(12) United States Patent
Schmees et al.

(10) Patent No.: US 11,964,953 B2
(45) Date of Patent: Apr. 23, 2024

(54) SUBSTITUTED AMINOTHIAZOLES AS DGKZETA INHIBITORS FOR IMMUNE ACTIVATION

(71) Applicants: Bayer Aktiengesellschaft, Leverkusen (DE); Deutsches Krebsforschungszentrum, Heidelberg (DE)

(72) Inventors: Norbert Schmees, Berlin (DE); Ulrike Roehn, Berlin (DE); Dennis Kirchhoff, Berlin (DE); Kirstin Petersen, Berlin (DE); Mareike Grees, Berlin (DE); Nicolas Werbeck, Freiburg (DE); Benjamin Bader, Berlin (DE); Rienk Offringa, Heidelberg (DE); Corinna Link, Heidelberg (DE)

(73) Assignees: Bayer Aktiengesellschaft, Leverkusen (DE); Deutsches Krebsforschungszentrum, Heidelberg (DE)

( * ) Notice: Subject to any disclaimer, the term of this patent is extended or adjusted under 35 U.S.C. 154(b) by 0 days.

(21) Appl. No.: 17/944,922

(22) Filed: Sep. 14, 2022

(65) Prior Publication Data

US 2023/0139936 A1  May 4, 2023

Related U.S. Application Data

(63) Continuation of application No. PCT/EP2021/060167, filed on Apr. 20, 2021.

(30) Foreign Application Priority Data

Apr. 24, 2020  (EP) .................... 20171280

(51) Int. Cl.
| | |
|---|---|
| C07D 277/42 | (2006.01) |
| A61P 35/00 | (2006.01) |
| C07D 277/46 | (2006.01) |
| C07D 417/06 | (2006.01) |
| C07D 417/10 | (2006.01) |
| C07D 417/12 | (2006.01) |
| C07D 417/14 | (2006.01) |
| C07D 471/08 | (2006.01) |
| C07D 487/04 | (2006.01) |
| C07K 16/28 | (2006.01) |

(52) U.S. Cl.
CPC ............ *C07D 277/42* (2013.01); *A61P 35/00* (2018.01); *C07D 277/46* (2013.01); *C07D 417/06* (2013.01); *C07D 417/10* (2013.01); *C07D 417/12* (2013.01); *C07D 417/14* (2013.01); *C07D 471/08* (2013.01); *C07D 487/04* (2013.01); *C07K 16/2818* (2013.01); *C07K 16/2827* (2013.01); *C07B 2200/07* (2013.01)

(58) Field of Classification Search
None
See application file for complete search history.

(56) References Cited

U.S. PATENT DOCUMENTS

| | | |
|---|---|---|
| 2005/0137239 A1 | 6/2005 | Hines et al. |
| 2023/0167078 A1 | 6/2023 | Schmees et al. |
| 2023/0167103 A1 | 6/2023 | Schmees et al. |

FOREIGN PATENT DOCUMENTS

| | | |
|---|---|---|
| AU | 2020413997 A1 | 6/2022 |
| CN | 103159695 A | 6/2013 |
| CN | 106109467 A | 11/2016 |
| EP | 1543824 A2 | 6/2005 |
| JP | 2011032254 A | 2/2011 |
| WO | 2004014884 A1 | 2/2004 |
| WO | 2005102318 A1 | 11/2005 |
| WO | 2005102325 A1 | 11/2005 |
| WO | 2005102326 A2 | 11/2005 |
| WO | 2005102346 A2 | 11/2005 |
| WO | 2005102455 A1 | 11/2005 |
| WO | 2005103022 A1 | 11/2005 |
| WO | 2005112920 A1 | 12/2005 |
| WO | 2005115304 A2 | 12/2005 |
| WO | 2005115385 A1 | 12/2005 |
| WO | 2006078287 A2 | 7/2006 |
| WO | 2006122011 A2 | 11/2006 |
| WO | 2007022415 A2 | 2/2007 |
| WO | 2007130075 A1 | 11/2007 |
| WO | 2008090382 A1 | 7/2008 |
| WO | 2009041790 A1 | 4/2009 |

(Continued)

OTHER PUBLICATIONS

Park et al., Bioorganic & Medicinal Chemistry Letters (2015), 25, pp. 3784-3787.*
Akiba, K-y. et al. (1975) "Formation of 2-Arylaminothiazoles by 1,3-Bipolar Cycloaddition on "Hector's Base" with Acetylenes," Tetrahedron Letters, 7:459-462.
Benziane, B. et al. (2017). "DGK deficiency protests against peripheral insulin resistance and improves energy metabolism," Journal of Lipid Research, 58:2324-2333.
Birkinshaw, T.N., et al. (1988). "Spectrometric and Chemical Studies of 5-Acyl- and 5-Nitroso-2-(N, N-disubstituted Amino)thiazoles," J. Chem. Soc. Perkin. Trans. 1:2209-2212.

(Continued)

*Primary Examiner* — Brian J Davis
(74) *Attorney, Agent, or Firm* — MORRISON & FOERSTER LLP

(57) ABSTRACT

The present invention covers aminothiazole compounds of general formula (I), in which $R^1$, $R^2$, $R^3$ and $R^4$ are as defined herein, methods of preparing said compounds, intermediate compounds useful for preparing said compounds, pharmaceutical compositions and combinations comprising said compounds and the use of said compounds for manufacturing pharmaceutical compositions for the treatment and/or prophylaxis of diseases, in particular of diacylglycerol kinase zeta (DGKζ) regulated disorders, as a sole agent or in combination with other active ingredients.

26 Claims, 5 Drawing Sheets
Specification includes a Sequence Listing.

(56) References Cited

FOREIGN PATENT DOCUMENTS

| WO | 2009149054 A1 | 12/2009 |
|---|---|---|
| WO | 2012064715 A1 | 5/2012 |
| WO | 2012075393 A2 | 6/2012 |
| WO | 2013033037 A2 | 3/2013 |
| WO | 2013056684 A2 | 4/2013 |
| WO | 2014173904 A1 | 10/2014 |
| WO | 2014181287 A1 | 11/2014 |
| WO | 2015046193 A1 | 4/2015 |
| WO | 2015199206 A1 | 12/2015 |
| WO | 2019133445 A1 | 7/2019 |
| WO | 2020006016 A1 | 1/2020 |
| WO | 2020006018 A1 | 1/2020 |
| WO | 2021028382 A1 | 2/2021 |
| WO | 2021041588 A1 | 3/2021 |
| WO | 2021043966 A1 | 3/2021 |
| WO | 2021091885 A2 | 5/2021 |
| WO | 2021132422 A1 | 7/2021 |
| WO | 2021214019 A1 | 10/2021 |
| WO | 2021214020 A1 | 10/2021 |
| WO | 2021214220 A1 | 10/2021 |

OTHER PUBLICATIONS

Brindley, J.C et al. (1987). "N'-Substituted N-Acyl- and N-Imidoyl-thioureas: Preparation and Conversion of N',N'-Disubstituted Compounds into 2-(N,N-Disubstituted Amino)thiazol-5-yl Ketones," J. Chem. Soc. Perkin. Trans. 1:1153-1158.
Cai, K. et al. (2014). "Increased diacylglycerol kinase expression inhuman metastatic colon cancer cells augments Rho GTPase activity and contributes to enhanced," BMC Cancer, 14(208):1-10.
Diao, J. et al. (2016) "Loss of Diacylglycerol Kinase-Inhibits Cell Proliferation and Survival in Human Gliomas," Mol Neurobiol, 53:5425-5435.
Eichmann, T. O. et al., (2015) "DAG tales: the multiple faces of diacylglycerol—stereochemistry, metabolism, and signaling," Cell. Mol. Life Sci.; 72:3931-3952.
Funnell, R. A. et al. (1987), "A Study of Three Reactions leading to Isomeric 2-(N,N-Disubstituted Amino)thiazol-5-yl Ketones" J. Chem. Soc. Perkin. Trans. 1:2311-2315.
Jing, W. et al. (2017). "T Cells Deficient in Diacylglycerol Kinase ζ AreResistant to PD-1 Inhibition and Help Create Persistent Host Immunity to Leukemia," Cancer Research, 77(20):5676-5686.
Joshi, R.P., et al. (2013). "Diacylglycerol Kinases: Regulated Controllers of T Cell Activation, Function, and Development," Int. J. Mol. Sci. 14: 6649-6673.
Jung, I-Y. et al., (2018) "Unleashing the Therapeutic Potential of CAR-T Cell Therapy Using Gene-Editing Technologies," Mol. Cells; 41 (8):717-723.
Jung, I-Y. et al., (Aug. 15, 2018) "CRISPR/Cas9-Mediated Knockout of DGK Improves Antitumor Activities of Human T Cells," Cancer Res; 78(16):4692-4703.
Keir, M.E. et al. (2008, e-pub. Jan. 2, 2008). "PD-1 and Its Ligands in Tolerance and Immunity," Front. Immunol., 178, 26:677-704.
Kikelj, D. et al. (2002) "Product Class 17: Thiazoles," Science of Synthesis 4(17):627-833.
Krishna, S. et al., (Jul. 2013) "Regulation of lipid signaling by diacylglycerol kinases during T cell development and function," T Cell Biology; 4:1-14.
Li, H. et al. (2019). "Knockdown of diacylglycerol kinase zeta (DGKZ) induces apoptosis and G2/M phase arrest in human acute myeloid leukemia HL-60 cells through MAPK/survivin/caspase pathway," Pharmazie, 74:418-422.
Meakins, G.D. et al. (1984) "An Unexpected Outcome of a General Thiazole Synthesis," J. Chem. Soc. Chem. Commun. 837-838.
Olenchock, B. A. et al., (Nov. 2006) "Disruption of diacylglycerol metabolism impairs the induction of T cell anergy," Nature Immunology; 7(11)1174-1181.

Quann, E. J. et al., (2011) "A Cascade of Protein Kinase C Isozymes Promotes Cytoskeletal Polarization in T Cells," Nat Immunol; 12(7):647-654.
Riese, M. J. et al., (Feb. 18, 2011) "Decreased Diacylglycerol Metabolism Enhances ERK Activation and Augments CD8+ T Cell Functional Responses," Journal of Biological Chemistry; 286(7):5254-5265.
Riese, M. J. et al., (Jun. 13, 2013) "Enhanced Effector Responses in Activated CD8+ T Cells Deficient in Diacylglycerol Kinases," Cancer Res; 73(12):3566-3577.
Ruffo, E. et al., (2016) "Inhibition of diacylglycerol kinase alpha restores restimulation-induced cell death and reduces immunopathology in XLP-1," Sci Transl Med.; 321ra7, 8(321):1-27.
Sandoval, E. et al. (2017), "The Discovery of Novel Antimalarial Aminoxadiazoles as a Promising Nonendoperoxide Scaffold," J. Med. Chem. 60: 6880-6896.
Singh B. K. et al., (Sep. 3, 2019) "Diacylglycerol kinase ζ promotes allergic airway inflammation and airway hyperresponsiveness through distinct mechanisms," Sci. Signal; eaax3332 12: 1-13.
Titus, S. et al. (2014) "One-pot four-component synthesis of 4-hydrazinothiazoles: novel scaffolds for drug discovery," Tetrahedron Letters, 55:5465-5467.
Velnati, S. et al., (2019) "Identification of a novel DGKα inhibitor for XLP-1 therapy by virtual screening," European Journal of Medicinal Chemistry;164:378-390.
Wee, S. et al. (2019) "Abstract 936: Regulation of CD8+ T-cell function and antitumor activity by DGKα and DGK ζ," Cancer Res, 79(13 Supplement): 936, 1-3.
Wesley, E.M. et al. (2018). "Diacylglycerol Kinase (DGK) and Casitas b-Lineage Proto-Oncogene b-Deficient Mice Have Similar Functional Outcomes in T Cells but DGK Deficient Mice Have Increased T Cell Activation and Tumor Clearance," Immuno Horizons, 2(4):107-118.
Xing, Y. et al. (2017). "AuIII-Catalyzed Formation of α-Halomethyl Ketones from Terminal Alkynes," Eur. J. Org. Chem.: 781-785.
Yang, E. et al. (2016). "Diacylglycerol kinase ζ Is a Target to Enhance NK Cell Function," J. Immunol. 179:934-941.
Yang, L. et al. (2015). "Diacylglycerol Kinase (DGK) Inhibitor II (R59949) Could Suppress Retinal Neovascularization and ProtectRetinal Astrocytes in an Oxygen-Induced Retinopathy Model," J. Mol. Neurosci. 56:78-88.
Yu, W. et al. (2019), "DGKZ Acts as a Potential Oncogene in Osteosarcoma Proliferation Through Its Possible Interaction WithERK1/2 and MYC Pathway," Frontiers in Oncology, 655, 8:1-11.
Zhong, X-P. et al., (Sep. 2003) "Enhanced T cell responses due to diacylglycerol kinase ζ deficiency," Nature Immunology; 4(9):882-890.
Zhu, Y-p. et al. (2013) "Target-oriented synthesis: miscellaneous synthetic routes to access 1,4-enediones through the coupling of 1,3-dicarbonyl compounds with multiform substrates," Tetrahedron, 69:6392-6398.
RN 1348293-02-6 Registry (Dec. 4, 2011) "Propanoic acid, 3-[[4-[[4-amino-5-(2,6-dichlorobenzoyl)-2-thiazolyl]methylamino]phenyl]sulfonyl]-, 1-methylethyl ester (CA Index Name)" 1 page.
RN 1349215-57-1 Registry (Dec. 5, 2011) "Methanone, [4-amino-2-[[4-[[3-(dimethylamino)propyl]sulfonyl]phenyl]methylamino]-5-thiazolyl](2,6-dichlorophenyl)—(CA Index Name)" 1 page.
RN 1349635-19-3 Registry (Dec. 6, 2011). "Methanone, [4-amino-2-[[4-[(2,3-dihydroxypropyl)sulfonyl]phenyl]methylamino]-5-thiazolyl](2,6-dichlorophenyl)—(CA Index Name)" 1 page.
Romagnoli, R. et al. (2009). "2-Arylamino-4-Amino-5-Aroylthiazoles. "One-Pot" Synthesis and Biological Evaluation of a New Class of Inhibitors of Tubulin Polymerization," J. Med. Chem. 52:5551-5555.
Riess R. et al (1998) "Evaluation of Protecting Groups for 3-Hydroxyisoxazoles 2 Short Access to 3-Alkoxyisoxazole-5-carbaldehydes and 3-Hydroxyisoxazole-5-carbaldehyde, the Putative Toxic Metabolite of Muscimol," Eur. J. Org. Chem., pp. 473-479.

* cited by examiner

Figure 1

```
MGDYKDDDDK MEPRDGSPEA RSSDSESASA SSSGSERDAG PEPDKAPRRL NKRRFPGLRL FGHRKAITKS GLQHLAPPPP TPGAPCSESE
RQIRSTVDWS ESATYGEHIW FETNVSGDFC YVGEQYCVAR MLKSVSRRKC AACKIVVHTP CIEQLEKINF RCKPSFRESG SRNVREPTFV
RHHWVHRRRQ DGKCRHCGKG FQQKFTFHSK EIVAISCSWC KQAYHSKVSC FMLQQIEEPC SLGVHAAVVI PPTWILRARR PQNTLKASKK
KKRASFKRKS SKKGPEEGRW RPFIIRPTPS PLMKPLLVFV NPKSGGNQGA KIIQSFLWYL NPRQVFDLSQ GGPKEALEMY RKVHNLRILA
CGGDGTVGWI LSTLDQLRLK PPPPVAILPL GTGNDLARTL NWGGGYTDEP VSKILSHVEE GNVVQLDRWD LHAEPNPEAG PEDRDEGATD
RLPLDVFNNY FSLGFDAHVT LEFHESREAN PEKFNSRFRN KMFYAGTAFS DFLMGSSKDL AKHIRVVCDG MDLTPKIQDL KPQCVVFLNI
PRYCAGTMPW GHPGEHHDFE PQRHDDGYLE VIGFTMTSLA ALQVGGHGER LTQCREVVLT TSKAIPVQVD GEPCKLAASR IRIALRNQAT
MVQKAKRRSA APLHSDQQPV PEQLRIQVSR VSMHDYEALH YDKEQLKEAS VPLGTVVVPG DSDLELCRAH IERLQQEPDG AGAKSPTCQK
LSPKWCFLDA TTASRFYRID RAQEHLNYVT EIAQDEIYIL DPELLGASAR PDLPTPTSPL PTSPCSPTPR SLQGDAAPPQ GEELIEAAKR
NDFCKLQELH RAGGDLMHRD EQSRTLLHHA VSTGSKDVVR YLLDHAPPEI LDAVEENGET CLHQAAALGQ RTICHYIVEA GASLMKTDQQ
GDTPRQRAEK AQDTELAAYL ENRQHYQMIQ REDQETAV
```

Figure 2

```
Ser Ile Ile Asn Phe Glu Lys Leu
1               5
```

Figure 3

```
Ser Met Leu Val Leu Leu Pro Asp Glu Val Ser Gly Leu Glu Gln Leu
1               5                   10                  15
Glu Ser Ile Ile Asn Phe Glu Lys Leu Thr Glu Trp Thr Ser
            20                  25                  30
```

Figure 4

```
Asp Tyr Lys Asp Asp Asp Lys
1               5
```

Figure 5

```
Gly Cys Cys Ala Cys Cys
1               5
```

SUBSTITUTED AMINOTHIAZOLES AS DGKZETA INHIBITORS FOR IMMUNE ACTIVATION

CROSS REFERENCE TO RELATED APPLICATIONS

This application is a continuation of International Application No. PCT/EP2021/060167, filed internationally on Apr. 20, 2021, which claims benefit of European Application No.: 20171280.9, filed Apr. 24, 2020, the disclosures of which are herein incorporated by reference in their entirety.

REFERENCE TO AN ELECTRONIC SEQUENCE LISTING

The contents of the electronic sequence listing (777052066101SEQLIST.xml; Size: 8,228 bytes; and Date of Creation: Aug. 9, 2022) is herein incorporated by reference in its entirety.

The present invention covers substituted aminothiazole compounds of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular of diacylglycerol kinase zeta (DGKzeta, DGKζ) regulated disorders, as a sole agent or in combination with other active ingredients.

The compounds of general formula (I) inhibit DGKζ and, by this, enhance T cell mediated immune response. This is a new strategy to use the patient's own immune system to overcome immunoevasive strategies utilized by many neoplastic disorders, respectively cancer and by this enhancing anti-tumor immunity. Furthermore, said compounds are used in particular to treat disorders such as viral infections or conditions with dysregulated immune responses or other disorders associated with aberrant DGKζ signaling.

The present invention further relates to the use of the compounds of general formula (I) for manufacturing pharmaceutical compositions for enhancement of T cell mediated immune response.

The present invention further relates to the use of the compounds of general formula (I) for manufacturing pharmaceutical compositions for the treatment of cancer.

The present invention further relates to the use of the compounds of general formula (I) for manufacturing pharmaceutical compositions for the treatment or prophylaxis of virus infections, lymphoproliferative disorders, asthma, eye diseases, and type 2 diabetes/insulin resistance.

BACKGROUND

Diacylglycerol kinases (DGKs) represent a family of enzymes that catalyze phosphorylation of the membrane lipid sn-1,2 diacylglycerol (DAG) to form phosphatidic acid (PA) (T. O. Eichmann and A. Lass, Cell. Mol. Life Sci. 2015, 72, 3931-3952). In T cells, DAG is formed downstream of the T cell receptor (TCR) after activation of the gamma 1 isoform of phospholipase C (PLCγ1) and cleavage of phosphatidylinositol 4,5-biphosphate (PIP2) into DAG and an additional second messenger, inositol 1,4,5-triphosphate (IP3) (S. Krishna and X.-P. Zhong, Front. Immunol. 2013, 4, 178). Whereas, IP3 is important in facilitating release of calcium from the endoplasmic reticulum, DAG interacts with other proteins important in TCR signal transduction, such as Protein kinase Cθ (E. J. Quann et al., Nat. Immunol. 2011, 12 (7), 647-654) and the Ras activating protein RasGRP1 (S. Krishna and X.-P. Zhong, Front. Immunol. 2013, 4, 178). Although, three isoforms of DGK are known to be present within T cells [DGKα (DGKalpha), DGKδ (DGKdelta), and DGKζ (DGKzeta)], only two, DGKα and DGKζ, are thought to play an important role in facilitating DAG metabolism downstream of the TCR (R. P. Joshi and G. A. Koretzky, Int. J. Mol. Sci. 2013, 14 (4), 6649-6673).

Targeting the activity of DGKζ in T cells, either by germline deletion, or with chemical inhibitors, results in enhanced and sustained signaling downstream of T cells, as assessed by prolonged phosphorylation of downstream molecules, such as extracellular signal-related kinases 1/2 (ERK1/2) and NFκB (X.-P.-Zhong et al., Nat. Immunol. 2003, 4, 882-890; B. A. Olenchock et al., Nat. Immunol. 2006, 7 (11), 1174-1181; M. J. Riese et al., J. Biol. Chem. 2011, 286, 5254-5265; E. M. Wesley et al., ImmunoHorizons 2018, 2 (4), 107-118).

Deletion of DGKζ in T cells leads to enhanced production of effector cytokines, such as IL2, IFNγ and enhanced proliferation (X.-P. Zhong et al., Nat. Immunol. 2003, 4, 882-890; B. A. Olenchock et al., Nat. Immunol. 2006, 7 (11), 1174-1181, E. M. Riese et al., J. Biol. Chem. 2011, 286, 5254-5264).

Adoptive transfer of DGKζ deficient T cell reduced leukaemia burden after inoculation of C1498.SIY leukaemia cells compared to control. Also, DGKζ deficient T cells are at least partially resistant to PD1 mediated inhibitory signals (W. Jing et al., Cancer Res. 2017, 77 (20), 5676-5686). In addition, DGKζ deficient mice have reduced tumor sizes compared to control after orthotopic tumor injection of a pancreatic tumor model (E. M. Wesley et al., ImmunoHorizons, 2018, 2 (4), 107-118). Also, S. Wee et al. inoculated C57BL/6 mice with a variety of syngeneic tumor cell lines—MC38 colon carcinoma, B16F1 melanoma, and C1498 leukemia—and analysed survival and tumor growth between mice deficient in DGKζ in the presence or absence of anti-PD1 treatment. DGKζ–/– mice suppressed growth of subcutaneously implanted tumor cells in the three model systems and the combination of DGKζ-deficiency and anti-PD1 was additive in tumor control (S. Wee et al., Proceedings of the American Association for Cancer Research Annual Meeting 2019; Cancer Res. 2019, 79 (13 Suppl): Abstract nr 936).

These findings suggest that DGKζ might serve as a useful target for enhancing T cell anti-tumor activity.

Additionally, the adoptive transfer of CAR (chimeric antigen receptor)-T cells deficient in DGKζ demonstrated increased efficacy compared to wild type CAR T cells in the treatment of murine mesothelioma (M. J. Riese et al., Cancer Res. 2013, 73 (12), 3566-3577) and a glioblastoma xenograft mouse model in combination with DGKα knockout (I.-Y. Jung et al., Cancer Res. 2018, 78 (16), 4692-4703).

Also, DGKζ-deficient mice mounted a more robust immune response to lymphocytic choriomeningitis virus infection than did wild-type mice (X.-P. Zhong et al., Nat. Immunol. 2003, 4, 882-890).

DGKζ is also relevant in natural killer (NK) cells. Upon stimulation through multiple activating receptors, NK cells from mice lacking DGKζ display increased cytokine production and degranulation in an ERK-dependent manner. Additionally, they have improved cytotoxic functions against tumor cell lines. (E. Yang et al. J. Immunol. 2016, 197(3), 934-41.)

Apart from immune-cell regulation, DGKζ also plays a role in cancer, mediating numerous aspects of cancer cell progression including proliferation, apoptosis, survival, invasion and tumorigenicity, e.g. in osteosarcoma, colon cancer, breast cancer, prostate cancer, glioma and leukemia models (W. Yu et al., Front. Oncol. 2019, 8:655; K. Cai et al., BMC Cancer 2014, 14:208; J. Diao et al., Mol. Neurobiol. 2016; 53, 5425-35; H. Li et al. Pharmazie 2019, 74(7): 418-422).

In addition, DGKζ knock-out diminished both airway inflammation and airway hyperresponsiveness in mice and also reduced bronchoconstriction of human airway samples in vitro by blocking T helper 2 (TH2) differentiation (B. A. Singh et al., Sci. Signal. 2019, 12: eaax3332).

Taken together, the findings from these studies argue that restraining DGKζ activity in T cells and tumor cells may prove valuable in generating more vigorous immune responses against pathogens and tumors and in ameliorating Th2 driven (auto-) immune diseases (in re-balancing the immune-system).

Furthermore, inhibition of DGKα has the potential to reverse the life-threatening Epstein-Barr virus (EBV)-associated immunopathology that occurs in X-linked lymphoproliferative disease (XLP-1) patients (E. Ruffo et al., Sci. Transl. Med. 2016, 8: (321):321ra7; S. Velnati et al., Eur. J. Med. Chem. 2019, 164, 378-390). Based on the underlying mode of action, it can be assumed that inhibition of DGKζ would have a similar effect.

The DGKα-inhibitor II (R59949) could suppress retinal neovascularization and protect retinal astrocytes in an Oxygen-Induced Retinopathy Model (L. Yang et al., J. Mol. Neurosci. 2015, 56, 78-88). Also, based on the underlying mode of action, it can be assumed that inhibition of DGKζ would have a similar effect.

In a DGKζ knock-out mouse it was shown that DGKζ deficiency increases protection against insulin resistance (B. Benziane et al., J. Lipid Res. 2017, 58 (12), 2324-2333).

In summary, inhibiting DGKζ activity has a therapeutic potential in targeting tumors directly as well as addressing virus infections, lymphoproliferative disorders, asthma, eye diseases, and type 2 diabetes/insulin resistance.

PRIOR ART

WO2020/006016 and WO2020/006018 describe Naphthyridinone compounds as T cell activators, which inhibit the activity of DGKα and/or DGKζ, for treatment of viral infections and proliferative disorders, such as cancer. WO2021/041588 describes pyridopyrimidinonyl compounds as T cell activators, which inhibit the activity of DGKα and/or DGKζ, for treatment of viral infections and proliferative disorders, such as cancer.

2,4,5-trisubstituted triazole derivatives featuring a substituted amino group attached to C-2 of the thiazole core have been disclosed in published patent applications in various technical contexts but not in the context of DGK inhibition.

WO 2014/181287 discloses heterocyclyl compounds as inhibitors of Interleukin 17 and Tumour Necrosis Factor alpha.

WO 2014/173904 discloses compounds having antibacterial activity.

WO 2009/149054 discloses small molecule inhibitors for the treatment or prevention of Dengue fever infection.

WO 2007/130075 discloses aminothiazole derivatives as human stearoyl-CoA desaturase inhibitors.

WO 2012/064715 discloses compositions and methods relating to heat shock transcription factor activating compounds and targets thereof.

WO 2005/103022 discloses substituted thiazole and pyrimidine derivatives as melanocortin receptor modulators.

CN 106109467 discloses the medical application of aromatic compounds, including thiazoles, in treating pyrazinamide-resistant tuberculosis.

WO 2015/199206 discloses compounds derived from a six-membered ring as TRPV4 inhibitors.

WO 2015/046193 discloses aromatic heterocyclic amine derivatives as TRPV4 inhibitors.

CN 103159695 discloses thiazole compounds capable of restraining human immunodeficiency (HIV) virus replication and effective against drug-resistant HIV virus strains.

WO 2013/056684 discloses thiazole derivatives as dihydroorotate dehydrogenase (DHODH) inhibitors.

WO 2013/033037 discloses compounds of various chemotypes, inter alia thiazole derivatives, as antiprion compounds.

WO 2012/075393 discloses compounds of various chemotypes, inter alia thiazole derivatives, as activators of proteasomal degradation.

JP 2011032254 discloses compounds of various chemotypes, inter alia thiazole derivatives, as pest controlling agents.

WO 2009/041790 discloses 2,4,5-trisubstituted thiazole derivatives as inhibitors of the sphingosylphosphorylcholine (SPC) receptor for treatment of inflammatory diseases.

WO 2008/090382 discloses thiazole and oxazole derivatives for use in the treatment of prion diseases, cancer, and conditions of the central nervous system as well as in the regulation of stem cells.

WO 2007/022415 discloses substituted 2-aminothiazoles for treating neurodegenerative diseases.

WO 2006/122011 discloses thiazole compounds and methods of use in treating viral infections, particularly hepatitis C virus infections.

WO 2006/078287 discloses derivatives of various 5-membered heteroarenes, inter alia thiazoles, as inhibitors of phosphodiesterase 4B.

WO 2005/102318, WO 2005/102325, WO 2005/102326, WO 2005/102346, WO 2005/102455, WO 2005/112920, WO 2005/115304, WO 2005/115385 all deal with c-Kit inhibitors of various chemotypes, including 2-aminothiazole derivatives, and various uses thereof.

EP 1543824 and US 2005/0137239 disclose thiazole derivatives to counter glycation.

WO 2004/014884 discloses thiazole derivatives as neuropeptide Y receptor ligands.

WO 2019/133445 discloses aminothiazole derivatives as inhibitors of Vanin-1.

WO 2021/043966 discloses substituted five-membered nitrogen containing heteroaryl compounds as inhibitors of the NOD-like receptor (NLR) family, pyrin domain-containing protein 3 (NLRP3).

2,4,5-trisubstituted triazole derivatives structurally related to the compounds of the present invention but yet structurally distinct have also been disclosed in several scientific publications.

D. Kikelj and U. Urleb, Science of Synthesis (2002), 11, 627-833, is a general review on the synthesis of thiazoles. By far most of the specific compounds disclosed are, besides having the thiazole core in common with the compounds of the present invention, structurally distant from these. Several individual compounds disclosed therein, namely those disclosed on pp 651, 681-683, and 719, and including {4-methyl-2-[methyl(phenyl)amino]-1,3-thiazol-5-yl}(phenyl)methanone, are somewhat structurally related to the compounds of the present invention but yet structurally distinct.

2,4,5-trisubstituted triazole derivatives structurally related to the compounds of the present invention but yet structurally distinct have also been disclosed in several journal articles.

None of the journal articles listed below, which also disclose some compounds which are somewhat structurally related to the compounds of the present invention but yet structurally distinct, disclose a therapeutic of pharmaceutical application of the compounds disclosed therein.

S. Titus et al., Tetrahedron Lett. 2014, 55, 5465-5467, disclose a four-component synthesis of 4-hydrazinothiazole derivatives.

T. N. Birkinshaw et al., J. Chem. Soc. Perkin Trans. 1, 1988, 2209-2212, disclose spectrometric and chemical studies on 5-acyl and 5-nitroso-2-(N,N-disubstituted amino) thiazoles.

R. A. Funnell et al., J. Chem. Soc. Perkin Trans. 1, 1987, 2311-2315 disclose a study on the formation of isomeric 2-(N,N-disubstituted amino) thiazol-5-yl ketones.

J. C. Brindley et al., J. Chem. Soc. Perkin Trans. 1, 1987, 1153-1158 disclose the conversion of N'-substituted N-acyl and N-imidoyl thioureas into 2-(N,N-disubstituted amino) thiazol-5-yl ketones.

G. D. Meakins et al., J. Chem. Soc. Chem. Comm. 1984, 837-838, disclose a chemical reaction unexpectedly yielding 5-benzoyl-4-methyl-2-(N-methyl-N-phenylamino)thiazole.

K. Akiba et al., Tetrahedron Lett. 1975, 7, 459-462, disclose the synthesis of certain 2-arylaminothiazoles by 1,3-cycloaddition of 4-aryl-3-arylimino-5-imino-1,2-4-thiadiazolidine (also known as Hector's base) and acetylenes.

Finally, three structures which are somewhat structurally related to the compounds of the present invention but yet structurally distinct, are disclosed in the database Chemical Abstracts Registry (CAS Registry), all without a reference and without a technical application, having the CAS Registry numbers 1349635-19-3, 1349215-57-1, and 1348293-02-6.

However, the state of the art does not describe:
the specific substituted aminothiazole compounds of general formula (I) of the present invention as described and defined herein, i.e. compounds having a 2-aminothiazole core bearing:
an optionally substituted benzoyl or 6-membered heteroaroyl group attached to C-5,
a —NH$_2$ or methyl group attached to C-4,
and (i) an optionally substituted phenyl or 5- or 6-membered heteroaryl group and (ii) an alkyl group laterally substituted with a group —S(=O)$_2$—NH$_2$, or, particularly, —C(=O)—NH$_2$, both (i) and (ii) being attached to the nitrogen atom attached to C-2, said laterally substituted alkyl group being essential for potent inhibition of DGKζ as shown in comparative experiments, infra,
or stereoisomers, tautomers, N-oxides, hydrates, solvates, salts thereof, or mixtures of same, as described and defined herein, and as hereinafter referred to as "compounds of general formula (I)" or "compounds of the present invention",
or their pharmacological activity.

WO 2021/028382, relating to a different chemotype ([1,2,4]triazolo[1.5-c]quinazolin-5-amine compounds) according to formula (I) and abstract, discloses a single compound name N$^2$-(4-amino-5-benzoyl-1,3-thiazol-2-yl)-N$^2$-(3-methylphenyl)alaninamide, without providing a synthesis protocol and without biological data relating to said compound name.

It is desirable to provide novel compounds having prophylactic and therapeutic properties.

Accordingly, it is an object of the present invention to provide compounds and pharmaceutical compositions comprising these compounds used for prophylactic and therapeutic use in DGKζ regulated disorders in a T cell immune-stimulatory or immune-modifying manner. DGKζ regulated disorders comprise conditions with dysregulated immune responses, particularly in an immunologically suppressed tumor microenvironment in cancer, autoimmune diseases, viral infections as well as other disorders associated with aberrant DGKζ signalling. Said compounds can be used as sole agent or in combination with other active ingredients.

It has now been found, and this constitutes the basis of the present invention, that the compounds of the present invention have surprising and advantageous properties.

In particular, the compounds of the present invention have surprisingly been found to effectively inhibit the DGKζ protein and, by this, enhance T-cell mediated immunity. Accordingly, they provide novel structures for the treatment diseases of mammals, including humans, in particular of cancers, and may therefore be used for the treatment or prophylaxis of hyperproliferative disorders, such as cancer, for example.

DESCRIPTION OF THE INVENTION

In accordance with a first aspect, the present invention covers compounds of general formula (I):

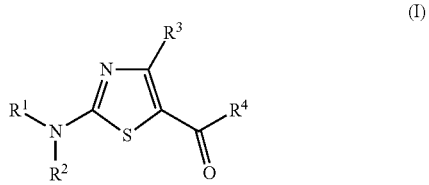

in which:
R$^1$ represents a phenyl or 6-membered heteroaryl group optionally substituted, one, two, or three times, each substituent independently selected from a halogen atom or a group selected from hydroxy, cyano, nitro, C$_1$-C$_6$-alkyl, (phenyl)-(C$_1$-C$_3$-alkyl)-, C$_1$-C$_6$-haloalkyl, C$_1$-C$_6$-alkoxy, (phenyl)-(C$_1$-C$_3$-alkoxy)-, C$_1$-C$_6$-haloalkoxy, —N(R$^5$)(R$^6$),
wherein the phenyl groups in said (phenyl)-(C$_1$-C$_3$-alkyl)- and (phenyl)-(C$_1$-C$_3$-alkoxy)-groups are optionally substituted one or two times, each substituent independently selected from a halogen atom or a group selected from cyano, methyl, ethyl, trifluoromethyl, methoxy, ethoxy, dimethylamino and trifluoromethoxy,
or two substituents attached to adjacent carbon atoms of said phenyl or 6-membered heteroaryl group together form a bivalent group selected from —(CH$_2$)—, —(CH$_2$)$_4$—, —(CH$_2$)$_2$—O—, —(CH$_2$)—O—, —CH$_2$—O—CH$_2$—, —(CH$_2$)$_2$—O—CH$_2$—, —O—CH$_2$—O—, —O—CH$_2$—CH$_2$—O—, —O-CF$_2$—O—, —O—CH$_2$—CF$_2$—O—, and —O—CF$_2$—CF$_2$—O—, or R$^1$ represents a 5-membered heteroaryl group optionally substituted one or two times, each substituent independently selected from a halogen atom or a group selected from cyano, C$_1$-C$_3$-alkyl, and C$_1$-C$_3$-alkoxy;

R$^2$ represents a group

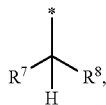

wherein "*" indicates the point of attachment to the nitrogen atom to which R$^2$ is attached;

R$^3$ represents a group selected from methyl and —NH$_2$;

R$^4$ represents a phenyl or 6-membered heteroaryl group optionally substituted, one, two, or three times, each substituent independently selected from a halogen atom or a group selected from cyano, nitro, C$_1$-C$_6$-alkyl, (phenyl)-(C$_1$-C$_3$-alkyl)-, (5- or 6-membered heteroaryl)-(C$_1$-C$_3$-alkyl)-, (C$_3$-C$_7$-cycloalkyl)-(C$_1$-C$_3$-alkyl)-, ((R$^9$)O)—(C$_1$-C$_6$-alkyl)-, C$_1$-C$_6$-haloalkyl, C$_3$-C$_7$-cycloalkyl, —OR$^9$, —N(R$^{10}$)(R$^{11}$), ((R$^{10}$)(R$^{11}$)N)—(C$_1$-C$_3$-alkyl)-, —C(═O)—N(R$^{12}$)(R$^{13}$), —S(═O), —R$^{14}$, —C(═O)R$^{14}$, —C(═O)—OR$^{17}$, and a 5- or 6-membered heteroaryl group which itself is optionally substituted with one or two substituents selected from a halogen atom and a methyl group, or two substituents attached to adjacent carbon atoms of said phenyl or 6-membered heteroaryl group together form a bivalent group selected from —(CH$_2$)$_3$—, —(CH$_2$)$_4$—, —(CH$_2$)$_2$—O—, —(CH$_2$)$_3$—O—, —CH$_2$—O—CH$_2$—, —(CH$_2$)$_2$—O—CH$_2$—, —O—CH$_2$—O—, —O—CH$_2$—CH$_2$O—, —O—CF$_2$—O—, —O—CH$_2$—CF$_2$—O—, and —O—CF$_2$—CF$_2$—O—;

R$^5$ and R$^6$ represent, independently from each occurrence, a hydrogen atom or a group selected from C$_1$-C$_4$-alkyl, (C$_1$-C$_4$-alkyl)-C(═O)—, C$_3$-C$_4$-cycloalkyl and (phenyl)-(C$_1$-C$_3$-alkyl)-, or R$^5$ and R$^6$, together with the nitrogen atom to which they are attached, represent a monocyclic nitrogen containing 4- to 7-membered heterocycloalkyl group which is optionally substituted one, two or three times, each substituent independently selected from a halogen atom or a group selected from oxo, hydroxy, C$_1$-C$_4$-alkyl, (C$_1$-C$_4$-alkyl)-C(═O)—, C$_3$-C$_4$-cycloalkyl and C$_1$-C$_4$-alkoxy;

R$^7$ represents a hydrogen atom or a C$_1$-C$_2$-alkyl group;

R$^8$ represents a group selected from —C(═O)—NH$_2$ and —S(═O)$_2$—NH$_2$;

R$^9$ represents a hydrogen atom or a group selected from C$_1$-C$_4$-alkyl, (5- or 6-membered heteroaryl)-(C$_1$-C$_3$-alkyl)-, (phenyl)-(C$_1$-C$_3$-alkyl)-, C$_1$-C$_6$-haloalkyl, C$_2$-C$_4$-hydroxyalkyl, (C$_1$-C$_3$-alkoxy)-C$_2$-C$_3$-alkyl-, ((C$_1$-C$_3$-alkyl)-C(═O)—O)—C$_2$-C$_3$-alkyl-, —C(R$^{18}$)(R$^{19}$)—C(═O)—OR$^{17}$, —C(R$^{18}$)(R$^{19}$)—C(═O)—N(R$^{20}$)(R$^{21}$), —C(═O)—N(R$^{20}$)(R$^{21}$), phenyl and 5- or 6-membered heteroaryl group, wherein the phenyl group within said (phenyl)-(C$_1$-C$_3$-alkyl)- group and said phenyl group itself, and the 5- or 6-membered heteroaryl group within said (5- or 6-membered heteroaryl)-(C$_1$-C$_3$-alkyl)- group and said 5- or 6-membered heteroaryl group itself are optionally substituted one or two times, each substituent independently selected from a halogen atom or a group selected from cyano, methyl, ethyl, trifluoromethyl, methoxy, ethoxy, dimethylamino and trifluoromethoxy;

R$^{10}$ and R$^{11}$ represent, independently from each occurrence, a hydrogen atom or a group selected from C$_1$-C$_4$-alkyl, C$_1$-C$_4$-haloalkyl, C$_2$-C$_4$-hydroxyalkyl, (C$_1$-C$_3$-alkoxy)-C$_2$-C$_3$-alkyl-, ((R$^{22}$)(R$^{23}$)N)—C$_2$-C$_3$-alkyl, (C$_3$-C$_7$-cycloalkyl)-(C$_1$-C$_3$-alkyl)-, (C$_1$-C$_4$-alkyl)-C(═O)—, C$_3$-C$_7$-cycloalkyl, (C$_3$-C$_7$-cycloalkyl)-C(═O)—, (phenyl)-(C$_1$-C$_3$-alkyl)-, (phenyl)-(C$_1$-C$_3$-alkyl)-C(═O)—, (phenyl)-(C$_1$-C$_3$-alkyl)-O—C(═O)—, phenyl and a 5- or 6-membered heteroaryl group, wherein C$_3$-C$_7$-cycloalkyl, and the C$_3$-C$_7$-cycloalkyl within said (C$_3$-C$_7$-cycloalkyl)-(C$_1$-C$_3$-alkyl)- and (C$_3$-C$_7$-cycloalkyl)-C(═O)— groups are optionally substituted one or two times, each substituent independently selected from a fluorine atom or a group selected from cyano, C$_1$-C$_2$-alkyl and C$_1$-C$_2$-haloalkyl, and wherein said phenyl and said 5- or 6-membered heteroaryl group, and the phenyl groups within said (phenyl)-(C$_1$-C$_3$-alkyl)-, (phenyl)-(C$_1$-C$_3$-alkyl)-C(═O)- and (phenyl)-(C$_1$-C$_3$-alkyl)-O—C(═O)— groups, are optionally substituted one or two times, each substituent independently selected from a halogen atom or a group selected from cyano, methyl, ethyl, trifluoromethyl, methoxy, ethoxy, dimethylamino and trifluoromethoxy, or R$^{10}$ and R$^{11}$, together with the nitrogen atom to which they are attached, represent a monocyclic nitrogen containing 4- to 7-membered heterocycloalkyl group, or a bicyclic nitrogen containing 5- to 11-membered heterocycloalkyl group, which are optionally substituted one, two or three times, each substituent independently selected from a halogen atom or a group selected from cyano, oxo, hydroxy, C$_1$-C$_4$-alkyl, C$_1$-C$_4$-haloalkyl, (C$_1$-C$_4$-alkyl)-C(═O)—, C$_3$-C$_7$-cycloalkyl, C$_1$-C$_4$-alkoxy, —N(R$^{22}$)(R$^{23}$), and a monocyclic 4- to 7-membered heterocycloalkyl group;

R$^{12}$ and R$^{13}$ represent, independently from each occurrence, a hydrogen atom or a group selected from C$_1$-C$_4$-alkyl, C$_1$-C$_4$-haloalkyl, C$_1$-C$_4$-hydroxyalkyl, (C$_1$-C$_4$-alkoxy)-C$_2$-C$_3$-alkyl-, (C$_1$-C$_4$-haloalkoxy)-C$_2$-C$_3$-alkyl-, (phenoxy)-C$_2$-C$_3$-alkyl-, C$_3$-C$_7$-cycloalkyl, monocyclic 4- to 7-membered heterocycloalkyl and (phenyl)-(C$_1$-C$_3$-alkyl)-, wherein C$_3$-C$_7$-cycloalkyl and monocyclic 4- to 7-membered heterocycloalkyl are optionally substituted one, two or three times, each substituent independently selected from a halogen atom or a group selected from cyano, oxo, hydroxy, C$_1$-C$_4$-alkyl, (C$_1$-C$_4$-alkyl)-C(═O)—, C$_3$-C$_4$-cycloalkyl and C$_1$-C$_4$-alkoxy, and wherein the phenyl groups within said (phenoxy)-C$_2$-C$_3$-alkyl- group and said (phenyl)-(C$_1$-C$_3$-alkyl)- group are optionally substituted one or two times, each substituent independently selected from a halogen atom or a group selected from cyano, methyl, ethyl, trifluoromethyl, methoxy, ethoxy, dimethylamino and trifluoromethoxy, or R$^{12}$ and R$^{13}$, together with the nitrogen atom to which they are attached, represent a monocyclic nitrogen containing 4- to 7-membered heterocycloalkyl group which is optionally substituted one, two or three times, each substituent independently selected from a halogen atom or a group selected from cyano, oxo, hydroxy, C$_1$-C$_4$-alkyl, (C$_1$-C$_4$-alkyl)-C(═O)—, C$_3$-C$_4$-cycloalkyl and C$_1$-C$_4$-alkoxy;

$R^{14}$ represents a group selected from $C_1$-$C_4$-alkyl, $C_1$-$C_4$-haloalkyl and phenyl, wherein the phenyl group is optionally substituted one or two times, each substituent independently selected from a halogen atom or a group selected from cyano, methyl, ethyl, trifluoromethyl, methoxy, ethoxy, dimethylamino and trifluoromethoxy;

$R^{17}$ represents a $C_1$-$C_4$-alkyl group;

$R^{18}$ and $R^{19}$ represent, independently from each occurrence, a hydrogen atom or a $C_1$-$C_4$-alkyl group;

$R^{20}$ represents a hydrogen atom or a group selected from $C_1$-$C_6$-alkyl, $C_3$-$C_4$-alkenyl, $C_3$-$C_4$-alkynyl, $C_1$-$C_3$-alkoxy, $C_3$-$C_7$-cycloalkyl, bicyclic $C_5$-$C_{11}$-cycloalkyl, adamantyl, monocyclic 4- to 7-membered heterocycloalkyl, bicyclic 5- to 11-membered heterocycloalkyl, phenyl, naphthyl, and 5- to 10-membered heteroaryl, wherein said $C_1$-$C_6$-alkyl group is optionally substituted one, two or three times, each substituent independently selected from a halogen atom or a group selected from hydroxy, cyano, $C_1$-$C_3$-alkoxy, —$N(R^{22})(R^{23})$, $C_3$-$C_7$-cycloalkyl, bicyclic $C_5$-$C_{11}$-cycloalkyl, adamantyl, monocyclic 4- to 7-membered heterocycloalkyl, bicyclic 5- to 11-membered heterocycloalkyl, phenyl, and 5- to 10-membered heteroaryl, said phenyl and 5- to 10-membered heteroaryl substituents themselves being optionally substituted one or two times, each substituent independently selected from a halogen atom or a group selected from cyano, methyl, ethyl, trifluoromethyl, methoxy, ethoxy, dimethylamino and trifluoromethoxy, and wherein $C_3$-$C_7$-cycloalkyl, bicyclic $C_5$-$C_{11}$-cycloalkyl, adamantyl, monocyclic 4- to 7-membered heterocycloalkyl and bicyclic 5- to 11-membered heterocycloalkyl are optionally substituted one, two or three times, each substituent independently selected from a halogen atom or a group selected from cyano, oxo, hydroxy, $C_1$-$C_4$-alkyl, ($C_1$-$C_4$-alkyl)-C(=O)—, $C_3$-$C_4$-cycloalkyl and $C_1$-$C_4$-alkoxy, and wherein said phenyl, naphthyl and 5- to 10-membered heteroaryl groups are optionally substituted one, two or three times, each substituent independently selected from a halogen atom or a group selected from cyano, $C_1$-$C_4$-alkyl, $C_1$-$C_4$-haloalkyl, $C_1$-$C_4$-alkoxy, $C_1$-$C_4$-haloalkoxy, —$N(R^{22})(R^{23})$ and —C(=O)—$N(R^{24})(R^{25})$, $R^{21}$ represents a hydrogen atom or a $C_1$-$C_4$-alkyl group, or $R^{20}$ and $R^{21}$, together with the nitrogen atom to which they are attached, represent a monocyclic nitrogen containing 4- to 7-membered heterocycloalkyl group which is optionally benzocondensed, and which is optionally substituted one, two or three times, each substituent independently selected from a halogen atom or a group selected from cyano, oxo, hydroxy, $C_1$-$C_4$-alkyl, $C_1$-$C_4$-haloalkyl, (phenyl)-($C_1$-$C_3$-alkyl)-, ($C_1$-$C_4$-alkyl)-C(=O)—, $C_3$-$C_4$-cycloalkyl, $C_1$-$C_4$-alkoxy, $C_1$-$C_3$-haloalkoxy, —$N(R^{22})(R^{23})$ and —C(=O)—$N(R^{24})(R^{25})$;

$R^{22}$ and $R^{23}$ represent, independently from each occurrence, a hydrogen atom or a group selected from $C_1$-$C_2$-alkyl and ($C_1$-$C_2$-alkyl)-C(=O)—;

$R^{24}$ and $R^{25}$ represent, independently from each occurrence, a hydrogen atom or a $C_1$-$C_4$-alkyl group, and n represents an integer 0, 1, or 2, and stereoisomers, tautomers, N-oxides, hydrates, solvates, and salts thereof, and mixtures of same.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3 or 4, in particular 1, 2 or 3.

When groups in the compounds according to the invention are substituted, it is possible for said groups to be mono-substituted or poly-substituted with substituent(s), unless otherwise specified. Within the scope of the present invention, the meanings of all groups which occur repeatedly are independent from one another. It is possible that groups in the compounds according to the invention are substituted with one, two or three identical or different substituents, particularly with one substituent.

As used herein, an oxo substituent represents an oxygen atom, which is bound to a carbon atom or to a sulfur atom via a double bond.

Should a composite substituent be composed of more than one part, e.g. ($C_1$-$C_2$alkoxy)-($C_1$-$C_6$-alkyl)-, it is possible for a given part to be attached at any suitable position of said composite substituent, e.g. it is possible for the $C_1$-$C_2$-alkoxy part to be attached to any suitable carbon atom of the $C_1$-$C_6$-alkyl part of said ($C_1$-$C_2$alkoxy)-($C_1$-$C_6$-alkyl)-group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen atom" means a fluorine, chlorine, bromine or iodine atom, particularly a fluorine, chlorine or bromine atom.

The term "$C_1$-$C_6$-alkyl" means a linear or branched, saturated, monovalent hydrocarbon group having 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group, or an isomer thereof. Particularly, said group has 1, 2, 3 or 4 carbon atoms ("$C_1$-$C_4$-alkyl"), e.g. a methyl, ethyl, propyl, isopropyl, butyl, sec-butyl isobutyl, or tert-butyl group, more particularly 1, 2 or 3 carbon atoms ("$C_1$-$C_3$-alkyl"), e.g. a methyl, ethyl, n-propyl or isopropyl group, more particularly 1 or 2 carbon atoms ("$C_1$-$C_2$-alkyl"), e.g. a methyl or ethyl group.

The term "$C_1$-$C_4$-hydroxyalkyl" means a linear or branched, saturated, monovalent hydrocarbon group in which the term "$C_1$-$C_4$-alkyl" is defined supra, and in which 1 or 2 hydrogen atoms are replaced with a hydroxy group, e.g. a hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl, 1-hydroxybutyl, 2-hydroxybutyl, 3-hydroxybutyl, 4-hydroxybutyl group, or an isomer thereof.

The term "$C_1$-$C_6$-haloalkyl" means a linear or branched, saturated, monovalent hydrocarbon group in which the term "$C_1$-$C_6$-alkyl" is as defined supra, and in which one or more of the hydrogen atoms are replaced, identically or differently, with a halogen atom. Particularly, said halogen atom is a fluorine atom. Said $C_1$-$C_6$-haloalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

The term "$C_1$-$C_6$-alkoxy" means a linear or branched, saturated, monovalent group of formula ($C_1$-$C_6$-alkyl)-O—, in which the term "$C_1$-$C_6$-alkyl" is as defined supra, e.g. a methoxy, ethoxy, n-propoxy, isopropoxy, n-butoxy, sec-butoxy, isobutoxy, tert-butoxy, pentyloxy, isopentyloxy or n-hexyloxy group, or an isomer thereof.

The term "$C_1$-$C_6$-haloalkoxy" means a linear or branched, saturated, monovalent $C_1$-$C_6$-alkoxy group, as defined supra, in which one or more of the hydrogen atoms is replaced, identically or differently, with a halogen atom. Particularly, said halogen atom is a fluorine atom. Said $C_1$-$C_6$-haloalkoxy group is, for example, fluoromethoxy, difluoromethoxy, trifluoromethoxy, 2,2,2-trifluoroethoxy or pentafluoroethoxy.

The term "$C_3$-$C_4$-alkenyl" means a linear or branched, monovalent hydrocarbon group, which contains one or two double bonds, and which has 3 or 4 carbon atoms. Said alkenyl group is, for example, a prop-2-en-1-yl (or "allyl"), prop-1-en-1-yl, but-3-enyl, but-2-enyl or but-1-enyl group.

The term "$C_3$-$C_4$-alkynyl" means a linear or branched, monovalent hydrocarbon group which contains one triple bond, and which contains 3 or 4 carbon atoms. Said $C_3$-$C_4$-alkynyl group is, for example, a prop-1-ynyl, prop-2-ynyl (or "propargyl"), but-1-ynyl, but-2-ynyl or but-3-ynyl group.

The term "$C_3$-$C_7$-cycloalkyl" means a saturated, monovalent, monocyclic hydrocarbon ring which contains 3, 4, 5, 6 or 7 carbon ring atoms ("$C_3$-$C_7$-cycloalkyl"). Said $C_3$-$C_7$-cycloalkyl group is for example, a cyclopropyl, cyclobutyl, cyclopentyl, cyclohexyl or cycloheptyl group.

The term "bicyclic $C_6$-$C_{11}$-cycloalkyl" means a spirocycloalkyl, fused $C_5$-$C_{10}$-cycloalkyl or bridged $C_7$-$C_{10}$-cycloalkyl group as defined below:

The term "spirocycloalkyl" means a bicyclic, saturated, monovalent $C_5$-$C_{11}$ hydrocarbon group in which the two rings share one common ring carbon atom, and wherein said bicyclic hydrocarbon group contains 5, 6, 7, 8, 9, 10 or 11 carbon atoms, it being possible for said spirocycloalkyl group to be attached to the rest of the molecule via any one of the carbon atoms except the spiro carbon atom. Said spirocycloalkyl group is, for spiro[2.6]nonyl, spiro[3.3]heptyl, spiro[3.4]octyl, spiro[3.5]nonyl, spiro[3.6]decyl, spiro[4.4]nonyl, spiro[4.5]decyl, spiro[4.6]undecyl or spiro[5.5]undecyl.

The term "fused $C_6$-$C_{10}$-cycloalkyl" means a bicyclic, saturated, monovalent hydrocarbon group, in which the two rings share two adjacent ring atoms, such as bicyclo[4.2.0]octyl, octahydropentalenyl or decalinyl.

The term "bridged $C_7$-$C_{10}$-cycloalkyl" means a bicyclic, saturated, monovalent hydrocarbon group which the two rings share two common ring atoms which are not adjacent, e.g. bicyclo[2.2.1]heptyl (also known as norbornyl).

The term "bicyclic $C_5$-$C_{11}$-cycloalkyl" means a spirocycloalkyl, fused $C_5$-$C_{10}$-cycloalkyl or bridged $C_5$-$C_{10}$-cycloalkyl group as defined below:

The term "spirocycloalkyl" means a bicyclic, saturated, monovalent $C_5$-$C_{11}$ hydrocarbon group in which the two rings share one common ring carbon atom, and wherein said bicyclic hydrocarbon group contains 5, 6, 7, 8, 9, 10 or 11 carbon atoms, it being possible for said spirocycloalkyl group to be attached to the rest of the molecule via any one of the carbon atoms except the spiro carbon atom. Said spirocycloalkyl group is, for spiro[2.6]nonyl, spiro[3.3]heptyl, spiro[3.4]octyl, spiro[3.5]nonyl, spiro[3.6]decyl, spiro[4.4]nonyl, spiro[4.5]decyl, spiro[4.6]undecyl or spiro[5.5]undecyl.

The term "fused $C_5$-$C_{10}$-cycloalkyl" means a bicyclic, saturated, monovalent hydrocarbon group, in which the two rings share two adjacent ring atoms, such as bicyclo[4.2.0]octyl, octahydropentalenyl or decalinyl.

The term "bridged $C_5$-$C_{10}$-cycloalkyl" means a bicyclic, saturated, monovalent hydrocarbon group which the two rings share two common ring atoms which are not adjacent, e.g. bicyclo[1.1.1]pentyl or bicyclo[2.2.1]heptyl (also known as norbornyl).

The term "monocyclic 4- to 7-membered heterocycloalkyl" means a monocyclic, saturated heterocycle with 4, 5, 6 or 7 ring atoms in total, which contains one or two identical or different ring heteroatoms from the series N, O and S.

Said monocyclic heterocycloalkyl group, without being limited thereto, can be a 4-membered ring, such as azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example, or a 7-membered ring, such as azepanyl, 1,4-diazepanyl or 1,4-oxazepanyl, for example.

The term "monocyclic nitrogen containing 4- to 7-membered heterocycloalkyl group" means a monocyclic, saturated heterocycle with 4, 5, 6 or 7 ring atoms in total, which contains one ring nitrogen atom and optionally one further ring heteroatom from the series N, O and S.

Said monocyclic nitrogen containing 4- to 7-membered heterocycloalkyl group, without being limited thereto, can be a 4-membered ring, such as azetidinyl, for example; or a 5-membered ring, such as pyrrolidinyl, imidazolidinyl, pyrazolidinyl, 1,2-oxazolidinyl, 1,3-oxazolidinyl or 1,3-thiazolidinyl, for example; or a 6-membered ring, such as piperidinyl, morpholinyl, thiomorpholinyl, piperazinyl, or 1,2-oxazinanyl, for example, or a 7-membered ring, such as azepanyl, 1,4-diazepanyl or 1,4-oxazepanyl, for example.

The term "monocyclic nitrogen containing 4- to 7-membered heterocycloalkyl group which is optionally benzocondensed" means a monocyclic, saturated heterocycle with 4, 5, 6 or 7 ring atoms in total, which contains one ring nitrogen atom and optionally one further ring heteroatom from the series N, O and S, in which two adjacent ring carbon atoms may be shared with a benzene ring optionally fused thereto, such group being one of the aforementioned monocyclic nitrogen containing 4- to 7-membered heterocycloalkyl groups, such as pyrrolidinyl, piperidinyl, and the like, or benzocondensed groups e.g. 3,4-dihydroquinolin-1(2H)-yl, 3,4-dihydroisoquinolin-2(1H)-yl, 1,3-dihydro-2H-isoindol-2-yl or 2,3-dihydro-1H-indol-1-yl.

The term "bicyclic 6-11 membered heterocycloalkyl" means a 6- to 11-membered heterospirocycloalkyl, a 6- to 10-membered fused heterocycloalkyl or a 7- to 10-membered bridged heterocycloalkyl group as defined below:

The term "6- to 11-membered heterospirocycloalkyl" means a bicyclic, saturated heterocycle with 6, 7, 8, 9, 10 or 11 ring atoms in total, in which the two rings share one common ring carbon atom, which "heterospirocycloalkyl" contains one or two identical or different ring heteroatoms from the series: N, O, S; it being possible for said heterospirocycloalkyl group to be attached to the rest of the molecule via any one of the carbon atoms, except the spiro carbon atom, or, if present, a nitrogen atom.

Said heterospirocycloalkyl group is, for example, azaspiro[2.3]hexyl, azaspiro[3.3]heptyl, oxaazaspiro[3.3]heptyl, thiaazaspiro[3.3]heptyl, oxaspiro[3.3]heptyl, oxazaspiro[5.3]nonyl, oxazaspiro[4.3]octyl, azaspiro[4,5]decyl, oxazaspiro[5.5]undecyl, diazaspiro[3.3]heptyl, thiazaspiro[3.3]heptyl, thiazaspiro[4.3]octyl, azaspiro[5.5]undecyl, or one of the further homologous scaffolds such as spiro[3.4]-, spiro[4.4]-, spiro[2.4]-, spiro[2.5]-, spiro[2.6]-, spiro[3.5]-, spiro[3.6]-, spiro[4.5]- and spiro[4.6]-.

The term "a 6- to 10-membered fused heterocycloalkyl" means a bicyclic, saturated heterocycle with 6, 7, 8, 9 or 10 ring atoms in total, in which the two rings share two adjacent ring atoms, which "fused heterocycloalkyl" contains one or two identical or different ring heteroatoms from the series: N, O, S; it being possible for said fused heterocycloalkyl group to be attached to the rest of the molecule via any one of the carbon atoms or, if present, a nitrogen atom.

Said fused heterocycloalkyl group is, for example, azabicyclo[3.3.0]octyl, azabicyclo[4.3.0]nonyl, diazabicyclo[4.3.0]nonyl, oxazabicyclo[4.3.0]nonyl, thiazabicyclo[4.3.0]nonyl or azabicyclo[4.4.0]decyl.

The term "a 7- to 10-membered bridged heterocycloalkyl" means a bicyclic, saturated heterocycle with 7, 8, 9 or 10 ring atoms in total, in which the two rings share two common ring atoms which are not adjacent, which "bridged heterocycloalkyl" contains one or two identical or different ring heteroatoms from the series: N, O, S; it being possible for said bridged heterocycloalkyl group to be attached to the rest of the molecule via any one of the carbon atoms, except the spiro carbon atom, or, if present, a nitrogen atom.

Said bridged heterocycloalkyl group is, for example, azabicyclo[2.2.1]heptyl, oxazabicyclo[2.2.1]heptyl, thiazabicyclo[2.2.1]heptyl, diazabicyclo[2.2.1]heptyl, azabicyclo[2.2.2]octyl, diazabicyclo[2.2.2]octyl, oxazabicyclo[2.2.2]octyl, thiazabicyclo[2.2.2]octyl, azabicyclo[3.2.1]octyl, diazabicyclo[3.2.1]octyl, oxazabicyclo[3.2.1]octyl, thiazabicyclo[3.2.1]octyl, azabicyclo[3.3.1]nonyl, diazabicyclo[3.3.1]nonyl, oxazabicyclo[3.3.1]nonyl, thiazabicyclo[3.3.1]nonyl, azabicyclo[4.2.1]nonyl, diazabicyclo[4.2.1]nonyl, oxazabicyclo[4.2.1]nonyl, thiazabicyclo[4.2.1]nonyl, azabicyclo[3.3.2]decyl, diazabicyclo[3.3.2]decyl, oxazabicyclo[3.3.2]decyl, thiazabicyclo[3.3.2]decyl or azabicyclo[4.2.2]decyl.

The term "bicyclic nitrogen containing 6-11 membered heterocycloalkyl" means a 6- to 11-membered heterospirocycloalkyl, 6- to 10-membered fused heterocycloalkyl or 7- to 10-membered bridged heterocycloalkyl group as defined supra, however containing one ring nitrogen atom and optionally one or two further ring heteroatoms from the series N, O and S; it being possible for said bicyclic nitrogen containing 6-11 membered heterocycloalkyl group to be attached to the rest of the molecule via a nitrogen atom or any one of the carbon atoms, except a spiro carbon atom.

The term "bicyclic 5-11 membered heterocycloalkyl" means a 5-11 membered heterospirocycloalkyl, a 5-11 membered fused heterocycloalkyl or a 5-11 membered bridged heterocycloalkyl group as defined below:

The term "5-11 membered heterospirocycloalkyl" means a bicyclic, saturated heterocycle with 5, 6, 7, 8, 9, 10 or 11 ring atoms in total, in which the two rings share one common ring carbon atom, which "heterospirocycloalkyl" contains one or two identical or different ring heteroatoms from the series: N, O, S; it being possible for said heterospirocycloalkyl group to be attached to the rest of the molecule via any one of the carbon atoms, except the spiro carbon atom, or, if present, a nitrogen atom.

Said heterospirocycloalkyl group is, for example, azaspiro[2.2]pentyl, azaspiro[2.3]hexyl, azaspiro[3.3]heptyl, oxaazaspiro[3.3]heptyl, thiaazaspiro[3.3]heptyl, oxaspiro[3.3]heptyl, oxazaspiro[5.3]nonyl, oxazaspiro[4.3]octyl, azaspiro[4,5]decyl, oxazaspiro[5.5]undecyl, diazaspiro[3.3]heptyl, thiazaspiro[3.3]heptyl, thiazaspiro[4.3]octyl, azaspiro[5.5]undecyl, or one of the further homologous scaffolds such as spiro[3.4]-, spiro[4.4]-, spiro[2.4]-, spiro[2.5]-, spiro[2.6]-, spiro[3.5]-, spiro[3.6]-, spiro[4.5]- and spiro[4.6]-.

The term "5-11 membered fused heterocycloalkyl" means a bicyclic, saturated heterocycle with 5, 6, 7, 8, 9 or 10 ring atoms in total, in which the two rings share two adjacent ring atoms, which "fused heterocycloalkyl" contains one or two identical or different ring heteroatoms from the series: N, O, S; it being possible for said fused heterocycloalkyl group to be attached to the rest of the molecule via any one of the carbon atoms or, if present, a nitrogen atom.

Said fused heterocycloalkyl group is, for example, azabicyclo[3.1.0]hexyl, azabicyclo[3.3.0]octyl, azabicyclo[4.3.0]nonyl, diazabicyclo[4.3.0]nonyl, oxazabicyclo[4.3.0]nonyl, thiazabicyclo[4.3.0]nonyl or azabicyclo[4.4.0]decyl.

The term "5-11 membered bridged heterocycloalkyl" means a bicyclic, saturated heterocycle with 5, 6, 7, 8, 9 or 10 ring atoms in total, in which the two rings share two common ring atoms which are not adjacent, which "bridged heterocycloalkyl" contains one or two identical or different ring heteroatoms from the series: N, O, S; it being possible for said bridged heterocycloalkyl group to be attached to the rest of the molecule via any one of the carbon atoms, except the spiro carbon atom, or, if present, a nitrogen atom.

Said bridged heterocycloalkyl group is, for example, azabicyclo[2.2.1]heptyl, oxazabicyclo[2.2.1]heptyl, thiazabicyclo[2.2.1]heptyl, diazabicyclo[2.2.1]heptyl, azabicyclo[2.2.2]octyl, diazabicyclo[2.2.2]octyl, oxazabicyclo[2.2.2]octyl, thiazabicyclo[2.2.2]octyl, azabicyclo[3.2.1]octyl, diazabicyclo[3.2.1]octyl, oxazabicyclo[3.2.1]octyl, thiazabicyclo[3.2.1]octyl, azabicyclo[3.3.1]nonyl, diazabicyclo[3.3.1]nonyl, oxazabicyclo[3.3.1]nonyl, thiazabicyclo[3.3.1]nonyl, azabicyclo[4.2.1]nonyl, diazabicyclo[4.2.1]nonyl, oxazabicyclo[4.2.1]nonyl, thiazabicyclo[4.2.1]nonyl, azabicyclo[3.3.2]decyl, diazabicyclo[3.3.2]decyl, oxazabicyclo[3.3.2]decyl, thiazabicyclo[3.3.2]decyl or azabicyclo[4.2.2]decyl.

The term "bicyclic nitrogen containing 5-11 membered heterocycloalkyl" means a 5-11 membered heterospirocycloalkyl, 5-11 membered fused heterocycloalkyl or 5-11 membered bridged heterocycloalkyl group as defined supra, however containing one ring nitrogen atom and optionally one or two further ring heteroatoms from the series N, O and S; it being possible for said bicyclic nitrogen containing 5-11 membered heterocycloalkyl group to be attached to the rest of the molecule via a nitrogen atom or any one of the carbon atoms, except a spiro carbon atom.

The term "heteroaryl" means a monovalent, monocyclic or bicyclic aromatic ring having 5, 6, 8, 9 or 10 ring atoms (a "5- to 10-membered heteroaryl" group), which contains at least one ring heteroatom and optionally one, two or three further ring heteroatoms from the series: N, O and/or S, and which is bound via a ring carbon atom, or, if valency allows as e.g. in pyrrol-1-yl, a nitrogen atom.

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl (herein also referred to as pyridyl), pyridazinyl, pyrimidinyl, pyrazinyl or triazinyl; or a 9-membered heteroaryl group, such as, for example, benzofuranyl, benzothienyl, benzoxazolyl, benzisoxazolyl, benzimidazolyl, benzothiazolyl, benzotriazolyl, thiazolopyridinyl, indazolyl, indolyl, isoindolyl, indolizinyl or purinyl; or a 10-membered heteroaryl group, such as, for example, quinolinyl, quinazolinyl, isoquinolinyl, cinnolinyl, phthalazinyl, quinoxalinyl or pteridinyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "$C_1$-$C_6$", as used in the present text, e.g. in the context of the definition of "$C_1$-$C_6$-alkyl", "$C_1$-$C_6$-haloalkyl", "$C_1$-$C_6$-hydroxyalkyl", "$C_1$-$C_6$-alkoxy" or "$C_1$-$C_6$-haloalkoxy" means an alkyl group having a finite number of carbon atoms of 1 to 6, i.e. 1, 2, 3, 4, 5 or 6 carbon atoms.

Further, as used herein, the term "$C_3$-$C_7$", as used in the present text, e.g. in the context of the definition of "$C_3$-$C_7$-cycloalkyl", means a cycloalkyl group having a finite number of carbon atoms of 3 to 7, i.e. 3, 4, 5, 6 or 7 carbon atoms.

When a range of values is given, said range encompasses each value and sub-range within said range.

For example:

"$C_1$-$C_6$" encompasses $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_5$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$.

As used herein, the term "leaving group" means an atom or a group of atoms that is displaced in a chemical reaction as stable species taking with it the bonding electrons. In particular, such a leaving group is selected from the group comprising: a halogen atom, in particular a fluorine atom, a chlorine atom, a bromine atom or an iodide atom, being displaced as halide, in particular fluoride, chloride, bromide or iodide; (methylsulfonyl)oxy, [(trifluoromethyl)sulfonyl]oxy, [(nonafluorobutyl)sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

As used herein, the term "dipolar aprotic solvent" means a solvent selected from acetone, acetonitrile, propionitrile, dimethylsulfoxide, diethylsulfoxide, N,N-dimethylformamide, N,N-dimethylacetamide, N,N-diethylformamide, N,N-diethylacetamide, 1-methyl-2-pyrrolidinone, 1-ethyl-2-pyrrolidinone, 1-methyl-2-piperidinone and 1-ethyl-2-piperidinone, or mixtures thereof. Particularly, said dipolar aprotic solvent is acetonitrile, dimethylsulfoxide, N,N-dimethylformamide, N,N-dimethylacetamide or 1-methyl-2-pyrrolidinone.

As used herein, the term "room temperature" means a temperature in the range from 15° C. to 25° C.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{125}$I, $^{129}$I and $^{131}$I, respectively.

With respect to the treatment and/or prophylaxis of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3$H or $^{14}$C, are incorporated are useful e.g. in drug and/or substrate tissue distribution studies. These isotopes are particularly preferred for the ease of their incorporation and detectability. Positron emitting isotopes such as $^{18}$F or $^{11}$C may be incorporated into a compound of general formula (I). These isotopic variants of the compounds of general formula (I) are useful for in vivo imaging applications. Deuterium-containing and $^{13}$-C-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

In another embodiment the present invention concerns a deuterium-containing compound of general formula (I) having 1, 2, 3 or 4 deuterium atoms, particularly with 1, 2 or 3 deuterium atoms.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, it is possible for some of the compounds of the present invention to exist as tautomers. For example, the compounds of the present invention may contain a pyridone moiety and can exist as a pyridone, or as an hydroxypyridine, or even a mixture in any amount of the two tautomers, namely:

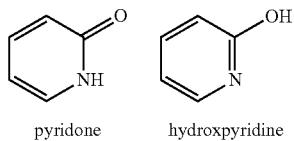

pyridone      hydroxpyridine

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge et al., "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethylglucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quaternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the "Experimental Section", for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x CF₃COOH", "x Na⁺", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

The invention further includes all possible cyclodextrin clathrates, i.e. alpha-, beta-, or gamma-cyclodextrins, hydroxypropyl-beta-cyclodextrins, methylbetacyclodextrins.

In accordance with a second embodiment of the first aspect, the present invention covers compounds of general formula (I), supra, in which:

$R^1$ represents a phenyl or pyridinyl group optionally substituted, one, two, or three times, each substituent independently selected from a halogen atom or a group selected from hydroxy, cyano, nitro, $C_1$-$C_4$-alkyl, (phenyl)-($C_1$-$C_2$-alkyl)-, $C_1$-$C_4$-haloalkyl, $C_1$-$C_4$-alkoxy, (phenyl)-($C_1$-$C_2$-alkoxy)-, $C_1$-$C_4$-haloalkoxy, —N($R^5$)($R^6$), wherein the phenyl groups in said (phenyl)-($C_1$-$C_2$-alkyl)- and (phenyl)-($C_1$-$C_2$-alkoxy)-groups are optionally substituted one or two times, each substituent independently selected from a fluorine atom, a chlorine atom and a bromine atom, or a group selected from methyl, trifluoromethyl and methoxy, or two substituents attached to adjacent carbon atoms of said phenyl or pyridinyl group together form a bivalent group selected from —(CH₂)₃—, —(CH₂)₄—, —(CH₂)₂—O—, —(CH₂)₃—O—, —CH₂—O—CH₂—, —O—CH₂—O—, —O—CH₂—CH₂—O— and —O—CF₂—O—, or
$R^1$ represents a pyrazolyl group optionally substituted one or two times, each substituent independently selected from a halogen atom or a group selected from cyano, $C_1$-$C_2$-alkyl, and $C_1$-$C_2$-alkoxy;

$R^2$ represents a group

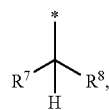

wherein "*" indicates the point of attachment to the nitrogen atom to which $R^2$ is attached;

$R^3$ represents a group selected from methyl and —NH₂;

$R^4$ represents a phenyl or pyridinyl group optionally substituted, one, two, or three times, each substituent independently selected from a halogen atom or a group selected from cyano, nitro, $C_1$-$C_4$-alkyl, (phenyl)-($C_1$-$C_2$-alkyl)-, (5-membered heteroaryl)-($C_1$-$C_2$-alkyl)-, ($C_3$-$C_7$-cycloalkyl)-($C_1$-$C_2$-alkyl)-, (($R^9$)O)—($C_1$-$C_4$-alkyl)-, $C_1$-$C_4$-haloalkyl, $C_3$-$C_7$-cycloalkyl, —O$R^9$, —N($R^{10}$)($R^{11}$), (($R^{10}$)($R^{11}$)N)—($C_1$-$C_3$-alkyl)-, —C(=O)—N($R^{12}$)($R^{13}$), S(=O)$_n$—$R^{14}$, —C(=O)$R^{14}$, —C(=O)—O$R^{17}$, and a 5-membered heteroaryl group which itself is optionally substituted with one or two methyl groups, or two substituents attached to adjacent carbon atoms of said phenyl or pyridinyl group together form a bivalent group selected from —(CH₂)₃—, —(CH₂)₄—, —(CH₂)₂—O—, —(CH₂)₃—O—, —CH₂—O—CH₂—, —O—CH₂—O—, —O—CH₂—CH₂—O— and —O—CF₂—O—;

$R^5$ and $R^6$ represent, independently from each occurrence, a hydrogen atom or a group selected from $C_1$-$C_2$-alkyl and ($C_1$-$C_2$-alkyl)-C(=O)—, or $R^5$ and $R^6$, together with the nitrogen atom to which they are attached, represent a monocyclic nitrogen containing 4- to 7-membered heterocycloalkyl group which is optionally substituted one or two times, each substituent independently selected from a fluorine atom, a chlorine atom and a bromine atom, or a group selected from oxo, hydroxy, $C_1$-$C_2$-alkyl and ($C_1$-$C_2$-alkyl)-C(=O)—;

$R^7$ represents a hydrogen atom or a $C_1$-$C_2$-alkyl group;

$R^8$ represents a —C(=O)—NH₂ group;

$R^9$ represents a hydrogen atom or a group selected from $C_1$-$C_4$-alkyl, (phenyl)-($C_1$-$C_2$-alkyl)-, $C_1$-$C_4$-haloalkyl, $C_2$-$C_3$-hydroxyalkyl, ($C_1$-$C_2$-alkoxy)-$C_2$-alkyl-, (($C_1$-$C_2$-alkyl)-C(=O)—O)—$C_2$-alkyl-, —C($R^{18}$)($R^{19}$)—C(=O)—O$R^{17}$, —C($R^{18}$)($R^{19}$)—C(=O)—N($R^{20}$)($R^{21}$), —C(=O)—N($R^{21}$)($R^{21}$) and phenyl, wherein the phenyl group within said (phenyl)-($C_1$-$C_2$-alkyl)- group and said phenyl group itself are optionally substituted one or two times, each substituent independently selected from a fluorine atom, a chlorine atom and a bromine atom, or a group selected from cyano, methyl, trifluoromethyl and methoxy;

$R^{10}$ and $R^{11}$ represent, independently from each occurrence, a hydrogen atom or a group selected from $C_1$-$C_2$-alkyl, $C_1$-$C_2$haloalkyl, $C_2$-$C_3$-hydroxyalkyl, ($C_1$-$C_2$-alkoxy)-$C_2$-alkyl-, (($R^{22}$)($R^{23}$)N)-$C_2$-alkyl-, ($C_3$-$C_7$-cycloalkyl)-($C_1$-$C_2$-alkyl)-, ($C_1$-$C_2$-alkyl)-C(=O)—, $C_3$-$C_7$-cycloalkyl, ($C_3$-$C_7$-cycloalkyl)-C(=O)—, (phenyl)-($C_1$-$C_2$-alkyl)-, (phenyl)-($C_1$-$C_2$-alkyl)-C(=O)- and (phenyl)-($C_1$-$C_2$-alkyl)-O—C(=O)—, wherein $C_3$-$C_7$-cycloalkyl, and the $C_3$-$C_7$-cycloalkyl within said ($C_3$-$C_7$-cycloalkyl)-($C_1$-$C_2$-alkyl)- and ($C_3$-$C_7$-cycloalkyl)-C(=O)— groups are optionally substituted one or two times, each substituent independently selected from a fluorine atom or a group selected from cyano, $C_1$-$C_2$-alkyl and $C_1$-$C_2$-haloalkyl, and wherein the phenyl groups within said (phenyl)-($C_1$-$C_2$-alkyl)-, (phenyl)-($C_1$-$C_2$-alkyl)-C(=O)- and (phenyl)-($C_1$-$C_2$-alkyl)-O—C(=O)— groups are optionally substituted one or two times, each substituent independently selected from a fluorine atom, a chlorine atom and a bromine atom, or a group selected from methyl, trifluoromethyl and methoxy, or $R^{10}$ and $R^{11}$, together with the nitrogen atom to which they are attached, represent a monocyclic nitrogen containing 4- to 7-membered heterocycloalkyl group, or a bicyclic nitrogen containing 5- to 10-membered heterocycloalkyl group, which are optionally substituted one, two or three times, each substituent independently selected from a halogen atom or a group selected from cyano, oxo, hydroxy, $C_1$-$C_2$-alkyl, $C_1$-$C_2$haloalkyl, ($C_1$-$C_2$-alkyl)-C (=O)—, $C_1$-$C_2$-alkoxy, —N($R^{22}$)($R^{23}$), and a monocyclic 4- to 7-membered heterocycloalkyl group;

$R^{12}$ and $R^{13}$ represent, independently from each occurrence, a hydrogen atom or a group selected from $C_1$-$C_4$-alkyl, $C_1$-$C_4$-haloalkyl, $C_1$-$C_4$-hydroxyalkyl, ($C_1$-$C_4$-alkoxy)-$C_2$-$C_3$-alkyl-, ($C_1$-$C_4$-haloalkoxy)-$C_2$-$C_3$-alkyl-, (phenoxy)-$C_2$-$C_3$-alkyl-, $C_3$-$C_7$-cycloalkyl, monocyclic 4- to 7-membered heterocycloalkyl and (phenyl)-($C_1$-$C_3$-alkyl)-, wherein $C_3$-$C_7$-cycloalkyl and monocyclic 4- to 7-membered heterocycloalkyl are optionally substituted one or two times, each substituent independently selected from a halogen atom or a group selected from oxo, $C_1$-$C_2$-alkyl and ($C_1$-$C_2$-alkyl)-C(=O)—, and wherein the phenyl groups within said (phenoxy)-$C_2$-$C_3$-alkyl- group and said (phenyl)-($C_1$-$C_3$-alkyl)- group are optionally substituted one or two times, each substituent independently selected from fluorine atom, a chlorine atom and a bromine atom, or a group selected from cyano, methyl, trifluoromethyl and methoxy, or $R^{12}$ and $R^{13}$, together with the nitrogen atom to which they are attached, represent a monocyclic nitrogen containing 4- to 7-membered heterocycloalkyl group which is optionally substituted one or two times, each substituent independently selected from a halogen atom or a group selected from oxo, $C_1$-$C_2$-alkyl and ($C_1$-$C_2$-alkyl)-C(=O)—;

$R^{14}$ represents a group selected from $C_1$-$C_2$-alkyl, $C_1$-$C_2$haloalkyl and phenyl, wherein the phenyl group is optionally substituted one or two times, each substituent independently selected from a fluorine atom, a chlorine atom and a bromine atom, or a group selected from methyl, trifluoromethyl and methoxy;

$R^{17}$ represents a $C_1$-$C_4$-alkyl group;

$R^{18}$ and $R^{19}$ represent, independently from each occurrence, a hydrogen atom or a $C_1$-$C_2$-alkyl group;

$R^{20}$ represents a hydrogen atom or a group selected from $C_1$-$C_6$-alkyl, $C_3$-$C_4$-alkenyl, $C_3$-$C_4$-alkynyl, $C_1$-$C_3$-alkoxy, $C_3$-$C_7$-cycloalkyl, bicyclic $C_5$-$C_{11}$-cycloalkyl, adamantyl, monocyclic 4- to 7-membered heterocycloalkyl, bicyclic 5- to 10-membered heterocycloalkyl, phenyl, naphthyl, and 5- to 10-membered heteroaryl, wherein said $C_1$-$C_6$-alkyl group is optionally substituted one, two or three times, each substituent independently selected from a halogen atom or a group selected from hydroxy, cyano, $C_1$-$C_3$-alkoxy, —N($R^{22}$)($R^{23}$), $C_3$-$C_7$-cycloalkyl, bicyclic $C_5$-$C_{11}$-cycloalkyl, adamantyl, monocyclic 4- to 7-membered heterocycloalkyl, bicyclic 5- to 10-membered heterocycloalkyl, phenyl, and 5- to 10-membered heteroaryl, said phenyl and 5- to 10-membered heteroaryl substituents themselves being optionally substituted one or two times, each substituent independently selected from a fluorine atom, a chlorine atom and a bromine atom, or a group selected from methyl, trifluoromethyl and methoxy, and wherein $C_3$-$C_7$-cycloalkyl, bicyclic $C_5$-$C_{11}$-cycloalkyl, adamantyl, monocyclic 4- to 7-membered heterocycloalkyl, bicyclic 5- to 10-membered heterocycloalkyl are optionally substituted one or two or three times, each substituent independently selected from a halogen atom or a group selected from cyano, oxo, hydroxy, $C_1$-$C_2$-alkyl and ($C_1$-$C_2$-alkyl)-C(=O)—, and wherein said phenyl, naphthyl and 5- to 10-membered heteroaryl groups are optionally substituted one, two or three times, each substituent independently selected from a halogen atom or a group selected from cyano, $C_1$-$C_2$-alkyl, $C_1$-$C_2$-haloalkyl, $C_1$-$C_2$alkoxy, $C_1$-$C_2$-haloalkoxy, —N($R^{22}$)($R^{23}$) and —C(=O)—N($R^{24}$)($R^{25}$), $R^{21}$ represents a hydrogen atom or a $C_1$-$C_2$-alkyl group, or $R^{20}$ and $R^{21}$, together with the nitrogen atom to which they are attached, represent a monocyclic nitrogen containing 4- to 7-membered heterocycloalkyl group which is optionally benzocondensed, and which is optionally substituted one, two or three times, each substituent independently selected from a halogen atom or a group selected from cyano, oxo, hydroxy, $C_1$-$C_2$-alkyl, $C_1$-$C_2$haloalkyl, (phenyl)-($C_1$-$C_2$-alkyl)-, ($C_1$-$C_2$-alkyl)-C(=O)—, $C_3$-$C_4$-cycloalkyl, $C_1$-$C_2$-alkoxy, $C_1$-$C_2$haloalkoxy, —N($R^{22}$)($R^{23}$) and —C(=O)—N($R^{24}$)($R^{25}$);

$R^{22}$ and $R^{23}$ represent, independently from each occurrence, a hydrogen atom or a group selected from $C_1$-$C_2$-alkyl and ($C_1$-$C_2$-alkyl)-C(=O)—;

$R^{24}$ and $R^{25}$ represent, independently from each occurrence, a hydrogen atom or a $C_1$-$C_2$-alkyl group, and n represents an integer 0, 1, or 2, and stereoisomers, tautomers, N-oxides, hydrates, solvates, and salts thereof, and mixtures of same.

In accordance with a third embodiment of the first aspect, the present invention covers compounds of general formula (I), supra, in which:

$R^1$ represents a phenyl or pyridinyl group optionally substituted, one, two, or three times, each substituent independently selected from a fluorine atom, a chlorine atom and a bromine atom, or a group selected from hydroxy, cyano, $C_1$-$C_4$-alkyl, $C_1$-$C_2$-fluoroalkyl, $C_1$-$C_2$-alkoxy, (phenyl)-($C_1$-$C_2$-alkoxy)-, $C_1$-$C_2$-fluoroalkoxy and —N($R^5$)($R^6$), or two substituents attached to adjacent carbon atoms of said phenyl or pyridinyl group together form a bivalent group selected from —($CH_2$)$_3$—, —O—$CH_2$—O— and —O—$CF_2$—O—, or $R^1$ represents a pyrazolyl group optionally substituted with one methyl group;

$R^2$ represents a group

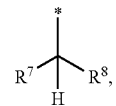

wherein "*" indicates the point of attachment to the nitrogen atom to which $R^2$ is attached;

$R^3$ represents a group selected from methyl and —$NH_2$;

$R^4$ represents a phenyl or pyridinyl group optionally substituted, one, two, or three times, each substituent independently selected from a halogen atom or a group selected from cyano, $C_1$-$C_3$-alkyl, (($R^9$)O)—($C_1$-$C_3$-alkyl)-, $C_1$-$C_3$-fluoroalkyl, —$OR^9$, —N($R^{10}$)($R^{11}$), —C(=O)—N($R^{12}$)($R^{13}$), S(=O)$_n$—$R^{14}$ and —C(=O)—$OR^{17}$, or two substituents attached to adjacent carbon atoms of said phenyl or pyridinyl group together form a bivalent group selected from —($CH_2$)$_3$—, —O—$CH_2$—O— and —O—$CF_2$—O—;

$R^5$ and $R^6$ represent, independently from each occurrence, a hydrogen atom or a $C_1$-$C_2$-alkyl group, or $R^5$ and $R^6$, together with the nitrogen atom to which they are attached, represent a monocyclic nitrogen containing 4- to 7-membered heterocycloalkyl group which is optionally substituted one or two times, each substituent independently selected from a fluorine atom or a group selected from hydroxy and $C_1$-$C_2$-alkyl;

$R^7$ represents a hydrogen atom or a $C_1$-$C_2$-alkyl group;

$R^8$ represents a —C(=O)—NH$_2$ group;

$R^9$ represents a hydrogen atom or a group selected from $C_1$-$C_2$-alkyl, benzyl, $C_1$-$C_2$-fluoroalkyl, $C_2$-hydroxyalkyl, ($C_1$-$C_2$-alkoxy)-$C_2$-alkyl-, (($C_1$-$C_2$-alkyl)-C(=O)—O)—$C_2$-alkyl-, —C($R^{18}$)($R^{19}$)—C(=O)—O$R^{17}$, —C($R^{18}$)($R^{19}$)—C(=O)—N($R^{20}$)($R^{21}$), —C(=O)—N($R^{20}$)($R^{21}$) and phenyl, wherein the phenyl group within said benzyl group and said phenyl group itself are optionally substituted one or two times, each substituent independently selected from a fluorine atom and a chlorine atom, or a group selected from cyano and methyl;

$R^{10}$ and $R^{11}$ represent, independently from each occurrence, a hydrogen atom or a group selected from $C_1$-$C_2$-alkyl, $C_1$-$C_2$-fluoroalkyl, ($C_3$-$C_5$-cycloalkyl)-($C_1$-$C_2$-alkyl)-, ($C_1$-$C_2$-alkyl)-C(=O)—, $C_3$-$C_7$-cycloalkyl, $C_3$-$C_7$-cycloalkyl-(C=O)—, (phenyl)-($C_1$-$C_2$-alkyl)-, (phenyl)-($C_1$-$C_2$-alkyl)-C(=O)- and (phenyl)-($C_1$-$C_2$-alkyl)-O—C(=O)—, wherein $C_3$-$C_7$-cycloalkyl, and the $C_3$-$C_5$-cycloalkyl within said ($C_3$-$C_5$-cycloalkyl)-($C_1$-$C_2$-alkyl)- and the $C_3$-$C_7$-cycloalkyl within the $C_3$-$C_7$-cycloalkyl-(C=O)— groups are optionally substituted one or two times, each substituent independently selected from a fluorine atom or a group selected from cyano, $C_1$-$C_2$-alkyl and $C_1$-$C_2$-fluoroalkyl, and wherein the phenyl groups within said (phenyl)-($C_1$-$C_2$-alkyl)-, (phenyl)-($C_1$-$C_2$-alkyl)-C(=O)- and (phenyl)-($C_1$-$C_2$-alkyl)-O—C(=O)— groups are optionally substituted one or two times, each substituent independently selected from a fluorine atom, a chlorine atom and a methyl group, or $R^{10}$ and $R^{11}$, together with the nitrogen atom to which they are attached, represent a monocyclic nitrogen containing 4- to 7-membered heterocycloalkyl group which is optionally substituted one or two times, each substituent independently selected from a fluorine atom or a group selected from cyano, oxo, $C_1$-$C_2$-alkyl, $C_1$-$C_2$-fluoroalkyl and ($C_1$-$C_2$-alkyl)-C(=O)—;

$R^{12}$ and $R^{13}$ represent, independently from each occurrence, a hydrogen atom or a group selected from $C_1$-$C_4$-alkyl, $C_1$-$C_4$-fluoroalkyl, $C_1$-$C_4$-hydroxyalkyl, ($C_1$-$C_4$-alkoxy)-$C_2$-$C_3$-alkyl-, ($C_1$-$C_2$-fluoroalkoxy)-$C_2$-$C_3$-alkyl-, (phenoxy)-$C_2$-$C_3$-alkyl-, $C_3$-$C_7$-cycloalkyl, monocyclic 4- to 7-membered heterocycloalkyl and (phenyl)-($C_1$-$C_2$-alkyl)-, wherein $C_3$-$C_7$-cycloalkyl and monocyclic 4- to 7-membered heterocycloalkyl are optionally substituted one or two times, each substituent independently selected from a fluorine atom or a group selected from oxo, $C_1$-$C_2$-alkyl and ($C_1$-$C_2$-alkyl)-C(=O)—, and wherein the phenyl groups within said (phenoxy)-$C_2$-$C_3$-alkyl- group and said (phenyl)-($C_1$-$C_2$-alkyl)- group are optionally substituted one or two times, each substituent independently selected from a fluorine atom and a chlorine atom, or a group selected from methyl, trifluoromethyl and methoxy, or $R^{12}$ and $R^{13}$, together with the nitrogen atom to which they are attached, represent a monocyclic nitrogen containing 4- to 7-membered heterocycloalkyl group which is optionally substituted one or two times, each substituent independently selected from a halogen atom or a group selected from oxo, $C_1$-$C_2$-alkyl and ($C_1$-$C_2$-alkyl)-C(=O)—;

$R^{14}$ represents a group selected from methyl and trifluoromethyl;

$R^{17}$ represents a $C_1$-$C_2$-alkyl group;

$R^{18}$ and $R^{19}$ represent, independently from each occurrence, a hydrogen atom or a methyl group;

$R^{20}$ represents a hydrogen atom or a group selected from optionally substituted $C_1$-$C_3$-alkyl, unsubstituted $C_4$-$C_6$-alkyl, prop-2-ynyl, methoxy, $C_3$-$C_6$-cycloalkyl, adamantyl, monocyclic 4- to 7-membered heterocycloalkyl, phenyl, and 5- to 10-membered heteroaryl, wherein said $C_1$-$C_3$-alkyl group is optionally substituted one, two or three times, each substituent independently selected from a halogen atom or a group selected from hydroxy, cyano, $C_1$-$C_3$-alkoxy, —N($R^{22}$)($R^{23}$), $C_3$-$C_6$-cycloalkyl, adamantyl, monocyclic 4- to 7-membered heterocycloalkyl, phenyl, and 5- to 10-membered heteroaryl, said phenyl and 5- to 10-membered heteroaryl substituents themselves being optionally substituted one or two times, each substituent independently selected from a fluorine atom, a chlorine atom and a methyl group, and wherein said $C_3$-$C_6$-cycloalkyl, adamantyl and monocyclic 4- to 7-membered heterocycloalkyl groups are optionally substituted one or two or three times, each substituent independently selected from a fluorine atom or a group selected from oxo, $C_1$-$C_2$-alkyl and ($C_1$-$C_2$-alkyl)-C(=O)—, and wherein said phenyl and 5- to 10-membered heteroaryl groups are optionally substituted one, two or three times, each substituent independently selected from a fluorine atom and a chlorine atom or a group selected from cyano, $C_1$-$C_2$-alkyl, $C_1$-$C_2$-fluoroalkyl, $C_1$-$C_2$-alkoxy, $C_1$-$C_2$-fluoroalkoxy, —N($R^{22}$)($R^{23}$) and —C(=O)—N($R^{24}$)($R^{25}$), $R^{21}$ represents a hydrogen atom or a $C_1$-$C_2$-alkyl group, or $R^{20}$ and $R^{21}$, together with the nitrogen atom to which they are attached, represent a monocyclic nitrogen containing 4- to 7-membered heterocycloalkyl group which is optionally benzocondensed, and which is optionally substituted one, two or three times, each substituent independently selected from a halogen atom or a group selected from cyano, oxo, hydroxy, $C_1$-$C_2$-alkyl, $C_1$-$C_2$-fluoroalkyl, benzyl, ($C_1$-$C_2$-alkyl)-C(=O)—, $C_3$-$C_4$-cycloalkyl, $C_1$-$C_2$-alkoxy, $C_1$-$C_2$-fluoroalkoxy, —N($R^{22}$)($R^{23}$) and —C(=O)—N($R^{24}$)($R^{25}$);

$R^{22}$ and $R^{23}$ represent, independently from each occurrence, a hydrogen atom or a group selected from $C_1$-$C_2$-alkyl and ($C_1$-$C_2$-alkyl)-C(=O)—;

$R^{24}$ and $R^{25}$ represent, independently from each occurrence, a hydrogen atom or a $C_1$-$C_2$-alkyl group, and n represents an integer 2, and stereoisomers, tautomers, N-oxides, hydrates, solvates, and salts thereof, and mixtures of same.

In accordance with a fourth embodiment of the first aspect, the present invention covers compounds of general formula (I), supra, in which:

$R^1$ represents a phenyl or pyridinyl group optionally substituted, one or two times, each substituent independently selected from a fluorine atom, a chlorine atom and a bromine atom, or a group selected from cyano, methyl, difluoromethyl, trifluoromethyl, methoxy, benzyloxy, difluoromethoxy and trifluoromethoxy, or two substituents attached to adjacent carbon atoms of said phenyl or pyridinyl group together form a bivalent group —O—CF$_2$—O—;

R$^2$ represents a group

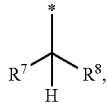

wherein "*" indicates the point of attachment to the nitrogen atom to which R$^2$ is attached;

R$^3$ represents a group selected from methyl and —NH$_2$;

R$^4$ represents a phenyl or pyridinyl group optionally substituted, one or two times, each substituent independently selected from a halogen atom or a group selected from C$_1$-C$_2$-alkyl, C$_1$-C$_2$-fluoroalkyl, —OR$^9$, —N(R$^{10}$)(R$^{11}$), —C(=O)—N(R$^{12}$)(R$^{13}$) and —C(=O)—OR$^{17}$;

R$^7$ represents a hydrogen atom or a C$_1$-C$_2$-alkyl group;

R$^8$ represents a —C(=O)—NH$_2$ group;

R$^9$ represents a hydrogen atom or a group selected from C$_1$-C$_2$-alkyl, benzyl, C$_1$-C$_2$-fluoroalkyl, (C$_1$-C$_2$-alkoxy)-C$_2$-alkyl-, ((C$_1$-C$_2$-alkyl)-C(=O)—O)—C$_2$-alkyl-, —C(R$^{18}$)(R$^{19}$)—C(=O)—N(R$^{20}$)(R$^{21}$), —C(=O)—N(R$^{20}$)(R$^{21}$) and phenyl, wherein the phenyl group within said benzyl group and said phenyl group itself are optionally substituted one or two times, each substituent independently selected from a fluorine atom and a chlorine atom, or a group selected from cyano and methyl;

R$^{10}$ and R$^{11}$ represent, independently from each occurrence, a hydrogen atom or a group selected from C$_1$-C$_2$-alkyl, (C$_3$-C$_5$-cycloalkyl)-(C$_1$-C$_2$-alkyl)-, C$_3$-C$_7$-cycloalkyl and (phenyl)-(C$_1$-C$_2$-alkyl)-O—C(=O)—, wherein C$_3$-C$_7$-cycloalkyl, and the C$_3$-C$_5$-cycloalkyl within said (C$_3$-C$_5$-cycloalkyl)-(C$_1$-C$_2$-alkyl)- group are optionally substituted one or two times, each substituent independently selected from a fluorine atom or a group selected from cyano, methyl and C$_1$-fluoroalkyl, and wherein the phenyl group within said (phenyl)-(C$_1$-C$_2$-alkyl)-O—C(=O)— group is optionally substituted one or two times, each substituent independently selected from a fluorine atom, a chlorine atom and a methyl group, or R$^{10}$ and R$^{11}$, together with the nitrogen atom to which they are attached, represent a monocyclic nitrogen containing 4- to 7-membered heterocycloalkyl group which is optionally substituted one or two times, each substituent independently selected from a fluorine atom or a group selected from cyano, methyl and C$_1$-fluoroalkyl;

R$^{12}$ and R$^{13}$ represent, independently from each occurrence, a hydrogen atom or a group selected from C$_1$-C$_4$-alkyl, C$_1$-C$_2$-fluoroalkyl, C$_1$-C$_2$-hydroxyalkyl, (C$_1$-C$_4$-alkoxy)-C$_2$-C$_3$-alkyl-, (C$_1$-C$_2$-fluoroalkoxy)-C$_2$-C$_3$-alkyl-, (phenoxy)-C$_2$-C$_3$-alkyl-, C$_3$-C$_7$-cycloalkyl and (phenyl)-(C$_1$-C$_2$-alkyl)-, wherein C$_3$-C$_7$-cycloalkyl is optionally substituted one or two times, each substituent independently selected from a fluorine atom or a methyl group, and wherein the phenyl groups within said (phenoxy)-C$_2$-C$_3$-alkyl- group and said (phenyl)-(C$_1$-C$_2$-alkyl)- group are optionally substituted one or two times, each substituent independently selected from a fluorine atom and a chlorine atom, or a group selected from methyl, trifluoromethyl and methoxy;

R$^{17}$ represents a C$_1$-C$_2$-alkyl group;

R$^{18}$ and R$^{19}$ represent, independently from each occurrence, a hydrogen atom or a methyl group;

R$^{20}$ represents a hydrogen atom or a group selected from C$_1$-C$_3$-alkyl and phenyl, wherein said C$_1$-C$_3$-alkyl group is optionally substituted one or two times, each substituent independently selected from a fluorine atom or a group selected from hydroxy, C$_1$-C$_3$-alkoxy and phenyl, said phenyl itself being optionally substituted one or two times, each substituent independently selected from a fluorine atom, a chlorine atom and a methyl group, and wherein said phenyl group is optionally substituted one, two or three times, each substituent independently selected from a fluorine atom and a chlorine atom or a group selected from methyl, trifluoromethyl, methoxy and trifluoromethoxy, and R$^{21}$ represents a hydrogen atom or a C$_1$-C$_2$-alkyl group, and stereoisomers, tautomers, N-oxides, hydrates, solvates, and salts thereof, and mixtures of same.

In accordance with a fifth embodiment of the first aspect, the present invention covers compounds of general formula (I), supra, in which:

R$^1$ represents a phenyl or pyridinyl group optionally substituted, one or two times, each substituent independently selected from a fluorine atom, a chlorine atom and a bromine atom, or a group selected from cyano, difluoromethyl, trifluoromethyl, methoxy, benzyloxy, difluoromethoxy and trifluoromethoxy, or two substituents attached to adjacent carbon atoms of said phenyl or pyridinyl group together form a bivalent group —O—CF$_2$—O—;

R$^2$ represents a group

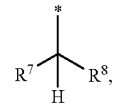

wherein "*" indicates the point of attachment to the nitrogen atom to which R$^2$ is attached;

R$^3$ represents a group selected from methyl and —NH$_2$;

R$^4$ represents a phenyl or pyridinyl group optionally substituted, one or two times, each substituent independently selected from a halogen atom or a group selected from C$_1$-C$_2$-alkyl, C$_1$-C$_2$-fluoroalkyl, —OR$^9$, —N(R$^{10}$)(R$^{11}$), —C(=O)—N(R$^{12}$)(R$^{13}$) and —C(=O)—OR$^{17}$;

R$^7$ represents a hydrogen atom or a C$_1$-C$_2$-alkyl group;

R$^8$ represents a —C(=O)—NH$_2$ group;

R$^9$ represents a hydrogen atom or a group selected from C$_1$-C$_2$-alkyl, benzyl, C$_1$-C$_2$-fluoroalkyl, (C$_1$-C$_2$-alkoxy)-C$_2$-alkyl-, ((C$_1$-C$_2$-alkyl)-C(=O)—O)—C$_2$-alkyl-, —C(R$^{18}$)(R$^{19}$)—C(=O)—N(R$^{20}$)(R$^{21}$), —C(=O)—N(R$^{20}$)(R$^{21}$) and phenyl, wherein the phenyl group within said benzyl group and said phenyl group itself are optionally substituted one or two times, each substituent independently selected from a fluorine atom and a chlorine atom, or a group selected from cyano and methyl;

R$^{10}$ and R$^{11}$ represent, independently from each occurrence, a hydrogen atom or a group selected from C$_1$-C$_2$-alkyl, (C$_3$-C$_5$-cycloalkyl)-(C$_1$-C$_2$-alkyl)-, C$_3$-C$_7$-cycloalkyl and (phenyl)-(C$_1$-C$_2$-alkyl)-O—C(=O)—, wherein C₃-C₇-cycloalkyl, and the C₃-C₅-cycloalkyl within said (C₃-C₅-cycloalkyl)-(C₁-C₂-alkyl)- group are optionally substituted one or two times, each substituent independently selected from a fluorine atom or a group selected from cyano, methyl and C₁-fluoroalkyl, and wherein the phenyl group within said (phenyl)-(C₁-C₂-alkyl)-O—C(=O)— group is optionally substituted one or two times, each substituent independently selected from a fluorine atom, a chlorine atom and a methyl group, or R¹⁰ and R¹¹, together with the nitrogen atom to which they are attached, represent a monocyclic nitrogen containing 4- to 7-membered heterocycloalkyl group which is optionally substituted one or two times, each substituent independently selected from a fluorine atom or a group selected from cyano, methyl and C₁-fluoroalkyl;

R¹² and R¹³ represent, independently from each occurrence, a hydrogen atom or a group selected from C₁-C₄-alkyl, C₁-C₂-fluoroalkyl, C₁-C₂-hydroxyalkyl, (C₁-C₄-alkoxy)-C₂-C₃-alkyl-, (C₁-C₂-fluoroalkoxy)-C₂-C₃-alkyl-, (phenoxy)-C₂-C₃-alkyl-, C₃-C₇-cycloalkyl and (phenyl)-(C₁-C₂-alkyl)-, wherein C₃-C₇-cycloalkyl is optionally substituted one or two times, each substituent independently selected from a fluorine atom or a methyl group, and wherein the phenyl groups within said (phenoxy)-C₂-C₃-alkyl- group and said (phenyl)-(C₁-C₂-alkyl)- group are optionally substituted one or two times, each substituent independently selected from a fluorine atom and a chlorine atom, or a group selected from methyl, trifluoromethyl and methoxy;

R¹⁷ represents a C₁-C₂-alkyl group;

R¹⁸ and R¹⁹ represent, independently from each occurrence, a hydrogen atom or a methyl group;

R²⁰ represents a hydrogen atom or a group selected from C₁-C₃-alkyl and phenyl, wherein said C₁-C₃-alkyl group is optionally substituted one or two times, each substituent independently selected from a fluorine atom or a group selected from hydroxy, C₁-C₃-alkoxy and phenyl, said phenyl itself being optionally substituted one or two times, each substituent independently selected from a fluorine atom, a chlorine atom and a methyl group, and wherein said phenyl group is optionally substituted one, two or three times, each substituent independently selected from a fluorine atom and a chlorine atom or a group selected from methyl, trifluoromethyl, methoxy and trifluoromethoxy, and R²¹ represents a hydrogen atom or a C₁-C₂-alkyl group, and stereoisomers, tautomers, N-oxides, hydrates, solvates, and salts thereof, and mixtures of same.

In accordance with a sixth embodiment of the first aspect, the present invention covers compounds of general formula (I), supra, in which:

R¹ represents a group

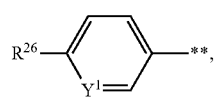

wherein "*" indicates the point of attachment to the nitrogen atom to which R¹ is attached;

R² represents a group

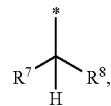

wherein "*" indicates the point of attachment to the nitrogen atom to which R² is attached;

R³ represents a group selected from methyl and —NH₂;

R⁴ represents a group

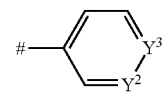

wherein "#" indicates the point of attachment to the carbonyl group to which R⁴ is attached;

R⁷ represents a hydrogen atom or a C₁-C₂-alkyl group;

R⁸ represents a —C(=O)—NH₂ group;

R⁹ represents a hydrogen atom or a group selected from C₁-C₂-alkyl, benzyl, C₁-C₂-fluoroalkyl, (C₁-C₂alkoxy)-C₂-alkyl-, ((C₁-C₂-alkyl)-C(=O)—O)—C₂-alkyl-, —C(R¹⁸)(R¹⁹)—C(=O)—N(R²⁰)(R²¹), —C(=O)—N(R²⁰)(R²¹) and phenyl, wherein the phenyl group within said benzyl group and said phenyl group itself are optionally substituted one or two times, each substituent independently selected from a fluorine atom and a chlorine atom, or a group selected from cyano and methyl;

R¹⁰ and R¹¹ represent, independently from each occurrence, a hydrogen atom or a group selected from C₁-C₂-alkyl, C₃-C₇-cycloalkyl and (benzyl)-O—C(=O)—, wherein C₃-C₇-cycloalkyl is optionally substituted one or two times, each substituent independently selected from a fluorine atom or a group selected from methyl and trifluoromethyl, and wherein the phenyl group within said (benzyl)-O—C(=O)— group is optionally substituted one or two times, each substituent independently selected from a fluorine atom, a chlorine atom and a methyl group, or R¹⁰ and R¹¹, together with the nitrogen atom to which they are attached, represent a monocyclic nitrogen containing 4- to 7-membered heterocycloalkyl group which is optionally substituted one or two times, each substituent independently selected from a fluorine atom or a group selected from cyano, methyl and trifluoromethyl;

R¹² and R¹³ represent, independently from each occurrence, a hydrogen atom or a group selected from C₁-C₄-alkyl, C₁-C₂-fluoroalkyl, C₁-C₂-hydroxyalkyl, (C₁-C₄-alkoxy)-C₂-alkyl-, (C₁-C₂-fluoroalkoxy)-C₂-alkyl-, (phenoxy)-C₂-alkyl-, C₃-C₇-cycloalkyl and (phenyl)-(C₁-C₂-alkyl)-, wherein the phenyl groups within said (phenoxy)-C₂-alkyl- group and said (phenyl)-(C₁-C₂-alkyl)- group are optionally substituted one or two times, each substituent independently selected from fluorine atom and a chlorine atom, or a group selected from methyl, trifluoromethyl and methoxy;

R¹⁷ represents a C₁-C₂-alkyl group;

R¹⁸ and R¹⁹ represent, independently from each occurrence, a hydrogen atom or a methyl group;

R²⁰ represents a group selected from benzyl and phenyl, wherein said phenyl group, and the phenyl group within said benzyl group, is optionally substituted one or two times, each substituent independently selected from a fluorine atom, a chlorine atom and a methyl group, $R^{21}$ represents a hydrogen atom or a methyl group, $Y^1$ represents —C(H)=, —C(F)=, —C(Cl)=, —C(CN)= or —N=;

$Y^2$ represents —C(H)= or —N=;

$Y^3$ represents —C($R^{27}$)= or —N=, with the proviso that if $Y^2$ represents —N=, $Y^3$ represents —C($R^{27}$)=, and if $Y^3$ represents —N=, $Y^2$ represents —C(H)=;

$R^{26}$ represents a fluorine atom, a chlorine atom or a bromine atom, or a group selected from methyl, difluoromethyl, trifluoromethyl, methoxy, benzyloxy, difluoromethoxy and trifluoromethoxy, and $R^{27}$ represents a halogen atom or a group selected from $C_1$-$C_2$-alkyl, $C_1$-$C_2$-fluoroalkyl, —O$R^9$, —N($R^{10}$)($R^{11}$), —C(=O)—N($R^{12}$)($R^{13}$) and —C(=O)—O$R^{17}$, and stereoisomers, tautomers, N-oxides, hydrates, solvates, and salts thereof, and mixtures of same.

In accordance with a seventh embodiment of the first aspect, the present invention covers compounds of general formula (I), supra, in which:

$R^1$ represents a group

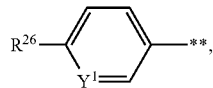

wherein "**" indicates the point of attachment to the nitrogen atom to which $R^1$ is attached;

$R^2$ represents a group

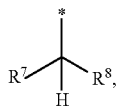

wherein "*" indicates the point of attachment to the nitrogen atom to which $R^2$ is attached;

$R^3$ represents a group selected from methyl and —NH$_2$;

$R^4$ represents a group

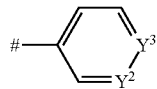

wherein "#" indicates the point of attachment to the carbonyl group to which $R^4$ is attached;

$R^7$ represents a hydrogen atom or a $C_1$-$C_2$-alkyl group;

$R^8$ represents a —C(=O)—NH$_2$ group;

$R^9$ represents a hydrogen atom or a group selected from $C_1$-$C_2$-alkyl, benzyl, $C_1$-$C_2$-fluoroalkyl and phenyl, wherein the phenyl group within said benzyl group and said phenyl group itself are optionally substituted one or two times, each substituent independently selected from a fluorine atom and a chlorine atom, or a group selected from cyano and methyl;

$R^{10}$ and $R^{11}$ represent, independently from each occurrence, a hydrogen atom or a group selected from $C_1$-$C_2$-alkyl and (benzyl)-O—C(=O)—, and wherein the phenyl group within said (benzyl)-O—C(=O)— group is optionally substituted one or two times, each substituent independently selected from a fluorine atom, a chlorine atom and a methyl group, or $R^{10}$ and $R^{11}$, together with the nitrogen atom to which they are attached, represent a monocyclic nitrogen containing 4- to 7-membered heterocycloalkyl group which is optionally substituted one or two times, each substituent independently selected from a fluorine atom or a group selected from cyano, methyl and trifluoromethyl;

$R^{12}$ and $R^{13}$ represent, independently from each occurrence, a hydrogen atom or a group selected from $C_1$-$C_2$-alkyl, ($C_1$-$C_4$-alkoxy)-$C_2$-alkyl-, ($C_1$-$C_2$-fluoroalkoxy)-$C_2$-alkyl-, (phenoxy)-$C_2$-alkyl-, $C_3$-$C_7$-cycloalkyl and (phenyl)-($C_1$-$C_2$-alkyl)-;

$Y^1$ represents —C(H)=, —C(F)=, —C(Cl)= or —N=;

$Y^2$ represents —C(H)= or —N=;

$Y^3$ represents —C($R^{27}$)= or —N=, with the proviso that if $Y^2$ represents —N=, $Y^3$ represents —C($R^{27}$)=, and if $Y^3$ represents —N=, $Y^2$ represents —C(H)=;

$R^{26}$ represents a fluorine atom, a chlorine atom or a bromine atom, or a group selected from difluoromethyl, methoxy, benzyloxy, difluoromethoxy and trifluoromethoxy, and $R^{27}$ represents a halogen atom or a group selected from —O$R^9$, —N($R^{10}$)($R^{11}$) and —C(=O)—N($R^{12}$)($R^{13}$), and stereoisomers, tautomers, N-oxides, hydrates, solvates, and salts thereof, and mixtures of same.

In accordance with an eighth embodiment of the first aspect, the present invention covers compounds of general formula (I):

in which:

$R^1$ represents a phenyl or 6-membered heteroaryl group optionally substituted, one, two, or three times, each substituent independently selected from a halogen atom or a group selected from cyano, nitro, $C_1$-$C_6$-alkyl, (phenyl)-($C_1$-$C_3$-alkyl)-, $C_1$-$C_6$-haloalkyl, $C_1$-$C_6$-alkoxy, (phenyl)-($C_1$-$C_3$-alkoxy)-, $C_1$-$C_6$-haloalkoxy, —N($R^5$)($R^6$), wherein the phenyl groups in said (phenyl)-($C_1$-$C_3$-alkyl)- and (phenyl)-($C_1$-$C_3$-alkoxy)-groups are optionally substituted one or two times, each substituent independently selected from a halogen atom or a group selected from cyano, methyl, ethyl, trifluoromethyl, methoxy, ethoxy, dimethylamino and trifluoromethoxy, or two substituents attached to adjacent carbon atoms of said phenyl or 6-membered heteroaryl group together form a bivalent group selected from —(CH$_2$)$_3$—, —(CH$_2$)$_4$—, —(CH$_2$)$_2$—O—, —(CH$_2$)$_3$—O—, —CH$_2$—O—CH$_2$—, —(CH$_2$)$_2$—O—CH$_2$—, —O—CH$_2$—O—, —O—CH$_2$—CH$_2$—O—, —O—CF$_2$—O—, —O—CH$_2$—CF$_2$—O—, and —O—CF$_2$—CF$_2$—O—, or $R^1$ represents a 5-membered heteroaryl group optionally substituted one or two times, each substituent independently selected from a halogen atom or a group selected from cyano, $C_1$-$C_3$-alkyl, and $C_1$-$C_3$-alkoxy;

$R^2$ represents a group

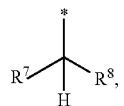

wherein "*" indicates the point of attachment to the nitrogen atom to which $R^2$ is attached;

$R^3$ represents a group selected from methyl and —$NH_2$;

$R^4$ represents a phenyl or 6-membered heteroaryl group optionally substituted, one, two, or three times, each substituent independently selected from a halogen atom or a group selected from cyano, nitro, $C_1$-$C_6$-alkyl, (phenyl)-($C_1$-$C_3$-alkyl)-, (5-membered heteroaryl)-($C_1$-$C_3$-alkyl)-, $C_1$-$C_6$-hydroxyalkyl, $C_1$-$C_6$-haloalkyl, —$OR^9$, —$N(R^{10})(R^{11})$, —C(=O)—$N(R^{12})(R^{13})$, $S(=O)_n$—$R^{14}$, and a 5-membered heteroaryl group which itself is optionally substituted with one or two methyl groups, or two substituents attached to adjacent carbon atoms of said phenyl or 6-membered heteroaryl group together form a bivalent group selected from —$(CH_2)_3$—, —$(CH_2)_4$—, —$(CH_2)_2$—O—, —$(CH_2)_3$—O—, —$CH_2$—O—$CH_2$—, —$(CH_2)_2$—O—$CH_2$—, —O—$CH_2$—O—, —O—$CH_2$—$CH_2$—O—, —O—$CF_2$—O—, —O—$CH_2$—$CF_2$—O—, and —O—$CF_2$—$CF_2$—O—;

$R^5$ and $R^6$ represent, independently from each occurrence, a hydrogen atom or a group selected from $C_1$-$C_4$-alkyl, ($C_1$-$C_4$-alkyl)-C(=O)—, $C_3$-$C_4$-cycloalkyl and (phenyl)-($C_1$-$C_3$-alkyl)-, or $R^5$ and $R^6$, together with the nitrogen atom to which they are attached, represent a monocyclic nitrogen containing 4- to 7-membered heterocycloalkyl group which is optionally substituted one, two or three times, each substituent independently selected from a halogen atom or a group selected from oxo, hydroxy, $C_1$-$C_4$-alkyl, ($C_1$-$C_4$-alkyl)-C(=O)—, $C_3$-$C_4$-cycloalkyl and $C_1$-$C_4$-alkoxy;

$R^7$ represents a hydrogen atom or a $C_1$-$C_2$-alkyl group;

$R^8$ represents a group selected from —C(=O)—$NH_2$ and —$S(=O)_2$—$NH_2$;

$R^9$ represents a hydrogen atom or a group selected from $C_1$-$C_6$-alkyl, (phenyl)-($C_1$-$C_3$-alkyl)-, $C_1$-$C_6$-haloalkyl, $C_2$-$C_4$-hydroxyalkyl, ($C_1$-$C_3$-alkoxy)-$C_2$-$C_3$-alkyl-, (($C_1$-$C_3$-alkyl)-C(=O)—O)—$C_2$-$C_3$-alkyl-, —$C(R^{18})(R^{19})$—C(=O)—$OR^{17}$, —$C(R^{18})(R^{19})$—C(=O)—$N(R^{20})(R^{21})$ and phenyl, wherein the phenyl group within said (phenyl)-($C_1$-$C_3$-alkyl)- group and said phenyl group itself are optionally substituted one or two times, each substituent independently selected from a halogen atom or a group selected from cyano, methyl, ethyl, trifluoromethyl, methoxy, ethoxy, dimethylamino and trifluoromethoxy;

$R^{10}$ and $R^{11}$ represent, independently from each occurrence, a hydrogen atom or a group selected from $C_1$-$C_4$-alkyl, $C_1$-$C_4$-haloalkyl, $C_2$-$C_4$-hydroxyalkyl, ($C_1$-$C_3$-alkoxy)-$C_2$-$C_3$-alkyl-, (($R^{22})(R^{23})$N)-$C_2$-$C_3$-alkyl, ($C_1$-$C_4$-alkyl)-C(=O)—, $C_3$-$C_7$-cycloalkyl, ($C_3$-$C_7$-cycloalkyl)-C(=O)—, (phenyl)-($C_1$-$C_3$-alkyl)-, (phenyl)-($C_1$-$C_3$-alkyl)-C(=O)— and (phenyl)-($C_1$-$C_3$-alkyl)-O—C(=O)—, wherein the phenyl groups within said (phenyl)-($C_1$-$C_3$-alkyl)-, (phenyl)-($C_1$-$C_3$-alkyl)-C(=O)— and (phenyl)-($C_1$-$C_3$-alkyl)-O—C(=O)— groups are optionally substituted one or two times, each substituent independently selected from a halogen atom or a group selected from cyano, methyl, ethyl, trifluoromethyl, methoxy, ethoxy, dimethylamino and trifluoromethoxy, or $R^{10}$ and $R^{11}$, together with the nitrogen atom to which they are attached, represent a monocyclic nitrogen containing 4- to 7-membered heterocycloalkyl group, or a bicyclic nitrogen containing 6- to 11-membered heterocycloalkyl group, which are optionally substituted one, two or three times, each substituent independently selected from a halogen atom or a group selected from cyano, oxo, hydroxy, $C_1$-$C_4$-alkyl, $C_1$-$C_4$-haloalkyl, ($C_1$-$C_4$-alkyl)-C(=O)—, $C_3$-$C_7$-cycloalkyl, $C_1$-$C_4$-alkoxy, —$N(R^{22})(R^{23})$, and a monocyclic 4- to 7-membered heterocycloalkyl group;

$R^{12}$ and $R^{13}$ represent, independently from each occurrence, a hydrogen atom or a group selected from $C_1$-$C_4$-alkyl, $C_1$-$C_4$-haloalkyl, $C_1$-$C_4$-hydroxyalkyl, ($C_1$-$C_3$-alkoxy)-$C_2$-$C_3$-alkyl-, $C_3$-$C_7$-cycloalkyl, monocyclic 4- to 7-membered heterocycloalkyl and (phenyl)-($C_1$-$C_3$-alkyl)-, wherein $C_3$-$C_7$-cycloalkyl and monocyclic 4- to 7-membered heterocycloalkyl are optionally substituted one, two or three times, each substituent independently selected from a halogen atom or a group selected from oxo, hydroxy, $C_1$-$C_4$-alkyl, ($C_1$-$C_4$-alkyl)-C(=O)—, $C_3$-$C_4$-cycloalkyl and $C_1$-$C_4$-alkoxy, or $R^{12}$ and $R^{13}$, together with the nitrogen atom to which they are attached, represent a monocyclic nitrogen containing 4- to 7-membered heterocycloalkyl group which is optionally substituted one, two or three times, each substituent independently selected from a halogen atom or a group selected from oxo, hydroxy, $C_1$-$C_4$-alkyl, ($C_1$-$C_4$-alkyl)-C(=O)—, $C_3$-$C_4$-cycloalkyl and $C_1$-$C_4$-alkoxy;

$R^{14}$ represents a group selected from $C_1$-$C_4$-alkyl and $C_1$-$C_4$-haloalkyl;

$R^{17}$ represents a $C_1$-$C_4$-alkyl group;

$R^{18}$ and $R^{19}$ represent, independently from each occurrence, a hydrogen atom or a $C_1$-$C_4$-alkyl group;

$R^{20}$ represents a hydrogen atom or a group selected from $C_1$-$C_6$-alkyl, $C_3$-$C_4$-alkenyl, $C_3$-$C_4$-alkynyl, $C_1$-$C_3$-alkoxy, $C_3$-$C_7$-cycloalkyl, bicyclic $C_6$-$C_{11}$-cycloalkyl, adamantyl, monocyclic 4- to 7-membered heterocycloalkyl, bicyclic 6- to 11-membered heterocycloalkyl, phenyl, naphthyl, and 5- to 10-membered heteroaryl, wherein said $C_1$-$C_6$-alkyl group is optionally substituted one, two or three times, each substituent independently selected from a halogen atom or a group selected from hydroxy, cyano, $C_1$-$C_3$-alkoxy, —$N(R^{22})(R^{23})$, $C_3$-$C_7$-cycloalkyl, bicyclic $C_6$-$C_{11}$-cycloalkyl, adamantyl, monocyclic 4- to 7-membered heterocycloalkyl, bicyclic 6- to 11-membered heterocycloalkyl, phenyl, and 5- to 10-membered heteroaryl, said phenyl and 5- to 10-membered heteroaryl substituents themselves being optionally substituted one or two times, each substituent independently selected from a halogen atom or a group selected from cyano, methyl, ethyl, trifluoromethyl, methoxy, ethoxy, dimethylamino and trifluoromethoxy, wherein $C_3$-$C_7$-cycloalkyl, bicyclic $C_6$-$C_{11}$-cycloalkyl, adamantyl, monocyclic 4- to 7-membered heterocycloalkyl and bicyclic 6- to 11-membered heterocycloalkyl are optionally substituted one, two or three times, each substituent independently selected from a halogen atom or a group selected from cyano, oxo, hydroxy, $C_1$-$C_4$-alkyl, ($C_1$-$C_4$-alkyl)-C(=O)—, $C_3$-$C_4$-cycloalkyl and $C_1$-$C_4$-alkoxy, and wherein said phenyl, naphthyl and 5- to 10-membered heteroaryl groups are optionally substituted one, two or three times, each substituent independently selected from a halogen atom or a group selected from cyano, $C_1$-$C_4$-alkyl, $C_1$-$C_4$-haloalkyl, $C_1$-$C_4$-alkoxy, $C_1$-$C_4$-haloalkoxy, —$N(R^{22})(R^{23})$ and —C(=O)—$N(R^{24})(R^{25})$, $R^{21}$ represents a hydrogen atom or a $C_1$-$C_4$-alkyl group,
or
$R^{20}$ and $R^{21}$, together with the nitrogen atom to which they are attached, represent a monocyclic nitrogen containing 4- to 7-membered heterocycloalkyl group which is optionally benzocondensed, and which is optionally substituted one, two or three times, each substituent independently selected from a halogen atom or a group selected from cyano, oxo, hydroxy, $C_1$-$C_4$-alkyl, $C_1$-$C_4$-haloalkyl, (phenyl)-($C_1$-$C_3$-alkyl)-, ($C_1$-$C_4$-alkyl)-C(=O)—, $C_3$-$C_4$-cycloalkyl, $C_1$-$C_4$-alkoxy, $C_1$-$C_3$-haloalkoxy, —N($R^{22}$)($R^{23}$) and —C(=O)—N($R^{24}$)($R^{25}$);
$R^{22}$ and $R^{23}$ represent, independently from each occurrence, a hydrogen atom or a group selected from $C_1$-$C_2$-alkyl and ($C_1$-$C_2$-alkyl)-C(=O)—;
$R^{24}$ and $R^{25}$ represent, independently from each occurrence, a hydrogen atom or a $C_1$-$C_4$-alkyl group, and
n represents an integer 0, 1, or 2,
and stereoisomers, tautomers, N-oxides, hydrates, solvates, and salts thereof, and mixtures of same.

In accordance with a ninth embodiment of the first aspect, the present invention covers compounds of general formula (I), supra, in which:
$R^1$ represents a phenyl or pyridinyl group optionally substituted, one, two, or three times, each substituent independently selected from a halogen atom or a group selected from cyano, nitro, $C_1$-$C_4$-alkyl, (phenyl)-($C_1$-$C_2$-alkyl)-, $C_1$-$C_4$-haloalkyl, $C_1$-$C_4$-alkoxy, (phenyl)-($C_1$-$C_2$-alkoxy)-, $C_1$-$C_4$-haloalkoxy, —N($R^5$)($R^6$),
wherein the phenyl groups in said (phenyl)-($C_1$-$C_2$-alkyl)- and (phenyl)-($C_1$-$C_2$-alkoxy)-groups are optionally substituted one or two times, each substituent independently selected from a fluorine atom, a chlorine atom and a bromine atom, or a group selected from methyl, trifluoromethyl and methoxy,
or two substituents attached to adjacent carbon atoms of said phenyl or pyridinyl group together form a bivalent group selected from —(CH$_2$)$_3$—, —(CH$_2$)$_4$—, —(CH$_2$)$_2$—O—, —(CH$_2$)—O—, —CH$_2$—O—CH$_2$—, —O—CH$_2$—O—, —O—CH$_2$—CH$_2$—O— and —O—CF$_2$—O—,
or
$R^1$ represents a pyrazolyl group optionally substituted one or two times, each substituent independently selected from a halogen atom or a group selected from cyano, $C_1$-$C_2$-alkyl, and $C_1$-$C_2$alkoxy;
$R^2$ represents a group

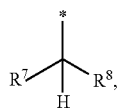

wherein "*" indicates the point of attachment to the nitrogen atom to which $R^2$ is attached;
$R^3$ represents a group selected from methyl and —NH$_2$;
$R^4$ represents a phenyl or pyridinyl group optionally substituted, one, two, or three times, each substituent independently selected from a halogen atom or a group selected from cyano, nitro, $C_1$-$C_4$-alkyl, (phenyl)-($C_1$-$C_2$-alkyl)-, (5-membered heteroaryl)-($C_1$-$C_2$-alkyl)-, $C_1$-$C_4$-hydroxyalkyl, $C_1$-$C_4$-haloalkyl, —O$R^9$, —N($R^{10}$)($R^{11}$), —C(=O)—N($R^{12}$)($R^{13}$), S(=O)$_n$—$R^{14}$, and a 5-membered heteroaryl group which itself is optionally substituted with one or two methyl groups,
or two substituents attached to adjacent carbon atoms of said phenyl or pyridinyl group together form a bivalent group selected from —(CH$_2$)$_3$—, —(CH$_2$)$_4$—, —(CH$_2$)$_2$—O—, —(CH$_2$)$_3$—O—, —CH$_2$—O—CH$_2$—, —O—CH$_2$—O—, —O—CH$_2$—CH$_2$—O— and —O—CF$_2$—O—;
$R^5$ and $R^6$ represent, independently from each occurrence, a hydrogen atom or a group selected from $C_1$-$C_2$-alkyl and ($C_1$-$C_2$-alkyl)-C(=O)—,
or
$R^5$ and $R^6$, together with the nitrogen atom to which they are attached, represent a monocyclic nitrogen containing 4- to 7-membered heterocycloalkyl group which is optionally substituted one or two times, each substituent independently selected from a fluorine atom, a chlorine atom and a bromine atom, or a group selected from oxo, hydroxy, $C_1$-$C_2$-alkyl and ($C_1$-$C_2$-alkyl)-C(=O)—;
$R^7$ represents a hydrogen atom or a $C_1$-$C_2$-alkyl group;
$R^8$ represents a —C(=O)—NH$_2$ group;
$R^9$ represents a hydrogen atom or a group selected from $C_1$-$C_4$-alkyl, (phenyl)-($C_1$-$C_2$-alkyl)-, $C_1$-$C_4$-haloalkyl, $C_2$-$C_3$-hydroxyalkyl, ($C_1$-$C_2$-alkoxy)-$C_2$-alkyl-, (($C_1$-$C_2$-alkyl)-C(=O)—O)—$C_2$-alkyl-, —C($R^{18}$)($R^{19}$)—C(=O)—O$R^{17}$, —C($R^{18}$)($R^{19}$)—C(=O)—N($R^{20}$)($R^{21}$) and phenyl,
wherein the phenyl group within said (phenyl)-($C_1$-$C_2$-alkyl)- group and said phenyl group itself are optionally substituted one or two times, each substituent independently selected from a fluorine atom, a chlorine atom and a bromine atom, or a group selected from methyl, trifluoromethyl and methoxy;
$R^{10}$ and $R^{11}$ represent, independently from each occurrence, a hydrogen atom or a group selected from $C_1$-$C_2$-alkyl, $C_1$-$C_2$haloalkyl, $C_2$-$C_3$-hydroxyalkyl, ($C_1$-$C_2$alkoxy)-$C_2$-alkyl-, (($R^{22}$)($R^{23}$)N)-$C_2$-alkyl, ($C_1$-$C_2$-alkyl)-C(=O)—, $C_3$-$C_5$-cycloalkyl, ($C_3$-$C_5$-cycloalkyl)-C(=O)—, (phenyl)-($C_1$-$C_2$-alkyl)-, (phenyl)-($C_1$-$C_2$-alkyl)-C(=O)— and (phenyl)-($C_1$-$C_2$-alkyl)-O—C(=O)—,
wherein the phenyl groups within said (phenyl)-($C_1$-$C_2$-alkyl)-, (phenyl)-($C_1$-$C_2$-alkyl)-C(=O)— and (phenyl)-($C_1$-$C_2$-alkyl)-O—C(=O)— groups are optionally substituted one or two times, each substituent independently selected from a fluorine atom, a chlorine atom and a bromine atom, or a group selected from methyl, trifluoromethyl and methoxy,
or
$R^{10}$ and $R^{11}$, together with the nitrogen atom to which they are attached, represent a monocyclic nitrogen containing 4- to 7-membered heterocycloalkyl group, or a bicyclic nitrogen containing 6- to 10-membered heterocycloalkyl group, which are optionally substituted one, two or three times, each substituent independently selected from a halogen atom or a group selected from cyano, oxo, hydroxy, $C_1$-$C_2$-alkyl, $C_1$-$C_2$haloalkyl, ($C_1$-$C_2$-alkyl)-C(=O)—, $C_1$-$C_2$alkoxy, —N($R^{22}$)($R^{23}$), and a monocyclic 4- to 7-membered heterocycloalkyl group;
$R^{12}$ and $R^{13}$ represent, independently from each occurrence, a hydrogen atom or a group selected from $C_1$-$C_4$-alkyl, $C_1$-$C_4$-haloalkyl, $C_1$-$C_4$-hydroxyalkyl, ($C_1$-$C_2$-alkoxy)-$C_2$-$C_3$-alkyl-, $C_3$-$C_7$-cycloalkyl, monocyclic 4- to 7-membered heterocycloalkyl and (phenyl)-($C_1$-$C_3$-alkyl)-,
wherein $C_3$-$C_7$-cycloalkyl and monocyclic 4- to 7-membered heterocycloalkyl are optionally substituted one or two times, each substituent independently selected from a halogen atom or a group selected from oxo, $C_1$-$C_2$-alkyl and ($C_1$-$C_2$-alkyl)-C(=O)—, or
R$^{12}$ and R$^{13}$, together with the nitrogen atom to which they are attached, represent a monocyclic nitrogen containing 4- to 7-membered heterocycloalkyl group which is optionally substituted one or two times, each substituent independently selected from a halogen atom or a group selected from oxo, C$_1$-C$_2$-alkyl and (C$_1$-C$_2$-alkyl)-C(=O)—;

R$^{14}$ represents a group selected from C$_1$-C$_2$-alkyl and C$_1$-C$_2$-haloalkyl;

R$^{17}$ represents a C$_1$-C$_4$-alkyl group;

R$^{18}$ and R$^{19}$ represent, independently from each occurrence, a hydrogen atom or a C$_1$-C$_2$-alkyl group;

R$^{20}$ represents a hydrogen atom or a group selected from C$_1$-C$_6$-alkyl, C$_3$-C$_4$-alkenyl, C$_3$-C$_4$-alkynyl, C$_1$-C$_3$-alkoxy, C$_3$-C$_7$-cycloalkyl, bicyclic C$_6$-C$_{11}$-cycloalkyl, adamantyl, monocyclic 4- to 7-membered heterocycloalkyl, bicyclic 6- to 10-membered heterocycloalkyl, phenyl, naphthyl, and 5- to 10-membered heteroaryl,
wherein said C$_1$-C$_6$-alkyl group is optionally substituted one, two or three times, each substituent independently selected from a halogen atom or a group selected from hydroxy, cyano, C$_1$-C$_3$-alkoxy, —N(R$^{22}$)(R$^{23}$), C$_3$-C$_7$-cycloalkyl, bicyclic C$_6$-C$_{11}$-cycloalkyl, adamantyl, monocyclic 4- to 7-membered heterocycloalkyl, bicyclic 6- to 10-membered heterocycloalkyl, phenyl, and 5- to 10-membered heteroaryl, said phenyl and 5- to 10-membered heteroaryl substituents themselves being optionally substituted one or two times, each substituent independently selected from a fluorine atom, a chlorine atom and a bromine atom, or a group selected from methyl, trifluoromethyl and methoxy,
wherein C$_3$-C$_7$-cycloalkyl, bicyclic C$_6$-C$_{11}$-cycloalkyl, adamantyl, monocyclic 4- to 7-membered heterocycloalkyl, bicyclic 6- to 10-membered heterocycloalkyl are optionally substituted one or two or three times, each substituent independently selected from a halogen atom or a group selected from cyano, oxo, hydroxy, C$_1$-C$_2$-alkyl and (C$_1$-C$_2$-alkyl)-C(=O)—,
and wherein said phenyl, naphthyl and 5- to 10-membered heteroaryl groups are optionally substituted one, two or three times, each substituent independently selected from a halogen atom or a group selected from cyano, C$_1$-C$_2$-alkyl, C$_1$-C$_2$-haloalkyl, C$_1$-C$_2$-alkoxy, C$_1$-C$_2$haloalkoxy, —N(R$^{22}$)(R$^{23}$) and —C(=O)—N(R$^{24}$)(R$^{25}$), R$^{21}$ represents a hydrogen atom or a C$_1$-C$_2$-alkyl group,
or
R$^{20}$ and R$^{21}$, together with the nitrogen atom to which they are attached, represent a monocyclic nitrogen containing 4- to 7-membered heterocycloalkyl group which is optionally benzocondensed, and which is optionally substituted one, two or three times, each substituent independently selected from a halogen atom or a group selected from cyano, oxo, hydroxy, C$_1$-C$_2$-alkyl, C$_1$-C$_2$haloalkyl, (phenyl)-(C$_1$-C$_2$-alkyl)-, (C$_1$-C$_2$-alkyl)-C(=O)—, C$_3$-C$_4$-cycloalkyl, C$_1$-C$_2$-alkoxy, C$_1$-C$_2$-haloalkoxy, —N(R$^{22}$)(R$^{23}$) and —C(=O)—N(R$^{24}$)(R$^{25}$);

R$^{22}$ and R$^{23}$ represent, independently from each occurrence, a hydrogen atom or a group selected from C$_1$-C$_2$-alkyl and (C$_1$-C$_2$-alkyl)-C(=O)—;

R$^{24}$ and R$^{25}$ represent, independently from each occurrence, a hydrogen atom or a C$_1$-C$_2$-alkyl group, and n represents an integer 0, 1, or 2,
and stereoisomers, tautomers, N-oxides, hydrates, solvates, and salts thereof, and mixtures of same.

In accordance with a tenth embodiment of the first aspect, the present invention covers compounds of general formula (I), supra, in which:

R$^1$ represents a phenyl or pyridinyl group optionally substituted, one, two, or three times, each substituent independently selected from a fluorine atom, a chlorine atom and a bromine atom, or a group selected from cyano, C$_1$-C$_4$-alkyl, C$_1$-C$_2$-fluoroalkyl, C$_1$-C$_2$-alkoxy, C$_1$-C$_2$-fluoroalkoxy, —N(R$^5$)(R$^6$),
or two substituents attached to adjacent carbon atoms of said phenyl or pyridinyl group together form a bivalent group selected from —(CH$_2$)$_3$—, —O—CH$_2$—O— and —O—CF$_2$—O—,
or
R$^1$ represents a pyrazolyl group optionally substituted with one methyl group, R$^2$ represents a group

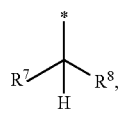

wherein "*" indicates the point of attachment to the nitrogen atom to which R$^2$ is attached;

R$^3$ represents a group selected from methyl and —NH$_2$;

R$^4$ represents a phenyl or pyridinyl group optionally substituted, one, two, or three times, each substituent independently selected from a fluorine atom, a chlorine atom and a bromine atom, or a group selected from cyano, C$_1$-C$_3$-alkyl, C$_1$-C$_3$-hydroxyalkyl, C$_1$-C$_3$-fluoroalkyl, —OR$^9$, —N(R$^{10}$)(R$^{11}$), —C(=O)—N(R$^{12}$)(R$^{13}$) and S(=O)$_n$—R$^{14}$,
or two substituents attached to adjacent carbon atoms of said phenyl or pyridinyl group together form a bivalent group selected from —(CH$_2$)$_3$—, —O—CH$_2$—O— and —O—CF$_2$—O—;

R$^5$ and R$^6$ represent, independently from each occurrence, a hydrogen atom or a C$_1$-C$_2$-alkyl group,
or
R$^5$ and R$^6$, together with the nitrogen atom to which they are attached, represent a monocyclic nitrogen containing 4- to 7-membered heterocycloalkyl group which is optionally substituted one or two times, each substituent independently selected from a fluorine atom or a group selected from hydroxy and C$_1$-C$_2$-alkyl;

R$^7$ represents a hydrogen atom or a C$_1$-C$_2$-alkyl group;

R$^8$ represents a —C(=O)—NH$_2$ group;

R$^9$ represents a hydrogen atom or a group selected from C$_1$-C$_2$-alkyl, benzyl, C$_1$-C$_2$-fluoroalkyl, (C$_1$-C$_2$-alkoxy)-C$_2$-alkyl-, ((C$_1$-C$_2$-alkyl)-C(=O)—O)—C$_2$-alkyl-, —C(R$^{18}$)(R$^{19}$)—C(=O)—OR$^{17}$, —C(R$^{18}$)(R$^{19}$)—C(=O)—N(R$^{20}$)(R$^{21}$) and phenyl,
wherein the phenyl group within said benzyl group and said phenyl group itself are optionally substituted one or two times, each substituent independently selected from a fluorine atom, a chlorine atom and a methyl group;

R$^{10}$ and R$^{11}$ represent, independently from each occurrence, a hydrogen atom or a group selected from C$_1$-C$_2$-alkyl, C$_1$-C$_2$-fluoroalkyl, (C$_1$-C$_2$-alkyl)-C(=O)—, (phenyl)-(C$_1$-C$_2$-alkyl)-, (phenyl)-(C$_1$-C$_2$-alkyl)-C(=O)— and (phenyl)-(C$_1$-C$_2$-alkyl)-O—C(=O)—,
wherein the phenyl groups within said (phenyl)-(C$_1$-C$_2$-alkyl)-, (phenyl)-(C$_1$-C$_2$-alkyl)-C(=O)— and (phenyl)-($C_1$-$C_2$-alkyl)-O—C(═O)— groups are optionally substituted one or two times, each substituent independently selected from a fluorine atom, a chlorine atom and a methyl group,
or
$R^{10}$ and $R^{11}$, together with the nitrogen atom to which they are attached, represent a monocyclic nitrogen containing 4- to 7-membered heterocycloalkyl group which is optionally substituted one or two times, each substituent independently selected from a fluorine atom or a group selected from oxo, $C_1$-$C_2$-alkyl, $C_1$-$C_2$-fluoroalkyl and ($C_1$-$C_2$-alkyl)-C(═O)—;

$R^{12}$ and $R^{13}$ represent, independently from each occurrence, a hydrogen atom or a group selected from $C_1$-$C_4$-alkyl, $C_1$-$C_4$-fluoroalkyl, $C_3$-$C_7$-cycloalkyl, monocyclic 4- to 7-membered heterocycloalkyl and (phenyl)-($C_1$-$C_2$-alkyl)-,
wherein $C_3$-$C_7$-cycloalkyl and monocyclic 4- to 7-membered heterocycloalkyl are optionally substituted one or two times, each substituent independently selected from a fluorine atom or a group selected from oxo, $C_1$-$C_2$-alkyl and ($C_1$-$C_2$-alkyl)-C(═O)—,
or
$R^{12}$ and $R^{13}$, together with the nitrogen atom to which they are attached, represent a monocyclic nitrogen containing 4- to 7-membered heterocycloalkyl group which is optionally substituted one or two times, each substituent independently selected from a halogen atom or a group selected from oxo, $C_1$-$C_2$-alkyl and ($C_1$-$C_2$-alkyl)-C(═O)—;

$R^{14}$ represents a group selected from methyl and trifluoromethyl;
$R^{17}$ represents a $C_1$-$C_2$-alkyl group;
$R^{18}$ and $R^{19}$ represent, independently from each occurrence, a hydrogen atom or a methyl group;
$R^{20}$ represents a hydrogen atom or a group selected from optionally substituted $C_1$-$C_3$-alkyl, unsubstituted $C_4$-$C_6$-alkyl, prop-2-ynyl, methoxy, $C_3$-$C_6$-cycloalkyl, adamantyl, monocyclic 4- to 7-membered heterocycloalkyl, phenyl, and 5- to 10-membered heteroaryl,
wherein said $C_1$-$C_3$-alkyl group is optionally substituted one, two or three times, each substituent independently selected from a halogen atom or a group selected from hydroxy, cyano, $C_1$-$C_3$-alkoxy, —N($R^{22}$)($R^{23}$), $C_3$-$C_6$-cycloalkyl, adamantyl, monocyclic 4- to 7-membered heterocycloalkyl, phenyl, and 5- to 10-membered heteroaryl, said phenyl and 5- to 10-membered heteroaryl substituents themselves being optionally substituted one or two times, each substituent independently selected from a fluorine atom, a chlorine atom and a methyl group,
wherein said $C_3$-$C_6$-cycloalkyl, adamantyl and monocyclic 4- to 7-membered heterocycloalkyl groups are optionally substituted one or two or three times, each substituent independently selected from a fluorine atom or a group selected from oxo, $C_1$-$C_2$-alkyl and ($C_1$-$C_2$-alkyl)-C(═O)—,
and wherein said phenyl and 5- to 10-membered heteroaryl groups are optionally substituted one, two or three times, each substituent independently selected from a fluorine atom and a chlorine atom or a group selected from cyano, $C_1$-$C_2$-alkyl, $C_1$-$C_2$-fluoroalkyl, $C_1$-$C_2$-alkoxy, $C_1$-$C_2$-haloalkoxy, —N($R^{22}$)($R^{23}$) and —C(═O)—N($R^{24}$)($R^{25}$), $R^{21}$ represents a hydrogen atom or a $C_1$-$C_2$-alkyl group,
or
$R^{20}$ and $R^{21}$, together with the nitrogen atom to which they are attached, represent a monocyclic nitrogen containing 4- to 7-membered heterocycloalkyl group which is optionally benzocondensed, and which is optionally substituted one, two or three times, each substituent independently selected from a halogen atom or a group selected from cyano, oxo, hydroxy, $C_1$-$C_2$-alkyl, $C_1$-$C_2$-fluoroalkyl, benzyl, ($C_1$-$C_2$-alkyl)-C(═O)—, $C_3$-$C_4$-cycloalkyl, $C_1$-$C_2$-alkoxy, $C_1$-$C_2$haloalkoxy, —N($R^{22}$)($R^{23}$) and —C(═O)—N($R^{24}$)($R^{25}$);

$R^{22}$ and $R^{23}$ represent, independently from each occurrence, a hydrogen atom or a group selected from $C_1$-$C_2$-alkyl and ($C_1$-$C_2$-alkyl)-C(═O)—;

$R^{24}$ and $R^{25}$ represent, independently from each occurrence, a hydrogen atom or a $C_1$-$C_2$-alkyl group, and n represents an integer 2, and stereoisomers, tautomers, N-oxides, hydrates, solvates, and salts thereof, and mixtures of same.

In accordance with an eleventh embodiment of the first aspect, the present invention covers compounds of general formula (I), supra, in which:
$R^1$ represents a phenyl or pyridinyl group optionally substituted, one or two times, each substituent independently selected from a fluorine atom and a chlorine atom, or a group selected from cyano, $C_1$-$C_2$-alkyl, $C_1$-$C_2$-fluoroalkyl, $C_1$-$C_2$-alkoxy, $C_1$-$C_2$-fluoroalkoxy;

$R^2$ represents a group

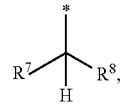

wherein "*" indicates the point of attachment to the nitrogen atom to which $R^2$ is attached;
$R^3$ represents a group selected from methyl and —$NH_2$;
$R^4$ represents a phenyl or pyridinyl group optionally substituted, one or two times, each substituent independently selected from a fluorine atom and a chlorine atom, or a group selected from $C_1$-$C_2$-alkyl, $C_1$-$C_2$-fluoroalkyl, —$OR^9$;
$R^7$ represents a hydrogen atom or a $C_1$-$C_2$-alkyl group;
$R^8$ represents a —C(═O)—$NH_2$ group, and
$R^9$ represents a group selected from $C_1$-$C_2$-alkyl, benzyl, $C_1$-$C_2$-fluoroalkyl, ($C_1$-$C_2$-alkoxy)-$C_2$-alkyl- and phenyl,
wherein the phenyl group within said benzyl group and said phenyl group itself are optionally substituted one or two times, each substituent independently selected from a fluorine atom, a chlorine atom and a methyl group;
and stereoisomers, tautomers, N-oxides, hydrates, solvates, and salts thereof, and mixtures of same.

In accordance with a twelfth embodiment of the first aspect, the present invention covers compounds of general formula (I), supra, in which:
$R^1$ represents a phenyl or pyridinyl group optionally substituted, one or two times, each substituent independently selected from a fluorine atom and a chlorine atom, or a group selected from cyano, $C_1$-$C_2$-fluoroalkyl, $C_1$-$C_2$alkoxy, $C_1$-$C_2$-fluoroalkoxy;

R² represents a group

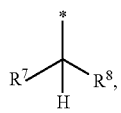

wherein "*" indicates the point of attachment to the nitrogen atom to which R² is attached;
R³ represents a group selected from methyl and —NH₂;
R⁴ represents a phenyl or pyridinyl group optionally substituted, one or two times, each substituent independently selected from a fluorine atom and a chlorine atom, or a group selected from $C_1$-$C_2$-alkyl, $C_1$-$C_2$-fluoroalkyl, —OR⁹;
R⁷ represents a hydrogen atom or a $C_1$-$C_2$-alkyl group;
R⁸ represents a —C(=O)—NH₂ group, and
R⁹ represents a group selected from $C_1$-$C_2$-alkyl, benzyl, $C_1$-$C_2$-fluoroalkyl, ($C_1$-$C_2$-alkoxy)-$C_2$-alkyl- and phenyl,
wherein the phenyl group within said benzyl group and said phenyl group itself are optionally substituted one or two times, each substituent independently selected from a fluorine atom, a chlorine atom and a methyl group;
and stereoisomers, tautomers, N-oxides, hydrates, solvates, and salts thereof, and mixtures of same.

In accordance with a thirteenth embodiment of the first aspect, the present invention covers compounds of general formula (I), supra, in which:
R¹ represents a group

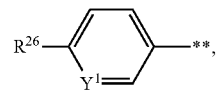

wherein "**" indicates the point of attachment to the nitrogen atom to which R¹ is attached;
R² represents a group

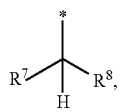

wherein "*" indicates the point of attachment to the nitrogen atom to which R² is attached;
R³ represents a group selected from methyl and —NH₂;
R⁴ represents a group

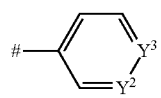

wherein "#" indicates the point of attachment to the carbonyl group to which R⁴ is attached;
R⁷ represents a hydrogen atom or a $C_1$-$C_2$-alkyl group;
R⁸ represents a —C(=O)—NH₂ group;
Y¹ represents —C(H)=, —C(F)=, —C(Cl)=, —C(CN)= or —N=;
Y² represents —C(H)= and —N=;
Y³ represents —C(R²⁷)= and —N=, with the proviso that if Y² represents —N=, Y³ represents —C(R²⁷)=, and if Y³ represents —N=, Y² represents —C(H)=;
R²⁶ represents a fluorine atom, a chlorine atom, or a group selected from $C_1$-$C_2$-alkyl, $C_1$-$C_2$-fluoroalkyl, $C_1$-$C_2$alkoxy and $C_1$-$C_2$-fluoroalkoxy, and
R²⁷ represents a fluorine atom, a chlorine atom, or a group selected from $C_1$-$C_2$alkoxy, benzyloxy and $C_1$-$C_2$-fluoroalkoxy,
and stereoisomers, tautomers, N-oxides, hydrates, solvates, and salts thereof, and mixtures of same.

In accordance with a fourteenth embodiment of the first aspect, the present invention covers compounds of general formula (I), supra, in which:
R¹ represents a group

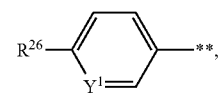

wherein "**" indicates the point of attachment to the nitrogen atom to which R¹ is attached;
R² represents a group

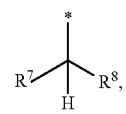

wherein "*" indicates the point of attachment to the nitrogen atom to which R² is attached;
R³ represents a group selected from methyl and —NH₂;
R⁴ represents a group

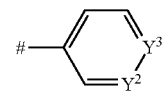

wherein "#" indicates the point of attachment to the carbonyl group to which R⁴ is attached;
R⁷ represents a hydrogen atom or a $C_1$-$C_2$-alkyl group;
R⁸ represents a —C(=O)—NH₂ group;
Y¹ represents —C(H)=, —C(F)=, —C(Cl)=, —C(CN)= or —N=;
Y² represents —C(H)= or —N=;
Y³ represents —C(R²⁷)= or —N=,
with the proviso that if Y² represents —N=, Y³ represents —C(R²⁷)=, and if Y³ represents —N=, Y² represents —C(H)=;
R²⁶ represents a fluorine atom, a chlorine atom, or a group selected from $C_1$-$C_2$-alkyl, $C_1$-$C_2$-fluoroalkyl, $C_1$-$C_2$-alkoxy and $C_1$-$C_2$-fluoroalkoxy, and
R²⁷ represents a fluorine atom, a chlorine atom, or a group selected from $C_1$-$C_2$-alkoxy, benzyloxy and $C_1$-$C_2$-fluoroalkoxy,
and stereoisomers, tautomers, N-oxides, hydrates, solvates, and salts thereof, and mixtures of same.

In accordance with a fifteenth embodiment of the first aspect, the present invention covers compounds of general formula (I), supra, in which:

$R^1$ represents a group

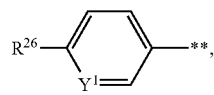

wherein "**" indicates the point of attachment to the nitrogen atom to which $R^1$ is attached;
$R^2$ represents a group

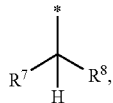

wherein "*" indicates the point of attachment to the nitrogen atom to which $R^2$ is attached;
$R^3$ represents a group selected from methyl and —$NH_2$;
$R^4$ represents a group

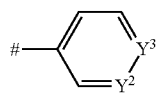

wherein "#" indicates the point of attachment to the carbonyl group to which $R^4$ is attached;
$R^7$ represents a hydrogen atom or a $C_1$-$C_2$-alkyl group;
$R^6$ represents a —C(=O)—$NH_2$ group;
$Y^1$ represents —C(H)=, —C(F)= or —N=;
$Y^2$ represents —C(H)= and —N=;
$Y^3$ represents —C($R^{27}$)= and —N=,
with the proviso that if $Y^2$ represents —N=, $Y^3$ represents —C($R^{27}$)=, and if $Y^3$ represents —N=, $Y^2$ represents —C(H)=;
$R^{26}$ represents a fluorine atom, a chlorine atom, or a group selected from methyl, difluoromethyl, trifluoromethyl, methoxy, difluoromethoxy and trifluoromethoxy, and
$R^{27}$ represents a chlorine atom, or a group selected from methoxy, benzyloxy, difluoromethoxy and trifluoromethoxy,
and stereoisomers, tautomers, N-oxides, hydrates, solvates, and salts thereof, and mixtures of same.

In accordance with a sixteenth embodiment of the first aspect, the present invention covers compounds of general formula (I), supra, in which:
$R^1$ represents a group

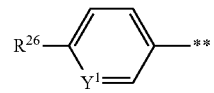

wherein "*" indicates the point of attachment to the nitrogen atom to which $R^1$ is attached;
$R^2$ represents a group

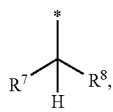

wherein "*" indicates the point of attachment to the nitrogen atom to which $R^2$ is attached;
$R^3$ represents a group selected from methyl and —$NH_2$;
$R^4$ represents a group

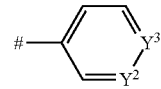

wherein "#" indicates the point of attachment to the carbonyl group to which $R^4$ is attached;
$R^7$ represents a hydrogen atom or a $C_1$-$C_2$-alkyl group;
$R^8$ represents a —C(=O)—$NH_2$ group;
$Y^1$ represents —C(H)=, —C(F)= or —N=;
$Y^2$ represents —C(H)= or —N=;
$Y^3$ represents —C($R^{27}$)= or —N=,
with the proviso that if $Y^2$ represents —N=, $Y^3$ represents —C($R^{27}$)=, and if $Y^3$ represents —N=, $Y^2$ represents —C(H)=;
$R^{26}$ represents a fluorine atom, a chlorine atom, or a group selected from methyl, difluoromethyl, trifluoromethyl, methoxy, difluoromethoxy and trifluoromethoxy, and
$R^{27}$ represents a chlorine atom, or a group selected from methoxy, benzyloxy, difluoromethoxy and trifluoromethoxy,
and stereoisomers, tautomers, N-oxides, hydrates, solvates, and salts thereof, and mixtures of same.

In accordance with a seventeenth embodiment of the first aspect, the present invention covers compounds of general formula (I), supra, in which:
$R^1$ represents a group

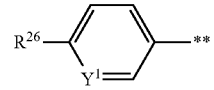

wherein "*" indicates the point of attachment to the nitrogen atom to which $R^1$ is attached;
$R^2$ represents a group

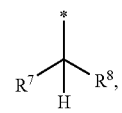

wherein "*" indicates the point of attachment to the nitrogen atom to which $R^2$ is attached;
$R^3$ represents a —$NH_2$ group;
$R^4$ represents a group

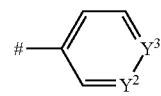

wherein "#" indicates the point of attachment to the carbonyl group to which $R^4$ is attached;
$R^7$ represents a hydrogen atom or a $C_1$-$C_2$-alkyl group;
$R^8$ represents a —C(=O)—$NH_2$ group;
$Y^1$ represents —C(H)=, —C(F)=, —C(Cl)=, —C(CN)= or —N=;

$Y^2$ represents —C(H)= and —N=;
$Y^3$ represents —C($R^{27}$)= and —N=,
with the proviso that if $Y^2$ represents —N=, $Y^3$ represents —C($R^{27}$)=, and if $Y^3$ represents —N=, $Y^2$ represents —C(H)=;
$R^{28}$ represents a fluorine atom, a chlorine atom, or a group selected from $C_1$-$C_2$-alkyl, $C_1$-$C_2$-fluoroalkyl, $C_1$-$C_2$-alkoxy and $C_1$-$C_2$-fluoroalkoxy, and
$R^{27}$ represents a fluorine atom, a chlorine atom, or a group selected from $C_1$-$C_2$-alkoxy, benzyloxy and $C_1$-$C_2$-fluoroalkoxy,
and stereoisomers, tautomers, N-oxides, hydrates, solvates, and salts thereof, and mixtures of same.

In accordance with an eighteenth embodiment of the first aspect, the present invention covers compounds of general formula (I), supra, in which:
$R^1$ represents a group

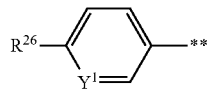

wherein "**" indicates the point of attachment to the nitrogen atom to which $R^1$ is attached;
$R^2$ represents a group

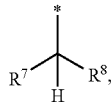

wherein "*" indicates the point of attachment to the nitrogen atom to which $R^2$ is attached;
$R^3$ represents a —NH$_2$ group;
$R^4$ represents a group

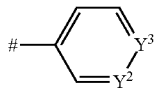

wherein "#" indicates the point of attachment to the carbonyl group to which $R^4$ is attached;
$R^7$ represents a hydrogen atom or a $C_1$-$C_2$-alkyl group;
$R^8$ represents a —C(=O)—NH$_2$ group;
$Y^1$ represents —C(H)=, —C(F)=, —C(Cl)=, —C(CN)= or —N=;
$Y^2$ represents —C(H)= or —N=;
$Y^3$ represents —C($R^{27}$)= or —N=,
with the proviso that if $Y^2$ represents —N=, $Y^3$ represents —C($R^{27}$)=, and if $Y^3$ represents —N=, $Y^2$ represents —C(H)=;
$R^{26}$ represents a fluorine atom, a chlorine atom, or a group selected from $C_1$-$C_2$-alkyl, $C_1$-$C_2$-fluoroalkyl, $C_1$-$C_2$-alkoxy and $C_1$-$C_2$-fluoroalkoxy, and
$R^{27}$ represents a fluorine atom, a chlorine atom, or a group selected from $C_1$-$C_2$-alkoxy, benzyloxy and $C_1$-$C_2$-fluoroalkoxy,
and stereoisomers, tautomers, N-oxides, hydrates, solvates, and salts thereof, and mixtures of same.

In accordance with a nineteenth embodiment of the first aspect, the present invention covers compounds of general formula (I), supra, in which:
$R^1$ represents a group

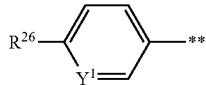

wherein "**" indicates the point of attachment to the nitrogen atom to which $R^1$ is attached;
$R^2$ represents a group

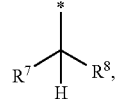

wherein "*" indicates the point of attachment to the nitrogen atom to which $R^2$ is attached;
$R^3$ represents a —NH$_2$ group;

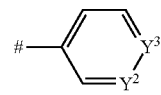

$R^4$ represents a group
wherein "#" indicates the point of attachment to the carbonyl group to which $R^4$ is attached;
$R^7$ represents a hydrogen atom or a $C_1$-$C_2$-alkyl group;
$R^8$ represents a —C(=O)—NH$_2$ group;
$Y^1$ represents —C(H)=, —C(F)= or —N=;
$Y^2$ represents —C(H)= and —N=;
$Y^3$ represents —C($R^{27}$)= and —N=,
with the proviso that if $Y^2$ represents —N=, $Y^3$ represents —C($R^{27}$)=, and if $Y^3$ represents —N=, $Y^2$ represents —C(H)=;
$R^{26}$ represents a fluorine atom, a chlorine atom, or a group selected from methyl, difluoromethyl, trifluoromethyl, methoxy, difluoromethoxy and trifluoromethoxy, and
$R^{27}$ represents a chlorine atom, or a group selected from methoxy, benzyloxy, difluoromethoxy and trifluoromethoxy,
and stereoisomers, tautomers, N-oxides, hydrates, solvates, and salts thereof, and mixtures of same.

In accordance with a twentieth embodiment of the first aspect, the present invention covers compounds of general formula (I), supra, in which:
$R^1$ represents a group

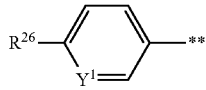

wherein "**" indicates the point of attachment to the nitrogen atom to which $R^1$ is attached;
$R^2$ represents a group

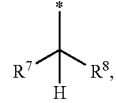

wherein "*" indicates the point of attachment to the nitrogen atom to which $R^2$ is attached;
$R^3$ represents a —$NH_2$ group;
$R^4$ represents a group

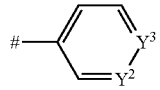

wherein "#" indicates the point of attachment to the carbonyl group to which $R^4$ is attached;
$R^7$ represents a hydrogen atom or a $C_1$-$C_2$-alkyl group;
$R^8$ represents a —C(=O)—$NH_2$ group;
$Y^1$ represents —C(H)=, —C(F)= or —N=;
$Y^2$ represents —C(H)= or —N=;
$Y^3$ represents —C($R^{27}$)= or —N=,
with the proviso that if $Y^2$ represents —N=, $Y^3$ represents —C($R^{27}$)=, and if $Y^3$ represents —N=, $Y^2$ represents —C(H)=;
$R^{28}$ represents a fluorine atom, a chlorine atom, or a group selected from methyl, difluoromethyl, trifluoromethyl, methoxy, difluoromethoxy and trifluoromethoxy, and
$R^{27}$ represents a chlorine atom, or a group selected from methoxy, benzyloxy, difluoromethoxy and trifluoromethoxy,
and stereoisomers, tautomers, N-oxides, hydrates, solvates, and salts thereof, and mixtures of same.

In accordance with a twenty-first embodiment of the first aspect, the present invention covers compounds of general formula (I), supra, in which:
$R^1$ represents a group

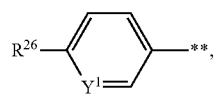

wherein "**" indicates the point of attachment to the nitrogen atom to which $R^1$ is attached,
or
$R^1$ represents a group

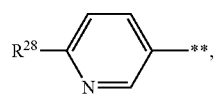

wherein "**" indicates the point of attachment to the nitrogen atom to which $R^1$ is attached;
$R^2$ represents a group

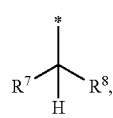

wherein "*" indicates the point of attachment to the nitrogen atom to which $R^2$ is attached;
$R^3$ represents a group selected from methyl and —$NH_2$;

$R^4$ represents a group selected from

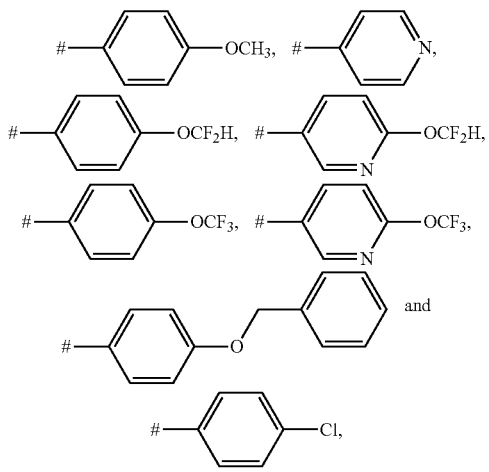

wherein "#" indicates the point of attachment to the carbonyl group to which $R^4$ is attached;
$R^7$ represents a methyl group;
$R^8$ represents a —C(=O)—$NH_2$ group;
$Y^1$ represents —C(H)= or —C(F)=;
$R^{26}$ represents a fluorine atom, a chlorine atom, or a group selected from difluoromethyl, trifluoromethyl, methoxy, difluoromethoxy and trifluoromethoxy;
$R^{28}$ represents a group selected from methyl, difluoromethyl, trifluoromethyl, methoxy, difluoromethoxy and trifluoromethoxy;
and stereoisomers, tautomers, N-oxides, hydrates, solvates, and salts thereof, and mixtures of same.

In accordance with a twenty-second embodiment of the first aspect, the present invention covers compounds of general formula (I), supra, in which:
$R^1$ represents a group

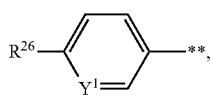

wherein "**" indicates the point of attachment to the nitrogen atom to which $R^1$ is attached,
or
$R^1$ represents a group

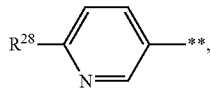

wherein "**" indicates the point of attachment to the nitrogen atom to which $R^1$ is attached;
$R^2$ represents a group

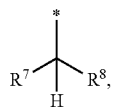

wherein "*" indicates the point of attachment to the nitrogen atom to which $R^2$ is attached;

$R^3$ represents a —$NH_2$ group;
$R^4$ represents a group selected from

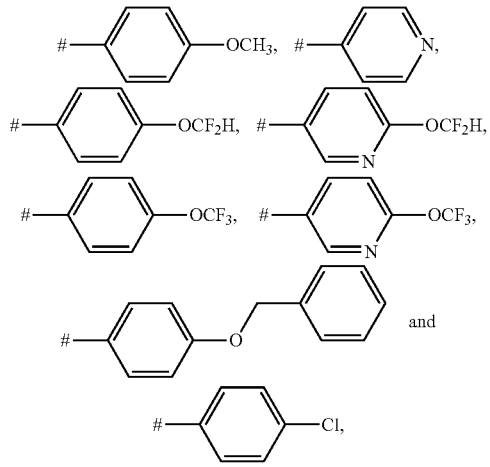

wherein "#" indicates the point of attachment to the carbonyl group to which $R^4$ is attached;
$R^7$ represents a methyl group;
$R^8$ represents a —C(=O)—$NH_2$ group;
$Y^1$ represents —C(H)= or —C(F)=;
$R^{26}$ represents a fluorine atom, a chlorine atom, or a group selected from difluoromethyl, trifluoromethyl, methoxy, difluoromethoxy and trifluoromethoxy;
$R^{28}$ represents a group selected from methyl, difluoromethyl, trifluoromethyl, methoxy, difluoromethoxy and trifluoromethoxy;
and stereoisomers, tautomers, N-oxides, hydrates, solvates, and salts thereof, and mixtures of same.

In accordance with a twenty-third embodiment of the first aspect, the present invention covers compounds of general formula (I), supra, in which:
$R^1$ represents a group

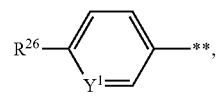

wherein "*" indicates the point of attachment to the nitrogen atom to which $R^1$ is attached,
or
$R^1$ represents a group

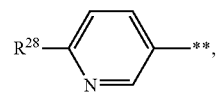

wherein "**" indicates the point of attachment to the nitrogen atom to which $R^1$ is attached;
$R^2$ represents a group

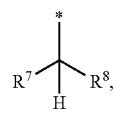

wherein "*" indicates the point of attachment to the nitrogen atom to which $R^2$ is attached;

$R^3$ represents a methyl group;
$R^4$ represents a group selected from

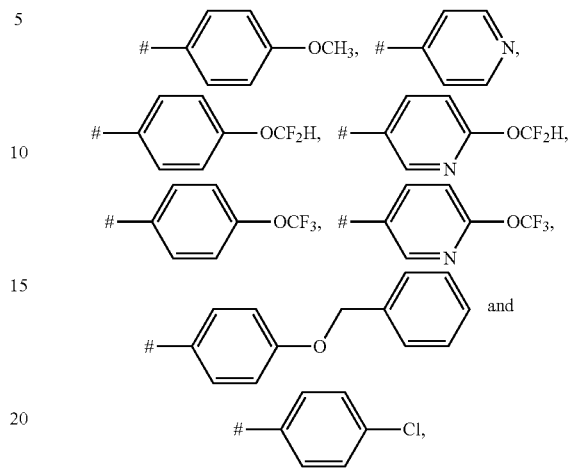

wherein "#" indicates the point of attachment to the carbonyl group to which $R^4$ is attached;
$R^7$ represents a methyl group;
$R^8$ represents a —C(=O)—$NH_2$ group;
$Y^1$ represents —C(H)= or —C(F)=;
$R^{26}$ represents a fluorine atom, a chlorine atom, or a group selected from difluoromethyl, trifluoromethyl, methoxy, difluoromethoxy and trifluoromethoxy;
$R^{28}$ represents a group selected from methyl, difluoromethyl, trifluoromethyl, methoxy, difluoromethoxy and trifluoromethoxy;
and stereoisomers, tautomers, N-oxides, hydrates, solvates, and salts thereof, and mixtures of same.

In accordance with a twenty-fourth embodiment of the first aspect, the present invention covers compounds of general formula (I), supra, in which:
$R^1$ represents a group selected from

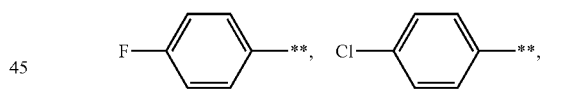
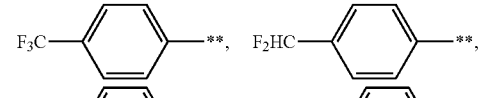
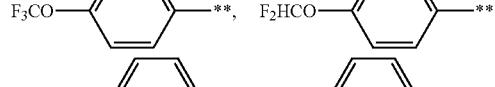
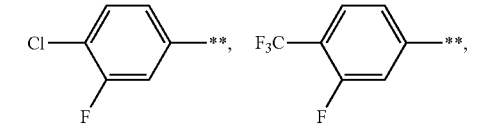
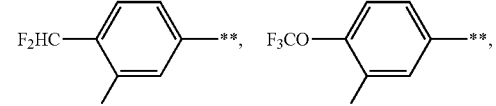

-continued

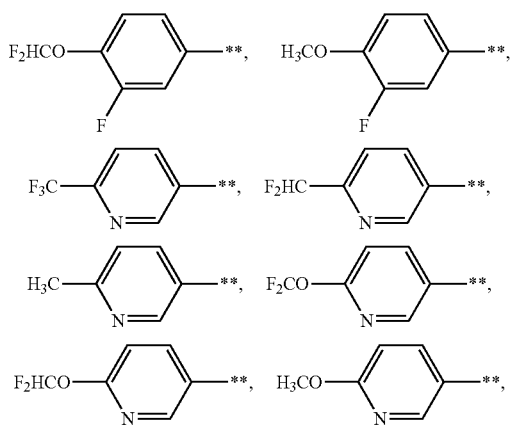

wherein "**" indicates the point of attachment to the nitrogen atom to which $R^1$ is attached;
$R^2$ represents a group

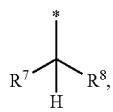

wherein "*" indicates the point of attachment to the nitrogen atom to which $R^2$ is attached;
$R^3$ represents a —$NH_2$ group;
$R^4$ represents a group selected from

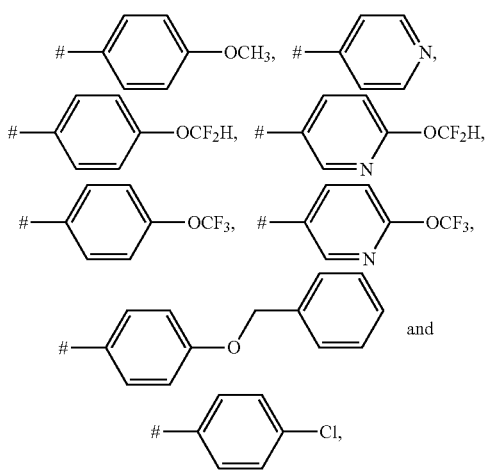

wherein "#" indicates the point of attachment to the carbonyl group to which $R^4$ is attached;
$R^7$ represents a methyl group;
$R^8$ represents a —C(=O)—$NH_2$ group;
and stereoisomers, tautomers, N-oxides, hydrates, solvates, and salts thereof, and mixtures of same.

In accordance with a twenty-fifth embodiment of the first aspect, the present invention covers compounds of general formula (I), supra, in which:

$R^1$ represents a group selected from

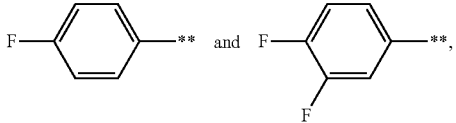

wherein "**" indicates the point of attachment to the nitrogen atom to which $R^1$ is attached;
$R^2$ represents a group

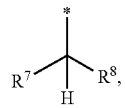

wherein "*" indicates the point of attachment to the nitrogen atom to which $R^2$ is attached;
$R^3$ represents a methyl group;
$R^4$ represents a group selected from

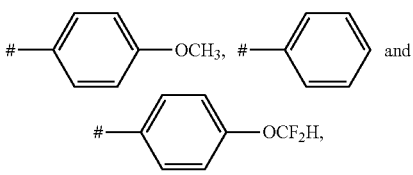

wherein "#" indicates the point of attachment to the carbonyl group to which $R^4$ is attached;
$R^7$ represents a methyl group;
$R^8$ represents a —C(=O)—$NH_2$ group;
and stereoisomers, tautomers, N-oxides, hydrates, solvates, and salts thereof, and mixtures of same.

FURTHER EMBODIMENTS OF THE FIRST ASPECT OF THE PRESENT INVENTION

In a further embodiment of the first aspect, the present invention covers compounds of formula (I), supra, in which:
$R^1$ represents a phenyl or pyridinyl group optionally substituted, one, two, or three times, each substituent independently selected from a halogen atom or a group selected from hydroxy, cyano, nitro, $C_1$-$C_4$-alkyl, (phenyl)-($C_1$-$C_2$-alkyl)-, $C_1$-$C_4$-haloalkyl, $C_1$-$C_4$-alkoxy, (phenyl)-($C_1$-$C_2$alkoxy)-, $C_1$-$C_4$-haloalkoxy, —N($R^5$)($R^6$),
wherein the phenyl groups in said (phenyl)-($C_1$-$C_2$-alkyl)- and (phenyl)-($C_1$-$C_2$-alkoxy)-groups are optionally substituted one or two times, each substituent independently selected from a fluorine atom, a chlorine atom and a bromine atom, or a group selected from methyl, trifluoromethyl and methoxy,
or two substituents attached to adjacent carbon atoms of said phenyl or pyridinyl group together form a bivalent group selected from —$(CH_2)_3$—, —$(CH_2)_4$—, —$(CH_2)_2$—O—, —$(CH_2)_3$—O—, —$CH_2$—O—$CH_2$—, —O—$CH_2$—O—, —O—$CH_2$—$CH_2$—O— and —O—$CF_2$—O—,
or
$R^1$ represents a pyrazolyl group optionally substituted one or two times, each substituent independently selected from a halogen atom or a group selected from cyano, $C_1$-$C_2$-alkyl, and $C_1$-$C_2$alkoxy, In a further embodiment of the first aspect, the present invention covers compounds of formula (I), supra, in which:
$R^1$ represents a phenyl or pyridinyl group optionally substituted, one, two, or three times, each substituent independently selected from a halogen atom or a group selected from hydroxy, cyano, nitro, $C_1$-$C_4$-alkyl, (phenyl)-($C_1$-$C_2$-alkyl)-, $C_1$-$C_4$-haloalkyl, $C_1$-$C_4$-alkoxy, (phenyl)-($C_1$-$C_2$alkoxy)-, $C_1$-$C_4$-haloalkoxy, —N($R^5$)($R^6$),
  wherein the phenyl groups in said (phenyl)-($C_1$-$C_2$-alkyl)- and (phenyl)-($C_1$-$C_2$-alkoxy)-groups are optionally substituted one or two times, each substituent independently selected from a fluorine atom, a chlorine atom and a bromine atom, or a group selected from methyl, trifluoromethyl and methoxy,
  or two substituents attached to adjacent carbon atoms of said phenyl or pyridinyl group together form a bivalent group selected from —(CH$_2$)$_3$—, —(CH$_2$)$_4$—, —(CH$_2$)$_2$—O—, —(CH$_2$)$_3$—O—, —CH$_2$—O—CH$_2$—, —O—CH$_2$—O—, —O—CH$_2$—CH$_2$—O— and —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl or pyridinyl group optionally substituted, one, two, or three times, each substituent independently selected from a halogen atom or a group selected from hydroxy, cyano, nitro, (phenyl)-($C_1$-$C_2$-alkyl)-, $C_1$-$C_4$-haloalkyl, $C_1$-$C_4$-alkoxy, (phenyl)-($C_1$-$C_2$-alkoxy)-, $C_1$-$C_4$-haloalkoxy, —N($R^5$)($R^6$),
  wherein the phenyl groups in said (phenyl)-($C_1$-$C_2$-alkyl)- and (phenyl)-($C_1$-$C_2$-alkoxy)-groups are optionally substituted one or two times, each substituent independently selected from a fluorine atom, a chlorine atom and a bromine atom, or a group selected from methyl, trifluoromethyl and methoxy,
  or two substituents attached to adjacent carbon atoms of said phenyl or pyridinyl group together form a bivalent group selected from —(CH$_2$)$_3$—, —(CH$_2$)$_4$—, —(CH$_2$)$_2$—O—, —(CH$_2$)$_3$—O—, —CH$_2$—O—CH$_2$—, —O—CH$_2$—O—, —O—CH$_2$—CH$_2$—O— and —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl or pyridinyl group optionally substituted, one, two, or three times, each substituent independently selected from a halogen atom or a group selected from cyano, nitro, $C_1$-$C_4$-alkyl, (phenyl)-($C_1$-$C_2$-alkyl)-, $C_1$-$C_4$-haloalkyl, $C_1$-$C_4$-alkoxy, (phenyl)-($C_1$-$C_2$-alkoxy)-, $C_1$-$C_4$-haloalkoxy, —N($R^5$)($R^6$),
  wherein the phenyl groups in said (phenyl)-($C_1$-$C_2$-alkyl)- and (phenyl)-($C_1$-$C_2$-alkoxy)-groups are optionally substituted one or two times, each substituent independently selected from a fluorine atom, a chlorine atom and a bromine atom, or a group selected from methyl, trifluoromethyl and methoxy,
  or two substituents attached to adjacent carbon atoms of said phenyl or pyridinyl group together form a bivalent group selected from —(CH$_2$)$_3$—, —(CH$_2$)$_4$—, —(CH$_2$)$_2$—O—, —(CH$_2$)$_3$—O—, —CH$_2$—O—CH$_2$—, —O—CH$_2$—O—, —O—CH$_2$—CH$_2$—O— and —O—CF$_2$—O—, and stereoisomers, tautomers, N-oxides, hydrates, solvates, and salts thereof, and mixtures of same.

or
$R^1$ represents a pyrazolyl group optionally substituted one or two times, each substituent independently selected from a halogen atom or a group selected from cyano, $C_1$-$C_2$-alkyl, and $C_1$-$C_2$alkoxy, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl or pyridinyl group optionally substituted, one, two, or three times, each substituent independently selected from a halogen atom or a group selected from cyano, nitro, $C_1$-$C_4$-alkyl, (phenyl)-($C_1$-$C_2$-alkyl)-, $C_1$-$C_4$-haloalkyl, $C_1$-$C_4$-alkoxy, (phenyl)-($C_1$-$C_2$-alkoxy)-, $C_1$-$C_4$-haloalkoxy, —N($R^5$)($R^6$),
  wherein the phenyl groups in said (phenyl)-($C_1$-$C_2$-alkyl)- and (phenyl)-($C_1$-$C_2$-alkoxy)-groups are optionally substituted one or two times, each substituent independently selected from a fluorine atom, a chlorine atom and a bromine atom, or a group selected from methyl, trifluoromethyl and methoxy,
  or two substituents attached to adjacent carbon atoms of said phenyl or pyridinyl group together form a bivalent group selected from —(CH$_2$)—, —(CH$_2$)$_4$—, —(CH$_2$)$_2$—O—, —(CH$_2$)—O—, —CH$_2$—O—CH$_2$—, —O—CH$_2$—O—, —O—CH$_2$—CH$_2$—O— and —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl or pyridinyl group optionally substituted, one, two, or three times, each substituent independently selected from a halogen atom or a group selected from cyano, nitro, (phenyl)-($C_1$-$C_2$-alkyl)-, $C_1$-$C_4$-haloalkyl, $C_1$-$C_4$-alkoxy, (phenyl)-($C_1$-$C_2$-alkoxy)-, $C_1$-$C_4$-haloalkoxy, —N($R^5$)($R^6$),
  wherein the phenyl groups in said (phenyl)-($C_1$-$C_2$-alkyl)- and (phenyl)-($C_1$-$C_2$-alkoxy)-groups are optionally substituted one or two times, each substituent independently selected from a fluorine atom, a chlorine atom and a bromine atom, or a group selected from methyl, trifluoromethyl and methoxy,
  or two substituents attached to adjacent carbon atoms of said phenyl or pyridinyl group together form a bivalent group selected from —(CH$_2$)$_3$—, —(CH$_2$)$_4$—, —(CH$_2$)$_2$—O—, —(CH$_2$)$_3$—O—, —CH$_2$—O—CH$_2$—, —O—CH$_2$—O—, —O—CH$_2$—CH$_2$—O— and —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl or pyridinyl group optionally substituted, one, two, or three times, each substituent independently selected from a fluorine atom, a chlorine atom and a bromine atom, or a group selected from hydroxy, cyano, $C_1$-$C_4$-alkyl, $C_1$-$C_2$-fluoroalkyl, $C_1$-$C_2$-alkoxy, (phenyl)-($C_1$-$C_2$-alkoxy)-, $C_1$-$C_2$-fluoroalkoxy and —N($R^5$)($R^6$),
  or two substituents attached to adjacent carbon atoms of said phenyl or pyridinyl group together form a bivalent group selected from —(CH$_2$)$_3$—, —O—CH$_2$—O— and —O—CF$_2$—O—,
  or
$R^1$ represents a pyrazolyl group optionally substituted with one methyl group, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl or pyridinyl group optionally substituted, one, two, or three times, each substituent independently selected from a fluorine atom, a chlorine atom and a bromine atom, or a group selected from hydroxy, cyano, $C_1$-$C_4$-alkyl, $C_1$-$C_2$-fluoroalkyl, $C_1$-$C_2$-alkoxy, (phenyl)-($C_1$-$C_2$-alkoxy)-, $C_1$-$C_2$-fluoroalkoxy and —N($R^5$)($R^6$),
or two substituents attached to adjacent carbon atoms of said phenyl or pyridinyl group together form a bivalent group selected from —(CH$_2$)$_3$—, —O—CH$_2$—O— and —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl or pyridinyl group optionally substituted, one, two, or three times, each substituent independently selected from a fluorine atom, a chlorine atom and a bromine atom, or a group selected from hydroxy, cyano, $C_1$-$C_2$-fluoroalkyl, $C_1$-$C_2$-alkoxy, (phenyl)-($C_1$-$C_2$-alkoxy)-, $C_1$-$C_2$-fluoroalkoxy and —N($R^5$)($R^6$),
or two substituents attached to adjacent carbon atoms of said phenyl or pyridinyl group together form a bivalent group selected from —(CH$_2$)$_3$—, —O—CH$_2$—O— and —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl group optionally substituted, one, two, or three times, each substituent independently selected from a fluorine atom, a chlorine atom and a bromine atom, or a group selected from hydroxy, cyano, $C_1$-$C_4$-alkyl, $C_1$-$C_2$-fluoroalkyl, $C_1$-$C_2$-alkoxy, (phenyl)-($C_1$-$C_2$-alkoxy)-, $C_1$-$C_2$-fluoroalkoxy and —N($R^5$)($R^6$),
or two substituents attached to adjacent carbon atoms of said phenyl group together form a bivalent group selected from —(CH$_2$)$_3$—, —O—CH$_2$—O— and —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl group optionally substituted, one, two, or three times, each substituent independently selected from a fluorine atom, a chlorine atom and a bromine atom, or a group selected from hydroxy, cyano, $C_1$-$C_2$-fluoroalkyl, $C_1$-$C_2$alkoxy, (phenyl)-($C_1$-$C_2$-alkoxy)-, $C_1$-$C_2$-fluoroalkoxy and —N($R^5$)($R^6$),
or two substituents attached to adjacent carbon atoms of said phenyl group together form a bivalent group selected from —(CH$_2$)—, —O—CH$_2$—O— and —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a pyridinyl group optionally substituted, one, two, or three times, each substituent independently selected from a fluorine atom, a chlorine atom and a bromine atom, or a group selected from hydroxy, cyano, $C_1$-$C_4$-alkyl, $C_1$-$C_2$-fluoroalkyl, $C_1$-$C_2$-alkoxy, (phenyl)-($C_1$-$C_2$alkoxy)-, $C_1$-$C_2$-fluoroalkoxy and —N($R^5$)($R^6$),
or two substituents attached to adjacent carbon atoms of said pyridinyl group together form a bivalent group selected from —(CH$_2$)—, —O—CH$_2$—O— and —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl or pyridinyl group optionally substituted, one, two, or three times, each substituent independently selected from a fluorine atom, a chlorine atom and a bromine atom, or a group selected from cyano, $C_1$-$C_4$-alkyl, $C_1$-$C_2$-fluoroalkyl, $C_1$-$C_2$-alkoxy, $C_1$-$C_2$-fluoroalkoxy, —N($R^5$)($R^6$),
or two substituents attached to adjacent carbon atoms of said phenyl or pyridinyl group together form a bivalent group selected from —(CH$_2$)—, —O—CH$_2$—O— and —O—CF$_2$—O—,
or
$R^1$ represents a pyrazolyl group optionally substituted with one methyl group,
and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl or pyridinyl group optionally substituted, one, two, or three times, each substituent independently selected from a fluorine atom, a chlorine atom and a bromine atom, or a group selected from cyano, $C_1$-$C_4$-alkyl, $C_1$-$C_2$-fluoroalkyl, $C_1$-$C_2$-alkoxy, $C_1$-$C_2$-fluoroalkoxy, —N($R^5$)($R^6$),
or two substituents attached to adjacent carbon atoms of said phenyl or pyridinyl group together form a bivalent group selected from —(CH$_2$)$_3$—, —O—CH$_2$—O— and —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl or pyridinyl group optionally substituted, one, two, or three times, each substituent independently selected from a fluorine atom, a chlorine atom and a bromine atom, or a group selected from cyano, $C_1$-$C_2$-fluoroalkyl, $C_1$-$C_2$-alkoxy, $C_1$-$C_2$-fluoroalkoxy, —N($R^5$)($R^6$),
or two substituents attached to adjacent carbon atoms of said phenyl or pyridinyl group together form a bivalent group selected from —(CH$_2$)$_3$—, —O—CH$_2$—O— and —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl group optionally substituted, one, two, or three times, each substituent independently selected from a fluorine atom, a chlorine atom and a bromine atom, or a group selected from cyano, $C_1$-$C_4$-alkyl, $C_1$-$C_2$-fluoroalkyl, $C_1$-$C_2$-alkoxy, $C_1$-$C_2$-fluoroalkoxy, —N($R^5$)($R^6$),
or two substituents attached to adjacent carbon atoms of said phenyl or pyridinyl group together form a bivalent group selected from —(CH$_2$)$_3$—, —O—CH$_2$—O— and —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:

$R^1$ represents a phenyl group optionally substituted, one, two, or three times, each substituent independently selected from a fluorine atom, a chlorine atom and a bromine atom, or a group selected from cyano, $C_1$-$C_2$-fluoroalkyl, $C_1$-$C_2$-alkoxy, $C_1$-$C_2$-fluoroalkoxy, —N($R^5$)($R^6$), or two substituents attached to adjacent carbon atoms of said phenyl group together form a bivalent group selected from —(CH$_2$)$_3$—, —O—CH$_2$—O— and —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a pyridinyl group optionally substituted, one, two, or three times, each substituent independently selected from a fluorine atom, a chlorine atom and a bromine atom, or a group selected from cyano, $C_1$-$C_4$-alkyl, $C_1$-$C_2$-fluoroalkyl, $C_1$-$C_2$alkoxy, $C_1$-$C_2$-fluoroalkoxy, —N($R^5$)($R^6$), or two substituents attached to adjacent carbon atoms of said phenyl or pyridinyl group together form a bivalent group selected from —(CH$_2$)$_3$—, —O—CH$_2$—O— and —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl or pyridinyl group optionally substituted, one or two times, each substituent independently selected from a fluorine atom and a chlorine atom, or a group selected from $C_1$-$C_2$-alkyl, $C_1$-$C_2$-fluoroalkyl, $C_1$-$C_2$-alkoxy, $C_1$-$C_2$-fluoroalkoxy, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl or pyridinyl group optionally substituted, one or two times, each substituent independently selected from a fluorine atom and a chlorine atom, or a group selected from $C_1$-$C_2$-fluoroalkyl, $C_1$-$C_2$alkoxy, $C_1$-$C_2$-fluoroalkoxy, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl group optionally substituted, one or two times, each substituent independently selected from a fluorine atom and a chlorine atom, or a group selected from cyano, $C_1$-$C_2$-alkyl, $C_1$-$C_2$-fluoroalkyl, $C_1$-$C_2$alkoxy, $C_1$-$C_2$-fluoroalkoxy, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl group optionally substituted, one or two times, each substituent independently selected from a fluorine atom and a chlorine atom, or a group selected from $C_1$-$C_2$-alkyl, $C_1$-$C_2$-fluoroalkyl, $C_1$-$C_2$alkoxy, $C_1$-$C_2$-fluoroalkoxy, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl group optionally substituted, one or two times, each substituent independently selected from a fluorine atom and a chlorine atom, or a group selected from cyano, $C_1$-$C_2$-fluoroalkyl, $C_1$-$C_2$alkoxy, $C_1$-$C_2$-fluoroalkoxy, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl group optionally substituted, one or two times, each substituent independently selected from a fluorine atom and a chlorine atom, or a group selected from $C_1$-$C_2$-fluoroalkyl, $C_1$-$C_2$-alkoxy, $C_1$-$C_2$-fluoroalkoxy, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a pyridinyl group optionally substituted, one or two times, each substituent independently selected from a fluorine atom and a chlorine atom, or a group selected from $C_1$-$C_2$-alkyl, $C_1$-$C_2$-fluoroalkyl, $C_1$-$C_2$-alkoxy, $C_1$-$C_2$-fluoroalkoxy, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl or pyridinyl group optionally substituted, one or two times, each substituent independently selected from a fluorine atom, a chlorine atom and a bromine atom, or a group selected from cyano, methyl, difluoromethyl, trifluoromethyl, methoxy, benzyloxy, difluoromethoxy and trifluoromethoxy, or two substituents attached to adjacent carbon atoms of said phenyl or pyridinyl group together form a bivalent group —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl or pyridinyl group optionally substituted, one or two times, each substituent independently selected from a fluorine atom, a chlorine atom and a bromine atom, or a group selected from cyano, difluoromethyl, trifluoromethyl, methoxy, benzyloxy, difluoromethoxy and trifluoromethoxy, or two substituents attached to adjacent carbon atoms of said phenyl or pyridinyl group together form a bivalent group —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl group optionally substituted, one or two times, each substituent independently selected from a fluorine atom, a chlorine atom and a bromine atom, or a group selected from cyano, methyl, difluoromethyl, trifluoromethyl, methoxy, benzyloxy, difluoromethoxy and trifluoromethoxy, or two substituents attached to adjacent carbon atoms of said phenyl group together form a bivalent group —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a phenyl group optionally substituted, one or two times, each substituent independently selected from a fluorine atom, a chlorine atom and a bromine atom, or a group selected from cyano, difluoromethyl, trifluoromethyl, methoxy, benzyloxy, difluoromethoxy and trifluoromethoxy,
or two substituents attached to adjacent carbon atoms of said phenyl group together form a bivalent group —O—CF$_2$—O—,
and stereoisomers, tautomers, N-oxides, hydrates, solvates, and salts thereof, and mixtures of same.

In a further embodiment of the first aspect, the present invention covers compounds of formula (I), supra, in which:
R$^1$ represents a pyridinyl group optionally substituted, one or two times, each substituent independently selected from a fluorine atom, a chlorine atom and a bromine atom, or a group selected from cyano, methyl, difluoromethyl, trifluoromethyl, methoxy, benzyloxy, difluoromethoxy and trifluoromethoxy,
or two substituents attached to adjacent carbon atoms of said pyridinyl group together form a bivalent group —O—CF$_2$—O—,
and stereoisomers, tautomers, N-oxides, hydrates, solvates, and salts thereof, and mixtures of same.

In a further embodiment of the first aspect, the present invention covers compounds of formula (I), supra, in which:
R$^1$ represents a phenyl or pyridinyl group optionally substituted, one or two times, each substituent independently selected from a fluorine atom, a chlorine atom and a bromine atom, or a group selected from methyl, difluoromethyl, trifluoromethyl, methoxy, benzyloxy, difluoromethoxy and trifluoromethoxy,
or two substituents attached to adjacent carbon atoms of said phenyl or pyridinyl group together form a bivalent group —O—CF$_2$—O—,
and stereoisomers, tautomers, N-oxides, hydrates, solvates, and salts thereof, and mixtures of same.

In a further embodiment of the first aspect, the present invention covers compounds of formula (I), supra, in which:
R$^1$ represents a phenyl or pyridinyl group optionally substituted, one or two times, each substituent independently selected from a fluorine atom, a chlorine atom and a bromine atom, or a group selected from difluoromethyl, trifluoromethyl, methoxy, benzyloxy, difluoromethoxy and trifluoromethoxy,
or two substituents attached to adjacent carbon atoms of said phenyl or pyridinyl group together form a bivalent group —O—CF$_2$—O—,
and stereoisomers, tautomers, N-oxides, hydrates, solvates, and salts thereof, and mixtures of same.

In a further embodiment of the first aspect, the present invention covers compounds of formula (I), supra, in which:
R$^1$ represents a phenyl group optionally substituted, one or two times, each substituent independently selected from a fluorine atom, a chlorine atom and a bromine atom, or a group selected from methyl, difluoromethyl, trifluoromethyl, methoxy, benzyloxy, difluoromethoxy and trifluoromethoxy,
or two substituents attached to adjacent carbon atoms of said phenyl group together form a bivalent group —O—CF$_2$—O—,
and stereoisomers, tautomers, N-oxides, hydrates, solvates, and salts thereof, and mixtures of same.

In a further embodiment of the first aspect, the present invention covers compounds of formula (I), supra, in which:
R$^1$ represents a phenyl group optionally substituted, one or two times, each substituent independently selected from a fluorine atom, a chlorine atom and a bromine atom, or a group selected from difluoromethyl, trifluoromethyl, methoxy, benzyloxy, difluoromethoxy and trifluoromethoxy,
or two substituents attached to adjacent carbon atoms of said phenyl group together form a bivalent group —O—CF$_2$—O—,
and stereoisomers, tautomers, N-oxides, hydrates, solvates, and salts thereof, and mixtures of same.

In a further embodiment of the first aspect, the present invention covers compounds of formula (I), supra, in which:
R$^1$ represents a pyridinyl group optionally substituted, one or two times, each substituent independently selected from a fluorine atom, a chlorine atom and a bromine atom, or a group selected from methyl, difluoromethyl, trifluoromethyl, methoxy, benzyloxy, difluoromethoxy and trifluoromethoxy,
or two substituents attached to adjacent carbon atoms of said pyridinyl group together form a bivalent group —O—CF$_2$—O—,
and stereoisomers, tautomers, N-oxides, hydrates, solvates, and salts thereof, and mixtures of same.

In a further embodiment of the first aspect, the present invention covers compounds of formula (I), supra, in which:
R$^1$ represents a group

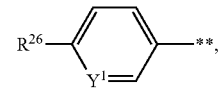

wherein "**" indicates the point of attachment to the nitrogen atom to which R$^1$ is attached,
and stereoisomers, tautomers, N-oxides, hydrates, solvates, and salts thereof, and mixtures of same.

In a further embodiment of the first aspect, the present invention covers compounds of formula (I), supra, in which:
R$^1$ represents a group

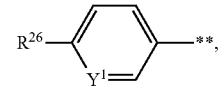

wherein "**" indicates the point of attachment to the nitrogen atom to which R$^1$ is attached;
Y$^1$ represents —C(H)═, —C(F)═, —C(Cl)═, —C(CN)═ or —N═;
R$^{26}$ represents a fluorine atom, a chlorine atom or a bromine atom, or a group selected from methyl, difluoromethyl, trifluoromethyl, methoxy, benzyloxy, difluoromethoxy and trifluoromethoxy,
and stereoisomers, tautomers, N-oxides, hydrates, solvates, and salts thereof, and mixtures of same.

In a further embodiment of the first aspect, the present invention covers compounds of formula (I), supra, in which:
R$^1$ represents a group

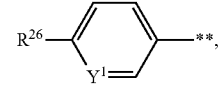

wherein "**" indicates the point of attachment to the nitrogen atom to which R$^1$ is attached;

Y¹ represents —C(H)=, —C(F)=, —C(Cl)=, —C(CN)= or —N=;

R²⁶ represents a fluorine atom, a chlorine atom or a bromine atom, or a group selected from difluoromethyl, trifluoromethyl, methoxy, benzyloxy, difluoromethoxy and trifluoromethoxy, and stereoisomers, tautomers, N-oxides, hydrates, solvates, and salts thereof, and mixtures of same.

In a further embodiment of the first aspect, the present invention covers compounds of formula (I), supra, in which:
R¹ represents a group

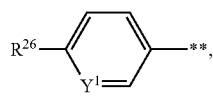

wherein "**" indicates the point of attachment to the nitrogen atom to which R¹ is attached;
Y¹ represents —C(H)=, —C(F)= or —N=;
R²⁶ represents a fluorine atom, a chlorine atom, or a group selected from $C_1$-$C_2$-alkyl, $C_1$-$C_2$-fluoroalkyl, $C_1$-$C_2$alkoxy and $C_1$-$C_2$-fluoroalkoxy, and stereoisomers, tautomers, N-oxides, hydrates, solvates, and salts thereof, and mixtures of same.

In a further embodiment of the first aspect, the present invention covers compounds of formula (I), supra, in which:
R¹ represents a group

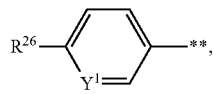

wherein "**" indicates the point of attachment to the nitrogen atom to which R¹ is attached;
Y¹ represents —C(H)=, —C(F)= or —N=;
R²⁶ represents a fluorine atom, a chlorine atom, or a group selected from $C_1$-$C_2$-fluoroalkyl, $C_1$-$C_2$alkoxy and $C_1$-$C_2$-fluoroalkoxy, and stereoisomers, tautomers, N-oxides, hydrates, solvates, and salts thereof, and mixtures of same.

In a further embodiment of the first aspect, the present invention covers compounds of formula (I), supra, in which:
R¹ represents a group

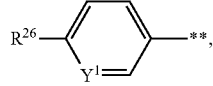

wherein "**" indicates the point of attachment to the nitrogen atom to which R¹ is attached;
Y¹ represents —C(H)=, —C(F)=, —C(Cl)= or —N=;
R²⁶ represents a fluorine atom, a chlorine atom or a bromine atom, or a group selected from difluoromethyl, methoxy, benzyloxy, difluoromethoxy and trifluoromethoxy, and stereoisomers, tautomers, N-oxides, hydrates, solvates, and salts thereof, and mixtures of same.

In a further embodiment of the first aspect, the present invention covers compounds of formula (I), supra, in which:

R¹ represents a group

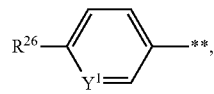

wherein "**" indicates the point of attachment to the nitrogen atom to which R¹ is attached,
Y¹ represents —C(H)= or —C(F)=, and
R²⁶ represents a fluorine atom, a chlorine atom, or a group selected from difluoromethyl, trifluoromethyl, methoxy, difluoromethoxy and trifluoromethoxy, and stereoisomers, tautomers, N-oxides, hydrates, solvates, and salts thereof, and mixtures of same.

In a further embodiment of the first aspect, the present invention covers compounds of formula (I), supra, in which:
R¹ represents a group

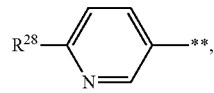

wherein "**" indicates the point of attachment to the nitrogen atom to which R¹ is attached, and
R²⁸ represents a group selected from methyl, difluoromethyl, trifluoromethyl, methoxy, difluoromethoxy and trifluoromethoxy, and stereoisomers, tautomers, N-oxides, hydrates, solvates, and salts thereof, and mixtures of same.

In a further embodiment of the first aspect, the present invention covers compounds of formula (I), supra, in which:
R¹ represents a group selected from

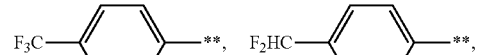
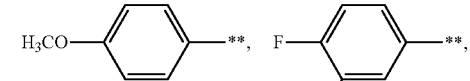
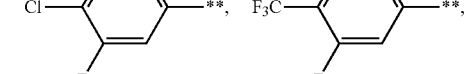
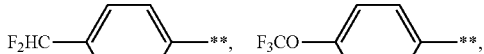

-continued

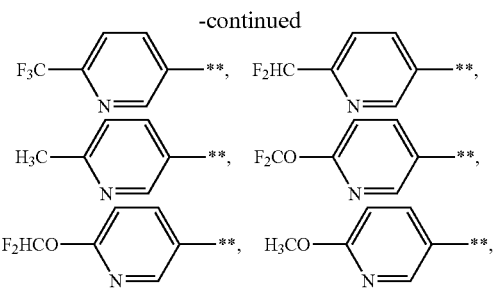

wherein "**" indicates the point of attachment to the nitrogen atom to which R¹ is attached,
and stereoisomers, tautomers, N-oxides, hydrates, solvates, and salts thereof, and mixtures of same.

In a further embodiment of the first aspect, the present invention covers compounds of formula (I), supra, in which:
R¹ represents a group selected from

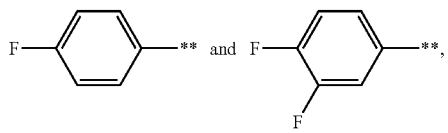

wherein "**" indicates the point of attachment to the nitrogen atom to which R¹ is attached,
and stereoisomers, tautomers, N-oxides, hydrates, solvates, and salts thereof, and mixtures of same.

In a further embodiment of the first aspect, the present invention covers compounds of formula (I), supra, in which:
R² represents a group

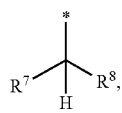

wherein "*" indicates the point of attachment to the nitrogen atom to which R² is attached;
R⁷ represents a hydrogen atom or a $C_1$-$C_2$-alkyl group;
R⁸ represents a —C(=O)—NH₂ group,
and stereoisomers, tautomers, N-oxides, hydrates, solvates, and salts thereof, and mixtures of same.

In a further embodiment of the first aspect, the present invention covers compounds of formula (I), supra, in which:
R² represents a group

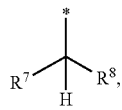

wherein "*" indicates the point of attachment to the nitrogen atom to which R² is attached;
R⁷ represents a $C_1$-$C_2$-alkyl group;
R⁸ represents a —C(=O)—NH₂ group,
and stereoisomers, tautomers, N-oxides, hydrates, solvates, and salts thereof, and mixtures of same.

In a further embodiment of the first aspect, the present invention covers compounds of formula (I), supra, in which:
R² represents a group

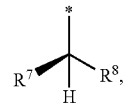

wherein "*" indicates the point of attachment to the nitrogen atom to which R² is attached;
R⁷ represents a $C_1$-$C_2$-alkyl group;
R⁸ represents a —C(=O)—NH₂ group,
and stereoisomers, tautomers, N-oxides, hydrates, solvates, and salts thereof, and mixtures of same.

In a further embodiment of the first aspect, the present invention covers isomeric mixtures of compounds of formula (I), supra, in which:
R² represents a group

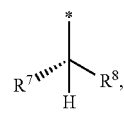

wherein "*" indicates the point of attachment to the nitrogen atom to which R² is attached;
R⁷ represents a $C_1$-$C_2$-alkyl group;
R⁸ represents a —C(=O)—NH₂ group,
and stereoisomers, tautomers, N-oxides, hydrates, solvates, and salts thereof, and mixtures of same.

In a further embodiment of the first aspect, the present invention covers isomeric mixtures of compounds of formula (I), supra, in which:
R² represents a group

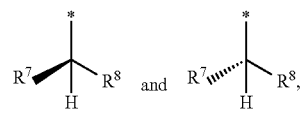

in a ratio of about 99:1 and higher, in favour of

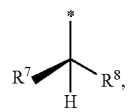

wherein "*" indicates the point of attachment to the nitrogen atom to which R² is attached;
R⁷ represents a $C_1$-$C_2$-alkyl group;
R⁸ represents a —C(=O)—NH₂ group, and tautomers, N-oxides, hydrates, solvates, and salts thereof, and mixtures of same.

In a further embodiment of the first aspect, the present invention covers isomeric mixtures of compounds of formula (I), supra, in which:
R² represents a group

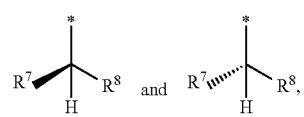

in a ratio of about 98:2 and higher, in favour of

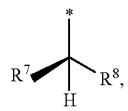

wherein "*" indicates the point of attachment to the nitrogen atom to which $R^2$ is attached;
$R^7$ represents a $C_1$-$C_2$-alkyl group;
$R^8$ represents a —C(=O)—NH$_2$ group,
and tautomers, N-oxides, hydrates, solvates, and salts thereof, and mixtures of same.

In a further embodiment of the first aspect, the present invention covers isomeric mixtures of compounds of formula (I), supra, in which:
$R^2$ represents a group

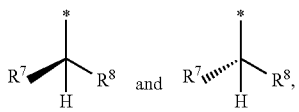

in a ratio of about 95:5 and higher, in favour of

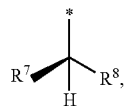

wherein "*" indicates the point of attachment to the nitrogen atom to which $R^2$ is attached;
$R^7$ represents a $C_1$-$C_2$-alkyl group;
$R^8$ represents a —C(=O)—NH$_2$ group, and tautomers, N-oxides, hydrates, solvates, and salts thereof, and mixtures of same.

In a further embodiment of the first aspect, the present invention covers isomeric mixtures of compounds of formula (I), supra, in which:
$R^2$ represents a group

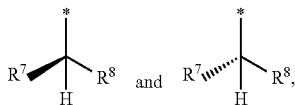

in a ratio of about 90:10 and higher, in favour of

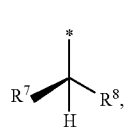

wherein "*" indicates the point of attachment to the nitrogen atom to which $R^2$ is attached;
$R^7$ represents a $C_1$-$C_2$-alkyl group;
$R^8$ represents a —C(=O)—NH$_2$ group,
and tautomers, N-oxides, hydrates, solvates, and salts thereof, and mixtures of same.

In a further embodiment of the first aspect, the present invention covers isomeric mixtures of compounds of formula (I), supra, in which:
$R^2$ represents a group

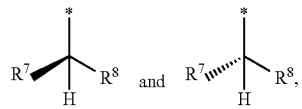

in a ratio of about 80:20 and higher, in favour of

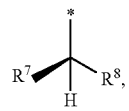

wherein "*" indicates the point of attachment to the nitrogen atom to which $R^2$ is attached;
$R^7$ represents a $C_1$-$C_2$-alkyl group;
$R^8$ represents a —C(=O)—NH$_2$ group,
and tautomers, N-oxides, hydrates, solvates, and salts thereof, and mixtures of same.

In a further embodiment of the first aspect, the present invention covers isomeric mixtures of compounds of formula (I), supra, in which:
$R^2$ represents a group

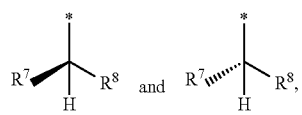

in a ratio of about 50:50, that is, racemic mixtures in case of compounds featuring no further element of chirality,
wherein "*" indicates the point of attachment to the nitrogen atom to which $R^2$ is attached;
$R^7$ represents a $C_1$-$C_2$-alkyl group;
$R^8$ represents a —C(=O)—NH$_2$ group,
and tautomers, N-oxides, hydrates, solvates, and salts thereof, and mixtures of same.

In a further embodiment of the first aspect, the present invention covers compounds of formula (I), supra, in which:
$R^2$ represents a group

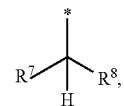

wherein "*" indicates the point of attachment to the nitrogen atom to which $R^2$ is attached;
$R^7$ represents a methyl group;
$R^8$ represents a —C(=O)—NH$_2$ group,
and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group

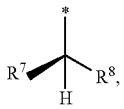

wherein "*" indicates the point of attachment to the nitrogen atom to which $R^2$ is attached;
$R^7$ represents a methyl group;
$R^8$ represents a —C(=O)—NH$_2$ group,
and stereoisomers, tautomers, N-oxides, hydrates, solvates, and salts thereof, and mixtures of same.

In a further embodiment of the first aspect, the present invention covers compounds of formula (I), supra, in which:
$R^2$ represents a group

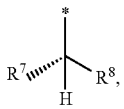

wherein "*" indicates the point of attachment to the nitrogen atom to which $R^2$ is attached;
$R^7$ represents a methyl group;
$R^8$ represents a —C(=O)—NH$_2$ group,
and stereoisomers, tautomers, N-oxides, hydrates, solvates, and salts thereof, and mixtures of same.

In a further embodiment of the first aspect, the present invention covers isomeric mixtures of compounds of formula (I), supra, in which:
$R^2$ represents a group

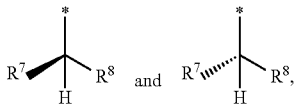

in a ratio of about 99:1 and higher, in favour of

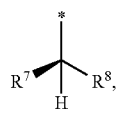

wherein "*" indicates the point of attachment to the nitrogen atom to which $R^2$ is attached;
$R^7$ represents a methyl group;
$R^8$ represents a —C(=O)—NH$_2$ group,
and tautomers, N-oxides, hydrates, solvates, and salts thereof, and mixtures of same.

In a further embodiment of the first aspect, the present invention covers isomeric mixtures of compounds of formula (I), supra, in which:
$R^2$ represents a group

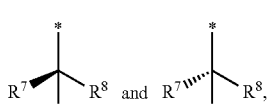

in a ratio of about 98:2 and higher, in favour of

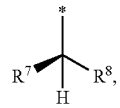

wherein "*" indicates the point of attachment to the nitrogen atom to which $R^2$ is attached;
$R^7$ represents a methyl group;
$R^8$ represents a —C(=O)—NH$_2$ group,
and tautomers, N-oxides, hydrates, solvates, and salts thereof, and mixtures of same.

In a further embodiment of the first aspect, the present invention covers isomeric mixtures of compounds of formula (I), supra, in which:
$R^2$ represents a group

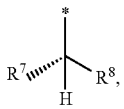

in a ratio of about 95:5 and higher, in favour of

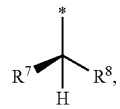

wherein "*" indicates the point of attachment to the nitrogen atom to which $R^2$ is attached;
$R^7$ represents a methyl group;
$R^8$ represents a —C(=O)—NH$_2$ group,
and tautomers, N-oxides, hydrates, solvates, and salts thereof, and mixtures of same.

In a further embodiment of the first aspect, the present invention covers isomeric mixtures of compounds of formula (I), supra, in which:
$R^2$ represents a group

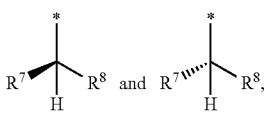

in a ratio of about 90:10 and higher, in favour of

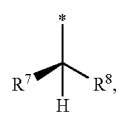

wherein "*" indicates the point of attachment to the nitrogen atom to which $R^2$ is attached;
$R^7$ represents a methyl group;
$R^8$ represents a —C(=O)—NH$_2$ group,
and tautomers, N-oxides, hydrates, solvates, and salts thereof, and mixtures of same.

In a further embodiment of the first aspect, the present invention covers isomeric mixtures of compounds of formula (I), supra, in which:

$R^2$ represents a group

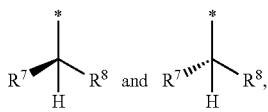

in a ratio of about 80:20 and higher, in favour of

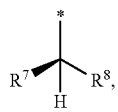

wherein "*" indicates the point of attachment to the nitrogen atom to which $R^2$ is attached;
$R^7$ represents a methyl group;
$R^8$ represents a —C(=O)—NH$_2$ group,
and tautomers, N-oxides, hydrates, solvates, and salts thereof, and mixtures of same.

In a further embodiment of the first aspect, the present invention covers isomeric mixtures of compounds of formula (I), supra, in which:
$R^2$ represents a group

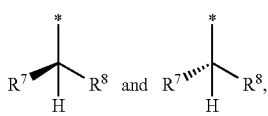

in a ratio of about 50:50, that is, racemic mixtures in case of compounds featuring no further element of chirality,
wherein "*" indicates the point of attachment to the nitrogen atom to which $R^2$ is attached;
$R^7$ represents a methyl group;
$R^8$ represents a —C(=O)—NH$_2$ group,
and tautomers, N-oxides, hydrates, solvates, and salts thereof, and mixtures of same.

In a further embodiment of the first aspect, the present invention covers compounds of formula (I), supra, in which:
$R^3$ represents a group selected from methyl and —NH$_2$,
and stereoisomers, tautomers, N-oxides, hydrates, solvates, and salts thereof, and mixtures of same.

In a further embodiment of the first aspect, the present invention covers compounds of formula (I), supra, in which:
$R^3$ represents a —NH$_2$ group,
and stereoisomers, tautomers, N-oxides, hydrates, solvates, and salts thereof, and mixtures of same.

In a further embodiment of the first aspect, the present invention covers compounds of formula (I), supra, in which:
$R^3$ represents a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^4$ represents a phenyl or pyridinyl group optionally substituted, one, two, or three times, each substituent independently selected from a halogen atom or a group selected from cyano, nitro, $C_1$-$C_4$-alkyl, (phenyl)-($C_1$-$C_2$-alkyl)-, (5-membered heteroaryl)-($C_1$-$C_2$-alkyl)-, ($C_3$-$C_7$-cycloalkyl)-($C_1$-$C_2$-alkyl)-, (($R^9$)O)—($C_1$-$C_4$-alkyl)-, $C_1$-$C_4$-haloalkyl, $C_3$-$C_7$-cycloalkyl, —OR$^9$, —N($R^{10}$)($R^{11}$), (($R^{10}$)($R^{11}$)N)—($C_1$-$C_2$-alkyl)-, —C(=O)—N($R^{12}$)($R^{13}$), S(=O)$_n$—R$^{14}$, —C(=O)R$^{14}$, —C(=O)—OR$^{17}$, and a 5-membered heteroaryl group which itself is optionally substituted with one or two methyl groups,
or two substituents attached to adjacent carbon atoms of said phenyl or pyridinyl group together form a bivalent group selected from —(CH$_2$)—, —(CH$_2$)$_4$—, —(CH$_2$)$_2$—O—, —(CH$_2$)—O—, —CH$_2$—O—CH$_2$—, —O—CH$_2$—O—, —O—CH$_2$—CH$_2$—O— and —O—CF$_2$—O—,
and stereoisomers, tautomers, N-oxides, hydrates, solvates, and salts thereof, and mixtures of same.

In a further embodiment of the first aspect, the present invention covers compounds of formula (I), supra, in which:
$R^4$ represents a phenyl or pyridinyl group optionally substituted, one, two, or three times, each substituent independently selected from a halogen atom or a group selected from cyano, nitro, $C_1$-$C_4$-alkyl, (phenyl)-($C_1$-$C_2$-alkyl)-, (5-membered heteroaryl)-($C_1$-$C_2$-alkyl)-, $C_1$-$C_4$-hydroxyalkyl, $C_1$-$C_4$-haloalkyl, —OR$^9$, —N($R^{10}$)($R^{11}$), —C(=O)—N($R^{12}$)($R^{13}$), S(=O)$_n$—R$^{14}$, and a 5-membered heteroaryl group which itself is optionally substituted with one or two methyl groups,
or two substituents attached to adjacent carbon atoms of said phenyl or pyridinyl group together form a bivalent group selected from —(CH$_2$)$_3$—, —(CH$_2$)$_4$—, —(CH$_2$)$_2$—O—, —(CH$_2$)$_3$—O—, —CH$_2$—O—CH$_2$—, —O—CH$_2$—O—, —O—CH$_2$—CH$_2$—O— and —O—CF$_2$—O—,
and stereoisomers, tautomers, N-oxides, hydrates, solvates, and salts thereof, and mixtures of same.

In a further embodiment of the first aspect, the present invention covers compounds of formula (I), supra, in which:
$R^4$ represents a phenyl or pyridinyl group optionally substituted, one, two, or three times, each substituent independently selected from a halogen atom or a group selected from cyano, $C_1$-$C_3$-alkyl, (($R^9$)O)—($C_1$-$C_3$-alkyl)-, $C_1$-$C_3$-fluoroalkyl, —OR$^9$, —N($R^{10}$)($R^{11}$), —C(=O)—N($R^{12}$)($R^{13}$), S(=O)$_n$—R$^{14}$ and —C(=O)—OR$^{17}$,
or two substituents attached to adjacent carbon atoms of said phenyl or pyridinyl group together form a bivalent group selected from —(CH$_2$)$_3$—, —O—CH$_2$—O— and —O—CF$_2$—O—,
and stereoisomers, tautomers, N-oxides, hydrates, solvates, and salts thereof, and mixtures of same.

In a further embodiment of the first aspect, the present invention covers compounds of formula (I), supra, in which:
$R^4$ represents a phenyl group optionally substituted, one, two, or three times, each substituent independently selected from a halogen atom or a group selected from cyano, $C_1$-$C_3$-alkyl, (($R^9$)O)—($C_1$-$C_3$-alkyl)-, $C_1$-$C_3$-fluoroalkyl, —OR$^9$, —N($R^{10}$)($R^{11}$), —C(=O)—N($R^{12}$)($R^{13}$), S(=O), —R$^{14}$ and —C(=O)—OR$^{17}$,
or two substituents attached to adjacent carbon atoms of said phenyl or pyridinyl group together form a bivalent group selected from —(CH$_2$)$_3$—, —O—CH$_2$—O— and —O—CF$_2$—O—,
and stereoisomers, tautomers, N-oxides, hydrates, solvates, and salts thereof, and mixtures of same.

In a further embodiment of the first aspect, the present invention covers compounds of formula (I), supra, in which:
$R^4$ represents a pyridinyl group optionally substituted, one, two, or three times, each substituent independently selected from a halogen atom or a group selected from cyano, $C_1$-$C_3$-alkyl, (($R^9$)O)—($C_1$-$C_3$-alkyl)-, $C_1$-$C_3$-fluoroalkyl, —OR$^9$, —N($R^{10}$)($R^{11}$), —C(=O)—N($R^{12}$)($R^{13}$), S(=O)$_n$—R$^{14}$ and —C(=O)—OR$^{17}$, or two substituents attached to adjacent carbon atoms of said phenyl or pyridinyl group together form a bivalent group selected from —(CH$_2$)—, —O—CH$_2$—O— and —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
R$^4$ represents a phenyl group optionally substituted, one, two, or three times, each substituent independently selected from a fluorine atom, a chlorine atom and a bromine atom, or a group selected from cyano, C$_1$-C$_3$-alkyl, C$_1$-C$_3$-hydroxyalkyl C$_1$-C$_3$-fluoroalkyl, —ORO, —N(R$^{10}$)(R$^{11}$), —C(=O)—N(R$^{12}$)(R$^{13}$) and S(=O)$_n$—R$^{14}$,
or two substituents attached to adjacent carbon atoms of said phenyl group together form a bivalent group selected from —(CH$_2$)—, —O—CH$_2$—O— and —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
R$^4$ represents a pyridinyl group optionally substituted, one, two, or three times, each substituent independently selected from a fluorine atom, a chlorine atom and a bromine atom, or a group selected from cyano, C$_1$-C$_3$-alkyl, C$_1$-C$_3$-hydroxyalkyl, C$_1$-C$_3$-fluoroalkyl, —ORO, —N(R$^{10}$)(R$^{11}$), —C(=O)—N(R$^{12}$)(R$^{13}$) and S(=O), —R$^{14}$,
or two substituents attached to adjacent carbon atoms of said pyridinyl group together form a bivalent group selected from —(CH$_2$)$_3$—, —O—CH$_2$—O— and —O—CF$_2$—O—, and stereoisomers, tautomers, N-oxides, hydrates, solvates, and salts thereof, and mixtures of same.

In a further embodiment of the first aspect, the present invention covers compounds of formula (I), supra, in which:
R$^4$ represents a phenyl or pyridinyl group optionally substituted, one or two times, each substituent independently selected from a fluorine atom and a chlorine atom, or a group selected from C$_1$-C$_2$-alkyl, C$_1$-C$_2$-fluoroalkyl, —OR$^9$;
R$^9$ represents a group selected from C$_1$-C$_2$-alkyl, benzyl, C$_1$-C$_2$-fluoroalkyl, (C$_1$-C$_2$-alkoxy)-C$_2$-alkyl- and phenyl, wherein the phenyl group within said benzyl group and said phenyl group itself are optionally substituted one or two times, each substituent independently selected from a fluorine atom, a chlorine atom and a methyl group, and stereoisomers, tautomers, N-oxides, hydrates, solvates, and salts thereof, and mixtures of same.

In a further embodiment of the first aspect, the present invention covers compounds of formula (I), supra, in which:
R$^4$ represents a phenyl or pyridinyl group optionally substituted, one or two times, each substituent independently selected from a halogen atom or a group selected from C$_1$-C$_2$-alkyl, C$_1$-C$_2$-fluoroalkyl, —OR$^9$, —N(R$^{10}$)(R$^{11}$), —C(=O)—N(R$^{12}$)(R$^{13}$) and —C(=O)—OR$^{17}$;

and stereoisomers, tautomers, N-oxides, hydrates, solvates, and salts thereof, and mixtures of same.

In a further embodiment of the first aspect, the present invention covers compounds of formula (I), supra, in which:
R$^4$ represents a phenyl group optionally substituted, one or two times, each substituent independently selected from a halogen atom or a group selected from C$_1$-C$_2$-alkyl, C$_1$-C$_2$-fluoroalkyl, —OR$^9$, —N(R$^{10}$)(R$^{11}$), —C(=O)—N(R$^{12}$)(R$^{13}$) and —C(=O)—OR$^{17}$;

and stereoisomers, tautomers, N-oxides, hydrates, solvates, and salts thereof, and mixtures of same.

In a further embodiment of the first aspect, the present invention covers compounds of formula (I), supra, in which:
R$^4$ represents a pyridinyl group optionally substituted, one or two times, each substituent independently selected from a halogen atom or a group selected from C$_1$-C$_2$-alkyl, C$_1$-C$_2$-fluoroalkyl, —OR$^9$, —N(R$^{10}$)(R$^{11}$), —C(=O)—N(R$^{12}$)(R$^{13}$) and —C(=O)—OR$^{17}$;

and stereoisomers, tautomers, N-oxides, hydrates, solvates, and salts thereof, and mixtures of same.

In a further embodiment of the first aspect, the present invention covers compounds of formula (I), supra, in which:
R$^4$ represents a phenyl or pyridinyl group optionally substituted, one or two times, each substituent independently selected from a fluorine atom and a chlorine atom, or a group selected from C$_1$-C$_2$-alkyl, C$_1$-C$_2$-fluoroalkyl, —OR$^9$, and stereoisomers, tautomers, N-oxides, hydrates, solvates, and salts thereof, and mixtures of same.

In a further embodiment of the first aspect, the present invention covers compounds of formula (I), supra, in which:
R$^4$ represents a phenyl group optionally substituted, one or two times, each substituent independently selected from a fluorine atom and a chlorine atom, or a group selected from C$_1$-C$_2$-alkyl, C$_1$-C$_2$-fluoroalkyl, —OR$^9$;
R$^9$ represents a group selected from C$_1$-C$_2$-alkyl, benzyl, C$_1$-C$_2$-fluoroalkyl, (C$_1$-C$_2$-alkoxy)-C$_2$-alkyl- and phenyl, wherein the phenyl group within said benzyl group and said phenyl group itself are optionally substituted one or two times, each substituent independently selected from a fluorine atom, a chlorine atom and a methyl group, and stereoisomers, tautomers, N-oxides, hydrates, solvates, and salts thereof, and mixtures of same.

In a further embodiment of the first aspect, the present invention covers compounds of formula (I), supra, in which:
R$^4$ represents a phenyl group optionally substituted, one or two times, each substituent independently selected from a fluorine atom and a chlorine atom, or a group selected from C$_1$-C$_2$-alkyl, C$_1$-C$_2$-fluoroalkyl, —OR$^9$, and stereoisomers, tautomers, N-oxides, hydrates, solvates, and salts thereof, and mixtures of same.

In a further embodiment of the first aspect, the present invention covers compounds of formula (I), supra, in which:
R$^4$ represents a pyridinyl group optionally substituted, one or two times, each substituent independently selected from a fluorine atom and a chlorine atom, or a group selected from C$_1$-C$_2$-alkyl, C$_1$-C$_2$-fluoroalkyl, —OR$^9$;
R$^9$ represents a group selected from C$_1$-C$_2$-alkyl, benzyl, C$_1$-C$_2$-fluoroalkyl, (C$_1$-C$_2$-alkoxy)-C$_2$-alkyl- and phenyl, wherein the phenyl group within said benzyl group and said phenyl group itself are optionally substituted one or two times, each substituent independently selected from a fluorine atom, a chlorine atom and a methyl group, and stereoisomers, tautomers, N-oxides, hydrates, solvates, and salts thereof, and mixtures of same.

In a further embodiment of the first aspect, the present invention covers compounds of formula (I), supra, in which:
R$^4$ represents a pyridinyl group optionally substituted, one or two times, each substituent independently selected from a fluorine atom and a chlorine atom, or a group selected from C$_1$-C$_2$-alkyl, C$_1$-C$_2$-fluoroalkyl, —OR$^9$, and stereoisomers, tautomers, N-oxides, hydrates, solvates, and salts thereof, and mixtures of same.

In a further embodiment of the first aspect, the present invention covers compounds of formula (I), supra, in which:
$R^4$ represents a group

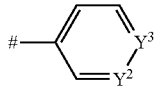

wherein "#" indicates the point of attachment to the carbonyl group to which $R^4$ is attached;
$Y^2$ represents —C(H)= or —N=;
$Y^3$ represents —C($R^{27}$)= or —N=,
with the proviso that if $Y^2$ represents —N=, $Y^3$ represents —C($R^{27}$)=, and if $Y^3$ represents —N=, $Y^2$ represents —C(H)=;
$R^{27}$ represents a halogen atom or a group selected from $C_1$-$C_2$-alkyl, $C_1$-$C_2$-fluoroalkyl, —$OR^9$, —N($R^{10}$)($R^{11}$), —C(=O)—N($R^{12}$)($R^{13}$) and —C(=O)—$OR^{17}$,
and stereoisomers, tautomers, N-oxides, hydrates, solvates, and salts thereof, and mixtures of same.

In a further embodiment of the first aspect, the present invention covers compounds of formula (I), supra, in which:
$R^4$ represents a group

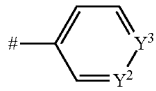

wherein "#" indicates the point of attachment to the carbonyl group to which $R^4$ is attached;
$Y^2$ represents —C(H)= or —N=;
$Y^3$ represents —C($R^{27}$)= or —N=,
with the proviso that if $Y^2$ represents —N=, $Y^3$ represents —C($R^{27}$)=, and if $Y^3$ represents —N=, $Y^2$ represents —C(H)=;
$R^{27}$ represents a fluorine atom, a chlorine atom, or a group selected from $C_1$-$C_2$-alkoxy, benzyloxy and $C_1$-$C_2$-fluoroalkoxy,
and stereoisomers, tautomers, N-oxides, hydrates, solvates, and salts thereof, and mixtures of same.

In a further embodiment of the first aspect, the present invention covers compounds of formula (I), supra, in which:
$R^4$ represents a group

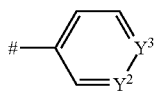

wherein "#" indicates the point of attachment to the carbonyl group to which $R^4$ is attached;
$Y^2$ represents —C(H)= and —N=;
$Y^3$ represents —C($R^{27}$)= and —N=,
with the proviso that if $Y^2$ represents —N=, $Y^3$ represents —C($R^{27}$)=, and if $Y^3$ represents —N=, $Y^2$ represents —C(H)=;
$R^{27}$ represents a fluorine atom, a chlorine atom, or a group selected from $C_1$-$C_2$-alkoxy, benzyloxy and $C_1$-$C_2$-fluoroalkoxy,
and stereoisomers, tautomers, N-oxides, hydrates, solvates, and salts thereof, and mixtures of same.

In a further embodiment of the first aspect, the present invention covers compounds of formula (I), supra, in which:
$R^4$ represents a group

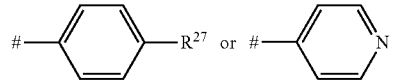

wherein "#" indicates the point of attachment to the carbonyl group to which $R^4$ is attached;
$R^{27}$ represents a fluorine atom, a chlorine atom, or a group selected from $C_1$-$C_2$-alkoxy, benzyloxy and $C_1$-$C_2$-fluoroalkoxy,
and stereoisomers, tautomers, N-oxides, hydrates, solvates, and salts thereof, and mixtures of same.

In a further embodiment of the first aspect, the present invention covers compounds of formula (I), supra, in which:
$R^4$ represents a group

wherein "#" indicates the point of attachment to the carbonyl group to which $R^4$ is attached;
$R^{27}$ represents a fluorine atom, a chlorine atom, or a group selected from $C_1$-$C_2$-alkoxy, benzyloxy and $C_1$-$C_2$-fluoroalkoxy,
and stereoisomers, tautomers, N-oxides, hydrates, solvates, and salts thereof, and mixtures of same.

In a further embodiment of the first aspect, the present invention covers compounds of formula (I), supra, in which:
$R^4$ represents a group selected from:

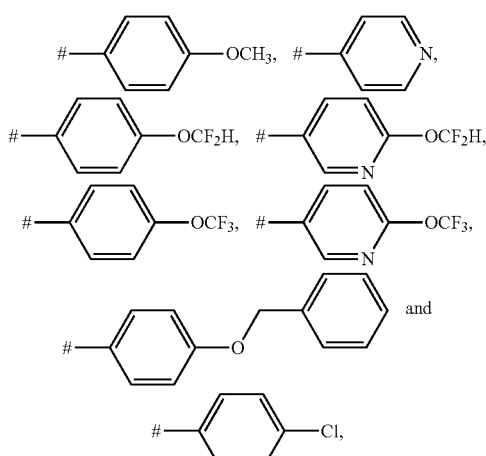

wherein "#" indicates the point of attachment to the carbonyl group to which $R^4$ is attached,
and stereoisomers, tautomers, N-oxides, hydrates, solvates, and salts thereof, and mixtures of same.

In a further embodiment of the first aspect, the present invention covers compounds of formula (I), supra, in which:

$R^4$ represents a group selected from:

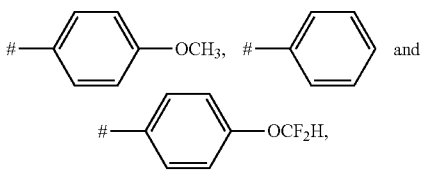

wherein "#" indicates the point of attachment to the carbonyl group to which $R^4$ is attached,
and stereoisomers, tautomers, N-oxides, hydrates, solvates, and salts thereof, and mixtures of same.

In a further embodiment of the first aspect, the present invention covers compounds of formula (I), supra, in which:
$R^5$ and $R^6$ represent, independently from each occurrence, a hydrogen atom or a group selected from $C_1$-$C_2$-alkyl and ($C_1$-$C_2$-alkyl)-C(=O)—,
or
$R^5$ and $R^6$, together with the nitrogen atom to which they are attached, represent a monocyclic nitrogen containing 4- to 7-membered heterocycloalkyl group which is optionally substituted one or two times, each substituent independently selected from a fluorine atom, a chlorine atom and a bromine atom, or a group selected from oxo, hydroxy, $C_1$-$C_2$-alkyl and ($C_1$-$C_2$-alkyl)-C(=O)—,
and stereoisomers, tautomers, N-oxides, hydrates, solvates, and salts thereof, and mixtures of same.

In a further embodiment of the first aspect, the present invention covers compounds of formula (I), supra, in which:
$R^5$ and $R^6$ represent, independently from each occurrence, a hydrogen atom or a group selected from $C_1$-$C_2$-alkyl and ($C_1$-$C_2$-alkyl)-C(=O)—,
and stereoisomers, tautomers, N-oxides, hydrates, solvates, and salts thereof, and mixtures of same.

In a further embodiment of the first aspect, the present invention covers compounds of formula (I), supra, in which:
$R^5$ and $R^6$, together with the nitrogen atom to which they are attached, represent a monocyclic nitrogen containing 4- to 7-membered heterocycloalkyl group which is optionally substituted one or two times, each substituent independently selected from a fluorine atom, a chlorine atom and a bromine atom, or a group selected from oxo, hydroxy, $C_1$-$C_2$-alkyl and ($C_1$-$C_2$-alkyl)-C(=O)—,
and stereoisomers, tautomers, N-oxides, hydrates, solvates, and salts thereof, and mixtures of same.

In a further embodiment of the first aspect, the present invention covers compounds of formula (I), supra, in which:
$R^5$ and $R^6$ represent, independently from each occurrence, a hydrogen atom or a $C_1$-$C_2$-alkyl group,
or
$R^5$ and $R^6$, together with the nitrogen atom to which they are attached, represent a monocyclic nitrogen containing 4- to 7-membered heterocycloalkyl group which is optionally substituted one or two times, each substituent independently selected from a fluorine atom or a group selected from hydroxy and $C_1$-$C_2$-alkyl,
and stereoisomers, tautomers, N-oxides, hydrates, solvates, and salts thereof, and mixtures of same.

In a further embodiment of the first aspect, the present invention covers compounds of formula (I), supra, in which:
$R^5$ and $R^6$ represent, independently from each occurrence, a hydrogen atom or a $C_1$-$C_2$-alkyl group,
and stereoisomers, tautomers, N-oxides, hydrates, solvates, and salts thereof, and mixtures of same.

In a further embodiment of the first aspect, the present invention covers compounds of formula (I), supra, in which:
$R^5$ and $R^6$, together with the nitrogen atom to which they are attached, represent a monocyclic nitrogen containing 4- to 7-membered heterocycloalkyl group which is optionally substituted one or two times, each substituent independently selected from a fluorine atom or a group selected from hydroxy and $C_1$-$C_2$-alkyl,
and stereoisomers, tautomers, N-oxides, hydrates, solvates, and salts thereof, and mixtures of same.

In a further embodiment of the first aspect, the present invention covers compounds of formula (I), supra, in which:
$R^7$ represents a hydrogen atom,
and stereoisomers, tautomers, N-oxides, hydrates, solvates, and salts thereof, and mixtures of same.

In a further embodiment of the first aspect, the present invention covers compounds of formula (I), supra, in which:
$R^7$ represents a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^7$ represents an ethyl group,
and stereoisomers, tautomers, N-oxides, hydrates, solvates, and salts thereof, and mixtures of same.

In a further embodiment of the first aspect, the present invention covers compounds of formula (I), supra, in which:
$R^7$ represents a hydrogen atom or a $C_1$-$C_2$-alkyl group;
and stereoisomers, tautomers, N-oxides, hydrates, solvates, and salts thereof, and mixtures of same.

In a further embodiment of the first aspect, the present invention covers compounds of formula (I), supra, in which:
$R^9$ represents a hydrogen atom or a group selected from $C_1$-$C_4$-alkyl, (phenyl)-($C_1$-$C_2$-alkyl)-, $C_1$-$C_4$-haloalkyl, $C_2$-$C_3$-hydroxyalkyl, ($C_1$-$C_2$alkoxy)-$C_2$-alkyl-, (($C_1$-$C_2$-alkyl)-C(=O)—O)—$C_2$-alkyl-, —C($R^{18}$)($R^{19}$)—C(=O)—OR$^{17}$, —C($R^{18}$)($R^{11}$)—C(=O)—N($R^{20}$)($R^{21}$), —C(=O)—N($R^{20}$)($R^{21}$) and phenyl,
wherein the phenyl group within said (phenyl)-($C_1$-$C_2$-alkyl)- group and said phenyl group itself are optionally substituted one or two times, each substituent independently selected from a fluorine atom, a chlorine atom and a bromine atom, or a group selected from cyano, methyl, trifluoromethyl and methoxy,
and stereoisomers, tautomers, N-oxides, hydrates, solvates, and salts thereof, and mixtures of same.

In a further embodiment of the first aspect, the present invention covers compounds of formula (I), supra, in which:
$R^9$ represents a hydrogen atom or a group selected from $C_1$-$C_4$-alkyl, (phenyl)-($C_1$-$C_2$-alkyl)-, $C_1$-$C_4$-haloalkyl, $C_2$-$C_3$-hydroxyalkyl, ($C_1$-$C_2$alkoxy)-$C_2$-alkyl-, (($C_1$-$C_2$-alkyl)-C(=O)—O)—$C_2$-alkyl-, —C($R^{18}$)($R^{19}$)—C(=O)—OR$^{17}$, —C($R^{18}$)($R^{19}$)—C(=O)—N($R^{20}$)($R^{21}$) and phenyl,
wherein the phenyl group within said (phenyl)-($C_1$-$C_2$-alkyl)- group and said phenyl group itself are optionally substituted one or two times, each substituent independently selected from a fluorine atom, a chlorine atom and a bromine atom, or a group selected from methyl, trifluoromethyl and methoxy,
and stereoisomers, tautomers, N-oxides, hydrates, solvates, and salts thereof, and mixtures of same.

In a further embodiment of the first aspect, the present invention covers compounds of formula (I), supra, in which:
$R^9$ represents a hydrogen atom or a group selected from $C_1$-$C_2$-alkyl, benzyl, $C_1$-$C_2$-fluoroalkyl, $C_2$-hydroxyalkyl, ($C_1$-$C_2$alkoxy)-$C_2$-alkyl-, (($C_1$-$C_2$-alkyl)-C(=O)—O)—

$C_2$-alkyl-, —C($R^{18}$)($R^{19}$)—C(=O)—$OR^{17}$, —C($R^{18}$)($R^{19}$)—C(=O)—N($R^{20}$)($R^{21}$), —C(=O)—N($R^{20}$)($R^{21}$) and phenyl, wherein the phenyl group within said benzyl group and said phenyl group itself are optionally substituted one or two times, each substituent independently selected from a fluorine atom and a chlorine atom, or a group selected from cyano and methyl, and stereoisomers, tautomers, N-oxides, hydrates, solvates, and salts thereof, and mixtures of same.

In a further embodiment of the first aspect, the present invention covers compounds of formula (I), supra, in which:
$R^9$ represents a hydrogen atom or a group selected from $C_1$-$C_2$-alkyl, benzyl, $C_1$-$C_2$-fluoroalkyl, ($C_1$-$C_2$-alkoxy)-$C_2$-alkyl-, (($C_1$-$C_2$-alkyl)-C(=O)—O)—$C_2$-alkyl-, —C($R^{18}$)($R^{19}$)—C(=O)—$OR^{17}$, —C($R^{18}$)($R^{19}$)—C(=O)—N($R^{20}$)($R^{21}$) and phenyl, wherein the phenyl group within said benzyl group and said phenyl group itself are optionally substituted one or two times, each substituent independently selected from a fluorine atom, a chlorine atom and a methyl group, and stereoisomers, tautomers, N-oxides, hydrates, solvates, and salts thereof, and mixtures of same.

In a further embodiment of the first aspect, the present invention covers compounds of formula (I), supra, in which:
$R^9$ represents a group selected from $C_1$-$C_2$-alkyl, benzyl, $C_1$-$C_2$-fluoroalkyl, ($C_1$-$C_2$-alkoxy)-$C_2$-alkyl- and phenyl, wherein the phenyl group within said benzyl group and said phenyl group itself are optionally substituted one or two times, each substituent independently selected from a fluorine atom, a chlorine atom and a methyl group;

and stereoisomers, tautomers, N-oxides, hydrates, solvates, and salts thereof, and mixtures of same.

In a further embodiment of the first aspect, the present invention covers compounds of formula (I), supra, in which:
$R^9$ represents a hydrogen atom or a group selected from $C_1$-$C_2$-alkyl, benzyl, $C_1$-$C_2$-fluoroalkyl, ($C_1$-$C_2$-alkoxy)-$C_2$-alkyl-, (($C_1$-$C_2$-alkyl)-C(=O)—O)—$C_2$-alkyl-, —C($R^{18}$)($R^{19}$)—C(=O)—N($R^{20}$)($R^{21}$), —C(=O)—N($R^{20}$)($R^{21}$) and phenyl, wherein the phenyl group within said benzyl group and said phenyl group itself are optionally substituted one or two times, each substituent independently selected from a fluorine atom and a chlorine atom, or a group selected from cyano and methyl, and stereoisomers, tautomers, N-oxides, hydrates, solvates, and salts thereof, and mixtures of same.

In a further embodiment of the first aspect, the present invention covers compounds of formula (I), supra, in which:
$R^9$ represents a hydrogen atom or a group selected from $C_1$-$C_2$-alkyl, benzyl, $C_1$-$C_2$-fluoroalkyl and phenyl, wherein the phenyl group within said benzyl group and said phenyl group itself are optionally substituted one or two times, each substituent independently selected from a fluorine atom and a chlorine atom, or a group selected from cyano and methyl, and stereoisomers, tautomers, N-oxides, hydrates, solvates, and salts thereof, and mixtures of same.

In a further embodiment of the first aspect, the present invention covers compounds of formula (I), supra, in which:
$R^{10}$ and $R^{11}$ represent, independently from each occurrence, a hydrogen atom or a group selected from $C_1$-$C_2$-alkyl, $C_1$-$C_2$haloalkyl, $C_2$-$C_3$-hydroxyalkyl, ($C_1$-$C_2$-alkoxy)-$C_2$-alkyl-, (($R^{22}$)($R^{23}$)N)-$C_2$-alkyl, ($C_3$-$C_7$-cycloalkyl)-($C_1$-$C_2$-alkyl)-, ($C_1$-$C_2$-alkyl)-C(=O)—, $C_3$-$C_7$-cycloalkyl, ($C_3$-$C_7$-cycloalkyl)-C(=O)—, (phenyl)-($C_1$-$C_2$-alkyl)-, (phenyl)-($C_1$-$C_2$-alkyl)-C(=O)— and (phenyl)-($C_1$-$C_2$-alkyl)-O—C(=O)—, wherein $C_3$-$C_7$-cycloalkyl, and the $C_3$-$C_7$-cycloalkyl within said ($C_3$-$C_7$-cycloalkyl)-($C_1$-$C_2$-alkyl)- and ($C_3$-$C_7$-cycloalkyl)-C(=O)— groups are optionally substituted one or two times, each substituent independently selected from a fluorine atom or a group selected from cyano, $C_1$-$C_2$-alkyl and $C_1$-$C_2$-haloalkyl, and wherein the phenyl groups within said (phenyl)-($C_1$-$C_2$-alkyl)-, (phenyl)-($C_1$-$C_2$-alkyl)-C(=O)— and (phenyl)-($C_1$-$C_2$-alkyl)-O—C(=O)— groups are optionally substituted one or two times, each substituent independently selected from a fluorine atom, a chlorine atom and a bromine atom, or a group selected from methyl, trifluoromethyl and methoxy, or $R^{10}$ and $R^{11}$, together with the nitrogen atom to which they are attached, represent a monocyclic nitrogen containing 4- to 7-membered heterocycloalkyl group, or a bicyclic nitrogen containing 5- to 10-membered heterocycloalkyl group, which are optionally substituted one, two or three times, each substituent independently selected from a halogen atom or a group selected from cyano, oxo, hydroxy, $C_1$-$C_2$-alkyl, $C_1$-$C_2$-haloalkyl, ($C_1$-$C_2$-alkyl)-C(=O)—, $C_1$-$C_2$-alkoxy, —N($R^{22}$)($R^{23}$), and a monocyclic 4- to 7-membered heterocycloalkyl group, and stereoisomers, tautomers, N-oxides, hydrates, solvates, and salts thereof, and mixtures of same.

In a further embodiment of the first aspect, the present invention covers compounds of formula (I), supra, in which:
$R^{10}$ and $R^{11}$ represent, independently from each occurrence, a hydrogen atom or a group selected from $C_1$-$C_2$-alkyl, $C_1$-$C_2$haloalkyl, $C_2$-$C_3$-hydroxyalkyl, ($C_1$-$C_2$-alkoxy)-Cr alkyl-, (($R^{22}$)($R^{23}$)N)-$C_2$-alkyl, ($C_3$-$C_7$-cycloalkyl)-($C_1$-$C_2$-alkyl)-, ($C_1$-$C_2$-alkyl)-C(=O)—, $C_3$-$C_7$-cycloalkyl, ($C_3$-$C_7$-cycloalkyl)-C(=O)—, (phenyl)-($C_1$-$C_2$-alkyl)-, (phenyl)-($C_1$-$C_2$-alkyl)-C(=O)— and (phenyl)-($C_1$-$C_2$-alkyl)-O—C(=O)—, wherein $C_3$-$C_7$-cycloalkyl, and the $C_3$-$C_7$-cycloalkyl within said ($C_3$-$C_7$-cycloalkyl)-($C_1$-$C_2$-alkyl)- and ($C_3$-$C_7$-cycloalkyl)-C(=O)— groups are optionally substituted one or two times, each substituent independently selected from a fluorine atom or a group selected from cyano, $C_1$-$C_2$-alkyl and $C_1$-$C_2$-haloalkyl, and wherein the phenyl groups within said (phenyl)-($C_1$-$C_2$-alkyl)-, (phenyl)-($C_1$-$C_2$-alkyl)-C(=O)— and (phenyl)-($C_1$-$C_2$-alkyl)-O—C(=O)— groups are optionally substituted one or two times, each substituent independently selected from a fluorine atom, a chlorine atom and a bromine atom, or a group selected from methyl, trifluoromethyl and methoxy, and stereoisomers, tautomers, N-oxides, hydrates, solvates, and salts thereof, and mixtures of same.

In a further embodiment of the first aspect, the present invention covers compounds of formula (I), supra, in which:
$R^{10}$ and $R^{11}$, together with the nitrogen atom to which they are attached, represent a monocyclic nitrogen containing 4- to 7-membered heterocycloalkyl group, or a bicyclic nitrogen containing 5- to 10-membered heterocycloalkyl group, which are optionally substituted one, two or three times, each substituent independently selected from a halogen atom or a group selected from cyano, oxo, hydroxy, $C_1$-$C_2$-alkyl, $C_1$-$C_2$haloalkyl, ($C_1$-$C_2$-alkyl)-C(=O)—, $C_1$-$C_2$alkoxy, —N($R^{22}$)($R^{23}$), and a monocyclic 4- to 7-membered heterocycloalkyl group, and stereoisomers, tautomers, N-oxides, hydrates, solvates, and salts thereof, and mixtures of same.

In a further embodiment of the first aspect, the present invention covers compounds of formula (I), supra, in which:
$R^{10}$ and $R^{11}$ represent, independently from each occurrence, a hydrogen atom or a group selected from $C_1$-$C_2$-alkyl, $C_1$-$C_2$haloalkyl, $C_2$-$C_3$-hydroxyalkyl, ($C_1$-$C_2$alkoxy)-$C_2$-alkyl-, (($R^{22}$)($R^{23}$)N)-$C_2$-alkyl, ($C_1$-$C_2$-alkyl)-C(=O)—, $C_3$-$C_5$-cycloalkyl, ($C_3$-$C_5$-cycloalkyl)-C(=O)—, (phenyl)-($C_1$-$C_2$-alkyl)-, (phenyl)-($C_1$-$C_2$-alkyl)-C(=O)— and (phenyl)-($C_1$-$C_2$-alkyl)-O—C(=O)—,
wherein the phenyl groups within said (phenyl)-($C_1$-$C_2$-alkyl)-, (phenyl)-($C_1$-$C_2$-alkyl)-C(=O)— and (phenyl)-($C_1$-$C_2$-alkyl)-O—C(=O)— groups are optionally substituted one or two times, each substituent independently selected from a fluorine atom, a chlorine atom and a bromine atom, or a group selected from methyl, trifluoromethyl and methoxy,
or
$R^{10}$ and $R^{11}$, together with the nitrogen atom to which they are attached, represent a monocyclic nitrogen containing 4- to 7-membered heterocycloalkyl group, or a bicyclic nitrogen containing 6- to 10-membered heterocycloalkyl group, which are optionally substituted one, two or three times, each substituent independently selected from a halogen atom or a group selected from cyano, oxo, hydroxy, $C_1$-$C_2$-alkyl, $C_1$-$C_2$haloalkyl, ($C_1$-$C_2$-alkyl)-C(=O)—, $C_1$-$C_2$-alkoxy, —N($R^{22}$)($R^{23}$), and a monocyclic 4- to 7-membered heterocycloalkyl group, and stereoisomers, tautomers, N-oxides, hydrates, solvates, and salts thereof, and mixtures of same.

In a further embodiment of the first aspect, the present invention covers compounds of formula (I), supra, in which:
$R^{10}$ and $R^{11}$ represent, independently from each occurrence, a hydrogen atom or a group selected from $C_1$-$C_2$-alkyl, $C_1$-$C_2$-haloalkyl, $C_2$-$C_3$-hydroxyalkyl, ($C_1$-$C_2$-alkoxy)-$C_2$-alkyl-, (($R^{22}$)($R^{23}$)N)-$C_2$-alkyl, ($C_1$-$C_2$-alkyl)-C(=O)—, $C_3$-$C_5$-cycloalkyl, ($C_3$-$C_5$-cycloalkyl)-C(=O)—, (phenyl)-($C_1$-$C_2$-alkyl)-, (phenyl)-($C_1$-$C_2$-alkyl)-C(=O)— and (phenyl)-($C_1$-$C_2$-alkyl)-O—C(=O)—,
wherein the phenyl groups within said (phenyl)-($C_1$-$C_2$-alkyl)-, (phenyl)-($C_1$-$C_2$-alkyl)-C(=O)— and (phenyl)-($C_1$-$C_2$-alkyl)-O—C(=O)— groups are optionally substituted one or two times, each substituent independently selected from a fluorine atom, a chlorine atom and a bromine atom, or a group selected from methyl, trifluoromethyl and methoxy,
and stereoisomers, tautomers, N-oxides, hydrates, solvates, and salts thereof, and mixtures of same.

In a further embodiment of the first aspect, the present invention covers compounds of formula (I), supra, in which:
$R^{10}$ and $R^{11}$, together with the nitrogen atom to which they are attached, represent a monocyclic nitrogen containing 4- to 7-membered heterocycloalkyl group, or a bicyclic nitrogen containing 6- to 10-membered heterocycloalkyl group, which are optionally substituted one, two or three times, each substituent independently selected from a halogen atom or a group selected from cyano, oxo, hydroxy, $C_1$-$C_2$-alkyl, $C_1$-$C_2$haloalkyl, ($C_1$-$C_2$-alkyl)-C(=O)—, $C_1$-$C_2$alkoxy, —N($R^{22}$)($R^{23}$), and a monocyclic 4- to 7-membered heterocycloalkyl group,
and stereoisomers, tautomers, N-oxides, hydrates, solvates, and salts thereof, and mixtures of same.

In a further embodiment of the first aspect, the present invention covers compounds of formula (I), supra, in which:

$R^{10}$ and $R^{11}$ represent, independently from each occurrence, a hydrogen atom or a group selected from $C_1$-$C_2$-alkyl, $C_1$-$C_2$-fluoroalkyl, ($C_3$-$C_5$-cycloalkyl)-($C_1$-$C_2$-alkyl)-($C_1$-$C_2$-alkyl)-C(=O)—, $C_3$-$C_7$-cycloalkyl, $C_3$-$C_7$-cycloalkyl-(C=O)—, (phenyl)-($C_1$-$C_2$-alkyl)-, (phenyl)-($C_1$-$C_2$-alkyl)-C(=O)— and (phenyl)-($C_1$-$C_2$-alkyl)-O—C(=O)—,
wherein $C_3$-$C_7$-cycloalkyl, and the $C_3$-$C_5$-cycloalkyl within said ($C_3$-$C_5$-cycloalkyl)-($C_1$-$C_2$-alkyl)- and the $C_3$-$C_7$-cycloalkyl within the $C_3$-$C_7$-cycloalkyl-(C=O)— groups are optionally substituted one or two times, each substituent independently selected from a fluorine atom or a group selected from cyano, $C_1$-$C_2$-alkyl and $C_1$-$C_2$-fluoroalkyl,
and wherein the phenyl groups within said (phenyl)-($C_1$-$C_2$-alkyl)-, (phenyl)-($C_1$-$C_2$-alkyl)-C(=O)— and (phenyl)-($C_1$-$C_2$-alkyl)-O—C(=O)— groups are optionally substituted one or two times, each substituent independently selected from a fluorine atom, a chlorine atom and a methyl group,
or
$R^{10}$ and $R^{11}$, together with the nitrogen atom to which they are attached, represent a monocyclic nitrogen containing 4- to 7-membered heterocycloalkyl group which is optionally substituted one or two times, each substituent independently selected from a fluorine atom or a group selected from cyano, oxo, $C_1$-$C_2$-alkyl, $C_1$-$C_2$-fluoroalkyl and ($C_1$-$C_2$-alkyl)-C(=O)—,
and stereoisomers, tautomers, N-oxides, hydrates, solvates, and salts thereof, and mixtures of same.

In a further embodiment of the first aspect, the present invention covers compounds of formula (I), supra, in which:
$R^{10}$ and $R^{11}$ represent, independently from each occurrence, a hydrogen atom or a group selected from $C_1$-$C_2$-alkyl, $C_1$-$C_2$-fluoroalkyl, ($C_3$-$C_5$-cycloalkyl)-($C_1$-$C_2$-alkyl)-($C_1$-$C_2$-alkyl)-C(=O)—, $C_3$-$C_7$-cycloalkyl, $C_3$-$C_7$-cycloalkyl-(C=O)—, (phenyl)-($C_1$-$C_2$-alkyl)-, (phenyl)-($C_1$-$C_2$-alkyl)-C(=O)— and (phenyl)-($C_1$-$C_2$-alkyl)-O—C(=O)—,
wherein $C_3$-$C_7$-cycloalkyl, and the $C_3$-$C_5$-cycloalkyl within said ($C_3$-$C_5$-cycloalkyl)-($C_1$-$C_2$-alkyl)- and the $C_3$-$C_7$-cycloalkyl within the $C_3$-$C_7$-cycloalkyl-(C=O)— groups are optionally substituted one or two times, each substituent independently selected from a fluorine atom or a group selected from cyano, $C_1$-$C_2$-alkyl and $C_1$-$C_2$-fluoroalkyl,
and wherein the phenyl groups within said (phenyl)-($C_1$-$C_2$-alkyl)-, (phenyl)-($C_1$-$C_2$-alkyl)-C(=O)— and (phenyl)-($C_1$-$C_2$-alkyl)-O—C(=O)— groups are optionally substituted one or two times, each substituent independently selected from a fluorine atom, a chlorine atom and a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^{10}$ and $R^{11}$, together with the nitrogen atom to which they are attached, represent a monocyclic nitrogen containing 4- to 7-membered heterocycloalkyl group which is optionally substituted one or two times, each substituent independently selected from a fluorine atom or a group selected from cyano, oxo, $C_1$-$C_2$-alkyl, $C_1$-$C_2$-fluoroalkyl and ($C_1$-$C_2$-alkyl)-C(=O)—,
and stereoisomers, tautomers, N-oxides, hydrates, solvates, and salts thereof, and mixtures of same.

In a further embodiment of the first aspect, the present invention covers compounds of formula (I), supra, in which:

$R^{10}$ and $R^{11}$ represent, independently from each occurrence, a hydrogen atom or a group selected from $C_1$-$C_2$-alkyl, $C_1$-$C_2$-fluoroalkyl, ($C_1$-$C_2$-alkyl)-C(=O)—, (phenyl)-($C_1$-$C_2$-alkyl)-, (phenyl)-($C_1$-$C_2$-alkyl)-C(=O)— and (phenyl)-($C_1$-$C_2$-alkyl)-O—C(=O)—,
  wherein the phenyl groups within said (phenyl)-($C_1$-$C_2$-alkyl)-, (phenyl)-($C_1$-$C_2$-alkyl)-C(=O)— and (phenyl)-($C_1$-$C_2$-alkyl)-O—C(=O)— groups are optionally substituted one or two times, each substituent independently selected from a fluorine atom, a chlorine atom and a methyl group,
or
$R^{10}$ and $R^{11}$, together with the nitrogen atom to which they are attached, represent a monocyclic nitrogen containing 4- to 7-membered heterocycloalkyl group which is optionally substituted one or two times, each substituent independently selected from a fluorine atom or a group selected from oxo, $C_1$-$C_2$-alkyl, $C_1$-$C_2$-fluoroalkyl and ($C_1$-$C_2$-alkyl)-C(=O)—,
and stereoisomers, tautomers, N-oxides, hydrates, solvates, and salts thereof, and mixtures of same.

In a further embodiment of the first aspect, the present invention covers compounds of formula (I), supra, in which:
$R^{10}$ and $R^{11}$ represent, independently from each occurrence, a hydrogen atom or a group selected from $C_1$-$C_2$-alkyl, $C_1$-$C_2$-fluoroalkyl, ($C_1$-$C_2$-alkyl)-C(=O)—, (phenyl)-($C_1$-$C_2$-alkyl)-(phenyl)-($C_1$-$C_2$-alkyl)-C(=O)— and (phenyl)-($C_1$-$C_2$-alkyl)-O—C(=O)—,
  wherein the phenyl groups within said (phenyl)-($C_1$-$C_2$-alkyl)-, (phenyl)-($C_1$-$C_2$-alkyl)-C(=O)— and (phenyl)-($C_1$-$C_2$-alkyl)-O—C(=O)— groups are optionally substituted one or two times, each substituent independently selected from a fluorine atom, a chlorine atom and a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^{10}$ and $R^{11}$, together with the nitrogen atom to which they are attached, represent a monocyclic nitrogen containing 4- to 7-membered heterocycloalkyl group which is optionally substituted one or two times, each substituent independently selected from a fluorine atom or a group selected from oxo, $C_1$-$C_2$-alkyl, $C_1$-$C_2$-fluoroalkyl and ($C_1$-$C_2$-alkyl)-C(=O)—,
and stereoisomers, tautomers, N-oxides, hydrates, solvates, and salts thereof, and mixtures of same.

In a further embodiment of the first aspect, the present invention covers compounds of formula (I), supra, in which:
$R^{10}$ and $R^{11}$ represent, independently from each occurrence, a hydrogen atom or a group selected from $C_1$-$C_2$-alkyl, ($C_3$-$C_5$-cycloalkyl)-($C_1$-$C_2$-alkyl)-, $C_3$-$C_7$-cycloalkyl and (phenyl)-($C_1$-$C_2$-alkyl)-O—C(=O)—,
  wherein $C_3$-$C_7$-cycloalkyl, and the $C_3$-$C_5$-cycloalkyl within said ($C_3$-$C_5$-cycloalkyl)-($C_1$-$C_2$-alkyl)- group are optionally substituted one or two times, each substituent independently selected from a fluorine atom or a group selected from cyano, methyl and $C_1$-fluoroalkyl,
  and wherein the phenyl group within said (phenyl)-($C_1$-$C_2$-alkyl)-O—C(=O)— group is optionally substituted one or two times, each substituent independently selected from a fluorine atom, a chlorine atom and a methyl group,
or
$R^{10}$ and $R^{11}$, together with the nitrogen atom to which they are attached, represent a monocyclic nitrogen containing 4- to 7-membered heterocycloalkyl group which is optionally substituted one or two times, each substituent independently selected from a fluorine atom or a group selected from cyano, methyl and $C_1$-fluoroalkyl,
and stereoisomers, tautomers, N-oxides, hydrates, solvates, and salts thereof, and mixtures of same.

In a further embodiment of the first aspect, the present invention covers compounds of formula (I), supra, in which:
$R^{10}$ and $R^{11}$ represent, independently from each occurrence, a hydrogen atom or a group selected from $C_1$-$C_2$-alkyl, ($C_3$-$C_5$-cycloalkyl)-($C_1$-$C_2$-alkyl)-, $C_3$-$C_7$-cycloalkyl and (phenyl)-($C_1$-$C_2$-alkyl)-O—C(=O)—,
  wherein $C_3$-$C_7$-cycloalkyl, and the $C_3$-$C_5$-cycloalkyl within said ($C_3$-$C_5$-cycloalkyl)-($C_1$-$C_2$-alkyl)- group are optionally substituted one or two times, each substituent independently selected from a fluorine atom or a group selected from cyano, methyl and $C_1$-fluoroalkyl,
  and wherein the phenyl group within said (phenyl)-($C_1$-$C_2$-alkyl)-O—C(=O)— group is optionally substituted one or two times, each substituent independently selected from a fluorine atom, a chlorine atom and a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^{10}$ and $R^{11}$, together with the nitrogen atom to which they are attached, represent a monocyclic nitrogen containing 4- to 7-membered heterocycloalkyl group which is optionally substituted one or two times, each substituent independently selected from a fluorine atom or a group selected from cyano, methyl and $C_1$-fluoroalkyl,
and stereoisomers, tautomers, N-oxides, hydrates, solvates, and salts thereof, and mixtures of same.

In a further embodiment of the first aspect, the present invention covers compounds of formula (I), supra, in which:
$R^{10}$ and $R^{11}$ represent, independently from each occurrence, a hydrogen atom or a group selected from $C_1$-$C_2$-alkyl, $C_3$-$C_7$-cycloalkyl and (benzyl)-O—C(=O)—,
  wherein $C_3$-$C_7$-cycloalkyl is optionally substituted one or two times, each substituent independently selected from a fluorine atom or a group selected from methyl and trifluoromethyl,
  and wherein the phenyl group within said (benzyl)-O—C(=O)— group is optionally substituted one or two times, each substituent independently selected from a fluorine atom, a chlorine atom and a methyl group,
or
$R^{10}$ and $R^{11}$, together with the nitrogen atom to which they are attached, represent a monocyclic nitrogen containing 4- to 7-membered heterocycloalkyl group which is optionally substituted one or two times, each substituent independently selected from a fluorine atom or a group selected from cyano, methyl and trifluoromethyl,
and stereoisomers, tautomers, N-oxides, hydrates, solvates, and salts thereof, and mixtures of same.

In a further embodiment of the first aspect, the present invention covers compounds of formula (I), supra, in which:
$R^{10}$ and $R^{11}$ represent, independently from each occurrence, a hydrogen atom or a group selected from $C_1$-$C_2$-alkyl, $C_3$-$C_7$-cycloalkyl and (benzyl)-O—C(=O)—,
  wherein $C_3$-$C_7$-cycloalkyl is optionally substituted one or two times, each substituent independently selected from a fluorine atom or a group selected from methyl and trifluoromethyl, and wherein the phenyl group within said (benzyl)-O—C(=O)— group is optionally substituted one or two times, each substituent independently selected from a fluorine atom, a chlorine atom and a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^{10}$ and $R^{11}$, together with the nitrogen atom to which they are attached, represent a monocyclic nitrogen containing 4- to 7-membered heterocycloalkyl group which is optionally substituted one or two times, each substituent independently selected from a fluorine atom or a group selected from cyano, methyl and trifluoromethyl,
and stereoisomers, tautomers, N-oxides, hydrates, solvates, and salts thereof, and mixtures of same.

In a further embodiment of the first aspect, the present invention covers compounds of formula (I), supra, in which:
$R^{10}$ and $R^{11}$ represent, independently from each occurrence, a hydrogen atom or a group selected from $C_1$-$C_2$-alkyl and (benzyl)-O—C(=O)—,
and wherein the phenyl group within said (benzyl)-O—C(=O)— group is optionally substituted one or two times, each substituent independently selected from a fluorine atom, a chlorine atom and a methyl group,
or
$R^{10}$ and $R^{11}$, together with the nitrogen atom to which they are attached, represent a monocyclic nitrogen containing 4- to 7-membered heterocycloalkyl group which is optionally substituted one or two times, each substituent independently selected from a fluorine atom or a group selected from cyano, methyl and trifluoromethyl,
and stereoisomers, tautomers, N-oxides, hydrates, solvates, and salts thereof, and mixtures of same.

In a further embodiment of the first aspect, the present invention covers compounds of formula (I), supra, in which:
$R^{10}$ and $R^{11}$ represent, independently from each occurrence, a hydrogen atom or a group selected from $C_1$-$C_2$-alkyl and (benzyl)-O—C(=O)—,
and wherein the phenyl group within said (benzyl)-O—C(=O)— group is optionally substituted one or two times, each substituent independently selected from a fluorine atom, a chlorine atom and a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^{12}$ and $R^{13}$ represent, independently from each occurrence, a hydrogen atom or a group selected from $C_1$-$C_4$-alkyl, $C_1$-$C_4$-haloalkyl, $C_1$-$C_4$-hydroxyalkyl, ($C_1$-$C_4$-alkoxy)-$C_2$-$C_3$-alkyl-, ($C_1$-$C_4$-haloalkoxy)-$C_2$-$C_3$-alkyl-, (phenoxy)-$C_2$-$C_3$-alkyl-, $C_3$-$C_7$-cycloalkyl, monocyclic 4- to 7-membered heterocycloalkyl and (phenyl)-($C_1$-$C_3$-alkyl)-,
wherein $C_3$-$C_7$-cycloalkyl and monocyclic 4- to 7-membered heterocycloalkyl are optionally substituted one or two times, each substituent independently selected from a halogen atom or a group selected from oxo, $C_1$-$C_2$-alkyl and ($C_1$-$C_2$-alkyl)-C(=O)—,
and wherein the phenyl groups within said (phenoxy)-$C_2$-$C_3$-alkyl- group and said (phenyl)-($C_1$-$C_3$-alkyl)- group are optionally substituted one or two times, each substituent independently selected from fluorine atom, a chlorine atom and a bromine atom, or a group selected from cyano, methyl, trifluoromethyl and methoxy,
or
$R^{12}$ and $R^{13}$, together with the nitrogen atom to which they are attached, represent a monocyclic nitrogen containing 4- to 7-membered heterocycloalkyl group which is optionally substituted one or two times, each substituent independently selected from a halogen atom or a group selected from oxo, $C_1$-$C_2$-alkyl and ($C_1$-$C_2$-alkyl)-C(=O)—,
and stereoisomers, tautomers, N-oxides, hydrates, solvates, and salts thereof, and mixtures of same.

In a further embodiment of the first aspect, the present invention covers compounds of formula (I), supra, in which:
$R^{12}$ and $R^{13}$ represent, independently from each occurrence, a hydrogen atom or a group selected from $C_1$-$C_4$-alkyl, $C_1$-$C_4$-haloalkyl, $C_1$-$C_4$-hydroxyalkyl, ($C_1$-$C_4$-alkoxy)-$C_2$-$C_3$-alkyl-, ($C_1$-$C_4$-haloalkoxy)-$C_2$-$C_3$-alkyl-, (phenoxy)-$C_2$-$C_3$-alkyl-, $C_3$-$C_7$-cycloalkyl, monocyclic 4- to 7-membered heterocycloalkyl and (phenyl)-($C_1$-$C_3$-alkyl)-,
wherein $C_3$-$C_7$-cycloalkyl and monocyclic 4- to 7-membered heterocycloalkyl are optionally substituted one or two times, each substituent independently selected from a halogen atom or a group selected from oxo, $C_1$-$C_2$-alkyl and ($C_1$-$C_3$-alkyl)-C(=O)—,
and wherein the phenyl groups within said (phenoxy)-$C_2$-$C_3$-alkyl- group and said (phenyl)-($C_1$-$C_3$-alkyl)- group are optionally substituted one or two times, each substituent independently selected from fluorine atom, a chlorine atom and a bromine atom, or a group selected from cyano, methyl, trifluoromethyl and methoxy,
and stereoisomers, tautomers, N-oxides, hydrates, solvates, and salts thereof, and mixtures of same.

In a further embodiment of the first aspect, the present invention covers compounds of formula (I), supra, in which:
$R^{12}$ and $R^{13}$, together with the nitrogen atom to which they are attached, represent a monocyclic nitrogen containing 4- to 7-membered heterocycloalkyl group which is optionally substituted one or two times, each substituent independently selected from a halogen atom or a group selected from oxo, $C_1$-$C_2$-alkyl and ($C_1$-$C_2$-alkyl)-C(=O)—,
and stereoisomers, tautomers, N-oxides, hydrates, solvates, and salts thereof, and mixtures of same.

In a further embodiment of the first aspect, the present invention covers compounds of formula (I), supra, in which:
$R^{12}$ and $R^{13}$ represent, independently from each occurrence, a hydrogen atom or a group selected from $C_1$-$C_4$-alkyl, $C_1$-$C_4$-haloalkyl, $C_1$-$C_4$-hydroxyalkyl, ($C_1$-$C_2$-alkoxy)-$C_2$-$C_3$-alkyl-, $C_3$-$C_7$-cycloalkyl, monocyclic 4- to 7-membered heterocycloalkyl and (phenyl)-($C_1$-$C_2$-alkyl)-,
wherein $C_3$-$C_7$-cycloalkyl and monocyclic 4- to 7-membered heterocycloalkyl are optionally substituted one or two times, each substituent independently selected from a halogen atom or a group selected from oxo, $C_1$-$C_2$-alkyl and ($C_1$-$C_2$-alkyl)-C(=O)—,
or
$R^{12}$ and $R^{13}$, together with the nitrogen atom to which they are attached, represent a monocyclic nitrogen containing 4- to 7-membered heterocycloalkyl group which is optionally substituted one or two times, each substituent independently selected from a halogen atom or a group selected from oxo, $C_1$-$C_2$-alkyl and ($C_1$-$C_2$-alkyl)-C(=O)—,
and stereoisomers, tautomers, N-oxides, hydrates, solvates, and salts thereof, and mixtures of same.

In a further embodiment of the first aspect, the present invention covers compounds of formula (I), supra, in which:

$R^{12}$ and $R^{13}$ represent, independently from each occurrence,
a hydrogen atom or a group selected from $C_1$-$C_4$-alkyl,
$C_1$-$C_4$-haloalkyl, $C_1$-$C_4$-hydroxyalkyl, ($C_1$-$C_2$-alkoxy)-$C_2$-$C_3$-alkyl-, $C_3$-$C_7$-cycloalkyl, monocyclic 4- to 7-membered heterocycloalkyl and (phenyl)-($C_1$-$C_2$-alkyl)-,
wherein $C_3$-$C_7$-cycloalkyl and monocyclic 4- to 7-membered heterocycloalkyl are optionally substituted one or two times, each substituent independently selected from a halogen atom or a group selected from oxo, $C_1$-$C_2$-alkyl and ($C_1$-$C_2$-alkyl)-C(=O)—,
and stereoisomers, tautomers, N-oxides, hydrates, solvates, and salts thereof, and mixtures of same.

In a further embodiment of the first aspect, the present invention covers compounds of formula (I), supra, in which:
$R^{12}$ and $R^{13}$, together with the nitrogen atom to which they are attached, represent a monocyclic nitrogen containing 4- to 7-membered heterocycloalkyl group which is optionally substituted one or two times, each substituent independently selected from a halogen atom or a group selected from oxo, $C_1$-$C_2$-alkyl and ($C_1$-$C_2$-alkyl)-C(=O)—,
and stereoisomers, tautomers, N-oxides, hydrates, solvates, and salts thereof, and mixtures of same.

In a further embodiment of the first aspect, the present invention covers compounds of formula (I), supra, in which:
$R^{12}$ and $R^{13}$ represent, independently from each occurrence,
a hydrogen atom or a group selected from $C_1$-$C_4$-alkyl, $C_1$-$C_4$-fluoroalkyl, $C_1$-$C_4$-hydroxyalkyl, ($C_1$-$C_4$-alkoxy)-$C_2$-$C_3$-alkyl-, ($C_1$-$C_2$-fluoroalkoxy)-$C_2$-$C_3$-alkyl-, (phenoxy)-$C_2$-$C_3$-alkyl-, $C_3$-$C_7$-cycloalkyl, monocyclic 4- to 7-membered heterocycloalkyl and (phenyl)-($C_1$-$C_2$-alkyl)-,
wherein $C_3$-$C_7$-cycloalkyl and monocyclic 4- to 7-membered heterocycloalkyl are optionally substituted one or two times, each substituent independently selected from a fluorine atom or a group selected from oxo, $C_1$-$C_2$-alkyl and ($C_1$-$C_2$-alkyl)-C(=O)—,
and wherein the phenyl groups within said (phenoxy)-$C_2$-$C_3$-alkyl- group and said (phenyl)-($C_1$-$C_2$-alkyl)- group are optionally substituted one or two times, each substituent independently selected from a fluorine atom and a chlorine atom, or a group selected from methyl, trifluoromethyl and methoxy,
or
$R^{12}$ and $R^{13}$, together with the nitrogen atom to which they are attached, represent a monocyclic nitrogen containing 4- to 7-membered heterocycloalkyl group which is optionally substituted one or two times, each substituent independently selected from a halogen atom or a group selected from oxo, $C_1$-$C_2$-alkyl and ($C_1$-$C_2$-alkyl)-C(=O)—,
and stereoisomers, tautomers, N-oxides, hydrates, solvates, and salts thereof, and mixtures of same.

In a further embodiment of the first aspect, the present invention covers compounds of formula (I), supra, in which:
$R^{12}$ and $R^{13}$ represent, independently from each occurrence,
a hydrogen atom or a group selected from $C_1$-$C_4$-alkyl, $C_1$-$C_4$-fluoroalkyl, $C_1$-$C_4$-hydroxyalkyl, ($C_1$-$C_4$-alkoxy)-$C_2$-$C_3$-alkyl-, ($C_1$-$C_2$-fluoroalkoxy)-$C_2$-$C_3$-alkyl-, (phenoxy)-$C_2$-$C_3$-alkyl-, $C_3$-$C_7$-cycloalkyl, monocyclic 4- to 7-membered heterocycloalkyl and (phenyl)-($C_1$-$C_2$-alkyl)-,
wherein $C_3$-$C_7$-cycloalkyl and monocyclic 4- to 7-membered heterocycloalkyl are optionally substituted one or two times, each substituent independently selected from a fluorine atom or a group selected from oxo, $C_1$-$C_2$-alkyl and ($C_1$-$C_2$-alkyl)-C(=O)—,
and wherein the phenyl groups within said (phenoxy)-$C_2$-$C_3$-alkyl- group and said (phenyl)-($C_1$-$C_2$-alkyl)- group are optionally substituted one or two times, each substituent independently selected from a fluorine atom and a chlorine atom, or a group selected from methyl, trifluoromethyl and methoxy,
and stereoisomers, tautomers, N-oxides, hydrates, solvates, and salts thereof, and mixtures of same.

In a further embodiment of the first aspect, the present invention covers compounds of formula (I), supra, in which:
$R^{12}$ and $R^{13}$ represent, independently from each occurrence,
a hydrogen atom or a group selected from $C_1$-$C_4$-alkyl, $C_1$-$C_4$-fluoroalkyl, $C_3$-$C_7$-cycloalkyl, monocyclic 4- to 7-membered heterocycloalkyl and (phenyl)-($C_1$-$C_2$-alkyl)-,
wherein $C_3$-$C_7$-cycloalkyl and monocyclic 4- to 7-membered heterocycloalkyl are optionally substituted one or two times, each substituent independently selected from a fluorine atom or a group selected from oxo, $C_1$-$C_2$-alkyl and ($C_1$-$C_2$-alkyl)-C(=O)—,
or
$R^{12}$ and $R^{13}$, together with the nitrogen atom to which they are attached, represent a monocyclic nitrogen containing 4- to 7-membered heterocycloalkyl group which is optionally substituted one or two times, each substituent independently selected from a halogen atom or a group selected from oxo, $C_1$-$C_2$-alkyl and ($C_1$-$C_2$-alkyl)-C(=O)—,
and stereoisomers, tautomers, N-oxides, hydrates, solvates, and salts thereof, and mixtures of same.

In a further embodiment of the first aspect, the present invention covers compounds of formula (I), supra, in which:
$R^{12}$ and $R^{13}$ represent, independently from each occurrence,
a hydrogen atom or a group selected from $C_1$-$C_4$-alkyl, $C_1$-$C_4$-fluoroalkyl, $C_3$-$C_7$-cycloalkyl, monocyclic 4- to 7-membered heterocycloalkyl and (phenyl)-($C_1$-$C_2$-alkyl)-,
wherein $C_3$-$C_7$-cycloalkyl and monocyclic 4- to 7-membered heterocycloalkyl are optionally substituted one or two times, each substituent independently selected from a fluorine atom or a group selected from oxo, $C_1$-$C_2$-alkyl and ($C_1$-$C_2$-alkyl)-C(=O)—,
and stereoisomers, tautomers, N-oxides, hydrates, solvates, and salts thereof, and mixtures of same.

In a further embodiment of the first aspect, the present invention covers compounds of formula (I), supra, in which:
$R^{12}$ and $R^{13}$, together with the nitrogen atom to which they are attached, represent a monocyclic nitrogen containing 4- to 7-membered heterocycloalkyl group which is optionally substituted one or two times, each substituent independently selected from a halogen atom or a group selected from oxo, $C_1$-$C_2$-alkyl and ($C_1$-$C_2$-alkyl)-C(=O)—,
and stereoisomers, tautomers, N-oxides, hydrates, solvates, and salts thereof, and mixtures of same.

In a further embodiment of the first aspect, the present invention covers compounds of formula (I), supra, in which:
$R^{12}$ and $R^{13}$ represent, independently from each occurrence,
a hydrogen atom or a group selected from $C_1$-$C_4$-alkyl, $C_1$-$C_2$-fluoroalkyl, $C_1$-$C_2$-hydroxyalkyl, ($C_1$-$C_4$-alkoxy)-$C_2$-$C_3$-alkyl-, ($C_1$-$C_2$-fluoroalkoxy)-$C_2$-$C_3$-alkyl-, (phenoxy)-$C_2$-$C_3$-alkyl-, $C_3$-$C_7$-cycloalkyl and (phenyl)-($C_1$-$C_2$-alkyl)-,
wherein $C_3$-$C_7$-cycloalkyl is optionally substituted one or two times, each substituent independently selected from a fluorine atom or a methyl group, and wherein the phenyl groups within said (phenoxy)-$C_2$-$C_3$-alkyl- group and said (phenyl)-($C_1$-$C_2$-alkyl)- group are optionally substituted one or two times, each substituent independently selected from a fluorine atom and a chlorine atom, or a group selected from methyl, trifluoromethyl and methoxy, and stereoisomers, tautomers, N-oxides, hydrates, solvates, and salts thereof, and mixtures of same.

In a further embodiment of the first aspect, the present invention covers compounds of formula (I), supra, in which:
$R^{12}$ and $R^{13}$ represent, independently from each occurrence, a hydrogen atom or a group selected from $C_1$-$C_4$-alkyl, $C_1$-$C_2$-fluoroalkyl, $C_1$-$C_2$-hydroxyalkyl, ($C_1$-$C_4$-alkoxy)-$C_2$-alkyl-, ($C_1$-$C_2$-fluoroalkoxy)-$C_2$-alkyl-, (phenoxy)-$C_2$-alkyl-, $C_3$-$C_7$-cycloalkyl and (phenyl)-($C_1$-$C_2$-alkyl)-,
wherein the phenyl groups within said (phenoxy)-$C_2$-alkyl- group and said (phenyl)-($C_1$-$C_2$-alkyl)- group are optionally substituted one or two times, each substituent independently selected from fluorine atom and a chlorine atom, or a group selected from methyl, trifluoromethyl and methoxy, and stereoisomers, tautomers, N-oxides, hydrates, solvates, and salts thereof, and mixtures of same.

In a further embodiment of the first aspect, the present invention covers compounds of formula (I), supra, in which:
$R^{12}$ and $R^{13}$ represent, independently from each occurrence, a hydrogen atom or a group selected from $C_1$-$C_2$-alkyl, ($C_1$-$C_4$-alkoxy)-$C_2$-alkyl-, ($C_1$-$C_2$-fluoroalkoxy)-$C_2$-alkyl-, (phenoxy)-$C_2$-alkyl-, $C_3$-$C_7$-cycloalkyl and (phenyl)-($C_1$-$C_2$-alkyl)-, and stereoisomers, tautomers, N-oxides, hydrates, solvates, and salts thereof, and mixtures of same.

In a further embodiment of the first aspect, the present invention covers compounds of formula (I), supra, in which:
$R^{14}$ represents a group selected from $C_1$-$C_2$-alkyl, $C_1$-$C_2$-haloalkyl and phenyl,
wherein the phenyl group is optionally substituted one or two times, each substituent independently selected from a fluorine atom, a chlorine atom and a bromine atom, or a group selected from methyl, trifluoromethyl and methoxy, and stereoisomers, tautomers, N-oxides, hydrates, solvates, and salts thereof, and mixtures of same.

In a further embodiment of the first aspect, the present invention covers compounds of formula (I), supra, in which:
$R^{14}$ represents a group selected from $C_1$-$C_2$-alkyl, $C_1$-$C_2$-haloalkyl and phenyl,
wherein the phenyl group is optionally substituted one or two times, each substituent independently selected from a fluorine atom, a chlorine atom and a bromine atom, or a group selected from methyl, trifluoromethyl and methoxy, and stereoisomers, tautomers, N-oxides, hydrates, solvates, and salts thereof, and mixtures of same.

In a further embodiment of the first aspect, the present invention covers compounds of formula (I), supra, in which:
$R^{14}$ represents a group selected from $C_1$-$C_2$-alkyl and $C_1$-$C_2$-haloalkyl, and stereoisomers, tautomers, N-oxides, hydrates, solvates, and salts thereof, and mixtures of same.

In a further embodiment of the first aspect, the present invention covers compounds of formula (I), supra, in which:
$R^{14}$ represents a group selected from methyl and trifluoromethyl, and stereoisomers, tautomers, N-oxides, hydrates, solvates, and salts thereof, and mixtures of same.

In a further embodiment of the first aspect, the present invention covers compounds of formula (I), supra, in which:
$R^{14}$ represents a methyl group, and stereoisomers, tautomers, N-oxides, hydrates, solvates, and salts thereof, and mixtures of same.

In a further embodiment of the first aspect, the present invention covers compounds of formula (I), supra, in which:
$R^{17}$ represents a $C_1$-$C_4$-alkyl group, and stereoisomers, tautomers, N-oxides, hydrates, solvates, and salts thereof, and mixtures of same.

In a further embodiment of the first aspect, the present invention covers compounds of formula (I), supra, in which:
$R^{17}$ represents a $C_1$-$C_3$-alkyl group, and stereoisomers, tautomers, N-oxides, hydrates, solvates, and salts thereof, and mixtures of same.

In a further embodiment of the first aspect, the present invention covers compounds of formula (I), supra, in which:
$R^{17}$ represents a $C_1$-$C_2$-alkyl group, and stereoisomers, tautomers, N-oxides, hydrates, solvates, and salts thereof, and mixtures of same.

In a further embodiment of the first aspect, the present invention covers compounds of formula (I), supra, in which:
$R^{17}$ represents a methyl group, and stereoisomers, tautomers, N-oxides, hydrates, solvates, and salts thereof, and mixtures of same.

In a further embodiment of the first aspect, the present invention covers compounds of formula (I), supra, in which:
$R^{17}$ represents an ethyl group, and stereoisomers, tautomers, N-oxides, hydrates, solvates, and salts thereof, and mixtures of same.

In a further embodiment of the first aspect, the present invention covers compounds of formula (I), supra, in which:
$R^{18}$ and $R^{19}$ represent, independently from each occurrence, a hydrogen atom or a $C_1$-$C_2$-alkyl group, and stereoisomers, tautomers, N-oxides, hydrates, solvates, and salts thereof, and mixtures of same.

In a further embodiment of the first aspect, the present invention covers compounds of formula (I), supra, in which:
$R^{18}$ and $R^{19}$ represent, independently from each occurrence, a hydrogen atom or a methyl group, and stereoisomers, tautomers, N-oxides, hydrates, solvates, and salts thereof, and mixtures of same.

In a further embodiment of the first aspect, the present invention covers compounds of formula (I), supra, in which:
$R^{18}$ and $R^{19}$ both represent a methyl group, and stereoisomers, tautomers, N-oxides, hydrates, solvates, and salts thereof, and mixtures of same.

In a further embodiment of the first aspect, the present invention covers compounds of formula (I), supra, in which:
$R^{18}$ and $R^{19}$ both represent a hydrogen atom, and stereoisomers, tautomers, N-oxides, hydrates, solvates, and salts thereof, and mixtures of same.

In a further embodiment of the first aspect, the present invention covers compounds of formula (I), supra, in which:
$R^{18}$ represents a hydrogen atom and $R^{19}$ represents a methyl group, and stereoisomers, tautomers, N-oxides, hydrates, solvates, and salts thereof, and mixtures of same.

In a further embodiment of the first aspect, the present invention covers compounds of formula (I), supra, in which:
$R^{20}$ represents a hydrogen atom or a group selected from $C_1$-$C_6$-alkyl, $C_3$-$C_4$-alkenyl, $C_3$-$C_4$-alkynyl, $C_1$-$C_3$-alkoxy, $C_3$-$C_7$-cycloalkyl, bicyclic $C_6$-$C_{11}$-cycloalkyl, adamantyl, monocyclic 4- to 7-membered heterocycloalkyl, bicyclic 6- to 10-membered heterocycloalkyl, phenyl, naphthyl, and 5- to 10-membered heteroaryl, wherein said $C_1$-$C_6$-alkyl group is optionally substituted one, two or three times, each substituent independently selected from a halogen atom or a group selected from hydroxy, cyano, $C_1$-$C_3$-alkoxy, —N($R^{22}$)($R^{23}$), $C_3$-$C_7$-cycloalkyl, bicyclic $C_6$-$C_{11}$-cycloalkyl, adamantyl, monocyclic 4- to 7-membered heterocycloalkyl, bicyclic 6- to 10-membered heterocycloalkyl, phenyl, and 5- to 10-membered heteroaryl, said phenyl and 5- to 10-membered heteroaryl substituents themselves being optionally substituted one or two times, each substituent independently selected from a fluorine atom, a chlorine atom and a bromine atom, or a group selected from methyl, trifluoromethyl and methoxy, wherein $C_3$-$C_7$-cycloalkyl, bicyclic $C_6$-$C_{11}$-cycloalkyl, adamantyl, monocyclic 4- to 7-membered heterocycloalkyl, bicyclic 6- to 10-membered heterocycloalkyl are optionally substituted one or two or three times, each substituent independently selected from a halogen atom or a group selected from cyano, oxo, hydroxy, $C_1$-$C_2$-alkyl and ($C_1$-$C_2$-alkyl)-C(═O)—, and wherein said phenyl, naphthyl and 5- to 10-membered heteroaryl groups are optionally substituted one, two or three times, each substituent independently selected from a halogen atom or a group selected from cyano, $C_1$-$C_2$-alkyl, $C_1$-$C_2$-haloalkyl, $C_1$-$C_2$-alkoxy, $C_1$-$C_2$haloalkoxy, —N($R^{22}$)($R^{23}$) and —C(═O)—N($R^{24}$)($R^{25}$), $R^{21}$ represents a hydrogen atom or a $C_1$-$C_2$-alkyl group, or $R^{20}$ and $R^{21}$, together with the nitrogen atom to which they are attached, represent a monocyclic nitrogen containing 4- to 7-membered heterocycloalkyl group which is optionally benzocondensed, and which is optionally substituted one, two or three times, each substituent independently selected from a halogen atom or a group selected from cyano, oxo, hydroxy, $C_1$-$C_2$-alkyl, $C_1$-$C_2$haloalkyl, (phenyl)-($C_1$-$C_2$-alkyl)-, ($C_1$-$C_2$-alkyl)-C(═O)—, $C_3$-$C_4$-cycloalkyl, $C_1$-$C_2$-alkoxy, $C_1$-$C_2$-haloalkoxy, —N($R^{22}$)($R^{23}$) and —C(═O)—N($R^{24}$)($R^{25}$);

$R^{22}$ and $R^{23}$ represent, independently from each occurrence, a hydrogen atom or a group selected from $C_1$-$C_2$-alkyl and ($C_1$-$C_2$-alkyl)-C(═O)—;

$R^{24}$ and $R^{25}$ represent, independently from each occurrence, a hydrogen atom or a $C_1$-$C_2$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^{20}$ represents a hydrogen atom or a group selected from $C_1$-$C_6$-alkyl, $C_3$-$C_4$-alkenyl, $C_3$-$C_4$-alkynyl, $C_1$-$C_3$-alkoxy, $C_3$-$C_7$-cycloalkyl, bicyclic $C_6$-$C_{11}$-cycloalkyl, adamantyl, monocyclic 4- to 7-membered heterocycloalkyl, bicyclic 6- to 10-membered heterocycloalkyl, phenyl, naphthyl, and 5- to 10-membered heteroaryl, wherein said $C_1$-$C_6$-alkyl group is optionally substituted one, two or three times, each substituent independently selected from a halogen atom or a group selected from hydroxy, cyano, $C_1$-$C_3$-alkoxy, —N($R^{22}$)($R^{23}$), $C_3$-$C_7$-cycloalkyl, bicyclic $C_6$-$C_{11}$-cycloalkyl, adamantyl, monocyclic 4- to 7-membered heterocycloalkyl, bicyclic 6- to 10-membered heterocycloalkyl, phenyl, and 5- to 10-membered heteroaryl, said phenyl and 5- to 10-membered heteroaryl substituents themselves being optionally substituted one or two times, each substituent independently selected from a fluorine atom, a chlorine atom and a bromine atom, or a group selected from methyl, trifluoromethyl and methoxy, wherein $C_3$-$C_7$-cycloalkyl, bicyclic $C_6$-$C_{11}$-cycloalkyl, adamantyl, monocyclic 4- to 7-membered heterocycloalkyl, bicyclic 6- to 10-membered heterocycloalkyl are optionally substituted one or two or three times, each substituent independently selected from a halogen atom or a group selected from cyano, oxo, hydroxy, $C_1$-$C_2$-alkyl and ($C_1$-$C_2$-alkyl)-C(═O)—, and wherein said phenyl, naphthyl and 5- to 10-membered heteroaryl groups are optionally substituted one, two or three times, each substituent independently selected from a halogen atom or a group selected from cyano, $C_1$-$C_2$-alkyl, $C_1$-$C_2$-haloalkyl, $C_1$-$C_2$alkoxy, $C_1$-$C_2$haloalkoxy, —N($R^{22}$)($R^{23}$) and —C(═O)—N($R^{24}$)($R^{25}$), $R^{21}$ represents a hydrogen atom or a $C_1$-$C_2$-alkyl group, $R^{22}$ and $R^{23}$ represent, independently from each occurrence, a hydrogen atom or a group selected from $C_1$-$C_2$-alkyl and ($C_1$-$C_2$-alkyl)-C(═O)—;

$R^{24}$ and $R^{25}$ represent, independently from each occurrence, a hydrogen atom or a $C_1$-$C_2$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^{20}$ and $R^{21}$, together with the nitrogen atom to which they are attached, represent a monocyclic nitrogen containing 4- to 7-membered heterocycloalkyl group which is optionally benzocondensed, and which is optionally substituted one, two or three times, each substituent independently selected from a halogen atom or a group selected from cyano, oxo, hydroxy, $C_1$-$C_2$-alkyl, $C_1$-$C_2$haloalkyl, (phenyl)-($C_1$-$C_2$-alkyl)-, ($C_1$-$C_2$-alkyl)-C(═O)—, $C_3$-$C_4$-cycloalkyl, $C_1$-$C_2$-alkoxy, $C_1$-$C_2$haloalkoxy, —N($R^{22}$)($R^{23}$) and —C(═O)—N($R^{24}$)($R^{25}$);

$R^{22}$ and $R^{23}$ represent, independently from each occurrence, a hydrogen atom or a group selected from $C_1$-$C_2$-alkyl and ($C_1$-$C_2$-alkyl)-C(═O)—;

$R^{24}$ and $R^{25}$ represent, independently from each occurrence, a hydrogen atom or a $C_1$-$C_2$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^{20}$ represents a hydrogen atom or a group selected from $C_1$-$C_6$-alkyl, $C_3$-$C_4$-alkenyl, $C_3$-$C_4$-alkynyl, $C_1$-$C_3$-alkoxy, $C_3$-$C_7$-cycloalkyl, bicyclic $C_5$-$C_{11}$-cycloalkyl, adamantyl, monocyclic 4- to 7-membered heterocycloalkyl, bicyclic 5- to 10-membered heterocycloalkyl, phenyl, naphthyl, and 5- to 10-membered heteroaryl, wherein said $C_1$-$C_6$-alkyl group is optionally substituted one, two or three times, each substituent independently selected from a halogen atom or a group selected from hydroxy, cyano, $C_1$-$C_3$-alkoxy, —N($R^{22}$)($R^{23}$), $C_3$-$C_7$-cycloalkyl, bicyclic $C_5$-$C_{11}$-cycloalkyl, adamantyl, monocyclic 4- to 7-membered heterocycloalkyl, bicyclic 5- to 10-membered heterocycloalkyl, phenyl, and 5- to 10-membered heteroaryl, said phenyl and 5- to 10-membered heteroaryl substituents themselves being optionally substituted one or two times, each substituent independently selected from a fluorine atom, a chlorine atom and a bromine atom, or a group selected from methyl, trifluoromethyl and methoxy, and wherein $C_3$-$C_7$-cycloalkyl, bicyclic $C_5$-$C_{11}$-cycloalkyl, adamantyl, monocyclic 4- to 7-membered heterocycloalkyl, bicyclic 5- to 10-membered heterocycloalkyl are optionally substituted one or two or three times, each substituent independently selected from a halogen atom or a group selected from cyano, oxo, hydroxy, $C_1$-$C_2$-alkyl and ($C_1$-$C_2$-alkyl)-C(=O)—, and wherein said phenyl, naphthyl and 5- to 10-membered heteroaryl groups are optionally substituted one, two or three times, each substituent independently selected from a halogen atom or a group selected from cyano, $C_1$-$C_2$-alkyl, $C_1$-$C_2$-haloalkyl, $C_1$-$C_2$alkoxy, $C_1$-$C_2$haloalkoxy, —N($R^{22}$)($R^{23}$) and —C(=O)—N($R^{24}$)($R^{25}$), and $R^{21}$ represents a hydrogen atom or a $C_1$-$C_2$-alkyl group, or $R^{20}$ and $R^{21}$, together with the nitrogen atom to which they are attached, represent a monocyclic nitrogen containing 4- to 7-membered heterocycloalkyl group which is optionally benzocondensed, and which is optionally substituted one, two or three times, each substituent independently selected from a halogen atom or a group selected from cyano, oxo, hydroxy, $C_1$-$C_2$-alkyl, $C_1$-$C_2$haloalkyl, (phenyl)-($C_1$-$C_2$-alkyl)-, ($C_1$-$C_2$-alkyl)-C(=O)—, $C_3$-$C_4$-cycloalkyl, $C_1$-$C_2$alkoxy, $C_1$-$C_2$haloalkoxy, —N($R^{22}$)($R^{23}$) and —C(=O)—N($R^{24}$)($R^{25}$), and stereoisomers, tautomers, N-oxides, hydrates, solvates, and salts thereof, and mixtures of same.

In a further embodiment of the first aspect, the present invention covers compounds of formula (I), supra, in which:

$R^{20}$ represents a hydrogen atom or a group selected from $C_1$-$C_6$-alkyl, $C_3$-$C_4$-alkenyl, $C_3$-$C_4$-alkynyl, $C_1$-$C_3$-alkoxy, $C_3$-$C_7$-cycloalkyl, bicyclic $C_5$-$C_{11}$-cycloalkyl, adamantyl, monocyclic 4- to 7-membered heterocycloalkyl, bicyclic 5- to 10-membered heterocycloalkyl, phenyl, naphthyl, and 5- to 10-membered heteroaryl, wherein said $C_1$-$C_6$-alkyl group is optionally substituted one, two or three times, each substituent independently selected from a halogen atom or a group selected from hydroxy, cyano, $C_1$-$C_3$-alkoxy, —N($R^{22}$)($R^{23}$), $C_3$-$C_7$-cycloalkyl, bicyclic $C_5$-$C_{11}$-cycloalkyl, adamantyl, monocyclic 4- to 7-membered heterocycloalkyl, bicyclic 5- to 10-membered heterocycloalkyl, phenyl, and 5- to 10-membered heteroaryl, said phenyl and 5- to 10-membered heteroaryl substituents themselves being optionally substituted one or two times, each substituent independently selected from a fluorine atom, a chlorine atom and a bromine atom, or a group selected from methyl, trifluoromethyl and methoxy, and wherein $C_3$-$C_7$-cycloalkyl, bicyclic $C_5$-$C_{11}$-cycloalkyl, adamantyl, monocyclic 4- to 7-membered heterocycloalkyl, bicyclic 5- to 10-membered heterocycloalkyl are optionally substituted one or two or three times, each substituent independently selected from a halogen atom or a group selected from cyano, oxo, hydroxy, $C_1$-$C_2$-alkyl and ($C_1$-$C_2$-alkyl)-C(=O)—, and wherein said phenyl, naphthyl and 5- to 10-membered heteroaryl groups are optionally substituted one, two or three times, each substituent independently selected from a halogen atom or a group selected from cyano, $C_1$-$C_2$-alkyl, $C_1$-$C_2$-haloalkyl, $C_1$-$C_2$alkoxy, $C_1$-$C_2$haloalkoxy, —N($R^{22}$)($R^{23}$) and —C(=O)—N($R^{24}$)($R^{25}$), and $R^{21}$ represents a hydrogen atom or a $C_1$-$C_2$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^{20}$ represents a hydrogen atom or a group selected from $C_1$-$C_6$-alkyl, $C_3$-$C_4$-alkenyl, $C_3$-$C_4$-alkynyl, $C_1$-$C_3$-alkoxy, $C_3$-$C_7$-cycloalkyl, bicyclic $C_6$-$C_{11}$-cycloalkyl, adamantyl, monocyclic 4- to 7-membered heterocycloalkyl, bicyclic 6- to 10-membered heterocycloalkyl, phenyl, naphthyl, and 5- to 10-membered heteroaryl, wherein said $C_1$-$C_6$-alkyl group is optionally substituted one, two or three times, each substituent independently selected from a halogen atom or a group selected from hydroxy, cyano, $C_1$-$C_3$-alkoxy, —N($R^{22}$)($R^{23}$), $C_3$-$C_7$-cycloalkyl, bicyclic $C_6$-$C_{11}$-cycloalkyl, adamantyl, monocyclic 4- to 7-membered heterocycloalkyl, bicyclic 6- to 10-membered heterocycloalkyl, phenyl, and 5- to 10-membered heteroaryl, said phenyl and 5- to 10-membered heteroaryl substituents themselves being optionally substituted one or two times, each substituent independently selected from a fluorine atom, a chlorine atom and a bromine atom, or a group selected from methyl, trifluoromethyl and methoxy, wherein $C_3$-$C_7$-cycloalkyl, bicyclic $C_6$-$C_{11}$-cycloalkyl, adamantyl, monocyclic 4- to 7-membered heterocycloalkyl, bicyclic 6- to 10-membered heterocycloalkyl are optionally substituted one or two or three times, each substituent independently selected from a halogen atom or a group selected from cyano, oxo, hydroxy, $C_1$-$C_2$-alkyl and ($C_1$-$C_2$-alkyl)-C(=O)—, and wherein said phenyl, naphthyl and 5- to 10-membered heteroaryl groups are optionally substituted one, two or three times, each substituent independently selected from a halogen atom or a group selected from cyano, $C_1$-$C_2$-alkyl, $C_1$-$C_2$-haloalkyl, $C_1$-$C_2$alkoxy, $C_1$-$C_2$-haloalkoxy, —N($R^{22}$)($R^{23}$) and —C(=O)—N($R^{24}$)($R^{25}$), $R^{21}$ represents a hydrogen atom or a $C_1$-$C_2$-alkyl group, or $R^{20}$ and $R^{21}$, together with the nitrogen atom to which they are attached, represent a monocyclic nitrogen containing 4- to 7-membered heterocycloalkyl group which is optionally benzocondensed, and which is optionally substituted one, two or three times, each substituent independently selected from a halogen atom or a group selected from cyano, oxo, hydroxy, $C_1$-$C_2$-alkyl, $C_1$-$C_2$haloalkyl, (phenyl)-($C_1$-$C_2$-alkyl)-, ($C_1$-$C_2$-alkyl)-C(=O)—, $C_3$-$C_4$-cycloalkyl, $C_1$-$C_2$-alkoxy, $C_1$-$C_2$haloalkoxy, —N($R^{22}$)($R^{23}$) and —C(=O)—N($R^{24}$)($R^{25}$);

and stereoisomers, tautomers, N-oxides, hydrates, solvates, and salts thereof, and mixtures of same.

In a further embodiment of the first aspect, the present invention covers compounds of formula (I), supra, in which:

$R^{20}$ represents a hydrogen atom or a group selected from $C_1$-$C_6$-alkyl, $C_3$-$C_4$-alkenyl, $C_3$-$C_4$-alkynyl, $C_1$-$C_3$-alkoxy, $C_3$-$C_7$-cycloalkyl, bicyclic $C_6$-$C_{11}$-cycloalkyl, adamantyl, monocyclic 4- to 7-membered heterocycloalkyl, bicyclic 6- to 10-membered heterocycloalkyl, phenyl, naphthyl, and 5- to 10-membered heteroaryl, wherein said $C_1$-$C_6$-alkyl group is optionally substituted one, two or three times, each substituent independently selected from a halogen atom or a group selected from hydroxy, cyano, $C_1$-$C_3$-alkoxy, —N($R^{22}$)($R^{23}$), $C_3$-$C_7$-cycloalkyl, bicyclic $C_6$-$C_{11}$-cycloalkyl, adamantyl, monocyclic 4- to 7-membered heterocycloalkyl, bicyclic 6- to 10-membered heterocycloalkyl, phenyl, and 5- to 10-membered heteroaryl, said phenyl and 5- to 10-membered heteroaryl substituents themselves being optionally substituted one or two times, each substituent independently selected from a fluorine atom, a chlorine atom and a bromine atom, or a group selected from methyl, trifluoromethyl and methoxy, wherein $C_3$-$C_7$-cycloalkyl, bicyclic $C_6$-$C_{11}$-cycloalkyl, adamantyl, monocyclic 4- to 7-membered heterocycloalkyl, bicyclic 6- to 10-membered heterocycloalkyl are optionally substituted one or two or three times, each substituent independently selected from a halogen atom or a group selected from cyano, oxo, hydroxy, $C_1$-$C_2$-alkyl and ($C_1$-$C_2$-alkyl)-C(=O)—, and wherein said phenyl, naphthyl and 5- to 10-membered heteroaryl groups are optionally substituted one, two or three times, each substituent independently selected from a halogen atom or a group selected from cyano, $C_1$-$C_2$-alkyl, $C_1$-$C_2$-haloalkyl, $C_1$-$C_2$alkoxy, $C_1$-$C_2$-haloalkoxy, —N($R^{22}$)($R^{23}$) and —C(=O)—N($R^{24}$)($R^{25}$), $R^{21}$ represents a hydrogen atom or a $C_1$-$C_2$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^{20}$ and $R^{21}$, together with the nitrogen atom to which they are attached, represent a monocyclic nitrogen containing 4- to 7-membered heterocycloalkyl group which is optionally benzocondensed, and which is optionally substituted one, two or three times, each substituent independently selected from a halogen atom or a group selected from cyano, oxo, hydroxy, $C_1$-$C_2$-alkyl, $C_1$-$C_2$haloalkyl, (phenyl)-($C_1$-$C_2$-alkyl)-, ($C_1$-$C_2$-alkyl)-C(=O)—, $C_3$-$C_4$-cycloalkyl, $C_1$-$C_2$-alkoxy, $C_1$-$C_2$haloalkoxy, —N($R^{22}$)($R^{23}$) and —C(=O)—N($R^{24}$)($R^{25}$);

and stereoisomers, tautomers, N-oxides, hydrates, solvates, and salts thereof, and mixtures of same.

In a further embodiment of the first aspect, the present invention covers compounds of formula (I), supra, in which:

$R^{20}$ represents a hydrogen atom or a group selected from optionally substituted $C_1$-$C_3$-alkyl, unsubstituted $C_4$-$C_6$-alkyl, prop-2-ynyl, methoxy, $C_3$-$C_6$-cycloalkyl, adamantyl, monocyclic 4- to 7-membered heterocycloalkyl, phenyl, and 5- to 10-membered heteroaryl, wherein said $C_1$-$C_3$-alkyl group is optionally substituted one, two or three times, each substituent independently selected from a halogen atom or a group selected from hydroxy, cyano, $C_1$-$C_3$-alkoxy, —N($R^{22}$)($R^{23}$), $C_3$-$C_6$-cycloalkyl, adamantyl, monocyclic 4- to 7-membered heterocycloalkyl, phenyl, and 5- to 10-membered heteroaryl, said phenyl and 5- to 10-membered heteroaryl substituents themselves being optionally substituted one or two times, each substituent independently selected from a fluorine atom, a chlorine atom and a methyl group, wherein said $C_3$-$C_6$-cycloalkyl, adamantyl and monocyclic 4- to 7-membered heterocycloalkyl groups are optionally substituted one or two or three times, each substituent independently selected from a fluorine atom or a group selected from oxo, $C_1$-$C_2$-alkyl and ($C_1$-$C_2$-alkyl)-C(=O)—, and wherein said phenyl and 5- to 10-membered heteroaryl groups are optionally substituted one, two or three times, each substituent independently selected from a fluorine atom and a chlorine atom or a group selected from cyano, $C_1$-$C_2$-alkyl, $C_1$-$C_2$-fluoroalkyl, $C_1$-$C_2$-alkoxy, $C_1$-$C_2$-haloalkoxy, —N($R^{22}$)($R^{23}$) and —C(=O)—N($R^{24}$)($R^{25}$), $R^{21}$ represents a hydrogen atom or a $C_1$-$C_2$-alkyl group, or $R^{20}$ and $R^{21}$, together with the nitrogen atom to which they are attached, represent a monocyclic nitrogen containing 4- to 7-membered heterocycloalkyl group which is optionally benzocondensed, and which is optionally substituted one, two or three times, each substituent independently selected from a halogen atom or a group selected from cyano, oxo, hydroxy, $C_1$-$C_2$-alkyl, $C_1$-$C_2$-fluoroalkyl, benzyl, ($C_1$-$C_2$-alkyl)-C(=O)—, $C_3$-$C_4$-cycloalkyl, $C_1$-$C_2$-alkoxy, $C_1$-$C_2$-haloalkoxy, —N($R^{22}$)($R^{23}$) and —C(=O)—N($R^{24}$)($R^{25}$);

$R^{22}$ and $R^{23}$ represent, independently from each occurrence, a hydrogen atom or a group selected from $C_1$-$C_2$-alkyl and ($C_1$-$C_2$-alkyl)-C(=O)—;

$R^{24}$ and $R^{25}$ represent, independently from each occurrence, a hydrogen atom or a $C_1$-$C_2$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^{20}$ represents a hydrogen atom or a group selected from optionally substituted $C_1$-$C_3$-alkyl, unsubstituted $C_4$-$C_6$-alkyl, prop-2-ynyl, methoxy, $C_3$-$C_6$-cycloalkyl, adamantyl, monocyclic 4- to 7-membered heterocycloalkyl, phenyl, and 5- to 10-membered heteroaryl, wherein said $C_1$-$C_3$-alkyl group is optionally substituted one, two or three times, each substituent independently selected from a halogen atom or a group selected from hydroxy, cyano, $C_1$-$C_3$-alkoxy, —N($R^{22}$)($R^{23}$), $C_3$-$C_6$-cycloalkyl, adamantyl, monocyclic 4- to 7-membered heterocycloalkyl, phenyl, and 5- to 10-membered heteroaryl, said phenyl and 5- to 10-membered heteroaryl substituents themselves being optionally substituted one or two times, each substituent independently selected from a fluorine atom, a chlorine atom and a methyl group, wherein said $C_3$-$C_6$-cycloalkyl, adamantyl and monocyclic 4- to 7-membered heterocycloalkyl groups are optionally substituted one or two or three times, each substituent independently selected from a fluorine atom or a group selected from oxo, $C_1$-$C_2$-alkyl and ($C_1$-$C_2$-alkyl)-C(=O)—, and wherein said phenyl and 5- to 10-membered heteroaryl groups are optionally substituted one, two or three times, each substituent independently selected from a fluorine atom and a chlorine atom or a group selected from cyano, $C_1$-$C_2$-alkyl, $C_1$-$C_2$-fluoroalkyl, $C_1$-$C_2$alkoxy, $C_1$-$C_2$-haloalkoxy, —N($R^{22}$)($R^{23}$) and —C(=O)—N($R^{24}$)($R^{25}$), $R^{21}$ represents a hydrogen atom or a $C_1$-$C_2$-alkyl group, $R^{22}$ and $R^{23}$ represent, independently from each occurrence, a hydrogen atom or a group selected from $C_1$-$C_2$-alkyl and ($C_1$-$C_2$-alkyl)-C(=O)—;

$R^{24}$ and $R^{25}$ represent, independently from each occurrence, a hydrogen atom or a $C_1$-$C_2$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^{20}$ and $R^{21}$, together with the nitrogen atom to which they are attached, represent a monocyclic nitrogen containing 4- to 7-membered heterocycloalkyl group which is optionally benzocondensed, and which is optionally substituted one, two or three times, each substituent independently selected from a halogen atom or a group selected from cyano, oxo, hydroxy, $C_1$-$C_2$-alkyl, $C_1$-$C_2$-fluoroalkyl, benzyl, ($C_1$-$C_2$-alkyl)-C(=O)—, $C_3$-$C_4$-cycloalkyl, $C_1$-$C_2$alkoxy, $C_1$-$C_2$-haloalkoxy, —N($R^{22}$)($R^{23}$) and —C(=O)—N($R^{24}$)($R^{25}$);

$R^{22}$ and $R^{23}$ represent, independently from each occurrence, a hydrogen atom or a group selected from $C_1$-$C_2$-alkyl and ($C_1$-$C_2$-alkyl)-C(=O)—;

$R^{24}$ and $R^{25}$ represent, independently from each occurrence, a hydrogen atom or a $C_1$-$C_2$-alkyl group, and stereoisomers, tautomers, N-oxides, hydrates, solvates, and salts thereof, and mixtures of same.

In a further embodiment of the first aspect, the present invention covers compounds of formula (I), supra, in which:
$R^{20}$ represents a hydrogen atom or a group selected from optionally substituted $C_1$-$C_3$-alkyl, unsubstituted $C_4$-$C_6$-alkyl, prop-2-ynyl, methoxy, $C_3$-$C_6$-cycloalkyl, adamantyl, monocyclic 4- to 7-membered heterocycloalkyl, phenyl, and 5- to 10-membered heteroaryl,
  wherein said $C_1$-$C_3$-alkyl group is optionally substituted one, two or three times, each substituent independently selected from a halogen atom or a group selected from hydroxy, cyano, $C_1$-$C_3$-alkoxy, —N($R^{22}$)($R^{23}$), $C_3$-$C_6$-cycloalkyl, adamantyl, monocyclic 4- to 7-membered heterocycloalkyl, phenyl, and 5- to 10-membered heteroaryl, said phenyl and 5- to 10-membered heteroaryl substituents themselves being optionally substituted one or two times, each substituent independently selected from a fluorine atom, a chlorine atom and a methyl group,
  wherein said $C_3$-$C_6$-cycloalkyl, adamantyl and monocyclic 4- to 7-membered heterocycloalkyl groups are optionally substituted one or two or three times, each substituent independently selected from a fluorine atom or a group selected from oxo, $C_1$-$C_2$-alkyl and ($C_1$-$C_2$-alkyl)-C(=O)—,
  and wherein said phenyl and 5- to 10-membered heteroaryl groups are optionally substituted one, two or three times, each substituent independently selected from a fluorine atom and a chlorine atom or a group selected from cyano, $C_1$-$C_2$-alkyl, $C_1$-$C_2$-fluoroalkyl, $C_1$-$C_2$alkoxy, $C_1$-$C_2$haloalkoxy, —N($R^{22}$)($R^{23}$) and —C(=O)—N($R^{24}$)($R^{25}$),
$R^{21}$ represents a hydrogen atom or a $C_1$-$C_2$-alkyl group,
or
$R^{20}$ and $R^{21}$, together with the nitrogen atom to which they are attached, represent a monocyclic nitrogen containing 4- to 7-membered heterocycloalkyl group which is optionally benzocondensed, and which is optionally substituted one, two or three times, each substituent independently selected from a halogen atom or a group selected from cyano, oxo, hydroxy, $C_1$-$C_2$-alkyl, $C_1$-$C_2$-fluoroalkyl, benzyl, ($C_1$-$C_2$-alkyl)-C(=O)—, $C_3$-$C_4$-cycloalkyl, $C_1$-$C_2$alkoxy, $C_1$-$C_2$-haloalkoxy, —N($R^{22}$)($R^{23}$) and —C(=O)—N($R^{24}$)($R^{25}$),
and stereoisomers, tautomers, N-oxides, hydrates, solvates, and salts thereof, and mixtures of same.

In a further embodiment of the first aspect, the present invention covers compounds of formula (I), supra, in which:
$R^{20}$ represents a hydrogen atom or a group selected from optionally substituted $C_1$-$C_3$-alkyl, unsubstituted $C_4$-$C_6$-alkyl, prop-2-ynyl, methoxy, $C_3$-$C_6$-cycloalkyl, adamantyl, monocyclic 4- to 7-membered heterocycloalkyl, phenyl, and 5- to 10-membered heteroaryl,
  wherein said $C_1$-$C_3$-alkyl group is optionally substituted one, two or three times, each substituent independently selected from a halogen atom or a group selected from hydroxy, cyano, $C_1$-$C_3$-alkoxy, —N($R^{22}$)($R^{23}$), $C_3$-$C_6$-cycloalkyl, adamantyl, monocyclic 4- to 7-membered heterocycloalkyl, phenyl, and 5- to 10-membered heteroaryl, said phenyl and 5- to 10-membered heteroaryl substituents themselves being optionally substituted one or two times, each substituent independently selected from a fluorine atom, a chlorine atom and a methyl group,
  wherein said $C_3$-$C_6$-cycloalkyl, adamantyl and monocyclic 4- to 7-membered heterocycloalkyl groups are optionally substituted one or two or three times, each substituent independently selected from a fluorine atom or a group selected from oxo, $C_1$-$C_2$-alkyl and ($C_1$-$C_2$-alkyl)-C(=O)—,
  and wherein said phenyl and 5- to 10-membered heteroaryl groups are optionally substituted one, two or three times, each substituent independently selected from a fluorine atom and a chlorine atom or a group selected from cyano, $C_1$-$C_2$-alkyl, $C_1$-$C_2$-fluoroalkyl, $C_1$-$C_2$-alkoxy, $C_1$-$C_2$haloalkoxy, —N($R^{22}$)($R^{23}$) and —C(=O)—N($R^{24}$)($R^{25}$),
$R^{21}$ represents a hydrogen atom or a $C_1$-$C_2$-alkyl group,
and stereoisomers, tautomers, N-oxides, hydrates, solvates, and salts thereof, and mixtures of same.

In a further embodiment of the first aspect, the present invention covers compounds of formula (I), supra, in which:
$R^{20}$ and $R^{21}$, together with the nitrogen atom to which they are attached, represent a monocyclic nitrogen containing 4- to 7-membered heterocycloalkyl group which is optionally benzocondensed, and which is optionally substituted one, two or three times, each substituent independently selected from a halogen atom or a group selected from cyano, oxo, hydroxy, $C_1$-$C_2$-alkyl, $C_1$-$C_2$-fluoroalkyl, benzyl, ($C_1$-$C_2$-alkyl)-C(=O)—, $C_3$-$C_4$-cycloalkyl, $C_1$-$C_2$-alkoxy, $C_1$-$C_2$haloalkoxy, —N($R^{22}$)($R^{23}$) and —C(=O)—N($R^{24}$)($R^{25}$),
and stereoisomers, tautomers, N-oxides, hydrates, solvates, and salts thereof, and mixtures of same.

In a further embodiment of the first aspect, the present invention covers compounds of formula (I), supra, in which:
$R^{20}$ represents a hydrogen atom or a group selected from optionally substituted $C_1$-$C_3$-alkyl, unsubstituted $C_4$-$C_6$-alkyl, prop-2-ynyl, methoxy, $C_3$-$C_6$-cycloalkyl, adamantyl, monocyclic 4- to 7-membered heterocycloalkyl, phenyl, and 5- to 10-membered heteroaryl,
  wherein said $C_1$-$C_3$-alkyl group is optionally substituted one, two or three times, each substituent independently selected from a halogen atom or a group selected from hydroxy, cyano, $C_1$-$C_3$-alkoxy, —N($R^{22}$)($R^{23}$), $C_3$-$C_6$-cycloalkyl, adamantyl, monocyclic 4- to 7-membered heterocycloalkyl, phenyl, and 5- to 10-membered heteroaryl, said phenyl and 5- to 10-membered heteroaryl substituents themselves being optionally substituted one or two times, each substituent independently selected from a fluorine atom, a chlorine atom and a methyl group,
  and wherein said $C_3$-$C_6$-cycloalkyl, adamantyl and monocyclic 4- to 7-membered heterocycloalkyl groups are optionally substituted one or two or three times, each substituent independently selected from a fluorine atom or a group selected from oxo, $C_1$-$C_2$-alkyl and ($C_1$-$C_2$-alkyl)-C(=O)—,
  and wherein said phenyl and 5- to 10-membered heteroaryl groups are optionally substituted one, two or three times, each substituent independently selected from a fluorine atom and a chlorine atom or a group selected from cyano, $C_1$-$C_2$-alkyl, $C_1$-$C_2$-fluoroalkyl, $C_1$-$C_2$-alkoxy, $C_1$-$C_2$-fluoroalkoxy, —N($R^{22}$)($R^{23}$) and —C(=O)—N($R^{24}$)($R^{25}$),
$R^{21}$ represents a hydrogen atom or a $C_1$-$C_2$-alkyl group,
or
$R^{20}$ and $R^{21}$, together with the nitrogen atom to which they are attached, represent a monocyclic nitrogen containing 4- to 7-membered heterocycloalkyl group which is optionally benzocondensed, and which is optionally substituted one, two or three times, each substituent independently selected from a halogen atom or a group selected from cyano, oxo, hydroxy, $C_1$-$C_2$-alkyl, $C_1$-$C_2$-fluoroalkyl, benzyl, ($C_1$-$C_2$-alkyl)-C(=O)—, $C_3$-$C_4$-cycloalkyl, $C_1$-$C_2$alkoxy, $C_1$-$C_2$-fluoroalkoxy, —N($R^{22}$)($R^{23}$) and —C(=O)—N($R^{24}$)($R^{25}$).

and stereoisomers, tautomers, N-oxides, hydrates, solvates, and salts thereof, and mixtures of same.

In a further embodiment of the first aspect, the present invention covers compounds of formula (I), supra, in which:
$R^{20}$ represents a hydrogen atom or a group selected from optionally substituted $C_1$-$C_3$-alkyl, unsubstituted $C_4$-$C_6$-alkyl, prop-2-ynyl, methoxy, $C_3$-$C_6$-cycloalkyl, adamantyl, monocyclic 4- to 7-membered heterocycloalkyl, phenyl, and 5- to 10-membered heteroaryl,
wherein said $C_1$-$C_3$-alkyl group is optionally substituted one, two or three times, each substituent independently selected from a halogen atom or a group selected from hydroxy, cyano, $C_1$-$C_3$-alkoxy, —N($R^{22}$)($R^{23}$), $C_3$-$C_6$-cycloalkyl, adamantyl, monocyclic 4- to 7-membered heterocycloalkyl, phenyl, and 5- to 10-membered heteroaryl, said phenyl and 5- to 10-membered heteroaryl substituents themselves being optionally substituted one or two times, each substituent independently selected from a fluorine atom, a chlorine atom and a methyl group,
and wherein said $C_3$-$C_6$-cycloalkyl, adamantyl and monocyclic 4- to 7-membered heterocycloalkyl groups are optionally substituted one or two or three times, each substituent independently selected from a fluorine atom or a group selected from oxo, $C_1$-$C_2$-alkyl and ($C_1$-$C_2$-alkyl)-C(=O)—,
and wherein said phenyl and 5- to 10-membered heteroaryl groups are optionally substituted one, two or three times, each substituent independently selected from a fluorine atom and a chlorine atom or a group selected from cyano, $C_1$-$C_2$-alkyl, $C_1$-$C_2$-fluoroalkyl, $C_1$-$C_2$-alkoxy, $C_1$-$C_2$-fluoroalkoxy, —N($R^{22}$)($R^{23}$) and —C(=O)—N($R^{24}$)($R^{25}$),
$R^{21}$ represents a hydrogen atom or a $C_1$-$C_2$-alkyl group,
and stereoisomers, tautomers, N-oxides, hydrates, solvates, and salts thereof, and mixtures of same.

In a further embodiment of the first aspect, the present invention covers compounds of formula (I), supra, in which:
$R^{20}$ and $R^{21}$, together with the nitrogen atom to which they are attached, represent a monocyclic nitrogen containing 4- to 7-membered heterocycloalkyl group which is optionally benzocondensed, and which is optionally substituted one, two or three times, each substituent independently selected from a halogen atom or a group selected from cyano, oxo, hydroxy, $C_1$-$C_2$-alkyl, $C_1$-$C_2$-fluoroalkyl, benzyl, ($C_1$-$C_2$-alkyl)-C(=O)—, $C_3$-$C_4$-cycloalkyl, $C_1$-$C_2$alkoxy, $C_1$-$C_2$-fluoroalkoxy, —N($R^{22}$)($R^{23}$) and —C(=O)—N($R^{24}$)($R^{25}$),
and stereoisomers, tautomers, N-oxides, hydrates, solvates, and salts thereof, and mixtures of same.

In a further embodiment of the first aspect, the present invention covers compounds of formula (I), supra, in which:
$R^{20}$ represents a hydrogen atom or a group selected from $C_1$-$C_3$-alkyl and phenyl,
wherein said $C_1$-$C_3$-alkyl group is optionally substituted one or two times, each substituent independently selected from a fluorine atom or a group selected from hydroxy, $C_1$-$C_3$-alkoxy and phenyl, said phenyl itself being optionally substituted one or two times, each substituent independently selected from a fluorine atom, a chlorine atom and a methyl group,
and wherein said phenyl group is optionally substituted one, two or three times, each substituent independently selected from a fluorine atom and a chlorine atom or a group selected from methyl, trifluoromethyl, methoxy and trifluoromethoxy;
$R^{21}$ represents a hydrogen atom or a $C_1$-$C_2$-alkyl group,
and stereoisomers, tautomers, N-oxides, hydrates, solvates, and salts thereof, and mixtures of same.

In a further embodiment of the first aspect, the present invention covers compounds of formula (I), supra, in which:
$R^{20}$ represents a group selected from benzyl and phenyl,
wherein said phenyl group, and the phenyl group within said benzyl group, is optionally substituted one or two times, each substituent independently selected from a fluorine atom, a chlorine atom and a methyl group,
$R^{21}$ represents a hydrogen atom or a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^{22}$ and $R^{23}$ represent, independently from each occurrence, a hydrogen atom or a group selected from $C_1$-$C_2$-alkyl and ($C_1$-$C_2$-alkyl)-C(=O)—,
and stereoisomers, tautomers, N-oxides, hydrates, solvates, and salts thereof, and mixtures of same.

In a further embodiment of the first aspect, the present invention covers compounds of formula (I), supra, in which:
$R^{22}$ and $R^{23}$ represent, independently from each occurrence, a hydrogen atom or a group selected from methyl and ($CH_3$)—C(=O)—,
and stereoisomers, tautomers, N-oxides, hydrates, solvates, and salts thereof, and mixtures of same.

In a further embodiment of the first aspect, the present invention covers compounds of formula (I), supra, in which:
$R^{24}$ and $R^{25}$ represent, independently from each occurrence, a hydrogen atom or a $C_1$-$C_2$-alkyl group,
and stereoisomers, tautomers, N-oxides, hydrates, solvates, and salts thereof, and mixtures of same.

In a further embodiment of the first aspect, the present invention covers compounds of formula (I), supra, in which:
$R^{24}$ and $R^{25}$ represent, independently from each occurrence, a hydrogen atom or a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^{20}$ represents a fluorine atom, a chlorine atom, or a group selected from $C_1$-$C_2$-alkyl, $C_1$-$C_2$-fluoroalkyl, $C_1$-$C_2$-alkoxy and $C_1$-$C_2$-fluoroalkoxy,
and stereoisomers, tautomers, N-oxides, hydrates, solvates, and salts thereof, and mixtures of same.

In a further embodiment of the first aspect, the present invention covers compounds of formula (I), supra, in which:
$R^{20}$ represents a fluorine atom, a chlorine atom or a bromine atom, or a group selected from methyl, difluoromethyl, trifluoromethyl, methoxy, benzyloxy, difluoromethoxy and trifluoromethoxy,
and stereoisomers, tautomers, N-oxides, hydrates, solvates, and salts thereof, and mixtures of same.

In a further embodiment of the first aspect, the present invention covers compounds of formula (I), supra, in which:
$R^{20}$ represents a fluorine atom, a chlorine atom, or a group selected from methyl, difluoromethyl, trifluoromethyl, methoxy, difluoromethoxy and trifluoromethoxy,
and stereoisomers, tautomers, N-oxides, hydrates, solvates, and salts thereof, and mixtures of same.

In a further embodiment of the first aspect, the present invention covers compounds of formula (I), supra, in which:

$R^{20}$ represents a fluorine atom, a chlorine atom or a bromine atom, or a group selected from difluoromethyl, methoxy, benzyloxy, difluoromethoxy and trifluoromethoxy,
and stereoisomers, tautomers, N-oxides, hydrates, solvates, and salts thereof, and mixtures of same.

In a further embodiment of the first aspect, the present invention covers compounds of formula (I), supra, in which:
$R^{20}$ represents a fluorine atom, a chlorine atom, or a group selected from difluoromethyl, trifluoromethyl, methoxy, difluoromethoxy and trifluoromethoxy,
and stereoisomers, tautomers, N-oxides, hydrates, solvates, and salts thereof, and mixtures of same.

In a further embodiment of the first aspect, the present invention covers compounds of formula (I), supra, in which:
$R^{27}$ represents a halogen atom or a group selected from $C_1$-$C_2$-alkyl, $C_1$-$C_2$-fluoroalkyl, —$OR^9$, —$N(R^{10})(R^{11})$, —$C(=O)$—$N(R^{12})(R^{13})$ and —$C(=O)$—$OR^{17}$,
and stereoisomers, tautomers, N-oxides, hydrates, solvates, and salts thereof, and mixtures of same.

In a further embodiment of the first aspect, the present invention covers compounds of formula (I), supra, in which:
$R^{27}$ represents a fluorine atom, a chlorine atom, or a group selected from $C_1$-$C_2$-alkoxy, benzyloxy and $C_1$-$C_2$-fluoroalkoxy,
and stereoisomers, tautomers, N-oxides, hydrates, solvates, and salts thereof, and mixtures of same.

In a further embodiment of the first aspect, the present invention covers compounds of formula (I), supra, in which:
$R^{27}$ represents a halogen atom or a group selected from —$OR^9$, —$N(R^{10})(R^{11})$ and —$C(=O)$—$N(R^{12})(R^{13})$,
and stereoisomers, tautomers, N-oxides, hydrates, solvates, and salts thereof, and mixtures of same.

In a further embodiment of the first aspect, the present invention covers compounds of formula (I), supra, in which:
$R^{27}$ represents a chlorine atom, or a group selected from methoxy, benzyloxy, difluoromethoxy and trifluoromethoxy,
and stereoisomers, tautomers, N-oxides, hydrates, solvates, and salts thereof, and mixtures of same.

In a further embodiment of the first aspect, the present invention covers compounds of formula (I), supra, in which:
n represents an integer 0, 1, or 2,
and stereoisomers, tautomers, N-oxides, hydrates, solvates, and salts thereof, and mixtures of same.

In a further embodiment of the first aspect, the present invention covers compounds of formula (I), supra, in which:
n represents an integer 0 or 2,
and stereoisomers, tautomers, N-oxides, hydrates, solvates, and salts thereof, and mixtures of same.

In a further embodiment of the first aspect, the present invention covers compounds of formula (I), supra, in which:
n represents an integer 0,
and stereoisomers, tautomers, N-oxides, hydrates, solvates, and salts thereof, and mixtures of same.

In a further embodiment of the first aspect, the present invention covers compounds of formula (I), supra, in which:
n represents an integer 2,
and stereoisomers, tautomers, N-oxides, hydrates, solvates, and salts thereof, and mixtures of same.

In a further embodiment of the first aspect, the present invention covers compounds of formula (I), supra, in which:
$Y^1$ represents —C(H)=, —C(F)=, —C(Cl)=, —C(CN)= or —N=,
and stereoisomers, tautomers, N-oxides, hydrates, solvates, and salts thereof, and mixtures of same.

In a further embodiment of the first aspect, the present invention covers compounds of formula (I), supra, in which:
$Y^1$ represents —C(H)=, —C(F)=, —C(Cl)= or —N=;
and stereoisomers, tautomers, N-oxides, hydrates, solvates, and salts thereof, and mixtures of same.

In a further embodiment of the first aspect, the present invention covers compounds of formula (I), supra, in which:
$Y^1$ represents —C(H)=, —C(F)= or —N=,
and stereoisomers, tautomers, N-oxides, hydrates, solvates, and salts thereof, and mixtures of same.

In a further embodiment of the first aspect, the present invention covers compounds of formula (I), supra, in which:
$Y^1$ represents —C(H)= or —C(F)=,
and stereoisomers, tautomers, N-oxides, hydrates, solvates, and salts thereof, and mixtures of same.

In a further embodiment of the first aspect, the present invention covers compounds of formula (I), supra, in which:
$Y^1$ represents —C(H)=,
and stereoisomers, tautomers, N-oxides, hydrates, solvates, and salts thereof, and mixtures of same.

In a further embodiment of the first aspect, the present invention covers compounds of formula (I), supra, in which:
$Y^1$ represents —C(Cl)=,
and stereoisomers, tautomers, N-oxides, hydrates, solvates, and salts thereof, and mixtures of same.

In a further embodiment of the first aspect, the present invention covers compounds of formula (I), supra, in which:
$Y^1$ represents —C(F)=,
and stereoisomers, tautomers, N-oxides, hydrates, solvates, and salts thereof, and mixtures of same.

In a further embodiment of the first aspect, the present invention covers compounds of formula (I), supra, in which:
$Y^1$ represents —N=,
and stereoisomers, tautomers, N-oxides, hydrates, solvates, and salts thereof, and mixtures of same.

In a further embodiment of the first aspect, the present invention covers compounds of formula (I), supra, in which:
$Y^2$ represents —C(H)= or —N=,
$Y^3$ represents —C($R^{27}$)= or —N=,
with the proviso that if $Y^2$ represents —N=, $Y^3$ represents —C($R^{27}$)=, and if $Y^3$ represents —N=, $Y^2$ represents —C(H)=,
and stereoisomers, tautomers, N-oxides, hydrates, solvates, and salts thereof, and mixtures of same.

In a further embodiment of the first aspect, the present invention covers compounds of formula (I), supra, in which:
$Y^2$ represents —C(H)= and —N=,
$Y^3$ represents —C($R^{27}$)= and —N=,
with the proviso that if $Y^2$ represents —N=, $Y^3$ represents —C($R^{27}$)=, and if $Y^3$ represents —N=, $Y^2$ represents —C(H)=,
and stereoisomers, tautomers, N-oxides, hydrates, solvates, and salts thereof, and mixtures of same.

In a further embodiment of the first aspect, the present invention covers compounds of formula (I), supra, in which:
$Y^2$ represents —N=;
$Y^3$ represents —C($R^{27}$)=,
and stereoisomers, tautomers, N-oxides, hydrates, solvates, and salts thereof, and mixtures of same.

In a further embodiment of the first aspect, the present invention covers compounds of formula (I), supra, in which:
$Y^2$ represents —C(H)=;
$Y^3$ represents —N=,
and stereoisomers, tautomers, N-oxides, hydrates, solvates, and salts thereof, and mixtures of same.

In a further embodiment of the first aspect, the present invention covers compounds of formula (I), supra, in which:
$Y^2$ represents —C(H)=;
$Y^3$ represents —C($R^{27}$)=, and stereoisomers, tautomers, N-oxides, hydrates, solvates, and salts thereof, and mixtures of same.

In a particular further embodiment of the first aspect, the present invention covers combinations of two or more of the above mentioned embodiments under the heading "further embodiments of the first aspect of the present invention".

The present invention covers any sub-combination within any embodiment or aspect of the present invention of compounds of general formula (I), supra.

The present invention covers the compounds of general formula (I) which are disclosed in the Example Section of this text, infra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Compounds of general formula (I) of the present invention demonstrate a valuable pharmacological spectrum of action, which could not have been predicted. Compounds of the present invention have surprisingly been found to effectively inhibit DGKζ and it is possible therefore that said compounds be used for the treatment or prophylaxis of diseases, preferably conditions with dysregulated immune responses, particularly cancer or other disorders associated with aberrant DGKζ signaling, in mammals, including humans.

Disorders and conditions particularly suitable for treatment with an DGKζ inhibitor of the present invention are liquid and solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancers include, but are not limited to, triple negative breast cancer, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypothalmic glioma, cerebellar and cerebral astrocytoma, glioblastoma, medulloblastoma, ependymoma, as well as neuroectodermal and pineal tumour.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Examples of ovarian cancer include, but are not limited to serous tumour, endometrioid tumour, mucinous cystadenocarcinoma, granulosa cell tumour, Sertoli-Leydig cell tumour and arrhenoblastoma.

Examples of cervical cancer include, but are not limited to squamous cell carcinoma, adenocarcinoma, adenosquamous carcinoma, small cell carcinoma, neuroendocrine tumour, glassy cell carcinoma and villoglandular adenocarcinoma.

Tumours of the digestive tract include, but are not limited to, anal, colon, colorectal, esophageal, gallbladder, gastric, pancreatic, rectal, small-intestine, and salivary gland cancers.

Examples of esophageal cancer include, but are not limited to esophageal cell carcinomas and adenocarcinomas, as well as squamous cell carcinomas, leiomyosarcoma, malignant melanoma, rhabdomyosarcoma and lymphoma.

Examples of gastric cancer include, but are not limited to intestinal type and diffuse type gastric adenocarcinoma.

Examples of pancreatic cancer include, but are not limited to ductal adenocarcinoma, adenosquamous carcinomas and pancreatic endocrine tumours.

Tumours of the urinary tract include, but are not limited to, bladder, penile, kidney, renal pelvis, ureter, urethral and human papillary renal cancers.

Examples of kidney cancer include, but are not limited to renal cell carcinoma, urothelial cell carcinoma, juxtaglomerular cell tumour (reninoma), angiomyolipoma, renal oncocytoma, Bellini duct carcinoma, clear-cell sarcoma of the kidney, mesoblastic nephroma and Wilms' tumour.

Examples of bladder cancer include, but are not limited to transitional cell carcinoma, squamous cell carcinoma, adenocarcinoma, sarcoma and small cell carcinoma.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, squamous cell cancer of the head and neck, laryngeal, hypopharyngeal, nasopharyngeal, oropharyngeal cancer, salivary gland cancer, lip and oral cavity cancer and squamous cell.

Lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

The term "treating" or "treatment" as stated throughout this document is used conventionally, for example the management or care of a subject for the purpose of combating, alleviating, reducing, relieving, improving the condition of a disease or disorder, such as a carcinoma.

The compounds of the present invention can be used in particular in therapy and prevention, i.e. prophylaxis, of tumour growth and metastases, especially in solid tumours of all indications and stages with or without pre-treatment of the tumour growth.

Generally, the use of chemotherapeutic agents and/or anti-cancer agents in combination with a compound or pharmaceutical composition of the present invention will serve to:

1. yield better efficacy in reducing the growth of a tumour or even eliminate the tumour as compared to administration of either agent alone,
2. provide for the administration of lesser amounts of the administered chemotherapeutic agents,
3. provide for a chemotherapeutic treatment that is well tolerated in the patient with fewer deleterious pharmacological complications than observed with single agent chemotherapies and certain other combined therapies,
4. provide for treating a broader spectrum of different cancer types in mammals, especially humans,
5. provide for a higher response rate among treated patients,
6. provide for a longer survival time among treated patients compared to standard chemotherapy treatments,
7. provide a longer time for tumour progression, and/or
8. yield efficacy and tolerability results at least as good as those of the agents used alone, compared to known instances where other cancer agent combinations produce antagonistic effects.

In addition, the compounds of general formula (I) of the present invention can also be used in combination with radiotherapy and/or surgical intervention.

In a further embodiment of the present invention, the compounds of general formula (I) of the present invention are used in combination with radiation: i.e. radiation treatment sensitizes cancers to anti-tumor immune responses by induction of tumor cell death and subsequent presentation of tumor neoantigens to tumor-reactive Tcells. As DGKζ is enhancing the antigen specific activation of T cells, the overall effect results in a much stronger cancer cell attack as compared to irradiation treatment alone.

Thus, the present invention also provides a method of killing a tumor, wherein conventional radiation therapy is employed previous to administering one or more of the compounds of the present invention.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with:

131I-chTNT, abarelix, abemaciclib, abiraterone, acalabrutinib, aclarubicin, adalimumab, ado-trastuzumab emtansine, afatinib, aflibercept, aldesleukin, alectinib, alemtuzumab, alendronic acid, alitretinoin, alpharadin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, apalutamide, aprepitant, arcitumomab, arglabin, arsenic trioxide, asparaginase, atezolizumab, avelumab, axicabtagene ciloleucel, axitinib, azacitidine, basiliximab, belotecan, bendamustine, besilesomab, belinostat, bevacizumab, bexarotene, bicalutamide, bisantrene, bleomycin, blinatumomab, bortezomib, bosutinib, buserelin, brentuximab vedotin, brigatinib, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, cemiplimab, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, durvalumab, eculizumab, edrecolomab, elimusertib (BAY1895344), elliptinium acetate, elotuzumab, eltrombopag, enasidenib, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, ibandronic acid, ibritumomab tiuxetan, ibrutinib, idarubicin, ifosfamide, imatinib, imiquimod, improsulfan, indisetron, incadronic acid, ingenol mebutate, inotuzumab ozogamicin, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, lutetium Lu 177 dotatate, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, midostaurin, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, mvasi, nabilone, nabiximols, nafarelin, naloxone+pentazocine, naltrexone, nartograstim, necitumumab, nedaplatin, nelarabine, neratinib, neridronic acid, netupitant/palonosetron, nivolumab, pentetreotide, nilotinib, nilutamide, nimorazole, nimotuzumab, nimustine, nintedanib, niraparib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, ribociclib, risedronic acid, rhenium-186 etidronate, rituximab, rolapitant, romidepsin, romiplostim, romurtide, rucaparib, samarium (153Sm) lexidronam, sargramostim, sarilumab, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tisagenlecleucel, tislelizumab, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

The compounds of the invention can further be combined with other reagents targeting the immune system, such as immune checkpoint inhibitors, e.g. aPD-1/-L1 axis antagonists.

PD-1, along with its ligands PD-L1 and PD-L2, function as negative regulators of T cell activation. PD-L1 is overexpressed in many cancers and overexpression of PD-1 often occurs concomitantly in tumor infiltrating T cells. This results in attenuation of T cell activation and evasion of immune surveillance, which contributes to impaired antitumor immune responses. (M. E. Keir et al., Annu. Rev. Immunol. 2008, 26, 677-704).

In accordance with a further aspect, the present invention covers combinations comprising one or more of the compounds of general formula (I), as described herein, or stereoisomers, tautomers, N-oxides, hydrates, solvates, and salts thereof, particularly pharmaceutically acceptable salts thereof, or mixtures of same, and one or more immune checkpoint inhibitors. Preferably, the immune checkpoint inhibitor is a aPD-1/-L1 axis antagonist.

The compounds of the invention can further be combined with inhibitors of DGKα, such as those inhibitors of DGKα disclosed in WO2020/006016, WO2020/006018 and WO 2021/041588. As DGKα in T cells operates in a similar fashion as DGKζ, a dual inhibition profoundly enhances T cell effector functions compared with cells with deletion of either DGK isoform alone or wild-type cells. (M. J. Riese et al. Cancer Res. (2013), 73(12); p. 3566-77).

The compounds of the invention can further be combined with chimeric antigen receptor T cells (CAR-T cells), such as Axicabtagen-Ciloleucel or Tisagenlecleucel. The activity of CAR-T cells can be suppressed by the tumor micro environment (TME). Knock out of DGKs by techniques such as Crispr had been shown to enhance CAR-T cell activity in a suppressive TME (I. Y. Jung et al., Mol. Cells 2018, 41 (8), 717-723).

In accordance with a further aspect, the present invention covers combinations comprising one or more compounds of general formula (I), as described herein, or stereoisomers, tautomers, N-oxides, hydrates, solvates, and salts thereof, particularly pharmaceutically acceptable salts thereof, or mixtures of same, with chimeric antigen receptor T cells, (CAR-T cells), CAR-NKT cells or CAR-NK cells.

Preferably, the chimeric antigen receptor T cells (CAR-T cells) are Axicabtagen-Ciloleucel or Tisagenlecleucel.

The present invention further provides the use of the compounds according to the invention for expansion of T cells including CAR-T and tumor infiltrated lymphocytes ex-vivo.

In accordance with a further aspect, the present invention covers compounds of general formula (I), as described herein, or stereoisomers, tautomers, N-oxides, hydrates, solvates, and salts thereof, particularly pharmaceutically acceptable salts thereof, or mixtures of same, for use in the expansion of T cells including CAR-T cells, CAR-NKT cells or CAR-NK cells and tumor infiltrated lymphocytes ex-vivo.

Hence, the present invention also relates to the use of the compounds according to the invention for the expansion of T cells, including CAR-T cell, CAR-NKT cells or CAR-NK cells and tumor infiltrated lymphocytes, ex-vivo.

The present invention also comprises an ex-vivo method for the expansion of T cells, including CAR-T cells, CAR-NKT cells or CAR-NK cells and tumor infiltrated lymphocytes, contacting said T cells with compounds according to the invention.

Compounds of the present invention can be utilized to inhibit, block, reduce or decrease DGKζ activity resulting in the modulation of dysregulated immune responses e.g. to block immunosuppression and increase immune cell activation and infiltration in the context of cancer and cancer immunotherapy that will eventually lead to reduction of tumour growth.

This method comprises administering to a mammal in need thereof, including a human, an amount of a compound of this invention, or a pharmaceutically acceptable salt, isomer, polymorph, metabolite, hydrate, solvate or ester thereof; which is effective to treat the disorder. The present invention also provides methods of treating a variety of other disorders wherein DGKζ is involved such as, but not limited to, disorders with dysregulated immune responses, inflammation, vaccination for infection & cancer, virus infections, lymphoproliferative disorders, asthma, eye diseases, and type 2 diabetes/insulin resistance.

These disorders have been well characterized in humans, but also exist with a similar etiology in other mammals, and can be treated by administering pharmaceutical compositions of the present invention.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prophylaxis of diseases, in particular cancer or conditions with dysregulated immune responses or other disorders associated with aberrant DGKζ signaling.

The pharmaceutical activity of the compounds according to the invention can be explained by their activity as DGKζ inhibitors.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, for the treatment or prophylaxis of diseases, in particular cancer or conditions with dysregulated immune responses or other disorders associated with aberrant DGKζ signaling, particularly liquid and solid tumours.

In accordance with a further aspect, the present invention covers the compounds of general formula (I), as described supra, or stereoisomers, tautomers, N-oxides, hydrates, solvates, and salts thereof, particularly pharmaceutically acceptable salts thereof, or mixtures of same, for the use in the treatment or prophylaxis of diseases, in particular cancer or conditions with dysregulated immune responses or other disorders associated with aberrant DGKζ signaling, particularly liquid and solid tumours.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prophylaxis of diseases, in particular cancer or conditions with dysregulated immune responses or other disorders associated with aberrant DGKζ signaling, particularly liquid and solid tumours.

In accordance with a further aspect, the present invention covers the use of a compound of general formula (I), as described supra, or stereoisomers, tautomers, N-oxides, hydrates, solvates, and salts thereof, particularly pharmaceutically acceptable salts thereof, or mixtures of same, in a method of treatment or prophylaxis of diseases, in particular cancer or conditions with dysregulated immune responses or other disorders associated with aberrant DGKζ signaling, particularly liquid and solid tumours.

In accordance with a further aspect, the present invention covers use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular cancer or conditions with dysregulated immune responses or other disorders associated with aberrant DGKζ signaling, particularly liquid and solid tumours.

In accordance with a further aspect, the present invention covers a method of treatment or prophylaxis of diseases, in particular cancer or conditions with dysregulated immune responses or other disorders associated with aberrant DGKζ signaling, particularly liquid and solid tumours, using an effective amount of a compound of general formula (I), as described supra, or stereoisomers, tautomers, N-oxides, hydrates, solvates, and salts thereof, particularly pharmaceutically acceptable salts thereof, or mixtures of same.

In accordance with a further aspect, the present invention covers pharmaceutical compositions, in particular a medicament, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore covers pharmaceutical compositions, in particular medicaments, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia,

- fillers and carriers (for example cellulose, microcrystalline cellulose (such as, for example, Avicel®), lactose, mannitol, starch, calcium phosphate (such as, for example, Di-Cafos®)),
- ointment bases (for example petroleum jelly, paraffins, triglycerides, waxes, wool wax, wool wax alcohols, lanolin, hydrophilic ointment, polyethylene glycols),
- bases for suppositories (for example polyethylene glycols, cacao butter, hard fat),
- solvents (for example water, ethanol, isopropanol, glycerol, propylene glycol, medium chain-length triglycerides fatty oils, liquid polyethylene glycols, paraffins),
- surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor), polyoxethylene fatty acid esters, polyoxyethylene fatty alcohol ethers, glycerol fatty acid esters, poloxamers (such as, for example, Pluronic®),
- buffers, acids and bases (for example phosphates, carbonates, citric acid, acetic acid, hydrochloric acid, sodium hydroxide solution, ammonium carbonate, trometamol, triethanolamine),
- isotonicity agents (for example glucose, sodium chloride),
- adsorbents (for example highly-disperse silicas),
- viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine),
- disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSom®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention covers pharmaceutical combinations, in particular medicaments, comprising at least one compound of general formula (I) of the present invention and at least one or more further active ingredients, in particular for the treatment and/or prophylaxis of cancer or conditions with dysregulated immune responses or other disorders associated with aberrant DGKζ signaling, particularly liquid and solid tumours.

Particularly, the present invention covers a pharmaceutical combination, which comprises:
one or more first active ingredients, in particular compounds of general formula (I) as defined supra, and
one or more further active ingredients, in particular in particular immune checkpoint inhibitors.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

Based upon standard laboratory techniques known to evaluate compounds useful for the treatment of cancer or conditions with dysregulated immune responses or other disorders associated with aberrant DGKζ signaling, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

General Syntheses of Compounds of the Present Invention

The compounds according to the invention of general formula (I) can be prepared according to the following Schemes 1, 2, 3 and 4. The schemes and procedures described below illustrate synthetic routes to the compounds of general formula (I) of the invention and are not intended to be limiting. It is clear to the person skilled in the art that the order of transformations as exemplified in Schemes 1, 2, 3 and 4 can be modified in various ways. The order of transformations exemplified in these schemes is therefore not intended to be limiting. In addition, modification of any of the substituents, $R^1$, $R^2$, $R^3$ or $R^4$ can be achieved before and/or after the exemplified transformations. These modifications can be such as the introduction of protecting groups, cleavage of protecting groups, reduction or oxidation of functional groups, halogenation, metalation, substitution, or coupling reactions such as amide couplings (couplings of carboxylic acids with amines) or transition metal catalysed coupling reactions (such as the well-known Suzuki coupling) known to the person skilled in the art. These transformations include those which introduce a functionality which allows for further modification of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

Suitable routes for the preparation of compounds of formulae (I-a) and (I-b), which are sub-sets of general formula (I), which when taken together they form, and for the preparation of compounds of formula (I-c) which, in turn constitutes a sub-set of formula (I-a), are described in Schemes 1, 2, 3 and 4.

Scheme 1: Route for the preparation of compounds of formula (I-a), a sub-set of general formula (I) in which $R^3$ represents an amino group, from isothiocyanates of formula (II) and ketones of formula (III).

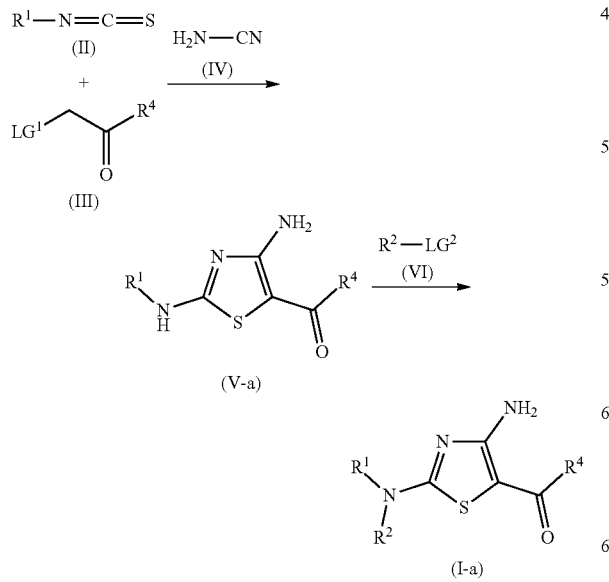

Compounds of formula (I-a), which constitutes a sub-set of general formula (I) in which $R^3$ represents an amino group, can be prepared from isothiocyanates of formula (II), in which $R^1$ has the meaning as given for general formula (I), and ketones of formula (III), in which $R^1$ has the meaning as given for general formula (I), and in which $LG^1$ represents a leaving group as defined herein, preferably a chlorine, bromine, or iodine atom, more preferably a bromine atom, by reacting with cyanamide (IV), in the presence of a non-nucleophilic base, preferably 1,8-diazabicyclo(5.4.0)undec-7-ene (herein also being referred to as DBU, CAS-RN 6674-22-2), in a dipolar aprotic solvent as defined herein, preferably acetonitrile, at a temperature in the range from 0° C. to 50° C., preferably 15° C. to 30° C., more preferably at room temperature, for a time in the range from 1 hour to 100 hours, preferably from 1 hour to 10 hours, more preferably from 2 hours to 4 hours, to give intermediate compounds of formula (V-a). Said intermediate compounds of formula (V-a) can subsequently be reacted with compounds of formula (VI), in which $R^2$ has the meaning as given for general formula (I), and in which $LG^2$ represents a leaving group as defined herein, preferably a chlorine, bromine, or iodine atom, or a (methylsulfonyl)oxy or [(4-methylphenyl)sulfonyl]oxy group, more preferably a bromine atom, in a dipolar aprotic solvent as defined herein, preferably N,N-dimethylformamide, at a temperature in the range from 60° C. to 120° C., preferably 80° C. to 100° C., more preferably 90° C., for a time in the range from 30 minutes to 24 hours, preferably from 1 hour to 4 hours, more preferably 2 hours, to give compounds of the present invention, of formula (I-a). Said conversion of intermediate compounds of formula (V-a) into compounds of the present invention of formula (I-a) by reacting with compounds of formula (VI) can also be accomplished advantageously in a dipolar aprotic solvent as defined herein, preferably N,N-dimethylformamide, at a temperature in the range from 0° C. to 60° C., preferably 10° C. to 40° C., more preferably at room temperature as defined herein, for a time in the range from 6 hours to 48 hours, preferably from 12 hour to 24 hours. Specific examples are described in the Experimental Section. As indicated in the introductory paragraph of this section, substituents, e.g. those attached to $R^1$ and $R^4$, can be modified by various methods known to the person skilled in the art during this synthesis route or on the final step. Specific examples are described in the Experimental Section.

Scheme 2: Alternative route for the preparation of compounds of formula (I-a), a sub-set of general formula (I) in which $R^3$ represents an amino group, from intermediates of formula (V-a).

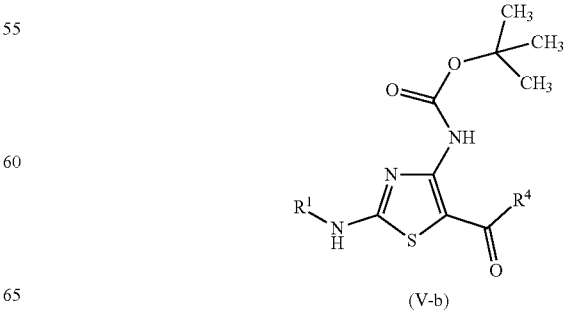

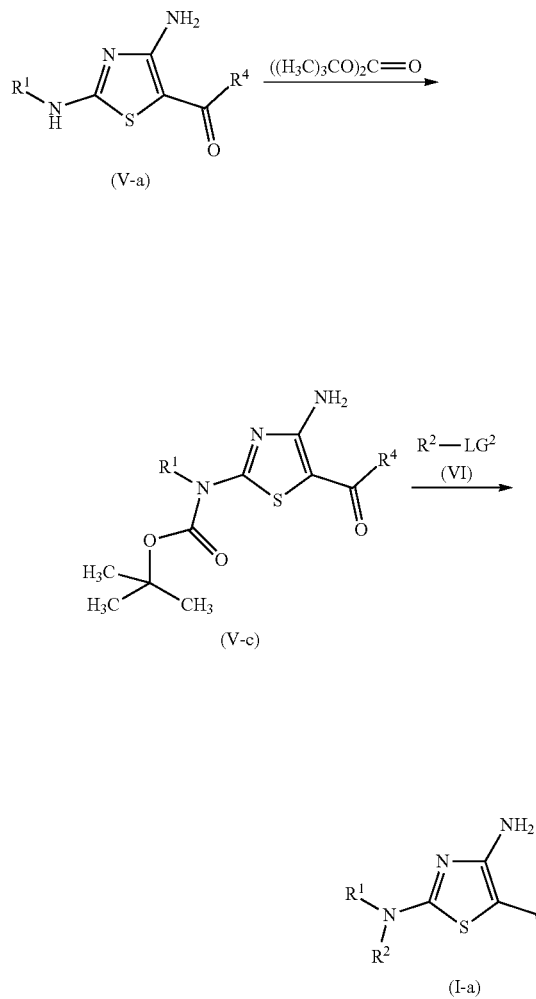

(V-a)

(V-c)

(I-a)

Scheme 3: Route for the preparation of compounds of formula (I-b), a sub-set of general formula (I) in which R³ represents a methyl group, from isothiocyanates of formula (II) and ketones of formula (III).

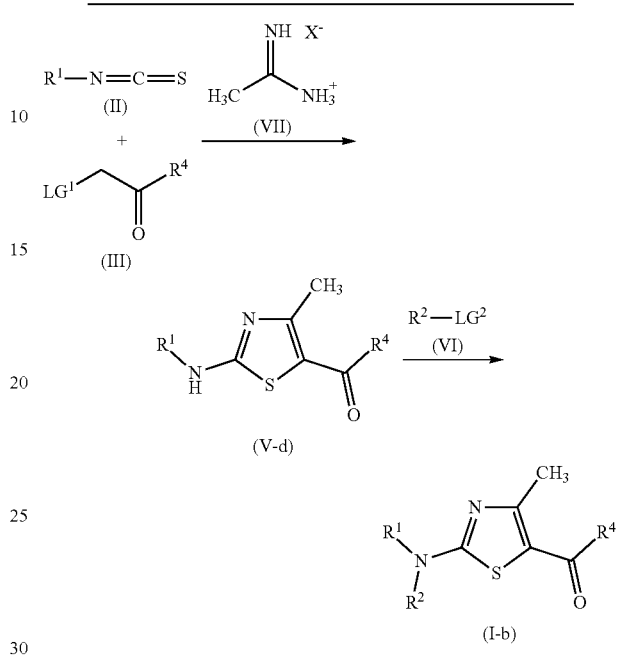

(II)

(VII)

(III)

(V-d)

(I-b)

The reaction between intermediates of the formula (V-a) and compounds of formula (VI) proceeds selectively at the nitrogen atom attached to C-2 of the thiazole, not involving the —NH₂ group attached to C-4. As shown in Scheme 2, this also applies to the analogous reaction with di-tert-butyl dicarbonate which gives compounds of formula (V-c) but not compounds of formula (V-b), said compounds of formula (V-c) being converted, upon reaction with compounds of formula (VI), in which R² has the meaning as given for general formula (I), and in which LG² represents a leaving group as defined herein, preferably a chlorine, bromine, or iodine atom, more preferably a bromine atom, in a dipolar aprotic solvent as defined herein, preferably N,N-dimethylformamide, at a temperature in the range from 60° C. to 120° C., preferably 80° C. to 100° C., more preferably 90° C., for a time in the range from 30 minutes to 24 hours, preferably from 1 hour to 4 hours, more preferably 2 hours, into compounds of the present invention, of formula (I-a), likewise. Specific examples are described in the Experimental Section.

Compounds of formula (I-b), which constitutes a sub-set of general formula (I) in which R³ represents a methyl group, can be prepared from isothiocyanates of formula (II), in which R¹ has the meaning as given for general formula (I), and ketones of formula (III), in which R⁴ has the meaning as given for general formula (I), and in which LG¹ represents a leaving group as defined herein, preferably a chlorine, bromine, or iodine atom, more preferably a bromine atom, by reacting with a salt of ethanimidamide of formula (VII), in which X⁻ represents a monovalent anion, preferably chloride, bromide, iodide or acetate, more preferably chloride, in the presence of a non-nucleophilic base, preferably 1,8-diazabicyclo(5.4.0)undec-7-ene (herein also being referred to as DBU, CAS-RN 6674-22-2), in a dipolar aprotic solvent as defined herein, preferably acetonitrile, at a temperature in the range from 0° C. to 50° C., preferably 15° C. to 30° C., more preferably at room temperature, for a time in the range from 1 hour to 100 hours, preferably from 1 hour to 10 hours, more preferably from 2 hours to 4 hours, to give intermediate compounds of formula (V-d). Said intermediate compounds of formula (V-d) can subsequently be reacted with compounds of formula (VI), in which R² has the meaning as given for general formula (I), and in which LG² represents a leaving group as defined herein, preferably a chlorine, bromine, or iodine atom, or a (methylsulfonyl)oxy or [(4-methylphenyl)sulfonyl]oxy group, more preferably a bromine atom, in a dipolar aprotic solvent as defined herein, preferably N,N-dimethylformamide, at a temperature in the range from 60° C. to 120° C., preferably 80° C. to 100° C., more preferably 90° C., for a time in the range from 30 minutes to 24 hours, preferably from 1 hour to 4 hours, more preferably 2 hours, to give compounds of the present invention, of formula (I-b). Specific examples are described in the Experimental Section.

Compounds of formulae (II), (III), (IV), (VI), and (VII) are largely commercially available or can be prepared using methods known to the person skilled in the art, see e.g. F. Calderon et al. Journal of Medicinal Chemistry 2017, 60 (16), 6880-6896, for the preparation of isothiocyanates of formula (II); see also the synthesis protocols of Intermediates 200-208 in the Experimental Section, or Y. Xing et al. European Journal of Organic Chemistry 2017, 2017 (4), 781-785; A. Wu et al. Tetrahedron 2013, 69 (31), 6392-6398, for the preparation of ketones of formula (III); see also the synthesis protocols of Intermediates 198 and 199 in the Experimental Section.

Alternatively, compounds of formula (I-a), which constitutes a sub-set of general formula (I) in which $R^3$ represents an amino group, can be prepared from precursors in which the $R^4$ group substituted with a group not covered within the definition of $R^4$ (such as a carboxy group), which however allows for establishing $R^4$ groups featuring diverse substituents from a common precursor, such as carboxamides of formula (I-c) (Scheme 4).

Scheme 4: Route for the preparation of further compounds of the invention, of formula (I-c), from advanced intermediate compounds of formula (VIII).

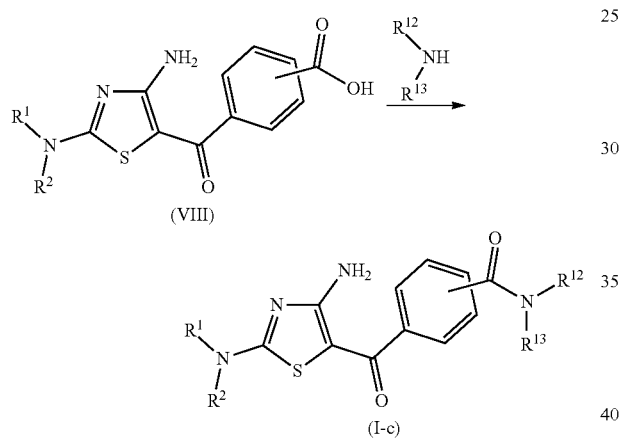

Scheme 4 exemplifies (without any limitation to the invention) the conversions of advanced intermediates of formula (VIII), which can be prepared using the methods described in the preceding Schemes, in combination with well-established methods such as the saponification of carboxylic esters, Thus, carboxylic acid derivatives of formula (VIII) can be reacted in well-known amide coupling reactions with amines $(R^{12})(R^{13})NH$, in the presence of a coupling reagent such as HATU and a tertiary amine such as triethylamine or N,N-diisopropylethylamine, and optionally in the presence of DMAP, in a dipolar aprotic solvent as defined herein, preferably N,N-dimethylformamide, at a temperature in the range from 0° C. to 50° C., preferably at room temperature as defined herein, for a time in the range from 2 hours to 24 hours, preferably from 12 hour to 20 hours, to give carboxamide compounds of the invention, of formula (I-c). Specific examples are described in the Experimental Section.

In accordance with a second aspect, the present invention covers methods of preparing compounds of formulae (I-a) and (I-b), which are sub-sets of general formula (I), supra, which when taken together they form.

In accordance with a second embodiment of the second aspect, said methods comprise the step of allowing an intermediate compound of formula (V-a):

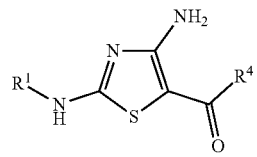

in which $R^1$ and $R^4$ are as defined for the compound of general formula (I) as defined supra, to react with a compound of formula (VI):

in which $R^2$ is as defined for the compound of general formula (I) as defined supra, and in which $LG^2$ represents a leaving group as defined herein, thereby giving a compound of formula (I-a):

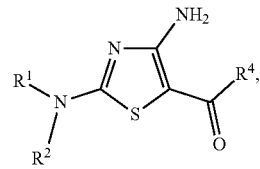

in which $R^1$, $R^2$ and $R^4$ are as defined supra.

In accordance with a third embodiment of the second aspect, the present invention covers methods of preparing compounds of formula (I-a), said methods comprising the step of allowing an intermediate compound of formula (V-c):

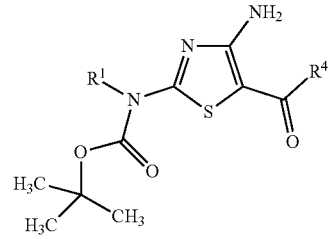

in which $R^1$ and $R^4$ are as defined for the compound of general formula (I) as defined supra, to react with a compound of formula (VI):

in which $R^2$ is as defined for the compound of general formula (I) as defined supra, and in which $LG^2$ represents a leaving group as defined herein, thereby giving a compound of formula (I-a):

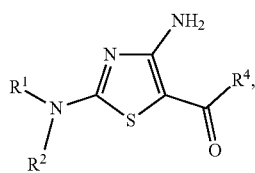
(I-a)

in which $R^1$, $R^2$ and $R^4$ are as defined supra.

In accordance with a fourth embodiment of the second aspect, the present invention covers methods of preparing compounds of formula (I-b), said methods comprising the step of allowing an intermediate compound of formula (V-d):

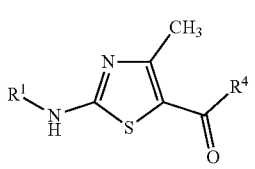
(V-d)

in which $R^1$ and $R^4$ are as defined for the compound of general formula (I) as defined supra, to react with a compound of formula (VI):

(VI)

in which $R^2$ is as defined for the compound of general formula (I) as defined supra, and in which $LG^2$ represents a leaving group as defined herein,
thereby giving a compound of formula (I-b):

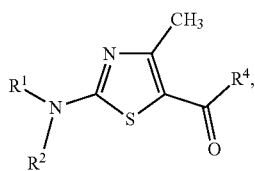
(I-b)

in which $R^1$, $R^2$ and $R^4$ are as defined supra.

In accordance with a third aspect, the present invention covers methods of preparing compounds of formulae (I-a) and (I-b), which are sub-sets of general formula (I), supra, which when taken together they form.

In accordance with a second embodiment of the third aspect, said methods comprise the step of allowing an intermediate compound of formula (V-a):

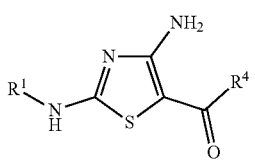
(V-a)

in which $R^1$ and $R^4$ are as defined for the compound of general formula (I) as defined supra, to react with a compound of formula (VI):

(VI)

in which $R^2$ is as defined for the compound of general formula (I) as defined supra, and in which $LG^2$ represents a leaving group as defined herein,
thereby giving a compound of formula (I-a):

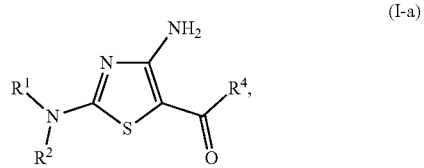
(I-a)

in which $R^1$, $R^2$ and $R^4$ are as defined supra,
then optionally converting said compound into solvates, salts and/or solvates of such salts using the corresponding (i) solvents and/or (ii) bases or acids.

In accordance with a third embodiment of the third aspect, the present invention covers methods of preparing compounds of formula (I-a), said methods comprising the step of allowing an intermediate compound of formula (V-c):

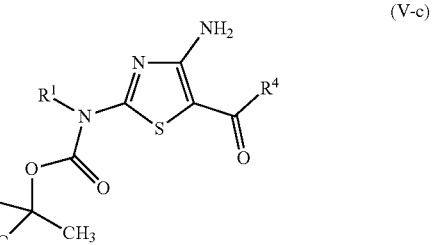
(V-c)

in which $R^1$ and $R^4$ are as defined for the compound of general formula (I) as defined supra, to react with a compound of formula (VI):

(VI)

in which $R^2$ is as defined for the compound of general formula (I) as defined supra, and in which $LG^2$ represents a leaving group as defined herein,
thereby giving a compound of formula (I-a):

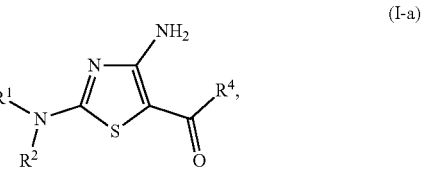
(I-a)

in which $R^4$, $R^2$ and $R^4$ are as defined supra, then optionally converting said compound into solvates, salts and/or solvates of such salts using the corresponding (i) solvents and/or (ii) bases or acids.

In accordance with a fourth embodiment of the third aspect, the present invention covers methods of preparing compounds of formula (I-b), said methods comprising the step of allowing an intermediate compound of formula (V-d):

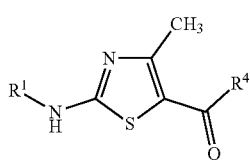
(V-d)

in which $R^1$ and $R^4$ are as defined for the compound of general formula (I) as defined supra, to react with a compound of formula (VI):

$$R^2-LG^2,$$ (VI)

in which $R^2$ is as defined for the compound of general formula (I) as defined supra, and in which $LG^2$ represents a leaving group as defined herein, thereby giving a compound of formula (I-b):

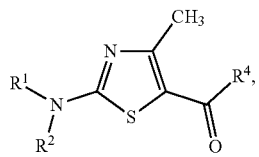
(I-b)

in which $R^1$, $R^2$ and $R^4$ are as defined supra, then optionally converting said compound into solvates, salts and/or solvates of such salts using the corresponding (i) solvents and/or (ii) bases or acids.

The present invention covers methods of preparing compounds of the present invention of general formula (I), said methods comprising the steps as described in the Experimental Section herein.

In accordance with a fourth aspect, the present invention covers intermediate compounds which are useful for the preparation of the compounds of formulae (I-a) and (I-b), which are sub-sets of general formula (I), supra, which when taken together they form.

In accordance with a second embodiment of the fourth aspect, the present invention covers the intermediate compounds of formula (V-c):

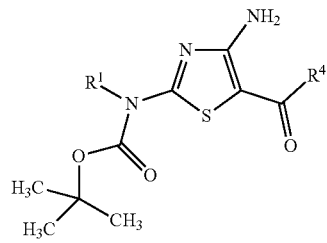
(V-c)

in which $R^1$ and $R^4$ are as defined for the compound of general formula (I) supra.

In accordance with a third embodiment of the fourth aspect, the present invention covers the intermediate compounds of formula (V-d):

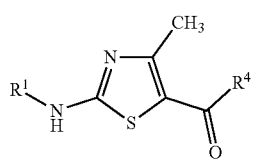
(V-d)

in which $R^1$ and $R^4$ are as defined for the compound of general formula (I) supra.

In accordance with a fifth aspect, the present invention covers the use of intermediate compounds for the preparation of the compounds of formulae (I-a) and (I-b), which are sub-sets of general formula (I), supra, which when taken together they form.

In accordance with a second embodiment of the fifth aspect, the present invention covers the intermediate compounds of formula (V-a):

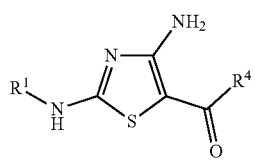
(V-a)

in which $R^1$ and $R^4$ are as defined for the compound of general formula (I) supra, for the preparation of a compound of formula (I-a) as defined supra.

In accordance with a third embodiment of the fifth aspect, the present invention covers the intermediate compounds of formula (V-c):

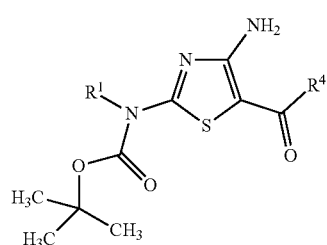
(V-c)

in which $R^1$ and $R^4$ are as defined for the compound of general formula (I) supra, for the preparation of a compound of formula (I-a) as defined supra.

In accordance with a fourth embodiment of the fifth aspect, the present invention covers the intermediate compounds of formula (V-d):

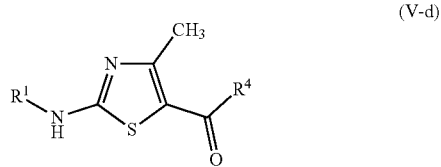

in which $R^1$ and $R^4$ are as defined for the compound of general formula (I) supra, for the preparation of a compound of formula (I-b) as defined supra.

The present invention covers intermediate compounds which are disclosed in the Example Section of this text, infra.

The present invention covers the use of intermediate compounds which are disclosed in the Example Section of this text, infra.

The present invention covers any sub-combination within any embodiment or aspect of the present invention of intermediate compounds of formulae (V-a), (V-c) and (V-d), supra.

DESCRIPTION OF THE FIGURES

FIG. 1: DGKz_hu_1 encoding human DGKζ M1 to V928 plus N-terminal Flag-Tag, as described under SEQ ID No. 1.

FIG. 2: SIINFEKL amino acid sequence, as described under SEQ ID No. 2.

FIG. 3: OVA-30 peptide sequence, as described under SEQ ID No. 3.

FIG. 4: FLAG-Tag, as described under SEQ ID No. 4.

FIG. 5: Kozak sequence for translation initiation, as described under SEQ ID No. 5.

EXPERIMENTAL SECTION—GENERAL PART

Figure 6:
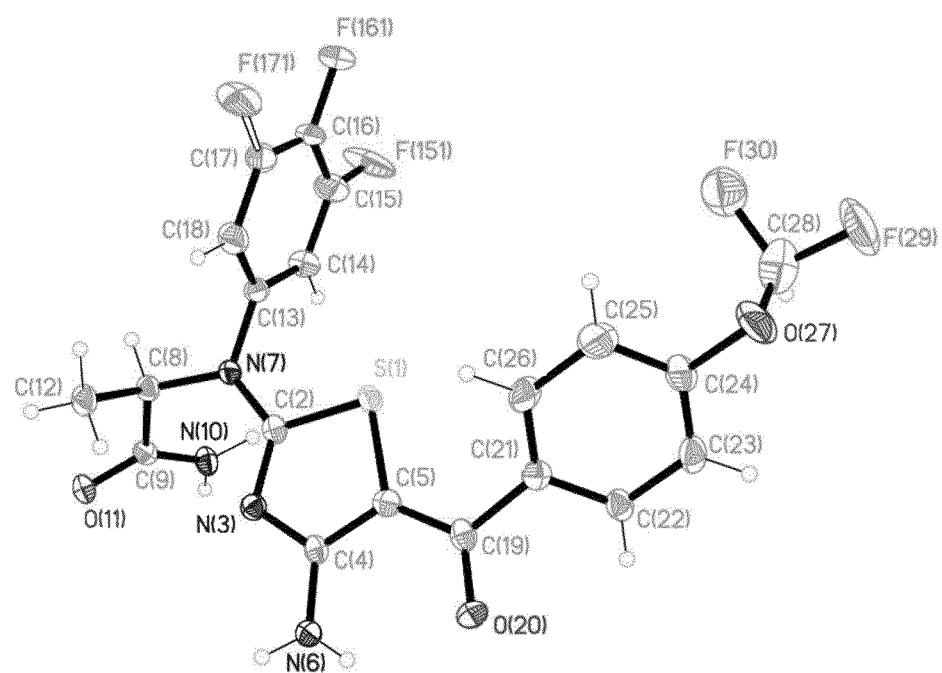
FIG. 6: 50% thermal ellipsoids of Example 49.2, Molecule 1. F171 and F151 represents the two refined positions for the 180° disorder over the C13-C16 axis.

NMR peak forms are stated as they appear in the spectra, possible higher order effects have not been considered. The multiplicities are stated according to the signal form which appears in the spectrum, NMR-spectroscopic effects of a higher order were not taken into consideration. Multiplicity of the NMR signals: s=singlet, d=doublet, t=triplet, q=quartet, quin=quintet, br=broad signal, m=multiplet. NMR signals: shift in [ppm]. Combinations of multiplicity could be e.g. dd=doublet from doublet.

Chemical names were generated using software programs such as the ACD/Name batch version 14.05 from ACD/Labs and BioVia Draw 2019 Version 19.1 NET, and chemical names were adapted if needed. In some cases generally accepted names of commercially available reagents were used in place of chemical names generated using above-mentioned software programs.

All reagents the synthesis of which is not described in the experimental part were purchased commercially, or said reagents are known compounds or can be formed from known compounds by known methods by a person skilled in the art.

Table 1 lists the abbreviations used in this paragraph and in the Examples section as far as they are not explained within the text body. Other abbreviations have their meanings customary per se to the skilled person.

TABLE 1

| | Abbreviations |
|---|---|
| $CDCl_3$ | deuterochloroform |
| DAD | diode array detector |
| SQD | single quadrupole detector |
| Azura UVD | single variable wavelength UV detector for HPLC |
| DMF | N,N-dimethylformamide |
| DMSO-d6 | deuterated dimethyl sulphoxide |
| DMSO | dimethyl sulphoxide |
| ELSD | evaporative light scattering detector |
| ESIpos | electrospray ionization positive |
| Expl. | example |
| HATU | (7-aza-1H-benzotriazol-1-yl)-1,1,3,3-tetramethyluronium hexafluorophosphate |
| HPLC | high-pressure liquid chromatography |
| LC-MS | liquid chromatography coupled with mass spectrometry |
| mL | milliliter |
| min | minute(s) |
| MTBE | methyl tert-butyl ether |
| RP-HPLC | reverse-phase high-pressure liquid chromatography |
| Rt | retention time |
| rt | room temperature |
| sat. | saturated |
| THF | tetrahydrofurane |
| EtOAc | ethyl acetate |
| TLC | thin layer chromatography |
| rac | racemic |
| μM | micromolar |
| M | molar |
| UPLC | Ultra high performance chromatography |
| UPLC-MS | Ultra high performance chromatography coupled with mass spectrometry |
| BEH | ethylene bridged hybrid |
| CSH | charged surface hybrid |
| UV | ultra violet |
| CAS-RN | chemical abstracts service registry number |
| NMR | nuclear magnetic resonance |
| MHz | Megahertz |

Analytical UPLC-MS Standard Procedures
Method 1/Acidic
Instrument: Waters Acquity UPLC-MS SQD 3001; column: Acquity UPLC BEH C18 1.7 50×2.1 mm; eluent A: water+0.1 vol % formic acid, eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD Method 2/Basic
Instrument: Waters Acquity UPLC-MS SQD 3001; column: Acquity UPLC BEH C18 1.7 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD Method 3/Basic
Instrument: Waters Acquity UPLC-MS SingleQuad; Column: Acquity UPLC CSH C18 1.7 μm 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; DAD scan: 210-400 nm.

Optical Rotation

Optical rotations were measured with a JASCO Polarimeter 2000 using the solvent and concentration stated in each case at 20° C., wavelength 589 nm, integration time 10 s, layer thickness 100 mm.

Compound Purification—General

The example compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartridges KP-Sil® or KP-NH® in combination with a Biotage autopurifier system (SP4® or Isolera Four®) and eluents such as gradients of hexane/ethyl acetate or dichloromethane/methanol. In some cases, the compounds may be purified by preparative HPLC using for example a Waters autopurifier system equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

Specific methods are described below, and in the respective protocols describing the preparations of example compounds and intermediates.

Preparative HPLC

Instrument: pump: Labomatic HD-3000, head HDK 280, low pressure gradient module ND-B1000; manual injection valve: Rheodyne 3725i038; detector: Knauer Azura UVD 2.15; collector: Labomatic Labocol Vario-4000; column: Chromatorex RP C-18 10 µm, 125×30 mm; eluent; gradient; UV-Detection. Eluent solvent A: water+0.1 vol % formic acid (99%; acidic) or 0.2 vol % aqueous ammonia (32%, basic), solvent B: acetonitrile; flow 150 mL/min.

Gradients:

Method A: 0.00-0.50 min 1% B, 0.50-6.00 min 1-25% B, 6.00-6.10 min 25-100% B, 6.10-8.00 min 100% B Method B: 0.00-0.50 min 10% B, 0.50-6.00 min 10-50% B, 6.00-6.10 min 50-100% B, 6.10-8.00 min 100% B Method C: 0.00-0.50 min 15% B, 0.50-6.00 min 15-55% B, 6.00-6.10 min 55-100% B, 6.10-8.00 min 100% B Method D: 0.00-0.50 min 30% B, 0.50-6.00 min 30-70% B, 6.00-6.10 min 70-100% B, 6.10-8.00 min 100% B Method E: 0.00-0.50 min 40% B, 0.50-6.00 min 40-80% B, 6.00-6.10 min 80-100% B, 6.10-8.00 min 100% B Method F:

Instrument: Waters autopurification system; column: Waters CSH C18 5µ 100×30 mm; eluent A: water+0.1 Vol-% aqueous ammonia (32%), eluent B: acetonitrile, DAD scan: 210-400 nm; MS Instrument: QDA (Waters); Collector-Trigger: DAD-MS flow rate: 60 mL/min Chiral HPLC and Stereochemistry Assignments Separations of stereoisomeric mixtures, such as racemic compounds, by chiral HPLC can result in the isolation of single stereoisomers without known configuration of the respective stereogenic centres in the isolated isomers. In the following, the full chemical names of all such separated isomers obtained from an isomeric mixture, including (R) and (S) configurations, are listed in alphabetical order together with all respective intermediate or example numbers, followed by the individual isomers with data on their analytics, isolation and yield, followed by descriptors such as "(enantiomer 1)", "(stereoisomer 2)", and the like. Likewise, example compounds obtained from starting materials being single stereoisomers of unknown absolute configuration are disclosed herein in an analogous fashion. The order of the full chemical names (including (R) and (S) configurations) cannot be construed as to encode for any correlation to the individual intermediate or example numbers.

Preparative Flash Chromatography

Instrument: Biotage Isolera Four; pump: Dual-Piston; flow rate: 1 to 200 mL/min; internal detector: 200-400 nm (variable UV detector); solvent inlets: 4; cartridges: Biotage SNAP Ultra™, sizes: 10 g, 25 g, 50 g, 100 g, 340 g, media: Biotage® HP-Sphere—25 micron spherical silica, resolution: minimum 7000 N/m (plates per meter) typical 10 000 N/m; solvent A: hexane, solvent B: ethyl acetate, solvent C: dichlormethane, solvent D: ethanol; solvent E: methanol; UV collection modes: single/dual/λ-All wavelengths (variable UV); fractionation modes: volume, threshold, threshold with volume, low slope, medium slope, custom slope or via external detection Method X: gradient with solvent A and B, λ-all Method Y: gradient with solvent C and D, λ-all Method Z: gradient with solvent C and E, λ-all The various aspects of the invention described in this application are illustrated by the following examples which are not meant to limit the invention in any way.

The example testing experiments described herein serve to illustrate the present invention and the invention is not limited to the examples given.

EXPERIMENTAL SECTION—PREPARATION OF INTERMEDIATES

Intermediate 1

1-(4-{[tert-butyl(dimethyl)silyl]oxy}phenyl)ethan-1-one

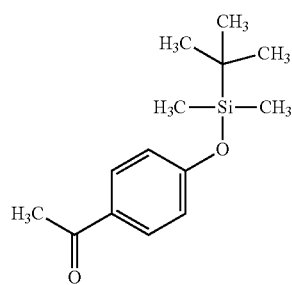 [SMILES: CC(=O)c1ccc(O[Si](C)(C)C(C)(C)C)cc1]

1-(4-Hydroxyphenyl)ethan-1-one (2.00 g, 14.7 mmol) was provided in dichloromethane (25 mL) at 0° C. 4-dimethylaminopyridine (100 mg, 819 µmol; CAS-RN 1122-58-3) and imidazole (2.00 g, 29.4 mmol; CAS-RN 288-32-4) were added. To the mixture was added dropwise a solution of tert-butyl(chloro)dimethylsilane (3.32 g, 22.0 mmol) dichloromethane. The reaction mixture was stirred for 2 h at rt. The mixture was poured into aqueous sodium bicarbonate solution and extracted with dichloromethane. The organic layer was washed with water, dried and concentrated under reduced pressure. The residue was purified by flash chromatography (silica gel, hexane/ethyl acetate gradient 0-10%) to give 3.7 g (96% yield) of the title compound.

$^1$H-NMR (400 MHz, CHLOROFORM-d): δ ppm=0.23 (s, 6H), 0.99 (s, 9H), 2.55 (s, 3H), 6.85-6.89 (m, 2H), 7.86-7.90 (m, 2H)

Intermediate 2 tert-butyl(dimethyl)(4-{1-[(trimethylsilyl)oxy]ethenyl}phenoxy)silane

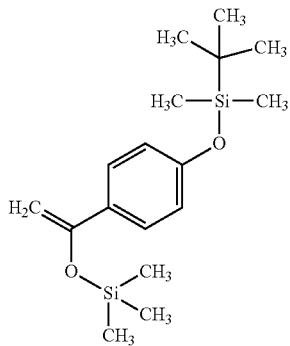 [SMILES: C=C(O[Si](C)(C)C)c1ccc(O[Si](C)(C)C(C)(C)C)cc1]

Lithium diisopropylamide solution in tetrahydrofurane (1.5 mL, 2.0 M, 3.0 mmol; CAS-RN 4111-54-0) was provided under argon at −70° C., and 1-(4-{[tert-butyl(dimethyl)silyl]oxy}phenyl)ethan-1-one (500 mg, 2.00 mmol, Intermediate 1) was added. The mixture was allowed to warm to 0° C. and was stirred for 30 min at 0° C. Chlorotrimethylsilane (1.6 mL, 13 mmol; CAS-RN 75-77-4) was added and the reaction mixture was stirred for 4 h at rt. The mixture was poured into water/brine and extracted with methyl tert-butylether. The combined organic layer was washed with brine, dried and concentrated under reduced pressure to give 700 mg (98% yield) of the title compound as a yellow oil.

$^1$H-NMR (400 MHz, CHLOROFORM-d): δ ppm=0.07 (s, 9H), 0.77-0.82 (m, 15H), 4.13-4.15 (m, 1H), 4.60 (d, J=1.77 Hz, 1H), 6.57-6.61 (m, 2H), 7.24-7.29 (m, 2H).

Intermediate 3

2-bromo-1-(4-{[tert-butyl(dimethyl)silyl]oxy}phenyl)ethan-1-one

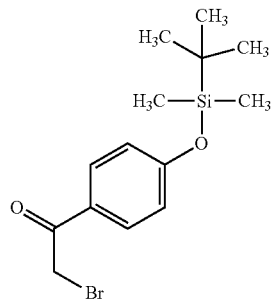 [SMILES: CC(C)(C)[Si](C)(C)Oc1ccc(C(=O)CBr)cc1]

Tert-butyl(dimethyl)(4-{1-[(trimethylsilyl)oxy]ethenyl}phenoxy)silane (695 mg, 2.15 mmol; Intermediate 2) was provided at 0° C. in tetrahydrofurane (57 mL) and N-bromosuccinimide (460 mg, 2.59 mmol; CAS-RN 128-08-5) was added. The reaction mixture was stirred overnight at rt. The mixture was treated with water/brine and extracted with ethyl acetate. The combined organic layer was washed with brine, dried and concentrated under reduced pressure. The residue was purified by flash chromatography (silica, hexane/ethyl acetate gradient 0-10%) to give 460 mg (62% yield) of the title compound.

$^1$H-NMR (400 MHz, CHLOROFORM-d): δ ppm=0.24-0.26 (m, 6H), 0.99 (s, 9H), 4.40 (s, 2H), 6.90 (d, J=8.87 Hz, 2H), 7.91 (d, J=8.87 Hz, 2H).

LC-MS (method 2): $R_t$=1.58 min; MS (ESIpos): m/z=329.2 [M+H]$^+$

Intermediate 4

[4-amino-2-(4-methoxy-2-methyl-anilino)thiazol-5-yl]-phenyl-methanone

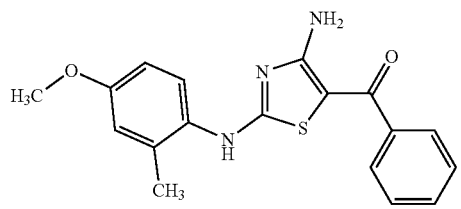 [SMILES: COc1ccc(Nc2nc(N)c(C(=O)c3ccccc3)s2)c(C)c1]

1-Isothiocyanato-4-methoxy-2-methylbenzene (225.1 mg, 1.26 mmol) was dissolved in acetonitrile (25 mL) followed by the addition of 1,8-diazabicyclo(5.4.0)undec-7-ene (190 mg, 1.26 mmol) and cyanamide (63.4 mg, 1.51 mmol). After stirring for 45 min at rt further 1,8-diazabicyclo(5.4.0)undec-7-ene (96 mg, 0.62 mmol) and 2-bromo-1-phenylethanone (225 mg, 1.26 mmol) were added. The reaction mixture was stirred at rt overnight. The suspension was treated with water and the precipitate was isolated by filtration, washed with water and some ethyl acetate and dried by lyophilization to give 351 mg (78% yield) of the title compound.

¹H-NMR: (400 MHz, DMSO-d6): δ ppm=2.19 (s, 3H), 3.74 (s, 3H), 6.78 (dd, J=8.62, 2.79 Hz, 1H), 6.88 (d, J=2.79 Hz, 1H), 7.26 (d, J=8.62 Hz, 1H), 7.34-7.47 (m, 3H), 7.50-7.62 (m, 2H), 7.75-8.52 (m, 2H), 9.90-10.16 (br s, 1H).

LC-MS (method 2) Rt=1.09 min; MS (ESIpos): m/z=340.1 [M+H]⁺

The following intermediates were prepared from commercial starting materials stated in Table 2, below, using the procedure as for Intermediate 4, followed by purification by chromatography if needed. If no purification is specified, the respective title compound was isolated as crude product.

The crude product was either purified by RP-HPLC (methods A-D depending on polarity) or by preparative flash chromatography (methods X, Y or Z depending on polarity) if necessary. In case of a missing precipitation, the reaction mixture was extracted three times with ethyl acetate. The combined organic phases were dried over sodium sulfate, filtrated and evaporated to dryness. The crude product was purified by chromatography as stated in Table 2.

TABLE 2

Intermediates 5-77

| Intermediate number | Chemical structure Compound name | Starting materials | Analytics/purification/yield |
|---|---|---|---|
| 5 | 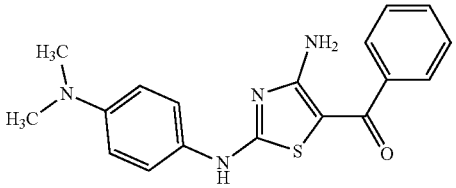 [SMILES: CN(C)c1ccc(Nc2nc(N)c(C(=O)c3ccccc3)s2)cc1] [4-amino-2-[4-(dimethylamino)anilino]thiazol-5-yl]-phenyl-methanone | 4-isothiocyanato-N,N-dimethylaniline; 2-bromo-1-phenylethanone | ¹H-NMR (400 MHz, DMSO-d6): δ ppm = 2.87 (s, 6 H), 6.72 (d, J = 9.13 Hz, 2 H), 7.30 (br d, J = 8.36 Hz, 2 H), 7.38-7.51 (m, 3 H), 7.61 (dd, J = 7.48, 2.15 Hz, 2 H), 7.82-8.55 (m, 2 H), 10.32-10.58 (br s, 1 H). LC-MS (method 1) Rt = 1.00 min; MS (ESIpos): m/z = 339.3 [M + H]⁺ RP-HPLC (method C, acidic) 10% yield |
| 6 | 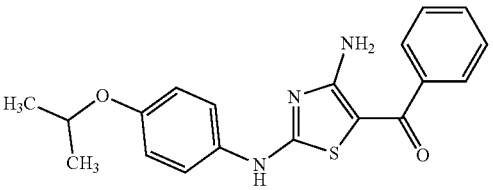 [SMILES: CC(C)Oc1ccc(Nc2nc(N)c(C(=O)c3ccccc3)s2)cc1] [4-amino-2-(4-isopropoxyanilino)thiazol-5-yl]-phenyl-methanone | 1-isopropoxy-4-isothiocyanatobenzene; 2-bromo-1-phenylethanone | ¹H-NMR (400 MHz, DMSO-d6): δ ppm = 1.24 (d, J = 6.08 Hz, 6 H), 4.56 (spt, J = 6.04 Hz, 1 H), 6.88-6.95 (m, 2 H), 7.42-7.49 (m, 5 H), 7.61-7.67 (m, 2 H), 7.89-8.41 (m, 2 H), 10.57-10.61 (br s, 1 H). LC-MS (method 1) Rt = 1.24 min; MS (ESIpos): m/z = 354.8 [M + H]⁺ RP-HPLC (method D, acidic) 66% yield |
| 7 | 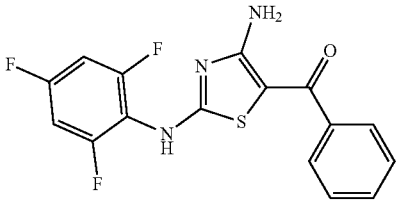 [SMILES: Nc1nc(Nc2c(F)cc(F)cc2F)sc1C(=O)c1ccccc1] [4-amino-2-(2,4,6-trifluoroanilino)thiazol-5-yl]-phenyl-methanone | 1,3,5-trifluoro-2-isothiocyanatobenzene; 2-bromo-1-phenylethanone | ¹H-NMR (400 MHz, DMSO-d6): δ ppm = 7.38 (m, 2 H), 7.43-7.52 (m, 3 H), 7.63 (m, 2 H), 7.97-8.42 (m, 2 H), 10.22-10.38 (br s, 1 H). LC-MS (method 2) Rt = 0.81 min; MS (ESIpos): m/z = 350.5 [M + H]⁺ RP-HPLC (method C, basic) 68% yield |
| 8 | 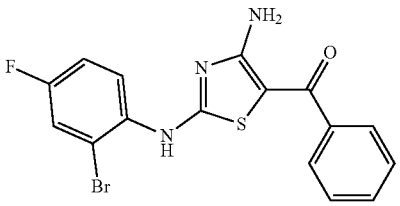 [SMILES: Nc1nc(Nc2ccc(F)cc2Br)sc1C(=O)c1ccccc1] [4-amino-2-(2-bromo-4-fluoro-anilino)thiazol-5-yl]-phenyl-methanone | 2-bromo-4-fluoro-1-isothiocyanatobenzene; 2-bromo-1-phenylethanone | ¹H-NMR (400 MHz, DMSO-d6): δ ppm = 7.33 (td, J = 8.55, 2.91 Hz, 1 H), 7.39-7.51 (m, 3 H), 7.61 (dd, J = 7.48, 1.90 Hz, 2 H), 7.66-7.75 (m, 2 H), 7.96-8.45 (m, 2 H), 10.20-10.49 (br s, 1 H). LC-MS (method 2) Rt = 0.81 min; MS (ESIpos): m/z = 350.5 [M + H]⁺ RP-HPLC (method C, basic) 33% yield |

TABLE 2-continued

Intermediates 5-77

| Intermediate number | Chemical structure / Compound name | Starting materials | Analytics/purification/yield |
|---|---|---|---|
| 9 | [4-amino-2-(4-fluoroanilino)thiazol-5-yl]-(6-methyl-3-pyridyl)methanone | 1-fluoro-4-isothiocyanatobenzene; 2-chloro-1-(6-methylpyridin-3-yl)ethanone | $^1$H-NMR (400 MHz, DMSO-d6): δ ppm = 2.52 (s, 3 H), 7.22 (t, J = 8.87 Hz, 2 H), 7.36 (d, J = 7.86 Hz, 1 H), 7.60-7.67 (m, 2 H), 7.92 (dd, J = 7.86, 2.28 Hz, 1 H), 8.14-8.48 (m, 2 H), 8.72 (d, J = 2.03 Hz, 1 H), 10.87 (s, 1 H). LC-MS (method 2) Rt = 0.86 min; MS (ESIpos): m/z = 329.2 [M + H]$^+$ 72% yield |
| 10 | [4-amino-2-(4-fluoroanilino)thiazol-5-yl]-(4-pyridyl)methanone | 1-fluoro-4-isothiocyanatobenzene; 2-bromo-1-(4-pyridyl)ethanone; hydrobromide (1:1) | $^1$H-NMR (400 MHz, DMSO-d6): δ ppm = 7.20-7.26 (m, 2 H), 7.54-7.59 (m, 1 H), 7.56-7.58 (m, 1 H), 7.60-7.67 (m, 2 H), 8.27-8.47 (m, 2 H), 8.70 (d, J = 5.83 Hz, 2 H), 10.83-11.02 (br s, 1 H). LC-MS (method 2) Rt = 0.77 min; MS (ESIpos): m/z = 315.1 [M + H]$^+$ 76% yield |
| 11 | [4-amino-2-(4-fluoroanilino)thiazol-5-yl]-(2-fluorophenyl)methanone | 1-fluoro-4-isothiocyanatobenzene; 2-bromo-1-(2-fluorophenyl)ethanone | $^1$H-NMR (400 MHz, DMSO-d6): δ ppm = 7.21 (t, J = 8.87 Hz, 2 H), 7.24-7.31 (m, 2 H), 7.44-7.53 (m, 2 H), 7.55-7.63 (m, 2 H), 8.16 (br s, 2 H), 10.79 (s, 1 H). LC-MS (method 2) Rt = 0.97 min; MS (ESIpos): m/z = 332.3 [M + H]$^+$ 92% yield |
| 12 | 4-[(4-amino-5-benzoyl-thiazol-2-yl)amino]benzonitrile | 4-isothiocyanatobenzonitrile; 2-bromo-1-phenylethanone | $^1$H-NMR (400 MHz, DMSO-d6): δ ppm = 7.45-7.52 (m, 3 H), 7.68 (dd, J = 7.73, 1.65 Hz, 2 H), 7.81 (s, 4 H), 8.17-8.40 (m, 2 H), 11.08-11.35 (br s, 1 H). LC-MS (method 2) Rt = 0.92 min; MS (ESIpos): m/z = 321.1 [M + H]$^+$ 56% yield |
| 13 | [4-amino-2-(4-fluoroanilino)thiazol-5-yl]-[4-chloro-3-(trifluoromethyl)phenyl]methanone | 1-fluoro-4-isothiocyanatobenzene; 2-bromo-1-[4-chloro-3-(trifluoromethyl)phenyl]ethanone | $^1$H-NMR (400 MHz, DMSO-d6): δ ppm = 7.22 (t, J = 8.87 Hz, 2 H), 7.66 (br d, J = 4.06 Hz, 2 H), 7.87 (s, 1 H), 7.95-8.01 (m, 1 H), 8.07 (s, 1 H), 8.28-8.49 (m, 2H), 10.90-10.96 (br s, 1 H). LC-MS (method 2) Rt = 1.26 min; MS (ESIpos): m/z = 416.2 [M + H]$^+$ RP-HPLC (method D, basic) 31% yield |

TABLE 2-continued

Intermediates 5-77

| Intermediate number | Chemical structure Compound name | Starting materials | Analytics/purification/yield |
|---|---|---|---|
| 14 | 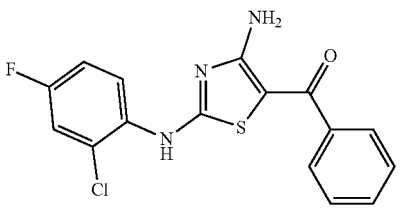<br>[4-amino-2-(2-chloro-4-fluoro-anilino)thiazol-5-yl]-phenyl-methanone | 2-chloro-4-fluoro-1-isothiocyanatobenzene; 2-bromo-1-phenylethanone | $^1$H-NMR (400 MHz, DMSO-d6): δ ppm = 7.25-7.31 (m, 1 H), 7.41-7.50 (m, 3 H), 7.58 (dd, J = 8.49, 2.91 Hz, 1 H), 7.60-7.66 (m, 2 H), 7.81 (dd, J = 9.12, 5.83 Hz, 1 H), 8.17 (br s, 2 H), 10.36 (br s, 1 H). LC-MS (method 2) Rt = 1.00 min; MS (ESIpos): m/z = 348.5 [M + H]$^+$<br>RP-HPLC (method C, basic)<br>67% yield |
| 15 | 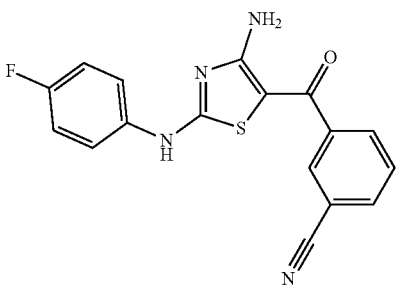 [SMILES: N#Cc1cccc(C(=O)c2sc(Nc3ccc(F)cc3)nc2N)c1]<br>3-[4-amino-2-(4-fluoroanilino)thiazole-5-carbonyl]benzonitrile | 1-fluoro-4-isothiocyanatobenzene; 3-(bromoacetyl)benzonitrile | $^1$H-NMR (400 MHz, DMSO-d6): δ ppm = 7.22 (t, J = 8.87 Hz, 2 H), 7.61-7.66 (m, 2 H), 7.69 (t, J = 7.98 Hz, 1 H), 7.97 (dd, J = 7.86, 1.77 Hz, 2 H), 8.06 (t, J = 1.52 Hz, 1 H), 8.33 (br s, 2 H), 10.81-10.97 (m, 1H). LC-MS (method 2) Rt = 0.97 min; MS (ESIpos): m/z = 339.2 [M + H]$^+$<br>78% yield |
| 16 | 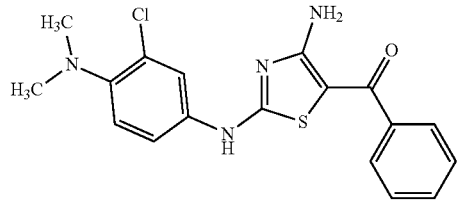 [SMILES: CN(C)c1ccc(Nc2nc(N)c(C(=O)c3ccccc3)s2)cc1Cl]<br>[4-amino-2-[3-chloro-4-(dimethylamino)anilino]thiazol-5-yl]-phenyl-methanone | 2-chloro-4-isothiocyanato-N,N-dimethylaniline; 2-bromo-1-phenylethanone | $^1$H-NMR (400 MHz, DMSO-d6): δ ppm = 2.68 (s, 6 H), 7.14 (d, J = 8.87 Hz, 1 H), 7.34 (dd, J = 8.62, 2.53 Hz, 1 H), 7.42-7.50 (m, 3 H), 7.60-7.69 (m, 2 H), 7.69-7.74 (m, 1 H), 8.22 (br s, 2 H), 10.58 (br s, 1 H). LC-MS (method 2) Rt = 1.14 min; MS (ESIpos): m/z = 373.2 [M + H]$^+$<br>RP-HPLC (method D, basic)<br>66% yield |
| 17 | 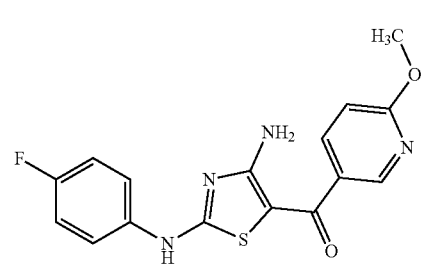 [SMILES: COc1ccc(C(=O)c2sc(Nc3ccc(F)cc3)nc2N)cn1]<br>[4-amino-2-(4-fluoroanilino)thiazol-5-yl]-(6-methoxy-3-pyridyl)methanone | 1-fluoro-4-isothiocyanatobenzene; 2-bromo-1-(6-methoxypyridin-3-yl)ethanone | $^1$H-NMR (400 MHz, DMSO-d6): δ ppm = 3.91 (s, 3 H), 6.91 (dd, J = 8.49, 0.63 Hz, 1 H), 7.19-7.26 (m, 2 H), 7.62-7.66 (m, 2 H), 7.98 (dd, J = 8.62, 2.53 Hz, 1 H), 8.24 (br s, 2 H), 8.51 (dd, J = 2.53, 0.76 Hz, 1 H), 10.85 (br s, 1 H). LC-MS (method 1) Rt = 1.09 min; MS (ESIpos): m/z = 345.2 [M + H]$^+$<br>72% yield |

TABLE 2-continued

Intermediates 5-77

| Intermediate number | Chemical structure Compound name | Starting materials | Analytics/purification/yield |
|---|---|---|---|
| 18 | 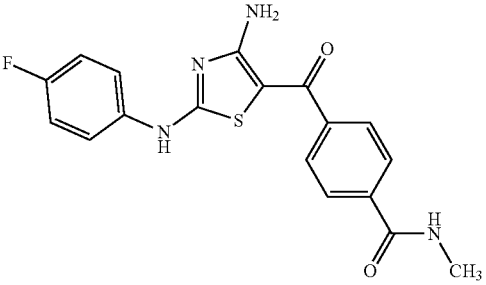 [SMILES: CNC(=O)c1ccc(C(=O)c2sc(Nc3ccc(F)cc3)nc2N)cc1]<br>4-[4-amino-2-(4-fluoroanilino)thiazole-5-carbonyl]-N-methyl-benzamide | 1-fluoro-4-isothiocyanatobenzene; 4-(bromoacetyl)-N-methylbenzamide | LC-MS (method 2) Rt = 0.79 min; MS (ESIpos): m/z = 371.2 [M + H]$^+$<br>RP-HPLC (method C, basic)<br>31% yield |
| 19 | 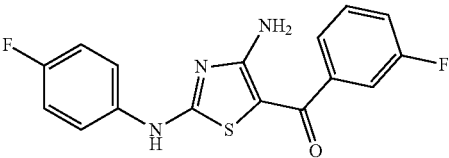 [SMILES: Nc1nc(Nc2ccc(F)cc2)sc1C(=O)c1cccc(F)c1]<br>[4-amino-2-(4-fluoroanilino)thiazol-5-yl]-(3-fluorophenyl)methanone | 1-fluoro-4-isothiocyanatobenzene; 2-bromo-1-(3-fluorophenyl)ethanone | LC-MS (method 2) Rt = 1.03 min; MS (ESIpos): m/z = 332.2 [M + H]$^+$<br>RP-HPLC (method D, basic)<br>13% yield |
| 20 | 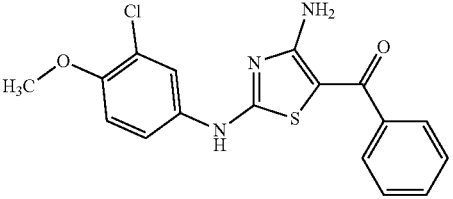 [SMILES: COc1ccc(Nc2nc(N)c(C(=O)c3ccccc3)s2)cc1Cl]<br>[4-amino-2-(3-chloro-4-methoxy-anilino)thiazol-5-yl]-phenyl-methanone | 2-chloro-4-isothiocyanato-1-methoxybenzene; 2-bromo-1-phenylethanone | $^1$H-NMR (400 MHz, DMSO-d6): δ ppm = 3.83 (s, 3 H), 7.15 (d, J = 8.87 Hz, 1 H), 7.41 (dd, J = 8.87. 2.79 Hz, 1 H), 7.44-7.51 (m, 3 H), 7.62-7.69 (m, 2 H), 7.82 (d, J = 2.03 Hz, 1 H), 8.27 (br s, 2 H), 10.71 (s, 1 H).<br>LC-MS (method 2) Rt = 0.98 min; MS (ESIpos): m/z = 360.2 [M + H]$^+$<br>39% yield |
| 21 | 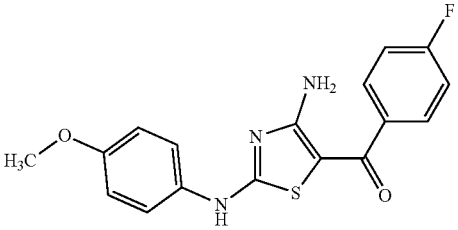 [SMILES: COc1ccc(Nc2nc(N)c(C(=O)c3ccc(F)cc3)s2)cc1]<br>[4-amino-2-(4-methoxyanilino)thiazol-5-yl]-(4-fluorophenyl)methanone | 1-isothiocyanato-4-methoxybenzene; 2-bromo-1-(4-fluorophenyl)thanone | $^1$H-NMR (400 MHz, DMSO-d6): δ ppm = 3.74 (s, 3 H), 6.94 (d, J = 8.87 Hz, 2 H), 7.28 (t, J = 8.87 Hz, 2 H), 7.45 (br d, J = 8.62 Hz, 2 H), 7.67-7.73 (m, 2 H), 7.89-8.50 (m, 2 H), 10.64 (br s, 1 H).<br>LC-MS (method 2) Rt = 1.09 min; MS (ESIpos): m/z = 344.5 [M + H]$^+$<br>preparative flash chromatography (method Y, 1-10%)<br>66% yield |
| 22 | 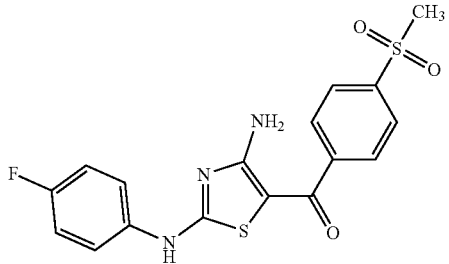 [SMILES: CS(=O)(=O)c1ccc(C(=O)c2sc(Nc3ccc(F)cc3)nc2N)cc1]<br>[4-amino-2-(4-fluoroanilino)thiazol-5-yl]-(4-methylsulfonylphenyl)methanone | 1-fluoro-4-isothiocyanatobenzene; 2-bromo-1-[4-(methylsulfonyl)phenyl]ethanone | $^1$H-NMR (400 MHz, DMSO-d6): δ ppm = 3.28 (s, 3 H), 7.22 (t, J = 8.87 Hz, 2 H), 7.60-7.65 (m, 2 H), 7.88 (d, J = 8.62 Hz, 2 H), 8.00-8.04 (m, 2 H), 8.31 (br s, 2 H), 9.20 (s, 1 H).<br>LC-MS (method 2) Rt = 0.83 min; MS (ESIpos): m/z = 392.2 [M + H]$^+$<br>92% yield |

TABLE 2-continued

Intermediates 5-77

| Intermediate number | Chemical structure / Compound name | Starting materials | Analytics/purification/yield |
|---|---|---|---|
| 23 | 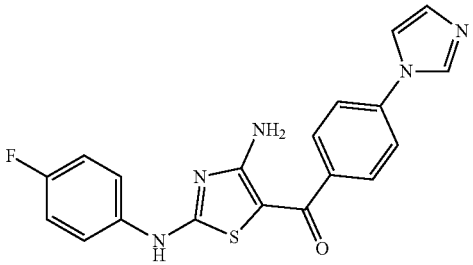 [SMILES: Nc1nc(Nc2ccc(F)cc2)sc1C(=O)c1ccc(-n2ccnc2)cc1]<br>[4-amino-2-(4-fluoroanilino)thiazol-5-yl]-(4-imidazol-1-ylphenyl)methanone | 1-fluoro-4-isothiocyanatobenzene; 2-bromo-1-[4-(1H-imidazol-1-yl)phenyl]ethanone | $^1$H-NMR (400 MHz, DMSO-d6): δ ppm = 7.14-7.15 (m, 1 H), 7.22 (t, J = 8.87 Hz, 2 H), 7.58-7.69 (m, 2 H), 7.75-7.82 (m, 4 H), 7.84 (t, J = 1.39 Hz, 1 H), 8.00-8.56 (m, 2 H), 8.37 (t, J = 1.14 Hz, 1 H), 10.84 (br s, 1 H).<br>LC-MS (method 2) Rt = 0.88 min; MS (ESIpos): m/z = 380.2 [M + H]$^+$<br>RP-HPLC (method C, basic)<br>16% yield |
| 24 | 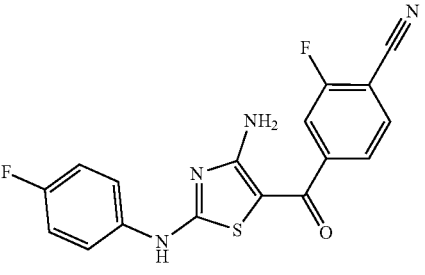 [SMILES: N#Cc1ccc(C(=O)c2sc(Nc3ccc(F)cc3)nc2N)cc1F]<br>4-[4-amino-2-(4-fluoroanilino)thiazole-5-carbonyl]-2-fluoro-benzonitrile | 1-fluoro-4-isothiocyanatobenzene; 4-(bromoacetyl)-2-fluorobenzonitrile | $^1$H-NMR (400 MHz, DMSO-d6): δ ppm = 7.22 (t, J = 8.87 Hz, 2 H), 7.58-7.63 (m, 2 H), 7.65 (dd, J = 7.98, 1.39 Hz, 1 H), 7.72 (dd, J = 9.76, 1.39 Hz, 1 H), 8.04 (dd, J = 7.86, 6.59 Hz, 1 H), 8.39 (br s, 2 H), 10.92 (br s, 1 H).<br>LC-MS (method 2) Rt = 0.92 min; MS (ESIpos): m/z = 357.2 [M + H]$^+$<br>RP-HPLC (method C, basic)<br>5% yield |
| 25 | 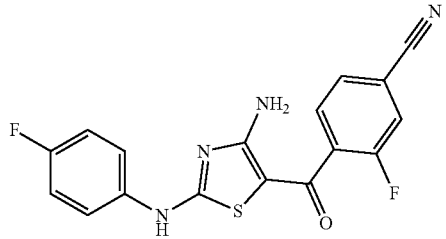 [SMILES: N#Cc1ccc(C(=O)c2sc(Nc3ccc(F)cc3)nc2N)c(F)c1]<br>4-[4-amino-2-(4-fluoroanilino)thiazole-5-carbonyl]-3-fluoro-benzonitrile | 1-fluoro-4-isothiocyanatobenzene; 4-(bromoacetyl)-3-fluorobenzonitrile | $^1$H-NMR (400 MHz, DMSO-d6): δ ppm = 7.23 (t, J = 8.87 Hz, 2 H), 7.60-7.67 (m, 3 H), 7.73 (dd, J = 9.89, 1.27 Hz, 1 H), 8.05 (dd, J = 7.86, 6.59 Hz, 1 H), 8.41 (br s, 2 H), 10.94 (br s, 1 H).<br>LC-MS (method 2) Rt = 0.92 min; MS (ESIpos): m/z = 357.2 [M + H]$^+$<br>RP-HPLC (method D, acidic)<br>13% yield |
| 26 | 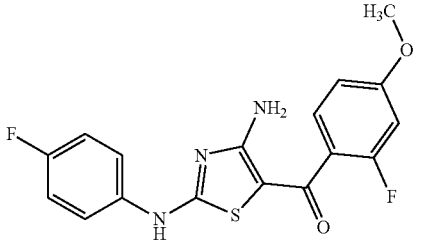 [SMILES: COc1ccc(C(=O)c2sc(Nc3ccc(F)cc3)nc2N)c(F)c1]<br>[4-amino-2-(4-fluoroanilino)thiazol-5-yl]-(2-fluoro-4-methoxy-phenyl)methanone | 1-fluoro-4-isothiocyanatobenzene; 2-bromo-1-(2-fluoro-4-methoxyphenyl)ethanone | $^1$H-NMR (400 MHz, DMSO-d6): δ ppm = 3.81 (s, 3 H), 6.83 (dd, J = 8.49, 2.41 Hz, 1 H), 6.89 (dd, J = 12.29, 2.41 Hz, 1 H), 7.21 (t, J = 8.87 Hz, 2 H), 7.42 (t, J = 8.49 Hz, 1 H), 7.56-7.63 (m, 2 H), 7.99-8.17 (br s, 2 H), 10.77 (br s, 1 H).<br>LC-MS (method 1) Rt = 1.13 min; MS (ESIpos): m/z = 362.4 [M + H]$^+$<br>81% yield |

TABLE 2-continued

Intermediates 5-77

| Intermediate number | Chemical structure Compound name | Starting materials | Analytics/purification/yield |
|---|---|---|---|
| 27 | 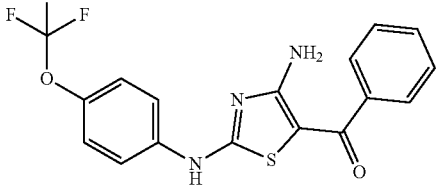<br>[4-amino-2-[4-(trifluoromethoxy)anilino]thiazol-5-yl]-phenyl-methanone | 1-isothiocyanato-4-(trifluoromethoxy)benzene; 2-bromo-1-phenylethanone | $^1$H-NMR (400 MHz, DMSO-d6): δ ppm = 7.38 (d, J = 8.36 Hz, 2 H), 7.45-7.52 (m, 3 H), 7.67 (dd, J = 7.60, 1.77 Hz, 2 H), 7.74 (d, J = 9.13 Hz, 2 H), 8.03-8.37 (br s, 2 H), 10.94 (br s, 1 H).<br>LC-MS (method 1) Rt = 1.13 min; MS (ESIpos): m/z = 380.5 [M + H]$^+$<br>preparative flash chromatography (method X, 25-90%)<br>21% yield |
| 28 | 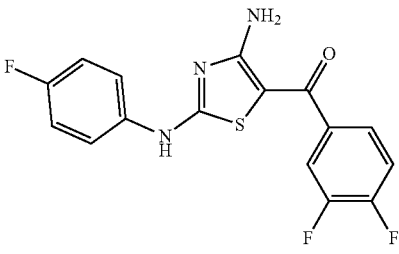 [SMILES: Nc1nc(Nc2ccc(F)cc2)sc1C(=O)c1ccc(F)c(F)c1]<br>[4-amino-2-(4-fluoroanilino)thiazol-5-yl]-(3,4-difluorophenyl)methanone | 1-fluoro-4-isothiocyanatobenzene; 2-chloro-1-(3,4-difluorophenyl)ethanone | $^1$H-NMR (400 MHz, DMSO-d6): δ ppm = 7.22 (t, J = 8.87 Hz, 2 H), 7.52-7.58 (m, 2 H), 7.61-7.73 (m, 3 H), 8.06-8.52 (br s, 2 H), 10.87 (br s, 1 H).<br>LC-MS (method 2) Rt = 1.13 min; MS (ESIpos): m/z = 350.2 [M + H]$^+$<br>RP-HPLC (method D, basic)<br>34% yield |
| 29 | 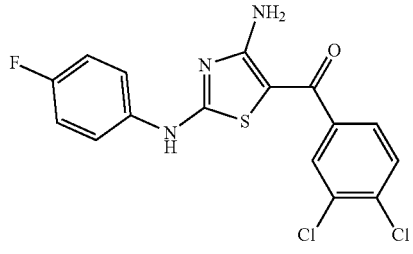 [SMILES: Nc1nc(Nc2ccc(F)cc2)sc1C(=O)c1ccc(Cl)c(Cl)c1]<br>[4-amino-2-(4-fluoroanilino)thiazol-5-yl]-(3,4-dichlorophenyl)methanone | 1-fluoro-4-isothiocyanatobenzene; 2-bromo-1-(3,4-dichlorophenyl)ethanone | $^1$H-NMR (400 MHz, DMSO-d6): δ ppm = 7.19 (t, J = 8.87 Hz, 2 H), 7.56 (br s, 2 H), 7.63 (dd, J = 8.36, 2.03 Hz, 1 H), 7.73 (d, J = 8.36 Hz, 1 H), 7.84 (d, J = 1.77 Hz, 1 H), 8.03-8.58 (m, 2 H), 10.83 (br s, 1 H).<br>LC-MS (method 2) Rt = 1.22 min; MS (ESIneg): m/z = 380.3 [M − H]$^+$<br>RP-HPLC (method D, basic)<br>32% yield |
| 30 | 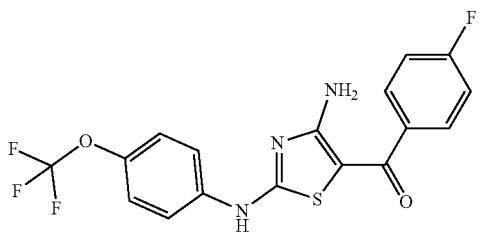 [SMILES: Nc1nc(Nc2ccc(OC(F)(F)F)cc2)sc1C(=O)c1ccc(F)cc1]<br>[4-amino-2-[4-(trifluoromethoxy)anilino]thiazol-5-yl]-(4-fluorophenyl)methanone | 1-isothiocyanato-4-(trifluoromethoxy)benzene; 2-bromo-1-(4-fluorophenyl)ethanone | $^1$H-NMR (400 MHz, DMSO-d6): δ ppm = 7.31 (t, J = 8.87 Hz, 2 H), 7.37 (d, J = 8.36 Hz, 2 H), 7.70-7.77 (m, 4 H), 8.07-8.34 (br s, 2 H), 10.98 (br s, 1 H).<br>LC-MS (method 2) Rt = 1.20 min; MS (ESIpos): m/z = 398.2 [M + H]$^+$<br>89% yield |
| 31 | 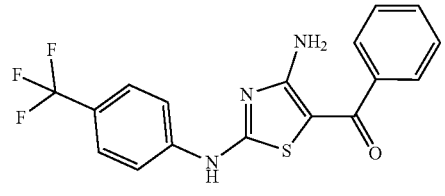 [SMILES: Nc1nc(Nc2ccc(C(F)(F)F)cc2)sc1C(=O)c1ccccc1]<br>[4-amino-2-[4-(trifluoromethyl)anilino]thiazol-5-yl]-phenyl-methanone | 1-isothiocyanato-4-(trifluoromethyl)benzene; 2-bromo-1-phenylethanone | $^1$H-NMR (400 MHz, DMSO-d6): δ ppm = 7.45-7.52 (m, 3 H), 7.66-7.73 (m, 4 H), 7.83 (br d, J = 8.36 Hz, 2 H), 8.24 (br s, 2 H), 11.13 (br s, 1 H).<br>LC-MS (method 2) Rt = 1.14 min; MS (ESIpos): m/z = 364.2 [M + H]$^+$<br>85% yield |

TABLE 2-continued

Intermediates 5-77

| Intermediate number | Chemical structure / Compound name | Starting materials | Analytics/purification/yield |
|---|---|---|---|
| 32 | 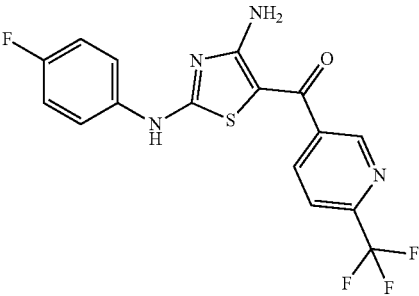 [SMILES: Nc1nc(Nc2ccc(F)cc2)sc1C(=O)c1ccc(C(F)(F)F)nc1]<br>[4-amino-2-(4-fluoroanilino)thiazol-5-yl]-[6-(trifluoromethyl)-3-pyridyl]methanone | 1-fluoro-4-isothiocyanatobenzene; 2-bromo-1-[6-(trifluoromethyl)pyridin-3-yl]ethanone | $^1$H-NMR (400 MHz, DMSO-d6): δ ppm = 7.22 (t, J = 8.87 Hz, 2 H), 7.55-7.64 (m, 2 H), 8.02 (d, J = 7.86 Hz, 1 H), 8.39 (br s, 1 H), 8.29 (dd, J = 7.86, 1.77 Hz, 2 H), 8.99 (d, J = 1.77 Hz, 1 H), 10.95 (br s, 1 H). LC-MS (method 2) Rt = 1.03 min; MS (ESIpos): m/z = 383.1 [M + H]$^+$ RP-HPLC (method C, basic) 97% yield |
| 33 | 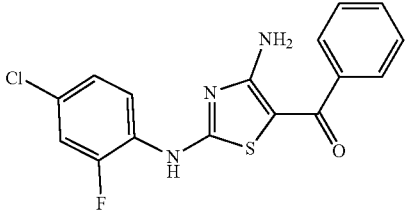 [SMILES: Nc1nc(Nc2ccc(Cl)cc2F)sc1C(=O)c1ccccc1]<br>[4-amino-2-(4-chloro-2-fluoro-anilino)thiazol-5-yl]-phenyl-methanone | 4-chloro-2-fluoro-1-isothiocyanatobenzene; 2-bromo-1-phenylethanone | LC-MS (method 2) Rt = 0.97 min; MS (ESIpos): m/z = 348.2 [M + H]$^+$ 94% yield |
| 34 | 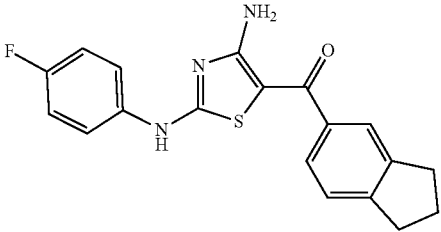 [SMILES: Nc1nc(Nc2ccc(F)cc2)sc1C(=O)c1ccc2c(c1)CCC2]<br>[4-amino-2-(4-fluoroanilino)thiazol-5-yl]-indan-5-yl-methanone | 1-fluoro-4-isothiocyanatobenzene; 2-bromo-1-(2,3-dihydro-1H-inden-5-yl)ethanone | LC-MS (method 2) Rt = 1.25 min; MS (ESIpos): m/z = 354.5 [M + H]$^+$ 89% yield |
| 35 | 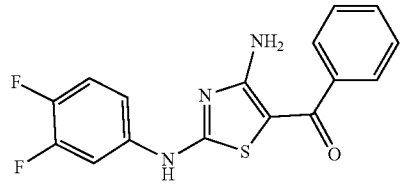 [SMILES: Nc1nc(Nc2ccc(F)c(F)c2)sc1C(=O)c1ccccc1]<br>[4-amino-2-(3,4-difluoroanilino)thiazol-5-yl]-phenyl-methanone | 1,2-difluoro-4-isothiocyanatobenzene; 2-bromo-1-phenylethanone | $^1$H-NMR (400 MHz, DMSO-d6); δ ppm = 7.21-7.28 (m, 1 H), 7.38-7.54 (m, 4 H), 7.63-7.72 (m, 2 H), 7.90-8.02 (m, 1 H), 8.10-8.46 (br s, 2 H), 10.86-11.07 (br s, 1 H). LC-MS (method 2) Rt = 1.05 min; MS (ESIpos): m/z = 332.2 [M + H]$^+$ 76% yield |

TABLE 2-continued

Intermediates 5-77

| Intermediate number | Chemical structure / Compound name | Starting materials | Analytics/purification/yield |
|---|---|---|---|
| 36 | 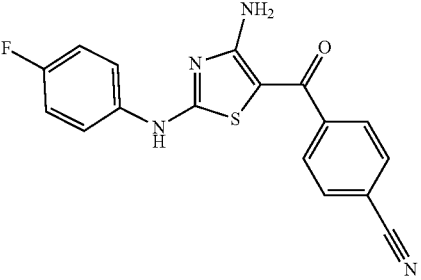 [SMILES: N#Cc1ccc(C(=O)c2sc(Nc3ccc(F)cc3)nc2N)cc1]<br>4-[4-amino-2-(4-fluoroanilino)thiazole-5-carbonyl]benzonitrile | 1-fluoro-4-isothiocyanatobenzene; 4-(bromoacetyl)benzonitrile | $^1$H-NMR (400 MHz, DMSO-d6); δ ppm = 7.22 (t, J = 8.87 Hz, 2 H), 7.62 (br dd, J = 8.87, 4.82 Hz, 2 H), 7.80 (d, J = 8.36 Hz, 2 H), 7.95 (d, J = 1.00 Hz, 2 H), 8.32 (br s, 2 H), 10.84-10.95 (br s, 1 H).<br>LC-MS (method 2) Rt = 0.97 min; MS (ESIpos): m/z = 339.2 [M + H]$^+$<br>84% yield |
| 37 | 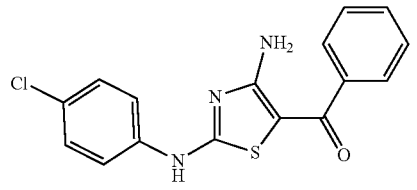 [SMILES: Nc1nc(Nc2ccc(Cl)cc2)sc1C(=O)c1ccccc1]<br>[4-amino-2-(4-chloroanilino)thiazol-5-yl]-phenyl-methanone | 1-chloro-4-isothiocyanatobenzene; 2-bromo-1-phenylethanone | LC-MS (method 1) Rt = 1.23 min; MS (ESIneg): m/z = 328.3<br>100% yield |
| 38 | 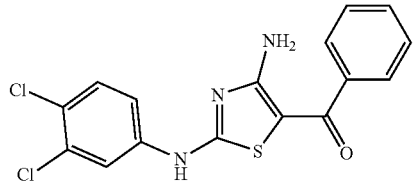 [SMILES: Nc1nc(Nc2ccc(Cl)c(Cl)c2)sc1C(=O)c1ccccc1]<br>[4-amino-2-(3,4-dichloroanilino)thiazol-5-yl]-phenyl-methanone | 1,2-dichloro-4-isothiocyanatobenzene; 2-bromo-1-phenylethanone | LC-MS (method 1) Rt = 1.32 min; MS (ESIneg): m/z = 362.3 [M − H]$^+$<br>preparative flash chromatography (method X, 10-80%)<br>65% yield |
| 39 | 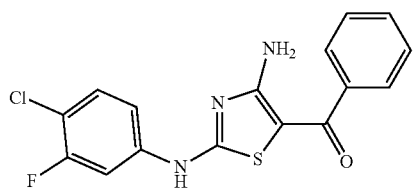 [SMILES: Nc1nc(Nc2ccc(Cl)c(F)c2)sc1C(=O)c1ccccc1]<br>[4-amino-2-(4-chloro-3-fluoro-anilino)thiazol-5-yl]-phenyl-methanone | 1-chloro-2-fluoro-4-isothiocyanatobenzene; 2-bromo-1-phenylethanone | $^1$H-NMR (400 MHz, DMSO-d6): δ ppm = 7.28 (br dt, J = 8.87, 1.27 Hz, 1 H), 7.45-7.57 (m, 4 H), 7.68 (dd, J = 7.60, 1.77 Hz, 2 H), 7.99 (dd, J = 11.91, 2.03 Hz, 1 H), 8.27 (br s, 2 H), 11.07 (br s, 1 H).<br>LC-MS (method 2) Rt = 1.04 min; MS (ESIpos): m/z = 348.1 [M + H]$^+$<br>67% yield |
| 40 | 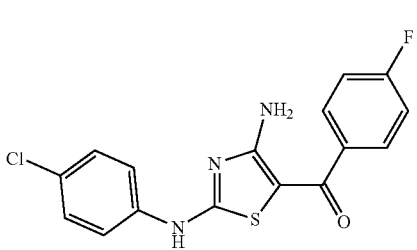 [SMILES: Nc1nc(Nc2ccc(Cl)cc2)sc1C(=O)c1ccc(F)cc1]<br>[4-amino-2-(4-chloroanilino)thiazol-5-yl]-(4-fluorophenyl)methanone | 1-fluoro-4-isothiocyanatobenzene; 2-bromo-1-(4-chlorophenyl)ethanone | LC-MS (method 2) Rt = 1.12 min; MS (ESIpos): m/z = 348.1 [M + H]$^+$<br>94% yield |

TABLE 2-continued

Intermediates 5-77

| Intermediate number | Chemical structure Compound name | Starting materials | Analytics/purification/yield |
|---|---|---|---|
| 41 | 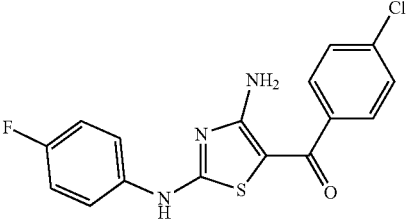 [SMILES: Nc1nc(Nc2ccc(F)cc2)sc1C(=O)c1ccc(Cl)cc1]<br>[4-amino-2-(4-fluoroanilino)thiazol-<br>5-yl]-(4-chlorophenyl)methanone | 1-fluoro-4-isothiocyanatobenzene; 2-bromo-1-(4-chlorophenyl)ethanone | $^1$H-NMR (400 MHz, DMSO-d6): δ ppm = 7.21 (t, J = 8.87 Hz, 2 H), 7.54 (d, J = 8.62 Hz, 2 H), 7.62 (br dd, J = 8.87, 5.07 Hz, 2 H), 7.68 (d, J = 8.62 Hz, 2 H), 8.28 (br s, 2 H), 10.83 (br s, 1 H).<br>LC-MS (method 1) Rt = 1.25 min; MS (ESIneg): m/z = 346.3 [M − H]$^+$<br>preparative flash chromatography (method Y, 0-15%)<br>53% yield |
| 42 | 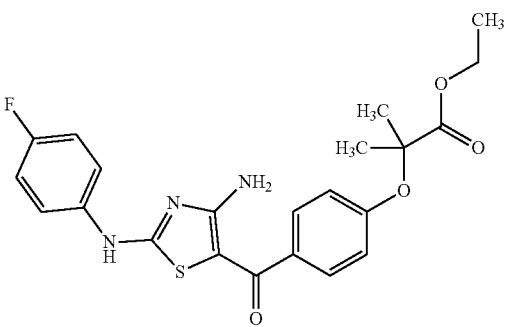 [SMILES: CCOC(=O)C(C)(C)Oc1ccc(C(=O)c2sc(Nc3ccc(F)cc3)nc2N)cc1]<br>ethyl 2-[4-[4-amino-2-(4-fluoroanilino)thiazole-5-carbonyl]phenoxy]-2-methyl-propanoate | 1-fluoro-4-isothiocyanatobenzene; ethyl 2-[4-(bromoacetyl)phenoxy]-2-methylpropanoate | $^1$H-NMR (400 MHz, DMSO-d6): δ ppm = 1.15 (t, J = 7.10 Hz, 3 H), 1.56 (s, 6 H), 4.17 (q, J = 7.10 Hz, 2 H), 6.78 (d, J = 8.87 Hz, 2 H), 7.12 (t, J = 8.87 Hz, 2 H), 7.34-7.51 (br s, 2 H), 7.58 (d, J = 8.62 Hz, 2 H), 7.62-8.80 (m, 2 H), 9.78-10.70 (m, 1 H).<br>LC-MS (method 2) Rt = 1.25 min; MS (ESIpos): m/z = 444.3 [M + H]$^+$<br>93% yield |
| 43 | 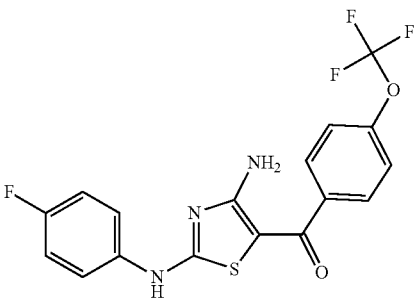 [SMILES: Nc1nc(Nc2ccc(F)cc2)sc1C(=O)c1ccc(OC(F)(F)F)cc1]<br>[4-amino-2-(4-fluoroanilino)thiazol-5-yl]-[4-(trifluoromethoxy)phenyl]methanone | 1-fluoro-4-isothiocyanatobenzene; 2-bromo-1-[4-(trifluoromethoxy)phenyl]ethanone | $^1$H-NMR (400 MHz, DMSO-d6): δ ppm = 7.21 (t, J = 8.87 Hz, 2 H), 7.46 (dd, J = 8.74, 0.89 Hz, 2 H), 7.55-7.66 (m, 2 H), 7.79 (d, J = 8.87 Hz, 2 H), 8.36 (br s, 2 H), 10.77 (br s, 1H).<br>LC-MS (method 2) Rt = 1.21 min; MS (ESIpos): m/z = 398.1 [M + H]$^+$<br>RP-HPLC (method D, basic)<br>50% yield |
| 44 | 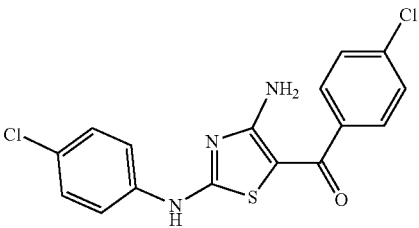 [SMILES: Nc1nc(Nc2ccc(Cl)cc2)sc1C(=O)c1ccc(Cl)cc1]<br>[4-amino-2-(4-chloroanilino)thiazol-5-yl]-(4-chlorophenyl)methanone | 1-chloro-4-isothiocyanatobenzene; 2-bromo-1-(4-chlorophenyl)ethanone | LC-MS (method 2) Rt = 1.19 min; MS (ESIpos): m/z = 364.1 [M + H]$^+$<br>87% yield |

TABLE 2-continued

Intermediates 5-77

| Intermediate number | Chemical structure / Compound name | Starting materials | Analytics/purification/yield |
|---|---|---|---|
| 45 | [4-amino-2-(4-fluoroanilino)thiazol-5-yl]-[4-(trifluoromethyl)phenyl]methanone | 1-fluoro-4-isothiocyanatobenzene; 2-bromo-1-[4-(trifluoromethyl)phenyl]ethanone | $^1$H-NMR (400 MHz, DMSO-d6): δ ppm = 7.22 (t, J = 8.87 Hz, 2 H), 7.61-7.65 (m, 2 H), 7.85 (s, 4 H), 8.36 (br s, 2 H), 10.88 (br s, 1 H). LC-MS (method 2) Rt = 1.15 min; MS (ESIpos): m/z = 382.2 [M + H]$^+$ 66% yield |
| 46 | [4-amino-2-[4-(trifluoromethyl)anilino]thiazol-5-yl]-[4-(difluoromethoxy)phenyl]methanone | 1-isothiocyanato-4-(trifluoromethyl)benzene; 2-bromo-1-[4-(difluoromethoxy)phenyl]ethanone | LC-MS (method 2) Rt = 1.15 min; MS (ESIpos): m/z = 430.2 [M + H]$^+$ 87% yield |
| 47 | [4-amino-2-(4-fluoroanilino)thiazol-5-yl]-[4-(difluoromethoxy)phenyl]methanone | 1-fluoro-4-isothiocyanatobenzene; 2-bromo-1-[4-(difluoromethoxy)phenyl]ethanone | $^1$H-NMR (400 MHz, DMSO-d6): δ ppm = 7.34 (t, J = 74.50 Hz, 1 H), 7.17-7.31 (m, 4 H), 7.61 (br dd, J = 8.62, 4.82 Hz, 2 H), 7.73 (d, J = 8.62 Hz, 2 H), 8.23 (br s, 2 H), 10.82 (br s, 1H). LC-MS (method 2) Rt = 1.11 min; MS (ESIpos): m/z = 380.4 [M + H]$^+$ RP-HPLC (method D, basic) 94% yield |
| 48 | (4-amino-2-anilino-thiazol-5-yl)-(4-hydroxyphenyl)methanone | phenylisothiocyanate; 2-bromo-4'-hydroxyacetophenone | $^1$H-NMR (400 MHz, DMSO-d6): δ ppm = 6.78 (d, 2 H), 7.04 (t 1 H), 7.33 (d, 2H), 7.54 (d, 2 H), 7.57 (d, 2 H), 8.06 (br s, 2 H), 9.95 (br s, 1 H), 10.68 (br s, 1 H) LC-MS (method 2) Rt = 0.61 min; MS (ESIpos): m/z = 312 [M + H]$^+$ preparative flash chromatography (ethyl acetate/heptane 4/1) 80% yield |

TABLE 2-continued

Intermediates 5-77

| Intermediate number | Chemical structure Compound name | Starting materials | Analytics/purification/yield |
|---|---|---|---|
| 49 | 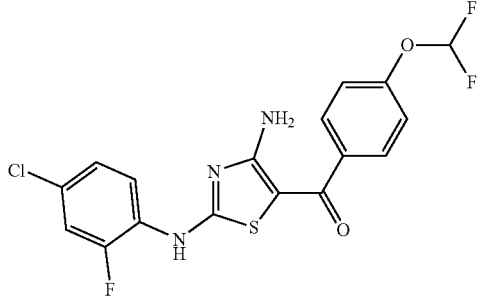 [SMILES: Nc1nc(Nc2ccc(Cl)cc2F)sc1C(=O)c1ccc(OC(F)F)cc1]<br>[4-amino-2-(4-chloro-2-fluoro-anilino)thiazol-5-yl]-[4-(difluoromethoxy)phenyl]methanone | 4-chloro-2-fluoro-1-isothiocyanatobenzene; 2-bromo-1-[4-(difluoromethoxy)phenyl]ethanone | LC-MS (method 2) Rt = 1.00 min; MS (ESIpos): m/z = 414.2 [M + H]$^+$ quantitave yield |
| 50 | 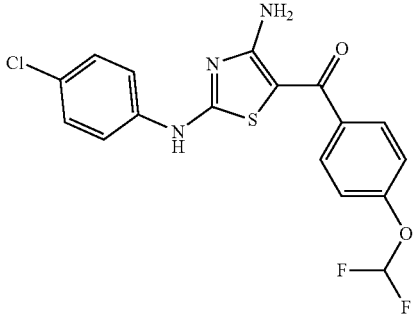 [SMILES: Nc1nc(Nc2ccc(Cl)cc2)sc1C(=O)c1ccc(OC(F)F)cc1]<br>[4-amino-2-(4-chloroanilino)thiazol-5-yl]-[4-(difluoromethoxy)phenyl]methanone | 1-chloro-4-isothiocyanatobenzene; 2-bromo-1-[4-(difluoromethoxy)phenyl]ethanone | $^1$H-NMR (400 MHz, DMSO-d6): δ ppm = 7.35 (t, J = 74.77 Hz, 1 H), 7.26 (d, J = 8.62 Hz, 2 H), 7.42 (d, J = 8.87 Hz, 1 H), 7.66 (d, J = 8.87 Hz, 2 H), 7.75 (d, J = 8.62 Hz, 2 H), 8.26 (br s, 2 H), 10.92 (br s, 1 H). LC-MS (method 2) Rt = 1.19 min; MS (ESIpos): m/z = 396.2 [M + H]$^+$ RP-HPLC (method D, acidic) quantitative yield |
| 51 | 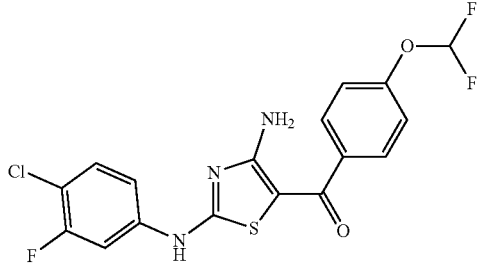 [SMILES: Nc1nc(Nc2ccc(Cl)c(F)c2)sc1C(=O)c1ccc(OC(F)F)cc1]<br>[4-amino-2-(4-chloro-3-fluoro-anilino)thiazol-5-yl]-[4-(difluoromethoxy)phenyl]methanone | 1-chloro-2-fluoro-4-isothiocyanatobenzene; 2-bromo-1-[4-(difluoromethoxy)phenyl]ethanone | LC-MS (method 2) Rt = 1.08 min; MS (ESIpos): m/z = 414.2 [M + H]$^+$ 95% yield |
| 52 | 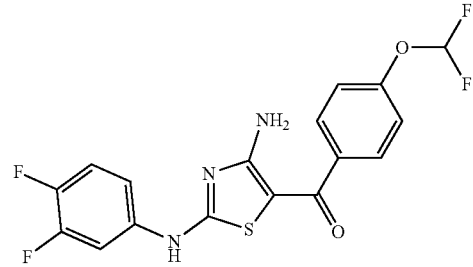<br>[4-amino-2-(3,4-difluoroanilino)thiazol-5-yl]-[4-(difluoromethoxy)phenyl]methanone | 1,2-difluoro-4-isothiocyanatobenzene; 2-bromo-1-[4-(difluoromethoxy)phenyl]ethanone | $^1$H-NMR (400 MHz, DMSO-d6): δ ppm = 7.35 (t, J = 76.04 Hz, 1 H), 7.27 (br d, J = 8.62 Hz, 3 H), 7.39-7.48 (m, 1 H), 7.75 (d, J = 8.87 Hz, 2 H), 7.97 (ddd, J = 12.99, 7.29, 2.28 Hz, 1 H), 8.27 (br s, 2 H), 10.99 (br s, 1 H). LC-MS (method 2) Rt = 1.06 min; MS (ESIpos): m/z = 398.2 [M + H]$^+$ 87% yield |

TABLE 2-continued

Intermediates 5-77

| Intermediate number | Chemical structure Compound name | Starting materials | Analytics/purification/yield |
|---|---|---|---|
| 53 | 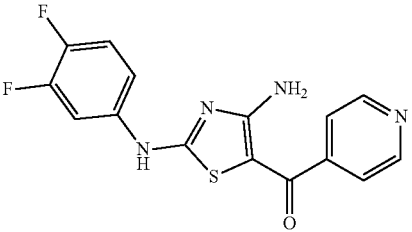 [SMILES: Nc1nc(Nc2ccc(F)c(F)c2)sc1C(=O)c1ccncc1]<br>[4-amino-2-(3,4-difluoroanilino)-1,3-thiazol-5-yl](pyridin-4-yl)methanone | 2-bromo-1-(pyridin-4-yl)ethan-1-one salt with hydrogen bromide; 1,2-difluoro-4-isothiocyanatobenzene | $^1$H-NMR (400 MHz, DMSO-d6): δ ppm = 7.22-7.28 (m, 1 H), 7.39-7.47 (m, 1 H), 7.56-7.59 (m, 2 H), 7.91-7.99 (m, 1 H), 8.39 (td, J = 6.46, 2.79 Hz, 1 H), 8.36-8.44 (m, 1 H), 8.68-8.74 (m, 2 H), 10.78-11.25 (m, 1 H).<br>LC-MS (method 1) Rt = 0.89 min; MS (ESIpos): m/z = 333.1 [M + H]$^+$<br><br>RP-HPLC (method C, acidic)<br>76% yield |
| 54 | 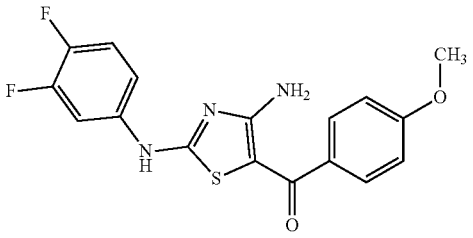 [SMILES: COc1ccc(C(=O)c2sc(Nc3ccc(F)c(F)c3)nc2N)cc1]<br>[4-amino-2-(3,4-difluoroanilino)-1,3-thiazol-5-yl](4-methoxyphenyl)methanone | 2-bromo-1-(4-methoxyphenyl)ethan-1-one; 1,2-difluoro-4-isothiocyanatobenzene | $^1$H-NMR (400 MHz, DMSO-d6): δ ppm = 3.82 (s, 3 H), 7.02 (d, J = 8.87 Hz, 2 H), 7.22-7.28 (m, 1 H), 7.38-7.47 (m, 1 H), 7.68 (d, J = 8.87 Hz, 2 H), 7.91-8.03 (m, 1 H), 8.19 (br s, 2 H), 10.81-11.06 (m, 1 H).<br>LC-MS (method 2) Rt = 1.07 min; MS (ESIpos): m/z = 362.1 [M + H]$^+$<br>92% yield |
| 55 | 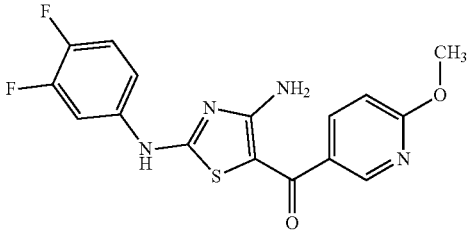 [SMILES: COc1ccc(C(=O)c2sc(Nc3ccc(F)c(F)c3)nc2N)cn1]<br>[4-amino-2-(3,4-difluoroanilino)-1,3-thiazol-5-yl](6-methoxypyridin-3-yl)methanone | 2-bromo-1-(6-methoxypyridin-3-yl)ethan-1-one; 1,2-difluoro-4-isothiocyanatobenzene | $^1$H-NMR (400 MHz, DMSO-d6): δ ppm = 2.54 (s, 3 H), 6.92 (dd, J = 8.62, 0.51 Hz, 1 H), 7.28 (br s, 1 H), 7.40-7.49 (m, 1 H), 7.94-8.03 (m, 2 H), 8.18-8.36 (m, 2 H), 8.53 (dd, J = 2.53, 0.76 Hz, 1 H), 10.98-11.04 (m, 1 H).<br>LC-MS (method 2) Rt = 0.92 min; MS (ESIpos): m/z = 363.2 [M + H]$^+$<br>77% yield |
| 56 | 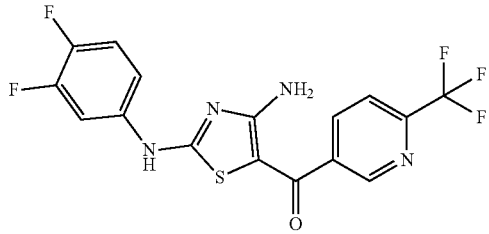 [SMILES: Nc1nc(Nc2ccc(F)c(F)c2)sc1C(=O)c1ccc(C(F)(F)F)nc1]<br>[4-amino-2-(3,4-difluoroanilino)-1,3-thiazol-5-yl][6-(trifluoromethyl)pyridin-3-yl]methanone | 2-bromo-1-[6-(trifluoromethyl)pyridin-3-yl]ethan-1-one; 1,2-difluoro-4-isothiocyanatobenzene | $^1$H-NMR (400 MHz, DMSO-d6): δ ppm = 7.21-7.27 (m, 1 H), 7.38-7.47 (m, 1 H), 7.87-7.98 (m, 1 H), 8.03 (d, J = 8.36 Hz, 1 H), 8.31 (dd, J = 8.11, 2.03 Hz, 1 H), 8.33-8.52 (m, 2 H), 9.00 (d, J = 1.52 Hz, 1 H), 11.04-11.24 (m, 1 H).<br>LC-MS (method 2) Rt = 0.96 min; MS (ESIpos): m/z = 401.3 [M + H]$^+$<br>74% yield |

TABLE 2-continued

Intermediates 5-77

| Intermediate number | Chemical structure Compound name | Starting materials | Analytics/purification/yield |
|---|---|---|---|
| 57 | [4-amino-2-(4-chloro-3-fluoroanilino)-1,3-thiazol-5-yl](pyridin-4-yl)methanone | 2-bromo-1-(pyridin-4-yl)ethan-1-one salt with hydrogen bromide; 1-chloro-2-fluoro-4-isothiocyanatobenzene | LC-MS (method 2) Rt = 0.77 min; MS (ESIpos): m/z = 349.1 [M + H]$^+$ 69% yield |
| 58 | [4-amino-2-(4-chloroanilino)-1,3-thiazol-5-yl](pyridin-4-yl)methanone | 2-bromo-1-(pyridin-4-yl)ethan-1-one salt with hydrogen bromide; 1-chloro-4-isothiocyanatobenzene | $^1$H-NMR (400 MHz, DMSO-d6): δ ppm = 3.78 (d, J = 12.42 Hz, 1 H), 4.08 (d, J = 12.17 Hz, 1 H), 7.18-7.23 (m, 2 H), 7.31-7.36 (m, 2 H), 7.56-7.60 (m, 2 H), 8.39 (s, 1 H), 8.48-8.55 (m, 2 H). LC-MS (method 2) Rt = 0.84 min; MS (ESIpos): m/z = 331.1 [M + H]$^+$ 57% yield |
| 59 | [4-amino-2-(4-chloroanilino)-1,3-thiazol-5-yl](4-methoxyphenyl)methanone | 2-bromo-1-(4-methoxyphenyl)ethan-1-one; 1-chloro-4-isothiocyanatobenzene | $^1$H-NMR (400 MHz, DMSO-d6): δ ppm = 3.82 (s, 3 H), 7.01 (d, J = 8.87 Hz, 2 H), 7.38-7.43 (m, 2 H), 7.61-7.70 (m, 4 H), 8.03-8.27 (m, 2 H), 10.78-10.92 (m, 1 H). LC-MS (method 2) Rt = 1.15 min; MS (ESIpos): m/z = 360.1 [M + H]$^+$ 94% yield |
| 60 | [4-amino-2-(4-chloro-3-fluoroanilino)-1,3-thiazol-5-yl](4-methoxyphenyl)methanone | 2-bromo-1-(4-methoxyphenyl)ethan-1-one; 1-chloro-2-fluoro-4-isothiocyanatobenzene | $^1$H-NMR (400 MHz, DMSO-d6): δ ppm = 3.82 (s, 3 H), 6.99-7.03 (m, 2 H), 7.25 (dd, J = 8.74, 1.65 Hz, 1 H), 7.51 (t J = 8.74 Hz, 1 H), 7.68 (d, J = 8.87 Hz, 2 H), 7.95 (br d, J = 12.17 Hz, 1 H), 8.06-8.29 (m, 2 H), 10.92-11.16 (m, 1H). LC-MS (method 2) Rt = 1.15 min; MS (ESIpos): m/z = 378.1 [M + H]$^+$ 80% yield |

TABLE 2-continued

Intermediates 5-77

| Intermediate number | Chemical structure Compound name | Starting materials | Analytics/purification/yield |
|---|---|---|---|
| 61 | 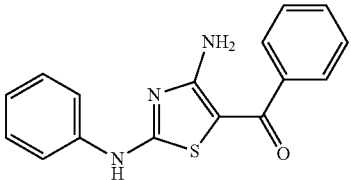 [SMILES: Nc1nc(Nc2ccccc2)sc1C(=O)c1ccccc1]<br>(4-amino-2-anilino-1,3-thiazol-5-yl)(phenyl)methanone | 2-bromo-1-phenylethan-1-one; isothiocyanatobenzene | $^1$H-NMR (400 MHz, DMSO-d6): δ ppm = 7.08 (t, J = 7.60 Hz, 1 H), 7.36 (t, J = 7.86 Hz, 2 H), 7.44-7.51 (m, 3 H), 7.61 (d, J = 7.86 Hz, 2 H), 7.64-7.69 (m, 2 H), 8.21 (br s, 2 H), 10.78 (br s, 1 H). LC-MS (method 2) Rt = 1.05 min; MS (ESIpos): m/z = 296.4 [M + H]$^+$<br>14% yield |
| 62 | 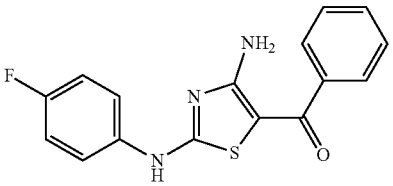 [SMILES: Nc1nc(Nc2ccc(F)cc2)sc1C(=O)c1ccccc1]<br>[4-amino-2-(4-fluoroanilino)-1,3-thiazol-5-yl](phenyl)methanone | 2-bromo-1-phenylethan-1-one; 1-fluoro-4-isothiocyanatobenzene | $^1$H-NMR (400 MHz, DMSO-d6): δ ppm = 7.21 (t, J = 8.87 Hz, 2 H), 7.43-7.52 (m, 3 H), 7.59-7.69 (m, 4 H), 8.22 (br s, 2 H), 10.79 (br s, 1 H). LC-MS (method 2) Rt = 1.04 min; MS (ESIpos): m/z = 314.4 [M + H]$^+$<br>preparative flash chromatography (method Z, 0-1%)<br>78% yield |
| 63 | 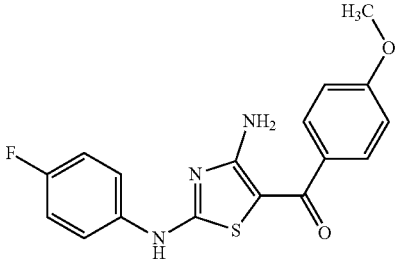 [SMILES: COc1ccc(C(=O)c2sc(Nc3ccc(F)cc3)nc2N)cc1]<br>[4-amino-2-(4-fluoroanilino)-1,3-thiazol-5-yl](4-methoxyphenyl)methanone | 2-bromo-1-(4-methoxyphenyl)ethan-1-one; 1-fluoro-4-isothiocyanatobenzene | $^1$H-NMR (400 MHz, DMSO-d6): δ ppm = 3.81 (s, 3 H), 7.01 (d, J = 8.87 Hz, 2 H), 7.21 (t, J = 8.87 Hz, 2 H), 7.66 (d, J = 8.87 Hz, 4 H), 8.15 (br s, 2 H), 10.77 (br s, 1 H). LC-MS (method 2) Rt = 1.09 min; MS (ESIpos): m/z = 344.4 [M + H]$^+$<br>preparative flash chromatography (method Z, 0-3%)<br>57% yield |
| 64 | 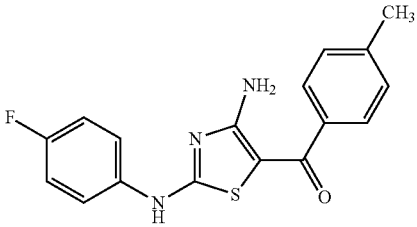 [SMILES: Cc1ccc(C(=O)c2sc(Nc3ccc(F)cc3)nc2N)cc1]<br>[4-amino-2-(4-fluoroanilino)-1,3-thiazol-5-yl](4-methylphenyl)methanone | 2-bromo-1-(4-methylphenyl)ethan-1-one; 1-fluoro-4-isothiocyanatobenzene | $^1$H-NMR (400 MHz, DMSO-d6): δ ppm = 2.35 (s, 3 H), 7.21 (t, J = 8.87 Hz, 2 H), 7.27 (d, J = 7.86 Hz, 2 H), 7.57 (d, J = 8.11 Hz, 2 H), 7.63 (dd, J = 9.13, 4.82 Hz, 2 H), 8.19 (br s, 2 H), 10.77 (s, 1 H). LC-MS (method 2) Rt = 1.14 min; MS (ESIpos): m/z = 328.4 [M + H]$^+$<br>preparative flash chromatography (method Z, 0-3%)<br>47% yield |
| 65 | 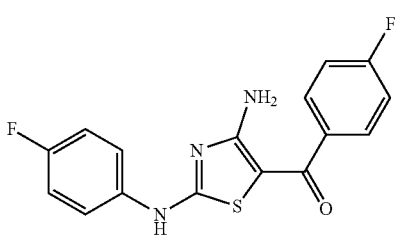 [SMILES: Nc1nc(Nc2ccc(F)cc2)sc1C(=O)c1ccc(F)cc1]<br>[4-amino-2-(4-fluoroanilino)-1,3-thiazol-5-yl](4-fluorophenyl)methanone | 2-bromo-1-(4-fluorophenyl)ethan-1-one; 1-fluoro-4-isothiocyanatobenzene | $^1$H NMR (400 MHz, DMSO-d6): δ ppm = 7.21 (t, J = 8.87 Hz, 2 H), 7.30 (t, J = 8.87 Hz, 2 H), 7.62 (dd, J = 8.87, 4.82 Hz, 2 H), 7.73 (dd, J = 8.74, 5.45 Hz, 2 H), 8.22 (br s, 2 H), 10.82 (br s, 1 H). LC-MS (method 2) Rt = 1.05 min; MS (ESIpos): m/z = 332.4 [M + H]$^+$<br>preparative flash chromatography (method Z, 0-2%)<br>66% yield |

TABLE 2-continued

Intermediates 5-77

| Intermediate number | Chemical structure Compound name | Starting materials | Analytics/purification/yield |
|---|---|---|---|
| 66 | 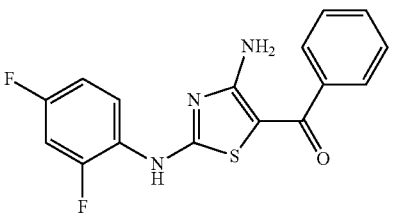 [SMILES: Nc1nc(Nc2ccc(F)cc2F)sc1C(=O)c1ccccc1]<br>[4-amino-2-(2,4-difluoroanilino)-1,3-thiazol-5-yl](phenyl)methanone | 2-bromo-1-phenylethan-1-one; 2,4-difluoro-1-isothiocyanatobenzene | $^1$H-NMR (400 MHz, DMSO-d6): δ ppm = 7.09-7.17 (m, 1 H), 7.39 (ddd, J = 11.15, 8.74, 2.91 Hz, 1 H), 7.43-7.50 (m, 3 H), 7.62-7.65 (m, 2 H), 8.01 (br td, J = 9.12, 6.34 Hz, 1 H), 8.08-8.39 (m, 2H), 10.50 (br s, 1 H). LC-MS (method 2) Rt = 0.88 min; MS (ESIpos): m/z = 332.4 [M + H]$^+$<br>preparative flash chromatography (method Z, 0-3%)<br>71% yield |
| 67 | 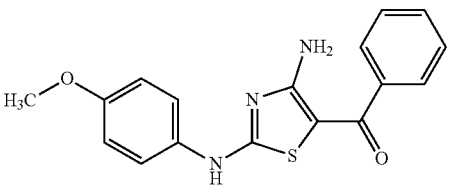 [SMILES: COc1ccc(Nc2nc(N)c(C(=O)c3ccccc3)s2)cc1]<br>[4-amino-2-(4-methoxyanilino)-1,3-thiazol-5-yl](phenyl)methanone | 2-bromo-1-phenylethan-1-one; 1-isothiocyanato-4-methoxybenzene | $^1$H-NMR (400 MHz, DMSO-d6): δ ppm = 3.70-3.76 (m, 3 H), 6.92-6.96 (m, 2 H), 7.42-7.50 (m, 5 H), 7.60-7.66 (m, 2 H), 7.93-8.48 (m, 2 H), 10.60 (br s, 1 H). LC-MS (method 2) Rt = 1.04 min; MS (ESIpos): m/z = 326.4 [M + H]$^+$<br>preparative flash chromatography (method Z, 0-1%)<br>76% yield |
| 68 | 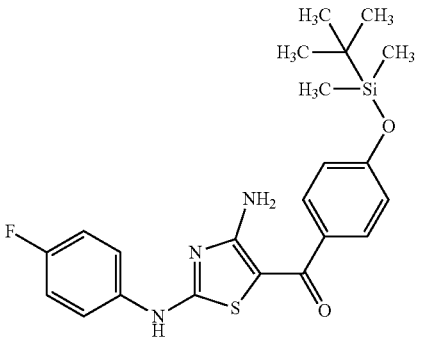 [SMILES: CC(C)(C)[Si](C)(C)Oc1ccc(C(=O)c2sc(Nc3ccc(F)cc3)nc2N)cc1]<br>[4-amino-2-(4-fluoroanilino)-1,3-thiazol-5-yl](4-{[tert-butyl(dimethyl)silyl]oxy}phenyl)methanone | 2-bromo-1-(4-{[tert-butyl(dimethyl)silyl]oxy}phenyl)ethan-1-one (Intermediate 3); 1-fluoro-4-isothiocyanatobenzene | $^1$H-NMR (400 MHz, DMSO-d6): δ ppm = 0.23 (s, 6 H), 0.96 (s, 9 H), 6.92 (d, J = 8.62 Hz, 2 H), 7.21 (t, J = 8.87 Hz, 2 H), 7.59-7.66 (m, 4 H), 8.15 (br s, 2 H), 10.76 (br s, 1 H). LC-MS (method 2) Rt = 1.56 min; MS (ESIpos): m/z = 444.2 [M + H]$^+$<br>preparative flash chromatography (method Z, 0-3%)<br>27% yield |
| 69 | 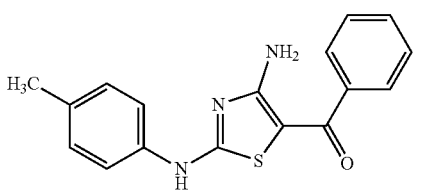 [SMILES: Cc1ccc(Nc2nc(N)c(C(=O)c3ccccc3)s2)cc1]<br>[4-amino-2-(4-methylanilino)-1,3-thiazol-5-yl](phenyl)methanone | 2-bromo-1-phenylethan-1-one; 1-isothiocyanato-4-methylbenzene | $^1$H-NMR (400 MHz, DMSO-d6): δ ppm = 2.27 (s, 3 H), 7.16 (d, J = 8.11 Hz, 2 H), 7.44-7.49 (m, 5 H), 7.63-7.67 (m, 2 H), 7.93-8.63 (m, 2 H), 10.69 (br s, 1 H). LC-MS (method 2) Rt = 1.15 min; MS (ESIpos): m/z = 310.5 [M + H]$^+$<br>preparative flash chromatography (method Z, 0-3%)<br>67% yield |
| 70 | 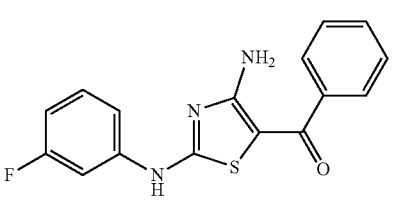 [SMILES: Nc1nc(Nc2cccc(F)c2)sc1C(=O)c1ccccc1]<br>[4-amino-2-(3-fluoroanilino)-1,3-thiazol-5-yl](phenyl)methanone | 2-bromo-1-phenylethan-1-one; 1-fluoro-3-isothiocyanatobenzene | $^1$H-NMR (400 MHz, DMSO-d6): δ ppm = 6.85-6.93 (m, 1 H), 7.27 (ddd, J = 8.24, 2.03, 0.89 Hz, 1 H), 7.38 (td, J = 8.17, 6.72 Hz, 1 H), 7.45-7.53 (m, 3 H), 7.66-7.70 (m, 2 H), 7.76 (dt, J = 11.66, 2.15 Hz, 1 H), 8.26 (br s, 2 H), 10.96 (s, 1 H). LC-MS (method 2) Rt = 1.07 min; MS (ESIpos): m/z = 314.4 [M + H]$^+$<br>preparative flash chromatography (method Z, 0-3%)<br>53% yield |

TABLE 2-continued

Intermediates 5-77

| Intermediate number | Chemical structure Compound name | Starting materials | Analytics/purification/yield |
|---|---|---|---|
| 71 | 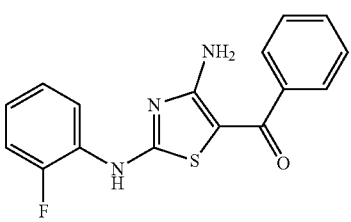 [SMILES: Nc1nc(Nc2ccccc2F)sc1C(=O)c1ccccc1]<br>[4-amino-2-(2-fluoroanilino)-1,3-thiazol-5-yl](phenyl)methanone | 2-bromo-1-phenylethan-1-one; 1-fluoro-2-isothiocyanatobenzene | $^1$H-NMR (400 MHz, DMSO-d6): δ ppm = 7.15-7.25 (m, 2 H), 7.27-7.34 (m, 1 H), 7.43-7.51 (m, 3 H), 7.62-7.68 (m, 2 H), 8.04-8.11 (m, 1 H), 8.10-8.32 (m, 2 H), 10.54 (s, 1 H). LC-MS (method 2) Rt = 0.96 min; MS (ESIpos): m/z = 314.5 [M + H]$^+$<br>preparative flash chromatography (method Z, 0-1%)<br>36% yield |
| 72 | 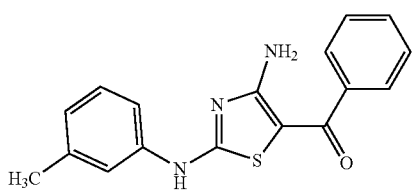 [SMILES: Cc1cccc(Nc2nc(N)c(C(=O)c3ccccc3)s2)c1]<br>[4-amino-2-(3-methylanilino)-1,3-thiazol-5-yl](phenyl)methanone | 2-bromo-1-phenylethan-1-one; 1-isothiocyanato-3-methylbenzene | $^1$H-NMR (400 MHz, DMSO-d6): δ ppm = 2.30 (s, 3 H), 6.91 (br d, J = 7.35 Hz, 1 H), 7.24 (br t, J = 7.73 Hz, 1 H), 7.38 (br s, 1 H), 7.41-7.54 (m, 4 H), 7.62-7.68 (m, 2 H), 8.20 (br s, 2 H), 10.70 (br s, 1 H). LC-MS (method 2) Rt = 1.15 min; MS (ESIpos): m/z = 310.5 [M + H]$^+$<br>preparative flash chromatography (method Z, 0-3%)<br>53% yield |
| 73 | 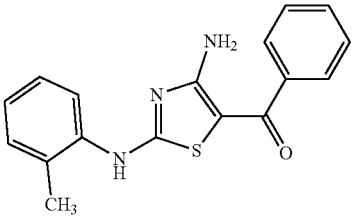 [SMILES: Cc1ccccc1Nc1nc(N)c(C(=O)c2ccccc2)s1]<br>[4-amino-2-(2-methylanilino)-1,3-thiazol-5-yl](phenyl)methanone | 2-bromo-1-phenylethan-1-one; 1-isothiocyanato-2-methylbenzene | $^1$H-NMR (400 MHz, DMSO-d6): δ ppm = 2.23 (s, 3 H), 7.14-7.26 (m, 2 H), 7.27-7.31 (m, 1 H), 7.38-7.52 (m, 4 H), 7.57-7.62 (m, 2 H), 8.15 (br s, 2 H), 10.18 (br s, 1 H). LC-MS (method 2) Rt = 1.10 min; MS (ESIpos): m/z = 310.5 [M + H]$^+$<br>preparative flash chromatography (method Z, 0-1%)<br>60% yield |
| 74 | 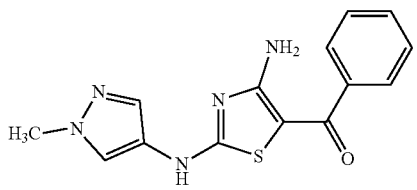 [SMILES: Cn1cc(Nc2nc(N)c(C(=O)c3ccccc3)s2)cn1]<br>{4-amino-2-[(1-methyl-1H-pyrazol-4-yl)amino]-1,3-thiazol-5-yl}(phenyl)methanone | 2-bromo-1-phenylethan-1-one; 4-isothiocyanato-1-methyl-1H-pyrazole | $^1$H-NMR (400 MHz, DMSO-d6): δ ppm = 3.81 (s, 3 H), 7.41-7.52 (m, 4 H), 7.58-7.66 (m, 2 H), 7.90 (s, 1 H), 7.94-8.50 (m, 2 H), 10.44-10.57 (m, 1 H). LC-MS (method 2) Rt = 0.78 min; MS (ESIpos): m/z = 300.5 [M + H]$^+$<br>preparative flash chromatography (method Z, 0-1%)<br>58% yield |
| 75 | 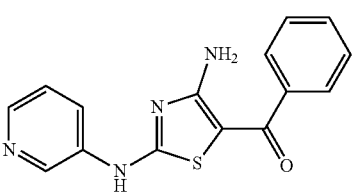 [SMILES: Nc1nc(Nc2cccnc2)sc1C(=O)c1ccccc1]<br>{4-amino-2-[(pyridin-3-yl)amino]-1,3-thiazol-5-yl}(phenyl)methanone | 2-bromo-1-phenylethan-1-one; 3-isothiocyanatopyridine | $^1$H-NMR (400 MHz, DMSO-d6): δ ppm = 7.37-7.42 (m, 1 H), 7.45-7.53 (m, 3 H), 7.65-7.69 (m, 2 H), 8.12 (br ddd, J = 8.36, 2.53, 1.52 Hz, 1 H), 8.16-8.39 (m, 2 H), 8.28 (dd, J = 4.69, 1.39 Hz, 1 H), 8.81 (d, J = 2.53 Hz, 1 H), 10.95 (br s, 1H). LC-MS (method 2) Rt = 0.70 min; MS (ESIpos): m/z = 297.4 [M + H]$^+$<br>preparative flash chromatography (method Z, 0-3%)<br>23% yield |

TABLE 2-continued

Intermediates 5-77

| Intermediate number | Chemical structure / Compound name | Starting materials | Analytics/purification/yield |
|---|---|---|---|
| 76 | 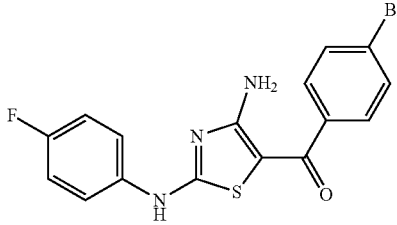<br>[4-amino-2-(4-fluoroanilino)-1,3-thiazol-5-yl](4-bromophenyl)methanone | 2-bromo-1-(4-bromophenyl)ethan-1-one;<br>1-fluoro-4-isothiocyanatobenzene | $^1$H-NMR (400 MHz, DMSO-d6): δ ppm = 7.21 (t, J = 8.87 Hz, 2 H), 7.56-7.65 (m, 4 H), 7.66-7.70 (m, 2 H), 8.26 (br s, 2 H), 10.85 (br s, 1 H).<br>LC-MS (method 2) Rt = 1.19 min; MS (ESIpos): m/z = 392.3 [M + H]$^+$<br>preparative flash chromatography (method Z, 0-1%)<br>77% yield |
| 77 | 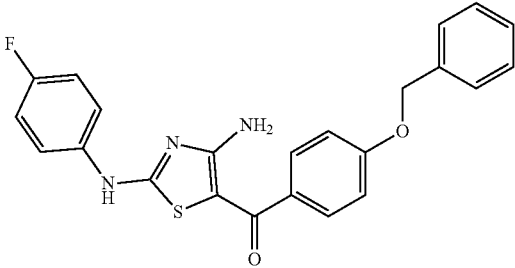 [SMILES: Nc1nc(Nc2ccc(F)cc2)sc1C(=O)c1ccc(OCc2ccccc2)cc1]<br>[4-amino-2-(4-fluoroanilino)-1,3-thiazol-5-yl][4-(benzyloxy)phenyl]methanone | 1-[4-(benzyloxy)phenyl]-2-bromoethan-1-one;<br>1-fluoro-4-isothiocyanatobenzene | $^1$H-NMR (400 MHz, DMSO-d6): δ ppm = 5.17 (s, 2 H), 7.09 (d, J = 8.87 Hz, 2 H), 7.21 (t, J = 8.87 Hz, 2 H), 7.31-7.37 (m, 1 H), 7.41 (t, J = 7.35 Hz, 2 H), 7.45-7.49 (m, 2 H), 7.60-7.69 (m, 4 H), 7.96-8.34 (m, 2 H), 10.71-10.79 (m, 1 H).<br>LC-MS (method 2) Rt = 1.30 min; MS (ESIpos): m/z = 420.2 [M + H]$^+$<br>87% yield |

Intermediate 78

[4-(difluoromethoxy)phenyl][2-(4-fluoroanilino)-4-methyl-1,3-thiazol-5-yl]methanone

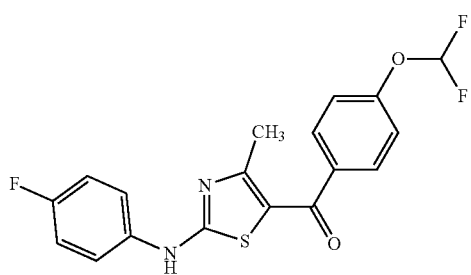

1-Fluoro-4-isothiocyanatobenzene (116 mg, 0.755 mmol) was dissolved in acetonitrile (7.5 mL) followed by the addition of 1,8-diazabicyclo(5.4.0)undec-7-ene (100 mg, 0.66 mmol) and ethanimidamide (salt with hydrogen chloride) (86 mg, 0.91 mmol). After stirring for 45 min at rt, further 1,8-diazabicyclo(5.4.0)undec-7-ene (70 mg, 0.47 mmol) and 2-bromo-1-[4-(difluoromethoxy)phenyl]ethan-1-one (200 mg, 0.755 mmol) were added. The reaction mixture was stirred at rt overnight. The reaction mixture was concentrated under vacuum and the residue was purified by preparative HPLC (method D, basic) to give 72 mg (25% yield) of the title compound.

LC-MS (method 2) Rt=1.30 min; MS (ESIpos): m/z=379.4 [M+H]$^+$

Intermediate 79

[2-(3,4-difluoroanilino)-4-methyl-1,3-thiazol-5-yl][4-(difluoromethoxy)phenyl]methanone

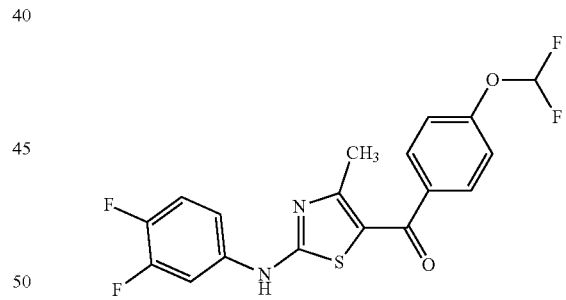

1,2-difluoro-4-isothiocyanatobenzene (129 mg, 0.755 mmol) was dissolved in acetonitrile (7.5 mL) followed by the addition of 1,8-diazabicyclo(5.4.0)undec-7-ene (100 mg, 0.66 mmol) and ethanimidamide (salt with hydrogen chloride) (86 mg, 0.91 mmol). After stirring for 45 min at rt, further 1,8-diazabicyclo(5.4.0)undec-7-ene (70 mg, 0.47 mmol) and 2-bromo-1-[4-(difluoromethoxy)phenyl]ethan-1-one (200 mg, 0.755 mmol) were added. The reaction mixture was stirred at rt overnight. The reaction mixture was concentrated under vacuum and the residue was purified by preparative HPLC (method E, basic) to give 31 mg (10% yield) of the title compound.

LC-MS (method 2) Rt=1.36 min; MS (ESIpos): m/z=397.3 [M+H]$^+$

Intermediate 80 ethyl 2-[4-[4-amino-2-(4-fluoroanilino)thiazole-5-carbonyl]phenoxy]acetate

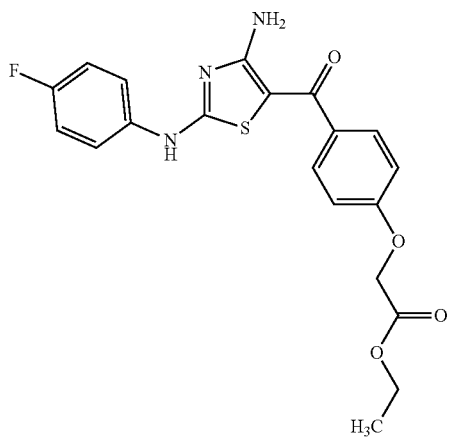 [SMILES: CCOC(=O)COc1ccc(C(=O)c2sc(Nc3ccc(F)cc3)nc2N)cc1]

1-fluoro-4-isothiocyanatobenzene (8.91 g, 58.20 mmol) was dissolved in acetonitrile (450 mL) followed by the addition of 1,8-diazabicyclo(5.4.0)undec-7-ene (8.86 g, 58.20 mmol) and cyanamide (2.94 g, 69.82 mmol). After stirring for 45 min at rt, further 1,8-diazabicyclo(5.4.0)undec-7-ene (4.43 g, 29.07 mmol) and ethyl [4-(bromoacetyl)phenoxy]acetate (17.52 g, 58.20 mmol) were added. The reaction mixture was stirred at rt overnight. The suspension was treated with water and the precipitate was isolated by filtration, washed with water and dried by lyophilization to give 18.54 g (77% yield) of the title compound.

$^1$H-NMR (500 MHz, DMSO-d6): δ ppm=1.22 (t, J=7.09 Hz, 3H), 4.18 (q, J=7.25 Hz, 2H), 4.86 (s, 2H), 7.00 (d, J=9.14 Hz, 2H), 7.21 (t, J=9.14 Hz, 2H), 7.61-7.67 (m, 4H), 8.21 (br s, 2H), 10.77 (s, 1H).

LC-MS (method 2) Rt=1.09 min; MS (ESIpos): m/z=416.3 [M+H]$^+$

Intermediate 81

[2-(4-fluoroanilino)-4-methyl-thiazol-5-yl]-phenyl-methanone

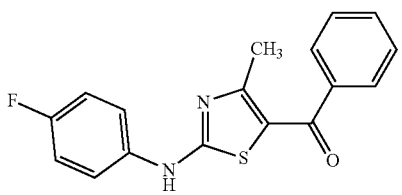 [SMILES: Cc1nc(Nc2ccc(F)cc2)sc1C(=O)c1ccccc1]

1-fluoro-4-isothiocyanatobenzene (77 mg, 0.50 mmol) was solved in acetonitrile (5 mL) followed by the addition of 1,8-diazabicyclo(5.4.0)undec-7-ene (77 mg, 0.50 mmol) and ethanimidamide (salt with hydrogen chloride) (57 mg, 0.60 mmol). After stirring for 45 min at rt, further 1,8-diazabicyclo(5.4.0)undec-7-ene (38 mg, 0.25 mmol) and 2-bromo-1-phenylethanone (100 mg, 0.50 mmol) were added. The reaction mixture was stirred at rt overnight. The solution was filtrated and purified by RP-HPLC (method D, basic). The title compound was isolated by lyophilization (53 mg, 33% yield).

$^1$H-NMR (400 MHz, DMSO-d6): δ ppm=2.28 (s, 3H), 7.18 (t, J=8.87 Hz, 2H), 7.51 (d, J=7.86 Hz, 2H), 7.53-7.58 (m, 3H), 7.63-7.67 (m, 2H), 10.67 (br s, 1H).

LC-MS (method 2) Rt=1.22 min; MS (ESIpos): m/z=313.1 [M+H]$^+$

Intermediate 82 rac-2-[4-[4-amino-2-(N-(2-amino-1-methyl-2-oxo-ethyl)-4-fluoro-anilino)thiazole-5-carbonyl]phenoxy]-2-methyl-propanoic acid

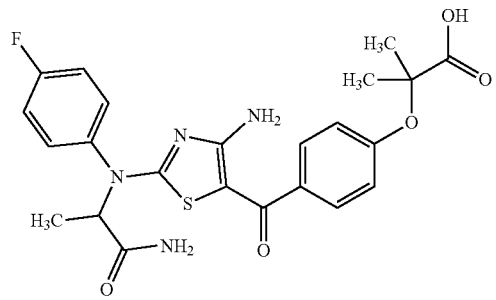 [SMILES: CC(C(N)=O)N(c1ccc(F)cc1)c1nc(N)c(C(=O)c2ccc(OC(C)(C)C(=O)O)cc2)s1]

Rac-ethyl 2-[4-[4-amino-2-(N-[2-amino-1-methyl-2-oxo-ethyl]-4-fluoro-anilino)thiazole-5-carbonyl]phenoxy]-2-methyl-propanoate (180 mg, 349 μmol, example 39) was dissolved in THF (1.8 ml), cooled to 0° C., and an aqueous solution of sodium hydroxide (350 μl, 1.0 M, 350 μmol) was added. The reaction mixture was stirred overnight at rt. Additional aqueous solution of sodium hydroxide (1.04 mmol) was added and the mixture was stirred for 3 days at rt. The reaction mixture was treated with water, and aqueous solution of hydrochloric acid (1 M) was added to adjust the pH to 5 and afterwards it was extracted three times with dichloromethane. The organic layer was concentrated under reduced pressure to give 36 mg (21% yield) of the title compound.

The aqueous layer was adjusted to pH 3 by addition of aqueous hydrochloric acid (1 M), the formed precipitate was isolated by filtration, washed with water and dried by lyophilization to give 90 mg (53% yield) of the title compound.

$^1$H NMR (400 MHz, DMSO-d$_6$): δ ppm=1.15 (d, J=7.35 Hz, 3H), 1.51 (s, 6H), 4.94-5.14 (m, 1H), 6.73-6.79 (m, 2H), 7.22-7.26 (m, 1H), 7.30-7.37 (m, 2H), 7.42-7.47 (m, 2H), 7.58 (br s, 1H), 7.64 (dd, J=8.87, 5.07 Hz, 2H), 7.77-8.44 (m, 2H), 12.81-13.47 (m, 1H)

LC-MS (method 1) Rt=1.00 min; MS (ESIpos): m/z=487.5 [M+H]⁺

Intermediate 83 tert-butyl N-(4-amino-5-benzoyl-thiazol-2-yl)-N-phenyl-carbamate

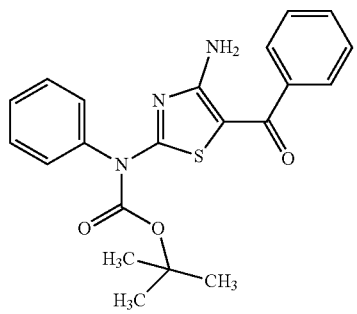 [SMILES: CC(C)(C)OC(=O)N(c1ccccc1)c1nc(N)c(C(=O)c2ccccc2)s1]

(4-amino-2-anilino-1,3-thiazol-5-yl)(phenyl)methanone (100 mg, 339 µmol, Intermediate 61) was provided in dichloromethane at rt. N,N-diisopropylethylamine (180 µl, 1.0 mmol; CAS-RN 7087-68-5), 4-(dimethylamino)pyridine (8 mg, 67.7 µmol; CAS-RN 1122-58-3) and di-tert-butyl dicarbonate (81 mg, 372 µmol; CAS-RN 24424-99-5) was added. The reaction mixture was stirred for 3 h at rt. The mixture was diluted with dichloromethane, washed with brine, dried and evaporated to give 120 mg (95% purity, 85% yield) of the title compound.

¹H-NMR (400 MHz, DMSO-d6): δ ppm=1.32 (s, 9H), 7.35-7.44 (m, 3H), 7.45-7.51 (m, 2H), 7.52-7.58 (m, 3H), 7.69-7.73 (m, 2H), 7.94 (s, 2H).

The following intermediates were prepared from the starting materials stated in Table 3, below, using the procedure as for Intermediate 83.

The crude product was either purified by RP-HPLC (methods A-D depending on polarity) or by preparative flash chromatography (methods X, Y or Z depending on polarity) after precipitation, extraction or filtration of the reaction mixture if necessary.

TABLE 3

| | Intermediates 84-96 | | |
|---|---|---|---|
| Intermediate number | Chemical structure Compound name | Starting materials | Analytics/purification/yield |
| 84 | ![structure] tert-butyl N-(4-amino-5-benzoyl-thiazol-2-yl)-N-(4-fluorophenyl)carbamate | Intermediate 62; di-tert-butyl dicarbonate | ¹H-NMR (400 MHz, DMSO-d6): δ ppm = 1.34 (s, 9 H), 7.31 (t, J = 8.87 Hz, 2 H), 7.44-7.48 (m, 2 H), 7.50-7.59 (m, 3 H), 7.68-7.74 (m, 2 H), 7.93 (s, 2 H). 91% yield |
| 85 | ![structure] tert-butyl N-[4-amino-5-(4-methoxybenzoyl)thiazol-2-yl]-N-(4-fluorophenyl)carbamate | Intermediate 63; di-tert-butyl dicarbonate | ¹H-NMR (400 MHz, DMSO-d6): δ ppm = 1.35 (s, 9 H), 3.84 (s, 3 H), 7.05-7.10 (m, 2 H), 7.31 (t, J = 8.74 Hz, 2 H), 7.46 (dd, J = 8.87, 5.07 Hz, 2 H), 7.73 (d, J = 8.87 Hz, 2 H), 7.86 (s, 2 H). 94% yield |

TABLE 3-continued

Intermediates 84-96

| Intermediate number | Chemical structure Compound name | Starting materials | Analytics/purification/yield |
|---|---|---|---|
| 86 | tert-butyl N-[4-amino-5-(4-methylbenzoyl)thiazol-2-yl]-N-(4-fluorophenyl)carbamate | Intermediate 64; di-tert-butyl dicarbonate | $^1$H-NMR (400 MHz, DMSO-d6): δ ppm = 1.34 (s, 9 H), 2.39 (s, 3 H), 7.31 (s, 4 H), 7.44-7.48 (m, 2 H), 7.61 (s, 2 H), 7.89 (s, 2 H). 79% yield |
| 87 | tert-butyl N-[4-amino-5-(4-fluorobenzoyl)thiazol-2-yl]-N-(4-fluorophenyl)carbamate | Intermediate 65; di-tert-butyl dicarbonate | $^1$H-NMR (400 MHz, DMSO-d6): δ ppm = 1.34 (s, 9 H), 7.31 (t, J = 8.87 Hz, 2 H), 7.37 (t, J = 9.00 Hz, 2 H), 7.46 (dd, J = 9.12, 5.07 Hz, 2 H), 7.79 (dd, J = 8.87, 5.58 Hz, 2 H), 7.95 (s, 2 H). quantitative yield |
| 88 | tert-butyl N-(4-amino-5-benzoyl-thiazol-2-yl)-N-(2,4-difluorophenyl)carbamate | Intermediate 66; di-tert-butyl dicarbonate | $^1$H-NMR (400 MHz, DMSO-d6): δ ppm = 1.35 (s, 9 H), 7.22-7.27 (m, 1 H), 7.49-7.57 (m, 4 H), 7.67-7.74 (m, 3 H), 7.95 (s, 2 H). 69% yield |

TABLE 3-continued

Intermediates 84-96

| Intermediate number | Chemical structure Compound name | Starting materials | Analytics/purification/yield |
|---|---|---|---|
| 89 | 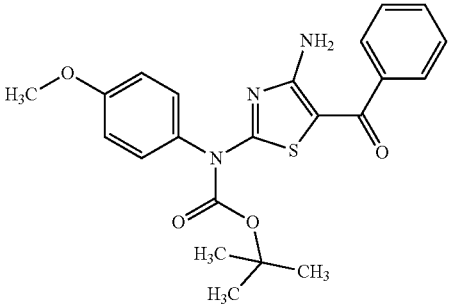 [SMILES: COc1ccc(N(C(=O)OC(C)(C)C)c2nc(N)c(C(=O)c3ccccc3)s2)cc1]<br>tert-butyl N-(4-amino-5-benzoyl-thiazol-2-yl)-N-(4-methoxyphenyl)carbamate | Intermediate 67; di-tert-butyl dicarbonate | $^1$H-NMR (400 MHz, DMSO-d6): δ ppm = 1.34 (s, 9 H), 3.80 (s, 3 H), 6.98-7.02 (m, 2 H), 7.25-7.30 (m, 2 H), 7.50-7.58 (m, 3 H), 7.68-7.74 (m, 2 H), 7.93 (s, 2 H).<br>91% yield |
| 90 | 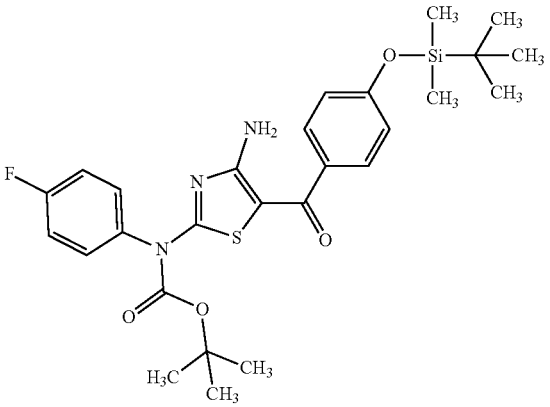 [SMILES: CC(C)(C)OC(=O)N(c1ccc(F)cc1)c1nc(N)c(C(=O)c2ccc(O[Si](C)(C)C(C)(C)C)cc2)s1]<br>tert-butyl N-[4-amino-5-[4-[tert-butyl(dimethyl)silyl]oxybenzoyl]thiazol-2-yl]-N-(4-fluorophenyl)carbamate | Intermediate 68; di-tert-butyl dicarbonate | $^1$H-NMR (400 MHz, DMSO-d6): δ ppm = 0.25 (s, 6 H), 0.96-0.99 (m, 9 H), 1.35 (s, 9 H), 6.99 (d, J = 8.62 Hz, 2 H), 7.28-7.34 (m, 2 H), 7.46 (dd, J = 8.87, 5.07 Hz, 2 H), 7.69 (d, J = 8.87 Hz, 2 H), 7.88 (s, 2 H).<br>92% yield |
| 91 | 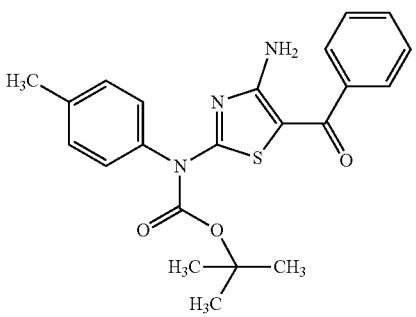 [SMILES: Cc1ccc(N(C(=O)OC(C)(C)C)c2nc(N)c(C(=O)c3ccccc3)s2)cc1]<br>tert-butyl N-(4-amino-5-benzoyl-thiazol-2-yl)-N-(p-tolyl)carbamate | Intermediate 69; di-tert-butyl dicarbonate | $^1$H-NMR (400 MHz, DMSO-d6): δ ppm = 1.33 (s, 9 H), 2.36 (s, 3 H), 7.25 (d, J = 9.38 Hz, 4 H), 7.54 (s, 3 H), 7.69-7.74 (m, 2 H), 7.93 (s, 2 H).<br>85% yield |

TABLE 3-continued

Intermediates 84-96

| Intermediate number | Chemical structure Compound name | Starting materials | Analytics/purification/yield |
|---|---|---|---|
| 92 | 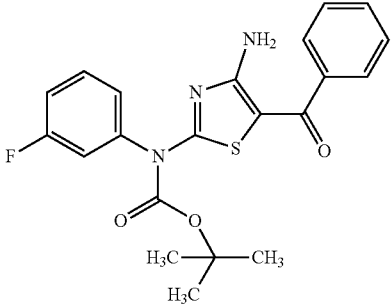 [SMILES: CC(C)(C)OC(=O)N(c1cccc(F)c1)c1nc(N)c(C(=O)c2ccccc2)s1]<br>tert-butyl N-(4-amino-5-benzoyl-thiazol-2-yl)-N-(3-fluorophenyl)carbamate | Intermediate 70; di-tert-butyl dicarbonate | $^1$H-NMR (400 MHz, DMSO-d6): δ ppm = 1.34 (s, 9 H), 7.22-7.32 (m, 2 H), 7.43 (br dt, J = 9.76, 2.22 Hz, 1 H), 7.48-7.60 (m, 4 H), 7.69-7.74 (m, 2 H), 7.95 (s, 2 H).<br>99% yield |
| 93 | 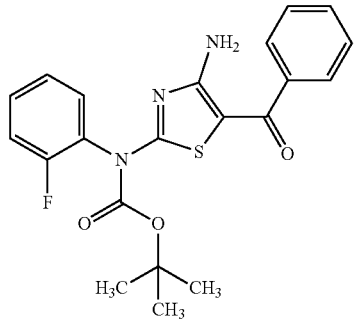 [SMILES: CC(C)(C)OC(=O)N(c1nc(N)c(C(=O)c2ccccc2)s1)c1ccccc1F]<br>tert-butyl N-(4-amino-5-benzoyl-thiazol-2-yl)-N-(2-fluorophenyl)carbamate | Intermediate 71; di-tert-butyl dicarbonate | $^1$H-NMR (400 MHz, DMSO-d6): δ ppm = 1.34 (s, 9 H), 7.33 (td, J = 7.67, 1.39 Hz, 1 H), 7.41 (ddd, J = 10.01, 8.49, 1.27 Hz, 1 H), 7.47-7.60 (m, 5 H), 7.70-7.75 (m, 2 H), 7.95 (s, 2 H).<br>88% yield |
| 94 | 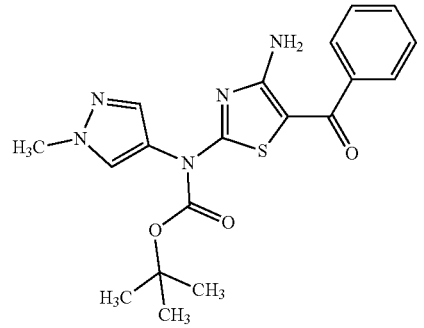 [SMILES: Cn1cc(N(C(=O)OC(C)(C)C)c2nc(N)c(C(=O)c3ccccc3)s2)cn1]<br>tert-butyl N-(4-amino-5-benzoyl-thiazol-2-yl)-N-(1-methylpyrazol-4-yl)carbamate | Intermediate 74; di-tert-butyl dicarbonate | $^1$H-NMR (400 MHz, DMSO-d6): δ ppm = 1.39 (s, 9 H), 3.85 (s, 3 H), 7.49-7.57 (m, 4 H), 7.68-7.73 (m, 2 H), 7.92 (s, 1 H), 7.98 (s, 2 H).<br>89% yield |

TABLE 3-continued

Intermediates 84-96

| Intermediate number | Chemical structure Compound name | Starting materials | Analytics/purification/yield |
|---|---|---|---|
| 95 | 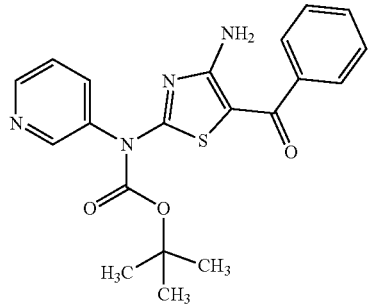 [SMILES: CC(C)(C)OC(=O)N(c1cccnc1)c1nc(N)c(C(=O)c2ccccc2)s1]<br>tert-butyl N-(4-amino-5-benzoyl-thiazol-2-yl)-N-(3-pyridyl)carbamate | Intermediate 75; di-tert-butyl dicarbonate | $^1$H-NMR (400 MHz, DMSO-d6): δ ppm = 1.34 (s, 9 H), 7.49-7.61 (m, 4 H), 7.68-7.75 (m, 2 H), 7.90-7.97 (m, 3 H), 8.60 (dd, J = 4.56, 1.52 Hz, 1 H), 8.63 (dd, J = 2.54, 0.51 Hz, 1 H). LC-MS (method 2) Rt = 1.24 min; MS (ESIpos): m/z = 397.5 [M + H]$^+$<br>85% yield |
| 96 | 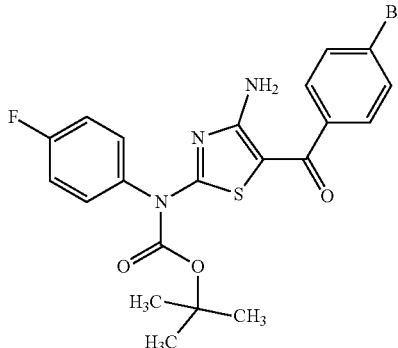<br>tert-butyl N-[4-amino-5-(4-bromobenzoyl)thiazol-2-yl]-N-(4-fluorophenyl)carbamate | Intermediate 76; di-tert-butyl dicarbonate | $^1$H-NMR (400 MHz, DMSO-d6): δ ppm = 1.34 (s, 9 H), 7.31 (t, J = 8.74 Hz, 2 H), 7.44-7.48 (m, 2 H), 7.64-7.68 (m, 2 H), 7.73-7.77 (m, 2 H), 7.98 (s, 2 H). LC-MS (method 2) Rt = 1.53 min; MS (ESIpos): m/z = 492.5 [M + H]$^+$<br>preparative flash chromatography (method Z, 0-3%)<br>92% yield |

Intermediate 97

2-bromo-1-[4-(methoxymethoxy)phenyl]ethan-1-one

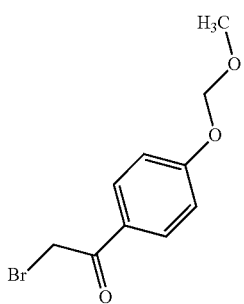

4-Hydroxyphenacyl bromide (2.50 g, 11.6 mmol) was provided in THF (50 mL). To this was added sodium hydride (511 mg, 60% in mineral oil, 12.8 mmol), and the suspension was stirred at rt for 1 h, after which time chloromethyl methyl ether (1.1 mL, 13.9 mmol) was added dropwise. The suspension was stirred at rt for 72 h. The reaction was stopped by the addition of a saturated aqueous solution of ammonium chloride and extracted with dichloromethane. The organics were washed with brine, dried over magnesium sulfate, filtered and concentrated under vacuum to give a brown oil. The residue was purified by normal phase column chromatography (10-80% EtOAc in heptane) to give 1.161 g (39% yield) of the title compound as a light yellow oil.

$^1$H-NMR (CDCl3, 400 MHz): δ ppm=3.48 (s, 3H); 4.40 (s, 2H); 5.23 (s, 2H); 7.09 (d, 2H); 7.96 (d, 2H)

LC-MS (method 2): Rt=0.79 min; MS(ESIpos) m/z=260 [M+H]$^+$

Intermediate 98

(4-amino-2-anilino-1,3-thiazol-5-yl)[4-(methoxymethoxy)phenyl]methanone

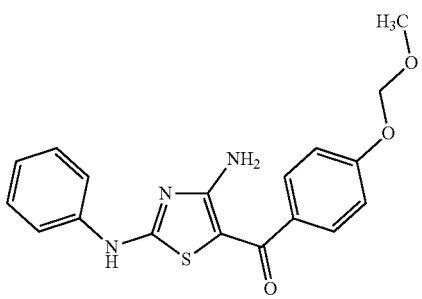 [SMILES: COCOc1ccc(C(=O)c2sc(Nc3ccccc3)nc2N)cc1]

Dry acetonitrile (65 mL) was provided and phenyl isothiocyanate (350 μl, 2.9 mmol; CAS-RN 103-72-0), cyanamide (146 mg, 3.47 mmol; CAS-RN 420-04-2) and 1,8-diazabicyclo[5.4.0]undec-7-en (0.75 mL, 5.1 mmol; CAS-RN 6674-22-2) were added and the solution was stirred at rt for 45 min, after which time more 1,8-diazabicyclo(5.4.0)undec-7-ene (0.75 mL, 5.1 mmol) was added, followed by 2-bromo-1-[4-(methoxymethoxy)phenyl]ethan-1-one (750 mg, 2.89 mmol in 10 mL acetonitrile; Intermediate 97). The solution was stirred at rt for 1.5 h. The mixture was partitioned between ethyl acetate and saturated aqueous sodium bicarbonate solution. The organics were washed with brine, and silica was added. The suspension was concentrated under vacuum. The residue was purified by normal phase column chromatography (10-80% EtOAc in heptane) to give 669 mg (65% yield) of the title compound as a yellow solid.

LC-MS (method 2): Rt=0.81 min; MS(ESIpos) m/z=356 [M+H]$^+$ $^1$H-NMR (CDCl3, 400 MHz): δ ppm=3.49 (s, 3H); 5.20 (s, 2H); 7.05 (d, 2H); 7.19 (t, 1H); 7.33-7.43 (m, 4H); 7.73 (d, 2H); 8.46 (br s, 1H); NH2 not observed.

Intermediate 99

[4-amino-2-(4-fluoroanilino)-1,3-thiazol-5-yl][4-(methoxymethoxy)phenyl]methanone

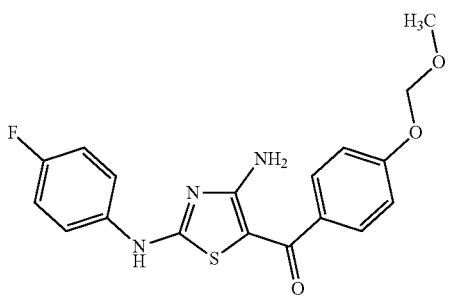 [SMILES: COCOc1ccc(C(=O)c2sc(Nc3ccc(F)cc3)nc2N)cc1]

Dry acetonitrile (25 mL) was provided and 4-fluorophenyl isothiocyanate (296 mg, 1.93 mmol), cyanamide (97.4 mg, 2.32 mmol; CAS-RN 420-04-2) and 1,8-diazabicyclo(5.4.0)undec-7-ene (0.5 mL, 3.4 mmol; CAS-RN 6674-22-2) were added and the solution was stirred at rt for 45 min, after which time more 1,8-diazabicyclo(5.4.0)undec-7-ene (0.5 mL, 3.4 mmol)) was added, followed by 2-bromo-1-[4-(methoxymethoxy)phenyl]ethan-1-one (500 mg, 1.93 mmol in 10 mL acetonitrile; Intermediate 98). The solution was stirred at rt for 18 h. The mixture was evaporated to dryness under vacuum, partitioned between water and ethyl acetate and extracted into ethyl acetate. The organic layers were combined and washed with saturated aqueous sodium hydrogen carbonate solution and brine, then dried over magnesium sulfate before being filtered. Silica was added and the suspension was evaporated. This was purified by normal phase column chromatography (15-100% EtOAc in heptane) to give 620 mg (72% yield) of the title compound.

$^1$H-NMR (DMSO-d6, 400 MHz): δ ppm=3.43 (s, 3H); 5.29 (s, 2H); 7.12 (d, 2H); 7.25 (2H, t); 7.64-7.72 (m, 4H); 8.20 (br s, 2H); 10.79 (s, 1H).

LC-MS (method 2): Rt=0.81 min; MS(ESIpos) m/z=374 [M+H]$^+$

Intermediate 100 rac-2-[4-[4-amino-2-(N-[2-amino-1-methyl-2-oxo-ethyl]-4-fluoro-anilino)thiazole-5-carbonyl]phenoxy]acetic acid

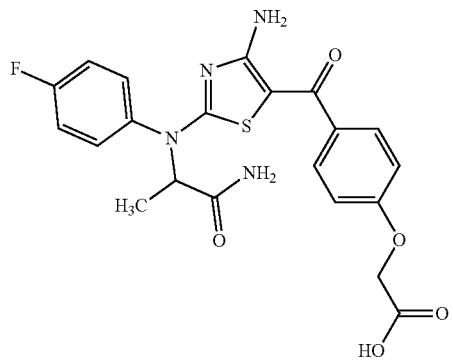 [SMILES: CC(C(N)=O)N(c1ccc(F)cc1)c1nc(N)c(C(=O)c2ccc(OCC(=O)O)cc2)s1]

To a solution of rac-ethyl 2-[4-[4-amino-2-(4-fluoro-N-[2-amino-1-methyl-2-oxo-ethyl]anilino)thiazole-5-carbonyl]phenoxy]acetate (24 mg, 0.05 mmol; Example 81) in tetrahydrofurane (2 mL) was added aqueous sodium hydroxide solution (0.1 mL, 1 M). The reaction mixture was stirred overnight at rt.

The reaction mixture was diluted with water, aqueous hydrochloride acid (1 M) was added dropwise to adjust the pH to 3 and afterwards the mixture was extracted with dichloromethane. The organic layer was washed with brine, filtered through a water repellent filter circle (MN 617 WA) and evaporated to dryness. The residue was dissolved in acetonitrile/water (1:1) and dried by lyophilization to give 15 mg (63% yield) of the title compound.

$^1$H-NMR (400 MHz, DMSO-d6): δ ppm=1.16 (d, J=7.35 Hz, 3H), 4.68 (s, 2H), 5.05 (br q, J=7.44 Hz, 1H), 6.89 (d, J=8.87 Hz, 2H), 7.24 (s, 1H), 7.33 (t, J=8.74 Hz, 2H), 7.47 (d, J=8.87 Hz, 2H), 7.58 (s, 1H), 7.64 (dd, J=8.87, 5.07 Hz, 2H), 8.08 (br s, 2H), 13.02 (br s, 1H).

LC-MS (method 1) Rt=0.87 min; MS (ESIpos): m/z=459.5 [M+H]$^+$

Intermediates 100.1 and 100.2:

(R)-2-[4-[4-amino-2-(N-[2-amino-1-methyl-2-oxo-ethyl]-4-fluoro-anilino)thiazole-5-carbonyl]phenoxy]acetic acid and (S)-2-[4-[4-amino-2-(N-[2-amino-1-methyl-2-oxo-ethyl]-4-fluoro-anilino)thiazole-5-carbonyl]phenoxy]acetic acid Intermediate 100.1

2-[4-[4-amino-2-(N-[2-amino-1-methyl-2-oxo-ethyl]-4-fluoro-anilino)thiazole-5-carbonyl]phenoxy]acetic acid (enantiomer 1)

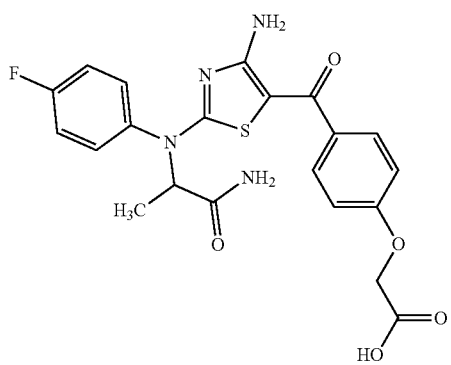 [SMILES: CC(C(N)=O)N(c1ccc(F)cc1)c1nc(N)c(C(=O)c2ccc(OCC(=O)O)cc2)s1]

To an ice cooled solution of ethyl 2-[4-[4-amino-2-(4-fluoro-N-[2-amino-1-methyl-2-oxo-ethyl]anilino)thiazole-5-carbonyl]phenoxy]acetate (enantiomer 1) (2.50 g, 5.14 mmol, Example 81.1) in tetrahydrofurane (26.3 mL) was added aqueous sodium hydroxide solution (5.1 mL, 1 M). The mixture was stirred overnight at rt.

The reaction mixture was diluted with water, aqueous hydrochloride acid (1 M) was added dropwise to adjust the pH to 3 and afterwards the mixture was treated with dichloromethane. The resulting precipitate was isolated by filtration, washed with water and some dichloromethane and dried by lyophilization to give 1.48 g (62% yield) of the title compound.

Intermediate 100.2

2-[4-[4-amino-2-(N-[2-amino-1-methyl-2-oxo-ethyl]-4-fluoro-anilino)thiazole-5-carbonyl]phenoxy]acetic acid (enantiomer 2)

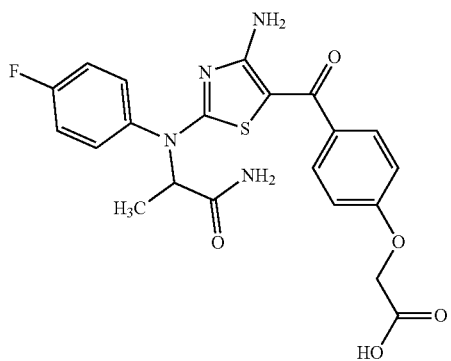 [SMILES: CC(C(N)=O)N(c1ccc(F)cc1)c1nc(N)c(C(=O)c2ccc(OCC(=O)O)cc2)s1]

To an ice cooled solution of ethyl 2-[4-[4-amino-2-(4-fluoro-N-[2-amino-1-methyl-2-oxo-ethyl]anilino)thiazole-5-carbonyl]phenoxy]acetate (enantiomer 2) (2.60 g, 5.34 mmol; Example 81.2) in tetrahydrofurane (27.3 mL) was added aqueous sodium hydroxide solution (5.3 mL, 1 M). The mixture was stirred overnight at rt.

The reaction mixture was diluted with water, aqueous hydrochloride acid (1 M) was added dropwise to adjust the pH to 3 and afterwards the mixture was treated with dichloromethane.

The resulting precipitate was isolated by filtration, washed with water and some dichloromethane and dried by lyophilization to give 0.95 g (37% yield) of the title compound.

The organic layer of the filtrate was separated, washed with brine, filtered through a water repellent filter circle (MN 617 WA) and evaporated to dryness to give further 695 mg (28% yield) of the title compound.

The following Intermediates were prepared from commercial starting materials stated in Table 4, below, using the procedure as for Intermediate 4, followed by purification by chromatography if needed. If no purification is specified, the respective title compound was isolated as crude product.

The crude product was either purified by RP-HPLC (methods A-D depending on polarity) or by preparative flash chromatography (methods X, Y or Z depending on polarity) if necessary. In case of a missing precipitation, the reaction mixture was extracted three times with ethyl acetate. The combined organic phases were dried over sodium sulfate, filtrated and evaporated to dryness. The crude product was purified by chromatography as stated in Table 4.

TABLE 4

Intermediates 101-197

| Intermediate number | Chemical structure Compound name | Starting materials | Analytics/purification/yield |
|---|---|---|---|
| 101 | 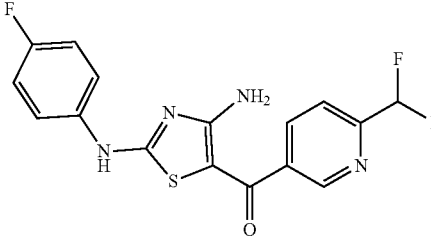<br>[4-amino-2-(4-fluoroanilino)thiazol-5-yl]-[6-(difluoromethyl)-3-pyridyl]methanone | 1-fluoro-4-isothiocyanato-benzene; 2-bromo-1-[6-(difluoromethyl)-3-pyridyl]ethanone | $^1$H NMR (400 MHz, DMSO-d$_6$) δ ppm = 7.03 (t, J = 60 Hz, 1 H), 7.23 (t, J = 8.87 Hz, 2 H), 7.64 (dd, J = 9.12, 4.82 Hz, 2 H), 7.81 (d, J = 8.11 Hz, 1 H), 8.22 (dd, J = 7.98, 2.15 Hz, 1 H), 8.35-8.40 (m, 2 H), 8.92 (d, J = 1.52 Hz, 1 H), 10.94 (s, 1 H).<br>LC-MS (method 1) Rt = 1.08 min; MS (ESIpos): m/z = 365.2 [M + H]$^+$<br>71% yield |
| 102 | 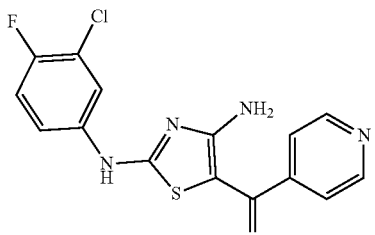<br>[4-amino-2-(3-chloro-4-fluoro-anilino)thiazol-5-yl]-(4-pyridyl) methanone | 2-chloro-1-fluoro-4-isothiocyanato-benzene; 2-bromo-1-(4-pyridyl)ethanone; hydrobromide | $^1$H NMR (400 MHz, DMSO-d$_6$) δ ppm = 7.22 (ddd, J = 8.87, 4.56, 2.53 Hz, 1 H), 7.33-7.37 (m, 1 H), 7.47 (dd, J = 6.84, 2.53 Hz, 1 H), 7.57-7.62 (m, 2 H), 8.41 (s, 1 H), 8.50-8.55 (m, 2 H).<br>LC-MS (method 2) Rt = 0.81 min; MS (ESIpos): m/z = 349.2 [M + H]$^+$<br>65% yield |
| 103 | 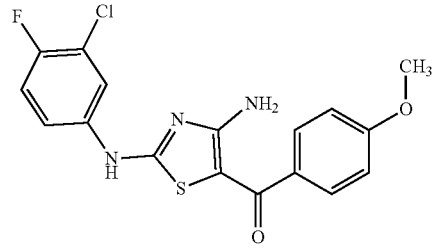 [SMILES: COc1ccc(C(=O)c2sc(Nc3ccc(F)c(Cl)c3)nc2N)cc1]<br>[4-amino-2-(3-chloro-4-fluoro-anilino)thiazol-5-yl]-4-methoxyphenyl)methanone | 2-chloro-1-fluoro-4-isothiocyanato-benzene; 2-bromo-1-(4-methoxyphenyl) ethanone | $^1$H NMR (400 MHz, DMSO-d$_6$) δ ppm = 3.79-3.84 (m, 3 H), 7.00 (d, 2 H), 7.32-7.43 (m, 2 H), 7.66 (d, 2 H), 7.88-7.98 (m, 1 H), 8.05-8.34 (m, 1 H).<br>LC-MS (method 2) Rt = 1.14 min; MS (ESIpos): m/z = 378.3 [M + H]$^+$<br>96% yield |
| 104 | 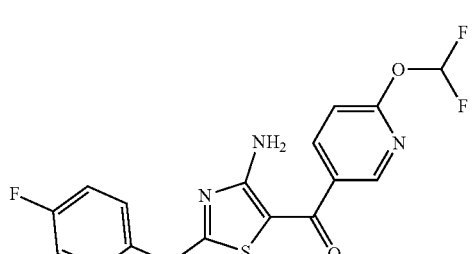<br>[4-amino-2-(4-fluoroanilino)thiazol-5-yl]-[6-(difluoromethoxy)-3-pyridyl]methanone | 1-fluoro-4-isothiocyanatobenzene; 2-bromo-1-[6-(difluoromethoxy) pyridin-3-yl]ethanone | $^1$H-NMR (400 MHz, DMSO-d$_6$): δ ppm = 7.15-7.26 (m, 3 H), 7.61-7.68 (m, 2 H), 7.77 (t, 1H), 8.12-8.19 (m, 1 H), 8.21-8.40 (m, 2 H), 8.53-8.57 (m, 1 H), 10.90 (br s, 1 H).<br>LC-MS (method 2) Rt = 1.03 min; MS (ESIpos): m/z = 381.2 [M + H]$^+$<br>73% yield |

TABLE 4-continued

Intermediates 101-197

| Intermediate number | Chemical structure Compound name | Starting materials | Analytics/purification/yield |
|---|---|---|---|
| 105 | 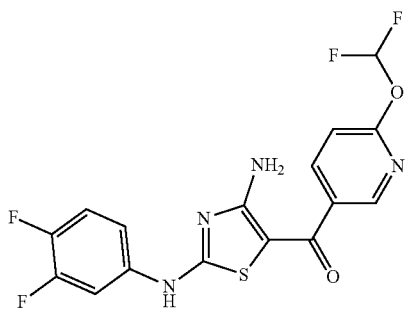 [SMILES: Nc1nc(Nc2ccc(F)c(F)c2)sc1C(=O)c1ccc(OC(F)F)nc1]<br>[4-amino-2-(3,4-difluoroanilino)thiazol-5-yl]-[6-(difluoromethoxy)-3-pyridyl]methanone | 1,2-difluoro-4-isothiocyanato-benzene; 2-bromo-1-[6-(difluoromethoxy)pyridin-3-yl]ethanone | $^1$H NMR (400 MHz, DMSO-d$_6$) δ ppm = 7.16-7.20 (m, 1 H), 7.24 (brd, J = 8.87 Hz, 1 H), 7.43 (d, J = 10.39 Hz, 1 H), 7.78 (t, J = 72 Hz, 1 H), 7.90-7.94 (m, 1 H), 8.17 (dd, J = 8.36, 2.53 Hz, 1 H), 8.28-8.33 (m, 2 H), 8.56 (d, J = 1.77 Hz, 1 H), 11.05 (br s, 1 H). LC-MS (method 2) Rt = 1.02 min; MS (ESIpos): m/z = 399.2 [M + H]$^+$ 63% yield |
| 106 | 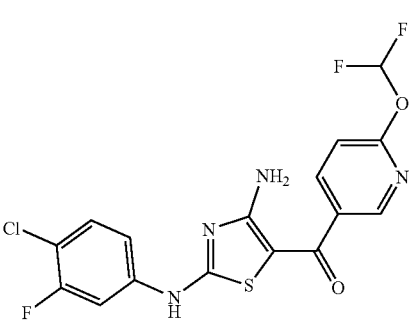 [SMILES: Nc1nc(Nc2ccc(Cl)c(F)c2)sc1C(=O)c1ccc(OC(F)F)nc1]<br>[4-amino-2-(4-chloro-3-fluoro-anilino)thiazol-5-yl]-[6-(difluoromethoxy)-3-pyridyl]methanone | 1-chloro-2-fluoro-4-isothiocyanatobenzene; 2-bromo-1-[6-(difluoromethoxy)pyridin-3-yl]ethanone | LC-MS (method 2) Rt = 1.03 min; MS (ESIpos): m/z = 415.2 [M + H]$^+$ 57% yield |
| 107 | 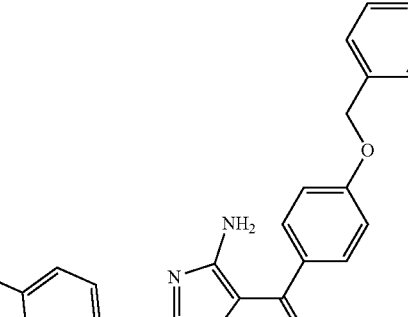<br>[4-amino-2-(3,4-difluoroanilino)-1,3-thiazol-5-yl][4-(benzyloxy)phenyl]methanone | 1,2-difluoro-4-isothiocyanato-benzene; 1-[4-(benzyloxy)phenyl]-2-bromoethanone | LC-MS (method 2) Rt = 1.29 min; MS (ESIpos): m/z = 438.3 [M + H]$^+$ 71% yield |

TABLE 4-continued

Intermediates 101-197

| Intermediate number | Chemical structure Compound name | Starting materials | Analytics/purification/yield |
|---|---|---|---|
| 108 | 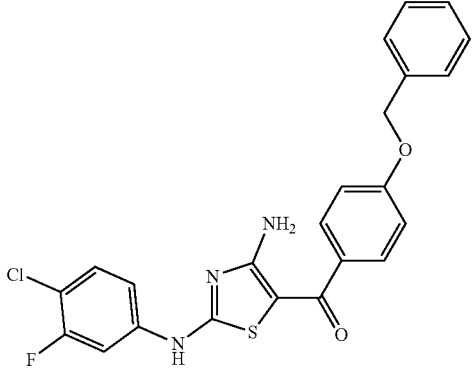 [SMILES: Nc1nc(Nc2ccc(Cl)c(F)c2)sc1C(=O)c1ccc(OCc2ccccc2)cc1]<br>[4-amino-2-(4-chloro-3-fluoro-anilino)thiazol-5-yl]-(4-benzyloxyphenyl)methanone | 1-chloro-2-fluoro-4-isothiocyanatobenzene; 1-[4-(benzyloxy)phenyl]-2-bromoethanone | LC-MS (method 2) Rt = 1.35 min; MS (ESIpos): m/z = 454.3 [M + H]$^+$<br>94% yield |
| 109 | 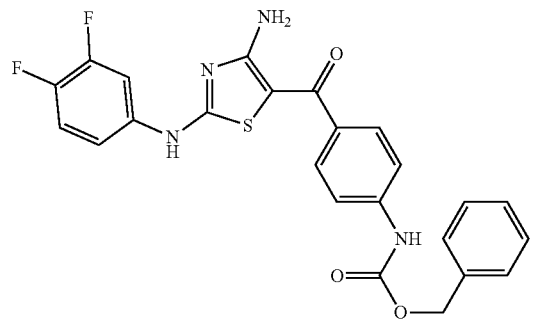 [SMILES: Nc1nc(Nc2ccc(F)c(F)c2)sc1C(=O)c1ccc(NC(=O)OCc2ccccc2)cc1]<br>Benzyl (4-{[4-amino-2-(3,4-difluoroanilino)-1,3-thiazol-5-yl]carbonyl}pheny)carbamate | 1,2-difluoro-4-isothiocyanato-benzene; benzyl N-[4-(2-bromoacetyl)phenyl]carbamate | LC-MS (method 2) Rt = 1.18 min; MS (ESIpos): m/z = 481.3 [M + H]$^+$<br>78% yield |
| 110 | 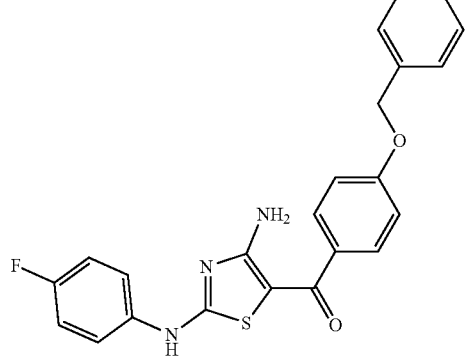<br>[4-amino-2-(4-fluoroanilino)thiazol-5-yl]-(4-benzyloxyphenyl)methanone | 1-fluoro-4-isothiocyanatobenzene; 1-[4-(benzyloxy)phenyl]-2-bromoethanone | $^1$H NMR (400 MHz, DMSO-d$_6$) δ ppm = 5.17 (s, 2 H), 7.06-7.10 (m, 2 H), 7.19-7.23 (m, 2 H), 7.39-7.43 (m, 5 H), 7.62-7.67 (m, 4 H), 8.11-8.15 (m, 2 H), 10.75 (br s, 1 H)<br>LC-MS (method 2) Rt = 1.30 min; MS (ESIpos): m/z = 420.2 [M + H]$^+$<br>86% yield |

TABLE 4-continued

Intermediates 101-197

| Intermediate number | Chemical structure Compound name | Starting materials | Analytics/purification/yield |
|---|---|---|---|
| 111 | [4-amino-2-(4-fluoroanilino)thiazol-5-yl]-(4-iodophenyl)methanone | 1-fluoro-4-isothiocyanatobenzene; 2-bromo-1-(4-iodophenyl)ethanone | LC-MS (method 2) Rt = 1.21 min; MS (ESIpos): m/z = 440.1 [M + H]$^+$ 82% yield |
| 112 | 2-[4-[4-amino-2-(4-fluoroanilino)thiazole-5-carbonyl]phenoxy]ethyl acetate | 1-fluoro-4-isothiocyanatobenzene; 2-[4-(bromoacetyl)phenoxy] ethyl acetate (Intermediate 198) | $^1$H NMR (400 MHz, DMSO-d$_6$) δ ppm = 3.73 (q, J = 5.15 Hz, 2 H), 4.03-4.07 (m, 2 H), 4.91 (t, J = 5.45 Hz, 1 H), 7.00-7.05 (m, 3 H), 7.19-7.23 (m, 2 H), 7.60-7.65 (m, 5 H), 8.15-8.19 (m, 2 H), 10.74-10.76 (m, 1 H). LC-MS (method 2) Rt = 1.06 min; MS (ESIpos): m/z = 416.3 [M + H]$^+$ 11% yield |
| 113 | [4-amino-2-(4-chloro-3-fluoroanilino)-1,3-thiazol-5-yl](6-methoxypyridin-3-yl)methanone | 1-chloro-2-fluoro-4-isothiocyanatobenzene; 2-bromo-1-(6-methoxy-3-pyridyl)ethanone | LC-MS (method 2) Rt = 1.05 min; MS (ESIpos): m/z = 379.2 [M + H]$^+$ 100% yield |
| 114 | [4-amino-2-(4-fluoroanilino)thiazol-5-yl]-(4-phenoxyphenyl)methanone | 1-fluoro-4-isothiocyanatobenzene; 2-bromo-1-(4-phenoxyphenyl) ethanone | $^1$H NMR (400 MHz, DMSO-d$_6$) δ ppm = 7.02-7.06 (m, 2 H), 7.09-7.13 (m, 2 H), 7.19-7.23 (m, 3 H), 7.43-7.47 (m, 2 H), 7.61-7.65 (m, 2 H), 7.69-7.71 (m, 2 H), 8.19-8.21 (m, 2 H), 10.77 (br s, 1 H) LC-MS (method 2) Rt = 1.27 min; MS (ESIpos): m/z = 406.2 [M + H]$^+$ 84% yield |

TABLE 4-continued

Intermediates 101-197

| Intermediate number | Chemical structure Compound name | Starting materials | Analytics/purification/yield |
|---|---|---|---|
| 115 | 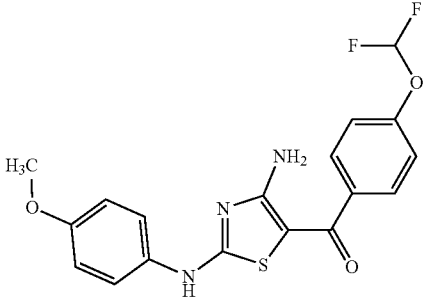<br>4-amino-2-(4-methoxyanilino)thiazol-5-yl]-[4-(difluoromethoxy)phenyl]methanone | 1-isothiocyanato-4-methoxybenzene; 2-bromo-1-[4-(difluoromethoxy)phenyl]ethanone | $^1$H NMR (500 MHz, DMSO-$d_6$) δ ppm = 3.73-3.76 (m, 3 H), 6.93-6.96 (m, 2 H), 7.22-7.26 (m, 2 H), 7.33 (t, 1 H), 7.45-7.48 (m, 2 H), 7.70-7.73 (m, 2 H), 8.19-8.21 (m, 2 H), 10.63 (m, 1 H) LC-MS (method 2) Rt = 1.27 min; MS (ESIpos): m/z = 406.2 [M + H]$^+$ 57% yield |
| 116 | 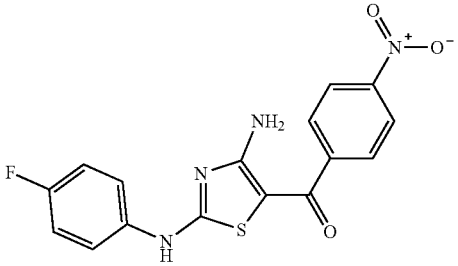 [SMILES: Nc1nc(Nc2ccc(F)cc2)sc1C(=O)c1ccc([N+](=O)[O-])cc1]<br>[4-amino-2-(4-fluoroanilino)thiazol-5-yl]-(4-nitrophenyl)methanone | 1-fluoro-4-isothiocyanatobenzene; 2-bromo-1-(4-nitrophenyl)ethanone | LC-MS (method 2) Rt = 0.95 min; MS (ESIpos): m/z = 359.1 [M + H]$^+$ 81% yield |
| 117 | 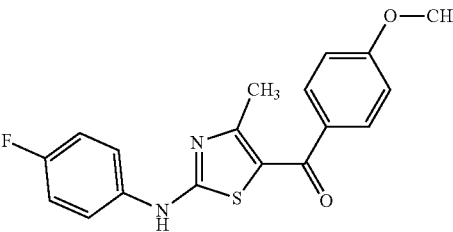 [SMILES: COc1ccc(C(=O)c2sc(Nc3ccc(F)cc3)nc2C)cc1]<br>[2-(4-fluoroanilino)-4-methyl-1,3-thiazol-5-yl](4-methoxyphenyl)methanone | 1-fluoro-4-isothiocyanatobenzene; ethanimidamide acetate (1:1); 2-bromo-1-(4-methoxyphenyl)ethanone | $^1$H NMR (400 MHz, DMSO-$d_6$) δ ppm = 2.34 (s, 3 H), 3.84 (s, 3 H), 7.05 (m, 2 H), 7.21 (m, 2 H), 7.64 (m, 2 H), 7.71 (m, 2 H), 10.76 (s, 1 H) LC-MS (method 2) Rt = 1.24 min; MS (ESIpos): m/z = 343.2 [M + H]$^+$ 8% yield |
| 118 | 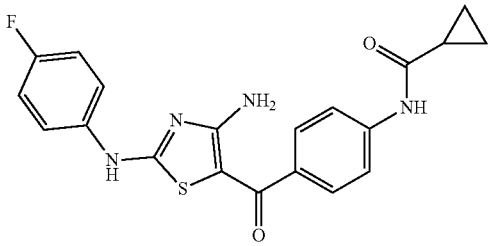 [SMILES: Nc1nc(Nc2ccc(F)cc2)sc1C(=O)c1ccc(NC(=O)C2CC2)cc1]<br>N-[4-[4-amino-2-(4-fluoroanilino)thiazole-5-carbonyl]phenyl]cyclopropanecarboxamide | 1-fluoro-4-isothiocyanatobenzene; N-[4-(bromoacetyl)phenyl]cyclopropanecarboxamide | LC-MS (method 2) Rt = 0.77 min; MS (ESIpos): m/z = 397.3 [M + H]$^+$ 69% yield |

TABLE 4-continued

Intermediates 101-197

| Intermediate number | Chemical structure Compound name | Starting materials | Analytics/purification/yield |
|---|---|---|---|
| 119 | 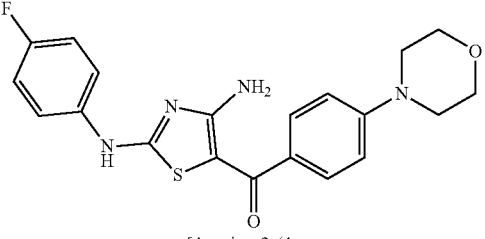<br>[4-amino-2-(4-fluoroanilino)thiazol-5-yl]-(4-morpholinophenyl)methanone | 1-fluoro-4-isothiocyanatobenzene; 2-bromo-1-[4-(morpholin-4-yl)phenyl]ethanone | LC-MS (method 2) Rt = 1.04 min; MS (ESIpos): m/z = 399.2 [M + H]$^+$ 66% yield |
| 120 | 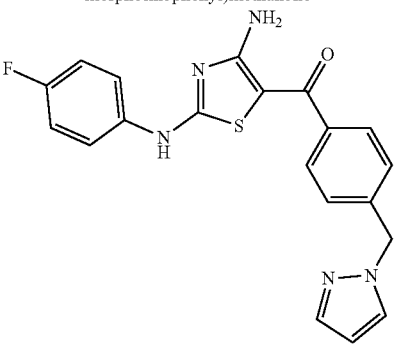<br>[4-amino-2-(4-fluoroanilino)-1,3-thiazol-5-yl][4-(1H-pyrazol-1-ylmethyl)phenyl]methanone | 1-fluoro-4-isothiocyanatobenzene; 2-bromo-1-{4-[(1H-pyrazol-1-yl)methyl]phenyl}ethan-1-one, hydrogen bromide | LC-MS (method 2) Rt = 1.01 min; MS (ESIpos): m/z = 394.3 [M + H]$^+$ 64% yield |
| 121 | 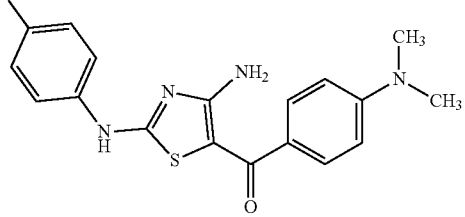<br>[4-amino-2-(4-fluoroanilino)-1,3-thiazol-5-yl][4-(dimethylamino)phenyl]methanone | 1-fluoro-4-isothiocyanatobenzene; 4-(dimethylamino)phenacyl bromide | LC-MS (method 2) Rt = 1.16 min; MS (ESIpos): m/z = 357.3 [M + H]$^+$ 86% yield |
| 122 | 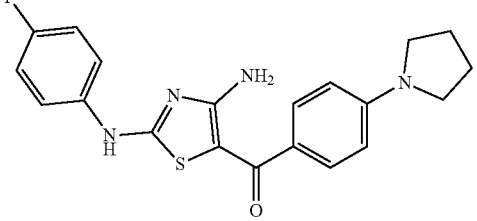<br>[4-amino-2-(4-fluoroanilino)thiazol-5-yl]-(4-pyrrolidin-1-ylphenyl)methanone | 1-fluoro-4-isothiocyanatobenzene; 2-bromo-1-[4-(pyrrolidin-1-yl)phenyl]ethanone | LC-MS (method 2) Rt = 1.26 min; MS (ESIpos): m/z = 383.2 [M + H]$^+$ 84% yield |

TABLE 4-continued

Intermediates 101-197

| Intermediate number | Chemical structure Compound name | Starting materials | Analytics/purification/yield |
|---|---|---|---|
| 123 | 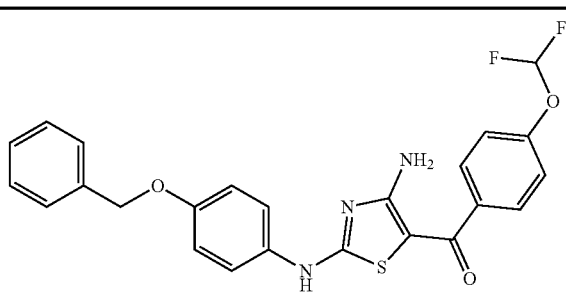<br>[4-amino-2-(4-benzyloxyanilino)thiazol-5-yl]-[4-(difluoromethoxy)phenyl]methanone | 1-(benzyloxy)-4-isothiocyanatobenzene; 2-bromo-1-[4-(difluoromethoxy)phenyl]ethanone | LC-MS (method 2) Rt = 1.32 min; MS (ESIpos): m/z = 468.3 [M + H]$^+$ 89% yield |
| 124 | 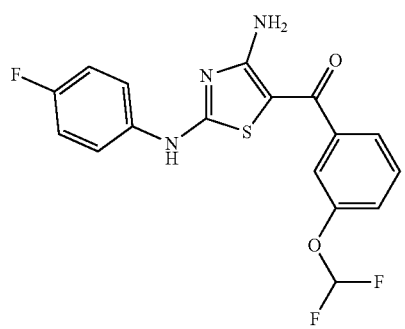 [SMILES: Nc1nc(Nc2ccc(F)cc2)sc1C(=O)c1cccc(OC(F)F)c1]<br>[4-amino-2-(4-fluoroanilino)-1,3-thiazol-5-yl][3-(difluoromethoxy)phenyl]methanone | 1-fluoro-4-isothiocyanatobenzene; 2-bromo-1-[3-(difluoromethoxy)phenyl]ethanone (intermediate 199) | LC-MS (method 2) Rt = 1.10 min; MS (ESIpos): m/z = 380.2 [M + H]$^+$ 91% yield |
| 125 | 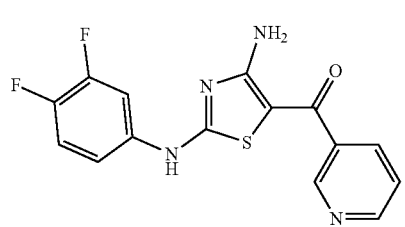 [SMILES: Nc1nc(Nc2ccc(F)c(F)c2)sc1C(=O)c1cccnc1]<br>[4-amino-2-(3,4-difluoroanilino)-1,3-thiazol-5-yl](pyridin-3-yl)methanone | 1,2-difluoro-4-isothiocyanatobenzene; 2-bromo-1-(pyridin-3-yl)ethanone hydrobromide (1:1) | LC-MS (method 2) Rt = 0.77 min; MS (ESIpos): m/z = 333.2 [M + H]$^+$ 88% yield |
| 126 | 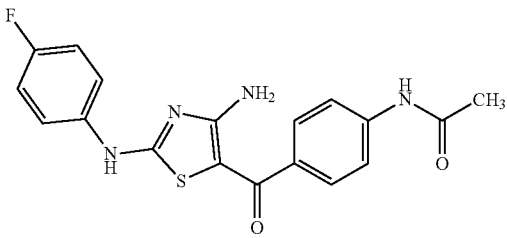 [SMILES: CC(=O)Nc1ccc(C(=O)c2sc(Nc3ccc(F)cc3)nc2N)cc1]<br>N-(4-{[4-amino-2-(4-fluoroanilino)-1,3-thiazol-5-yl]carbonyl}phenyl)acetamide | 1-fluoro-4-isothiocyanatobenzene; 4-acetamidophenacyl bromide | LC-MS (method 2) Rt = 0.87 min; MS (ESIpos): m/z = 371.3 [M + H]$^+$ 58% yield |

TABLE 4-continued

Intermediates 101-197

| Intermediate number | Chemical structure Compound name | Starting materials | Analytics/purification/yield |
|---|---|---|---|
| 127 | 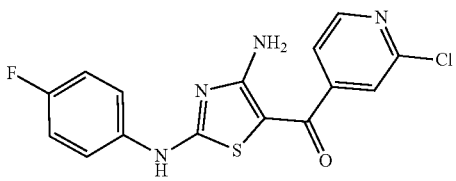 [SMILES: Nc1nc(Nc2ccc(F)cc2)sc1C(=O)c1ccnc(Cl)c1]<br>[4-amino-2-(4-fluoroanilino)-1,3-thiazol-5-yl](2-chloropyridin-4-yl)methanone | 1-fluoro-4-isothiocyanatobenzene; 2-bromo-1-(2-chloropyridin-4-yl)ethanone | LC-MS (method 2) Rt = 0.86 min; MS (ESIpos): m/z = 349.2 [M + H]⁺ 88% yield |
| 128 | 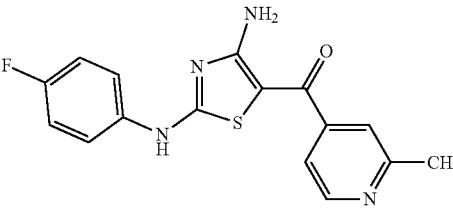<br>[4-amino-2-(4-fluoroanilino)thiazol-5-yl]-(2-methyl-4-pyridyl)methanone | 1-fluoro-4-isothiocyanatobenzene; 2-bromo-1-(2-methylpyridin-4-yl)ethanone hydrobromide (1:1) | LC-MS (method 2) Rt = 0.80 min; MS (ESIpos): m/z = 329.2 [M + H]⁺ 80% yield |
| 129 | 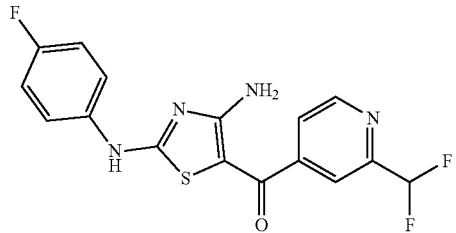 [SMILES: Nc1nc(Nc2ccc(F)cc2)sc1C(=O)c1ccnc(C(F)F)c1]<br>[4-amino-2-(4-fluoroanilino)-1,3-thiazol-5-yl][2-(difluoromethyl)pyridin-4-yl]methanone | 1-fluoro-4-isothiocyanatobenzene; 2-bromo-1-[2-(difluoromethyl)-4-pyridyl]ethanone | LC-MS (method 2) Rt = 0.87 min; MS (ESIpos): m/z = 365.2 [M + H]⁺ 78% yield |
| 130 | 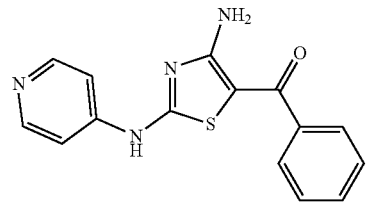 [SMILES: Nc1nc(Nc2ccncc2)sc1C(=O)c1ccccc1]<br>[4-amino-2-(pyridin-4-ylamino)-1,3-thiazol-5-yl](phenyl)methanone | 4-isothiocyanatopyridine; 2-bromo-1-phenylethanone | LC-MS (method 2) Rt = 0.69 min; MS (ESIpos): m/z = 297.2 [M + H]⁺ 17% yield |

TABLE 4-continued

Intermediates 101-197

| Intermediate number | Chemical structure Compound name | Starting materials | Analytics/purification/yield |
|---|---|---|---|
| 131 | 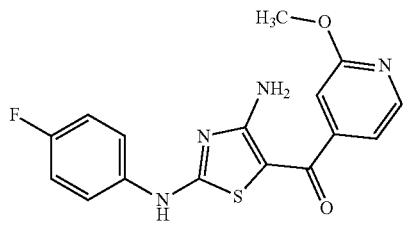 [SMILES: COc1cc(C(=O)c2sc(Nc3ccc(F)cc3)nc2N)ccn1]<br>[4-amino-2-(4-fluoroanilino)thiazol-5-yl]-(2-methoxy-4-pyridyl)methanone | 1-fluoro-4-isothiocyanatobenzene; 2-bromo-1-(2-methoxypyridin-4-yl)ethanone | LC-MS (method 2) Rt = 0.91 min; MS (ESIpos): m/z = 345.2 [M + H]$^+$ 80% yield |
| 132 | 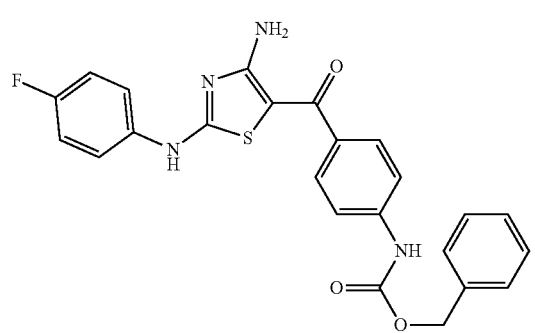 [SMILES: Nc1nc(Nc2ccc(F)cc2)sc1C(=O)c1ccc(NC(=O)OCc2ccccc2)cc1]<br>Benzyl (4-{4-amino-2-(4-fluoroanilino)-1,3-thiazol-5-yl]carbonyl}phenyl)carbamate | 1-fluoro-4-isothiocyanatobenzene; benzyl N-[4-(2-bromoacetyl)phenyl]carbamate | LC-MS (method 2) Rt = 1.20 min; MS (ESIpos): m/z = 463.3 [M + H]$^+$ 72% yield |
| 133 | 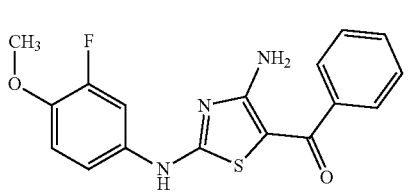 [SMILES: COc1ccc(Nc2nc(N)c(C(=O)c3ccccc3)s2)cc1F]<br>[4-amino-2-(3-fluoro-4-methoxyanilino)-1,3-thiazol-5-yl](phenyl)methanone | 2-fluoro-4-isothiocyanato-1-methoxybenzene; 2-bromo-1-phenylethanone | $^1$H NMR (400 MHz, DMSO-d$_6$) δ ppm = 10.75 (s, 1H), 8.23 (br s, 2H), 7.68-7.75 (m, 1H), 7.64-7.68 (m, 2H), 7.44-7.52 (m, 3H), 7.13-7.22 (m, 2H), 3.82 (s, 3H). LC-MS (method 2) Rt = 1.08 min MS (ESIpos): m/z = 344.6 [M + H]$^+$ 96% yield |
| 134 | 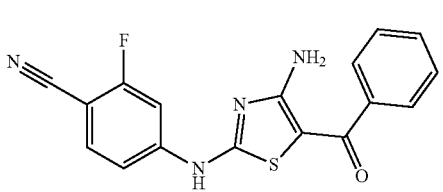 [SMILES: N#Cc1ccc(Nc2nc(N)c(C(=O)c3ccccc3)s2)cc1F]<br>4-[(4-amino-5-benzoyl-1,3-thiazol-2-yl)amino]-2-fluorobenzonitrile | 2-fluoro-4-isothiocyanatobenzonitrile; 2-bromo-1-phenylethanone | $^1$H NMR (400 MHz, DMSO-d$_6$) δ ppm = 11.42 (br s, 1H), 8.28 (br s, 2H), 8.10 (dd, J = 12.5, 1.9 Hz, 1H), 7.86 (dd, J = 8.6, 7.9 Hz, 1H), 7.67-7.72 (m, 2H), 7.46-7.56 (m, 3H), 7.39 (dd, J = 8.6, 2.0 Hz, 1H). LC-MS (method 2) Rt = 0.9 min MS (ESIpos): m/z = 339.5 [M + H]$^+$ 87% yield |

TABLE 4-continued

Intermediates 101-197

| Intermediate number | Chemical structure Compound name | Starting materials | Analytics/purification/yield |
|---|---|---|---|
| 135 | 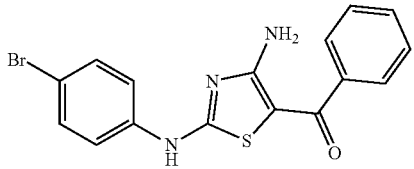 [SMILES: Nc1nc(Nc2ccc(Br)cc2)sc1C(=O)c1ccccc1]<br>[4-amino-2-(4-bromoanilino)-1,3-thiazol-5-yl](phenyl)methanone | 1-bromo-4-isothiocyanatobenzene; 2-bromo-1-phenylethanone | $^1$H NMR (400 MHz, DMSO-d$_6$) δ ppm = 10.89 (br s, 1H), 8.22 (br s, 2H), 7.64-7.70 (m, 2H), 7.57-7.64 (m, 2H), 7.44-7.57 (m, 5H). LC-MS (method 2) Rt = 1.18 min MS (ESIpos): m/z = 375.2 [M + H]$^+$ 100% yield |
| 136 | 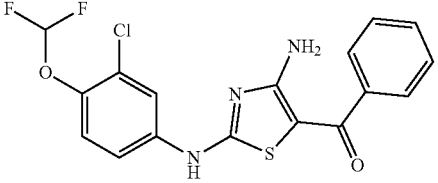 [SMILES: Nc1nc(Nc2ccc(OC(F)F)c(Cl)c2)sc1C(=O)c1ccccc1]<br>{4-amino-2-[3-chloro-4-(difluoromethoxy)anilino]-1,3-thiazol-5-yl}(phenyl)methanone | 2-chloro-1-(difluoromethoxy)-4-isothiocyanatobenzene; 2-bromo-1-phenylethanone | $^1$H NMR (400 MHz, DMSO-d$_6$) δ ppm = 10.97 (br s, 1H), 8.26 (br s, 2H), 8.05 (d, J = 2.5 Hz, 1H), 7.64-7.70 (m, 2H), 7.45-7.54 (m, 4H), 7.36 (d, J = 8.9 Hz, 1H), 7.20 (t, J = 73.3 Hz, 1H). LC-MS (method 2) Rt = 1.14 min MS (ESIpos): m/z = 396.3 [M + H]$^+$ 92% yield |
| 137 | 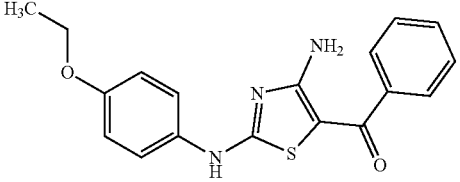 [SMILES: CCOc1ccc(Nc2nc(N)c(C(=O)c3ccccc3)s2)cc1]<br>[4-amino-2-(4-ethoxyanilino)-1,3-thiazol-5-yl](phenyl)methanone | 1-ethoxy-4-isothiocyanatobenzene; 2-bromo-1-phenylethanone | $^1$H NMR (400 MHz, DMSO-d$_6$) δ ppm = 10.58 (br s, 1H), 7.69-8.55 (m, 2H), 7.60-7.66 (m, 2H), 7.40-7.51 (m, 5H), 6.88-6.95 (m, 2H), 4.00 (q, J = 7.1 Hz, 2H), 1.31 (t, J = 7.0 Hz, 3H). LC-MS (method 2) Rt = 1.14 min MS (ESIpos): m/z = 340.4 [M + H]$^+$ 100% yield |
| 138 | 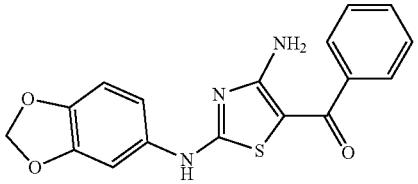 [SMILES: Nc1nc(Nc2ccc3c(c2)OCO3)sc1C(=O)c1ccccc1]<br>[4-amino-2-(1,3-benzodioxol-5-ylamino)-1,3-thiazol-5-yl](phenyl)methanone | 5-isothiocyanato-1,3-benzodioxole; 2-bromo-1-phenylethanone | $^1$H NMR (400 MHz, DMSO-d$_6$) δ ppm = 10.64 (s, 1H), 8.20 (br s, 2H), 7.62-7.67 (m, 2H), 7.43-7.52 (m, 3H), 7.32-7.37 (m, 1H), 6.88-6.95 (m, 2H), 6.02 (s, 2H). LC-MS (method 2) Rt = 0.99 min MS (ESIpos): m/z = 340.2 [M + H]$^+$ 57% yield |
| 139 | 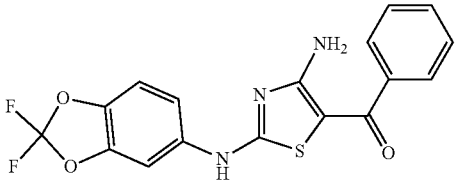 [SMILES: Nc1nc(Nc2ccc3c(c2)OC(F)(F)O3)sc1C(=O)c1ccccc1]<br>{4-amino-2-[(2,2-difluoro-1,3-benzodioxol-5-yl)amino]-1,3-thiazol-5-yl}(phenyl)methanone | 2,2-difluoro-5-isothiocyanato-1,3-benzodioxole; 2-bromo-1-phenylethanone | $^1$H NMR (400 MHz, DMSO-d$_6$) δ ppm = 10.95 (br s, 1H), 8.24 (br s, 2H), 7.94 (d, J = 2.0 Hz, 1H), 7.64-7.69 (m, 2H), 7.45-7.53 (m, 3H), 7.40 (d, J = 8.6 Hz, 1H), 7.24 (dd, J = 8.7, 2.2 Hz, 1H). LC-MS (method 2) Rt = 1.17 min MS (ESIpos): m/z = 376.4 [M + H]$^+$ 78% yield |

TABLE 4-continued

Intermediates 101-197

| Intermediate number | Chemical structure Compound name | Starting materials | Analytics/purification/yield |
|---|---|---|---|
| 140 | {4-amino-2-[4-(difluoromethoxy)-3-fluoroanilino]-1,3-thiazol-5-yl}(phenyl)methanone | 1-(difluoromethoxy)-2-fluoro-4-isothiocyanatobenzene; 2-bromo-1-phenylethanone | $^1$H NMR (400 MHz, DMSO-$d_6$) δ ppm = 11.00 (s, 1H), 8.26 (br s, 2H), 7.97 (dd, J = 12.9, 2.5 Hz, 1H), 7.65-7.70 (m, 2H), 7.45-7.54 (m, 3H), 7.33-7.39 (m, 1H), 7.24-7.29 (m, 1H), 7.18 (t, J = 73.3 Hz, 1H). LC-MS (method 2) Rt = 1.08 min MS (ESIpos): m/z = 380.2 [M + H]$^+$ 92% yield |
| 141 | {4-amino-2-[4-(benzyloxy)anilino]-1,3-thiazol-5-yl}(phenyl)methanone | 1-(benzyloxy)-4-isothiocyanatobenzene; 2-bromo-1-phenylethanone | $^1$H NMR (400 MHz, DMSO-$d_6$) δ ppm = 10.61 (br s, 1H), 8.17 (br s, 2H), 7.64 (dd, J = 7.6, 1.8 Hz, 2H), 7.42-7.50 (m, 7H), 7.36-7.42 (m, 2H), 7.30-7.36 (m, 1H), 6.99-7.04 (m, 2H), 5.09 (s, 2H). LC-MS (method 2) Rt = 1.3 min MS (ESIpos): m/z = 402.4 [M + H]$^+$ 98% yield |
| 142 | {4-amino-2-[3-chloro-4-(difluoromethoxy)anilino]-1,3-thiazol-5-yl}(4-methoxyphenyl)methanone | 2-chloro-1-(difluoromethoxy)-4-isothiocyanatobenzene; 2-bromo-1-(4-methoxyphenyl)ethanone | $^1$H NMR (400 MHz, DMSO-$d_6$) δ ppm = 10.94 (br s, 1H), 8.21 (br s, 2H), 8.06 (d, J = 2.5 Hz, 1H), 7.66-7.71 (m, 2H), 7.48 (dd, J = 8.9, 2.5 Hz, 1H), 7.36 (d, J = 8.9 Hz, 1H), 7.20 (t, J = 73.8 Hz, 1H), 7.02-7.05 (m, 1H), 7.00-7.02 (m, 1H), 3.82 (s, 3H). LC-MS (method 2) Rt = 1.17 min MS (ESIpos): m/z = 426.2 [M + H]$^+$ 99% yield |
| 143 | {4-amino-2-[3-chloro-4-(difluoromethoxy)anilino]-1,3-thiazol-5-yl}[4-(difluoromethoxy)phenyl]methanone | 2-chloro-1-(difluoromethoxy)-4-isothiocyanatobenzene; 2-bromo-1-[4-(difluoromethoxy)phenyl]ethanone | $^1$H NMR (400 MHz, DMSO-$d_6$) δ ppm = 11.00 (br s, 1H), 8.14-8.42 (m, 2H), 8.05 (d, J = 2.5 Hz, 1H), 7.73-7.78 (m, 2H), 7.48 (dd, J = 9.0, 2.7 Hz, 1H), 7.38 (d, J = 6.1 Hz, 1H), 7.35 (t, J = 73.8 Hz, 1H), 7.24-7.29 (m, 2H), 7.20 (t, J = 73.3 Hz, 1H). LC-MS (method 2) Rt = 1.15 min MS (ESIpos): m/z = 462.2 [M + H]$^+$ 87% yield |

TABLE 4-continued

Intermediates 101-197

| Intermediate number | Chemical structure Compound name | Starting materials | Analytics/purification/yield |
|---|---|---|---|
| 144 | {4-amino-2-[3-chloro-4-(difluoromethoxy)anilino]-1,3-thiazol-5-yl}(4-chlorophenyl)methanone | 2-chloro-1-(difluoromethoxy)-4-isothiocyanatobenzene; 2-bromo-1-(4-chlorophenyl)ethanone | $^1$H NMR (400 MHz, DMSO-$d_6$) δ ppm = 11.02 (br s, 1H), 8.31 (br s, 2H), 8.05 (d, J = 2.3 Hz, 1H), 7.67-7.72 (m, 2H), 7.53-7.58 (m, 2H), 7.47 (dd, J = 9.0, 2.7 Hz, 1H), 7.36 (d, J = 8.9 Hz, 1H), 7.20 (t, J = 73.5 Hz, 1H).<br>LC-MS (method 2) Rt = 1.20 min<br>MS (ESIpos): m/z = 430.2 [M + H]$^+$<br>100% yield |
| 145 | {4-amino-2-[3-chloro-4-(difluoromethoxy)anilino]-1,3-thiazol-5-yl}(pyridin-4-yl)methanone | 2-chloro-1-(difluoromethoxy)-4-isothiocyanatobenzene; 2-bromo-1-(pyridin-4-yl)ethanone hydrobromide | $^1$H NMR (400 MHz, DMSO-$d_6$) δ ppm = 11.08 (br s, 1H), 8.70-8.74 (m, 2H), 8.42 (br s, 2H), 8.06 (d, J = 2.5 Hz, 1H), 7.56-7.60 (m, 2H), 7.46-7.51 (m, 1H), 7.37 (d, J = 9.1 Hz, 1H), 7.21 (t, J = 73.3 Hz, 1H).<br>LC-MS (method 2) Rt = 0.82 min<br>MS (ESIpos): m/z = 397.2 [M + H]$^+$<br>45% yield |
| 146 | {4-amino-2-[3-chloro-4-(difluoromethoxy)anilino]-1,3-thiazol-5-yl}[6-(difluoromethoxy)pyridin-3-yl]methanone | 2-chloro-1-(difluoromethoxy)-4-isothiocyanatobenzene; 2-bromo-1-[6-(difluoromethoxy)pyridin-3-yl]ethanone | $^1$H NMR (400 MHz, DMSO-$d_6$) δ ppm = 11.07 (br s, 1H), 8.55-8.58 (m, 1H), 8.34 (br s, 2H), 8.18 (dd, J = 8.6, 2.5 Hz, 1H), 8.04 (d, J = 2.0 Hz, 1H), 7.78 (t, J = 72.5 Hz, 1H), 7.47 (dd, J = 9.0, 2.7 Hz, 1H), 7.37 (d, J = 8.9 Hz, 1H), 7.21 (t, J = 73.5 Hz, 1H), 7.18-7.21 (m, 1H).<br>LC-MS (method 2) Rt = 1.06 min<br>MS (ESIpos): m/z = 463.2 [M + H]$^+$<br>92% yield |
| 147 | {4-amino-2-[4-(difluoromethoxy)-3-fluoroanilino]-1,3-thiazol-5-yl}(4-methoxyphenyl)methanone | 1-(difluoromethoxy)-2-fluoro-4-isothiocyanatobenzene; 2-bromo-1-(4-methoxyphenyl)ethanone | $^1$H NMR (400 MHz, DMSO-$d_6$) δ ppm = 10.99 (br s, 1H), 8.20 (br s, 2H), 7.97 (dd, J = 13.1, 2.4 Hz, 1H), 7.66-7.71 (m, 2H), 7.33-7.39 (m, 1H), 7.24-7.30 (m, 1H), 7.17 (t, J = 73.3 Hz, 1H), 7.00-7.05 (m, 2H), 3.82 (s, 3H).<br>LC-MS (method 2) Rt = 1.13 min<br>MS (ESIpos): m/z = 410.2 [M + H]$^+$<br>96% yield |

TABLE 4-continued

Intermediates 101-197

| Intermediate number | Chemical structure Compound name | Starting materials | Analytics/purification/yield |
|---|---|---|---|
| 148 | 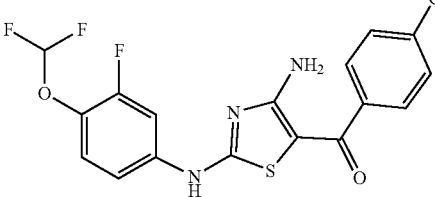<br>{4-amino-2-[4-(difluoromethoxy)-3-fluoroanilino]-1,3-thiazol-5-yl}(4-chlorophenyl)methanone | 1-(difluoromethoxy)-2-fluoro-4-isothiocyanatobenzene; 2-bromo-1-(4-chlorophenyl)ethanone | $^1$H NMR (400 MHz, DMSO-d$_6$) δ ppm = 11.06 (br s, 1H), 8.30 (br s, 2H), 7.96 (dd, J = 12.9, 2.5 Hz, 1H), 7.68-7.72 (m, 2H), 7.53-7.58 (m, 2H), 7.33-7.39 (m, 1H), 7.24-7.29 (m, 1H), 7.18 (t, J = 73.3 Hz, 1H).<br>LC-MS (method 2) Rt = 1.18 min<br>MS (ESIpos): m/z = 414.2 [M + H]$^+$<br>95% yield |
| 149 | 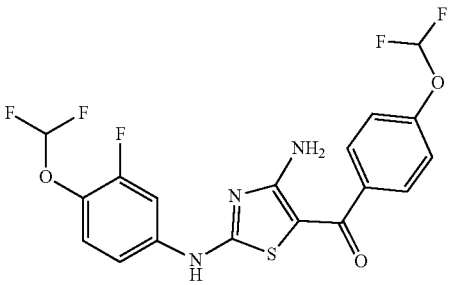 [SMILES: Nc1nc(Nc2ccc(OC(F)F)c(F)c2)sc1C(=O)c1ccc(OC(F)F)cc1]<br>{4-amino-2-[4-(difluoromethoxy)-3-fluoroanilino]-1,3-thiazol-5-yl}[4-(difluoromethoxy)phenyl]methanone | 1-(difluoromethoxy)-2-fluoro-4-isothiocyanatobenzene; 2-bromo-1-[4-(difluoromethoxy)phenyl]ethanone | $^1$H NMR (400 MHz, DMSO-d$_6$) δ ppm = 11.03 (br s, 1H), 8.28 (br s, 2H), 7.96 (dd, J = 12.9, 2.3 Hz, 1H), 7.73-7.78 (m, 2H), 7.32-7.55 (m, 2H), 6.99-7.30 (m, 4H).<br>LC-MS (method 2) Rt = 1.14 min<br>MS (ESIpos): m/z = 446.2 [M + H]$^+$<br>88% yield |
| 150 | 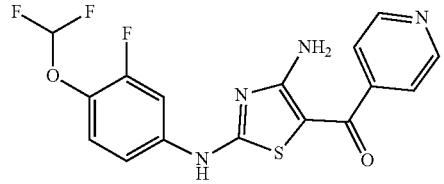 [SMILES: Nc1nc(Nc2ccc(OC(F)F)c(F)c2)sc1C(=O)c1ccncc1]<br>{4-amino-2-[4-(difluoromethoxy)-3-fluoroanilino]-1,3-thiazol-5-yl}(pyridin-4-yl)methanone | 1-(difluoromethoxy)-2-fluoro-4-isothiocyanatobenzene; 2-bromo-1-(pyridin-4-yl)ethanone hydrobromide | $^1$H NMR (400 MHz, DMSO-d$_6$) δ ppm = 11.12 (s, 1H), 8.70-8.74 (m, 2H), 8.41 (br s, 2H), 7.97 (dd, J = 12.9, 2.5 Hz, 1H), 7.57-7.60 (m, 2H), 7.34-7.38 (m, 1H), 7.25-7.30 (m, 1H), 7.18 (t, J = 73.3 Hz,1H).<br>LC-MS (method 2) Rt = 0.8 min<br>MS (ESIpos): m/z = 381.2 [M + H]$^+$<br>15% yield |
| 151 | 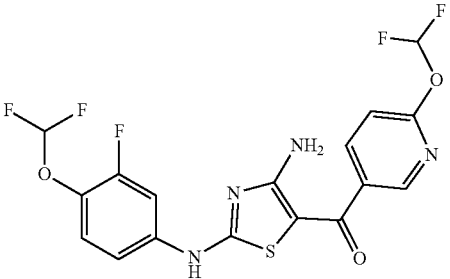 [SMILES: Nc1nc(Nc2ccc(OC(F)F)c(F)c2)sc1C(=O)c1ccc(OC(F)F)nc1]<br>{4-amino-2-[4-(difluoromethoxy)-3-fluoroanilino]-1,3-thiazol-5-yl}[6-(difluoromethoxy)pyridin-3-yl]methanone | 1-(difluoromethoxy)-2-fluoro-4-isothiocyanatobenzene; 2-bromo-1-[6-(difluoromethoxy)pyridin-3-yl]ethanone | $^1$H NMR (400 MHz, DMSO-d$_6$) δ ppm = 11.02-11.23 (m, 1H), 8.57 (d, J = 2.3 Hz, 1H), 8.25-8.41 (m, 2H), 8.18 (dd, J = 8.5, 2.4 Hz, 1H), 7.92-7.98 (m, 1H), 7.78 (t, J = 72.2 Hz, 1H), 7.33-7.40 (m, 1H), 7.24-7.30 (m, 1H), 7.20 (d, J = 9.1 Hz, 1H), 7.18 (t, J = 73.5 Hz, 1H).<br>LC-MS (method 2) Rt = 1.06 min<br>MS (ESIpos): m/z = 447.2 [M + H]$^+$<br>86% yield |

TABLE 4-continued

Intermediates 101-197

| Intermediate number | Chemical structure Compound name | Starting materials | Analytics/purification/yield |
|---|---|---|---|
| 152 | 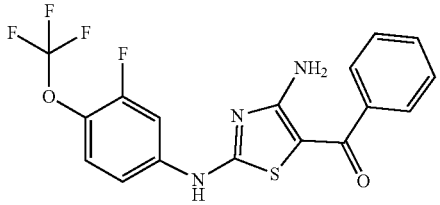 [SMILES: Nc1nc(Nc2ccc(OC(F)(F)F)c(F)c2)sc1C(=O)c1ccccc1]<br>{4-amino-2-[3-fluoro-4-(trifluoromethoxy)anilino]-1,3-thiazol-5-yl}(phenyl)methanone | 2-fluoro-4-isothiocyanato-1-(trifluoromethoxy)benzene (Intermediate 200); 2-bromo-1-phenylethanone | $^1$H NMR (400 MHz, DMSO-d$_6$) δ ppm = 11.12 (br s, 1H), 8.26 (br s, 2H), 8.08 (dd, J = 12.9, 2.5 Hz, 1H), 7.66-7.70 (m, 2H), 7.45-7.59 (m, 4H), 7.29-7.34 (m, 1H).<br>LC-MS (method 2) Rt = 1.21 min MS (ESIpos): m/z = 398.2 [M + H]$^+$<br>96% yield |
| 153 | 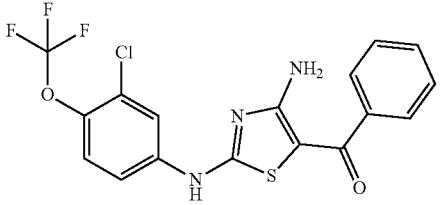 [SMILES: Nc1nc(Nc2ccc(OC(F)(F)F)c(Cl)c2)sc1C(=O)c1ccccc1]<br>{4-amino-2-[3-chloro-4-(trifluoromethoxy)anilino]-1,3-thiazol-5-yl}(phenyl)methanone | 2-chloro-4-isothiocyanato-1-(trifluoromethoxy)benzene; 2-bromo-1-phenylethanone | $^1$H NMR (400 MHz, DMSO-d$_6$) δ ppm = 11.08 (br s, 1H), 8.28 (br s, 2H), 8.16 (d, J = 2.3 Hz, 1H), 7.65-7.72 (m, 2H), 7.45-7.59 (m, 5H).<br>LC-MS (method 2) Rt = 1.22 min MS (ESIpos): m/z = 414.2 [M + H]$^+$<br>91% yield |
| 154 | 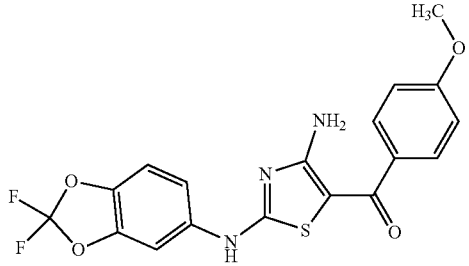 [SMILES: COc1ccc(C(=O)c2sc(Nc3ccc4c(c3)OC(F)(F)O4)nc2N)cc1]<br>{4-amino-2-[(2,2-difluoro-1,3-benzodioxol-5-yl)amino]-1,3-thiazol-5-yl}(4-methoxyphenyl)methanone | 2,2-difluoro-5-isothiocyanato-1,3-benzodioxole; 2-bromo-1-(4-methoxyphenyl)ethanone | $^1$H NMR (400 MHz, DMSO-d$_6$) δ ppm = 10.92 (br s, 1H), 8.17 (br s, 2H), 7.95 (d, J = 2.0 Hz, 1H), 7.65-7.70 (m, 2H), 7.40 (d, J = 8.6 Hz, 1H), 7.24 (dd, J = 8.7, 2.2 Hz, 1H), 6.99-7.05 (m, 2H), 3.82 (s, 3H).<br>LC-MS (method 2) Rt = 1.21 min MS (ESIpos): m/z = 406.2 [M + H]$^+$<br>89% yield |
| 155 | 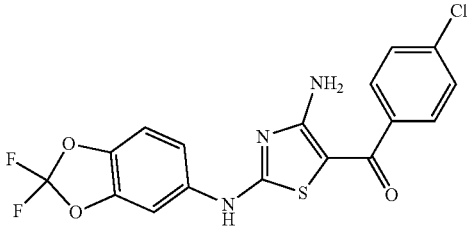 [SMILES: Nc1nc(Nc2ccc3c(c2)OC(F)(F)O3)sc1C(=O)c1ccc(Cl)cc1]<br>{4-amino-2-[(2,2-difluoro-1,3-benzodioxol-5-yl)amino]-1,3-thiazol-5-yl}(4-chlorophenyl)methanone | 2,2-difluoro-5-isothiocyanate-1,3-benzodioxole; 2-bromo-1-(4-chlorophenylethanone | $^1$H NMR (400 MHz, DMSO-d$_6$) δ ppm = 11.00 (br d, J = 1.3 Hz, 1H), 8.28 (br s, 2H), 7.94 (d, J = 2.0 Hz, 1H), 7.66-7.73 (m, 2H), 7.51-7.58 (m, 2H), 7.40 (d, J = 8.6 Hz, 1H), 7.24 (dd, J = 8.9, 2.3 Hz, 1H).<br>LC-MS (method 2) Rt = 1.25 min MS (ESIpos): m/z = 410.2 [M + H]$^+$<br>93% yield |

TABLE 4-continued

Intermediates 101-197

| Intermediate number | Chemical structure Compound name | Starting materials | Analytics/purification/yield |
|---|---|---|---|
| 156 | 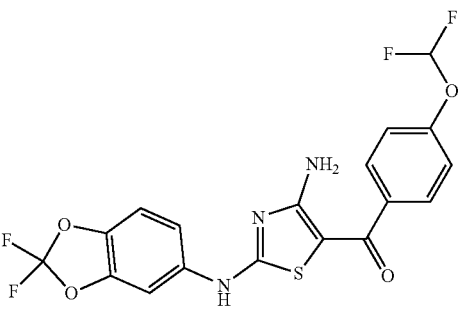<br>{4-amino-2-[(2,2-difluoro-1,3-benzodioxol-5-yl)amino]-1,3-thiazol-5-yl}[4-(difluoromethoxy)phenyl]methanone | 2,2-difluoro-5-isothiocyanate-1,3-benzodioxole; 2-bromo-1-[4-(difluoromethoxy)phenyl]ethanone | $^1$H NMR (400 MHz, DMSO-d$_6$) δ ppm = 10.98 (br s, 1H), 8.24 (br s, 2H), 7.93 (d, J = 1.5 Hz, 1H), 7.71-7.78 (m, 2H), 7.40 (d, J = 8.6 Hz, 1H), 7.35 (t, J = 73.8 Hz, 1H), 7.21-7.29 (m, 3H).<br>LC-MS (method 2) Rt = 1.23 min<br>MS (ESIpos): m/z = 442.2 [M + H]$^+$<br>61% yield |
| 157 | 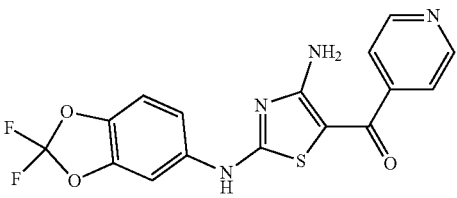 [SMILES: Nc1nc(Nc2ccc3c(c2)OC(F)(F)O3)sc1C(=O)c1ccncc1]<br>{4-amino-2-[(2,2-difluoro-1,3-benzodioxol-5-yl)amino]-1,3-thiazol-5-yl}(pyridin-4-yl)methanone | 2,2-difluoro-5-isothiocyanate-1,3-benzodioxole; 2-bromo-1-(pyridin-4-yl)ethanone hydrobromide | $^1$H NMR (400 MHz, DMSO-d$_6$) δ ppm = 11.06 (s, 1H), 8.69-8.74 (m, 2H), 8.38 (br s, 2H), 7.94 (d, J = 1.8 Hz, 1H), 7.56-7.60 (m, 2H), 7.41 (d, J = 8.9 Hz, 1H), 7.25 (dd, J = 8.7, 2.2 Hz, 1H).<br>LC-MS (method 2) Rt = 0.85 min<br>MS (ESIpos): m/z = 377.2 [M + H]$^+$<br>13% yield |
| 158 | 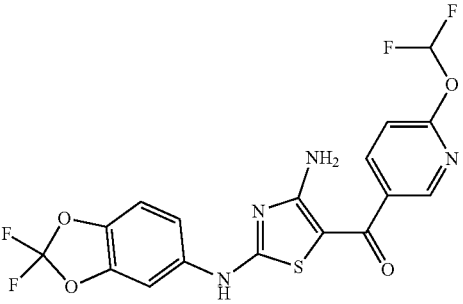 [SMILES: Nc1nc(Nc2ccc3c(c2)OC(F)(F)O3)sc1C(=O)c1ccc(OC(F)F)nc1]<br>{4-amino-2-[(2,2-difluoro-1,3-benzodioxol-5-yl)amino]-1,3-thiazol-5-yl}[6-(difluoromethoxy)pyridin-3-yl]methanone | 2,2-difluoro-5-isothiocyanate-1,3-benzodioxole; 2-bromo-1-[6-(difluoromethoxy)pyridin-3-yl]ethanone | $^1$H NMR (400 MHz, DMSO-d$_6$) δ ppm = 11.05 (br s, 1H), 8.54-8.58 (m, 1H), 8.31 (br s, 2H), 8.17 (dd, J = 8.6, 2.5 Hz, 1H), 7.94 (d, J = 1.8 Hz, 1H), 7.78 (t, J = 72.5 Hz, 1H), 7.41 (d, J = 8.9 Hz, 1H), 7.25 (dd, J = 8.9, 2.3 Hz, 1H), 7.17-7.22 (m, 1H).<br>LC-MS (method 2) Rt = 1.15 min<br>MS (ESIpos): m/z = 443.2 [M + H]$^+$<br>85% yield |

TABLE 4-continued

Intermediates 101-197

| Intermediate number | Chemical structure Compound name | Starting materials | Analytics/purification/yield |
|---|---|---|---|
| 159 | {4-amino-2-[3-fluoro-4-(trifluoromethoxy)anilino]-1,3-thiazol-5-yl}(4-methoxyphenyl)methanone | 2-fluoro-4-isothiocyanato-1-(trifluoromethoxy) benzene (Intermediate 200); 2-bromo-1-(4-methoxyphenyl) ethanone | $^1$H NMR (400 MHz, DMSO-d$_6$) δ ppm = 11.10 (br s, 1H), 8.20 (br s, 2H), 8.08 (dd, J = 12.9, 2.5 Hz, 1H), 7.66-7.72 (m, 2H), 7.55 (td, J = 8.9, 1.0 Hz, 1H), 7.30-7.35 (m, 1H), 7.00-7.05 (m, 2H), 3.82 (s, 3H). LC-MS (method 2) Rt = 1.24 min MS (ESIpos): m/z = 428.2 [M + H]$^+$ 90% yield |
| 160 | {4-amino-2-[3-fluoro-4-(trifluoromethoxy)anilino]-1,3-thiazol-5-yl}(4-chlorophenyl)methanone | 2-fluoro-4-isothiocyanato-1-(trifluoromethoxy) benzene (Intermediate 200); 2-bromo-1-(4-chlorophenyl)ethanone | $^1$H NMR (400 MHz, DMSO-d$_6$) δ ppm = 11.10 (br s, 1H), 8.20 (br s, 2H), 8.08 (dd, J = 12.9, 2.5 Hz, 1H), 7.66-7.72 (m, 2H), 7.55 (td, J = 9.0, 1.0 Hz, 1H), 7.30-7.35 (m, 1H), 7.00-7.06 (m, 2H), 3.82 (s, 3H). LC-MS (method 2) Rt = 1.23 min MS (ESIpos): m/z = 432.2 [M + H]$^+$ 91% yield |
| 161 | {4-amino-2-[3-fluoro-4-(trifluoromethoxy)anilino]-1,3-thiazol-5-yl}[4-(difluoromethoxy)phenyl]methanone | 2-fluoro-4-isothiocyanato-1-(trifluoromethoxy) benzene (Intermediate 200); 2-bromo-1-[4-(difluoromethoxy) phenyl]ethanone | $^1$H NMR (400 MHz, DMSO-d$_6$) δ ppm = 11.15 (br s, 1H), 8.28 (br s, 2H), 8.07 (dd, J = 12.9, 2.5 Hz, 1H), 7.73-7.80 (m, 2H), 7.51-7.62 (m, 1H), 7.36 (t, J = 73.8 Hz, 1H), 7.30-7.34 (m, 1H), 7.25-7.30 (m, 2H). LC-MS (method 2) Rt = 1.24 min MS (ESIpos): m/z = 464.2 [M + H]$^+$ 86% yield |
| 162 | {4-amino-2-[3-fluoro-4-(trifluoromethoxy)anilino]-1,3-thiazol-5-yl}(pyridin-4-yl)methanone | 2-fluoro-4-isothiocyanato-1-(trifluoromethoxy) benzene (Intermediate 200); 2-bromo-1-(pyridin-4-yl)ethanone hydrobromide | $^1$H NMR (400 MHz, DMSO-d$_6$) δ ppm = 11.23 (s, 1H), 8.70-8.75 (m, 2H), 8.42 (br s, 2H), 8.08 (dd, J = 12.9, 2.5 Hz, 1H), 7.53-7.62 (m, 3H), 7.30-7.35 (m, 1H). LC-MS (method 2) Rt = 0.89 min MS (ESIpos): m/z = 399.2 [M + H]$^+$ 21% yield |

TABLE 4-continued

Intermediates 101-197

| Intermediate number | Chemical structure Compound name | Starting materials | Analytics/purification/yield |
|---|---|---|---|
| 163 | 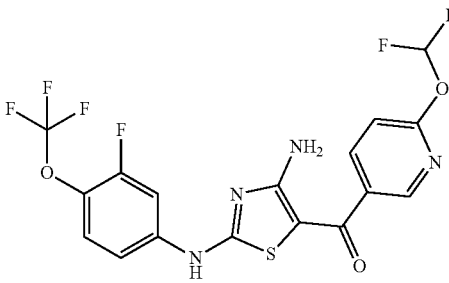<br>{4-amino-2-[3-fluoro-4-(trifluoromethoxy)anilino]-1,3-thiazol-5-yl}[6-(difluoromethoxy)pyridin-3-yl]methanone | 2-fluoro-4-isothiocyanato-1-(trifluoromethoxy)benzene (Intermediate 200); 2-bromo-1-[6-(difluoromethoxy)pyridin-3-yl]ethanone | $^1$H NMR (400 MHz, DMSO-$d_6$) δ ppm = 11.22 (br s, 1H), 8.55-8.61 (m, 1H), 8.34 (br s, 2H), 8.19 (dd, J = 8.5, 2.4 Hz, 1H), 8.07 (dd, J = 12.9, 2.5 Hz, 1H), 7.78 (t, J = 72.5 Hz, 1H), 7.56 (td, J = 8.9, 1.0 Hz, 1H), 7.30-7.36 (m, 1H), 7.18-7.22 (m, 1H).<br>LC-MS (method 2) Rt = 1.15 min<br>MS (ESIpos): m/z = 465.2 [M + H]$^+$<br>84% yield |
| 164 | 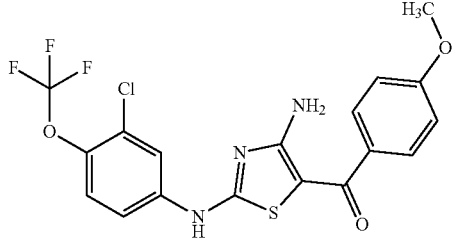<br>{4-amino-2-[3-chloro-4-(trifluoromethoxy)anilino]-1,3-thiazol-5-yl}(4-methoxyphenyl)methanone | 2-chloro-4-isothiocyanato-1-(trifluoromethoxy)benzene; 2-bromo-1-(4-methoxyphenyl)ethanone | $^1$H NMR (400 MHz, DMSO-$d_6$) δ ppm = 11.06 (br s, 1H), 8.05-8.37 (m, 3H), 7.66-7.72 (m, 2H), 7.50-7.58 (m, 2H), 7.00-7.05 (m, 2H), 3.82 (s, 3H).<br>LC-MS (method 2) Rt = 1.22 min<br>MS (ESIpos): m/z = 444.2 [M + H]$^+$<br>79% yield |
| 165 | 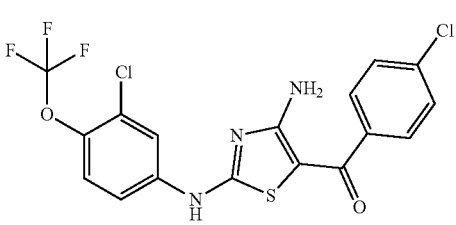 [SMILES: Nc1nc(Nc2ccc(OC(F)(F)F)c(Cl)c2)sc1C(=O)c1ccc(Cl)cc1]<br>{4-amino-2-[3-chloro-4-(trifluoromethoxy)anilino]-1,3-thiazol-5-yl}(4-chlorophenyl)methanone | 2-chloro-4-isothiocyanato-1-(trifluoromethoxy)benzene; 2-bromo-1-(4-chlorophenyl)ethanone | 1H NMR (400 MHz, DMSO-$d_6$) δ ppm = 7.87-7.99 (m, 1H), 7.64-7.71 (m, 2H), 7.48-7.54 (m, 2H), 7.43 (s, 1H), 7.37 (br d, J = 0.8 Hz, 1H).<br>LC-MS (method 2) Rt = 1.3 min<br>MS (ESIpos): m/z = 448.2 [M + H]$^+$<br>53% yield |
| 166 | 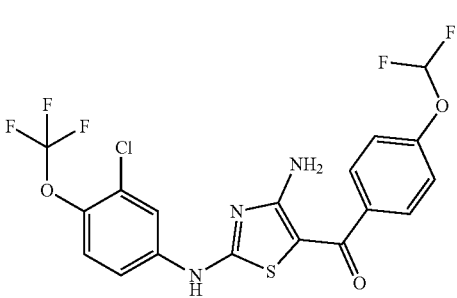 [SMILES: Nc1nc(Nc2ccc(OC(F)(F)F)c(Cl)c2)sc1C(=O)c1ccc(OC(F)F)cc1]<br>{4-amino-2-[3-chloro-4-(trifluoromethoxy)anilino]-1,3-thiazol-5-yl}[4-(difluoromethoxy)phenyl]methanone | 2-chloro-4-isothiocyanato-1-(trifluoromethoxy)benzene; 2-bromo-1-[4-(difluoromethoxy)phenyl]ethanone | $^1$H NMR (400 MHz, DMSO-$d_6$) δ ppm = 11.11 (br s, 1H), 8.29 (br s, 2H), 8.15 (d, J = 2.5 Hz, 1H), 7.73-7.79 (m, 2H), 7.50-7.58 (m, 2H), 7.36 (t, J = 73.2 Hz, 1H), 7.25-7.30 (m, 2H).<br>LC-MS (method 2) Rt = 1.24 min<br>MS (ESIpos): m/z = 480.2 [M + H]$^+$<br>71% yield |

TABLE 4-continued

Intermediates 101-197

| Intermediate number | Chemical structure Compound name | Starting materials | Analytics/purification/yield |
|---|---|---|---|
| 167 | 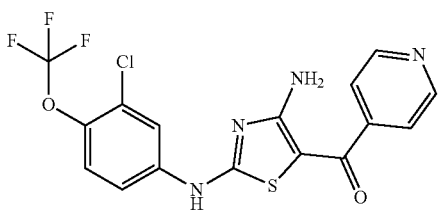 [SMILES: Nc1nc(Nc2ccc(OC(F)(F)F)c(Cl)c2)sc1C(=O)c1ccncc1]　{4-amino-2-[3-chloro-4-(trifluoromethoxy)anilino]-1,3-thiazol-5-yl}(pyridin-4-yl)methanone | 2-chloro-4-isothiocyanato-1-(trifluoromethoxy) benzene; 2-bromo-1-(pyridin-4-yl)ethanone hydrobromide | $^1$H NMR (400 MHz, DMSO-$d_6$) δ ppm = 11.19 (s, 1H), 8.70-8.75 (m, 2H), 8.43 (br s, 2H), 8.17 (d, J = 2.3 Hz, 1H), 7.51-7.61 (m, 4H). LC-MS (method 2) Rt = 0.93 min MS (ESIpos): m/z = 415.2 [M + H]$^+$ 47% yield |
| 168 | 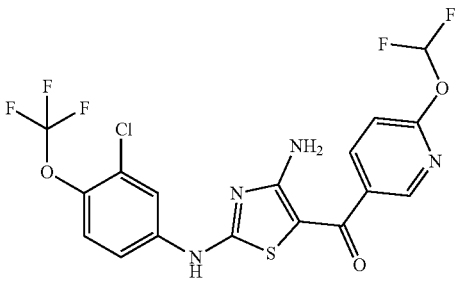　{4-amino-2-[3-chloro-4-(trifluoromethoxy)anilino]-1,3-thiazol-5-yl}[6-(difluoromethoxy)pyridin-3-yl]methanone | 2-chloro-4-isothiocyanato-1-(trifluoromethoxy) benzene; 2-bromo-1-[6-(difluoromethoxy) pyridin-3-yl]ethanone | $^1$H NMR (400 MHz, DMSO-$d_6$) δ ppm = 11.20 (br s, 1H), 8.54-8.59 (m, 1H), 8.21-8.52 (m, 2H), 8.18 (dd, J = 8.4, 2.5 Hz, 1H), 8.11 (br s, 1H), 7.78 (t, J = 72.5 Hz, 1H), 7.46-7.58 (m, 2H), 7.17-7.21 (m, 1H). LC-MS (method 2) Rt = 1.19 min MS (ESIpos): m/z = 481.2 [M + H]$^+$ 34% yield |
| 169 | 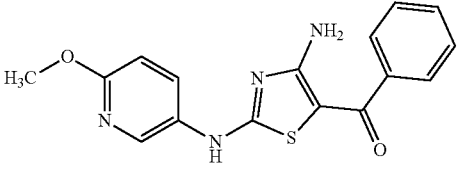 [SMILES: COc1ccc(Nc2nc(N)c(C(=O)c3ccccc3)s2)cn1]　{4-amino-2-[(6-methoxypyridin-3-yl)amino]-1,3-thiazol-5-yl}(phenyl)methanone | 5-isothiocyanato-2-methoxypyridine; 2-bromo-1-phenylethanone | $^1$H NMR (400 MHz, DMSO-$d_6$) δ ppm = 10.69 (br s, 1H), 8.40 (d, J = 2.5 Hz, 1H), 7.96-8.38 (m, 2H), 7.93 (dd, J = 8.9, 2.8 Hz, 1H), 7.62-7.67 (m, 2H), 7.43-7.52 (m, 3H), 6.84-6.88 (m, 1H), 3.83 (s, 3H). LC-MS (method 2) Rt = 0.91 min MS (ESIpos): m/z = 327.2 [M + H]$^+$ 87% yield |
| 170 | 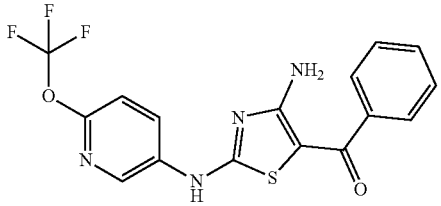 [SMILES: Nc1nc(Nc2ccc(OC(F)(F)F)nc2)sc1C(=O)c1ccccc1]　(4-amino-2-{[6-(trifluoromethoxy)pyridin-3-yl]amino}-1,3-thiazol-5-yl)(phenyl)methanone | 5-isothiocyanato-2-(trifluoromethoxy) pyridine (Intermediate 201); 2-bromo-1-phenylethanone | $^1$H NMR (400 MHz, DMSO-$d_6$) δ ppm = 11.10 (br s, 1H), 8.67 (d, J = 2.8 Hz, 1H), 8.27 (dd, J = 8.9, 2.8 Hz, 3H), 7.66-7.70 (m, 2H), 7.46-7.53 (m, 3H), 7.34 (d, J = 8.9 Hz, 1H). LC-MS (method 2) Rt = 0.96 min MS (ESIpos): m/z = 381.2 [M + H]$^+$ 82% yield |

TABLE 4-continued

Intermediates 101-197

| Intermediate number | Chemical structure Compound name | Starting materials | Analytics/purification/yield |
|---|---|---|---|
| 171 | 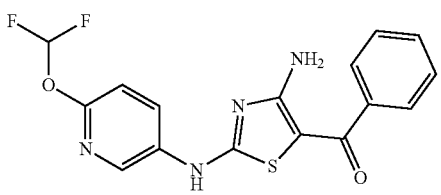 [SMILES: Nc1nc(Nc2ccc(OC(F)F)nc2)sc1C(=O)c1ccccc1]<br>(4-amino-2-{[6-(difluoromethoxy)pyridin-3-yl]amino}-1,3-thiazol-5-yl)(phenyl)methanone | 2-(difluoromethoxy)-5-isothiocyanatopyridine (Intermediate 202); 2-bromo-1-phenylethanone | $^1$H NMR (400 MHz, DMSO-$d_6$) δ ppm = 10.94 (br s, 1H), 8.56 (d, J = 2.8 Hz, 1H), 8.16 (dd, J = 8.9, 2.8 Hz, 1H), 7.67 (dd, J = 7.6, 1.8 Hz, 2H), 7.65 (t, J = 73.0 Hz, 1H), 7.45-7.53 (m, 3H), 7.14 (d, J = 8.9 Hz, 1H).<br>LC-MS (method 2) Rt = 0.93 min<br>MS (ESIpos): m/z = 363.2 [M + H]$^+$<br>90% yield |
| 172 | 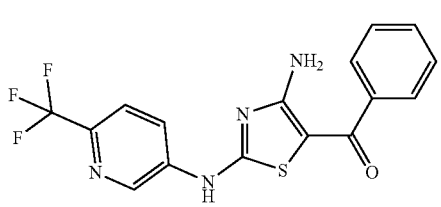 [SMILES: Nc1nc(Nc2ccc(C(F)(F)F)nc2)sc1C(=O)c1ccccc1]<br>(4-amino-2-{[6-(trifluoromethyl)pyridin-3-yl]amino}-1,3-thiazol-5-yl)(phenyl)methanone | 5-isothiocyanato-2-(trifluoromethyl)pyridine; 2-bromo-1-phenylethanone | $^1$H NMR (400 MHz, DMSO-$d_6$) δ ppm = 11.26-11.46 (m, 1H), 8.93 (d, J = 2.5 Hz, 1H), 8.40 (dd, J = 8.5, 2.2 Hz, 1H), 8.25 (br s, 2H), 7.89 (d, J = 8.6 Hz, 1H), 7.67-7.72 (m, 2H), 7.46-7.56 (m, 3H).<br>LC-MS (method 2) Rt = 0.88 min<br>MS (ESIpos): m/z = 365.2 [M + H]$^+$<br>69% yield |
| 173 | 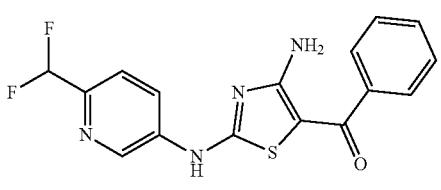 [SMILES: Nc1nc(Nc2ccc(C(F)F)nc2)sc1C(=O)c1ccccc1]<br>(4-amino-2-{[6-(difluoromethyl)pyridin-3-yl]amino}-1,3-thiazol-5-yl)(phenyl)methanone | 2-(difluoromethyl)-5-isothiocyanatopyridine (Intermediate 203); 2-bromo-1-phenylethanone | $^1$H NMR (400 MHz, DMSO-$d_6$) δ ppm = 11.21 (br s, 1H), 8.88 (d, J = 2.3 Hz, 1H), 8.15-8.37 (m, 3H), 7.66-7.72 (m, 3H), 7.46-7.55 (m, 3H), 6.92 (t, J = 55.3 Hz, 1H).<br>LC-MS (method 2) Rt = 0.79 min<br>MS (ESIpos): m/z = 347.2 [M + H]$^+$<br>66% yield |
| 174 | 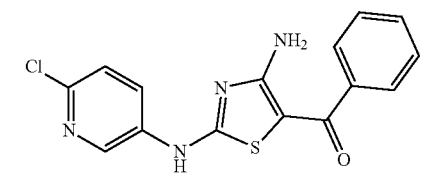 [SMILES: Nc1nc(Nc2ccc(Cl)nc2)sc1C(=O)c1ccccc1]<br>{4-amino-2-[(6-chloropyridin-3-yl)amino]-1,3-thiazol-5-yl}(phenyl)methanone | 2-chloro-5-isothiocyanatopyridine; 2-bromo-1-phenylethanone | $^1$H NMR (400 MHz, DMSO-$d_6$) δ ppm = 11.09 (br s, 1H), 8.68 (d, J = 2.5 Hz, 1H), 8.12-8.37 (m, 3H), 7.65-7.71 (m, 2H), 7.45-7.55 (m, 4H).<br>LC-MS (method 2) Rt = 0.79 min<br>MS (ESIpos): m/z = 331.2 [M + H]$^+$<br>60% yield |
| 175 | 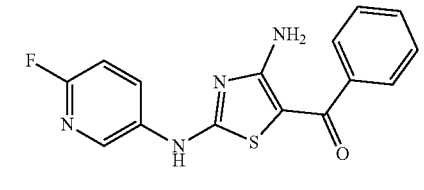 [SMILES: Nc1nc(Nc2ccc(F)nc2)sc1C(=O)c1ccccc1]<br>{4-amino-2-[(6-fluoropyridin-3-yl)amino]-1,3-thiazol-5-yl}(phenyl)methanone | 2-fluoro-5-isothiocyanatopyridine; 2-bromo-1-phenylethanone | $^1$H NMR (400 MHz, DMSO-$d_6$) δ ppm = 10.99 (br s, 1H), 8.52 (dd, J = 2.5, 1.3 Hz, 1H), 7.96-8.46 (m, 3H), 7.65-7.70 (m, 2H), 7.44-7.54 (m, 3H), 7.22 (dd, J = 8.9, 3.0 Hz, 1H).<br>LC-MS (method 2) Rt = 0.79 min<br>MS (ESIpos): m/z = 315.2 [M + H]$^+$<br>yield 70% |

TABLE 4-continued

Intermediates 101-197

| Intermediate number | Chemical structure Compound name | Starting materials | Analytics/purification/yield |
|---|---|---|---|
| 176 | 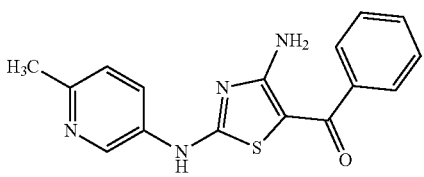 [SMILES: Cc1ccc(Nc2nc(N)c(C(=O)c3ccccc3)s2)cn1]<br>{4-amino-2-[(6-methylpyridin-3-yl)amino]-1,3-thiazol-5-yl}(phenyl)methanone | 5-isothiocyanato-2-methylpyridine; 2-bromo-1-phenylethanone | $^1$H NMR (400 MHz, DMSO-$d_6$) δ ppm = 10.83 (br s, 1H), 8.63 (d, J = 2.5 Hz, 1H), 8.03-8.52 (m, 2H), 8.00 (dd, J = 8.4, 2.5 Hz, 1H), 7.63-7.70 (m, 2H), 7.44-7.53 (m, 3H), 7.25 (d, J = 8.4 Hz, 1H), 2.43 (s, 3H). LC-MS (method 2) Rt = 0.81 min MS (ESIpos): m/z = 311.2 [M + H]$^+$ 88% yield |
| 177 | 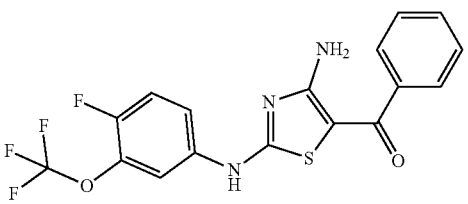 [SMILES: Nc1nc(Nc2ccc(F)c(OC(F)(F)F)c2)sc1C(=O)c1ccccc1]<br>{4-amino-2-[4-fluoro-3-(trifluoromethoxy)anilino]-1,3-thiazol-5-yl}(phenyl)methanone | 1-fluoro-4-isothiocyanato-2-(trifluoromethoxy)benzene (Intermediate 204); 2-bromo-1-phenylethanone | $^1$H NMR (400 MHz, DMSO-$d_6$) δ ppm = 11.01 (br s, 1H), 8.09-8.42 (m, 2H), 7.99 (dd, J = 7.1, 1.3 Hz, 1H), 7.66-7.70 (m, 2H), 7.56-7.61 (m, 1H), 7.45-7.55 (m, 4H). LC-MS (method 2) Rt = 1.21 min MS (ESIpos): m/z = 398.2 [M + H]$^+$ 94% yield |
| 178 | 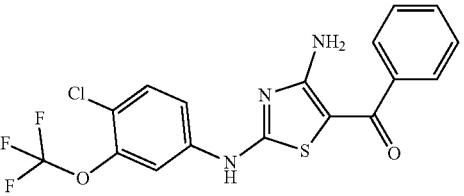 [SMILES: Nc1nc(Nc2ccc(Cl)c(OC(F)(F)F)c2)sc1C(=O)c1ccccc1]<br>{4-amino-2-[4-chloro-3-(trifluoromethoxy)anilino]-1,3-thiazol-5-yl}phenyl)methanone | 1-chloro-4-isothiocyanato-2-(trifluoromethoxy)benzene; 2-bromo-1-phenylethanone | $^1$H NMR (400 MHz, DMSO-$d_6$) δ ppm = 11.12 (br s, 1H), 8.25 (br s, 2H), 8.01 (d, J = 0.8 Hz, 1H), 7.60-7.71 (m, 4H), 7.45-7.55 (m, 3H). LC-MS (method 2) Rt = 1.28 min MS (ESIpos): m/z = 414.2 [M + H]$^+$ 90% yield |
| 179 | 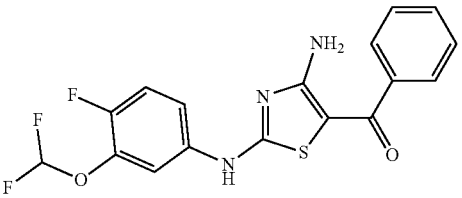 [SMILES: Nc1nc(Nc2ccc(F)c(OC(F)F)c2)sc1C(=O)c1ccccc1]<br>{4-amino-2-[3-(difluoromethoxy)-4-fluoroanilino]-1,3-thiazol-5-yl}(phenyl)methanone | 2-(difluoromethoxy)-1-fluoro-4-isothiocyanatobenzene (Intermediate 205); 2-bromo-1-phenylethanone | $^1$H NMR (400 MHz, DMSO-$d_6$) δ ppm = 10.91 (br s, 1H), 8.06-8.43 (m, 2H), 7.74 (dd, J = 6.7, 2.2 Hz, 1H), 7.64-7.70 (m, 2H), 7.45-7.53 (m, 4H), 7.37-7.42 (m, 1H), 7.25 (t, J = 73.0 Hz, 1H). LC-MS (method 2) Rt = 1.1 min MS (ESIpos): m/z = 380.2 [M + H]$^+$ 95% yield |
| 180 | 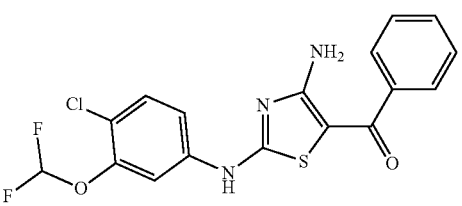 [SMILES: Nc1nc(Nc2ccc(Cl)c(OC(F)F)c2)sc1C(=O)c1ccccc1]<br>{4-amino-2-[4-chloro-3-(difluoromethoxy)anilino]-1,3-thiazol-5-yl}(phenyl)methanone | 1-chloro-2-(difluoromethoxy)-4-isothiocyanatobenzene; 2-bromo-1-phenylethanone | $^1$H NMR (400 MHz, DMSO-$d_6$) δ ppm = 11.03 (br s, 1H), 8.23 (br s, 2H), 7.75 (d, J = 2.0 Hz, 1H), 7.65-7.70 (m, 2H), 7.46-7.58 (m, 5H), 7.27 (t, J = 73.0 Hz, 1H). LC-MS (method 2) Rt = 1.12 min MS (ESIpos): m/z = 396.2 [M + H]$^+$ 98% yield |

TABLE 4-continued

Intermediates 101-197

| Intermediate number | Chemical structure Compound name | Starting materials | Analytics/purification/yield |
|---|---|---|---|
| 181 | 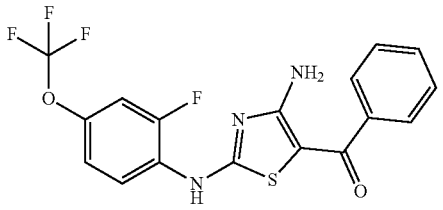 [SMILES: Nc1nc(Nc2ccc(OC(F)(F)F)cc2F)sc1C(=O)c1ccccc1]{4-amino-2-[2-fluoro-4-(trifluoromethoxy)anilino]-1,3-thiazol-5-yl}(phenyl)methanone | 2-fluoro-1-isothiocyanato-4-(trifluoromethoxy)benzene (Intermediate 206); 2-bromo-1-phenylethanone | $^1$H NMR (400 MHz, DMSO-$d_6$) δ ppm = 10.69 (br s, 1H), 8.25 (br t, J = 9.0 Hz, 3H), 7.63-7.69 (m, 2H), 7.43-7.56 (m, 4H), 7.28 (dd, J = 9.1, 1.0 Hz, 1H). LC-MS (method 2) Rt = 1.02 min MS (ESIpos): m/z = 398.2 [M + H]$^+$ 100% yield |
| 182 | 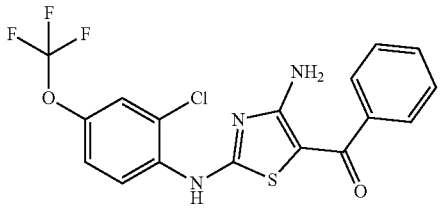 [SMILES: Nc1nc(Nc2ccc(OC(F)(F)F)cc2Cl)sc1C(=O)c1ccccc1]{4-amino-2-[2-chloro-4-(trifluoromethoxy)anilino]-1,3-thiazol-5-yl}(phenyl)methanone | 2-chloro-1-isothiocyanato-4-(trifluoromethoxy)benzene; 2-bromo-1-phenylethanone | $^1$H NMR (400 MHz, DMSO-$d_6$) δ ppm = 9.25-9.70 (m, 1H), 8.46 (s, 1H), 7.55-7.68 (m, 3H), 7.32-7.46 (m, 4H), 7.16-7.25 (m, 1H). LC-MS (method 2) Rt = 1.05 min MS (ESIpos): m/z = 414.2 [M + H]$^+$ 45% yield |
| 183 | 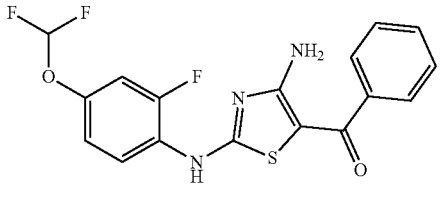 [SMILES: Nc1nc(Nc2ccc(OC(F)F)cc2F)sc1C(=O)c1ccccc1]{4-amino-2-[4-(difluoromethoxy)-2-fluoroanilino]-1,3-thiazol-5-yl}(phenyl)methanone | 4-(difluoromethoxy)-2-fluoro-1-isothiocyanatobenzene (Intermediate 207); 2-bromo-1-phenylethanone | 1H NMR (400 MHz, DMSO-$d_6$) δ ppm = 10.25-10.79 (m, 1H), 7.90-8.47 (m, 3H), 7.61-7.66 (m, 2H), 7.40-7.50 (m, 4H), 7.24-7.29 (m, 2H), 7.02-7.09 (m, 1H). LC-MS (method 2) Rt = 0.98 min MS (ESIpos): m/z = 380.2 [M + H]$^+$ 100% yield |
| 184 | 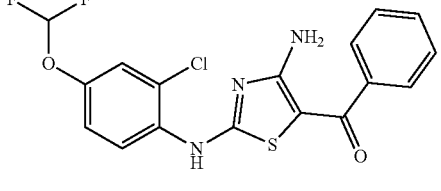{4-amino-2-[2-chloro-4-(difluoromethoxy)anilino]-1,3-thiazol-5-yl}(phenyl)methanone | 2-chloro-4-(difluoromethoxy)-1-isothiocyanatobenzene (Intermediate 208); 2-bromo-1-phenylethanone | $^1$H NMR (400 MHz, DMSO-$d_6$) δ ppm = 10.43 (br s, 1H), 7.88-8.41 (m, 2H), 7.84 (d, J = 8.6 Hz, 1H), 7.62 (dd, J = 7.6, 1.8 Hz, 2H), 7.41-7.48 (m, 4H), 7.30 (t, J = 73.8 Hz, 1H), 7.21 (dd, J = 8.7, 2.7 Hz, 1H). LC-MS (method 2) Rt = 1.02 min MS (ESIpos): m/z = 396.2 [M + H]$^+$ 99% yield |

TABLE 4-continued

Intermediates 101-197

| Intermediate number | Chemical structure Compound name | Starting materials | Analytics/purification/yield |
|---|---|---|---|
| 185 | 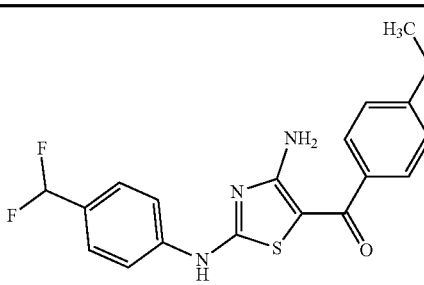{4-amino-2-[4-(difluoromethyl)anilino]-1,3-thiazol-5-yl}(4-methoxyphenyl)methanone | 1-(difluoromethyl)-4-isothiocyanatobenzene; 2-bromo-1-(4-methoxyphenyl)ethanone | $^1$H NMR (400 MHz, DMSO-d$_6$) δ ppm = 10.97 (br s, 1H), 8.17 (br s, 2H), 7.77 (d, J = 8.6 Hz, 2H), 7.66-7.71 (m, 2H), 7.56 (d, J = 8.6 Hz, 2H), 7.00-7.05 (m, 2H), 6.98 (t, J = 56.0 Hz, 1H), 3.82 (s, 3H). LC-MS (method 2) Rt = 1.07 min MS (ESIpos): m/z = 376.1 [M + H]$^+$ 88% yield |
| 186 | 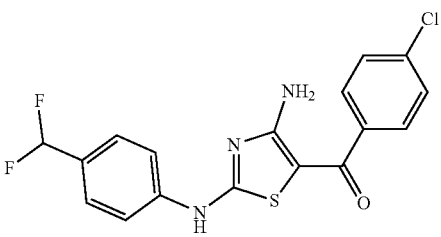 [SMILES: Nc1nc(Nc2ccc(C(F)F)cc2)sc1C(=O)c1ccc(Cl)cc1]{4-amino-2-[4-(difluoromethyl)anilino]-1,3-thiazol-5-yl}(4-chlorophenyl)methanone | 1-(difluoromethyl)-4-isothiocyanatobenzene; 2-bromo-1-(4-chlorophenyl)ethanone | $^1$H NMR (400 MHz, DMSO-d$_6$) δ ppm = 11.06 (br s, 1H), 8.28 (br s, 2H), 7.75 (brd, J = 8.4 Hz, 2H), 7.68-7.72 (m, 2H), 7.52-7.58 (m, 4H), 6.98 (t, J = 56.0 Hz, 1H). LC-MS (method 2) Rt = 1.11 min MS (ESIpos): m/z = 380.1 [M + H]$^+$ 94% yield |
| 187 | 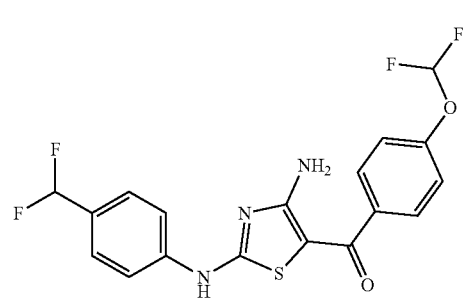 [SMILES: Nc1nc(Nc2ccc(C(F)F)cc2)sc1C(=O)c1ccc(OC(F)F)cc1]{4-amino-2-[4-(difluoromethyl)anilino]-1,3-thiazol-5-y)[4-(difluoromethoxy)phenyl]methanone | 1-(difluoromethyl)-4-isothiocyanatobenzene; 2-bromo-1-[4-(difluoromethoxy)phenyl]ethanone | $^1$H NMR (400 MHz, DMSO-d$_6$) δ ppm = 11.03 (br s, 1H), 8.24 (br s, 2H), 7.73-7.78 (m, 4H), 7.56 (d, J = 8.6 Hz, 2H), 7.35 (t, J = 73.8 Hz, 1H), 7.24-7.29 (m, 2H), 6.99 (t, J = 56.0 Hz, 1H). LC-MS (method 2) Rt = 1.09 min MS (ESIpos): m/z = 412.1 [M + H]$^+$ 91% yield |
| 188 | 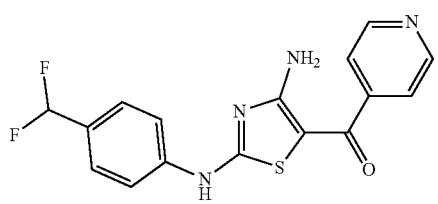 [SMILES: Nc1nc(Nc2ccc(C(F)F)cc2)sc1C(=O)c1ccncc1]{4-amino-2-[4-(difluoromethyl)anilino]-1,3-thiazol-5-yl}(pyridin-4-yl)methanone | 1-(difluoromethyl)-4-isothiocyanatobenzene; 2-bromo-1-(pyridin-4-yl)ethanone hydrobromide | $^1$H NMR (400 MHz, DMSO-d$_6$) δ ppm = 10.83-11.29 (m, 1H), 8.67-8.76 (m, 2H), 8.39 (br s, 2H), 7.77 (d, J = 8.6 Hz, 2H), 7.53-7.63 (m, 4H), 6.99 (t J = 55.8 Hz, 1H). LC-MS (method 2) Rt = 0.72 min MS (ESIpos): m/z = 347.1 [M + H]$^+$ 39% yield |

TABLE 4-continued

Intermediates 101-197

| Intermediate number | Chemical structure Compound name | Starting materials | Analytics/purification/yield |
|---|---|---|---|
| 189 | 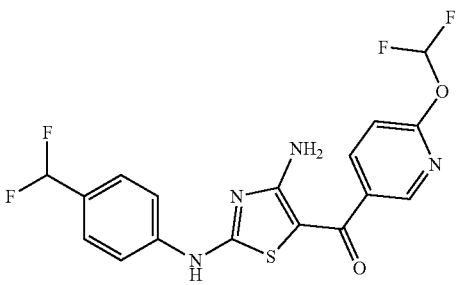 [SMILES: Nc1nc(Nc2ccc(C(F)F)cc2)sc1C(=O)c1ccc(OC(F)F)nc1]{4-amino-2-[4-(difluoromethyl)anilino]-1,3-thiazol-5-yl}[6-(difluoromethoxy)pyridin-3-yl]methanone | 1-(difluoromethyl)-4-isothiocyanatobenzene; 2-bromo-1-[6-(difluoromethoxy)pyridin-3-yl]ethanone | $^1$H NMR (400 MHz, DMSO-$d_6$) δ ppm = 11.10 (br s, 1H), 8.56-8.60 (m, 1H), 8.32 (br s, 2H), 8.18 (dd, J = 8.4, 2.5 Hz, 1H), 7.78 (t, J = 72.5 Hz, 1H), 7.77 (d, J = 8.4 Hz, 2H), 7.57 (d, J = 8.6 Hz, 2H), 7.18-7.22 (m, 1H), 6.99 (t, J = 55.8 Hz, 1H).<br>LC-MS (method 2) Rt = 1.04 min<br>MS (ESIpos): m/z = 413 [M + H]$^+$<br>89% yield |
| 190 | 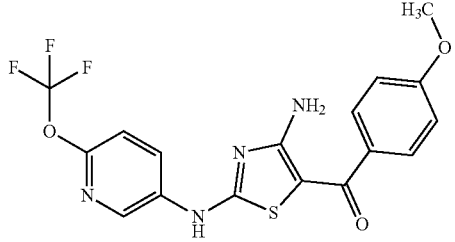 [SMILES: COc1ccc(C(=O)c2sc(Nc3ccc(OC(F)(F)F)nc3)nc2N)cc1](4-amino-2-{[6-(trifluoromethoxy)pyridin-3-yl]amino}-1,3-thiazol-5-yl)(4-methoxyphenyl)methanone | 5-isothiocyanato-2-(trifluoromethoxy)pyridine (Intermediate 201); 2-bromo-1-(4-methoxyphenyl)ethanone | $^1$H NMR (400 MHz, DMSO-$d_6$) δ ppm = 11.07 (br s, 1H), 8.67 (d, J = 2.8 Hz, 1H), 8.27 (dd, J = 8.9, 2.8 Hz, 1H), 8.17 (br s, 2H), 7.65-7.71 (m, 2H), 7.34 (d, J = 8.9 Hz, 1H), 7.00-7.05 (m, 2H), 3.82 (s, 3H).<br>LC-MS (method 2) Rt = 0.95 min<br>MS (ESIpos): m/z = 411.2 [M + H]$^+$<br>63% yield |
| 191 | 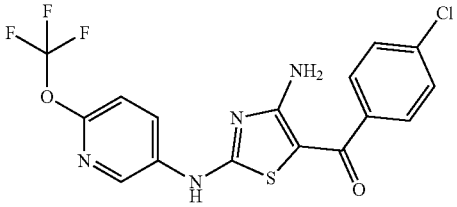 [SMILES: Nc1nc(Nc2ccc(OC(F)(F)F)nc2)sc1C(=O)c1ccc(Cl)cc1](4-amino-2-{[6-(trifluoromethoxy)pyridin-3-yl]amino}-1,3-thiazol-5-yl)(4-chlorophenyl)methanone | 5-isothiocyanato-2-(trifluoromethoxy)pyridine (Intermediate 201); 2-bromo-1-(4-chlorophenyl)ethanone | $^1$H NMR (400 MHz, DMSO-$d_6$) δ ppm = 11.18 (br s, 1H), 8.64 (d, J = 2.5 Hz, 1H), 8.25 (br dd, J = 8.9, 3.0 Hz, 3H), 7.67-7.73 (m, 2H), 7.53-7.58 (m, 2H), 7.33 (d, J = 8.9 Hz, 1H).<br>LC-MS (method 2) Rt = 0.98 min<br>MS (ESIpos): m/z = 415.2 [M + H]$^+$<br>68% yield |

TABLE 4-continued

Intermediates 101-197

| Intermediate number | Chemical structure Compound name | Starting materials | Analytics/purification/yield |
|---|---|---|---|
| 192 | 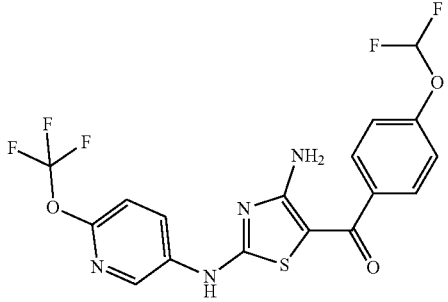 [SMILES: Nc1nc(Nc2ccc(OC(F)(F)F)nc2)sc1C(=O)c1ccc(OC(F)F)cc1]<br>(4-amino-2-{[6-(trifluoromethoxy)pyridin-3-yl]amino}-1,3-thiazol-5-yl)[4-(difluoromethoxy)phenyl]methanone | 5-isothiocyanato-2-(trifluoromethoxy)pyridine (Intermediate 201); 2-bromo-1-[4-(difluoromethoxy)phenyl]ethanone | $^1$H NMR (400 MHz, DMSO-$d_6$) δ ppm = 11.13 (br s, 1H), 8.67 (d, J = 2.8 Hz, 1H), 8.27 (dd, J = 8.9, 2.8 Hz, 3H), 7.72-7.79 (m, 2H), 7.16-7.55 (m, 4H).<br>LC-MS (method 2) Rt = 0.97 min<br>MS (ESIpos): m/z = 447.4 [M + H]$^+$<br>90% yield |
| 193 | 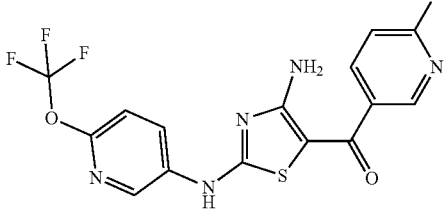<br>(4-amino-2-{[6-(trifluoromethoxy)pyridin-3-yl]amino}-1,3-thiazol-5-yl)[6-(difluoromethoxy)pyridin-3-yl]methanone | 5-isothiocyanato-2-(trifluoromethoxy)pyridine (Intermediate 201); 2-bromo-1-[6-(difluoromethoxy)pyridin-3-yl]ethanone | $^1$H NMR (400 MHz, DMSO-$d_6$) δ ppm = 11.23 (br s, 1H), 8.65 (d, J = 2.5 Hz, 1H), 8.55-8.59 (m, 1H), 8.21-8.48 (m, 3H), 8.18 (dd, J = 8.6, 2.5 Hz, 1H), 7.78 (t, J = 72.9 Hz, 1H), 7.34 (d, J = 8.9 Hz, 1H), 7.17-7.22 (m, 1H).<br>LC-MS (method 2) Rt = 0.85 min<br>MS (ESIpos): m/z = 448.2 [M + H]$^+$<br>70% yield |
| 194 | 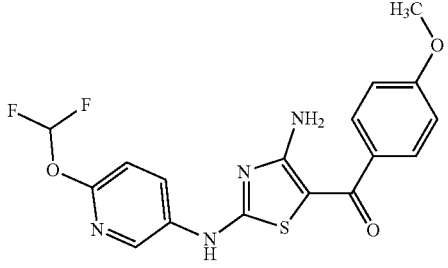 [SMILES: COc1ccc(C(=O)c2sc(Nc3ccc(OC(F)F)nc3)nc2N)cc1]<br>(4-amino-2-{[6-(difluoromethoxy)pyridin-3-yl]amino}-1,3-thiazol-5-yl)(4-methoxyphenyl)methanone | 2-(difluoromethoxy)-5-isothiocyanatopyridine (Intermediate 202); 2-bromo-1-(4-methoxyphenyl)ethanone | $^1$H NMR (400 MHz, DMSO-$d_6$) δ ppm = 10.91 (s, 1H), 8.57 (d, J = 2.5 Hz, 1H), 8.17 (dd, J = 8.9, 2.8 Hz, 3H), 7.65-7.70 (m, 2H), 7.65 (t, J = 73.0 Hz, 1H), 7.13 (d, J = 8.9 Hz, 1H), 6.99-7.05 (m, 2H), 3.82 (s, 3H).<br>LC-MS (method 2) Rt = 0.94 min<br>MS (ESIpos): m/z = 393.2 [M + H]$^+$<br>86% yield |

TABLE 4-continued

Intermediates 101-197

| Intermediate number | Chemical structure Compound name | Starting materials | Analytics/purification/yield |
|---|---|---|---|
| 195 | 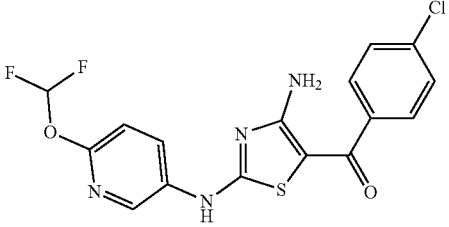 [SMILES: Nc1nc(Nc2ccc(OC(F)F)nc2)sc1C(=O)c1ccc(Cl)cc1]<br>(4-amino-2-{[6-(difluoromethoxy)pyridin-3-yl]amino}-1,3-thiazol-5-yl)(4-chlorophenyl)methanone | 2-(difluoromethoxy)-5-isothiocyanatopyridine (Intermediate 202); 2-bromo-1-(4-chlorophenyl)ethanone | $^1$H NMR (400 MHz, DMSO-$d_6$) δ ppm = 11.00 (br s, 1H), 8.52 (d, J = 2.5 Hz, 1H), 8.14 (dd, J = 8.9, 2.8 Hz, 3H), 7.66-7.71 (m, 2H), 7.65 (t, J = 73.3 Hz, 1H), 7.54 (d, J = 8.6 Hz, 2H), 7.12 (d, J = 8.9 Hz, 1H).<br>LC-MS (method 2) Rt = 0.94 min MS (ESIpos): m/z = 397.1 [M + H]$^+$<br>82% yield |
| 196 | 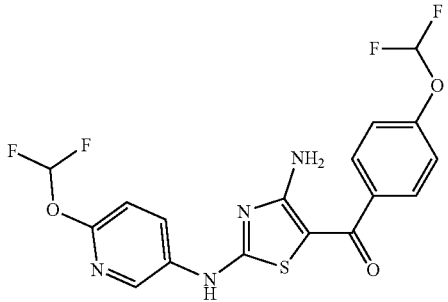 [SMILES: Nc1nc(Nc2ccc(OC(F)F)nc2)sc1C(=O)c1ccc(OC(F)F)cc1]<br>(4-amino-2-{[6-(difluoromethoxy)pyridin-3-yl]amino}-1,3-thiazol-5-yl)[4-(difluoromethoxy)phenyl]methanone | 2-(difluoromethoxy)-5-isothiocyanatopyridine (Intermediate 202); 2-bromo-1-[4-(difluoromethoxy)phenyl]ethanone | $^1$H NMR (400 MHz, DMSO-$d_6$) δ ppm = 8.56-10.12 (m, 1H), 7.70-8.09 (m, 2H), 7.65 (d, J = 8.6 Hz, 2H), 7.57 (t J = 73.8 Hz, 1H), 7.27 (t, J = 74.1 Hz, 1H), 7.14 (d, J = 8.6 Hz, 2H), 6.88 (d, J = 8.9 Hz, 1H).<br>LC-MS (method 2) Rt = 1.04 min MS (ESIpos): m/z = 429.1 [M + H]$^+$<br>87% yield |
| 197 | 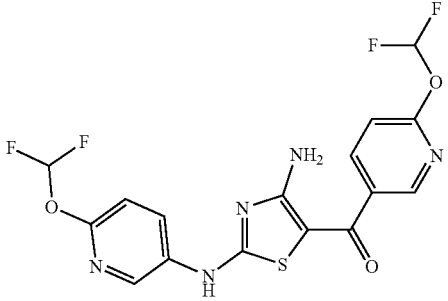 [SMILES: Nc1nc(Nc2ccc(OC(F)F)nc2)sc1C(=O)c1ccc(OC(F)F)nc1]<br>(4-amino-2-{[6-(difluoromethoxy)pyridin-3-yl]amino}-1,3-thiazol-5-yl)[6-(difluoromethoxy)pyridin-3-yl]methanone | 2-(difluoromethoxy)-5-isothiocyanatopyridine (Intermediate 202); 2-bromo-1-[6-(difluoromethoxy)pyridin-3-yl]ethanone | $^1$H NMR (400 MHz, DMSO-$d_6$) δ ppm = 1H NMR (400 MHz, DMSO-d6, 22° C.): Shift = 11.04 (br s, 1H), 8.53-8.59 (m, 2H), 8.31 (br s, 2H), 8.14-8.19 (m, 2H), 7.78 (t, J = 72.5 Hz, 1H), 7.65 (t, J = 73.0 Hz, 1H), 7.20 (dd, J = 8.6, 0.8 Hz, 1H), 7.14 (d, J = 8.9 Hz, 1H).<br>LC-MS (method 2) Rt = 0.92 min MS (ESIpos): m/z = 430.4 [M + H]$^+$<br>86% yield |

Intermediate 198

2-[4-(2-bromoacetyl)phenoxy]ethyl acetate

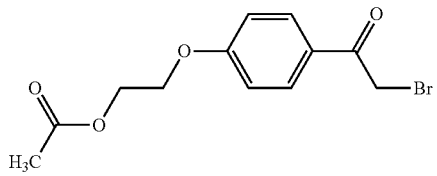 [SMILES: CC(=O)OCCOc1ccc(C(=O)CBr)cc1]

2-(4-acetylphenoxy)ethyl acetate (940 mg, 4.23 mmol) in THF (12.5 mL) at 0° C. was treated with phenyl trimethyl ammonium tribromide (1.59 g, 4.23 mmol). The reaction mixture was stirred at rt overnight, diluted with water and extracted three times with dichloromethane. The combined organic phases were washed with brine, filtered through a water repellent filter circle (MN 617 WA) and evaporated to dryness. The crude product was purified by Biotage (method X) to give 237 mg (0.79 mmol, 18% yield) of the title compound.

LC-MS (method 1): Rt=1.05 min; MS(ESIpos) m/z=300.0 [M+H]$^+$

Intermediate 199

2-bromo-1-[3-(difluoromethoxy)phenyl]ethanone

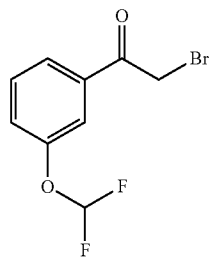 [SMILES: O=C(CBr)c1cccc(OC(F)F)c1]

3'-(difluoromethoxy)acetophenone (1 g, 5.37 mmol) in THF (15 mL) at 0° C. was treated with phenyl trimethyl ammonium tribromide (2.02 g, 5.37 mmol). The reaction mixture was stirred at rt overnight, diluted with water and extracted three times with ethyl acetate. The combined organic phases were washed with brine, filtered through a water repellent filter circle (MN 617 WA) and evaporated to dryness. The crude product (quant.) was used without further purification.

LC-MS (method 1): Rt=1.14 min; MS(ESIpos) m/z=264.9 [M+H]$^+$

Intermediate 200

2-Fluoro-4-isothiocyanato-1-(trifluoromethoxy)benzene

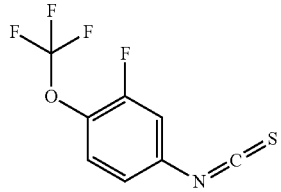 [SMILES: Fc1cc(N=C=S)ccc1OC(F)(F)F]

3-fluoro-4-(trifluoromethoxy)aniline (560 mg, 2.81 mmol) was suspended in dichloromethane (12 mL) followed by the addition of triethylamine (1.76 mL, 12.65 mmol). The mixture was cooled to 0° C. and carbonothioyl dichloride (356 mg, 3.09 mmol) diluted in dichloromethane (1.5 mL) was added slowly. After removal of the ice bath the batch was stirred at room temperature for one hour. Water (12 mL) and dichloromethane (7.5 mL) were added, the organic layer was separated, and the aqueous phase was extracted with dichloromethane. The combined organic phases were filtered through a water repellent filter circle (MN 617 WA) and evaporated to dryness. The crude material was purified via Biotage (hexanes/ethyl acetate) to yield 350 mg (1.36 mmol, 48%) of the title compound.

$^1$H NMR (400 MHz, DMSO-d$_6$) δ ppm=7.79 (dd, J=11.0, 2.4 Hz, 1H), 7.65-7.71 (m, 1H), 7.43 (ddd, J=8.9, 2.5, 1.5 Hz, 1H).

The following Intermediates were prepared from the starting materials stated in Table 5, below, using the procedure as for 2-fluoro-4-isothiocyanato-1-(trifluoromethoxy)benzene/Intermediate 200.

TABLE 5

| Intermediates 201-208 | | | |
|---|---|---|---|
| Intermediate number | Chemical structure Compound name | Starting materials | Analytics/yield |
| 201 | ![structure] <br> 5-isothiocyanato-2-(trifluoromethoxy)pyridine | 6-(trifluoromethoxy)pyridin-3-amine dihydrochloride; carbonothioyl dichloride | $^1$H NMR (400 MHz, DMSO-d$_6$) δ ppm = 8.52 (d, J = 2.8 Hz, 1H), 8.13 (dd, J = 8.7, 2.7 Hz, 1H), 7.39-7.43 (m, 1H). 79% yield |

TABLE 5-continued

Intermediates 201-208

| Intermediate number | Chemical structure Compound name | Starting materials | Analytics/yield |
|---|---|---|---|
| 202 | 2-(difluoromethoxy)-5-isothiocyanato-pyridine | 6-(difluoromethoxy)pyridin-3-amine; carbonothioyl dichloride | $^1$H NMR (400 MHz, DMSO-d$_6$) δ ppm = 8.43 (d, J = 2.8 Hz, 1H), 8.05 (dd, J = 8.7, 2.7 Hz, 1H), 7.69 (t, J = 72.5 Hz, 1H), 7.20 (d, J = 8.9 Hz, 1H). 86% yield |
| 203 | 2-(difluoromethyl)-5-isothiocyanato-pyridine | 6-(difluoromethyl)pyridin-3-amine dihydrochloride; carbonothioyl dichloride | $^1$H NMR (400 MHz, DMSO-d$_6$) δ ppm = 1H NMR (400 MHz, DMSO-d6, 22° C.): Shift = 8.78 (d, J = 2.0 Hz, 1H), 8.06 (dd, J = 8.4, 2.3 Hz, 1H), 7.78 (d, J = 8.4 Hz, 1H), 7.00 (t, J = 54.8 Hz, 1H). 77% yield |
| 204 | 1-fluoro-4-isothiocyanato-2-(trifluoromethoxy)-benzene | 4-fluoro-3-(trifluoromethoxy)aniline; carbonothioyl dichloride | $^1$H NMR (400 MHz, DMSO-d$_6$) δ ppm = 7.83-7.88 (m, 1H), 7.59-7.65 (m, 2H). 53% yield |
| 205 | 2-(difluoromethoxy)-1-fluoro-4-isothiocyanato-benzene | 3-(difluoromethoxy)-4-fluoroaniline hydrochloride; carbonothioyl dichloride | $^1$H NMR (400 MHz, DMSO-d$_6$) δ ppm = 7.60 (dd, J = 7.0, 2.4 Hz, 1H), 7.51 (dd, J = 10.4, 8.9 Hz, 1H), 7.39-7.44 (m, 1H), 7.30 (t, J = 72.8 Hz, 1H). 73% yield |
| 206 | 2-fluoro-1-isothiocyanato-4-(trifluoromethoxy)-benzene | 2-fluoro-4-(trifluoromethoxy)aniline; carbonothioyl dichloride | $^1$H NMR (400 MHz, DMSO-d$_6$) δ ppm = 7.70 (dd, J = 10.0, 2.4 Hz, 1H), 7.64 (t, J = 8.7 Hz, 1H), 7.33 (ddt, J = 8.9, 2.4, 1.3 Hz, 1H). 35% yield |
| 207 | 4-(difluoromethoxy)-2-fluoro-1-isothiocyanato-benzene | 4-(difluoromethoxy)-2-fluoroaniline; carbonothioyl dichloride | $^1$H NMR (400 MHz, DMSO-d$_6$) δ ppm = 7.58 (t, J = 8.9 Hz, 1H), 7.43 (dd, J = 11.0, 2.7 Hz, 1H), 7.34 (t, J = 73.3 Hz, 1H), 7.07-7.13 (m. 1H). 70% yield |

TABLE 5-continued

Intermediates 201-208

| Intermediate number | Chemical structure Compound name | Starting materials | Analytics/yield |
|---|---|---|---|
| 208 | 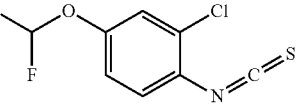<br>2-chloro-4-(difluoromethoxy)-1-isothiocyanato-benzene | 2-chloro-4-(difluoromethoxy) aniline; carbonothioyl dichloride | $^1$H NMR (400 MHz, DMSO-$d_6$) δ ppm = 7.64 (d, J = 8.9 Hz, 1H), 7.57 (d, J = 2.8 Hz, 1H), 7.34 (t, J = 73.3 Hz, 1H), 7.25 (dd, J = 8.9, 2.8 Hz, 1H). 48% yield |

Intermediate 209

[4-amino-2-(4-fluoroanilino)thiazol-5-yl]-[4-(2-hydroxyethoxy)phenyl]methanone

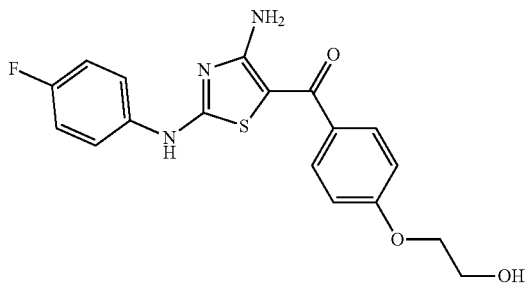 [SMILES: Nc1nc(Nc2ccc(F)cc2)sc1C(=O)c1ccc(OCCO)cc1]

The title compound (36 mg, 0.09 mmol, 11% yield) was isolated as a byproduct in the formation of 2-(4-{[4-amino-2-(4-fluoroanilino)-1,3-thiazol-5-yl]carbonyl}phenoxy)ethyl acetate (Intermediate 112).

LC-MS (method 2): Rt=0.90 min; MS(ESIpos) m/z=374.3 [M+H]$^+$

Intermediate 210

Ethyl 4-[4-amino-2-(4-fluoroanilino)thiazole-5-carbonyl]benzoate

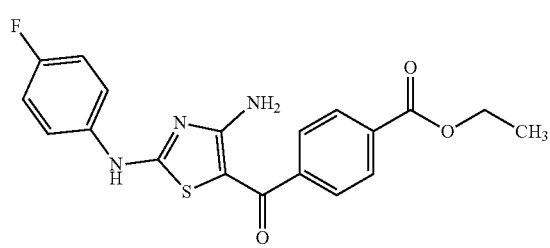 [SMILES: CCOC(=O)c1ccc(C(=O)c2sc(Nc3ccc(F)cc3)nc2N)cc1]

1-fluoro-4-isothiocyanatobenzene (5.65 g, 36.9 mmol) was dissolved in acetonitrile (200 mL) followed by the addition of 1,8-diazabicyclo(5.4.0)undec-7-ene (5.61 g, 36.9 mmol) and cyanamide (1.86 g, 44.3 mmol). After stirring for 45 min at rt, further 1,8-diazabicyclo(5.4.0)undec-7-ene (2.8 g, 18.5 mmol) and ethyl 4-(bromoacetyl)benzoate (10 g, 36.9 mmol) dissolved in acetonitrile (80 mL) were added. The reaction mixture was stirred at rt for 2.5 h and treated with water. The precipitate was filtered off, washed with water and dried in vacuo to give 14.2 g (quant.) of the title compound.

$^1$H NMR (400 MHz, DMSO-$d_6$) δ ppm=1.34 (t, J=7.1 Hz, 3H), 4.34 (d, J=7.1 Hz, 3H), 7.22 (m, 2H), 7.61 (m, 1H), 7.78 (d, J=8.62 Hz, 2H), 8.04 (d, J=8.62 Hz, 2H), 8.32 (m, 2H), 10.87 (br s, 1H).

LC-MS (method 2): Rt=1.10 min; MS(ESIpos) m/z=386.3 [M+H]$^+$

Intermediate 211 rac-4-[(4-amino-2-{[(2RS)-1-amino-1-oxopropan-2-yl](4-fluorophenyl)amino}-1,3-thiazol-5-yl)carbonyl]benzoic acid

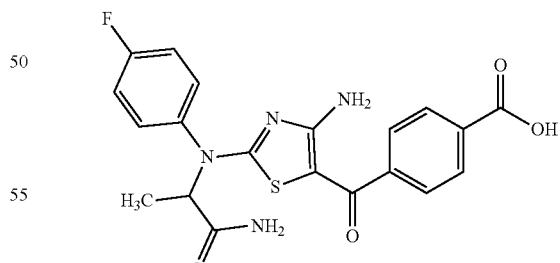

rac-Ethyl 4-[4-amino-2-(N-(2-amino-1-methyl-2-oxo-ethyl)-4-fluoro-anilino)thiazole-5-carbonyl]benzoate (15.47 g, 33 mmol, Example 257) was suspended in THF (150 mL) and treated with 1M aqueous sodium hydroxide (43 mL, 43 mmol). The reaction mixture was stirred overnight followed by the addition of 1M aqueous hydrochloric acid up to pH 3. The solution was extracted three times with ethyl acetate. The combined organic phases were washed with brine, filtered through a water repellent filter circle (MN 617 WA) and evaporated to dryness to give 11.63 g (25 mmol, 87% yield) of the title compound.

LC-MS (method 2): Rt=0.53 min; MS(ESIpos) m/z=429.4 [M+H]$^+$

Intermediate 212

Ethyl 4-[4-amino-2-(4-chloro-3-fluoro-anilino)thiazole-5-carbonyl]benzoate

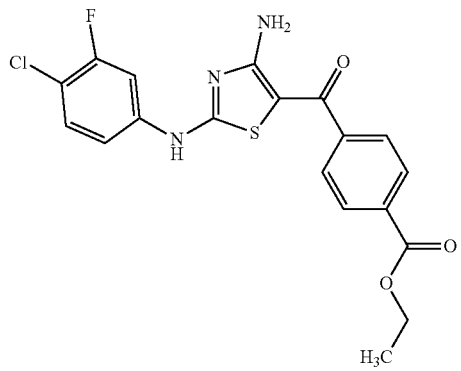 [SMILES: CCOC(=O)c1ccc(C(=O)c2sc(Nc3ccc(Cl)c(F)c3)nc2N)cc1]

1-chloro-2-fluoro-4-isothiocyanatobenzene (692 mg, 3.7 mmol) was dissolved in acetonitrile (20 mL) followed by the addition of 1,8-diazabicyclo(5.4.0)undec-7-ene (561.5 mg, 3.68 mmol) and cyanamide (186 mg, 4.43 mmol). After stirring for 45 min at rt, further 1,8-diazabicyclo(5.4.0)undec-7-ene (280.75 mg, 1.84 mmol) and ethyl 4-(bromoacetyl)benzoate (1 g, 3.7 mmol) dissolved in acetonitrile (14 mL) were added. The reaction mixture was stirred 2 h at rt. The suspension was treated with water and the precipitate was isolated by filtration, washed with water and some ethyl acetate and dried in vacuo to give 1.24 g (2.52 mmol, 68%, purity 85%) of the title compound.

LC-MS (method 2): Rt=1.12 min; MS(ESIpos) m/z=420.2 [M+H]$^+$

Intermediate 213 rac-4-[4-amino-2-(N-(2-amino-1-methyl-2-oxo-ethyl)-4-chloro-3-fluoro-anilino)thiazole-5-carbonyl]benzoic acid

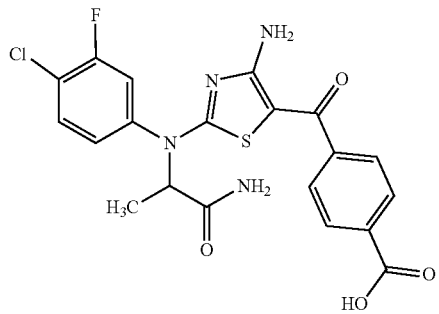 [SMILES: CC(C(N)=O)N(c1ccc(Cl)c(F)c1)c1nc(N)c(C(=O)c2ccc(C(=O)O)cc2)s1]

rac-Ethyl 4-[4-amino-2-(N-(2-amino-1-methyl-2-oxo-ethyl)-4-chloro-3-fluoro-anilino)thiazole-5-carbonyl]benzoate (830 mg, 1.7 mmol, Example 258) was suspended in THF (10 mL) and treated with 2M aqueous sodium hydroxide (8.5 mL, 17 mmol). The reaction mixture was stirred at room temperature overnight followed by the addition of 2M aqueous hydrochloric acid up to pH 3. The precipitate was filtered off, washed with water and dried in vacuo to yield 680 mg (1.47 mmol, 88%) of the title compound.

LC-MS (method 1): Rt=1.07 min; MS(ESIpos) m/z=463.1 [M+H]$^+$

Intermediate 214

Ethyl 2-[4-[4-amino-2-(4-fluoroanilino)thiazole-5-carbonyl]phenoxy]-2-methyl-propanoate

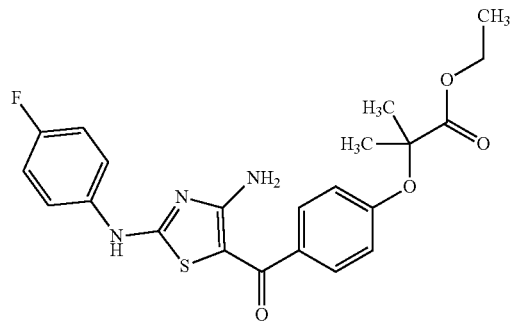 [SMILES: CCOC(=O)C(C)(C)Oc1ccc(C(=O)c2sc(Nc3ccc(F)cc3)nc2N)cc1]

1-fluoro-4-isothiocyanatobenzene (349 mg, 2.28 mmol) was dissolved in acetonitrile (8 mL) followed by the addition of 1,8-diazabicyclo(5.4.0)undec-7-ene (346 mg, 2.28 mmol) and cyanamide (115 mg, 2.7 mmol). After stirring for 45 min at rt, further 1,8-diazabicyclo(5.4.0)undec-7-ene (173 mg, 1.14 mmol) and ethyl 2-[4-(2-bromoacetyl)phenoxy]-2-methyl-propanoate (750 mg, 2.28 mmol) dissolved in acetonitrile (4 mL) were added. The reaction mixture was stirred overnight at rt. The suspension was treated with water and the precipitate was isolated by filtration, washed with water and dried in vacuo to give 1.01 g (2.28 mmol, 70%) of the title compound.

$^1$H NMR (400 MHz, DMSO-d6) δ ppm=1.15 (t, J=7.1 Hz, 3H), 1.57 (s, 6H), 4.17 (q, J=7.1 Hz, 2H), 6.80 (m, 2H), 7.15 (m, 2H), 7.50 (m, 2H), 7.59 (m, 2H), 8.12 (m, 2H), 10.51 (m, 1H).

LC-MS (method 2): Rt=1.24 min; MS(ESIpos) m/z=444.3 [M+H]$^+$

Intermediate 215 rac-2-[4-[4-amino-2-(N-(2-amino-1-methyl-2-oxo-ethyl)-4-fluoro-anilino)thiazole-5-carbonyl]phenoxy]-2-methyl-propanoic acid

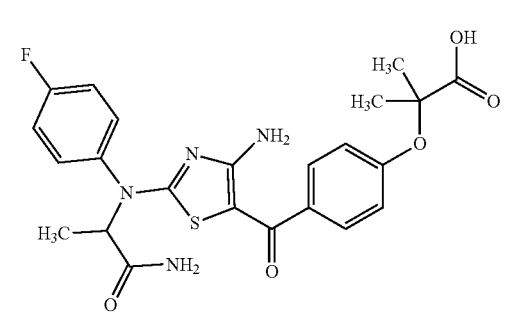 [SMILES: CC(C(N)=O)N(c1ccc(F)cc1)c1nc(N)c(C(=O)c2ccc(OC(C)(C)C(=O)O)cc2)s1]

Rac-Ethyl 2-[4-[4-amino-2-(N-(2-amino-1-methyl-2-oxo-ethyl)-4-fluoro-anilino)thiazole-5-carbonyl]phenoxy]-2-methyl-propanoate (925 mg, 1.79 mmol, Example 259) was suspended in THF (10 mL) and treated with 1M aqueous sodium hydroxide (2.7 mL, 2.7 mmol). The reaction mixture was stirred at room temperature overnight followed by the addition of 1M aqueous hydrochloric acid up to pH 3. The reaction mixture was extracted three times with ethyl acetate. The combined organic phases were washed with brine, filtered through a water repellent filter circle (MN 617 WA) and evaporated to dryness to yield 861 mg (1.6 mmol, 91%) of the title compound.

$^1$H NMR (400 MHz, DMSO-d$_6$) δ ppm=1.16 (d, J=7.35 Hz, 3H), 1.52 (s, 6H), 5.06 (m, 1H), 6.76 (m, 2H), 7.24 (s, 1H), 7.33 (t, J=8.74 Hz, 2H), 7.45 (m, 2H), 7.57 (s, 1H), 7.64 (m, 2H), 8.10 (m, 2H), 13.15 (m, 1H).

LC-MS (method 2): Rt=0.63 min; MS(ESIpos) m/z=487.4 [M+H]$^+$

Intermediate 216

[4-amino-2-(4-fluoroanilino)thiazol-5-yl]-(6-amino-3-pyridyl)methanone

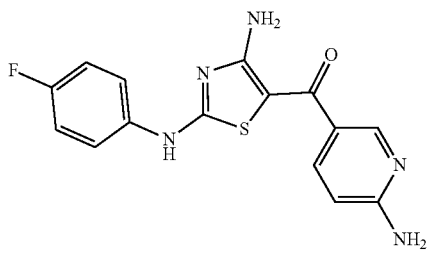 [SMILES: Nc1ccc(C(=O)c2sc(Nc3ccc(F)cc3)nc2N)cn1]

1-fluoro-4-isothiocyanatobenzene (250 mg, 1.63 mmol) was dissolved in acetonitrile (8 mL) followed by the addition of 1,8-diazabicyclo(5.4.0)undec-7-ene (248.5 mg, 1.63 mmol) and cyanamide (82 mg, 1.96 mmol). After stirring for 45 min at rt, further 1,8-diazabicyclo(5.4.0)undec-7-ene (124.2 mg, 0.82 mmol) and 1-(8-amino-3-pyridyl)-2-bromo-ethanone (351 mg, 1.63 mmol) dissolved in acetonitrile (7 mL) were added. The reaction mixture was stirred 2.5 h at rt. The suspension was treated with water and the precipitate was isolated by filtration, washed with water and dried in vacuo to give 350 mg (1.05 mmol, 64%) of the title compound.

$^1$H NMR (400 MHz, DMSO-de) δ ppm=4.65 (s, 2H), 6.96 (d, J=9.63 Hz, 1H), 7.03 (d, J=9.38 Hz, 2H), 8.24 (m, 3H), 8.62 (d, J=2.28 Hz, 2H), 8.82 (d, J=2.28 Hz, 1H).

LC-MS (method 2): Rt=0.82 min; MS(ESIpos) m/z=330.2 [M+H]$^+$

Intermediate 217

Benzyl N-[5-[4-amino-2-(4-fluoroanilino)thiazole-5-carbonyl]-2-pyridyl]carbamate

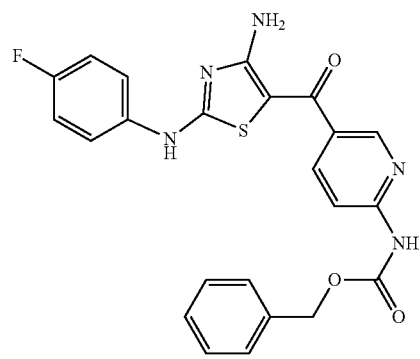 [SMILES: Nc1nc(Nc2ccc(F)cc2)sc1C(=O)c1ccc(NC(=O)OCc2ccccc2)nc1]

[4-amino-2-(4-fluoroanilino)thiazol-5-yl]-(6-amino-3-pyridyl)methanone (205 mg, 0.62 mmol, Intermediate 216) was suspended in THF (5 mL) and treated with benzyl carbonochloridate (106 mg, 0.62 mmol) and triethylamine (94 mg, 0.93 mmol). The reaction mixture was stirred overnight at rt followed by the addition of further benzyl carbonochloridate (106 mg, 0.62 mmol), triethylamine (94 mg, 0.93 mmol) and DMAP (1 mg). After 4.5 h water was added and the reaction mixture was extracted three times with ethyl acetate. The combined organic phases were washed with brine, filtered through a water repellent filter circle (MN 617 WA) and evaporated to dryness. The residue was purified via Biotage chromatography (method Y) to yield 25 mg (0.05 mmol, 9%) of the title compound.

LC-MS (method 2): Rt=1.11 min; MS(ESIpos) m/z=464.3 [M+H]$^+$

Intermediate 218

[4-amino-2-(4-fluoroanilino)-1,3-thiazol-5-yl](6-bromopyridin-3-yl)methanone

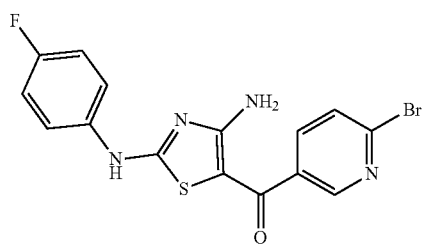 [SMILES: Nc1nc(Nc2ccc(F)cc2)sc1C(=O)c1ccc(Br)nc1]

1-fluoro-4-isothiocyanatobenzene (1.29 g, 8.43 mmol) was dissolved in acetonitrile (65 mL) followed by the addition of 1,8-diazabicyclo(5.4.0)undec-7-ene (1.28 g, 8.43 mmol) and cyanamide (0.43 g, 10.1 mmol). After stirring for 45 min at rt, further 1,8-diazabicyclo(5.4.0)undec-7-ene (0.64 g, 4.2 mmol) and 2-bromo-1-(6-bromo-3-pyridyl)etha-none (2.35 g, 8.43 mmol) dissolved in acetonitrile (15 mL) were added. The reaction mixture was stirred at rt overnight and treated with water. The precipitate was filtered off, washed with water and dried in vacuo to give 2.52 g (6.4 mmol, 76%) of the title compound.

LC-MS (method 2): Rt=0.95 min; MS(ESIpos) m/z=395.1 [M+H]+

EXPERIMENTAL SECTION—PREPARATION OF EXAMPLE COMPOUNDS

Example 1 rac-2-(N-(4-amino-5-benzoyl-thiazol-2-yl)-4-methoxy-2-methyl-anilino)propanamide

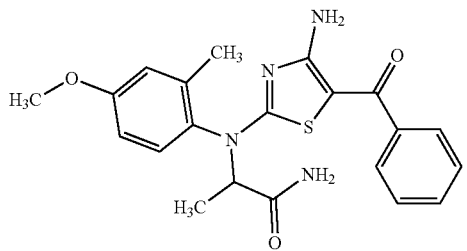 [SMILES: COc1ccc(N(c2nc(N)c(C(=O)c3ccccc3)s2)C(C)C(N)=O)c(C)c1]

[4-amino-2-(4-methoxy-2-methyl-anilino)thiazol-5-yl]-phenyl-methanone (100 mg, 0.295 mmol; Intermediate 4) were dissolved in N,N-dimethylformamide (3 mL) followed by the addition of potassium carbonate (407 mg, 2.95 mmol) and rac-2-bromopropanamide (224 mg, 1.47 mmol). The reaction mixture was stirred at 90° C. for 2 h. The reaction mixture was filtrated and purified by RP-HPLC (method D, basic) to give 57 mg (47% yield) of the title compound.

$^1$H-NMR: (400 MHz, DMSO-d6): δ ppm=1.03 (d, J=7.35 Hz, 3H), 2.13 (s, 3H), 3.75-3.78 (m, 3H), 4.93-5.13 (m, 1H), 6.85-6.93 (m, 2H), 7.17-7.24 (m, 1H), 7.34-7.42 (m, 3H), 7.42-7.50 (m, 2H), 7.54 (br s, 1H), 7.64 (d, J=8.62 Hz, 1H), 7.73-8.60 (m, 2H).

LC-MS (method 2) Rt=1.08 min; MS (ESIpos): m/z=411.5 [M+H]+

The following examples were prepared from the starting materials stated in Table 6, below, using the procedure as for Example 1.

The crude product was either purified by RP-HPLC (methods A-D depending on polarity) or by preparative flash chromatography (methods X, Y or Z depending on polarity) after precipitation, extraction or filtration of the reaction mixture if necessary.

Enantiomers were separated from their racemate by chiral HPLC using the column and solvent conditions stated.

TABLE 6

Examples 2-80

| Example number | Chemical structure Compound name | Starting materials | Analytics/purification/yield |
|---|---|---|---|
| 2 | rac-2-[N-(4-amino-5-benzoyl-thiazol-2-yl)-4-(dimethylamino)anilino]propanamide | Intermediate 5 rac-2-bromo-propanamide | $^1$H-NMR (400 MHz, DMSO-d6): δ ppm = 1.14 (d, J = 7.35 Hz, 3 H), 2.93 (s, 6 H), 5.06 (br d, J = 6.08 Hz, 1 H), 6.70 (d, J = 9.38 Hz, 2 H), 7.15-7.20 (m, 1 H), 7.28 (d, J = 8.87 Hz, 2 H), 7.34-7.41 (m, 3 H), 7.43-7.50 (m, 3 H), 7.74-8.53 (m, 2 H). LC-MS (method 2) Rt = 1.11 min; MS (ESIpos): m/z = 410.6 [M + H]+ RP-HPLC (method D, basic) 51% yield |
| 3 | rac-2-(N-(4-amino-5-benzoyl-thiazol-2-yl)-4-isopropoxy-anilino)propanamide | Intermediate 6 rac-2-bromo-propanamide | $^1$H-NMR (400 MHz, DMSO-d6): δ ppm = 1.15 (d, J =7.35 Hz, 3 H), 1.27 (d, J =6.08 Hz, 6 H), 4.62 (spt, J =6.04 Hz, 1 H), 5.01-5.11 (m, 1 H), 6.96 (d, J = 9.12 Hz, 2 H), 7.21 (s, 1 H), 7.35-7.49 (m, 7 H), 7.52 (s, 1 H), 7.75-8.51 (m, 2 H). LC-MS (method 1) Rt = 1.18 min; MS (ESIpos): m/z = 425.7 [M + H]+ RP-HPLC (method D, basic) 42% yield |

TABLE 6-continued

Examples 2-80

| Example number | Chemical structure Compound name | Starting materials | Analytics/purification/yield |
|---|---|---|---|
| 4 | 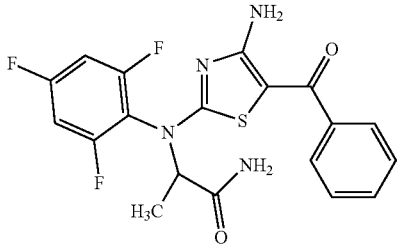 [SMILES: CC(C(N)=O)N(c1nc(N)c(C(=O)c2ccccc2)s1)c1c(F)cc(F)cc1F]<br>rac-2-(N-(4-amino-5-benzoyl-thiazol-2-yl)-2,4,6-trifluoro-anilino)propanamide | Intermediate 7; rac-2-bromo-propanamide | ¹H-NMR (500 MHz, DMSO-d6): δ ppm = 1.32 (d, J = 6.99 Hz, 3 H), 4.95 (q, J = 6.57 Hz, 1 H), 7.04-7.11 (m, 1 H), 7.33 (brs, 2 H), 7.39-7.48 (m, 4 H), 7.56 (dd, J = 7.79, 1.75 Hz, 2 H), 7.96 (br s, 2 H) LC-MS (method 2) Rt = 1.08 min; MS (ESIpos): m/z = 421.5 [M + H]⁺ RP-HPLC (method D, basic) preparative flash chromatography (method X, 40-100%) 33% yield |
| 5 | 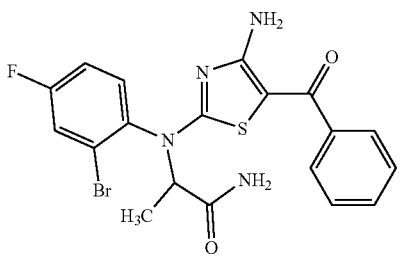 [SMILES: CC(C(N)=O)N(c1nc(N)c(C(=O)c2ccccc2)s1)c1ccc(F)cc1Br]<br>rac-2-(N-(4-amino-5-benzoyl-thiazol-2-yl)-2-bromo-4-fluoro-anilino)propanamide | Intermediate 8; rac-2-bromo-propanamide | ¹H-NMR (400 MHz, DMSO-d6): δ ppm = 1.03-1.15 (m, 3 H), 4.98-5.13 (m, 1 H), 7.21-7.34 (m, 1 H), 7.34-7.55 (m, 6 H), 7.57-7.87 (m, 2 H), 7.90-8.49 (m, 3 H). LC-MS (method 2) Rt = 1.11 min; MS (ESIpos): m/z = 463.2 [M + H]⁺ RP-HPLC (method D, basic) 83% yield |
| 6 | 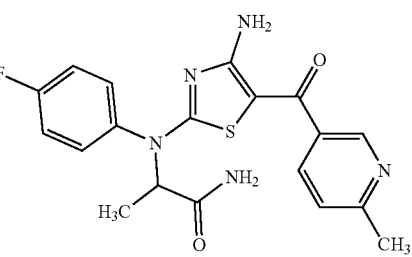<br>rac-2-(N-[4-amino-5-(6-methylpyridine-3-carbonyl)thiazol-2-yl]-4-fluoro-anilino)propanamide | Intermediate 9; rac-2-bromo-propanamide | ¹H-NMR (400 MHz, DMSO-d6): δ ppm = 1.16 (d, J = 7.60 Hz, 3 H), 2.45 (s, 3 H), 5.00-5.11 (m, 1 H), 7.24-7.28 (m, 2 H), 7.33 (t, J = 8.87 Hz, 2 H), 7.59 (s, 1 H), 7.62-7.67 (m, 2 H), 7.74 (dd, J = 8.11, 2.28 Hz, 1 H), 7.97-8.46 (m, 2 H), 8.54 (d, J = 2.03 Hz, 1 H). LC-MS (method 2) Rt = 0.93 min; MS (ESIpos): m/z = 400.4 [M + H]⁺ RP-HPLC (method C, basic) 59% yield |
| 7 | 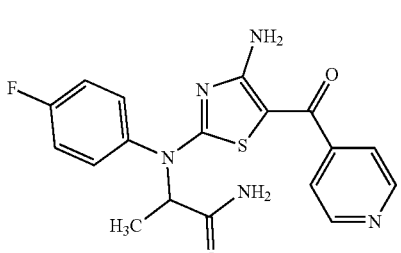<br>rac-2-(N-[4-amino-5-(pyridine-4-carbonyl)thiazol-2-yl]-4-fluoro-anilino)propanamide | Intermediate 10; rac-2-bromo-propanamide | ¹H-NMR (400 MHz, DMSO-d6): δ ppm = 1.16 (d, J = 7.60 Hz, 3 H), 5.06 (br d, J = 7.10 Hz, 1 H), 7.26 (s, 1 H), 7.33 (t, J = 8.74 Hz, 2 H), 7.38-7.42 (m, 2 H), 7.59 (s, 1 H), 7.61-7.67 (m, 2 H), 8.10-8.50 (m, 2 H), 8.59-8.64 (m, 2 H). LC-MS (method 2) Rt = 0.85 min; MS (ESIpos): m/z = 386.3 [M + H]⁺ RP-HPLC (method C, acidic) 17% yield |

TABLE 6-continued

Examples 2-80

| Example number | Chemical structure / Compound name | Starting materials | Analytics/purification/yield |
|---|---|---|---|
| 8 | rac-2-(N-[4-amino-5-(2-fluorobenzoyl)thiazol-2-yl]-4-fluoro-anilino)propanamide | Intermediate 11; rac-2-bromo-propanamide | ¹H-NMR (400 MHz, DMSO-d6): δ ppm = 1.14 (d, J = 7.35 Hz, 3 H), 4.89-5.13 (m, 1 H), 7.15-7.34 (m, 7 H), 7.40 (tdd, J = 7.73, 7.73, 5.58, 1.77 Hz, 1 H), 7.53-7.66 (m, 3 H), 8.09 (brs, 2 H). LC-MS (method 1) Rt = 1.05 min; MS (ESIpos): m/z = 403.4 [M + H]⁺ RP-HPLC (method D, basic) 71% yield |
| 9 | rac-2-(N-(4-amino-5-benzoyl-thiazol-2-yl)-4-cyano-anilino)propanamide | Intermediate 12; rac-2-bromo-propanamide | ¹H-NMR (400 MHz, DMSO-d6): δ ppm = 1.18 (d, J = 7.35 Hz, 3 H), 5.05 (q, J = 7.69 Hz, 1 H), 7.31 (s, 1 H), 7.36-7.43 (m, 3 H), 7.48-7.52 (m, 2 H), 7.64 (s, 1 H), 7.81 (d, J = 8.62 Hz, 2 H), 8.16 (brs, 2 H), 7.99 (d, J = 8.36 Hz, 2 H). LC-MS (method 1) Rt = 0.99 min; MS (ESIpos): m/z = 392.3 [M + H]⁺ RP-HPLC (method C, basic) 8% yield |
| 10 | rac-2-(N-[4-amino-5-[4-chloro-3-(trifluoromethyl)benzoyl]thiazol-2-yl]-4-fluoro-anilino)propanamide | Intermediate 13; rac-2-bromo-propanamide | ¹H-NMR (400 MHz, DMSO-d6): δ ppm = 1.16 (d, J = 7.35 Hz, 3 H), 5.01-5.14 (m, 1 H), 7.27 (s, 1 H), 7.34 (t, J = 8.87 Hz, 2 H), 7.59 (s, 1 H), 7.62-7.67 (m, 2 H), 7.77 (s, 2 H), 7.89-7.91 (m, 1 H), 8.08-8.64 (m, 2 H). LC-MS (method 2) Rt = 1.30 min; MS (ESIpos): m/z = 487.2 [M + H]⁺ RP-HPLC (method D, basic) 22% yield |
| 11 | rac-2-(N-(4-amino-5-benzoyl-thiazol-2-yl)-2-chloro-4-fluoro-anilino)propanamide | Intermediate 14; rac-2-bromo-propanamide | ¹H-NMR (400 MHz, DMSO-d6): δ ppm = 1.09 (d, J = 7.35 Hz, 3 H), 4.98-5.21 (m, 1 H), 7.26-7.34 (m, 1 H), 7.36-7.55 (m, 6 H), 7.59-7.76 (m, 2 H), 7.89-8.45 (m, 2 H), 8.03 (dd, J = 8.87, 5.83 Hz, 1 H). LC-MS (method 2) Rt = 1.13 min; MS (ESIpos): m/z = 419.4 [M + H]⁺ RP-HPLC (method D, basic) 48% yield |

TABLE 6-continued

Examples 2-80

| Example number | Chemical structure Compound name | Starting materials | Analytics/purification/yield |
|---|---|---|---|
| 12 | 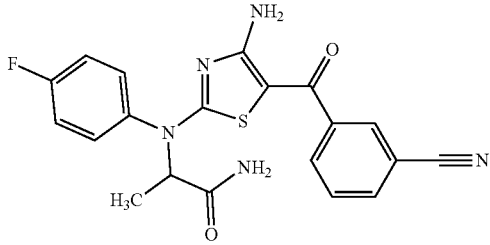 [SMILES: CC(C(N)=O)N(c1ccc(F)cc1)c1nc(N)c(C(=O)c2cccc(C#N)c2)s1]<br>rac-2-(N-[4-amino-5-(3-cyanobenzoyl)thiazol-2-yl]-4-fluoro-anilino)propanamide | Intermediate 15; rac-2-bromo-propanamide | $^1$H-NMR (400 MHz, DMSO-d6): δ ppm = 1.16 (d, J = 7.35 Hz, 3 H), 5.01-5.10 (m, 1 H), 7.24-7.28 (m, 1 H), 7.33 (t, J = 8.87 Hz, 2 H), 7.57-7.66 (m, 4 H), 7.78 (dt, J = 7.79, 1.30 Hz, 1 H), 7.86-7.89 (m, 2 H), 8.25 (br s, 2 H). LC-MS (method 2) Rt = 1.02 min; MS (ESIpos): m/z = 410.3 [M + H]$^+$ RP-HPLC (method C, basic) 31% yield |
| 13 | 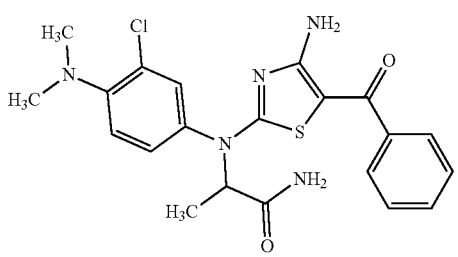 [SMILES: CC(C(N)=O)N(c1ccc(N(C)C)c(Cl)c1)c1nc(N)c(C(=O)c2ccccc2)s1]<br>rac-2-[N-(4-amino-5-benzoyl-thiazol-2-yl)-3-chloro-4-(dimethylamino)anilino]propanamide | Intermediate 16; rac-2-bromo-propanamide | $^1$H-NMR (400 MHz, DMSO-d6): δ ppm = 1.16 (d, J = 7.35 Hz, 3 H), 2.77 (s, 6 H), 4.99-5.09 (m, 1 H), 7.18 (d, J = 8.62 Hz, 1 H), 7.22-7.27 (m, 1 H), 7.35-7.46 (m, 4 H), 7.47-7.52 (m, 2 H), 7.57 (s, 1 H), 7.63 (d, J = 2.28 Hz, 1 H), 8.16 (brs, 2 H). LC-MS (method 2) Rt = 0.91 min; MS (ESIpos): m/z = 444.5 [M + H]$^+$ RP-HPLC (method C, basic) 51% yield |
| 14 | 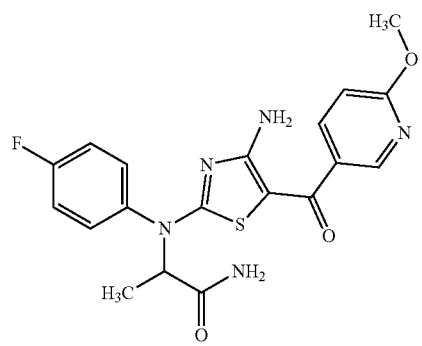 [SMILES: COc1ccc(C(=O)c2sc(N(c3ccc(F)cc3)C(C)C(N)=O)nc2N)cn1]<br>rac-2-(N-[4-amino-5-(6-methoxypyridine-3-carbonyl)thiazol-2-yl]-4-fluoro-anilino)propanamide | Intermediate 17; rac-2-bromo-propanamide | $^1$H-NMR (400 MHz, DMSO-d6): δ ppm = 1.16 (d, J = 7.60 Hz, 3 H), 3.85 (s, 3 H), 5.01-5.11 (m, 1 H), 6.83 (dd, J = 8.62, 0.51 Hz, 1 H), 7.24-7.28 (m, 1 H), 7.34 (t, J = 8.87 Hz, 2 H), 7.59 (s, 1 H), 7.62-7.68 (m, 2 H), 7.82 (dd, J = 8.62, 2.53 Hz, 1 H), 8.17 (br s, 2 H), 8.33 (d, J = 2.03 Hz, 1 H). LC-MS (method 2) Rt = 1.02 min; MS (ESIpos): m/z = 416.4 [M + H]$^+$ RP-HPLC (method C, basic) 43% yield |
| 15 | 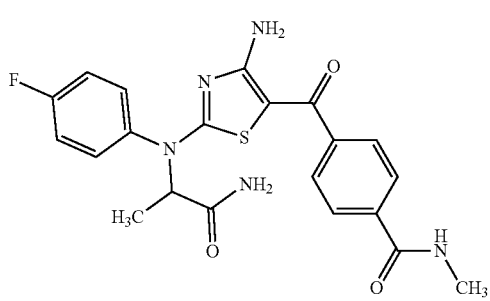 [SMILES: CNC(=O)c1ccc(C(=O)c2sc(N(c3ccc(F)cc3)C(C)C(N)=O)nc2N)cc1]<br>rac-4-[4-amino-2-(N-[2-amino-1-methyl-2-oxo-ethyl]-4-fluoro-anilino)thiazole-5-carbonyl]-N-methyl-benzamide | Intermediate 18; rac-2-bromo-propanamide | $^1$H-NMR (400 MHz, DMSO-d6): δ ppm = 1.16 (d, J = 7.35 Hz, 3 H), 2.75 (d, J = 4.56 Hz, 3 H), 4.99-5.12 (m, 1 H), 7.25 (s, 1 H), 7.32 (t, J = 8.87 Hz, 2 H), 7.53 (d, J = 8.36 Hz, 2 H), 7.58 (brs, 1 H), 7.60-7.66 (m, 2 H), 7.78 (d, J = 8.36 Hz, 2 H), 8.17 (brs, 2 H), 8.46 (q, J = 4.48 Hz, 1 H). LC-MS (method 2) Rt = 0.85 min; MS (ESIpos): m/z = 442.5 [M + H]$^+$ RP-HPLC (method C, basic) 10% yield |

TABLE 6-continued

Examples 2-80

| Example number | Chemical structure / Compound name | Starting materials | Analytics/purification/yield |
|---|---|---|---|
| 16 | rac-2-(N-[4-amino-5-(3-fluorobenzoyl)thiazol-2-yl]-4-fluoro-anilino)propanamide | Intermediate 19; rac-2-bromo-propanamide | $^1$H-NMR (400 MHz, DMSO-d6): δ ppm = 1.16 (d, J = 7.35 Hz, 3 H), 4.98-5.17 (m, 1 H), 7.22-7.29 (m, 3 H), 7.29-7.36 (m, 3 H), 7.39-7.48 (m, 1 H), 7.58 (s, 1 H), 7.64 (dd, J = 8.62, 5.07 Hz, 2 H), 7.97-8.59 (m, 2 H). LC-MS (method 1) Rt = 1.10 min; MS (ESIpos): m/z = 403.3 [M + H]+ RP-HPLC (method D, basic) 68% yield |
| 17 | rac-2-(N-(4-amino-5-benzoyl-thiazol-2-yl)-3-chloro-4-methoxy-anilino)propanamide | Intermediate 20; rac-2-bromo-propanamide | $^1$H-NMR (400 MHz, DMSO-d6): δ ppm = 1.16 (d, J = 7.35 Hz, 3 H), 3.89 (s, 3 H), 4.96-5.10 (m, 1 H), 7.22 (d, J = 8.87 Hz, 1 H), 7.25 (s, 1 H), 7.35-7.43 (m, 3 H), 7.46-7.54 (m, 3 H), 7.59 (s, 1 H), 7.71 (d, J = 2.53 Hz, 1 H), 7.87-8.37 (m, 2 H). LC-MS (method 2) Rt = 1.10 min; MS (ESIpos): m/z = 431.3 [M + H]$^+$ RP-HPLC (method D, basic) 60% yield |
| 18 | rac-2-(N-[4-amino-5-(4-fluorobenzoyl)thiazol-2-yl]-4-methoxy-anilino)propanamide | Intermediate 21; rac-2-bromo-propanamide | $^1$H-NMR (400 MHz, DMSO-d6): δ ppm = 1.14 (d, J = 7.35 Hz, 3 H), 3.78 (s, 3 H), 5.01-5.10 (m, 1 H), 7.01 (d, J = 9.13 Hz, 2 H), 7.17-7.24 (m, 3 H), 7.46 (d, J = 8.62 Hz, 2 H), 7.51-7.58 (m, 3 H), 8.09 (brs, 2 H). LC-MS (method 1) Rt = 1.08 min; MS (ESIpos): m/z = 415.6 [M + H]$^+$ RP-HPLC (method C, acidic) 36% yield |
| 19 | rac-2-(N-[4-amino-5-(4-methylsulfonylbenzoyl)thiazol-2-yl]-4-fluoro-anilino)propanamide | Intermediate 22; rac-2-bromo-propanamide | $^1$H-NMR (400 MHz, DMSO-d6): δ ppm = 1.16 (d, J = 7.35 Hz, 3 H), 3.23 (s, 3 H), 4.96-5.15 (m, 1 H), 7.26 (s, 1 H), 7.33 (t, J = 8.74 Hz, 2 H), 7.59 (s, 1 H), 7.64 (dd, J = 8.87, 5.07 Hz, 2 H), 7.70 (d, J = 8.36 Hz, 2 H), 7.93 (d, J = 8.62 Hz, 2 H), 8.04-8.56 (m, 2 H). LC-MS (method 1) Rt = 0.91 min; MS (ESIpos): m/z = 463.4 [M + H]$^+$ RP-HPLC (method C, basic) 31% yield |

TABLE 6-continued

Examples 2-80

| Example number | Chemical structure Compound name | Starting materials | Analytics/purification/yield |
|---|---|---|---|
| 20 | 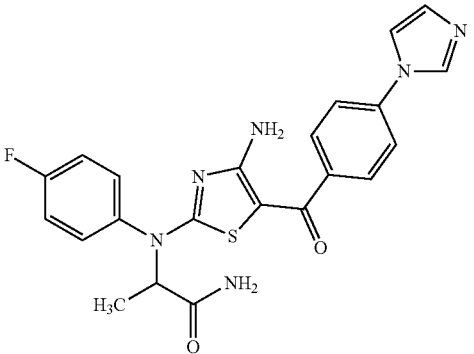 [SMILES: CC(C(N)=O)N(c1ccc(F)cc1)c1nc(N)c(C(=O)c2ccc(-n3ccnc3)cc2)s1]<br>rac-2-(N-[4-amino-5-(4-imidazol-1-ylbenzoyl)thiazol-2-yl]-4-fluoro-anilino)propanamide | Intermediate 23; rac-2-bromo-propanamide | $^1$H-NMR (400 MHz, DMSO-d6): δ ppm = 1.16 (d, J = 7.35 Hz, 3 H), 5.00-5.13 (m, 1 H), 7.10 (s, 1 H), 7.26 (s, 1 H), 7.34 (t, J = 8.74 Hz, 2 H), 7.56-7.73 (m, 7 H), 7.78 (t, J = 1.27 Hz, 1 H), 7.88-8.62 (m, 2 H), 8.30 (s, 1 H). LC-MS (method 1) Rt = 0.70 min; MS (ESIpos): m/z = 451.5 [M + H]$^+$ RP-HPLC (method C, basic) 68% yield |
| 21 | 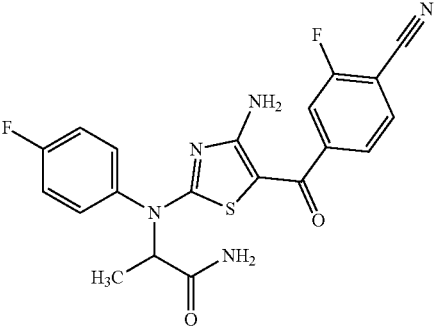 [SMILES: CC(C(N)=O)N(c1ccc(F)cc1)c1nc(N)c(C(=O)c2ccc(C#N)c(F)c2)s1]<br>rac-2-(N-[4-amino-5-(4-cyano-3-fluoro-benzoyl)thiazol-2-yl]-4-fluoro-anilino)propanamide | Intermediate 24; rac-2-bromo-propanamide | $^1$H-NMR (400 MHz, DMSO-d6): δ ppm = 1.15 (d, J = 7.35 Hz, 3 H), 5.01-5.11 (m, 1 H), 7.25 (s, 1 H), 7.33 (t, J = 8.87 Hz, 2 H), 7.45 (dd, J = 7.86, 1.27 Hz, 1 H), 7.55 (dd, J = 9.89, 1.27 Hz, 1 H), 7.58-7.66 (m, 3 H), 7.93 (dd, J = 7.86, 6.59 Hz, 1 H), 8.11-8.52 (m, 2 H). LC-MS (method 1) Rt = 1.08 min; MS (ESIpos): m/z = 428.3 [M + H]$^+$ RP-HPLC (method C, basic) 5% yield |
| 21.1 and 21.2 | (R)-2-(N-[4-amino-5-(4-cyano-3-fluoro-benzoyl)thiazol-2-yl]-4-fluoro-anilino)propanamide and (S)-2-(N-[4-amino-5-(4-cyano-3-fluoro-benzoyl)thiazol-2-yl]-4-fluoro-anilino)propanamide | | |

TABLE 6-continued

Examples 2-80

| Example number | Chemical structure Compound name | Starting materials | Analytics/purification/yield |
|---|---|---|---|
| 21.1 | 2-(N-[4-amino-5-(4-cyano-3-fluoro-benzoyl)thiazol-2-yl]-4-fluoro-anilino)propanamide (enantiomer 1) | Example 21 | $^1$H-NMR (400 MHz, DMSO-d6): δ ppm = 1.15 (d, J = 7.35 Hz, 3 H), 5.01-5.11 (m, 1 H), 7.25 (s, 1 H), 7.33 (t, J = 8.87 Hz, 2 H), 7.45 (dd, J = 7.86, 1.27 Hz, 1 H), 7.55 (dd, J = 9.89, 1.27 Hz, 1 H), 7.58-7.66 (m, 3 H), 7.93 (dd, J = 7.86, 6.59 Hz, 1 H), 8.11-8.52 (m, 2 H). LC-MS (method 1) Rt = 1.07 min; MS (ESIpos): m/z = 428.3 [M + H]$^+$ RP-HPLC (method C, basic) 8% yield |

Chiral HPLC Example 21.1
HPLC separation of rac-2-(N-[4-amino-5-(4-cyano-3-fluoro-benzoyl)thiazol-2-yl]-4-fluoro-anilino)propanamide (Example 21, 106 mg. 0.25 mmol) on a chiral column followed by another preparative HPLC gave 9.2 mg (8% yield) of 2-(N-[4-amino-5-(4-cyano-3-fluoro-benzoyl)thiazol-2-yl]-4-fluoro-anilino)propanamide, enantiomer 1.
Preparative chiral HPLC
Instrument: PrepCon Labomatic HPLC; Column: YMC Cellulose SB 5μ, 250 × 30; eluent A: hexane + 0.1 vol % diethylamine; eluent B: ethanol + 0.1 vol % diethylamine; isocratic: 80% A + 20% B; flow: 50 mL/min; temperature: 25° C.; UV: 254 nm
Analytical chiral HPLC: Rt = 5.46 min
Instrument: Waters Alliance 2695; Column: YMC Cellulose SB 3μ, 100 × 4.6; eluent A: hexane + 0.1 vol % diethylamine; eluent B: ethanol; isocratic: 80% A + 20% B; flow: 1.4 mL/min; temperature: 25° C.; UV: 254 nm

| 21.2 | 2-(N-[4-amino-5-(4-cyano-3-fluoro-benzoyl)thiazol-2-yl]-4-fluoro-anilino)propanamide (enantiomer 2) | Example 21 | $^1$H-NMR (400 MHz, DMSO-d6): δ ppm = 1.15 (d, J = 7.35 Hz, 3 H), 5.01-5.11 (m, 1 H), 7.25 (s, 1 H), 7.33 (t, J = 8.87 Hz, 2 H), 7.45 (dd, J = 7.86, 1.27 Hz, 1 H), 7.55 (dd, J = 9.89, 1.27 Hz, 1 H), 7.58-7.66 (m, 3 H), 7.93 (dd, J = 7.86, 6.59 Hz, 1 H), 8.11-8.52 (m, 2 H). LC-MS (method 1) Rt = 1.07 min; MS (ESIpos): m/z = 428.3 [M + H]$^+$ RP-HPLC (method C, basic) 7% yield |

Chiral HPLC Example 21.2
HPLC separation of rac-2-(N-[4-amino-5-(4-cyano-3-fluoro-benzoyl)thiazol-2-yl]-4-fluoro-anilino)propanamide (Example 21, 106 mg. 0.25 mmol) on a chiral column followed by another preparative HPLC gave 7 mg (6% yield) of 2-(N-[4-amino-5-(4-cyano-3-fluoro-benzoyl)thiazol-2-yl]-4-fluoro-anilino)propanamide, enantiomer 2.
Preparative chiral HPLC
Instrument: PrepCon Labomatic HPLC; Column: YMC Cellulose SB 5μ, 250 × 30; eluent A: hexane + 0.1 vol % diethylamine; eluent B: ethanol + 0.1 vol % diethylamine; isocratic: 80% A + 20% B; flow: 50 mL/min; temperature: 25° C.; UV: 254 nm
Analytical chiral HPLC: Rt = 7.71 min
Instrument: Waters Alliance 2695; Column: YMC Cellulose SB 3μ, 100 × 4.6; eluent A: hexane + 0.1 vol % diethylamine; eluent B: ethanol; isocratic: 80% A + 20% B; flow: 1.4 mL/min; temperature: 25° C.; UV: 254 nm TABLE 6-continued Examples 2-80

| Example number | Chemical structure Compound name | Starting materials | Analytics/purification/yield |
|---|---|---|---|
| 22 | 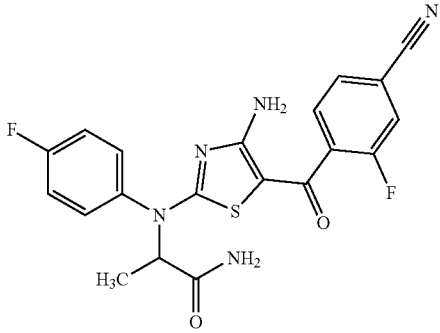 [SMILES: CC(C(N)=O)N(c1ccc(F)cc1)c1nc(N)c(C(=O)c2ccc(C#N)cc2F)s1]<br>rac-2-(N-[4-amino-5-(4-cyano-2-fluoro-benzoyl)thiazol-2-yl]-4-fluoro-anilino)propanamide | Intermediate 25; rac-2-bromo-propanamide | $^1$H-NMR (400 MHz, DMSO-d6): δ ppm = 1.16 (d, J = 7.35 Hz, 3 H), 5.01-5.11 (m, 1 H), 7.27 (s, 1 H), 7.34 (t, J = 8.87 Hz, 2 H), 7.45 (dd, J = 8.11, 1.27 Hz, 1 H), 7.56 (dd, J = 9.76, 1.14 Hz, 1 H), 7.59 (s, 1 H), 7.64 (dd, J = 8.74, 4.94 Hz, 2 H), 7.92-7.97 (m, 1 H), 8.18-8.50 (m, 2 H). LC-MS (method 1) Rt = 1.07 min; MS (ESIpos): m/z = 428.3 [M + H]$^+$ RP-HPLC (method D, basic) 40% yield |
| 23 | 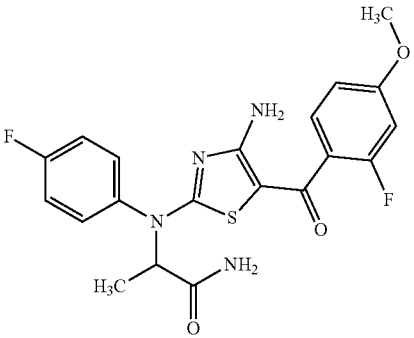 [SMILES: COc1ccc(C(=O)c2sc(N(c3ccc(F)cc3)C(C)C(N)=O)nc2N)c(F)c1]<br>rac-2-(N-[4-amino-5-(2-fluoro-4-methoxy-benzoyl)thiazol-2-yl]-4-fluoro-anilino)propanamide | Intermediate 26; rac-2-bromo-propanamide | $^1$H-NMR (400 MHz, DMSO-d6): δ ppm = 1.14 (d, J = 7.60 Hz, 3 H), 3.75 (s, 3 H), 4.98-5.09 (m, 1 H), 6.76 (d, J = 20.28 Hz, 1 H), 6.78 (br d, J = 23.32 Hz, 1 H), 7.22-7.27 (m, 2 H), 7.31 (t, J = 8.87 Hz, 2 H), 7.57 (s, 1 H), 7.59-7.64 (m, 2 H), 8.03 (br s, 2 H). LC-MS (method 2) Rt = 1.06 min; MS (ESIpos): m/z = 433.4 [M + H]$^+$ RP-HPLC (method D, basic) 47% yield |
| 24 | 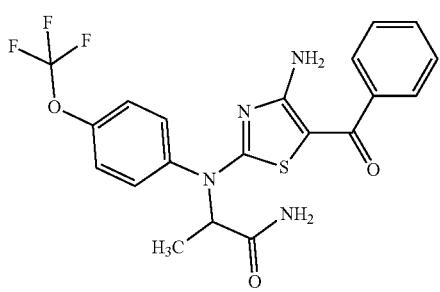 [SMILES: CC(C(N)=O)N(c1ccc(OC(F)(F)F)cc1)c1nc(N)c(C(=O)c2ccccc2)s1]<br>rac-2-[N-(4-amino-5-benzoyl-thiazol-2-yl)-4-(trifluoromethoxy)anilino] propanamide | Intermediate 27; rac-2-bromo-propanamide | $^1$H-NMR (400 MHz, DMSO-d6): δ ppm = 1.17 (d, J = 7.35 Hz, 3 H), 5.05 (q, J = 7.18 Hz, 1 H), 7.28 (s, 1 H), 7.36-7.42 (m, 3 H), 7.45-7.52 (m, 4 H), 7.61 (s, 1 H), 7.69-7.75 (m, 2 H), 8.16 (brs, 2 H). LC-MS (method 2) Rt = 1.20 min; MS (ESIpos): m/z = 451.5 [M + H]$^+$ RP-HPLC (method D, basic) 49% yield |

TABLE 6-continued

Examples 2-80

| Example number | Chemical structure Compound name | Starting materials | Analytics/purification/yield |
|---|---|---|---|
| 25 | 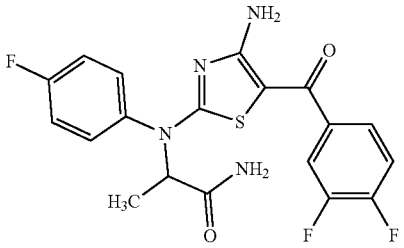 [SMILES: CC(C(N)=O)N(c1ccc(F)cc1)c1nc(N)c(C(=O)c2ccc(F)c(F)c2)s1]<br>rac-2-(N-[4-amino-5-(3,4-difluorobenzoyl)thiazol-2-yl]-4-fluoro-anilino)propanamide | Intermediate 28; rac-2-bromo-propanamide | ¹H-NMR (400 MHz, DMSO-d6): δ ppm = 1.16 (d, J = 7.35 Hz, 3 H), 5.02-5.10 (m, 1 H), 7.26 (s, 1 H), 7.34 (t, J = 8.62 Hz, 3 H), 7.41-7.49 (m, 1 H), 7.52 (ddd, J = 11.15, 7.98, 2.15 Hz, 1 H), 7.58 (s, 1 H), 7.62-7.66 (m, 2 H), 7.98-8.50 (m, 2 H).<br>LC-MS (method 2) Rt = 1.14 min; MS (ESIpos): m/z = 419.3 [M + H]⁺<br>RP-HPLC (method D, basic)<br>30% yield |
| 26 | 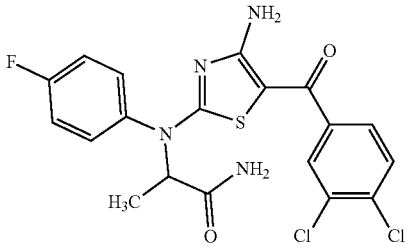 [SMILES: CC(C(N)=O)N(c1ccc(F)cc1)c1nc(N)c(C(=O)c2ccc(Cl)c(Cl)c2)s1]<br>rac-2-(N-[4-amino-5-(3,4-dichlorobenzoyl)thiazol-2-yl]-4-fluoro-anilino)propanamide | Intermediate 29; rac-2-bromo-propanamide | ¹H-NMR (400 MHz, DMSO-d6): δ ppm = 1.16 (d, J = 7.35 Hz, 3 H), 5.00-5.11 (m, 1 H), 7.26 (s, 1 H), 7.34 (t, J = 8.74 Hz, 2 H), 7.44 (dd, J = 8.36, 2.03 Hz, 1 H), 7.57-7.61 (m, 1 H), 7.62-7.66 (m, 2 H), 7.67 (d, J = 11.66 Hz, 1 H), 7.67 (d, J = 1.27 Hz, 1 H), 8.03-8.48 (m, 2 H).<br>LC-MS (method 2) Rt = 1.24 min; MS (ESIpos): m/z = 453.1 [M + H]⁺<br>RP-HPLC (method D, basic)<br>38% yield |
| 27 | 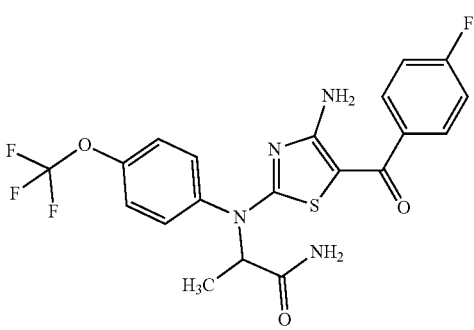 [SMILES: CC(C(N)=O)N(c1ccc(OC(F)(F)F)cc1)c1nc(N)c(C(=O)c2ccc(F)cc2)s1]<br>rac-2-[N-[4-amino-5-(4-fluorobenzoyl)thiazol-2-yl]-4-(trifluoromethoxy)anilino]propanamide | Intermediate 30; rac-2-bromo-propanamide | ¹H-NMR (400 MHz, DMSO-d6): δ ppm = 1.15-1.19 (m, 3 H), 5.02-5.09 (m, 1 H), 7.22 (t, J = 8.87 Hz, 2 H), 7.28 (s, 1 H), 7.50 (d, J = 8.11 Hz, 2 H), 7.56 (dd, J = 8.62, 5.58 Hz, 2 H), 7.61 (s, 1 H), 7.73 (d, J = 9.13 Hz, 2 H), 7.90-8.49 (m, 2 H).<br>LC-MS (method 2) Rt = 1.23 min; MS (ESIpos): m/z = 469.3 [M + H]⁺<br>59% yield |

TABLE 6-continued

Examples 2-80

| Example number | Chemical structure Compound name | Starting materials | Analytics/purification/yield |
|---|---|---|---|
| 27.1 and 27.2 | (R)-2-[N-[4-amino-5-(4-fluorobenzoyl)thiazol-2-yl]-4-(trifluoromethoxy)anilino]propanamide and (S)-2-[N-[4-amino-5-(4-fluorobenzoyl)thiazol-2-yl]-4-(trifluoromethoxy)anilino]propanamide | | |
| 27.1 | 2-[N-[4-amino-5-(4-fluorobenzoyl)thiazol-2-yl]-4-(trifluoromethoxy)anilino]propanamide (enantiomer 1) | Example 27 | ¹H-NMR (400 MHz, DMSO-d6): δ ppm = 1.17 (d, J = 7.35 Hz, 3 H), 5.05 (q, J = 7.27 Hz, 1 H), 7.22 (t, J = 9.00 Hz, 2 H), 7.28 (s, 1 H), 7.48-7.53 (m, 2 H), 7.53-7.59 (m, 2 H), 7.61 (s, 1 H), 7.70-7.75 (m, 2 H), 7.95-8.42 (m, 2 H). LC-MS (method 1) Rt = 1.23 min; MS (ESIpos): m/z = 469.3 [M + H]⁺ 39% yield |

Chiral HPLC Example 27.1
HPLC separation of rac-2-[N-[4-amino-5-(4-fluorobenzoyl)thiazol-2-yl]-4-(trifluoromethoxy)anilino]propanamide (1130 mg, 2.4 mmol; Example 27) on a chiral column gave 448 mg (39% yield) of 2-[N-[4-amino-5-(4-fluorobenzoyl)thiazol-2-yl]-4-(trifluoromethoxy)anilino]propanamide, enantiomer 1.
Preparative chiral HPLC
Instrument: PrepCon Labomatic HPLC; Column: YMC Cellulose SB 5u, 250 × 30; eluent A: hexane + 0.1 vol % diethylamine; eluent B: ethanol + 0.1 vol % diethylamine; isocratic: 80% A + 20% B; flow: 60 mL/min; temperature: 25° C.; UV: 254 nm
Analytical chiral HPLC: Rt = 2.99 min
Instrument: Waters Alliance 2695; Column: YMC Cellulose SB 3μ, 100 × 4.6; eluent A: hexane + 0.1 vol % diethylamine; eluent B: ethanol; isocratic: 80% A + 20% B; flow: 1.4 mL/min; temperature: 25° C.; UV: 254 nm

| 27.2 | 2-[N-(4-amino-5-(4-fluorobenzoyl)thiazol-2-yl]-4-(trifluoromethoxy)anilino]propanamide (enantiomer 2) | Example 27 | ¹H-NMR (400 MHz, DMSO-d6): δ ppm = 1.17 (d, J = 7.60 Hz, 3 H), 5.05 (br d, J =7.10 Hz, 1 H), 7.19-7.25 (m, 2 H), 7.28 (s, 1 H), 7.47-7.53 (m, 2 H), 7.53-7.59 (m, 2 H), 7.59-7.63 (m, 1 H), 7.70-7.76 (m, 2 H), 7.96-8.40 (m, 2 H). LC-MS (method 1) Rt = 1.23 min; MS (ESIpos): m/z = 469.2 [M + H]⁺ 37% yield |

Chiral HPLC Example 27.2
HPLC separation of rac-2-[N-[4-amino-5-(4-fluorobenzoyl)thiazol-2-yl]-4-(trifluoromethoxy)anilino]propanamide (1130 mg, 2.4 mmol; Example 27) on a chiral column gave 430 mg (37% yield) of 2-[N-[4-amino-5-(4-fluorobenzoyl)thiazol-2-yl]-4-(trifluoromethoxy)anilino]propanamide, enantiomer 2.
Preparative chiral HPLC
Instrument: PrepCon Labomatic HPLC; Column: YMC Cellulose SB 5μ, 250 × 30; eluent A: hexane + 0.1 vol % diethylamine; eluent B: ethanol + 0.1 vol % diethylamine; isocratic: 80% A + 20% B; flow: 60 mL/min; temperature: 25° C.; UV: 254 nm
Analytical chiral HPLC: Rt = 3.81 min
Instrument: Waters Alliance 2695; Column: YMC Cellulose SB 3μ, 100×4.6; eluent A: hexane + 0.1 vol % diethylamine; eluent B: ethanol; isocratic: 80% A + 20% B; flow: 1.4 mL/min; temperature: 25° C.; UV: 254 nm

TABLE 6-continued

Examples 2-80

| Example number | Chemical structure / Compound name | Starting materials | Analytics/purification/yield |
|---|---|---|---|
| 28 | rac-2-[N-(4-amino-5-benzoyl-thiazol-2-yl)-4-(trifluoromethyl)anilino]propanamide | Intermediate 31; rac-2-bromo-propanamide | $^1$H-NMR (400 MHz, DMSO-d6): δ ppm = 1.18 (d, J = 7.35 Hz, 3 H), 5.06 (q, J = 7.52 Hz, 1 H), 7.30 (s, 1 H), 7.36-7.44 (m, 3 H), 7.47-7.52 (m, 2 H), 7.63 (s, 1 H), 7.80-7.91 (m, 4 H), 8.18 (br s, 2 H). LC-MS (method 1) Rt = 1.18 min; MS (ESIpos): m/z = 435.3 $[M + H]^+$ RP-HPLC (method D, basic) 29% yield |
| 29 | rac-2-(N-[4-amino-5-[6-(trifluoromethyl)pyridine-3-carbonyl]thiazol-2-yl]-4-fluoro-anilino)propanamide | Intermediate 32; rac-2-bromo-propanamide | $^1$H-NMR (400 MHz, DMSO-d6): δ ppm = 1.16 (d, J = 7.60 Hz, 3 H), 5.02-5.13 (m, 1 H), 7.25 (s, 1 H), 7.30-7.38 (m, 2 H), 7.60 (s, 1 H), 7.64 (dd, J = 8.87, 5.07 Hz, 2 H), 7.94 (d, J = 7.86 Hz, 1 H), 8.12 (dd, J = 8.11, 1.77 Hz, 1 H), 8.23-8.46 (m, 2 H), 8.84 (br d, J = 1.80 Hz, 1 H). LC-MS (method 1) Rt = 1.13 min; MS (ESIpos): m/z = 454.5 $[M + H]^+$ RP-HPLC (method C, basic) 42% yield |
| 29.1 and 29.2 | (R)-2-(N-[4-amino-5-(6-(trifluoromethyl)pyridine-3-carbonyl]thiazol-2-yl]-4-fluoro-anilino)propanamide and (S)-2-(N-[4-amino-5-[6-(trifluoromethyl)pyridine-3-carbonyl]thiazol-2-yl]-4-fluoro-anilino)propanamide | | |
| 29.1 | 2-(N-[4-amino-5-[6-(trifluoromethyl)pyridine-3-carbonyl]thiazol-2-yl]-4-fluoro-anilino)propanamide (enantiomer 1) | Example 29 | $^1$H-NMR (400 MHz, DMSO-d6): δ ppm = 1.16 (d, J = 7.35 Hz, 3 H), 5.00-5.16 (m, 1 H), 7.27 (s, 1 H), 7.33 (t, J = 8.74 Hz, 2 H), 7.58-7.69 (m, 3 H), 7.93 (d, J = 8.11 Hz, 1 H), 8.11 (br d, J = 1.77 Hz, 1 H), 8.17-8.50 (m, 2 H), 8.84 (d, J = 1.27 Hz, 1 H). LC-MS (method 1) Rt = 1.13 min; MS (ESIpos): m/z = 454.5 $[M + H]^+$ $[α]_D^{20}$ = +53.2° (c = 1.00, dimethylsulfoxide) 13% yield |

Chiral HPLC Example 29.1
HPLC separation of rac-2-(N-[4-amino-5-[6-(trifluoromethyl)pyridine-3-carbonyl]thiazol-2-yl]-4-fluoro-anilino)propanamide (394 mg, 1.0 mmol; Example 29) on a chiral column gave 163 mg (33% yield) of 2-(N-[4-amino-5-[6-(trifluoromethyl)pyridine-3-carbonyl]thiazol-2-yl]-4-fluoro-anilino)propanamide, enantiomer 1.
Preparative chiral HPLC
Instrument: PrepCon Labomatic HPLC; Column: YMC Cellulose SB 10µ, 250 × 50; eluent A: hexane + 0.1 vol % diethylamine; eluent B: 2-propanol + 0.1 vol % diethylamine; isocratic: 60% A + 40% B; flow: 140 mL/min; temperature: 25° C.; UV: 254 nm
Analytical chiral HPLC: Rt = 2.24 min TABLE 6-continued Examples 2-80

| Example number | Chemical structure Compound name | Starting materials | Analytics/purification/yield |
|---|---|---|---|

Instrument: Waters Alliance 2695; Column: YMC Cellulose SB 3µ, 100 × 4.6; eluent A: hexane + 0.1 vol % diethylamine; eluent B: 2-propanol; isocratic: 60% A + 40% B; flow: 1.4 mL/min; temperature: 25° C.; UV: 254 nm

29.2

2-(N-[4-amino-5-[6-(trifluoromethyl)pyridine-3-carbonyl]thiazol-2-yl]-4-fluoro-anilino)propanamide (enantiomer 2)

Example 29

$^1$H-NMR (400 MHz, DMSO-d6): δ ppm = 1.17 (d, J = 7.35 Hz, 3 H), 5.01-5.17 (m, 1 H), 7.28 (s, 1 H), 7.33 (t, J = 8.74 Hz, 2 H), 7.54-7.72 (m, 3 H), 7.93 (d, J = 8.11 Hz, 1 H), 8.12 (dd, J = 8.11, 1.77 Hz, 1 H), 8.21-8.54 (m, 2 H), 8.84 (d, J = 1.27 Hz, 1 H).
LC-MS (method 1) Rt = 1.12 min; MS (ESIpos): m/z = 454.5 [M + H]$^+$
$[\alpha]_D^{20}$ = −44.3° (c = 1.00, dimethylsulfoxide) 13% yield Chiral HPLC Example 29.2
HPLC separation of rac-2-(N-[4-amino-5-[6-(trifluoromethyl)pyridine-3-carbonyl]thiazol-2-yl]-4-fluoro-anilino)propanamide (394 mg, 1.0 mmol; Example 29) on a chiral column gave 164 mg (33% yield) of 2-(N-[4-amino-5-[6-(trifluoromethyl)pyridine-3-carbonyl]thiazol-2-yl]-4-fluoro-anilino)propanamide, enantiomer 2.
Preparative chiral HPLC
Instrument: PrepCon Labomatic HPLC; Column: YMC Cellulose SB 10µ, 250 × 50; eluent A: hexane + 0.1 vol % diethylamine; eluent B: 2-propanol + 0.1 vol % diethylamine; isocratic: 60% A + 40% B; flow: 140 mL/min; temperature: 25° C.; UV: 254 nm
Analytical chiral HPLC: Rt = 3.26 min
Instrument: Waters Alliance 2695; Column: YMC Cellulose SB 3µ, 100 × 4.6; eluent A: hexane + 0.1 vol % diethylamine; eluent B: 2-propanol; isocratic: 60% A + 40% B; flow: 1.4 mL/min; temperature: 25° C.; UV: 254 nm

30 rac-2-(N-(4-amino-5-benzoyl-thiazol-2-yl)-4-chloro-2-fluoro-anilino)propanamide

Intermediate 33; rac-2-bromo-propanamide $^1$H-NMR (400 MHz, DMSO-d6): δ ppm = 1.11-1.22 (m, 3 H), 4.92-5.22 (m, 1 H), 7.28-7.36 (m, 1 H), 7.39-7.54 (m, 6 H), 7.59-7.76 (m, 2 H), 7.79-7.93 (m, 1 H), 7.97-8.32 (m, 2 H).
LC-MS (method 1) Rt = 1.16 min; MS (ESIpos): m/z = 417.2 [M + H]$^+$
RP-HPLC (method D, basic)
37% yield

31 rac-2-(N-[4-amino-5-(indane-5-carbonyl)thiazol-2-yl]-4-fluoro-anilino)propanamide Intermediate 34; rac-2-bromo-propanamide $^1$H-NMR (400 MHz, DMSO-d6): δ ppm = 1.15 (d, J = 7.35 Hz, 3 H), 1.98 (quin, J = 7.41 Hz, 2 H), 2.82 (td, J = 7.29, 4.18 Hz, 4 H), 5.04 (brq, J = 6.67 Hz, 1 H), 7.18-7.23 (m, 2 H), 7.24 (s, 1 H), 7.29-7.35 (m, 3 H), 7.56-7.59 (m, 1 H), 7.60-7.65 (m, 2 H), 7.80-8.40 (m, 2 H).
LC-MS (method 2) Rt = 1.23 min; MS (ESIpos): m/z = 425.6 [M + H]$^+$
RP-HPLC (method D, basic)
24% yield TABLE 6-continued Examples 2-80

| Example number | Chemical structure Compound name | Starting materials | Analytics/purification/yield |
|---|---|---|---|
| 32 | 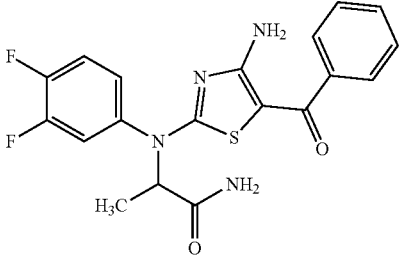 [SMILES: CC(C(N)=O)N(c1ccc(F)c(F)c1)c1nc(N)c(C(=O)c2ccccc2)s1]<br>rac-2-(N-(4-amino-5-benzoyl-thiazol-2-yl)-3,4-difluoro-anilino)propanamide | Intermediate 35; rac-2-bromo-propanamide | $^1$H-NMR (400 MHz, DMSO-d6): δ ppm = 1.18 (d, J =7.35 Hz, 3 H), 5.02 (q, J = 7.69 Hz, 1 H), 7.29 (s, 1 H), 7.36-7.44 (m, 3 H), 7.47-7.53 (m, 3 H), 7.54-7.60 (m, 1 H), 7.61-7.65 (m, 1 H), 7.77 (ddd, J = 11.47, 7.54, 2.28 Hz, 1 H), 8.15 (br s, 2 H). LC-MS (method 1) Rt = 1.11 min; MS (ESIpos): m/z = 403.3 $[M + H]^+$ RP-HPLC (method C, basic) 48% yield |
| 33 | 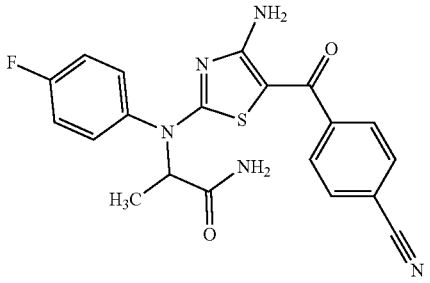 [SMILES: CC(C(N)=O)N(c1ccc(F)cc1)c1nc(N)c(C(=O)c2ccc(C#N)cc2)s1]<br>rac-2-(N-[4-amino-5-(4-cyanobenzoyl)thiazol-2-yl]-4-fluoro-anilino)propanamide | Intermediate 36; rac-2-bromo-propanamide | $^1$H-NMR (400 MHz, DMSO-d6): δ ppm = 1.16 (d, J = 7.35 Hz, 3 H), 4.90-5.24 (m, 1 H), 7.23-7.29 (m, 1 H), 7.33 (t, J = 8.74 Hz, 2 H), 7.59 (s, 1 H), 7.60-7.66 (m, 4 H), 7.86 (d, J = 8.36 Hz, 2 H), 8.05-8.57 (m, 2 H). LC-MS (method 2) Rt = 1.02 min; MS (ESIpos): m/z = 410.3 $[M + H]^+$ RP-HPLC (method C, basic) 78% yield |
| 33.1 and 33.2 | (R)-2-(N-[4-amino-5-(4-cyanobenzoyl)thiazol-2-yl]-4-fluoro-anilino)propanamide and (S)-2-(N-[4-amino-5-(4-cyanobenzoyl)thiazol-2-yl]-4-fluoro-anilino)propanamide | | |
| 33.1 | 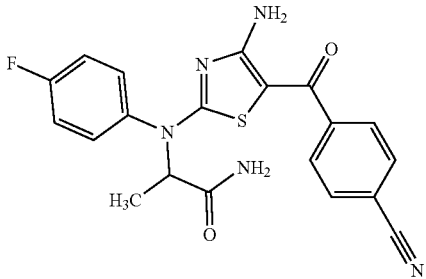 [SMILES: CC(C(N)=O)N(c1ccc(F)cc1)c1nc(N)c(C(=O)c2ccc(C#N)cc2)s1]<br>2-(N-[4-amino-5-(4-cyanobenzoyl)thiazol-2-yl]-4-fluoro-anilino)propanamide (enantiomer 1) | Example 33 | $^1$H-NMR (400 MHz, DMSO-d6): δ ppm = 1.16 (d, J = 7.35 Hz, 3 H), 5.02-5.11 (m, 1 H), 7.24-7.28 (m, 1 H), 7.33 (t, J = 8.74 Hz, 2 H), 7.58 (s, 1 H), 7.61-7.66 (m, 4 H), 7.86 (d, J = 8.62 Hz, 2 H), 8.05-8.50 (m, 2 H). LC-MS (method 2) Rt = 1.02 min; MS (ESIpos): m/z = 410.3 $[M + H]^+$ $[α]_D^{20}$ = +93.9° (c = 1.00, dimethylsulfoxide) 31% yield |

Chiral HPLC Example 33.1
HPLC separation of rac-2-(N-[4-amino-5-(4-cyanobenzoyl)thiazol-2-yl]-4-fluoro-anilino)propanamide (96 mg, 0.23 mmol; Example 33) on a chiral column gave 30 mg (30% yield) of 2-(N-[4-amino-5-(4-cyanobenzoyl)thiazol-2-yl]-4-fluoro-anilino)propanamide, enantiomer 1.
Preparative chiral HPLC
Instrument: PrepCon Labomatic HPLC; Column: YMC Cellulose SB 10μ, 250 × 50; eluent A: hexane + 0.1 vol % diethylamine; eluent B: ethanol; isocratic: 60% A + 40% B; flow: 150 mL/min; temperature: 25° C.; UV: 254 nm
Analytical chiral HPLC: Rt = 2.26 min
Instrument: Waters Alliance 2695; Column: YMC Cellulose SB 3μ, 100 × 4.6; eluent A: hexane + 0.1 vol % diethylamine; eluent B: ethanol; isocratic: 60% A + 40% B; flow: 1.4 mL/min; temperature: 25° C.; UV: 254 nm

TABLE 6-continued

Examples 2-80

| Example number | Chemical structure Compound name | Starting materials | Analytics/purification/yield |
|---|---|---|---|
| 33.2 | 2-(N-[4-amino-5-(4-cyanobenzoyl)thiazol-2-yl]-4-fluoro-anilino)propanamide (enantiomer 2) | Example 33 | $^1$H-NMR (400 MHz, DMSO-d6): δ ppm = 1.16 (d, J = 7.60 Hz, 3 H), 5.01-5.12 (m, 1 H), 7.26 (s, 1 H), 7.33 (t, J = 8.87 Hz, 2 H), 7.58 (s, 1 H), 7.63 (d, J = 8.36 Hz, 4 H), 7.86 (d, J = 8.36 Hz, 2 H), 8.05-8.53 (m, 2 H). LC-MS (method 2) Rt = 1.02 min; MS (ESIpos): m/z = 410.3 [M + H]$^+$ $[α]_D^{20}$ = −89.9° (c = 1.00, dimethylsulfoxide) 30% yield |

Chiral HPLC Example 33.2

HPLC separation of rac-2-(N-[4-amino-5-(4-cyanobenzoyl)thiazol-2-yl]-4-fluoro-anilino)propanamide (96 mg, 0.23 mmol; Example 33) on a chiral column gave 32 mg (31% yield) of 2-(N-[4-amino-5-(4-cyanobenzoyl)thiazol-2-yl]-4-fluoro-anilino)propanamide, enantiomer 2.

Preparative chiral HPLC

Instrument: PrepCon Labomatic HPLC; Column: YMC Cellulose SB 10μ, 250 × 50; eluent A: hexane + 0.1 vol % diethylamine; eluent B: ethanol; isocratic: 60% A + 40% B; flow: 150 mL/min; temperature: 25° C.; UV: 254 nm Analytical chiral HPLC: Rt = 3.05 min Instrument: Waters Alliance 2695; Column: YMC Cellulose SB 3μ, 100 × 4.6; eluent A: hexane + 0.1 vol % diethylamine; eluent B: ethanol; isocratic: 60% A + 40% B; flow: 1.4 mL/min; temperature: 25° C.; UV: 254 nm

| Example number | Chemical structure Compound name | Starting materials | Analytics/purification/yield |
|---|---|---|---|
| 34 | rac-2-(N-(4-amino-5-benzoyl-thiazol-2-yl)-4-chloro-anilino)propanamide | Intermediate 37; rac-2-bromo-propanamide | $^1$H-NMR (400 MHz, DMSO-d6): δ ppm = 1.16 (d, J = 7.35 Hz, 3 H), 5.05 (q, J = 7.18 Hz, 1 H), 7.26 (s, 1 H), 7.35-7.42 (m, 3 H), 7.47-7.50 (m, 2 H), 7.54-7.63 (m, 5 H), 8.16 (brs, 2 H). LC-MS (method 2) Rt = 1.15 min; MS (ESIpos): m/z = 402.2 [M + H]$^+$ RP-HPLC (method D, basic) 9% yield |
| 35 | rac-2-(N-(4-amino-5-benzoyl-thiazol-2-yl)-3,4-dichloro-anilino)propanamide | Intermediate 38; rac-2-bromo-propanamide | $^1$H-NMR (400 MHz, DMSO-d6): δ ppm = 1.19 (d, J = 7.35 Hz, 3 H), 5.01 (q, J = 7.18 Hz, 1 H), 7.31 (s, 1 H), 7.37-7.45 (m, 3 H), 7.49-7.54 (m, 2 H), 7.62 (dd, J = 8.90, 2.53 Hz, 1 H), 7.64 (s, 1 H), 7.79 (d, J = 8.36 Hz, 1 H), 7.95 (d, J = 2.28 Hz, 1 H), 8.24 (br s, 2 H). LC-MS (method 1) Rt = 1.23 min; MS (ESIneg): m/z = 433.4 [M − H]$^+$ RP-HPLC (method D, basic) 27% yield |

TABLE 6-continued

Examples 2-80

| Example number | Chemical structure Compound name | Starting materials | Analytics/purification/yield |
|---|---|---|---|
| 36 | rac-2-(N-(4-amino-5-benzoyl-thiazol-2-yl)-4-chloro-3-fluoro-anilino)propanamide | Intermediate 39; rac-2-bromo-propanamide | ¹H-NMR (400 MHz, DMSO-d6): δ ppm = 1.19 (d, J = 7.35 Hz, 3 H), 5.02 (q, J = 7.35 Hz, 1 H), 7.30 (s, 1 H), 7.38-7.45 (m, 3 H), 7.49-7.53 (m, 3 H), 7.63 (s, 1 H), 7.72-7.77 (m, 2 H), 8.15 (br s, 2 H). LC-MS (method 1) Rt = 1.17 min; MS (ESIpos): m/z = 419.3 [M + H]⁺ RP-HPLC (method D, basic) 39% yield |
| 37 | rac-2-(N-[4-amino-5-(4-fluorobenzoyl)thiazol-2-yl]-4-chloro-anilino)propanamide | Intermediate 40; rac-2-bromo-propanamide | ¹H-NMR (400 MHz, DMSO-d6): δ ppm = 1.16 (d, J = 7.60 Hz, 3 H), 5.02-5.11 (m, 1 H), 7.25 (s, 1 H), 7.33 (t, J = 8.87 Hz, 2 H), 7.43-7.52 (m, 4 H), 7.58 (s, 1 H), 7.64 (dd, J = 8.87, 5.07 Hz, 2 H), 7.98-8.43 (m, 2 H). LC-MS (method 2) Rt = 1.18 min; MS (ESIpos): m/z = 419.2 [M + H]⁺ 55% yield |
| 37.1 and 37.2 | (R)-2-(N-[4-amino-5-(4-fluorobenzoyl)thiazol-2-yl]-4-chloro-anilino)propanamide and (S)-2-(N-[4-amino-5-(4-fluorobenzoyl)thiazol-2-yl]-4-chloro-anilino)propanamide | | |
| 37.1 | 2-(N-[4-amino-5-(4-fluorobenzoyl)thiazol-2-yl]-4-chloro-anilino)propanamide (enantiomer 1) | Example 37 | ¹H-NMR (400 MHz, DMSO-d6): δ ppm = 1.13-1.19 (m, 3 H), 5.01-5.11 (m, 1 H), 7.25 (s, 1 H), 7.33 (t, J = 8.87 Hz, 2 H), 7.43-7.53 (m, 4 H), 7.58 (s, 1 H), 7.64 (dd, J = 8.87, 5.07 Hz, 2 H), 7.88-8.52 (m, 2 H). LC-MS (method 1) Rt = 1.19 min; MS (ESIpos): m/z = 419.2 [M + H]⁺ 31% yield |

Chiral HPLC Example 37.1
HPLC separation of rac-2-(N-[4-amino-5-(4-fluorobenzoyl)thiazol-2-yl]-4-chloro-anilino)propanamide (170 mg, 0.41 mmol, Example 37) on a chiral column gave 54 mg (31% yield) of 2-(N-[4-amino-5-(4-fluorobenzoyl)thiazol-2-yl]-4-chloro-anilino)propanamide, enantiomer 1.
Preparative chiral HPLC
Instrument: PrepCon Labomatic HPLC; Column: YMC Cellulose SB 5µ, 250 × 30; eluent A: hexane + 0.1 vol % diethylamine; eluent B: ethanol + 0.1 vol % diethylamine; isocratic: 60% A + 40% B; flow: 50 mL/min; temperature: 25° C.; UV: 254 nm
Analytical chiral HPLC: Rt = 1.66 min
Instrument: Waters Alliance 2695; Column: YMC Cellulose SB 3µ, 100 × 4.6; eluent A: hexane + 0.1 vol % diethylamine; eluent B: ethanol; isocratic: 60% A + 40% B; flow: 1.4 mL/min; temperature: 25° C.; UV: 254 nm

| Example number | Chemical structure Compound name | Starting materials | Analytics/purification/yield |
| --- | --- | --- | --- |
| 37.2 | 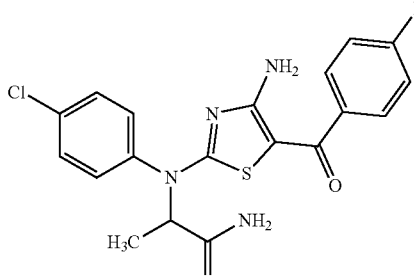<br><br>2-(N-[4-amino-5-(4-fluorobenzoyl)thiazol-2-yl]-4-chloro-anilino)propanamide<br>(enantiomer 2) | Example 37 | $^1$H-NMR (400 MHz, DMSO-d6): δ ppm = 1.16 (d, J = 7.35 Hz, 3 H), 5.01-5.11 (m, 1 H), 7.23-7.27 (m, 1 H), 7.33 (t J = 8.87 Hz, 2 H), 7.43-7.53 (m, 4 H), 7.58 (s, 1 H), 7.64 (dd, J = 8.87, 5.07 Hz, 2 H), 7.92-8.37 (m, 2 H).<br>LC-MS (method 1) Rt = 1.19 min; MS (ESIpos): m/z = 419.2 [M + H]$^+$<br>32% yield |

Chiral HPLC Example 37.2

HPLC separation of rac-2-(N-[4-amino-5-(4-fluorobenzoyl)thiazol-2-yl]-4-chloro-anilino)propanamide (170 mg, 0.41 mmol, Example 37) on a chiral column gave 57 mg (32% yield) 2-(N-[4-amino-5-(4-fluorobenzoyl)thiazol-2-yl]-4-chloro-anilino)propanamide, enantiomer 2.

Preparative chiral HPLC

Instrument: PrepCon Labomatic HPLC; Column: YMC Cellulose SB 5µ, 250 × 30; eluent A: hexane + 0.1 vol % diethylamine; eluent B: ethanol + 0.1 vol % diethylamine; isocratic: 60% A + 40% B; flow: 50 mL/min; temperature: 25° C.; UV: 254 nm Analytical chiral HPLC: Rt = 2.20 min Instrument: Waters Alliance 2695; Column: YMC Cellulose SB 3µ, 100 × 4.6; eluent A: hexane + 0.1 vol % diethylamine; eluent B: ethanol; isocratic: 60% A + 40% B; flow: 1.4 mL/min; temperature: 25° C.; UV: 254 nm

| Example number | Chemical structure Compound name | Starting materials | Analytics/purification/yield |
| --- | --- | --- | --- |
| 38 | 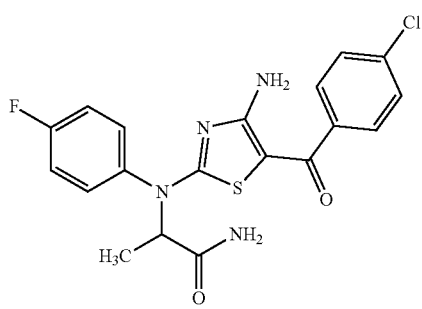<br><br>rac-2-(N-[4-amino-5-(4-chlorobenzoyl)thiazol-2-yl]-4-fluoro-anilino)propanamide | Intermediate 41; rac-2-bromo-propanamide | $^1$H-NMR (400 MHz, DMSO-d6): δ ppm = 1.16 (d, J = 7.60 Hz, 3 H), 5.01-5.12 (m, 1 H), 7.25 (s, 1 H), 7.29-7.37 (m, 2 H), 7.43-7.53 (m, 4 H), 7.58 (s, 1 H), 7.63 (dd, J = 8.87, 5.07 Hz; 2 H), 7.92-8.44 (m, 2 H).<br>LC-MS (method 1) Rt = 1.19 min; MS (ESIpos): m/z = 419.2 [M + H]$^+$<br>RP-HPLC (method C, basic)<br>42% yield |
| 38.1 and 38.2 | (R)-2-(N-[4-amino-5-(4-chlorobenzoyl)thiazol-2-yl]-4-fluoro-anilino)propanamide and (S)-2-(N-[4-amino-5-(4-chlorobenzoyl)thiazol-2-yl]-4-fluoro-anilino)propanamide | | |

TABLE 6-continued

Examples 2-80

| Example number | Chemical structure Compound name | Starting materials | Analytics/purification/yield |
|---|---|---|---|
| 38.1 | 2-(N-[4-amino-5-(4-chlorobenzoyl)thiazol-2-yl]-4-fluoro-anilino)propanamide (enantiomer 1) | Example 38 | $^1$H-NMR (400 MHz, DMSO-d6): δ ppm = 1.16 (d, J = 7.35 Hz, 3 H), 4.98-5.16 (m, 1 H), 7.25 (s, 1 H), 7.33 (t, J = 8.87 Hz, 2 H), 7.43-7.52 (m, 4 H), 7.58 (s, 1 H), 7.63 (dd, J = 8.87, 5.07 Hz, 2 H), 7.92-8.50 (m, 2 H). LC-MS (method 1) Rt = 1.19 min; MS (ESIpos): m/z = 419.2 [M + H]$^+$ RP-HPLC (method D, basic) 16% yield |

Chiral HPLC Example 38.1

HPLC separation of rac-2-(N-[4-amino-5-(4-chlorobenzoyl)thiazol-2-yl]-4-fluoro-anilino)propanamide (115 mg, 0.27 mmol; Example 38) on a chiral column, followed by an additional RP-HPLC gave 19 mg (16% yield) of 2-(N-[4-amino-5-(4-chlorobenzoyl)thiazol-2-yl]-4-fluoro-anilino)propanamide, enantiomer 1.

Preparative chiral HPLC

Instrument: PrepCon Labomatic HPLC; Column: YMC Cellulose SB 10μ, 250 × 50; eluent A: hexane + 0.1 vol % diethylamine; eluent B: 2-propanol + 0.1 vol % diethylamine; isocratic: 60% A + 40% B; flow: 140 mL/min; temperature: 25° C.; UV: 254 nm Analytical chiral HPLC: Rt = 2.23 min Instrument: Waters Alliance 2695; Column: YMC Cellulose SB 3μ, 100 × 4.6; eluent A: exane + 0.1 vol % diethylamine; eluent B: 2-propanol; isocratic: 60% A + 40% B; flow: 1.4 mL/mi n; temperature: 25° C.; UV: 254 nm

| Example number | Chemical structure Compound name | Starting materials | Analytics/purification/yield |
|---|---|---|---|
| 38.2 | 2-(N-[4-amino-5-(4-chlorobenzoyl)thiazol-2-yl]-4-fluoro-anilino)propanamide (enantiomer 2) | Example 38 | $^1$H-NMR (400 MHz, DMSO-d6): δ ppm = 1.16 (d, J = 7.35 Hz, 3 H), 5.02-5.10 (m, 1 H), 7.25 (s, 1 H), 7.33 (t, J = 8.87 Hz, 2 H), 7.43-7.52 (m, 4H), 7.57-7.60 (m, 1 H), 7.63 (dd, J = 8.87, 5.07 Hz, 2 H), 7.95-8.47 (m, 2 H). LC-MS (method 1) Rt = 1.19 min; MS (ESIpos): m/z = 419.2 [M + H]$^+$ RP-HPLC (method D, basic) 38% yield |

Chiral HPLC Example 38.2

HPLC separation of rac-2-(N-[4-amino-5-(4-chlorobenzoyl)thiazol-2-yl]-4-fluoro-anilino)propanamide (115 mg, 0.27 mmol; Example 38) on a chiral column, followed by an additional RP-HPLC gave 20 mg (17% yield) of 2-(N-[4-amino-5-(4-chlorobenzoyl)thiazol-2-yl]-4-fluoro-anilino)propanamide, enantiomer 2.

Preparative chiral HPLC

Instrument: PrepCon Labomatic HPLC; Column: YMC Cellulose SB 10μ, 250 × 50; eluent A: hexane + 0.1 vol % diethylamine; eluent B: 2-propanol + 0.1 vol % diethylamine; isocratic: 60% A + 40% B; flow: 140 mL/min; temperature: 25° C.; UV: 254 nm Analytical chiral HPLC: Rt = 3.79 min Instrument: Waters Alliance 2695; Column: YMC Cellulose SB 3μ, 100 × 4.6; eluent A: exane + 0.1 vol % diethylamine; eluent B: 2-propanol; isocratic: 60% A + 40% B, flow: 1.4 mL/mi n; temperature: 25° C.; UV: 254 nm

TABLE 6-continued

Examples 2-80

| Example number | Chemical structure Compound name | Starting materials | Analytics/purification/yield |
|---|---|---|---|
| 39 | 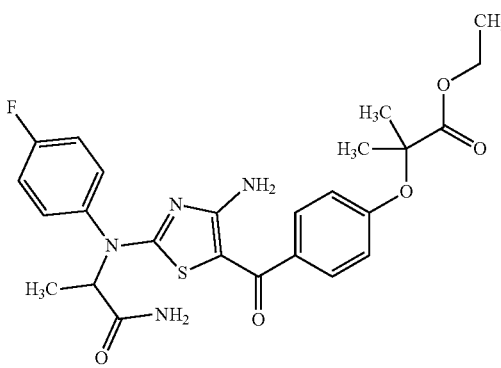<br><br>rac-ethyl 2-[4-[4-amino-2-(N-[2-amino-1-methyl-2-oxo-ethyl]-4-fluoro-anilino)thiazole-5-carbonyl]phenoxy]-2-methyl-propanoate | Intermediate 42; rac-2-bromo-propanamide | $^1$H-NMR (400 MHz, DMSO-d6): δ ppm = 1.07 (t, J = 7.10 Hz, 3 H), 1.15 (d, J = 7.35 Hz, 3 H), 1.53 (s, 6 H), 4.12 (q, J = 7.01 Hz, 2 H), 5.02-5.09 (m, 1 H), 6.72-6.76 (m, 2 H), 7.24 (s, 1 H), 7.33 (t, J = 8.87 Hz, 2 H), 7.44 (d, J = 8.87 Hz, 2 H), 7.58 (s, 1 H), 7.63 (dd, J = 9.00, 5.20 Hz, 2 H), 7.88 (brs, 2 H). LC-MS (method 1) Rt = 1.21 min; MS (ESIpos): m/z = 515.4 [M + H]$^+$ RP-HPLC (method D, basic) 50% yield |
| 40 | 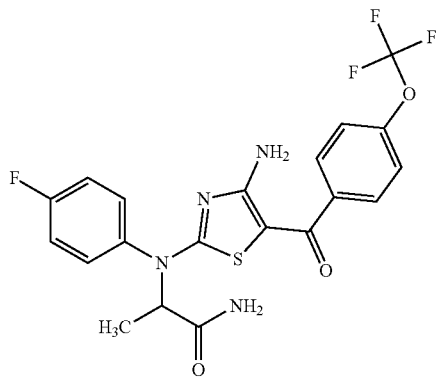 [SMILES: CC(C(N)=O)N(c1ccc(F)cc1)c1nc(N)c(C(=O)c2ccc(OC(F)(F)F)cc2)s1]<br><br>rac-2-(N-[4-amino-5-[4-(trifluoromethoxy)benzoyl]thiazol-2-yl]-4-fluoro-anilino)propanamide | Intermediate 43; rac-2-bromo-propanamide | $^1$H-NMR (400 MHz, DMSO-d6): δ ppm = 1.16 (d, J = 7.35 Hz, 3 H), 5.06 (br d, J = 6.84 Hz, 1 H), 7.26 (s, 1 H), 7.33 (t, J = 8.74 Hz, 2 H), 7.38 (d, J = 7.86 Hz, 2 H), 7.58 (s, 1 H), 7.60-7.67 (m, 4 H), 7.95-8.56 (m, 2 H). LC-MS (method 1) Rt = 1.25 min; MS (ESIpos): m/z = 469.5 [M + H]$^+$ RP-HPLC (method D, basic) 83% yield |
| 40.1 and 40.2 | (R)-2-(N-[4-amino-5-[4-(trifluoromethoxy)benzoyl]thiazol-2-yl]-4-fluoro-anilino)propanamide and (S)-2-(N-[4-amino-5-[4-(trifluoromethoxy)benzoyl]thiazol-2-yl]-4-fluoro-anilino)propanamide | | |

TABLE 6-continued

Examples 2-80

| Example number | Chemical structure Compound name | Starting materials | Analytics/purification/yield |
|---|---|---|---|
| 40.1 | 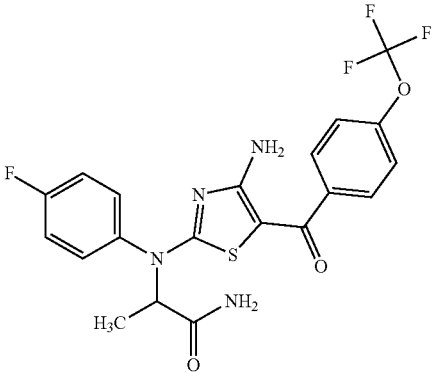 [SMILES: CC(C(N)=O)N(c1ccc(F)cc1)c1nc(N)c(C(=O)c2ccc(OC(F)(F)F)cc2)s1]<br>2-(N-[4-amino-5-[4-(trifluoromethoxy)benzoyl]thiazol-2-yl]-4-fluoro-anilino)propanamide (enantiomer 1) | Example 40 | $^1$H-NMR (400 MHz, DMSO-d6): δ ppm = 1.16 (d, J = 7.35 Hz, 3 H), 5.02-5.11 (m, 1 H), 7.26 (s, 1 H), 7.33 (t, J = 8.74 Hz, 2 H), 7.38 (d, J = 8.11 Hz, 2 H), 7.58 (s, 1 H), 7.60-7.67 (m, 4 H), 7.95-8.46 (m, 2 H).<br>LC-MS (method 2) Rt = 1.24 min; MS (ESIpos): m/z = 469.4 [M + H]+<br>20% yield |

Chiral HPLC Example 40.1

HPLC separation of rac-2-(N-[4-amino-5-[4-(trifluoromethoxy)benzoyl]thiazol-2-yl]-4-fluoro-anilino)propanamide (69 mg, 0.15 mmol; Example 40) on a chiral column gave 20 mg (20% yield) of 2-(N-[4-amino-5-[4-(trifluoromethoxy)benzoyl]thiazol-2-yl]-4-fluoro-anilino)propanamide, enantiomer 1.

Preparative chiral HPLC

Instrument: Sepiatec: Prep SFC100; Column: Chiralpak IC 5μ 250 × 30mm; eluent A: CO$_2$; eluent B: ethanol + 0.2 vol % aqueous ammonia (32%); isocratic: 15% B; flow: 100 mL/min; temperature: 40° C.; BPR: 150 bar; UV: 254 nm Analytical chiral HPLC: Rt = 2.73 min Instrument: Agilent: 1260, Aurora SFC-Modul; Column: Chiralpak IC 5μ 100 × 4.6 mm; eluent A: CO$_2$; eluent B: ethanol + 0.2 vol % aqueous ammonia (32%); isocratic: 15% B; flow: 4 mL/min; temperature: 37.5° C.; BPR: 100 bar; UV: 254 nm

| Example number | Chemical structure Compound name | Starting materials | Analytics/purification/yield |
|---|---|---|---|
| 40.2 | 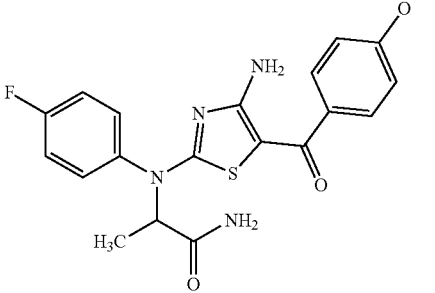<br>2-(N-[4-amino-5-[4-(trifluoromethoxy)benzoyl]thiazol-2-yl]-4-fluoro-anilino)propanamide (enantiomer 2) | Example 40 | $^1$H-NMR (400 MHz, DMSO-d6): δ ppm = 1.16 (d, J = 7.35 Hz, 3 H), 5.02-5.11 (m, 1 H), 7.26 (s, 1 H), 7.33 (t, J = 8.87 Hz, 2 H), 7.38 (d, J = 8.11 Hz, 2 H), 7.58 (s, 1 H), 7.60-7.67 (m, 4 H), 7.95-8.48 (m, 2 H).<br>LC-MS (method 2) Rt = 1.25 min; MS (ESIpos): m/z = 469.3 [M + H]+<br>21% yield |

Chiral HPLC Example 40.2

HPLC separation of rac-2-(N-[4-amino-5-[4-(trifluoromethoxy)benzoyl]thiazol-2-yl]-4-fluoro-anilino)propanamide (69 mg, 0.15 mmol; Example 40) on a chiral column gave 20 mg (21% yield) of 2-(N-[4-amino-5-[4-(trifluoromethoxy)benzoyl]thiazol-2-yl]-4-fluoro-anilino)propanamide, enantiomer 2.

Preparative chiral HPLC

Instrument: Sepiatec: Prep SFC100; Column: Chiralpak IC 5μ 250 × 30mm; eluent A: CO$_2$; eluent B: 1thanol + 0.2 vol % aqueous ammonia (32%); isocratic: 15% B; flow: 100 mL/min; temperature: 40° C.; BPR: 150 bar; UV: 254 nm Analytical chiral HPLC: Rt = 3.48 min Instrument: Agilent: 1260, Aurora SFC-Modul; Column: Chiralpak IC 5μ 100 × 4.6mm; eluent A: CO$_2$; eluent B: ethanol + 0.2 vol % aqueous ammonia (32%); isocratic: 15% B; flow: 4 mL/min; temperature: 37.5° C.; BPR: 100 bar; UV: 254 nm TABLE 6-continued Examples 2-80

| Example number | Chemical structure Compound name | Starting materials | Analytics/purification/yield |
| --- | --- | --- | --- |
| 41 | rac-2-(N-[4-amino-5-(4-chlorobenzoyl)thiazol-2-yl]-4-chloro-anilino)propanamide | Intermediate 44; rac-2-bromo-propanamide | $^1$H-NMR (400 MHz, DMSO-d6): δ ppm = 1.16 (d, J = 7.35 Hz, 3 H), 5.06 (q, J = 7.27 Hz, 1 H), 7.23-7.28 (m, 1 H), 7.44-7.53 (m, 4 H), 7.55-7.63 (m, 5 H), 7.96-8.44 (m, 2 H). LC-MS (method 2) Rt = 1.27 min; MS (ESIpos): m/z = 435.2 [M + H]$^+$ 47% yield |
| 41.1 and 41.2 | (R)-2-(N-(4-amino-5-(4-chlorobenzoyl)thiazol-2-yl]-4-chloro-anilino)propanamide and (S)-2-(N-[4-amino-5-(4-chlorobenzoyl)thiazol-2-yl]-4-chloro-anilino)propanamide | | |
| 41.1 | 2-(N-[4-amino-5-(4-chlorobenzoyl)thiazol-2-yl]-4-chloro-anilino)propanamide (enantiomer 1) | Example 41 | $^1$H-NMR (400 MHz, DMSO-d6): δ ppm = 1.14-1.19 (m, 3 H), 5.06 (q, J =7.10 Hz, 1 H), 7.27 (s, 1 H), 7.44-7.53 (m, 4 H), 7.55-7.64 (m, 5 H), 7.99-8.41 (m, 2 H). LC-MS (method 1) Rt = 1.27 min; MS (ESIpos): m/z = 435.2 [M + H]$^+$ $[α]_D^{20}$ = +83.8° (c = 1.00, dimethylsulfoxide) 25% yield |

Chiral HPLC Example 41.1

HPLC separation of rac-2-(N-[4-amino-5-(4-chlorobenzoyl)thiazol-2-yl]-4-chloro-anilino)propanamide (144 mg, 0.33 mmol; Example 41) on a chiral column gave 36 mg (25% yield) of 2-(N-[4-amino-5-(4-chlorobenzoyl)thiazol-2-yl]-4-chloro-anilino)propanamide, enantiomer 1.

Preparative chiral HPLC

Instrument: PrepCon Labomatic HPLC; Column: YMC Cellulose SB 10μ, 250 × 50; eluent A: hexane; eluent B: ethanol; isocratic: 60% A + 40% B; flow: 150 mL/min; temperature: 25° C.; UV: 254 nm Analytical chiral HPLC: Rt = 1.84 min Instrument: Waters Alliance 2695; Column: YMC Cellulose SB 3μ, 100 × 4.6; eluent A: hexane + 0.1 vol % diethylamine; eluent B: ethanol; isocratic: 60% A + 40% B; flow: 1.4 mL/min; temperature: 25° C.; UV: 254 nm

TABLE 6-continued

Examples 2-80

| Example number | Chemical structure Compound name | Starting materials | Analytics/purification/yield |
|---|---|---|---|
| 41.2 | 2-(N-[4-amino-5-(4-chlorobenzoyl)thiazol-2-yl]-4-chloro-anilino)propanamide (enantiomer 2) | Example 41 | $^1$H-NMR (400 MHz, DMSO-d6): δ ppm = 1.16 (d, J = 7.35 Hz, 3 H), 5.06 (q, J = 7.10 Hz, 1 H), 7.26-7.29 (m, 1 H), 7.44-7.52 (m, 4 H), 7.55-7.63 (m, 5 H), 7.94-8.68 (m, 2 H). LC-MS (method 1) Rt = 1.27 min; MS (ESIpos): m/z = 435.2 [M + H]$^+$ $[α]_D^{20}$ = −78.4° (c = 1.00, dimethylsulfoxide) 18% yield |

Chiral HPLC Example 41.2

HPLC separation of rac-2-(N-[4-amino-5-(4-chlorobenzoyl)thiazol-2-yl]-4-chloro-anilino)propanamide (144 mg, 0.33 mmol; Example 41) on a chiral column gave 26 mg (18% yield) of 2-(N-[4-amino-5-(4-chlorobenzoyl)thiazol-2-yl]-4-chloro-anilino)propanamide, enantiomer 2.

Preparative chiral HPLC

Instrument: PrepCon Labomatic HPLC; Column: YMC Cellulose SB 10μ, 250 × 50; eluent A: hexane; eluent B: ethanol; isocratic: 60% A + 40% B; flow: 150 mL/min; temperature: 25° C.; UV: 254 nm Analytical chiral HPLC: Rt = 2.34 min Instrument: Waters Alliance 2695; Column: YMC Cellulose SB 3μ, 100 × 4.6; eluent A: hexane + 0.1 vol % diethylamine; eluent B: ethanol; isocratic: 60% A + 40% B; flow: 1.4 mL/min; temperature: 25° C.; UV: 254 nm

| 42 | rac-2-(N-[4-amino-5-[4-(trifluoromethyl)benzoyl]thiazol-2-yl]-4-fluoro-anilino)propanamide | Intermediate 45; rac-2-bromo-propanamide | $^1$H-NMR (400 MHz, DMSO-d6): δ ppm = 1.16 (d, J = 7.35 Hz, 3 H), 5.00-5.13 (m, 1 H), 7.26 (s, 1 H), 7.33 (t, J = 8.87 Hz, 2 H), 7.59 (s, 1 H), 7.64 (dd, J = 8.87, 5.07 Hz, 2 H), 7.72 (dd, J = 37.13, 8.24 Hz, 4 H), 7.98-8.51 (m, 2 H). LC-MS (method 1) Rt = 1.22 min; MS (ESIpos): m/z = 453.4 [M + H]$^+$ RP-HPLC (method D, basic) 71% yield |

TABLE 6-continued

Examples 2-80

| Example number | Chemical structure Compound name | Starting materials | Analytics/purification/yield |
|---|---|---|---|
| 43 | rac-2-[N-[4-amino-5-[4-(difluoromethoxy)benzoyl]thiazol-2-yl-4-(trifluoromethyl)anilino]propanamide | Intermediate 46; rac-2-bromo-propanamide | $^1$H-NMR (400 MHz, DMSO-d6): δ ppm = 1.18 (d, J = 7.35 Hz, 3 H), 5.07 (q, J = 7.27 Hz, 1 H), 7.28 (t, J = 72.24 Hz, 1 H), 7.18 (d, J = 9.38 Hz, 2 H), 7.30 (s, 1 H), 7.57 (d, J = 8.87 Hz, 2 H), 7.64 (s, 1 H), 7.86 (dd, J = 27.88, 8.36 Hz, 4 H), 8.18 (br s, 2 H). LC-MS (method 1) Rt = 1.22 min; MS (ESIpos): m/z = 501.4 [M + H]$^+$ RP-HPLC (method D, basic) 54% yield |
| 43.1 and 43.2 | (R)-2-[N-[4-amino-5-[4-(difluoromethoxy)benzoyl]thiazol-2-yl]-4-(trifluoromethyl)anilino]propanamide and (S)-2-[N-[4-amino-5-[4-(difluoromethoxy)benzoyl]thiazol-2-yl-4-(trifluoromethyl)anilino]propanamide | | |
| 43.1 | 2-[N-[4-amino-5-[4-(difluoromethoxy)benzoyl]thiazol-2-yl)-4-(trifluoromethyl)anilino]propanamide (enantiomer 1) | Example 43 | $^1$H-NMR (400 MHz, DMSO-d6): δ ppm = 1.18 (d, J = 7.35 Hz, 3 H), 5.07 (q, J = 7.35 Hz, 1 H), 7.28 (t, J = 74.01 Hz, 1 H), 7.18 (d, J = 8.62 Hz, 2 H), 7.31 (s, 1 H), 7.57 (d, J = 8.87 Hz, 2 H), 7.63 (s, 1 H), 7.86 (dd, J = 27.88, 8.62 Hz, 4 H), 7.99-8.36 (m, 2 H). LC-MS (method 1) Rt = 1.22 min; MS (ESIpos): m/z = 501.4 [M + H]$^+$ 34% yield |

Chiral HPLC Example 43.1
HPLC separation of rac-2-[N-[4-amino-5-[4-(difluoromethoxy)benzoyl]thiazol-2-yl]-4-(trifluoromethyl)anilino]propanamide (280 mg, 0.56 mmol; Example 43) on a chiral column gave 99 mg (35% yield) of 2-[N-[4-amino-5-[4-(difluoromethoxy)benzoyl]thiazol-2-yl]-4-(trifluoromethyl)anilino]propanamide, enantiomer 1.
Preparative chiral HPLC
Instrument: PrepCon Labomatic HPLC; Column: YMC Cellulose SB 5μ, 250 × 30;
eluent A: hexane + 0.1 vol % diethylamine; eluent B: ethanol + 0.1 vol % diethylamine;
isocratic: 80% A + 20% B; flow: 50 mL/min; temperature: 25° C.; UV: 254 nm
Analytical chiral HPLC: Rt = 4.50 min
Instrument: Waters Alliance 2695; Column: YMC Cellulose SB 3μ, 100 × 4.6;
eluent A: hexane + 0.1 vol % diethylamine; eluent B: ethanol; isocratic: 80% A + 20% B; flow: 1.4 mL/min; temperature: 25° C.; UV: 254 nm

TABLE 6-continued

Examples 2-80

| Example number | Chemical structure Compound name | Starting materials | Analytics/purification/yield |
|---|---|---|---|
| 43.2 | 2-[N-[4-amino-5-[4-(difluoromethoxy)benzoyl]thiazol-2-yl-4-(trifluoromethyl)anilino]propanamide (enantiomer 2) | Example 43 | $^1$H-NMR (400 MHz, DMSO-d6): δ ppm = 1.18 (d, J = 7.35 Hz, 3 H), 5.07 (q, J = 7.35 Hz, 1 H), 7.28 (t, J = 73.76 Hz, 1 H), 7.18 (d, J = 8.62 Hz, 2 H), 7.31 (s, 1 H), 7.57 (d, J = 8.87 Hz, 2 H), 7.63 (s, 1 H), 7.86 (dd, J = 27.88, 8.62 Hz, 4 H), 8.18 (br s, 2 H). LC-MS (method 1) Rt = 1.22 min; MS (ESIpos): m/z = 501.3 [M + H]$^+$ 27% yield |

Chiral HPLC Example 43.2
HPLC separation of rac-2-[N-[4-amino-5-[4-(difluoromethoxy)benzoyl]thiazol-2-yl]-4-(trifluoromethyl)anilino]propanamide (280 mg, 0.56 mmol; Example 43) on a chiral column gave 79 mg (27% yield) of 2-[N-[4-amlno-5-[4-(difluoromethoxy)benzoyl]thiazol-2-yl]-4-(trifluoromethyl)anilino]propanamide, enantiomer 2.
Preparative chiral HPLC
Instrument: PrepCon Labomatic HPLC; Column: YMC Cellulose SB 5μ, 250 × 30;
eluent A: hexane + 0.1 vol % diethylamine; eluent B: ethanol + 0.1 vol % diethylamine;
isocratic: 80% A + 20% B; flow: 50 mL/min; temperature: 25° C.; UV: 254 nm
Analytical chiral HPLC: Rt = 5.44 min
Instrument: Waters Alliance 2695; Column: YMC Cellulose SB 3μ, 100 × 4.6;
eluent A: hexane + 0.1 vol % diethylamine; eluent B: ethanol; isocratic: 80% A + 20% B; flow: 1.4
mL/min; temperature: 25° C.; UV: 254 nm

| | | | |
|---|---|---|---|
| 44 | rac-2-(N-[4-amino-5-[4-(difluoromethoxy)benzoyl]thiazol-2-yl]-4-fluoro-anilino)propanamide | Intermediate 47; rac-2-bromo-propanamide | $^1$H-NMR (400 MHz, DMSO-d6): δ ppm = 1.16 (d, J = 7.35 Hz, 3 H), 5.06 (q, J = 7.10 Hz, 1 H), 7.28 (t, J = 73.76 Hz, 1 H), 7.17 (d, J = 8.62 Hz, 2 H), 7.25 (br s, 1 H), 7.33 (t, J = 8.87 Hz, 2 H), 7.55 (d, J = 8.87 Hz, 2 H), 7.58 (br s, 1 H), 7.64 (dd, J = 8.87, 5.07 Hz, 2 H), 8.21 (brs, 2 H). LC-MS (method 2) Rt = 1.13 min; MS (ESIpos): m/z = 451.6 [M + H]$^+$ RP-HPLC (method D, basic) 87% yield |
| 44.1 and 44.2 | (R)-2-(N-(4-amino-5-[4-(difluoromethoxy)benzoyl]thiazol-2-yl]-4-fluoro-anilino)propanamide and (S)-2-(N-[4-amino-5-[4-(difluoromethoxy)benzoyl]thiazol-2-yl]-4-fluoro-anilino)propanamide | | |

TABLE 6-continued

Examples 2-80

| Example number | Chemical structure Compound name | Starting materials | Analytics/purification/yield |
|---|---|---|---|
| 44.1 | 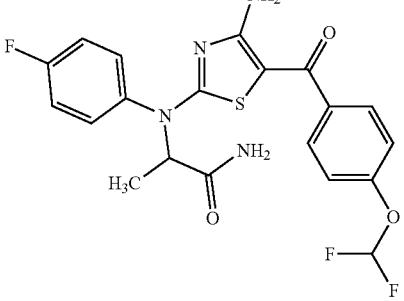<br>2-(N-[4-amino-5-[4-(difluoromethoxy)benzoyl]thiazol-2-yl]-4-fluoro-anilino)propanamide (enantiomer 1) | Example 44 | $^1$H-NMR (400 MHz, DMSO-d6): δ ppm = 1.16 (d, J = 7.35 Hz, 3 H), 5.02-5.10 (m, 1 H), 7.26 (t, J = 74.01 Hz, 1 H), 7.17 (d, J = 9.38 Hz, 2 H), 7.25 (s, 1 H), 7.33 (t, J = 8.74 Hz, 2 H), 7.55 (d, J = 8.87 Hz, 2 H), 7.58 (br s, 1 H), 7.64 (dd, J = 8.87, 5.07 Hz, 2 H), 7.86-8.45 (m, 2 H). LC-MS (method 2) Rt = 1.12 min; MS (ESIpos): m/z = 451.3 [M + H]$^+$ $[\alpha]_D^{20}$ = +77.2% (c = 1.00, dimethylsulfoxide) 38% yield |

Chiral HPLC Example 44.1

HPLC separation of rac-2-(N-[4-amino-5-[4-(difluoromethoxy)benzoyl]thiazol-2-yl]-4-fluoro-anilino)propanamide (2552 mg, 5.61 mmol; Example 44) on a chiral column gave 1096 mg (35% yield) of 2-(N-[4-amino-5-[4-(difluoromethoxy)benzoyl]thiazol-2-yl]-4-fluoro-anilino)propanamide, enantiomer 1.

Preparative chiral HPLC

Instrument: PrepCon Labomatic HPLC; Column: YMC Cellulose SB 10µ, 250 × 50; eluent A: hexane + 0.1 vol % diethylamine; eluent B: 2-propanol + 0.1 vol % diethylamine; isocratic: 60% A + 40% B; flow: 140 mL/min; temperature: 25° C.; UV: 254 nm Analytical chiral HPLC: Rt = 2.81 min Instrument: Waters Alliance 2695; Column: YMC Cellulose SB 3µ, 100 × 4.6; eluent A: hexane + 0.1 vol % diethylamine; eluent B: 2-propanol; isocratic: 80% A + 20% B; flow: 1.4 mL/min; temperature: 25° C.; UV: 254 nm

| 44.2 | 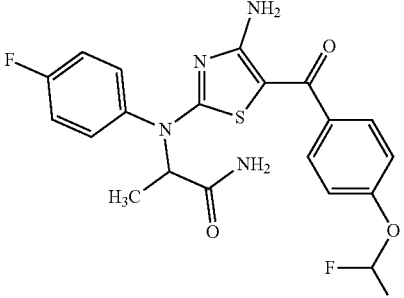<br>2-(N-[4-amino-5-[4-(difluoromethoxy)benzoyl]thiazol-2-yl]-4-fluoro-anilino)propanamide (enantiomer 2) | Example 44 | $^1$H-NMR (400 MHz, DMSO-d6): δ ppm = 1.16 (d, J = 7.35 Hz, 3 H), 5.01-5.12 (m, 1 H), 7.28 (t, J = 73.76 Hz, 1 H), 7.17 (d, J = 8.62 Hz, 2 H), 7.25 (s, 1 H), 7.33 (t, J = 8.87 Hz, 2 H), 7.55 (d, J = 8.87 Hz, 2 H), 7.58 (br s, 1 H), 7.64 (dd, J = 8.87, 5.07 Hz, 2 H), 8.15 (br s, 2 H). LC-MS (method 2) Rt = 1.12 min; MS (ESIpos): m/z = 451.4 [M + H]$^+$ $[\alpha]_D^{20}$ = −79.7° (c = 1.00, dimethylsulfoxide) 38% yield |

Chiral HPLC Example 44.2

HPLC separation of rac-2-(N-[4-amino-5-[4-(difluoromethoxy)benzoyl]thiazol-2-yl]-4-fluoro-anilino)propanamide (2552 mg, 5.61 mmol; Example 44) on a chiral column gave 1139 mg (37% yield) of 2-(N-[4-amino-5-[4-(difluoromethoxy)benzoyl]thiazol-2-yl]-4-fluoro-anilino)propanamide, enantiomer 2.

Preparative chiral HPLC

Instrument: PrepCon Labomatic HPLC; Column: YMC Cellulose SB 10µ, 250 × 50; eluent A: hexane + 0.1 vol % diethylamine; eluent B: 2-propanol + 0.1 vol % diethylamine; isocratic: 60% A + 40% B; flow: 140 mL/min; temperature: 25° C.; UV: 254 nm Analytical chiral HPLC: Rt = 4.61 min Instrument: Waters Alliance 2695; Column: YMC Cellulose SB 3µ, 100 × 4.6; eluent A: hexane + 0.1 vol % diethylamine; eluent B: 2-propanol; isocratic: 80% A + 20% B; flow: 1.4 mL/min; temperature: 25° C.; UV: 254 nm

TABLE 6-continued

Examples 2-80

| Example number | Chemical structure Compound name | Starting materials | Analytics/purification/yield |
|---|---|---|---|
| 45 | 2-(N-[4-amino-5-[4-[2-amino-1-methyl-2-oxo-ethoxy]benzoyl]thiazol-2-yl]anilino)propanamide (mixture of stereoisomers) | Intermediate 48; rac-2-bromo-propanamide | $^1$H-NMR (400 MHz, DMSO-d6): δ ppm = 1.16 (d, J = 7.35 Hz, 3 H), 1.41 (d, J = 6.59 Hz, 3 H), 4.63 (q, J = 6.59 Hz, 1 H), 5.04-5.12 (m, 1 H), 6.86 (d, J = 8.87 Hz, 2 H), 7.24 (br d, J = 3.80 Hz, 2 H), 7.42-7.52 (m, 6 H), 7.53-7.58 (m, 3 H), 8.08 (br s, 2 H). LC-MS (method 2) Rt = 0.85 min; MS (ESIpos): m/z = 454.4 [M + H]$^+$ RP-HPLC (method C, basic) 70% yield |
| 45.1, 45.2, 45.3 and 45.4 | (2R)-(N-[4-amino-5-[4-[2-amino-(1R)-methyl-2-oxo-ethoxy]benzoyl]thiazol-2-yl]anilino)propanamide, (2R)-(N-[4-amino-5-[4-[2-amino-(1S)-methyl-2-oxo-ethoxy]benzoyl]thiazol-2-yl]anilino)propanamide, (2S)-(N-[4-amino-5-[4-[2-amino-(1R)-methyl-2-oxo-ethoxy]benzoyl]thiazol-2-yl]anilino)propanamide, and (2S)-(N-[4-amino-5-[4-[2-amino-(1S)-methyl-2-oxo-ethoxy]benzoyl]thiazol-2-yl]anilino)propanamide | | |
| 45.1 | 2-(N-[4-amino-5-[4-[2-amino-1-methyl-2-oxo-ethoxy]benzoyl]thiazol-2-yl]anilino)propanamide (stereoisomer 1) | Example 45 | $^1$H-NMR (400 MHz, DMSO-d6): δ ppm = 1.16 (d, J = 7.35 Hz, 3 H), 1.41 (d, J = 6.59 Hz, 3 H), 4.63 (q, J = 6.76 Hz, 1 H), 5.08 (q, J = 7.35 Hz, 1 H), 6.86 (d, J = 8.87 Hz, 2 H), 7.23 (br d, J = 3.30 Hz, 2 H), 7.43-7.52 (m, 6 H), 7.53-7.60 (m, 3 H), 7.75-8.37 (m, 2 H). LC-MS (method 1) Rt = 0.86 min; MS (ESIpos): m/z = 454.3 [M + H]$^+$ 4% yield |

TABLE 6-continued

Examples 2-80

| Example number | Chemical structure Compound name | Starting materials | Analytics/purification/yield |
|---|---|---|---|
| | Chiral HPLC Example 45.1 HPLC separation of 2-(N-[4-amino-5-[4-[2-amino-1-methyl-2-oxo-ethoxy]benzoyl]thiazol-2-yl]anilino)propanamide (mixture of stereoisomers; 449 mg, 0.99 mmol; Example 45) on a chiral column gave 29 mg (6% yield) of 2-(N-[4-amino-5-[4-[2-amino-1-methyl-2-oxo-ethoxy]benzoyl]thiazol-2-yl]anilino)propanamide, stereoisomer 1. Preparative chiral HPLC Instrument: PrepCon Labomatic HPLC; Column: YMC Amylose SA 10µ, 250 × 50; eluent A: methyl tert-butyl ether; eluent B: acetonitrile; isocratic: 80% A + 20% B; flow: 100 mL/min; temperature: 25° C.; UV: 254 nm Analytical chiral HPLC: Rt = 6.48 min Instrument: Waters Alliance 2695; Column: YMC Amylose SA 3µ, 100 × 4.6; eluent A: methyl tert-butyl ether; eluent B: acetonitrile; isocratic: 80% A + 20% B; flow: 1.4 ml/min; temperature: 25° C.; UV: 254 nm | | |
| 45.2 | <br>2-(N-[4-amino-5-[4-[2-amino-1-methyl-2-oxo-ethoxy]benzoyl]thiazol-2-yl]anilino)propanamide (stereoisomer 2) | Example 45 | $^1$H-NMR (400 MHz, DMSO-d6): δ ppm = 1.16 (d, J = 7.35 Hz, 3 H), 1.41 (d, J = 6.59 Hz, 3 H), 4.63 (q, J = 6.59 Hz, 1 H), 5.08 (q, J = 7.27 Hz, 1 H), 6.86 (d, J = 8.87 Hz, 2 H), 7.23 (br d, J = 4.82 Hz, 2 H), 7.42-7.52 (m, 6 H), 7.55 (br d, J = 1.27 Hz, 3 H), 8.14 (brs, 2 H). LC-MS (method 1) Rt = 0.85 min; MS (ESIpos): m/z = 454.3 [M + H]$^+$ 5% yield |
| | Chiral HPLC Example 45.2 HPLC separation of 2-(N-[4-amino-5-[4-[2-amino-1-methyl-2-oxo-ethoxy]benzoyl]thiazol-2-yl]anilino)propanamide (mixture of stereoisomers; 449 mg, 0.99 mmol; Example 45) on a chiral column gave 36 mg (7% yield) of 2-(N-[4-amino-5-[4-[2-amino-1-methyl-2-oxo-ethoxy]benzoyl]thiazol-2-yl]anilino)propanamide, stereoisomer 2. Preparative chiral HPLC Instrument: PrepCon Labomatic HPLC; Column: YMC Amylose SA 10µ, 250 × 50; eluent A: methyl tert-butyl ether; eluent B: acetonitrile; isocratic: 80% A + 20% B; flow: 100 mL/min; temperature: 25° C.; UV: 254 nm Analytical chiral HPLC: Rt = 6.48 min Instrument: Waters Alliance 2695; Column: YMC Amylose SA 3µ, 100 × 4.6; eluent A: methyl tert-butyl ether; eluent B: acetonitrile; isocratic: 80% A + 20% B; flow: 1.4 ml/min; temperature: 25° C.; UV: 254 nm | | |
| 45.3 | 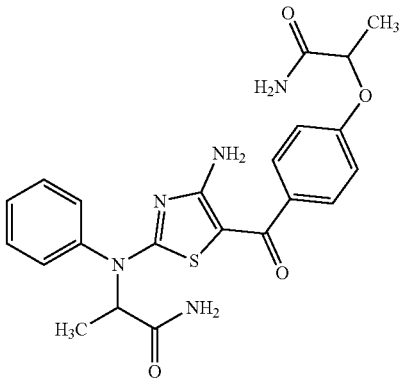<br>2-(N-[4-amino-5-[4-[2-amino-1-methyl-2-oxo-ethoxy]benzoyl]thiazol-2-yl]anilino)propanamide (stereoisomer 3) | Example 45 | $^1$H-NMR (400 MHz, DMSO-d6): δ ppm = 1.16 (d, J = 7.35 Hz, 3 H), 1.41 (d, J = 6.59 Hz, 3 H), 4.59-4.66 (m, 1 H), 5.08 (q, J = 7.77 Hz, 1 H), 6.86 (d, J = 8.87 Hz, 2 H), 7.23 (br d, J = 4.06 Hz, 2 H), 7.42-7.52 (m, 6 H), 7.53-7.59 (m, 3 H), 8.05 (br s, 2 H). LC-MS (method 1) Rt = 0.85 min; MS (ESIpos): m/z = 454.3 [M + H]$^+$ 5% yield |

TABLE 6-continued

Examples 2-80

| Example number | Chemical structure Compound name | Starting materials | Analytics/purification/yield |
|---|---|---|---|
| 45.4 | 2-(N-[4-amino-5-[4-[2-amino-1-methyl-2-oxo-ethoxy]benzoyl]thiazol-2-yl]anilino)propanamide (stereoisomer 4) | Example 45 | $^1$H-NMR (400 MHz, DMSO-d6): δ ppm = 1.16 (d, J = 7.35 Hz, 3 H), 1.41 (d, J = 6.59 Hz, 3 H), 4.63 (q, J = 6.59 Hz, 1 H), 5.08 (q, J = 6.93 Hz, 1 H), 6.86 (d, J = 8.87 Hz, 2 H), 7.23 (br d, J = 3.04 Hz, 2 H), 7.43-7.52 (m, 6 H), 7.53-7.58 (m, 3 H), 8.04 (br s, 2 H). LC-MS (method 2) Rt = 0.86 min; MS (ESIpos): m/z = 454.3 [M + H]$^+$ 5% yield |

Chiral HPLC Example 45.3
HPLC separation of 2-(N-[4-amino-5-[4-[2-amino-1-methyl-2-oxo-ethoxy]benzoyl]thiazol-2-yl]anilino)propanamide (mixture of stereoisomers; 449 mg, 0.99 mmol; Example 45) on a chiral column gave 36 mg (8% yield) of 2-(N-[4-amino-5-[4-[2-amino-1-methyl-2-oxo-ethoxy]benzoyl]thiazol-2-yl]anilino)propanamide, stereoisomer 3.
Preparative chiral HPLC
Instrument: PrepCon Labomatic HPLC; Column: YMC Amylose SA 10µ, 250 × 50; eluent A: methyl tert-butyl ether; eluent B: acetonitrile; isocratic: 80% A + 20% B; flow: 100 mL/min; temperature: 25° C.; UV: 254 nm
Analytical chiral HPLC: Rt = 6.48 min
Instrument: Waters Alliance 2695; Column: YMC Amylose SA 3µ, 100 × 4.6; eluent A: methyl tert-butyl ether; eluent B: acetonitrile; isocratic: 80% A + 20% B; flow: 1.4 ml/min; temperature: 25° C.; UV: 254 nm Chiral HPLC Example 45.4
HPLC-separation of 2-(N-[4-amino-5-[4-[2-amino-1-methyl-2-oxo-ethoxy]benzoyl]thiazol-2-yl]anilino)propanamide (mixture of stereoisomers; 449 mg, 0.99 mmol; Example 45) on a chiral column gave 36 mg (8% yield) of 2-(N-[4-amino-5-[4-[2-amino-1-methyl-2-oxo-ethoxy]benzoyl]thiazol-2-yl]anilino)propanamide, stereoisomer 4.
Preparative chiral HPLC
Instrument: PrepCon Labomatic HPLC; Column: YMC Amylose SA 10µ, 250 × 50; eluent A: methyl tert-butyl ether; eluent B: acetonitrile; isocratic: 80% A + 20% B; flow: 100 mL/min; temperature: 25° C.; UV: 254 nm
Analytical chiral HPLC: Rt = 6.48 min
Instrument: Waters Alliance 2695; Column: YMC Amylose SA 3µ, 100 × 4.6; eluent A: methyl tert-butyl ether; eluent B: acetonitrile; isocratic: 80% A + 20% B; flow: 1.4 ml/min; temperature: 25° C.; UV: 254 nm

| Example number | Chemical structure Compound name | Starting materials | Analytics/purification/yield |
|---|---|---|---|
| 46 | rac-2-(N-[4-amino-5-[4-(difluoromethoxy)benzoyl]thiazol-2-yl]-4-chloro-2-fluoro-anilino)propanamide | Intermediate 49; rac-2-bromo-propanamide | $^1$H-NMR (400 MHz, DMSO-d6): δ ppm = 1.17 (s, 3 H), 4.98-5.23 (m, 1 H), 7.30 (br t, J = 73.76 Hz, 1 H), 7.19 (br d, J = 8.36 Hz, 2 H), 7.32 (br s, 1 H), 7.48 (br d, J = 8.90 Hz, 1 H), 7.59 (br d, J = 7.35 Hz, 2 H), 7.65 (br s, 1 H), 7.71 (br d, J = 9.12 Hz, 1 H), 7.80-7.91 (m, 1 H), 8.18 (br s, 2 H). LC-MS (method 1) Rt = 1.21 min; MS (ESIpos): m/z = 485.3 [M + H]$^+$ RP-HPLC (method D, basic) 40% yield |

TABLE 6-continued

Examples 2-80

| Example number | Chemical structure Compound name | Starting materials | Analytics/purification/yield |
|---|---|---|---|
| 46.1 and 46.2 | (R)-2-(N-(4-amino-5-[4-(difluoromethoxy)benzoyl]thiazol-2-yl]-4-chloro-2-fluoro-anilino)propanamide and (S)-2-(N-[4-amino-5-[4-(difluoromethoxy)benzoyl]thiazol-2-yl]-4-chloro-2-fluoro-anilino)propanamide | | |
| 46.1 | 2-(N-[4-amino-5-[4-(difluoromethoxy)benzoyl]thiazol-2-yl]-4-chloro-2-fluoro-anilino)propanamide (enantiomer 1) | Example 46 | $^1$H-NMR (400 MHz, DMSO-d6) δ ppm = 1.13-1.22 (m, 3 H), 5.02-5.22 (m, 1 H), 7.19 (br d, J = 8.36 Hz, 2 H), 7.30 (t, 1 H), 7.32 (brs, 1 H), 7.47-7.50 (m, 1 H), 7.56-7.63 (m, 2 H), 7.63-7.67 (m, 1 H), 7.68-7.75 (m, 1 H), 7.81-7.94 (m, 1 H), 8.02-8.36 (m, 2 H). LC-MS (method 1) Rt = 1.21 min; MS (ESIpos): m/z = 485.3 [M + H]$^+$ 35% yield |

Chiral HPLC Example 46.1
HPLC separation of rac-2-(N-[4-amino-5-[4-(difluoromethoxy)benzoyl]thiazol-2-yl]-4-chloro-2-fluoro-anilno)propanamide (253 mg, 0.52 mmol; Example 46) on a chiral column gave 90 mg (35% yield) of 2-(N-[4-amino-5-[4-(difluoromethoxy)benzoyl]thiazol-2-yl]-4-chloro-2-fluoro-anilino)propanamide, enantiomer 1.
Preparative chiral HPLC
Instrument: PrepCon Labomatic HPLC; Column: YMC Cellulose SB 5μ 250 × 30;
eluent A: exane + 0.1 vol % diethylamine; eluent B: ethanol + 0.1 vol % diethylamine;
isocratic: 70% A + 30% B; flow: 40 mL/min; temperature: 25° C.; UV: 254 nm
Analytical chiral HPLC: Rt = 2.42 min
Instrument: Waters Alliance 2695; Column: YMC Cellulose SB 3μ, 100 × 4.6; eluent A: hexane + 0.1 vol % diethylamine; eluent B: ethanol; isocratic; 70% A + 30% B; flow: 1.4 mL/min; temperature: 25° C.; UV: 254 nm

| 46.2 | 2-(N-[4-amino-5-[4-(difluoromethoxy)benzoyl]thiazol-2-yl]-4-chloro-2-fluoro-anilino)propanamide (enantiomer 2) | Example 46 | $^1$H-NMR (400 MHz, DMSO-d6): δ ppm = 1.12-1.22 (m, 3 H), 4.97-5.23 (m, 1 H), 7.19 (br d, J = 8.36 Hz, 2 H), 7.30 (s, 1 H), 7.32 (brs, 1 H), 7.47-7.51 (m, 1 H), 7.59 (br d, J = 7.60 Hz, 2 H), 7.65 (brs, 1 H), 7.69-7.76 (m, 1 H), 7.82-7.92 (m, 1 H), 7.99-8.31 (m, 2 H). LC-MS (method 1) Rt = 1.21 min; MS (ESIpos): m/z = 485.2 [M + H]$^+$ 52% yield |

Chiral HPLC Example 46.2
HPLC separation of rac-2-(N-[4-amino-5-[4-(difluoromethoxy)benzoyl]thiazol-2-yl]-4-chloro-2-fluoro-anilno)propanamide (253 mg, 0.52 mmol; Example 46) on a chiral column gave 135 mg (52% yield) of 2-(N-[4-amino-5-[4-(difluoromethoxy)benzoyl]thiazol-2-yl]-4-chloro-2-fluoro-anilino)prepanamide, enantiomer 2.
Preparative chiral HPLC
Instrument PrepCon Labomatic HPLC; Column: YMC Cellulose SB 5μ, 250 × 30;
eluent A: exane + 0.1 vol % diethylamine; eluent B: ethanol + 0.1 vol % diethylamine;
isocratic: 70% A + 30% B; flow: 40 mL/min; temperature: 25° C.; UV: 254 nm

TABLE 6-continued

Examples 2-80

| Example number | Chemical structure Compound name | Starting materials | Analytics/purification/yield |
|---|---|---|---|
| | Analytical chiral HPLC: Rt = 3.13 min Instrument: Waters Alliance 2695; Column: YMC Cellulose SB 3μ, 100 × 4.6; eluent A: hexane + 0.1 vol % diethylamine; eluent B: ethanol; isocratic: 70% A + 30% B; flow: 1.4 mL/min; temperature: 25° C.; UV: 254 nm | | |
| 47 | 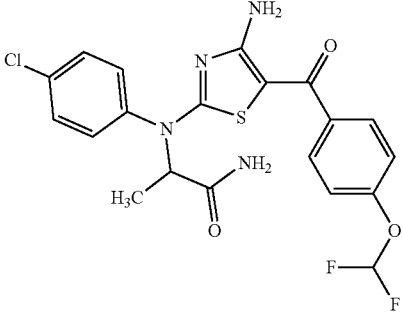 rac-2-(N-[4-amino-5-[4-(difluoromethoxy)benzoyl]thiazol-2-yl]-4-chloro-anilino)propanamide | Intermediate 50; rac-2-bromo-propanamide | $^1$H-NMR (400 MHz, DMSO-d6): δ ppm = 1.16 (d, J = 7.35 Hz, 3 H), 5.06 (br q, J = 7.27 Hz, 1 H), 7.28 (t, J = 73.51 Hz, 1 H), 7.17 (d, J = 8.62 Hz, 2 H), 7.26 (s, 1 H), 7.54-7.64 (m, 7 H), 8.14 (br s, 2 H). LC-MS (method 2) Rt = 1.19 min; MS (ESIpos): m/z = 467.3 [M + H]$^+$ 40% yield |
| 47.1 and 47.2 | (R)-2-(N-[4-amino-5-[4-(difluoromethoxy)benzoyl]thiazol-2-yl]-4-chloro-anilino)propanamide and (S)-2-(N-[4-amino-5-[4-(difluoromethoxy)benzoyl]thiazol-2-yl]-4-chloro-anilino)propanamide | | |
| 47.1 | 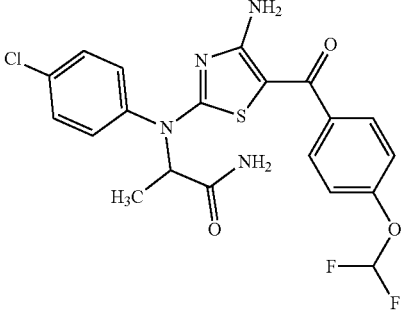 2-(N-[4-amino-5-[4-(difluoromethoxy)benzoyl]thiazol-2-yl]-4-chloro-anilino)propanamide (enantiomer 1) | Example 47 | $^1$H-NMR (400 MHz, DMSO-d6): δ ppm = 1.17 (d, J = 7.35 Hz, 3 H), 5.06 (q, J = 7.18 Hz, 1 H), 7.28 (t, J = 73.76 Hz, 1 H), 7.18 (d, J = 8.62 Hz, 2 H), 7.27 (s, 1 H), 7.54-7.64 (m, 7 H), 8.14 (br s, 2 H). LC-MS (method 2) Rt = 1.19 min; MS (ESIpos): m/z = 467.2 [M + H]+ $[\alpha]_D^{20}$ = +73.5° (c = 1.00, dimethylsulfoxide). RP-HPLC (method D, basic) 11% yield |

Chiral HPLC Example 47.1
HPLC separation of rac-2-(N-[4-amino-5-[4-(difluoromethoxy)benzoyl]thiazol-2-yl]-4-chloro-anilino)propanamide (524 mg, 1.12 mmol; Example 47) on a chiral column gave 147 mg (29% yield) of 2-(N-[4-amino-5-[4-(difluoromethoxy)benzoyl]thiazol-2-yl]-4-chloro-anilino)propanamide, enantiomer 1.
Preparative chiral HPLC
Instrument: PrepCon Labomatic HPLC; Column: YMC Cellulose SB 5μ, 250 × 30; eluent A: hexane + 0.1 vol % diethylamine; eluent B: 2-propanol; isocratic: 60% A + 40% B; flow: 40 mL/min; temperature: 25° C.; UV: 254 nm
Analytical chiral HPLC: Rt = 2.99 min
Instrument: Waters Alliance 2695; Column: YMC Cellulose SB 3μ, 100 × 4.6; eluent A: hexane + 0.1 vol % diethylamine; eluent B: 2-propanol; isocratic: 60% A + 40% B; flow: 1.4 mL/min; temperature: 25° C.; UV: 254 nm

TABLE 6-continued

Examples 2-80

| Example number | Chemical structure Compound name | Starting materials | Analytics/purification/yield |
|---|---|---|---|
| 47.2 | 2-(N-[4-amino-5-[4-(difluoromethoxy)benzoyl]thiazol-2-yl]-4-chloro-anilino)propanamide (enantiomer 2) | Example 47 | $^1$H-NMR (400 MHz, DMSO-d6): δ ppm = 1.17 (d, J = 7.35 Hz, 3 H), 5.06 (q, J = 7.18 Hz, 1 H), 7.28 (t, J = 73.76 Hz, 1 H), 7.18 (d, J = 8.62 Hz, 2 H), 7.27 (s, 1 H), 7.54-7.64 (m, 7 H), 8.14 (br s, 2 H).<br>LC-MS (method 2) Rt = 1.19 min; MS (ESIpos): m/z = 467.2 [M + H]+<br>$[\alpha]_D^{20}$ = −67.1° (c = 1.00, dimethylsulfoxide).<br>RP-HPLC (method D, basic) 13% yield |

Chiral HPLC Example 47.2

HPLC separation of rac-2-(N-[4-amino-5-[4-(difluoromethoxy)benzoyl]thiazol-2-yl]-4-chloro-anilino)propanamide (524 mg, 1.12 mmol; Example 47) on a chiral column gave 178 mg (34% yield) of 2-(N-[4-amino-5-[4-(difluoromethoxy)benzoyl]thiazol-2-yl]-4-chloro-anilino)propanamide, enantiomer 2.

Preparative chiral HPLC

Instrument: PrepCon Labomatic HPLC; Column: YMC Cellulose SB 5μ, 250 × 30; eluent A: hexane + 0.1 vol % diethylamine; eluent B: 2-propanol; isocratic: 60% A + 40% B; flow: 40 mL/min; temperature: 25° C.; UV: 254 nm Analytical chiral HPLC: Rt = 4.37 min Instrument: Waters Alliance 2695; Column: YMC Cellulose SB 3μ, 100 × 4.6; eluent A: hexane + 0.1 vol % diethylamine; eluent B: 2-propanol; isocratic: 60% A + 40% B; flow: 1.4 mL/min; temperature: 25° C.; UV: 254 nm

| Example number | Chemical structure Compound name | Starting materials | Analytics/purification/yield |
|---|---|---|---|
| 48 | rac-2-(N-[4-amino-5-[4-(difluoromethoxy)benzoyl]thiazol-2-yl]-4-chloro-3-fluoro-anilino)propanamide | Intermediate 51; rac-2-bromo-propanamide | $^1$H-NMR (400 MHz, DMSO-d6): δ ppm = 1.19 (d, J = 7.35 Hz, 3 H), 5.00-5.07 (m, 1 H), 7.29 (t, J = 73.76 Hz, 1 H), 7.19 (d, J = 8.62 Hz, 2 H), 7.30 (s, 1 H), 7.49-7.54 (m, 1 H), 7.58 (d, J = 8.87 Hz, 2 H), 7.63 (s, 1 H), 7.73-7.79 (m, 2 H), 8.19 (br s, 2 H).<br>LC-MS (method 1) Rt = 1.22 min; MS (ESIpos): m/z = 485.4 [M + H]+<br>RP-HPLC (method D, basic) 25% yield |
| 48.1 and 48.2 | (R)-2-(N-[4-amino-5-[4-(difluoromethoxy)benzoyl]thiazol-2-yl]-4-chloro-3-fluoro-anilino)propanamide and (S)-2-(N-[4-amino-5-[4-(difluoromethoxy)benzoyl]thiazol-2-yl]-4-chloro-3-fluoro-anilino)propanamide | | |

TABLE 6-continued

Examples 2-80

| Example number | Chemical structure Compound name | Starting materials | Analytics/purification/yield |
|---|---|---|---|
| 48.1 | 2-(N-[4-amino-5-[4-(difluoromethoxy)benzoyl]thiazol-2-yl]-4-chloro-3-fluoro-anilino)propanamide (enantiomer 1) | Example 48 | $^1$H-NMR (400 MHz, DMSO-d6): δ ppm = 1.19 (d, J = 7.60 Hz, 3 H), 5.03 (q, J = 7.44 Hz, 1 H), 7.29 (t, J = 73.76 Hz, 1 H), 7.19 (d, J = 8.62 Hz, 2 H), 7.30 (s, 1 H), 7.49-7.54 (m, 1 H), 7.58 (d, J = 8.87 Hz, 2 H), 7.63 (s, 1 H), 7.73-7.78 (m, 2 H), 8.17 (br s, 2 H). LC-MS (method 1) Rt = 1.22 min; MS (ESIpos): m/z = 485.2 [M + H]$^+$ 19% yield |

Chiral HPLC Example 48.1
HPLC separation of rac-2-(N-[4-amino-5-[4-(difluoromethoxy)benzoyl]thiazol-2-yl]-4-chloro-3-fluoro-anilno)propanamide (144 mg, 0.3 mmol; Example 48) on a chiral column gave 29 mg (20% yield) of 2-(N-[4-amino-5-[4-(difluoromethoxy)benzoyl]thiazol-2-yl]-4-chloro-3-fluoro-anilino)propanamide, enantiomer 1.
Preparative chiral HPLC
Instrument: PrepCon Labomatic HPLC; Column: YMC Amylose SA 5μ, 250 × 30; eluent A: methyl tert-butyl ether + 0.1 vol % diethylamine; eluent B: acetonitrile; isocratic: 85% A + 15% B; flow: 50 m L/min; temperature: 25° C.; UV: 254 nm
Analytical chiral HPLC: Rt = 1.54 min
Instrument: Waters Alliance 2695; Column: YMC Amylose SA 3μ, 100 × 4.6; eluent A: methyl tert-butyl ether + 0.1 vol % diethylamine; eluent B: acetonitrile; isocratic: 85% A + 15% B; flow: 1.4 mL/min; temperature: 25° C.; UV: 254 nm

| | | | |
|---|---|---|---|
| 48.2 | 2-(N-[4-amino-5-[4-(difluoromethoxy)benzoyl]thiazol-2-yl]-4-chloro-3-fluoro-anilino)propanamide (enantiomer 2) | Example 48 | $^1$H-NMR (400 MHz, DMSO-d6): δ ppm = 1.19 (d, J = 7.35 Hz, 3 H), 5.03 (q, J = 7.10 Hz, 1 H), 7.29 (t, J = 73.76 Hz, 1 H), 7.19 (d, J = 8.87 Hz, 2 H), 7.30 (s, 1 H), 7.51 (dt, J = 8.62, 1.27 Hz, 1 H), 7.58 (d, J = 8.62 Hz, 2 H), 7.63 (s, 1 H), 7.73-7.79 (m, 2 H), 8.18 (br s, 2 H). LC-MS (method 1) Rt = 1.22 min; MS (ESIpos): m/z = 485.3 [M + H]$^+$ 24% yield |

Chiral HPLC Example 48.2
HPLC separation of rac-2-(N-[4-amino-5-[4-(difluoromethoxy)benzoyl]thiazol-2-yl]-4-chloro-3-fluoro-anilno)propanamide (144 mg, 0.3 mmol; Example 48) on a chiral column gave 36 mg (24% yield) of 2-(N-[4-amino-5-[4-(difluoromethoxy)benzoyl]thiazol-2-yl]-4-chloro-3-fluoro-anilino)propanamide, enantiomer 2.
Preparative chiral HPLC
Instrument: PrepCon Labomatic HPLC; Column: YMC Amylose SA 5μ, 250 × 30; eluent A: methyl tert-butyl ether + 0.1 vol % diethylamine; eluent B: acetonitrile; isocratic: 85% A + 15% B; flow: 50 mL/min; temperature: 25° C.; UV: 254 nm
Analytical chiral HPLC: Rt = 2.09 min
Instrument: Waters Alliance 2695; Column: YMC Amylose SA 3μ, 100 × 4.6; eluent A: methyl tert-butyl ether + 0.1 vol % diethylamine; eluent B: acetonitrile; isocratic: 85% A + 15% B; flow: 1.4 mL/min; temperature: 25° C.; UV: 254 nm TABLE 6-continued Examples 2-80

| Example number | Chemical structure Compound name | Starting materials | Analytics/purification/yield |
|---|---|---|---|
| 49 | 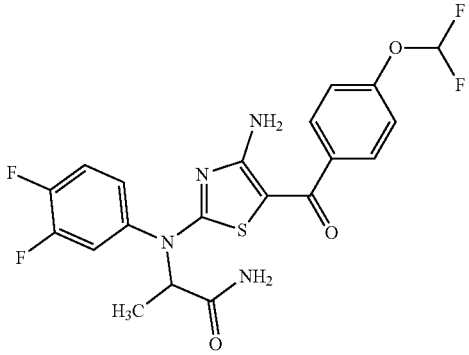 [SMILES: CC(C(N)=O)N(c1ccc(F)c(F)c1)c1nc(N)c(C(=O)c2ccc(OC(F)F)cc2)s1]<br>rac-2-(N-[4-amino-5-[4-(difluoromethoxy)benzoyl]thiazol-2-yl]-3,4-difluoro-anilino)propanamide | Intermediate 52; rac-2-bromo-propanamide | $^1$H-NMR (400 MHz, DMSO-d6): δ ppm = 1.18 (d, J = 7.35 Hz, 3 H), 5.03 (q, J = 6.76 Hz, 1 H), 7.28 (t, J = 73.76 Hz, 1 H), 7.18 (d, J = 8.62 Hz, 2 H), 7.30 (s, 1 H), 7.48-7.53 (m, 1 H), 7.58 (d, J = 8.62 Hz, 4 H), 7.78 (ddd, J = 11.34, 7.41, 2.53 Hz, 1 H), 8.13 (brs, 2 H).<br>LC-MS (method 1) Rt = 1.16 min; MS (ESIpos): m/z = 469.3 [M + H]$^+$<br>RP-HPLC (method D, basic) 65% yield |
| 49.1 and 49.2 | (R)-2-(N-[4-amino-5-(4-(difluoromethoxy)benzoyl]thiazol-2-yl]-3,4-difluoro-anilino)propanamide and (S)-2-(N-[4-amino-5-[4-(difluoromethoxy)benzoyl]thiazol-2-yl]-3,4-difluoro-anilino)propanamide | | |
| 49.1 | 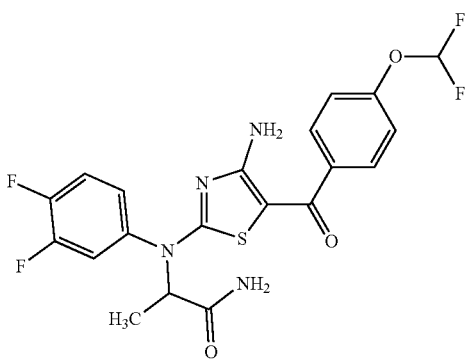 [SMILES: CC(C(N)=O)N(c1ccc(F)c(F)c1)c1nc(N)c(C(=O)c2ccc(OC(F)F)cc2)s1]<br>2-(N-[4-amino-5-[4-(difluoromethoxy)benzoyl]thiazol-2-yl]-3,4-difluoro-anilino)propanamide (enantiomer 1) | Example 49 | $^1$H-NMR (400 MHz, DMSO-d6): δ ppm = 1.18 (d, J = 7.35 Hz, 3 H), 5.03 (brq, J = 7.18 Hz, 1 H), 7.29 (t, J = 73.51 Hz, 3 H), 7.18 (d, J = 8.36 Hz, 1 H), 7.30 (s, 1 H), 7.48-7.53 (m, 1 H), 7.56-7.64 (m, 4 H), 7.78 (ddd, J = 11.34, 7.54, 2.41 Hz, 1 H), 8.17 (brs, 2 H).<br>LC-MS (method 1) Rt = 1.16 min; MS (ESIpos): m/z = 469.3 [M + H]$^+$<br>39% yield |

Chiral HPLC Example 49.1
HPLC separation of rac-2-(N-[4-amino-5-[4-(difluoromethoxy)benzoyl]thiazol-2-yl]-3,4-difluoro-anilino)propanamide (381 mg, 0.81 mmol; Example 49) on a chiral column gave 155 mg (39% yield) of 2-(N-[4-amino-5-[4-(difluoromethoxy)benzoyl]thiazol-2-yl]-3,4-difluoro-anilino)propanamide, enantiomer 1.
Preparative chiral HPLC
Instrument: PrepCon Labomatic HPLC; Column: YMC Cellulose SB 5μ, 250 × 30; eluent A: hexane + 0.1 vol % diethylamine; eluent B: ethanol + 0.1 vol % diethylamine; isocratic: 80% A + 20% B; flow: 50 mL/min; temperature: 25° C.; UV: 254 nm
Analytical chiral HPLC: Rt = 4.31 min
Instrument: Waters Alliance 2695; Column: YMC Cellulose SB 3μ, 100 × 4.6; eluent A: hexane + 0.1 vol % diethylamine; eluent B: ethanol; isocratic: 80% A + 20% B; flow: 1.4 mL/min; temperature: 25° C.; UV: 254 nm TABLE 6-continued Examples 2-80

| Example number | Chemical structure Compound name | Starting materials | Analytics/purification/yield |
|---|---|---|---|
| 49.2 | 2-(N-[4-amino-5-[4-(difluoromethoxy)benzoyl]thiazol-2-yl]-3,4-difluoro-anilino)propanamide (enantiomer 2) | Example 49 | ¹H-NMR (400 MHz, DMSO-d6): δ ppm = 1.18 (d, J = 7.35 Hz, 3 H), 5.03 (q, J = 7.35 Hz, 1 H), 7.28 (t, J = 74.01 Hz, 1 H), 7.18 (d, J = 8.62 Hz, 2 H), 7.30 (s, 1 H), 7.48-7.53 (m, 1 H), 7.55-7.65 (m, 4 H), 7.78 (ddd, J = 11.34, 7.54, 2.41 Hz, 1 H), 8.19 (brs, 2 H). LC-MS (method 1) Rt = 1.16 min; MS (ESIpos): m/z = 469.3 [M + H]⁺ 34% yield |

Chiral HPLC Example 49.2
HPLC separation of rac-2-(N-[4-amino-5-[4-(difluoromethoxy)benzoyl]thiazol-2-yl]-3,4-difluoro-anilino)propanamide (381 mg, 0.81 mmol; Example 49) on a chiral column gave 136 mg (34% yield) of 2-(N-[4-amino-5-[4-(difluoromethoxy)benzoyl]thiazol-2-yl]-3,4-difluoro-anilino)propanamide, enantiomer 2.
Preparative chiral HPLC
Instrument: PrepCon Labomatic HPLC; Column: YMC Cellulose SB 5μ, 250 × 30; eluent A: hexane + 0.1 vol % diethylamine; eluent B: ethanol + 0.1 vol % diethylamine; isocratic: 80% A + 20% B; flow: 50 mL/min; temperature: 25° C.; UV: 254 nm
Analytical chiral HPLC Rt = 5.54 min
Instrument: Waters Alliance 2695; Column: YMC Cellulose SB 3μ, 100 × 4.6; eluent A: hexane + 0.1 vol % diethylamine; eluent B: ethanol; isocratic: 80% A + 20% B; flow: 1.4 mL/min; temperature: 25° C.; UV: 254 nm

| 49.2 | | | Example 49.2 was determined to be (R)-2-(N-[4-amino-5-[4-(difluoromethoxy)benzoyl]thiazol-2-yl]-3,4-difluoro-anilino)propanamide, by means of X-ray crystal structure analysis. |
|---|---|---|---|
| 50 | rac-2-(N-[4-amino-5-(pyridine-4-carbonyl)thiazol-2-yl]-3,4-difluoro-anilino)propanamide | Intermediate 53; rac-2-bromo-propanamide | ¹H-NMR (400MHz, DMSO-d6): δ ppm = 1.18 (d, J = 7.60 Hz, 3 H), 5.03 (q, J = 7.35 Hz, 1 H), 7.30 (s, 1 H), 7.40-7.44 (m, 2 H), 7.47-7.53 (m, 1 H), 7.55-7.66 (m, 2 H), 7.77 (ddd, J = 11.34, 7.54, 2.41 Hz, 1 H), 8.13-8.49 (m, 2 H), 8.60-8.66 (m, 2 H). LC-MS (method 2) Rt = 0.90 min; MS (ESIpos): m/z = 404.3 [M + H]⁺ 97% yield |

TABLE 6-continued

Examples 2-80

| Example number | Chemical structure Compound name | Starting materials | Analytics/purification/yield |
|---|---|---|---|
| 50.1 and 50.2 | (R)-2-(N-[4-amino-5-(pyridine-4-carbonyl)thiazol-2-yl]-3,4-difluoro-anilino)propanamide and (S)-2-(N-[4-amino-5-(pyridine-4-carbonyl)thiazol-2-yl]-3,4-difluoro-anilino)propanamide | | |
| 50.1 | 2-(N-[4-amino-5-(pyridine-4-carbonyl)thiazol-2-yl]-3,4-difluoro-anilino)propanamide (enantiomer 1) | Example 50 | $^1$H-NMR (400 MHz, DMSO-d6): δ ppm = 1.18 (d, J = 7.35 Hz, 3 H), 5.03 (br q, J =7.27 Hz, 1 H), 7.30 (s, 1 H), 7.40-7.45 (m, 2 H), 7.47-7.53 (m, 1 H), 7.55-7.65 (m, 2 H), 7.78 (br ddd, J = 11.34, 7.54, 2.41 Hz, 1 H), 8.17-8.47 (m, 2 H), 8.60-8.66 (m, 2 H). LC-MS (method 2) Rt = 0.87 min; MS (ESIpos): m/z = 404.2 [M + H]$^+$ [α]$_D^{20}$ = −79.8° (c = 1.00, dimethylsulfoxide) 21% yield |

Chiral HPLC Example 50.1
HPLC separation of rac-2-(N-[4-amino-5-(pyridine-4-carbonyl)thiazol-2-yl]-3,4-difluoro-anilino)propanamide (974 mg, 2.35 mmol; Example 50) on a chiral column gave 205 mg (21% yield) of 2-(N-[4-amino-5-(pyridine-4-carbonyl)thiazol-2-yl]-3,4-difluoro-anilino)propanamide, enantiomer 1.
Preparative chiral HPLC
Instrument: PrepCon Labomatic HPLC; Column: YMC Cellulose SC 10μ, 250 × 50; eluent A: methyl tert-butyl ether; eluent B: acetonitrile; isocratic: 20%A + 80% B; flow: 140 mL/min; temperature: 25° C.; UV: 254 nm
Analytical chiral HPLC: Rt = 2.71 min
Instrument: Thermo Fisher UltiMate 3000; Column: YMC Cellulose SC 3μ, 100 × 4.6; eluent A: methyl tert-butyl ether + 0.1 vol % diethylamine; eluent B: acetonitrile; isocratic: 20% A + 80% B; flow: 1.4 mL/min; temperature: 25° C.; UV: 254 nm

| | | | |
|---|---|---|---|
| 50.2 | 2-(N-[4-amino-5-(pyridine-4-carbonyl)thiazol-2-yl]-3,4-difluoro-anilino)propanamide (enantiomer 2) | Example 50 | $^1$H-NMR (400 MHz, DMSO-d6): δ ppm = 1.18 (d, J =7.60 Hz, 3 H), 5.03 (q, J = 6.67 Hz, 1 H), 7.30 (s, 1 H), 7.40-7.44 (m, 2 H), 7.47-7.53 (m, 1 H), 7.55-7.65 (m, 2 H), 7.77 (ddd, J = 11.34, 7.54, 2.41 Hz, 1 H), 8.14-8.46 (m, 2 H), 8.60-8.66 (m, 2 H). LC-MS (method 2) Rt = 0.87 min; MS (ESIpos): m/z = 404.2 [M + H]$^+$ [α]$_D^{20}$ = +84.9° (c = 1.00, dimethylsulfoxide) 21% yield |

Chiral HPLC Example 50.2
HPLC separation of rac-2-(N-[4-amino-5-(pyridine-4-carbonyl)thiazol-2-yl]-3,4-difluoro-anilino)propanamide (974 mg, 2.35 mmol; Example 50) on a chiral column gave 204 mg (21% yield) of 2-(N-[4-amino-5-(pyridine-4-carbonyl)thiazol-2-yl]-3,4-difluoro-anilino)propanamide, enantiomer 2.
Preparative chiral HPLC
Instrument: PrepCon Labomatic HPLC; Column: YMC Cellulose SC 10μ, 250 × 50; eluent A: methyl tert-butyl ether; eluent B: acetonitrile; isocratic: 20% A + 80% B; flow: 140 mL/min; temperature: 25° C.; UV: 254 nm
Analytical chiral HPLC: Rt = 3.06 min
Instrument: Thermo Fisher UltiMate 3000; Column: YMC Cellulose SC 3μ, 100 × 4.6; eluent A: methyl tert-butyl ether + 0.1 vol % diethylamine; eluent B: acetonitrile; isocratic: 20% A + 80% B; flow: 1.4 mL/min; temperature: 25° C.; UV: 254 nm

TABLE 6-continued

Examples 2-80

| Example number | Chemical structure Compound name | Starting materials | Analytics/purification/yield |
|---|---|---|---|
| 51 | rac-2-(N-[4-amino-5-(4-methoxybenzoyl)thiazol-2-yl]-3,4-difluoro-anilino)propanamide | Intermediate 54; rac-2-bromo-propanamide | $^1$H-NMR (400 MHz, DMSO-d6): δ ppm = 1.18 (d, J = 7.60 Hz, 3 H), 3.76 (s, 3 H), 5.02 (q, J = 7.27 Hz, 1 H), 6.94 (d, J = 8.87 Hz, 2 H), 7.29 (s, 1 H), 7.50 (d, J = 8.62 Hz, 3 H), 7.56-7.65 (m, 2 H), 7.78 (ddd, J =11.41, 7.48, 2.41 Hz, 1 H), 7.89-8.45 (m, 2 H) LC-MS (method 2) Rt = 1.09 min; MS (ESIpos): m/z = 433.2 [M + H]$^+$ 85% yield |
| 51.1 and 51.2 | (R)-2-(N-[4-amino-5-(4-methoxybenzoyl)thiazol-2-yl]-3,4-difluoro-anilino)propanamide and (S)-2-(N-[4-amino-5-(4-methoxybenzoyl)thiazol-2-yl]-3,4-difluoro-anilino)propanamide | | |
| 51.1 | 2-(N-[4-amino-5-(4-methoxybenzoyl)thiazol-2-yl]-3,4-difluoro-anilino)propanamide (enantiomer 1) | Example 51 | $^1$H-NMR (400 MHz, DMSO-d6): δ ppm = 1.19 (d, J = 7.35 Hz, 3 H), 3.76 (s, 3 H), 5.03 (q, J = 7.18 Hz, 1 H), 6.94 (d, J = 8.87 Hz, 2 H), 7.29 (s, 1 H), 7.48-7.53 (m, 3 H), 7.55-7.64 (m, 2 H), 7.78 (ddd, J =11.47, 7.41, 2.41 Hz, 1 H), 7.87-8.36 (m, 2 H). LC-MS (method 1) Rt = 1.10 min; MS (ESIpos): m/z = 433.5 [M + H]$^+$ 33% yield |

Chiral HPLC Example 51.1
HPLC separation of rac-2-(N-[4-amino-5-(4-methoxybenzoyl)thiazol-2-yl]-3,4-difluoro-anilino)propanamide (88 mg, 0.20 mmol; Example 51) on a chiral column gave 19 mg (21% yield) of 2-(N-[4-amino-5-(4-methoxybenzoyl)thiazol-2-yl]-3,4-difluoro-anilino)propanamide, enantiomer 1.
Preparative chiral HPLC
Instrument: PrepCon Labomatic HPLC; Column: YMC Cellulose SC 10μ, 250 × 50; eluent A: methyl tert-butyl ether + 0.1 vol % diethylamine; eluent B: acetonitrile; isocratic: 50% A + 50% B; flow: 100 nL/min; temperature: 25° C.; UV: 254 nm
Analytical chiral HPLC: Rt =1.57 min
Instrument: Waters Alliance 2695; Column: YMC Cellulose SC 3μ, 100 × 4.6; eluent A: methyl tert-butyl ether + 0.1 vol % diethylamine; eluent B: acetonitrile; isocratic: 50% A + 50% B; flow: 1.4 mL/mi n; temperature: 25° C.; UV: 254 nm

| | | | |
|---|---|---|---|
| 51.2 | 2-(N-[4-amino-5-(4-methoxybenzoyl)thiazol-2-yl]-3,4-difluoro-anilino)propanamide (enantiomer 2) | Example 51 | $^1$H-NMR (400 MHz, DMSO-d6): δ ppm = 1.19 (d, J = 7.35 Hz, 3 H), 3.76 (s, 3 H), 5.03 (q, J =7.10 Hz, 1 H), 6.94 (d, J = 8.87 Hz, 2 H), 7.29 (s, 1 H), 7.48-7.53 (m, 3 H), 7.56-7.65 (m, 2 H), 7.75-7.82 (m, 1 H), 7.89-8.38 (m, 2 H). LC-MS (method 1) Rt = 1.10 min; MS (ESIpos): m/z = 433.5 [M + H]$^+$ 36% yield |

TABLE 6-continued

Examples 2-80

| Example number | Chemical structure Compound name | Starting materials | Analytics/purification/yield |
|---|---|---|---|
| | Chiral HPLC Example 51.2 HPLC separation of rac-2-(N-[4-amino-5-(4-methoxybenzoyl)thiazol-2-yl]-3,4-difluoro-anilino)propanamide (88 mg, 0.20 mmol; Example 51) on a chiral column gave 22 mg (24% yield) of 2 (N-[4-amino-5-(4-methoxybenzoyl)thiazol-2-yl]-3,4-difluoro-anilino)propanamide, enantiomer 2. Preparative chiral HPLC Instrument: PrepCon Labomatic HPLC; Column: YMC Cellulose SC 10μ, 250 × 50; eluent A: methyl tert-butyl ether + 0.1 vol % diethylamine; eluent B: acetonitrile; isocratic: 50% A + 50% B; flow: 100 nL/min; temperature: 25° C.; UV: 254 nm Analytical chiral HPLC: Rt = 1.84 min Instrument: Waters Alliance 2695; Column: YMC Cellulose SC 3μ, 100 × 4.6; eluent A: methyl tert-butyl ether + 0.1 vol % diethylamine; eluent B: acetonitrile; isocratic: 50% A + 50% B; flow: 1.4 mL/min; temperature: 25° C.; UV: 254 nm | | |
| 52 52.1 and 52.2 | [chemical structure] rac-2-(N-[4-amino-5-(6-methoxypyridine-3-carbonyl)thiazol-2-yl]-3,4-difluoro-anilino)propanamide (R)-2-(N-[4-amino-5-(6-methoxypyridine-3-carbonyl)thiazol-2-yl]-3,4-difluoro-anilino)propanamide and (S)-2-(N-[4-amino-5-(6-methoxypyridine-3-carbonyl)thiazol-2-yl]-3,4-difluoro-anilino)propanamide | Intermediate 55; rac-2-bromo-propanamide | $^1$H-NMR (400 MHz, DMSO-d6): δ ppm = 1.19 (d, J = 7.35 Hz, 3 H), 3.86 (s, 3 H), 5.03 (q, J = 7.69 Hz, 1 H), 6.84 (dd, J = 8.62, 0.76 Hz, 1 H), 7.30 (s, 1 H), 7.49-7.54 (m, 1 H), 7.56-7.65 (m, 2 H), 7.79 (ddd, J =11.41, 7.35, 2.53 Hz, 1 H), 7.84 (dd, J = 8.62, 2.28 Hz, 1 H), 8.16 (br s, 2 H), 8.36 (dd, J = 2.41, 0.63 Hz, 1 H). LC-MS (method 1) Rt = 1.07 min; MS (ESIpos): m/z = 434.3 [M + H]$^+$ RP-HPLC (method C, basic) 48% yield |
| 52.1 | [chemical structure] 2-(N-[4-amino-5-(6-methoxypyridine-3-carbonyl)thiazol-2-yl]-3,4-difluoro-anilino)propanamide (enantiomer 1) | Example 52 | $^1$H-NMR (400 MHz, DMSOd6): δ ppm = 1.19 (d, J = 7.35 Hz, 3 H), 3.86 (s, 3 H), 5.03 (q, J = 6.84 Hz, 1 H), 6.84 (dd, J = 8.49, 0.63 Hz, 1 H), 7.30 (s, 1 H), 7.49-7.54 (m, 1 H), 7.56-7.65 (m, 2 H), 7.79 (ddd, J =11.34, 7.54, 2.41 Hz, 1 H), 7.84 (dd, J = 8.62, 2.28 Hz, 1 H), 7.97-8.32 (m, 2 H), 8.35-8.37 (m, 1 H). LC-MS (method 1) Rt = 1.07 min; MS (ESIpos): m/z = 434.3 [M + H]$^+$ 31% yield |
| | Chiral HPLC Example 52.1 HPLC separation of rac-2-(N-[4-amjno-5-(6-methoxypyridine-3-carbonyl)thiazol-2-yl]-3,4-difluoro-anilino)propanamide (31 mg, 0.07 mmol; Example 52) on a chiral column gave 9 mg (27% yield) of 2-(N-[4-amino-5-(6-methoxypyridine-3-carbonyl)thiazol-2-yl]-3,4-difluoro-anilino)propanamide, enantiomer 1. Preparative chiral HPLC Instrument: PrepCon Labomatic HPLC; Column: YMC Amylose SA 5μ, 250 × 30; eluent A: methyl tert-butyl ether + 0.1 vol % diethylamine; eluent B: acetonitrile + 0.1 vol % diethylamine; isocratic: 50% A + 50% B; flow: 40 mL/min; temperature: 25° C.; UV: 254 nm Analytical chiral HPLC: Rt = 1.25 min Instrument: Waters Alliance 2695; Column: YMC Amylose SA 3μ, 100 × 4.6; eluent A: methyl tert-butyl ether + 0.1 vol % diethylamine; eluent B: acetonitrile; isocratic: 50% A + 50% B; flow: 1.4 mL/min; temperature: 25°C.; UV: 254 nm | | |

TABLE 6-continued

Examples 2-80

| Example number | Chemical structure / Compound name | Starting materials | Analytics/purification/yield |
|---|---|---|---|
| 52.2 | 2-(N-[4-amino-5-(6-methoxypyridine-3-carbonyl)thiazol-2-yl]-3,4-difluoro-anilino)propanamide (enantiomer 2) | Example 52 | ¹H-NMR (400 MHz, DMSO-d6): δ ppm = 1.19 (d, J = 7.35 Hz, 3 H), 3.86 (s, 3 H), 5.03 (q, J = 6.93 Hz, 1 H), 6.82-6.86 (m, 1 H), 7.30 (s, 1 H), 7.49-7.54 (m, 1 H), 7.56-7.64 (m, 2 H), 7.79 (ddd, J = 11.28, 7.48, 2.28 Hz, 1 H), 7.84 (dd, J = 8.62, 2.53 Hz, 1 H), 7.96-8.31 (m, 2 H), 8.36 (d, J = 2.03 Hz, 1 H). LC-MS (method 1) Rt = 1.07 min; MS (ESIpos): m/z = 434.3 [M + H]⁺ 31% yield |

Chiral HPLC Example 52.2

HPLC separation of rac-2-(N-[4-amino-5-(6-methoxypyridine-3-carbonyl)thiazol-2-yl]-3,4-difluoro-anilino)propanamide (31 mg, 0.07 mmol; Example 52) on a chiral column gave 7 mg (20% yield) of 2-(N-[4-amino-5-(6-methoxypyridine-3-carbonyl)thiazol-2-yl]-3,4-difluoro-anilino)propanamide, enantiomer 2.

Preparative chiral HPLC

Instrument: PrepCon Labomatic HPLC; Column: YMC Amylose SA 5μ, 250 × 30; eluent A: methyl tert-butyl ether + 0.1 vol % diethylamine; eluent B: acetonitrile + 0.1 vol % diethylamine; isocratic: 50% A + 50% B; flow: 40 mL/min; temperature: 25° C.; UV: 254 nm Analytical chiral HPLC: Rt = 1.74 min Instrument: Waters Alliance 2695; Column: YMC Amylose SA 3μ, 100 × 4.6; eluent A: methyl tert-butyl ether + 0.1 vol % diethylamine; eluent B: acetonitrile; isocratic: 50% A + 50% B; flow: 1.4 mL/min; temperature: 25° C.; UV: 254 nm

| Example number | Chemical structure / Compound name | Starting materials | Analytics/purification/yield |
|---|---|---|---|
| 53<br><br>53.1 and 53.2 | rac-2-(N-[4-amino-5-[6-(trifluoromethyl)pyridine-3-carbonyl]thiazol-2-yl]-3,4-difluoro-anilino)propanamide<br>(R)-2-(N-[4-amino-5-[6-(trifluoromethyl)pyridine-3-carbonyl]thiazol-2-yl]-3,4-difluoro-anilino)propanamide<br>and<br>(S)-2-(N-[4-amino-5-[6-(trifluoromethyl)pyridine-3-carbonyl]thiazol-2-yl]-3,4-difluoro-anilino)propanamide | Intermediate 56; rac-2-bromo-propanamide | ¹H-NMR (400 MHz, DMSO-d6): δ ppm = 1.19 (d, J = 7.60 Hz, 3 H), 4.99-5.09 (m, 1 H), 7.31 (s, 1 H), 7.47-7.54 (m, 1 H), 7.55-7.67 (m, 2 H), 7.78 (ddd, J = 11.22, 7.54, 2.53 Hz, 1 H), 7.95 (d, J = 7.60 Hz, 1 H), 8.15 (dd, J = 7.98, 1.90 Hz, 1 H), 8.24-8.49 (m, 2 H), 8.86 (d, J = 1.77 Hz, 1 H). LC-MS (method 1) Rt = 1.16 min; MS (ESIpos): m/z = 472.3 [M + H]⁺ RP-HPLC (method C, basic) 55% yield |

TABLE 6-continued

Examples 2-80

| Example number | Chemical structure Compound name | Starting materials | Analytics/purification/yield |
|---|---|---|---|
| 53.1 | 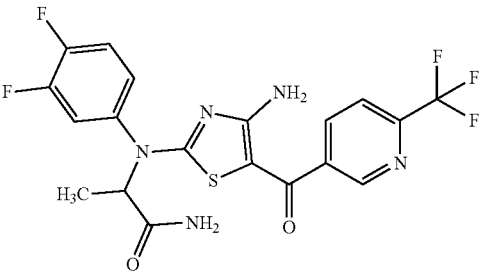 [SMILES: CC(C(N)=O)N(c1ccc(F)c(F)c1)c1nc(N)c(C(=O)c2ccc(C(F)(F)F)nc2)s1]<br>2-(N-[4-amino-5-[6-(trifluoromethyl)pyridine-3-carbonyl]thiazol-2-yl]-3,4-difluoro-anilino)propanamide (enantiomer 1) | Example 53 | $^1$H-NMR (400 MHz, DMSO-d6): δ ppm = 1.19 (d, J = 7.60 Hz, 3 H), 5.04 (br q, J = 6.84 Hz, 1 H), 7.31 (s, 1 H), 7.48-7.53 (m, 1 H), 7.55-7.66 (m, 2 H), 7.78 (ddd, J = 11.28, 7.48, 2.28 Hz, 1 H), 7.95 (dd, J = 8.24, 0.63 Hz, 1 H), 8.15 (dd, J = 7.98, 1.90 Hz, 1 H), 8.23-8.51 (m, 2 H), 8.86 (d, J =1.77 Hz, 1 H). LC-MS (method 1) Rt = 1.13 min; MS (ESIpos): m/z = 472.2 [M + H]$^+$ 30 % yield |

Chiral HPLC Example 53.1
HPLC separation of rac-2-(N-[4-amino-5-[6-(trifluoromethyl)pyridine-3-carbonyl]thiazol-2-yl]-3,4-difluoro-anilino)propanamide (164 mg, 0.35 mmol; Example 53) on a chiral column gave 51 mg (30% yield) of 2-(N-[4-amino-5-[6-(trifluoromethyl)pyridine-3-carbonyl]thiazol-2-yl]-3,4-difluoro-anilino)propanamide, enantiomer 1.
Preparative chiral HPLC
Instrument: PrepCon Labomatic HPLC; Column: YMC Amylose SA 5μ, 250 × 30; eluent A: methyl tert-butyl ether + 0.1 vol % diethylamine; eluent B: acetonitrile; isocratic: 50% A + 50% B; flow: 50 m L/min; temperature: 25° C.; UV: 254 nm
Analytical chiral HPLC: Rt = 1.05 min
Instrument: Waters Alliance 2695; Column: YMC Amylose SA 3μ, 100 × 4.6; eluent A: methyl tert-butyl ether + 0.1 vol % diethylamine; eluent B: acetonitrile; isocratic: 50% A + 50% B; flow: 1.4 mL/min; temperature: 25° C.; UV: 254 nm

| 53.2 | 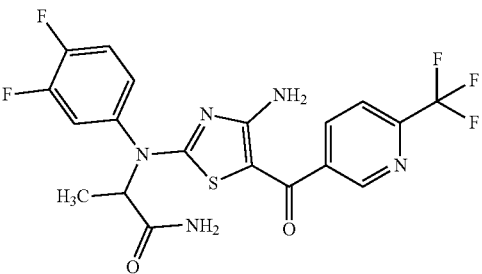 [SMILES: CC(C(N)=O)N(c1ccc(F)c(F)c1)c1nc(N)c(C(=O)c2ccc(C(F)(F)F)nc2)s1]<br>2-(N-[4-amino-5-[6-(trifluoromethyl)pyridine-3-carbonyl]thiazol-2-yl]-3,4-difluoro-anilino)propanamide (enantiomer 2) | Example 53 | $^1$H-NMR (400 MHz, DMSO-d6): δ ppm = 1.19 (d, J = 7.35 Hz, 3 H), 5.04 (br q, J = 7.10 Hz, 1 H), 7.31 (s, 1 H), 7.46-7.53 (m, 1 H), 7.55-7.66 (m, 2 H), 7.78 (ddd, J =1 1.34, 7.54, 2.41 Hz, 1 H), 7.95 (dd, J = 8.24, 0.63 Hz, 1 H), 8.15 (dd, J = 7.98, 1.90 Hz, 1 H), 8.23-8.56 (m, 2 H), 8.86 (d, J = 1.77 Hz, 1 H). LC-MS (method 1) Rt = 1.13 min; MS (ESIpos): m/z = 472.2 [M + H]$^+$ 27% yield |

Chiral HPLC Example 53.2
HPLC separation of rac-2-(N-[4-amino-5-[6-(trifluoromethyl)pyridine-3-carbonyl]thiazol-2-yl]-3,4-difluoro-anilino)propanamide (164 mg, 0.35 mmol; Example 53) on a chiral column gave 47 mg (27% yield) of 2-(N-[4-amino-5-[6-(trifluoromethyl)pyridine-3-carbonyl]thiazol-2-yl]-3,4-difluoro-anilino)propanamide, enantiomer 2.
Preparative chiral HPLC
Instrument: PrepCon Labomatic HPLC; Column: YMC Amylose SA 5μ, 250 × 30; eluent A: methyl tert-butyl ether + 0.1 vol % diethylamine; eluent B: acetonitrile; isocratic: 50% A + 50% B; flow: 50 m L/min; temperature: 25° C.; UV: 254 nm
Analytical chiral HPLC: Rt = 1.36 min
Instrument: Waters Alliance 2695; Column: YMC Amylose SA 3μ, 100 × 4.6; eluent A: methyl tert-butyl ether + 0.1 vol % diethylamine; eluent B: acetonitrile; isocratic: 50% A + 50% B; flow: 1.4 mL/min; temperature: 25° C.; UV: 254 nm TABLE 6-continued Examples 2-80

| Example number | Chemical structure Compound name | Starting materials | Analytics/purification/yield |
|---|---|---|---|
| 54 | 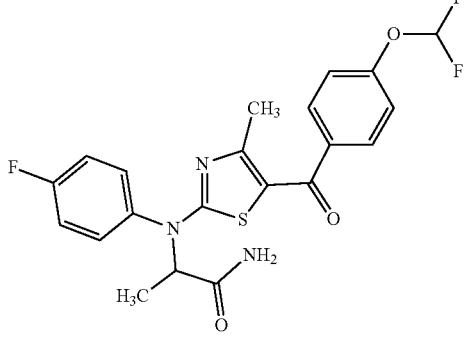rac-2-(N-[5-[4-(difluoromethoxy)benzoyl]-4-methyl-thiazol-2-yl]-4-fluoro-anilino)propanamide | Intermediate 78; rac-2-bromo-propanamide | $^1$H-NMR (400 MHz, DMSO-d6): δ ppm = 1.16 (d, J = 7.60 Hz, 3 H), 2.28 (s, 3 H), 5.11 (q, J = 7.10 Hz, 1 H), 7.15-7.25 (m, 3 H), 7.33-7.39 (m, 3 H), 7.61-7.71 (m, 5 H). LC-MS (method 1) Rt = 1.20 min; MS (ESIpos): m/z = 449.1 [M + H]$^+$ RP-HPLC (method D, basic) 52% yield |
| 55 | 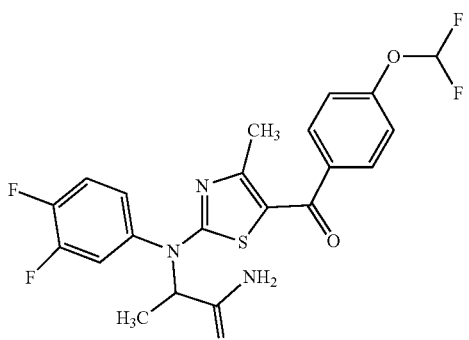rac-2-(N-[5-[4-(difluoromethoxy)benzoyl]-4-methyl-thiazol-2-yl]-3,4-difluoro-anilino)propanamide | Intermediate 79; rac-2-bromo-propanamide | $^1$H-NMR (400 MHz, DMSO-d6): δ ppm = 1.19 (d, J = 7.35 Hz, 3 H), 2.27 (s, 3 H), 5.09 (q, J = 7.27 Hz, 1 H), 7.16-7.38 (m, 4 H), 7.51-7.56 (m, 1 H), 7.58-7.69 (m, 4 H), 7.82 (ddd, J = 11.34, 7.54, 2.41 Hz, 1 H). LC-MS (method 1) Rt = 1.23 min; MS (ESIpos): m/z = 466.3 [M + H]$^+$ RP-HPLC (method D, basic) 7% yield |
| 55.1 and 55.2 | (R)-2-(N-[5-4-(difluoromethoxy)benzoyl]-4-methyl-thiazol-2-yl]-3,4-difluoro-anilino)propanamide and (S)-2-(N-[5-[4-(difluoromethoxy)benzoyl]-4-methyl-thiazol-2-yl]-3,4-difluoro-anilino)propanamide | | |
| 55.1 | 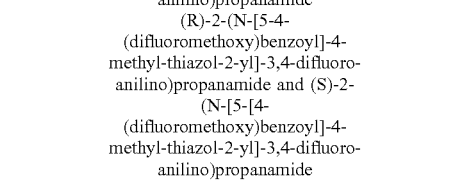2-(N-[5-[4-(difluoromethoxy)benzoyl]-4-methyl-thiazol-2-yl]-3,4-difluoro-anilino)propanamide (enantiomer 1) | Example 55 | $^1$H NMR (400 MHz, DMSO-d6) δ ppm = 1.19 (d, J = 7.35 Hz, 3 H), 2.27 (s, 3 H), 5.08-5.10 (m, 1 H), 7.20-7.24 (m, 3 H), 7.35 (t, J = 72 Hz, 1 H), 7.52-7.54 (m, 1 H), 7.60-7.66 (m, 4 H), 7.81-7.83 (m, 1 H) LC-MS (method 1) Rt = 1.23 min MS (ESIpos): m/z = 468.5 [M + H]$^+$ 35% yield |

TABLE 6-continued

Examples 2-80

| Example number | Chemical structure Compound name | Starting materials | Analytics/purification/yield |
|---|---|---|---|

Chiral HPLC Example 55.1
HPLC separation of rac-2-(N-[5-[4-(difluoromethoxy)benzoyl]-4-methyl-thiazol-2-yl]-3,4-difluoro-anilino)propanamide (59 mg, 0.13 mmol, Example 55) on a chiral column gave 21 mg (35% yield) of 2-(N-[5-[4-(difluoromethoxy)benzoyl]-4-methyl-thiazol-2-yl]-3,4-difluoro-anilino)propanamide, enantiomer 1.
Preparative chiral HPLC
Instrument: PrepCon Labomatic HPLC-2; Column: Chiralpak AS 5μ, 250 × 20; eluent A: hexane + 0.1 vol % diethylamine; eluent B: 2-propanol; isocratic: 80% A + 20% B; flow: 20 mL/min; temperature: 25° C.; UV: 254 nm
Analytical chiral HPLC: Rt = 5.43 min
Instrument: Thermo Fisher UltiMate 3000; Column: Chiralpak AS 3μ, 100 × 4.6; eluent A: hexane + 0.1 vol % diethylamine; eluent B: 2-propanol; isocratic; 80% A + 20% B; flow: 1.4 mL/min; temperature: 25° C.; UV: 254 nm

| 55.2 | 2-(N-[5-[4-(difluoromethoxy)benzoyl]-4-methyl-thiazol-2-yl]-3,4-difluoro-anilino)propanamidepropanamide (enantiomer 2) | Example 55 | $^1$H NMR (400 MHz, DMSO-d6) δ ppm = 1.19 (d, J = 7.35 Hz, 3 H), 2.27 (s, 3 H), 5.08-5.10 (m, 1 H), 7.20-7.24 (m, 3 H), 7.35 (t, J = 72 Hz, 1 H), 7.52-7.54 (m, 1 H), 7.60-7.66 (m, 4 H), 7.81-7.83 (m, 1 H)<br>LC-MS (method 1) Rt = 1.23 min MS (ESIpos): m/z = 468.5 [M + H]$^+$<br>17% yield |

Chiral HPLC Example 55.2
HPLC separation of rac-2-(N-[5-[4-(difluoromethoxy)benzoyl]-4-methyl-thiazol-2-yl]-3,4-difluoro-anilino)propanamide (59 mg, 0.13 mmol, Example 55) on a chiral column gave 10 mg (17% yield) of 2-(N-[5-[4-(difluoromethoxy)benzoyl]-4-methyl-thiazol-2-yl]-3,4-difluoro-anilino)propanamide, enantiomer 2.
Preparative chiral HPLC
Instrument: PrepCon Labomatic HPLC-2; Column: Chiralpak AS 5μ, 250 × 20; eluent A: hexane + 0.1 vol % diethylamine; eluent B: 2-propanol; isocratic: 80% A + 20% B; flow: 20 mL/min; temperature: 25° C.; UV: 254 nm
Analytical chiral HPLC: Rt = 9.88 min
Instrument: Thermo Fisher UltiMate 3000; Column: Chiralpak AS 3μ, 100 × 4.6; eluent A: hexane + 0.1 vol % diethylamine; eluent B: 2-propanol; isocratic: 80% A + 20% B; flow: 1.4 mL/min; temperature: 25° C.; UV: 254 nm

| 56<br><br>56.1 and 56.2 | rac-2-(N-[4-amino-5-(pyridine-4-carbonyl)thiazol-2-yl]-4-chloro-3-fluoro-anilino)propanamide<br>(R)-2-(N-[4-amino-5-(pyridine-4-carbonyl)thiazol-2-yl]-4-chloro-3-fluoro-anilino)propanamide and (S)-2-(N-[4-amino-5-(pyridine-4-carbonyl)thiazol-2-yl]-4-chloro-3-fluoro-anilino)propanamide | Intermediate 57; rac-2-bromo-propanamide | $^1$H-NMR (400 MHz, DMSO-d6): δ ppm = 1.19 (d, J = 7.35 Hz, 3 H), 5.03 (q, J = 7.35 Hz, 1 H), 7.31 (s, 1 H), 7.43 (br d, J = 4.31 Hz, 2 H), 7.49-7.53 (m, 1 H), 7.64 (s, 1 H), 7.71-7.78 (m, 2 H), 8.13-8.48 (m, 2 H), 8.63 (br s, 2 H).<br>LC-MS (method 2) Rt = 0.96 min; MS (ESIpos): m/z = 420.3 [M + H]$^+$<br>RP-HPLC (method C, basic)<br>33% yield |

TABLE 6-continued

Examples 2-80

| Example number | Chemical structure Compound name | Starting materials | Analytics/purification/yield |
|---|---|---|---|
| 56.1 | 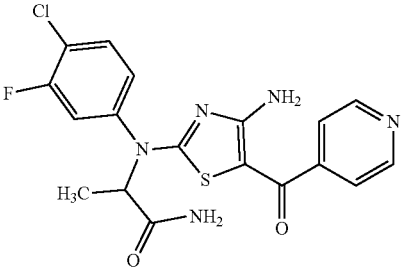 [SMILES: CC(C(N)=O)N(c1ccc(Cl)c(F)c1)c1nc(N)c(C(=O)c2ccncc2)s1]<br>2-(N-[4-amino-5-(pyridine-4-carbonyl)thiazol-2-yl]-4-chloro-3-fluoro-anilino)propanamide (enantiomer 1) | Example 56 | $^1$H-NMR (400 MHz, DMSO-d6): δ ppm = 1.19 (d, J = 7.60 Hz, 3 H), 4.98-5.08 (m, 1 H), 7.31 (s, 1 H), 7.41-7.45 (m, 2 H), 7.48-7.53 (m, 1 H), 7.64 (s, 1 H), 7.72-7.77 (m, 2 H), 8.07-8.45 (m, 2 H), 8.62-8.65 (m, 2 H).<br>LC-MS (method 2) Rt = 0.94 min; MS (ESIpos): m/z = 420.2 [M + H]$^+$<br>19% yield |

Chiral HPLC Example 56.1

HPLC separation of rac-2-(N-[4-amino-5-(pyridine-4-carbonyl)thiazol-2-yl]-4-chloro-3-fluoro-anilino)propanamide (133 mg, 0.32 mmol; Example 56) on a chiral column gave 26 mg (20% yield) of 2-(N-[4-amino-5-(pyridine-4-carbonyl)thiazol-2-yl]-4-chloro-3-fluoro-anilino)propanamide, enantiomer 1.

Preparative chiral HPLC

Instrument: PrepCon Labomatic HPLC; Column: YMC Cellulose SC 10μ, 250 × 50; eluent A: methyl tert-butyl ether; eluent B: acetonitrile; isocratic: 60% A + 40% B; flow: 140 mL/min; temperature: 25° C.; UV: 254 nm Analytical chiral HPLC: Rt = 3.10 min Instrument: Thermo Fisher UltiMate 3000; Column: YMC Cellulose SC 3μ, 100 × 4.6; eluent A: methyl tert-butyl ether + 0.1 vol % diethylamine; eluent B: acetonitrile; isocratic: 60% A + 40% B; flow: 1.4 mL/min; temperature: 25° C.; UV: 254 nm

| Example number | Chemical structure Compound name | Starting materials | Analytics/purification/yield |
|---|---|---|---|
| 56.2 | 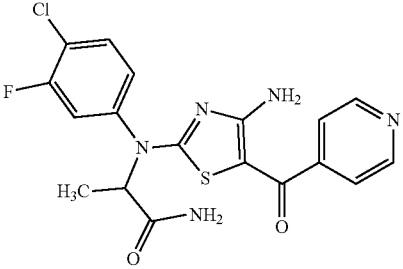 [SMILES: CC(C(N)=O)N(c1ccc(Cl)c(F)c1)c1nc(N)c(C(=O)c2ccncc2)s1]<br>2-(N-[4-amino-5-(pyridine-4-carbonyl)thiazol-2-yl]-4-chloro-3-fluoro-anilino)propanamide (enantiomer 2) | Example 56 | $^1$H-NMR (400 MHz, DMSO-d6): δ ppm = 1.19 (d, J =7.60 Hz, 3 H), 5.03 (q, J = 7.35 Hz, 1 H), 7.31 (s, 1 H), 7.40-7.46 (m, 2 H), 7.49-7.53 (m, 1 H), 7.64 (s, 1 H), 7.72-7.79 (m, 2 H), 8.12-8.47 (m, 2 H), 8.61-8.66 (m, 2 H)<br>LC-MS (method 2) Rt = 0.94 min; MS (ESIpos): m/z = 420.2 [M + H]$^+$<br>20% yield |

Chiral HPLC Example 56.2

HPLC separation of rac-2-(N-[4-amino-5-(pyridine-4-carbonyl)thiazol-2-yl]-4-chloro-3-fluoro-anilino)propanamide (133 mg, 0.32 mmol; Example 56) on a chiral column gave 27 mg (20% yield) of 2-(N-[4-amino-5-(pyridine-4-carbonyl)thiazol-2-yl]-4-chloro-3-fluoro-anilino)propanamide, enantiomer 2.

Preparative chiral HPLC

Instrument: PrepCon Labomatic HPLC; Column: YMC Cellulose SC 10μ, 250 × 50; eluent A: methyl tert-butyl ether; eluent B: acetonitrile; isocratic: 60% A + 40% B; flow: 140 mL/min; temperature: 25° C.; UV: 254 nm Analytical chiral HPLC: Rt = 3.34 min Instrument: Thermo Fisher UltiMate 3000; Column: YMC Cellulose SC 3μ, 100 × 4.6; eluent A: methyl tert-butyl ether + 0.1 vol % diethylamine; eluent B: acetonitrile; isocratic: 60% A + 40% B; flow: 1.4 mL/min; temperature: 25° C.; UV: 254 nm TABLE 6-continued Examples 2-80

| Example number | Chemical structure Compound name | Starting materials | Analytics/purification/yield |
|---|---|---|---|
| 57 | rac-2-(N-[4-amino-5-(pyridine-4-carbonyl)thiazol-2-yl]-4-chloro-anilino)propanamide | Intermediate 58; rac-2-bromo-propanamide | $^1$H-NMR (400 MHz, DMSO-d6): δ ppm = 1.16 (d, J = 7.35 Hz, 3 H), 5.06 (q, J = 7.27 Hz, 1 H), 7.27 (s, 1 H), 7.41 (d, J = 6.08 Hz, 2 H), 7.59 (d, J = 10.90 Hz, 5 H), 8.08-8.48 (m, 2 H), 8.62 (d, J = 6.08 Hz, 2 H). LC-MS (method 2) Rt = 0.91 min; MS (ESIpos): m/z = 402.2 [M + H]$^+$ 50% yield |
| 57.1 and 57.2 | (R)-2-(N-[4-amino-5-(pyridine-4-carbonyl)thiazol-2-yl]-4-chloro-anilino)propanamide and (S)-2-(N-[4-amino-5-(pyridine-4-carbonyl)thiazol-2-yl]-4-chloro-anilino)propanamide | | |
| 57.1 | 2-(N-[4-amino-5-(pyridine-4-carbonyl)thiazol-2-yl]-4-chloro-anilino)propanamide (enantiomer 1) | Example 57 | $^1$H NMR (400 MHz, DMSO-d$_6$) δ ppm = 1.17 (d, J = 7.35 Hz, 3 H), 5.06 (m, 1 H), 7.28 (s, 1 H), 7.41 (m, 2 H), 7.59 (m, 5 H), 8.28 (m, 2 H), 8.62 (m, 2 H) LC-MS (method 1) Rt = 0.85 min MS (ESIpos): m/z = 402.4 [M + H]$^+$ $[\alpha]_D^{20}$ = −67° c = 8.2 mg/mL in DMSO 38% yield |

Chiral HPLC Example 57.1
HPLC separation of rac-2-(N-[4-amino-5-(pyridine-4-carbonyl)thiazol-2-yl]-4-chloro-anilino)propanamide (590 mg, 1.47 mmol, Example 57) on a chiral column gave 234 mg (38% yield) of 2 (N-[4-amino-5-(pyridine-4-carbonyl)thiazol-2-yl]-4-chloro-anilino)propanamide, enantiomer 1.
Preparative chiral HPLC
Instrument: Sepiatec: Prep SFC100; Column: Chiralpak IG 5μ 250 × 30mm; eluent A: CO$_2$; eluent B: 6 thanol + 0.2 vol % aqueous ammonia (32%); isocratic: 30% B; flow: 100 mL/min; temperature: 40° C.; BPR: 150 bar; UV: 254 nm
Analytical chiral HPLC: Rt = 4.76 min
Instrument: Agilent: 1260, Aurora SFC-Modul; Column: Chiralpak IG 5μ 100 × 4.6 mm; eluent A: CO$_2$; eluent B: ethanol + 0.2 vol % aqueous ammonia (32%); isocratic: 30% B; flow: 4 mL/min; temperature: 37.5° C.; BPR: 100 bar; UV: 254 nm

| 57.2 | 2-(N-[4-amino-5-(pyridine-4-carbonyl)thiazol-2-yl]-4-chloro-anilino)propanamide (enantiomer 2) | Example 57 | $^1$H NMR (400 MHz, DMSO-d$_6$) δ ppm = 1.17 (d, J =7.35 Hz, 3 H), 5.06 (m, 1 H), 7.28 (s, 1 H), 7.41 (m, 2 H), 7.59 (m, 5 H), 8.28 (m, 2 H), 8.62 (m, 2 H) LC-MS (method 1) Rt = 0.85 min MS (ESIpos): m/z = 402.4 [M + H]$^+$ $[\alpha]_D^{20}$ = 76° c = 9.6 mg/mL in DMSO 36% yield |

TABLE 6-continued

Examples 2-80

| Example number | Chemical structure Compound name | Starting materials | Analytics/purification/yield |
|---|---|---|---|

Chiral HPLC Example 57.2
HPLC separation of rac-2-(N-[4-amino-5-(pyridine-4-carbonyl)thiazol-2-yl]-4-chloro-anilino)propanamide (590 mg, 1.47 mmol, Example 57) on a chiral column gave 225 mg (36% yield) of 2 (N-[4-amino-5-(pyridine-4-carbonyl)thiazol-2-yl]-4-chloro-anilino)propanamide, enantiomer 2.
Preparative chiral HPLC
Instrument: Sepiatec: Prep SFC100; Column: Chiralpak IG 5µ 250 × 30mm; eluent A: $CO_2$; eluent B: 6 thanol + 0.2 vol % aqueous ammonia (32%); isocratic: 30% B; flow: 100 mL/min; temperature: 40° C.; BPR: 150 bar; UV: 254 nm
Analytical chiral HPLC: Rt = 2.59 min
Instrument: Agilent: 1260, Aurora SFC-Modul; Column: Chiralpak IG 5µ 100 × 4.6 mm; eluent A: $CO_2$; eluent B: ethanol + 0.2 vol % aqueous ammonia (32%); isocratic: 30% B; flow: 4 mL/min; temperature: 37.5° C.; BPR: 100 bar; UV: 254 nm

| 58 | rac-2-(N-[4-amino-5-(4-methoxybenzoyl)thiazol-2-yl]-4-chloro-anillno)propanamide | Intermediate 59; rac-2-bromo-propanamide | $^1$H-NMR (400 MHz, DMSO-d6): δ ppm = 1.16 (d, J =7.35 Hz, 3 H), 3.76 (s, 3 H), 5.05 (q, J = 7.18 Hz, 1 H), 6.93 (d, J = 8.87 Hz, 2 H), 7.26 (s, 1 H), 7.49 (d, J = 8.87 Hz, 2 H), 7.55-7.64 (m, 5 H), 7.82-8.39 (m, 2 H). LC-MS (method 2) Rt = 1.13 min; MS (ESIpos): m/z = 431.2 [M + H]$^+$ 77% yield |
| 58.1 and 58.2 | (R)-2-(N-[4-amino-5-(4-methoxybenzoyl)thiazol-2-yl]-4-chloro-anilino)propanamide and (S)-2-(N-[4-amino-5-(4-methoxybenzoyl)thiazol-2-yl]-4-chloro-anilino)propanamide | | |
| 58.1 | 2-(N-[4-amino-5-(4-methoxybenzoyl)thiazol-2-yl]-4-chloro-anilino)propanamide (enantiomer 1) | Example 58 | $^1$H NMR (400 MHz, DMSO-d$_6$) δ ppm = 1.16 (d, J =7.35 Hz, 3 H), 3.76 (s, 3 H), 5.06 (m, 1 H), 6.93 (m, 2 H), 7.25 (m, 1 H), 7.49 (m, 2 H), 7.60 (m, 5 H), 8.04 (m, 2 H) LC-MS (method 1) Rt = 1.14 min MS (ESIpos): m/z = 431.4 [M + H]$^+$ $[α]_D^{20}$ = −80° c = 11.1 mg/mL in DMSO 36% yield |

Chiral HPLC Example 58.1
HPLC separation of rac-2-(N-[4-amino-5-(4-methoxybenzoyl)thiazol-2-yl]-4-chloro-anilino)propanamide (2.83 g, 6.57 mmol, Example 58) on a chiral column gave 1.03 g (36% yield) of 2-(N-[4-amino-5-(4-methoxybenzoyl)thiazol-2-yl]-4-chloro-anilino)propanamide, enantiomer 1.
Preparative chiral HPLC
Instrument: Labomatic HD3000, Knauer Pump 100, Labcol Vario 4000 Plus, Knauer DAD 2600; Column: Cellulose SB 5µ 250x50mm Nr. 034; eluent A: hexane + 0.1 Vol-% diethylamine (99%); eluent B: ethanol + 0.1 Vol-% diethylamine (99%); isocratic: 60% A + 40% B; flow 100.0 mL/min, UV @ 254 nm
Analytical chiral HPLC: Rt = 4.15 min
Instrument: Agilent HPLC 1260; Column: Cellulose SB 3µ 100x4,6mm; eluent A: hexane + 0.1 Vol-% diethylamine (99%); eluent B: ethanol + 0.1 Vol-% diethylamine (99%); isocratic: 60% A + 40% B; flow 1.0 mL/min; temperature: 25° C.; DAD 254 nm TABLE 6-continued Examples 2-80

| Example number | Chemical structure Compound name | Starting materials | Analytics/purification/yield |
|---|---|---|---|
| 58.2 | 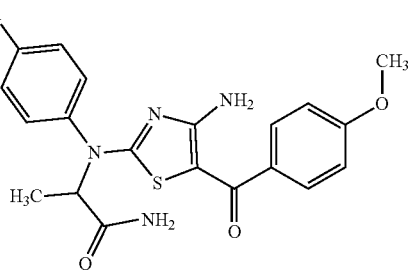<br>2-(N-[4-amino-5-(4-methoxybenzoyl)thiazol-2-yl]-4-chloro-anilino)propanamide (enantiomer 2) | Example 58 | $^1$H NMR (400 MHz, DMSO-d$_6$) δ ppm = 1.16 (d, J = 7.35 Hz, 3 H), 3.76 (s, 3 H), 5.06 (m, 1 H), 6.93 (m, 2 H), 7.25 (m, 1 H), 7.49 (m, 2 H), 7.60 (m, 5 H), 8.04 (m, 2 H) LC-MS (method 1) Rt = 1.14 min MS (ESIpos): m/z = 431.4 [M + H]$^+$ [α]$_D^{20}$ = 79° c = 11.1 mg/mL in DMSO 41% yield |

Chiral HPLC Example 58.2
HPLC separation of rac-2-(N-[4-amino-5-(4-methoxybenzoyl)thiazol-2-yl]-4-chloro-anilino)propanamide (2.83 g, 6.57 mmol, Example 58) on a chiral column gave 1.18 g (41% yield) of 2-(N-[4-amino-5-(4-methoxybenzoyl)thiazol-2-yl]-4-chloro-anilino)propanamide, enantiomer 2.
Preparative chiral HPLC
Instrument: Labomatic HD3000, Knauer Pump 100, Labcol Vario 4000 Plus, Knauer DAD 2600; Column: Cellulose SB 5μ 250x50mm Nr. 034; eluent A: hexane + 0.1 Vol-% diethylamine (99%); eluent B: ethanol + 0.1 Vol-% diethylamine (99%); isocratic: 60% A + 40% B; flow 100.0 mL/min, UV @ 254 nm
Analytical chiral HPLC: Rt = 3.40 min
Instrument: Agilent HPLC 1260; Column: Cellulose SB 3μ 100x4,6mm; eluent A: hexane + 0.1 Vol-% diethylamine (99%); eluent B: ethanol + 0.1 Vol-% diethylamine (99%); isocratic: 60% A + 40% B; flow 1.0 mL/min; temperature: 25° C.; DAD 254 nm

| | | | |
|---|---|---|---|
| 59 | 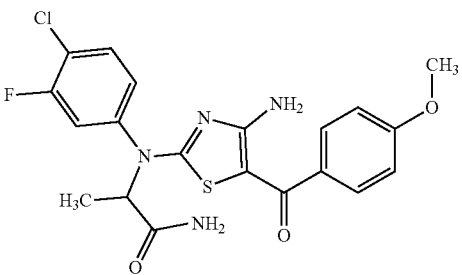 [SMILES: COc1ccc(C(=O)c2sc(N(c3ccc(Cl)c(F)c3)C(C)C(N)=O)nc2N)cc1]<br>rac-2-(N-[4-amino-5-(4-methoxybenzoyl)thiazol-2-yl]-4-chloro-3-fluoro-anilino)propanamide | Intermediate 60; rac-2-bromo-propanamide | $^1$H-NMR (400 MHz, DMSO-d6): δ ppm = 1.20 (d, J = 7.35 Hz, 3 H), 3.77 (s, 3 H), 5.03 (q, J = 7.35 Hz, 1 H), 6.94 (d, J = 8.87 Hz, 2 H), 7.30 (s, 1 H), 7.49-7.53 (m, 3 H), 7.63 (s, 1 H), 7.73-7.79 (m, 2 H), 7.88-8.31 (m, 2 H). LC-MS (method 2) Rt = 1.17 min; MS (ESIpos): m/z = 449.3 [M + H]$^+$ 83% yield |
| 59.1 and 59.2 | (R)-2-(N-[4-amino-5-(4-methoxybenzoyl)thiazol-2-yl]-4-chloro-3-fluoro-anilino)propanamide and (S)-2-(N-[4-amino-5-(4-methoxybenzoyl)thiazol-2-yl]-4-chloro-3-fluoro-anilino)propanamide | | |

TABLE 6-continued

Examples 2-80

| Example number | Chemical structure Compound name | Starting materials | Analytics/purification/yield |
|---|---|---|---|
| 59.1 | 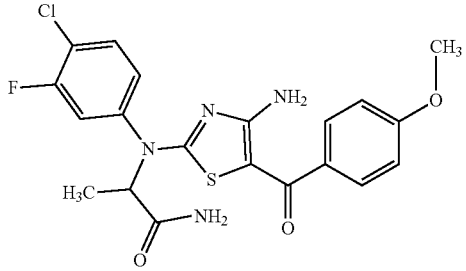 [SMILES: COc1ccc(C(=O)c2sc(N(c3ccc(Cl)c(F)c3)C(C)C(N)=O)nc2N)cc1]

2-(N-[4-amino-5-(4-methoxybenzoyl)thiazol-2-yl]-4-chloro-3-fluoro-anilino)propanamide (enantiomer 1) | Example 59 | $^1$H NMR (400 MHz, DMSO-d$_6$) δ ppm = 1.20 (d, J = 7.35 Hz, 3 H), 3.76 (s, 3 H), 5.03 (q, J = 7.35 Hz, 1 H), 6.94 (m, 2 H), 7.30 (s, 1 H), 7.52 (m, 3 H), 7.63 (s, 1 H), 7.75 (m, 2 H), 8.10 (m, 2 H) LC-MS (method 1) Rt = 1.16 min MS (ESIpos): m/z = 449.4 [M + H]$^+$ [α]$_D^{20}$ = −82° c = 8.2 mg/mL in DMSO 29% yield |

Chiral HPLC Example 59.1

HPLC separation of rac-2-(N-[4-amino-5-(4-methoxybenzoyl)thiazol-2-yl]-4-chloro-3-fluoro-anilino)propanamide (442 mg, 0.98 mmol, Example 59) on a chiral column gave 132 mg (29% yield) of 2 -(N-[4-amino-5-(4-methoxybenzoyl)thiazol-2-yl]-4-chloro-3-fluoro-anilino)propanamide, enantiomer 1.

Preparative chiral HPLC

Instrument: PrepCon Labomatic HPLC-4; Column: YMC Amylose SA 5µ, 250 × 30;
eluent A: nethyl tert-butyl ether + 0.1 vol % diethylamine; eluent B: acetonitrile; isocratic:
70% A + 30% B; flow: 50 mL/min; temperature: 25° C.; UV: 254 nm Analytical chiral HPLC: Rt = 1.49 min Instrument: Waters Alliance 2695; Column: YMC Amylose SA 3µ, 100 × 4.6;
eluent A: nethyl tert-butyl ether + 0.1 vol % diethylamine; eluent B: acetonitrile; isocratic:
70%A + 30% B; flow: 1.4 mL/min; temperature: 25° C.; UV: 254 nm

| | | | |
|---|---|---|---|
| 59.1 | 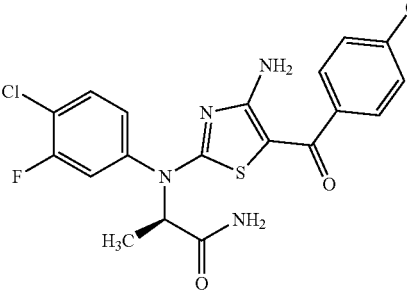 | | Example 59.1 was determined to be (R)-2-(N-[4-amino-5-(4-methoxybenzoyl)thiazol-2-yl]-4-chloro-3-fluoro-anilino)propanamide, by means of X-ray crystal structure analysis. |
| 59.2 | 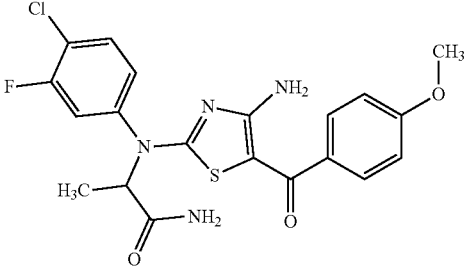

2-(N-[4-amino-5-(4-methoxybenzoyl)thiazol-2-yl]-4-chloro-3-fluoro-anilino)propanamide (enantiomer 2) | Example 59 | $^1$H NMR (400 MHz, DMSO-d$_6$) δ ppm = 1.20 (d, J = 7.35 Hz, 3 H), 3.76 (s, 3 H), 5.03 (q, J = 7.35 Hz, 1 H), 6.94 (m, 2 H), 7.30 (s, 1 H), 7.52 (m, 3 H), 7.63 (s, 1 H), 7.75 (m, 2 H), 8.10 (m, 2 H) LC-MS (method 1) Rt = 1.16 min MS (ESIpos): m/z = 449.4 [M + H]$^+$ [α]$_D^{20}$ = 87° c = 7.6 mg/mL in DMSO 15% yield |

TABLE 6-continued

Examples 2-80

| Example number | Chemical structure Compound name | Starting materials | Analytics/purification/yield |
|---|---|---|---|
| | Chiral HPLC Example 59.2 HPLC separation of rac-2-(N-[4-amino-5-(4-methoxybenzoyl)thiazol-2-yl]-4-chloro-3-fluoro-anilino)propanamide (442 mg, 0.98 mmol, Example 59) on a chiral column gave 68 mg (15% yield) of 2 -(N-[4-amino-5-(4-methoxybenzoyl)thiazol-2-yl]-4-chloro-3-fluoro-anilino)propanamide, enantiomer 2. Preparative chiral HPLC Instrument: PrepCon Labomatic HPLC-4; Column: YMC Amylose SA 5μ, 250 × 30; eluent A: nethyl tert-butyl ether + 0.1 vol % diethylamine; eluent B: acetonitrile; isocratic: 70% A + 30% B; flow: 50 mL/min; temperature: 25° C.; UV: 254 nm Analytical chiral HPLC: Rt = 2.03 min Instrument: Waters Alliance 2695; Column: YMC Amylose SA 3μ, 100 × 4.6; eluent A: nethyl tert-butyl ether + 0.1 vol % diethylamine; eluent B: acetonitrile; isocratic: 70% A + 30% B; flow: 1.4 mL/min; temperature: 25° C.; UV: 254 nm | | |
| 60 | rac-2-(N-(4-amino-5-benzoyl-thiazol-2-yl)anilino)propanamide | Intermediate 83; rac-2-bromo-propanamide | $^1$H-NMR (600 MHz, DMSO-d6): δ ppm = 1.16 (d, J =7.25 Hz, 3 H), 5.09 (q, J =7.25 Hz, 1 H), 7.24 (s, 1 H), 7.35-7.40 (m, 3 H), 7.42-7.50 (m, 5 H), 7.54-7.57 (m, 3 H), 7.74-8.52 (m, 2 H). LC-MS (method 2) Rt= 1.02 min; MS (ESIpos): m/z = 367.1 [M + H]$^+$ preparative flash chromatography (method Z, 0-3%) 46% yield |
| 61 | rac-2-(N-(4-amino-5-benzoyl-thiazol-2-yl)-4-fluoro-anilino)propanamide | Intermediate 84; rac-2-bromo-propanamide | $^1$H-NMR (400 MHz, DMSO-d6): δ ppm = 1.16 (d, J = 7.35 Hz, 3 H), 5.00-5.10 (m, 1 H), 7.25 (s, 1 H), 7.32 (t, J = 8.87 Hz, 2 H), 7.35-7.42 (m, 3 H), 7.45-7.52 (m, 2 H), 7.58 (s, 1 H), 7.63 (dd, J = 9.00, 5.20 Hz, 2 H), 7.80-8.46 (m, 2 H). LC-MS (method 2) Rt = 1.07 min; MS (ESIpos): m/z = 385.3 [M + H]$^+$ preparative flash chromatography (method Z, 0-3%) 87% yield |
| 61.1 and 61.2 | (R)-2-(N-(4-amino-5-benzoyl-thiazol-2-yl)-4-fluoro-aniiino)propanamide and (S)-2-(N-(4-amino-5-benzoyl-thiazol-2-yl)-4-fluoro-anilino)propanamide | | |
| 61.1 | 2-(N-(4-amino-5-benzoyl-thiazol-2-yl)-4-fluoro-anilino)propanamide (enantiomer 1) | Example 61 | $^1$H-NMR (400 MHz, DMSO-d6): δ ppm = 1.15 (d, J = 7.60 Hz, 3 H), 5.02-5.09 (m, 1 H), 7.25 (s, 1 H), 7.32 (t, J =8.87 Hz, 2 H), 7.36-7.42 (m, 3 H), 7.46-7.50 (m, 2 H), 7.58 (s, 1 H), 7.63 (dd, J = 8.74, 5.20 Hz, 2 H), 7.80-8.50 (m, 2 H). LC-MS (method 1) Rt = 1.07 min; MS (ESIpos): m/z = 385.5 [M + H]$^+$ 24% yield |

TABLE 6-continued

Examples 2-80

| Example number | Chemical structure Compound name | Starting materials | Analytics/purification/yield |
| --- | --- | --- | --- |

Chiral HPLC Example 61.1
HPLC separation of rac-2-(N-(4-amino-5-benzoyl-thiazol-2-yl)-4-fluoro-anilino)propanamide
(414 mg, 1.08 mmol; Example 61) on a chiral column gave 139 mg (33% yield) of 2-(N-(4-amino-5-benzoyl-thiazol-2-yl)-4-fluoro-anilino)propanamide, enantiomer 1.
Preparative chiral HPLC
Instrument: Sepiatec: Prep SFC100; Column: Chiralpak IA 5μ 250 × 30mm; eluent A: $CO_2$;
eluent B: 2-propanol + 0.4 vol % diethylamine; isocratic: 25% B; flow: 100 mL/min; temperature:
40° C.; BPR: 150 bar; UV: 280 nm
Analytical chiral HPLC: Rt = 2.10 min
Instrument: Agilent: 1260, Aurora SFC-Modul;column Chiralpak IA 5μ 100 × 4.6mm; eluent A:
$CO_2$; eluent B: 2-propanol + 0.4% diethylamine (99%); isocratic: 25% B; flow: 4 mL/min;
temperature: 37.5° C.; BPR: 100 bar; UV: 280 nm

| 61.2 | 2-(N-(4-amino-5-benzoyl-thiazol-2-yl)-4-fluoro-anilino)propanamide (enantiomer 2) | Example 61 | $^1$H-NMR (400 MHz, DMSO-d6): δ ppm = 1.15 (d, J = 7.60 Hz, 3 H), 5.02-5.09 (m, 1 H), 7.25 (s, 1 H), 7.32 (t, J = 8.87 Hz, 2 H), 7.36-7.42 (m, 3 H), 7.46-7.50 (m, 2 H), 7.58 (s, 1 H), 7.63 (dd, J = 8.74, 5.20 Hz, 2 H), 7.80-8.50 (m, 2 H). LC-MS (method 1) Rt = 1.07 min; MS (ESIpos): m/z = 385.5 [M + H]$^+$ 26% yield |

Chiral HPLC Example 61.2
HPLC separation of rac-2-(N-(4-amino-5-benzoyl-thiazol-2-yl)-4-fluoro-anilino)propanamide
(414 mg, 1.08 mmol; Example 61) on a chiral column gave 103 mg (24% yield) of 2-(N-(4-amino-5-benzoyl-thiazol-2-yl)-4-fluoro-anilino)propanamide, enantiomer 2.
Preparative chiral HPLC
Instrument: Sepiatec: Prep SFC100; Column: Chiralpak IA 5μ 250 × 30mm; eluent A: $CO_2$;
eluent B: 2-propanol + 0.4 vol % diethylamine; isocratic: 25% B; flow: 100 mL/min; temperature:
40° C.; BPR: 150 bar; UV: 280 nm
Analytical chiral HPLC: Rt = 3.08 min
Instrument: Agilent: 1260, Aurora SFC-Modul; column: Chiralpak IA 5μ 100 × 4.6mm; eluent A:
$CO_2$; eluent B: 2-Propanol + 0.4% diethylamine (99%); isocratic; 25%B; flow: 4 mL/min;
temperature: 37.5° C.; BPR: 100 bar; UV: 280 nm

| 61.2 | | | Example 61.2 was determined to be (R)-2-(N-(4-amino-5-benzoyl-thiazol-2-yl)-4-fluoro-anilino)propanamide, by means of X-ray crystal structure analysis. |

TABLE 6-continued

Examples 2-80

| Example number | Chemical structure Compound name | Starting materials | Analytics/purification/yield |
|---|---|---|---|
| 62 | rac-2-(N-[4-amino-5-(4-methoxybenzoyl)thiazol-2-yl]-4-fluoro-anilino)propanamide | Intermediate 85; rac-2-bromo-propanamide | ¹H-NMR (400 MHz, DMSO-d6): δ ppm = 1.16 (d, J = 7.60 Hz, 3 H), 3.75 (s, 3 H), 5.06 (q, J = 6.76 Hz, 1 H), 6.93 (d, J = 8.87 Hz, 2 H), 7.22-7.27 (m, 1 H), 7.34 (t, J = 8.87 Hz, 2 H), 7.48 (d, J = 8.87 Hz, 2 H), 7.57 (s, 1 H), 7.64 (dd, J = 8.87, 5.07 Hz, 2 H), 7.79-8.38 (m, 2 H). LC-MS (method 2) Rt = 1.06 min; MS (ESIpos): m/z = 415.5 [M + H]⁺ preparative flash chromatography (method Z, 0-3%) 49% yield |
| 62.1 and 62.2 | (R)-2-(N-[4-amino-5-(4-methoxybenzoyl)thiazol-2-yl]-4-fluoro-anilino)propanamide and (S)-2-(N-[4-amino-5-(4-methoxybenzoyl)thiazol-2-yl]-4-fluoro-anilino)propanamide | | |
| 62.1 | 2-(N-[4-amino-5-(4-methoxybenzoyl)thiazol-2-yl]-4-fluoro-anilino)propanamide (enantiomer 1) | Example 62 | ¹H-NMR (400 MHz, DMSO-d6): δ ppm = 1.16 (d, J = 7.60 Hz, 3 H), 3.75 (s, 3 H), 5.06 (q, J = 6.76 Hz, 1 H), 6.93 (d, J = 8.87 Hz, 2 H), 7.22-7.27 (m, 1 H), 7.34 (t, J = 8.87 Hz, 2 H), 7.48 (d, J = 8.87 Hz, 2 H), 7.57 (s, 1 H), 7.64 (dd, J = 8.87, 5.07 Hz, 2 H), 7.79-8.38 (m, 2 H). $[\alpha]_D^{20}$ = −142.9° (c = 1.00, chloroform) 45% yield |

Chiral HPLC Example 62.1

HPLC separation of rac-2-(N-[4-amino-5-(4-methoxybenzoyl)thiazol-2-yl]-4-fluoro-anilino)propanamide (350 mg, 0.80 mmol; Example 62) on a chiral column gave 135 mg (45% yield) of 2-(N-[4-amino-5-(4-methoxybenzoyl)thiazol-2-yl]-4-fluoro-anilino)propanamide, enantiomer 1.

Preparative chiral HPLC

Instrument: Sepiatec: Prep SFC100; Column: Chiralpak IA 5μ 250 × 30mm; eluent A: CO₂; eluent B: 2-propanol + 0.4 vol % diethylamine; isocratic: 30% B; flow: 100 mL/min; temperature: 40° C.; BPR: 150 bar; UV: 254 nm Analytical chiral HPLC: Rt = 1.72 min Instrument: Agilent: 1260, Aurora SFC-Modul; Column: Chiralpak IA 5μ 100 × 4.6mm; eluent A: CO₂; eluent B: 2-propanol + 0.4 vol % diethylamine; isocratic: 30% B; flow: 4 mL/min; temperature: 37.5° C.; BPR: 100 bar; UV: 254 nm

TABLE 6-continued

Examples 2-80

| Example number | Chemical structure Compound name | Starting materials | Analytics/purification/yield |
|---|---|---|---|
| 62.2 | 2-(N-[4-amino-5-(4-methoxybenzoyl)thiazol-2-yl]-4-fluoro-anilino)propanamide (enantiomer 2) | Example 62 | $^1$H-NMR (400 MHz, DMSO-d6): δ ppm = 1.16 (d, J = 7.60 Hz, 3 H), 3.75 (s, 3 H), 5.06 (q, J = 6.76 Hz, 1 H), 6.93 (d, J = 8.87 Hz, 2 H), 7.22-7.27 (m, 1 H), 7.34 (t, J = 8.87 Hz, 2 H), 7.48 (d, J = 8.87 Hz, 2 H), 7.57 (s, 1 H), 7.64 (dd, J = 8.87, 5.07 Hz, 2 H), 7.79-8.38 (m, 2 H). $[α]_D^{20}$ = +114.5° (c = 1.00, chloroform) 49% yield |

Chiral HPLC Example 62.2
HPLC separation of rac-2-(N-[4-amino-5-(4-methoxybenzoyl)thiazol-2-yl]-4-fluoro-anilino)propanamide (350 mg, 0.80 mmol; Example 62) on a chiral column gave 15 mg (49% yield) of 2-(N-[4-amino-5-(4-methoxybenzoyl)thiazol-2-yl]-4-fluoro-anilino)propanamide, enantiomer 2.
Preparative chiral HPLC
Instrument: Sepiatec: Prep SFC100; Column: Chiralpak IA 5µ 250 × 30mm; eluent A: CO$_2$; eluent B: 2-propanol + 0.4 vol % diethylamine; isocratic: 30% B; flow: 100 mL/min; temperature: 40° C.; BPR: 150 bar; UV: 254 nm
Analytical chiral HPLC: Rt = 2.61 min
Instrument: Agilent: 1260, Aurora SFC-Modul; Column: Chiralpak IA 5µ 100 × 4.6mm; eluent A: CO$_2$; eluent B: 2-propanol + 0.4 vol % diethylamine; isocratic: 30% B; flow: 4 mL/min; temperature: 37.5° C.; BPR: 100 bar; UV: 254 nm

| Example number | Chemical structure Compound name | Starting materials | Analytics/purification/yield |
|---|---|---|---|
| 62.2 | | | Example 62.2 was determined to be (R)-2-(N-[4-amino-5-(4-methoxybenzoyl)thiazol-2-yl]-4-fluoro-anilino)propanamide, by means of X-ray crystal structure analysis. |
| 63 | | Intermediate 86; rac-2-bromo-propanamide | $^1$H-NMR (400 MHz, DMSO-d6): δ ppm = 1.16 (d, J =7.60 Hz, 3 H), 2.29 (s, 3 H), 5.05 (q, J = 6.67 Hz, 1 H), 7.18 (d, J = 8.11 Hz, 2 H), 7.24 (s, 1 H), 7.32 (t, J = 8.87 Hz, 2 H), 7.38 (d, J = 8.11 Hz, 2 H), 7.57 (s, 1 H), 7.63 (dd, J = 8.62, 5.07 Hz, 2 H), 8.10 (br s, 2 H). LC-MS (method 2) Rt = 1.15 min; MS (ESIpos): m/z = 399.3 [M + H]$^+$ preparative flash chromatography (method Z, 0-3%) 18% yield |
| | rac-2-(N-[4-amino-5-(4-methylbenzoyl)thiazol-2-yl]-4-fluoro-anilino)propanamide | | |
| 63.1 and 63.2 | (R)-2-(N-[4-amino-5-(4-methylbenzoyl)thiazol-2-yl]-4-fluoro-anilino)propanamide and (S)-2-(N-[4-amino-5-(4-methylbenzoyl)thiazol-2-yl]-4-fluoro-anilino)propanamide | | |

TABLE 6-continued

Examples 2-80

| Example number | Chemical structure Compound name | Starting materials | Analytics/purification/yield |
|---|---|---|---|
| 63.1 | 2-(N-[4-amino-5-(4-methylbenzoyl)thiazol-2-yl]-4-fluoro-anilino)propanamide (enantiomer 1) | Example 63 | $^1$H-NMR (400 MHz, DMSO-d6): δ ppm = 1.16 (d, J =7.60 Hz, 3 H), 2.29 (s, 3 H), 5.05 (q, J = 6.67 Hz, 1 H), 7.18 (d, J = 8.11 Hz, 2 H), 7.24 (s, 1 H), 7.32 (t, J = 8.87 Hz, 2 H), 7.38 (d, J = 8.11 Hz, 2 H), 7.57 (s, 1 H), 7.63 (dd, J = 8.62, 5.07 Hz, 2 H), 8.10 (br s, 2 H). $[\alpha]_D^{20}$ = −159.9° (c = 1.00, chloroform) 13% yield |

Chiral HPLC Example 63.1

HPLC separation of rac-2-(N-[4-amino-5-(4-methylbenzoyl)thiazol-2-yl]-4-fluoro-anilino)propanamide (1.5 g, 3.58 mmol; Example 63) on a chiral column gave 660 mg (45% yield) of 2-(N-[4-amino-5-(4-methylbenzoyl)thiazol-2-yl]-4-fluoro-anilino)propanamlde, enantiomer 1.

Preparative chiral HPLC

Instrument: PrepCon Labomatic HPLC; Column: YMC Cellulose SB 10μ, 250 × 50; eluent A: hexane + 0.1 vol % diethylamine; eluent B: 2-propanol + 0.1 vol % diethylamine; isocratic: 60% A + 40% B; flow: 140 mL/min; temperature: 25° C.; UV: 254 nm Analytical chiral HPLC: Rt = 2.46 min Instrument: Waters Alliance 2695; Column: YMC Cellulose SB 3μ, 100 × 4.6; eluent A: hexane + 0.1 vol % diethylamine; eluent B: 2-propanol; isocratic: 60% A + 40% B; flow: 1.4 mL/min; temperature: 25° C.; UV: 254 nm

| | | | |
|---|---|---|---|
| 63.2 | 2-(N-[4-amino-5-(4-methylbenzoyl)thiazol-2-yl]-4-fluoro-anilino)propanamide (enantiomer 2) | Example 63 | $^1$H-NMR (400 MHz, DMSO-d6): δ ppm = 1.16 (d, J = 7.60 Hz, 3 H), 2.29 (s, 3 H), 5.05 (q, J = 6.67 Hz, 1 H), 7.18 (d, J = 8.11 Hz, 2 H), 7.24 (s, 1 H), 7.32 (t, J = 8.87 Hz, 2 H), 7.38 (d, J = 8.11 Hz, 2 H), 7.57 (s, 1 H), 7.63 (dd, J = 8.62, 5.07 Hz, 2 H), 8.10 (br s, 2 H). $[\alpha]_D^{20}$ = +147.0° (c = 1.00, chloroform) 13% yield |

Chiral HPLC Example 63.2

HPLC separation of rac-2-(N-[4-amino-5-(4-methylbenzoyl)thiazol-2-yl]-4-fluoro-anilino)propanamide (1.5 g, 3.58 mmol; Example 63) on a chiral column gave 680 mg (44% yield) of 2-(N-[4-amino-5-(4-methylbenzoyl)thiazol-2-yl]-4-fluoro-anilino)propanamlde, enantiomer 2.

Preparative chiral HPLC

Instrument: PrepCon Labomatic HPLC; Column: YMC Cellulose SB 10μ, 250 × 50; eluent A: hexane + 0.1 vol % diethylamine; eluent B: 2-propanol + 0.1 vol % diethylamine; isocratic: 60%A + 40% B; flow: 140 mL/min; temperature: 25° C.; UV: 254 nm Analytical chiral HPLC: Rt = 3.69 min Instrument: Waters Alliance 2695; Column: YMC Cellulose SB 3μ, 100 × 4.6; eluent A: hexane + 0.1 vol % diethylamine; eluent B: 2-propanol; isocratic: 60% A + 40% B; flow: 1.4 mL/min; temperature: 25° C.; UV: 254 nm

TABLE 6-continued

Examples 2-80

| Example number | Chemical structure / Compound name | Starting materials | Analytics/purification/yield |
|---|---|---|---|
| 64 | rac-2-(N-[4-amino-5-(4-fluorobenzoyl)thiazol-2-yl]-4-fluoro-anilino)propanamide | Intermediate 87; rac-2-bromo-propanamide | ¹H-NMR (400 MHz, DMSO-d6): δ ppm = 1.16 (d, J = 7.35 Hz, 3 H), 5.06 (br q, J = 6.84 Hz, 1 H), 7.22 (t, J = 8.87 Hz, 2 H), 7.25 (s, 1 H), 7.33 (t, J = 8.87 Hz, 2 H), 7.55 (dd, J = 8.74, 5.45 Hz, 2 H), 7.58 (br s, 1 H), 7.64 (dd, J = 8.87, 5.07 Hz, 2 H), 7.86-8.56 (m, 2 H). LC-MS (method 2) Rt = 1.09 min; MS (ESIpos): m/z = 403.3 [M +H]⁺ preparative flash chromatography (method Z, 0-3%) 7% yield |
| 65 | rac-2-(N-(4-amino-5-benzoyl-thiazol-2-yl)-2,4-difluoro-anilino)propanamide | Intermediate 88; rac-2-bromo-propanamide | ¹H-NMR (400 MHz, CHLOROFORM-d): δ ppm = 1.27 (d, J = 7.10 Hz, 3 H), 5.23 (q, J = 7.18 Hz, 1 H), 5.39-5.48 (m, 1 H), 6.58-6.70 (m, 1 H), 6.94-7.02 (m, 2 H), 7.33-7.43 (m, 4 H), 7.58-7.64 (m, 2 H) (NH2 missing). LC-MS (method 2) Rt = 1.08 min; MS (ESIpos): m/z = 403.3 [M + H]⁺ preparative flash chromatography (method Z, 0-3%) 29% yield |
| 66 | rac-2-(N-(4-amino-5-benzoyl-thiazol-2-yl)-4-methoxy-anilino)propanamide | Intermediate 89; rac-2-bromo-propanamide | ¹H-NMR (400 MHz, DMSO-d6): δ ppm = 1.15 (d, J = 6.84 Hz, 3 H), 3.78 (s, 3 H), 5.06 (q, J = 6.59 Hz, 1 H), 7.00 (d, J = 9.12 Hz, 2 H), 7.21 (s, 1 H), 7.35-7.42 (m, 3 H), 7.43-7.49 (m, 4 H), 7.52 (s, 1 H), 7.65-8.49 (m, 2 H). LC-MS (method 2) Rt = 1.03 min; MS (ESIpos): m/z = 397.4 [M + H]⁺ preparative flash chromatography (method Z, 0-3%) 19% yield |
| 67 | rac-2-[(4-amino-5-benzoyl-1,3-thiazol-2-yl)(phenyl)amino]butanamide | Intermediate 83; rac-2-bromo-butanamide | ¹H-NMR (400 MHz, DMSO-d6): δ ppm = 0.84 (t, J = 7.35 Hz, 3 H), 1.47-1.60 (m, 1 H), 1.69-1.81 (m, 1 H), 4.87-4.95 (m, 1 H), 7.30 (s, 1 H), 7.34-7.51 (m, 8 H), 7.54-7.58 (m, 3 H), 7.78-8.48 (m, 2 H). LC-MS (method 2) Rt = 1.09 min; MS (ESIpos): m/z = 381.3 [M + H]⁺ preparative flash chromatography (method Z, 0-3%) 43% yield |

TABLE 6-continued

Examples 2-80

| Example number | Chemical structure Compound name | Starting materials | Analytics/purification/yield |
|---|---|---|---|
| 68 | rac-2-[(4-amino-5-benzoyl-1,3-thiazol-2-yl)(4-fluorophenyl)amino]butanamide | Intermediate 84; rac-2-bromo-butanamide | $^1$H-NMR (400 MHz, DMSO-d6): δ ppm = 0.84 (t, J = 7.35 Hz, 3 H), 1.46-1.58 (m, 1 H), 1.68-1.79 (m, 1 H), 4.85-4.92 (m, 1 H), 7.32 (s, 3 H), 7.37-7.42 (m, 3 H), 7.47-7.50 (m, 2 H), 7.59 (s, 1 H), 7.64 (dd, J = 9.12, 5.07 Hz, 2 H), 7.83-8.36 (m, 2 H). LC-MS (method 2) Rt = 1.12 min; MS (ESIpos): m/z = 399.3 [M + H]$^+$ preparative flash chromatography (method Z, 0-3%) 29% yield |
| 69 | 2-(N-[4-amino-5-[4-(2-amino-1-methyl-2-oxo-ethoxy)benzoyl]thiazol-2-yl]-4-fluoro-anilino)propanamide (mixture of stereoisomers) | Intermediate 90; rac-2-bromo-propanamide | $^1$H-NMR (400 MHz, DMSO-d6): δ ppm = 1.16 (d, J = 7.35 Hz, 3 H), 1.41 (d, J = 6.59 Hz, 3 H), 4.64 (q, J = 6.59 Hz, 1 H), 5.05 (q, J = 6.76 Hz, 1 H), 6.87 (d, J = 8.87 Hz, 2 H), 7.25 (br s, 2 H), 7.33 (t, J = 8.74 Hz, 2 H), 7.46 (d, J = 8.62 Hz, 2 H), 7.50 (s, 1 H), 7.57 (s, 1 H), 7.64 (dd, J = 9.00, 5.20 Hz, 2 H), 7.78-8.35 (m, 2 H). LC-MS (method 2) Rt = 0.87 min; MS (ESIpos): m/z = 472.2 [M + H]$^+$ preparative flash chromatography (method Z, 0-8%) 28% yield |
| 70 | rac-2-{[4-amino-5-(4-methoxybenzoyl)-1,3-thiazol-2-yl](4-fluorophenyl)amino}butanamide | Intermediate 85; rac-2-bromo-butanamide | $^1$H-NMR (400 MHz, DMSO-d6): δ ppm = 0.84 (t, J =7.22 Hz, 3 H), 1.46-1.58 (m, 1 H), 1.67-1.78 (m, 1 H), 3.76 (s, 3 H), 4.85-4.93 (m, 1 H), 6.93 (d, J = 8.87 Hz, 2 H), 7.33 (t J = 8.74 Hz, 2 H), 7.32 (br s, 1 H), 7.49 (d, J = 8.87 Hz, 2 H), 7.59 (s, 1 H), 7.65 (dd, J = 9.00, 4.94 Hz, 2 H), 8.11 (brs, 2 H). LC-MS (method 2) Rt = 1.12 min; MS (ESIpos): m/z = 429.3 [M + H]$^+$ preparative flash chromatography (method Z, 0-3%) 28% yield |

TABLE 6-continued

Examples 2-80

| Example number | Chemical structure Compound name | Starting materials | Analytics/purification/yield |
|---|---|---|---|
| 71 | 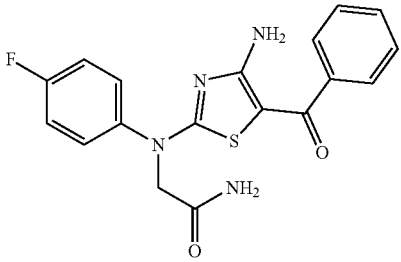 [SMILES: NC(=O)CN(c1ccc(F)cc1)c1nc(N)c(C(=O)c2ccccc2)s1]<br>2-(N-(4-amino-5-benzoyl-thiazol-2-yl)-4-fluoro-anilino)acetamide | Intermediate 84; 2-bromo-acetamide | $^1$H-NMR (500 MHz, DMSO-d6): δ ppm = 4.44 (s, 2 H), 7.23 (s, 1 H), 7.32 (t, J = 8.67 Hz, 2 H), 7.38-7.43 (m, 3 H), 7.50-7.53 (m, 2 H), 7.56 (s, 1 H), 7.61 (dd, J = 8.83, 5.04 Hz, 2 H), 7.94-8.44 (m, 2 H).<br>LC-MS (method 2) Rt = 1.00 min; MS (ESIpos): m/z = 371.4 [M + H]$^+$ preparative flash chromatography (method Z, 0-3%) 8% yield |
| 72 | 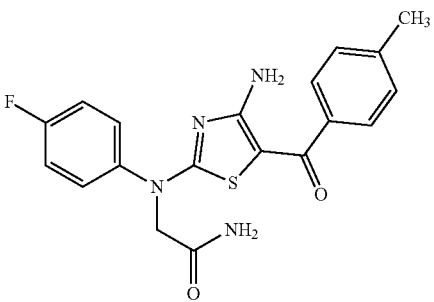 [SMILES: Cc1ccc(C(=O)c2sc(N(CC(N)=O)c3ccc(F)cc3)nc2N)cc1]<br>2-(N-[4-amino-5-(4-methylbenzoyl)thiazol-2-yl]-4-fluoro-anilino)acetamide | Intermediate 86; 2-bromo-acetamide | $^1$H-NMR (400 MHz, DMSO-d6): δ ppm = 2.30 (s, 3 H), 4.44 (s, 2 H), 7.18-7.24 (m, 3 H), 7.32 (t, J = 8.87 Hz, 2 H), 7.42 (d, J = 8.11 Hz, 2 H), 7.55 (s, 1 H), 7.61 (dd, J = 9.13, 5.07 Hz, 2 H), 7.79-8.41 (m, 2 H).<br>LC-MS (method 2) Rt = 1.07 min; MS (ESIpos): m/z = 385.5 [M + H]$^+$ preparative flash chromatography (method Z, 0-3%) 6% yield |
| 73 | 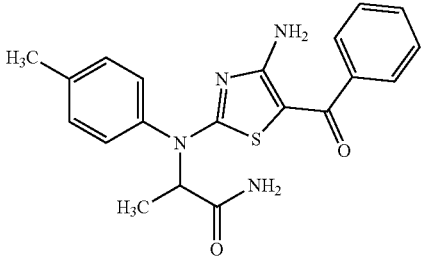 [SMILES: Cc1ccc(N(c2nc(N)c(C(=O)c3ccccc3)s2)C(C)C(N)=O)cc1]<br>rac-2-(N-(4-amino-5-benzoyl-thiazol-2-yl)-4-methyl-anilino)propanamide | Intermediate 91; rac-2-bromo-propanamide | $^1$H-NMR (400 MHz, DMSO-d6): δ ppm = 1.15 (d, J = 7.35 Hz, 3 H), 2.33 (s, 3 H), 5.07 (q, J = 7.01 Hz, 1 H), 7.21 (s, 1 H), 7.27 (d, J = 8.11 Hz, 2 H), 7.35-7.43 (m, 5 H), 7.44-7.48 (m, 2 H), 7.52 (s, 1 H), 8.10 (brs, 2 H).<br>LC-MS (method 2) Rt = 1.10 min; MS (ESIpos): m/z = 381.5 [M + H]$^+$ preparative flash chromatography (method Z, 0-3%) 35% yield |
| 73.1 and 73.2 | (R)-2-(N-(4-amino-5-benzoyl-thiazol-2-yl)-4-methyl-anilino)propanamide and (S)-2-(N-(4-amino-5-benzoyl-thiazol-2-yl)-4-methyl-anilino)propanamide | | |

TABLE 6-continued

Examples 2-80

| Example number | Chemical structure Compound name | Starting materials | Analytics/purification/yield |
|---|---|---|---|
| 73.1 | 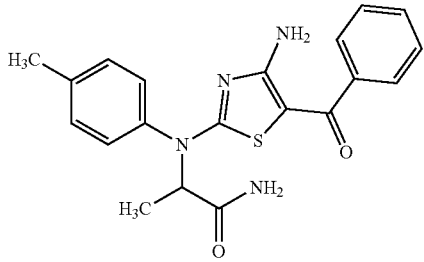 [SMILES: Cc1ccc(N(c2nc(N)c(C(=O)c3ccccc3)s2)C(C)C(N)=O)cc1]<br>2-(N-(4-amino-5-benzoyl-thiazol-2-yl)-4-methyl-anilino)propanamide<br>(enantiomer 1) | Example 73 | $^1$H-NMR (400 MHz, DMSO-d6): δ ppm = 1.15 (d, J = 7.35 Hz, 3 H), 2.33 (s, 3 H), 5.07 (q, J = 7.01 Hz, 1 H), 7.21 (s, 1 H), 7.27 (d, J = 8.11 Hz, 2 H), 7.35-7.43 (m, 5 H), 7.44-7.48 (m, 2 H), 7.52 (s, 1 H), 8.10 (br s, 2 H).<br>$[\alpha]_D^{20}$ = −173.6° (c = 1.00, chloroform)<br>35% yield |

Chiral HPLC Example 73.1

HPLC separation of rac-2-(N-(4-amino-5-benzoyl-thiazol-2-yl)-4-methyl-anilino)propanamide (440 mg, 1.10 mmol; Example 73) on a chiral column gave 160 mg (36% yield) of 2-(N-(4-amino-5-benzoyl-thiazol-2-yl)-4-methyl-anilino)propanamide; enantiomer 1.

Preparative chiral HPLC

Instrument: Sepiatec: Prep SFC100; Column: Chiralpak IA 5μ 250 × 30mm; eluent A: CO$_2$; eluent B: 2-propanol + 0.4 vol % diethylamine; isocratic: 25% B; flow: 100 mL/min; temperature: 40° C.; BPR: 150 bar; UV: 280 nm Analytical chiral HPLC: Rt = 2.88 min Instrument: Agilent: 1260, Aurora SFC-module; column: Chiralpak IA 5μ 100 × 4.6mm; eluent A: CO$_2$; eluent B: 2-propanol + 0.4 vol % diethylamine, isocratic: 25% B; flow: 4 mL/min; temperature: 37.5° C.; BPR: 100 bar; UV: 280 nm

| | | | |
|---|---|---|---|
| 73.2 | 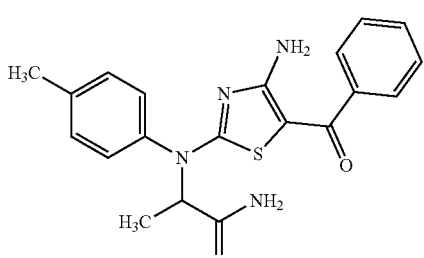<br>2-(N-(4-amino-5-benzoyl-thiazol-2-yl)-4-methyl-anilino)propanamide<br>(enantiomer 2) | Example 73 | $^1$H-NMR (400 MHz, DMSO-d6): δ ppm = 1.15 (d, J = 7.35 Hz, 3 H), 2.33 (s, 3 H), 5.07 (q, J = 7.01 Hz, 1 H), 7.21 (s, 1 H), 7.27 (d, J = 8.1 1 Hz, 2 H), 7.35-7.43 (m, 5 H), 7.44-7.48 (m, 2 H), 7.52 (s, 1 H), 8.10 (br s, 2 H).<br>$[\alpha]_D^{20}$ = +161.4% (c = 1.00, chloroform)<br>8% yield |

Chiral HPLC Example 73.2

HPLC separation of rac-2-(N-(4-amino-5-benzoyl-thiazol-2-yl)-4-methyl-anilino)propanamide (440 mg, 1.10 mmol; Example 73) on a chiral column gave 100 mg (23% yield) of 2-(N-(4-amino-5-benzoyl-thiazol-2-yl)-4-methyl-anilino)propanamide; enantiomer 2.

Preparative chiral HPLC

Instrument: Sepiatec: Prep SFC100; Column: Chiralpak IA 5μ 250 × 30 mm; eluent A: CO$_2$; eluent B: 2-propanol + 0.4 vol % diethylamine; isocratic: 25% B; flow: 100 mL/min; temperature: 40° C.; BPR: 150 bar; UV: 280 nm Analytical chiral HPLC: Rt = 4.57 min Instrument: Agilent: 1260, Aurora SFC-module; column: Chiralpak IA 5μ 100 × 4.6 mm; eluent A: CO$_2$; eluent B: 2-propanol + 0.4 vol % diethylamine, isocratic: 25% B; flow: 4 mL/min; temperature: 37.5° C.; BPR: 100 bar; UV: 280 nm TABLE 6-continued Examples 2-80

| Example number | Chemical structure Compound name | Starting materials | Analytics/purification/yield |
|---|---|---|---|
| 74 | rac-2-(N-(4-amino-5-benzoyl-thiazol-2-yl)-3-fluoro-anilino)propanamide | Intermediate 92; rac-2-bromo-propanamide | $^1$H-NMR (400 MHz, DMSO-d6): δ ppm = 1.18 (d, J = 7.35 Hz, 3 H), 5.05 (q, J = 7.18 Hz, 1 H), 7.28 (s, 1 H), 7.32 (td, J = 8.30, 2.15 Hz, 1 H), 7.37-7.46 (m, 4 H), 7.47-7.56 (m, 4 H), 7.60 (s, 1 H), 7.85-8.35 (m, 2 H). LC-MS (method 2) Rt = 1.06 min; MS (ESIpos): m/z = 385.5 [M + H]$^+$ preparative flash chromatography (method Z, 0-3%) 15% yield |
| 74.1 and 74.2 | (R)-2-(N-(4-amino-5-benzoyl-thiazol-2-yl)-3-fluoro-anilino)propanamide and (S)-2-(N-(4-amino-5-benzoyl-thiazol-2-yl)-3-fluoro-anilino)propanamide | | |
| 74.1 | 2-(N-(4-amino-5-benzoyl-thiazol-2-yl)-3-fluoro-anilino)propanamide (enantiomer 1) | Example 74 | $^1$H-NMR (400 MHz, DMSO-d6): δ ppm = 1.18 (d, J = 7.35 Hz, 3 H), 5.05 (q, J = 7.18 Hz, 1 H), 7.28 (s, 1 H), 7.32 (td, J = 8.30, 2.15 Hz, 1 H), 7.37-7.46 (m, 4 H), 7.47-7.56 (m, 4 H), 7.60 (s, 1 H), 7.85-8.35 (m, 2 H). $[α]_D^{20}$ = −143.6° (c = 1.00, chloroform) 4% yield |

Chiral HPLC Example 74.1
HPLC separation of rac-2-(N-(4-amino-5-benzoyl-thiazol-2-yl)-3-fluoro-anilino)propanamide (260 mg, 0.64 mmol; Example 74) on a chiral column gave 65 mg (25% yield) of 2-(N-(4-amino-5-benzoyl-thiazol-2-yl)-3-fluoro-anilino)propanamide, enantiomer 1.
Preparative chiral HPLC
Instrument PrepCon Labomatic HPLC; Column: YMC Cellulose SC 10µ, 250 × 50; eluent A: hexane; eluent B: 2-propanol; isocratic: 70% A + 30% B; flow: 150 mL/min; temperature: 25° C.; UV: 254 nm
Analytical chiral HPLC: Rt = 5.46 min
Instrument: Waters Alliance 2695; Column: YMC Cellulose SC 3µ, 100 × 4.6; eluent A: hexane; eluent B: 2-propanol; isocratic: 70% A + 30% B; flow: 1.4 mL/min; temperature: 25° C.; UV: 254 nm

| 74.2 | 2-(N-(4-amino-5-benzoyl-thiazol-2-yl)-3-fluoro-anilino)propanamide (enantiomer 2) | Example 74 | $^1$H-NMR (400 MHz, DMSO-d6): δ ppm = 1.18 (d, J = 7.35 Hz, 3 H), 5.05 (q, J = 7.18 Hz, 1 H), 7.28 (s, 1 H), 7.32 (td, J = 8.30, 2.15 Hz, 1 H), 7.37-7.46 (m, 4 H), 7.47-7.56 (m, 4 H), 7.60 (s, 1 H), 7.85-8.35 (m, 2 H). $[α]_D^{20}$ = +151.0° (c = 1.00, chloroform) 4% yield |

Chiral HPLC Example 74.2
HPLC separation of rac-2-(N-(4-amino-5-benzoyl-thiazol-2-yl)-3-fluoro-anilino)propanamide (260 mg, 0.64 mmol; Example 74) on a chiral column gave 65 mg (25% yield) of 2-(N-(4-amino-5-benzoyl-thiazol-2-yl)-3-fluoro-anilino)propanamide, enantiomer 2.
Preparative chiral HPLC

TABLE 6-continued

Examples 2-80

| Example number | Chemical structure Compound name | Starting materials | Analytics/purification/yield |
|---|---|---|---|
| | Instrument: PrepCon Labomatic HPLC; Column: YMC Cellulose SC 10μ, 250 × 50; eluent A: hexane; eluent B: 2-propanol; isocratic: 70% A + 30% B; flow: 150 mL/min; temperature: 25° C.; UV: 254 nm<br>Analytical chiral HPLC: Rt = 6.76 min<br>Instrument: Waters Alliance 2695; Column: YMC Cellulose SC 3μ, 100 × 4.6; eluent A: hexane; eluent B: 2-propanol; isocratic: 70% A + 30% B; flow: 1.4 mL/min; temperature: 25° C.; UV: 254 nm | | |
| 75 | rac-2-(N-(4-amino-5-benzoyl-thiazol-2-yl)-2-fluoro-anilino)propanamide | Intermediate 93; rac-2-bromo-propanamide | $^1$H-NMR (500 MHz, DMSO-d6): δ ppm = 1.22 (d, J = 7.31 Hz, 3 H), 5.04 (q, J = 7.10 Hz, 1 H), 6.87-7.30 (m, 2 H), 7.32 (td, J = 7.63, 1.27 Hz, 1 H), 7.34-7.43 (m, 4 H), 7.49-7.55 (m, 3 H), 7.77 (td, J = 7.95, 1.59 Hz, 1 H), 7.92 (br s, 2 H). LC-MS (method 2) Rt = 1.04 min; MS (ESIpos): m/z = 385.4 [M + H]$^+$ preparative flash chromatography (method Z, 0-3%) 52% yield |
| 75.1 and 75.2 | (R)-2-(N-(4-amino-5-benzoyl-thiazol-2-yl)-2-fluoro-anilino)propanamide and (S)-2-(N-(4-amino-5-benzoyl-thiazol-2-yl)-2-fluoro-anilino)propanamide | | |
| 75.1 | 2-(N-(4-amino-5-benzoyl-thiazol-2-yl)-2-fluoro-anilino)propanamide (enantiomer 1) | Example 75 | $^1$H-NMR (500 MHz, DMSO-d6): δ ppm = 1.22 (d, J = 7.31 Hz, 3 H), 5.04 (q, J = 7.10 Hz, 1 H), 6.87-7.30 (m, 2 H), 7.32 (td, J = 7.63, 1.27 Hz, 1 H), 7.34-7.43 (m, 4 H), 7.49-7.55 (m, 3 H), 7.77 (td, J = 7.95, 1.59 Hz, 1 H), 7.92 (brs, 2 H). $[\alpha]_D^{20}$ = −116.9° (c = 1.00, chloroform) 13% yield |
| | Chiral HPLC Example 75.1<br>HPLC separation of rac-2-(N-(4-amino-5-benzoyl-thiazol-2-yl)-2-fluoro-anilino)propanamide (560 mg, 1.38 mmol; Example 75) on a chiral column gave 135 mg (24% yield) of 2-(N-(4-amino-5-benzoyl-thiazol-2-yl)-2-fluoro-anilino)propanamide, enantiomer 1.<br>Preparative chiral HPLC<br>Instrument PrepCon Labomatic HPLC; Column: YMC Cellulose SB 5μ, 250 × 30; eluent A: hexane + 0.1 vol % diethylamine; eluent B: 2-propanol; isocratic: 70% A + 30% B; flow: 50 mL/min; temperature: 25° C.; UV: 254 nm<br>Analytical chiral HPLC: Rt = 3.50 min<br>Instrument: Waters Alliance 2695; Column: YMC Cellulose SB 3μ, 100 × 4.6; eluent A: hexane + 0.1 vol % diethylamine; eluent B: 2-propanol; isocratic: 70% A + 30% B; flow: 1.4 mL/min; temperature: 25° C.; UV: 254 nm | | |
| 75.2 | | Example 75 | $^1$H-NMR (500 MHz, DMSO-d6): δ ppm = 1.22 (d, J = 7.31 Hz, 3 H), 5.04 (q, J = 7.10 Hz, 1 H), 6.87-7.30 (m, 2 H), 7.32 (td, J = 7.63, 1.27 Hz, 1 H), 7.34-7.43 (m, 4 H), 7.49-7.55 (m, 3 H), 7.77 (td, J = 7.95, 1.59 Hz, 1 H), 7.92 (br s, 2 H). $[\alpha]_D^{20}$ = +109.3° (c = 1.00, chloroform) 15% yield |

TABLE 6-continued

Examples 2-80

| Example number | Chemical structure Compound name | Starting materials | Analytics/purification/yield |
|---|---|---|---|
| | 2-(N-(4-amino-5-benzoyl-thiazol-2-yl)-2-fluoro-anilino)propanamide (enantiomer 2) Chiral HPLC Example 75.2 HPLC separation of rac-2-(N-(4-amino-5-benzoyl-thiazol-2-yl)-2-fluoro-anilino)propanamide (560 mg, 1.38 mmol; Example 75) on a chiral column gave 165 mg (31% yield) of 2-(N-(4-amino-5-benzoyl-thiazol-2-yl)-2-fluoro-anilino)propanamide, enantiomer 2. Preparative chiral HPLC Instrument PrepCon Labomatic HPLC; Column: YMC Cellulose SB 5μ, 250 × 30; eluent A: hexane + 0.1 vol % diethylamine; eluent B: 2-propanol; isocratic: 70% A + 30% B; flow: 50 mL/min; temperature: 25° C.; UV: 254 nm Analytical chiral HPLC: Rt = 4.39 min Instrument: Waters Alliance 2695; Column: YMC Cellulose SB 3μ, 100 × 4.6; eluent A: hexane + 0.1 vol % diethylamine; eluent B: 2-propanol; isocratic: 70% A + 30% B; flow: 1.4 mL/min; temperature: 25° C.; UV: 254 nm | | |
| 76 | 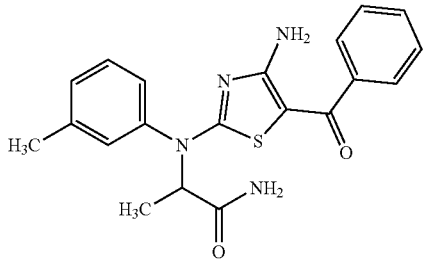 [SMILES: Cc1cccc(N(c2nc(N)c(C(=O)c3ccccc3)s2)C(C)C(N)=O)c1]<br>rac-2-(N-(4-amino-5-benzoyl-thiazol-2-yl)-3-methyl-anilino)propanamide | Intermediate 72; rac-2-bromo-propanamide | $^1$H-NMR (400 MHz, DMSO-d6): δ ppm = 1.16 (d, J = 7.35 Hz, 3 H), 2.31 (s, 3 H), 5.05 (q, J = 7.18 Hz, 1 H), 7.22 (s, 1 H), 7.23-7.27 (m, 1 H), 7.33-7.41 (m, 6 H), 7.45-7.50 (m, 2 H), 7.53 (s, 1 H), 7.70-8.47 (m, 2 H). LC-MS (method 2) Rt = 1.10 min; MS (ESIpos): m/z = 381.5 [M + H]$^+$ preparative flash chromatography (method Z, 0-3%) 71% yield |
| 76.1 and 76.2 | (R)-2-(N-(4-amino-5-benzoyl-thiazol-2-yl)-3-methyl-anilino)propanamide and (S)-2-(N-(4-amino-5-benzoyl-thiazol-2-yl)-3-methyl-anilino)propanamide | | |
| 76.1 | 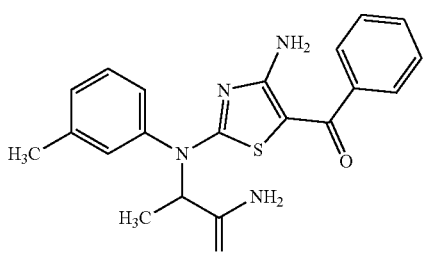<br>2-(N-(4-amino-5-benzoyl-thiazol-2-yl)-3-methyl-anilino)propanamide (enantiomer 1) Chiral HPLC Example 76.1 HPLC separation of rac-2-(N-(4-amino-5-benzoyl-thiazol-2-yl)-3-methyl-anilino)propanamide (1170 mg, 3.00 mmol; Example 76) on a chiral column gave 525 mg (44% yield) of 2-(N-(4-amino-5-benzoyl-thiazol-2-yl)-3-methyl-anilino)propanamide, enantiomer 1. Preparative chiral HPLC Instrument: PrepCon Labomatic HPLC; Column: YMC Cellulose SC 10μ, 250 × 50; eluent A: methyl tert-butyl ether; eluent B: acetonitrile; isocratic: 95% A + 5% B; flow: 150 mL/min; temperature: 25° C.; UV: 254 nm Analytical chiral HPLC: Rt = 6.56 min Instrument: Waters Alliance 2695; Column: YMC Cellulose SC 3μ, 100 × 4.6; eluent A: methyl tert-butyl ether; eluent B: acetonitrile; isocratic: 95% A + 5% B; flow: 1.4 mL/min; temperature: 25° C.; UV: 254 nm | Example 76 | $^1$H-NMR (400 MHz, DMSO-d6): δ ppm = 1.16 (d, J = 7.35 Hz, 3 H), 2.31 (s, 3 H), 5.05 (q, J = 7.18 Hz, 1 H), 7.22 (s, 1 H), 7.23-7.27 (m, 1 H), 7.33-7.41 (m, 6 H), 7.45-7.50 (m, 2 H), 7.53 (s, 1 H), 7.70-8.47 (m, 2 H). $[α]_D^{20}$ = +177.3° (c = 1.00, chloroform) 31% yield |

TABLE 6-continued

Examples 2-80

| Example number | Chemical structure Compound name | Starting materials | Analytics/purification/yield |
|---|---|---|---|
| 76.2 | 2-(N-(4-amino-5-benzoyl-thiazol-2-yl)-3-methyl-anilino)propanamide (enantiomer 2) | Example 76 | $^1$H-NMR (400 MHz, DMSO-d6): δ ppm = 1.16 (d, J = 7.35 Hz, 3 H), 2.31 (s, 3 H), 5.05 (q, J = 7.18 Hz, 1 H), 7.22 (s, 1 H), 7.23-7.27 (m, 1 H), 7.33-7.41 (m, 6 H), 7.45-7.50 (m, 2 H), 7.53 (s, 1 H), 7.70-8.47 (m, 2 H). $[α]_D^{20}$ = +177.3% (c = 1.00, chloroform) 34% yield |

Chiral HPLC Example 76.2
HPLC separation of rac-2-(N-(4-amino-5-benzoyl-thiazol-2-yl)-3-methyl-anilino)propanamide (1170 mg, 3.00 mmol; Example 76) on a chiral column gave 525 mg (45% yield) of 2-(N-(4-amino-5-benzoyl-thiazol-2-yl)-3-methyl-anilino)propanamide, enantiomer 2.
Preparative chiral HPLC
Instrument: PrepCon Labomatic HPLC; Column: YMC Cellulose SC 10μ, 250 × 50; eluent A: methyl tert-butyl ether; eluent B: acetonitrile; isocratic: 95% A + 5% B; flow: 150 mL/min; temperature: 25° C.; UV: 254 nm
Analytical chiral HPLC: Rt = 8.91 min
Instrument: Waters Alliance 2695; Column: YMC Cellulose SC 3μ, 100 × 4.6; eluent A: methyl tert-butyl ether; eluent B: acetonitrile; isocratic: 95% A + 5% B; flow: 1.4 mL/min; temperature: 25° C.; UV: 254 nm

| | | | |
|---|---|---|---|
| 77 | rac-2-(N-(4-amino-5-benzoyl-thiazol-2-yl)-2-methyl-anilino)propanamide | Intermediate 73; rac-2-bromo-propanamide | $^1$H-NMR (400 MHz, DMSO-d6): δ ppm = 0.97-1.08 (m, 3 H), 2.17 (s, 3 H), 4.97-5.12 (m, 1 H), 7.24 (br s, 1 H), 7.33-7.40 (m, 6 H), 7.46 (br d, J = 5.32 Hz, 2 H), 7.57 (br s, 1 H), 7.71-7.77 (m, 1 H), 7.85-8.48 (m, 2 H). LC-MS (method 2) Rt = 1.08 min; MS (ESIpos): m/z = 381.4 [M + H]+ preparative flash chromatography (method Z, 0-3%) 56% yield |
| 77.2 | thiazol-2-yl)-2-methyl-aniiino)propanamide and (S)-2-(N-(4-amino-5-benzoyl-thiazol-2-yl)-2-methyl-anilino)propanamide | | |
| 77.1 | 2-(N-(4-amino-5-benzoyl-thiazol-2-yl)-2-methyl-anilino)propanamide (enantiomer 1) | Example 77 | $^1$H-NMR (400 MHz, DMSO-d6): δ ppm = 0.97-1.08 (m, 3 H), 2.17 (s, 3 H), 4.97-5.12 (m, 1 H), 7.24 (br s, 1 H), 7.33-7.40 (m, 6 H), 7.46 (br d, J = 5.32 Hz, 2 H), 7.57 (br s, 1 H), 7.71-7.77 (m, 1 H), 7.85-8.48 (m, 2 H). $[α]_D^{20}$= +166.1° (c = 1.00, chloroform) 23% yield |

Chiral HPLC Example 77.1
HPLC separation of rac-2-(N-(4-amino-5-benzoyl-thiazol-2-yl)-2-methyl-anilino)propanamide (1010 mg, 2.52 mmol; Example 77) on a chiral column gave 420 mg (42% yield) of 2-(N-(4-amino-5-benzoyl-thiazol-2-yl)-2-methyl-anilino)propanamide, enantiomer 1.

TABLE 6-continued

Examples 2-80

| Example number | Chemical structure Compound name | Starting materials | Analytics/purification/yield |
|---|---|---|---|
| | Preparative chiral HPLC Instrument: PrepCon Labomatic HPLC; Column: Chiralpak IG 5µ, 250 × 30; eluent A: hexane + 0.1 vol % diethylamine; eluent B: ethanol + 0.1 vol % diethylamine; isocratic: 85% A + 15% B; flow: 60 m L/min; temperature: 25° C.; UV: 254 nm Analytical chiral HPLC: Rt = 7.09 min Instrument: Waters Alliance 2695; Column: Chiralpak IG 3µ, 100 × 4.6; eluent A: hexane + 0.1 vol % diethylamine; eluent B: ethanol; isocratic: 85% A + 15% B; flow: 1.4 mL/min; temperature: 25° C.; UV: 254 nm | | |
| 77.2 | 2-(N-(4-amino-5-benzoyl-thiazol-2-yl)-2-methyl-anilino)propanamide (enantiomer 1) | Example 77 | $^1$H-NMR (400 MHz, DMSO-d6): δ ppm = 0.97-1.08 (m, 3 H), 2.17 (s, 3 H), 4.97-5.12 (m, 1 H), 7.24 (br s, 1 H), 7.33-7.40 (m, 6 H), 7.46 (br d, J = 5.32 Hz, 2 H), 7.57 (brs, 1 H), 7.71-7.77 (m, 1 H), 7.85-8.48 (m, 2 H). $[α]_D^{20}$ = −152.0° (c = 1.00, chloroform) 23% yield |
| | Chiral HPLC Example 77.2 HPLC separation of rac-2-(N-(4-amino-5-benzoyl-thiazol-2-yl)-2-methyl-anilino)propanamide (1010 mg, 2.52 mmol; Example 77) on a chiral column gave 420 mg (42% yield) of 2-(N-(4-amino-5-benzoyl-thiazol-2-yl)-2-methyl-anilino)propanamide, enantiomer 2. Preparative chiral HPLC Instrument: PrepCon Labomatic HPLC; Column: Chiralpak IG 5µ, 250 × 30; eluent A: hexane + 0.1 vol % diethylamine; eluent B: ethanol + 0.1 vol % diethylamine; isocratic: 85% A + 15% B; flow: 60 m L/min; temperature: 25° C.; UV: 254 nm Analytical chiral HPLC: Rt = 10.30 min Instrument: Waters Alliance 2695; Column: Chiralpak IG 3µ, 100 × 4.6; eluent A: hexane + 0.1 vol % diet ylamine; eluent B: ethanol; isocratic: 85% A + 15% B; flow: 1.4 mL/min; temperature: 25° C.; UV: 254 nm | | |
| 78 | rac-2-[(4-amino-5-benzoyl-thiazol-2-yl)-(1-methylpyrazol-4-yl)amino]propanamide | Intermediate 94; rac-2-bromo-propanamide | $^1$H-NMR (400 MHz, DMSO-d6): δ ppm = 1.19 (d, J = 7.35 Hz, 3 H), 3.83 (s, 3 H), 4.99-5.18 (m, 1 H), 7.18 (s, 1 H), 7.37-7.44 (m, 3 H), 7.48 (s, 1 H), 7.49-7.53 (m, 3 H), 7.80-8.48 (m, 2 H), 7.90 (s, 1 H). LC-MS (method 2) Rt = 0.80 min; MS (ESIpos): m/z = 371.3 [M + H]$^+$ preparative flash chromatography (method Z, 0-3%) 17% yield |
| 78.1 and 78.2 | (R)-2-[(4-amino-5-benzoyl-thiazol-2-yl)-(1-methylpyrazol-4-yl)amino]propanamide and (S)-2-[(4-amino-5-benzoyl-thiazol-2-yl)-(1-methylpyrazol-4-yl)amino]propanamide | | |

TABLE 6-continued

Examples 2-80

| Example number | Chemical structure Compound name | Starting materials | Analytics/purification/yield |
|---|---|---|---|
| 78.1 | 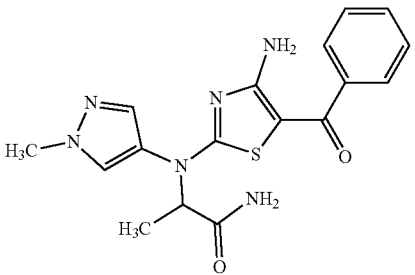 [SMILES: CC(C(N)=O)N(c1cnn(C)c1)c1nc(N)c(C(=O)c2ccccc2)s1]<br>2-[(4-amino-5-benzoyl-thiazol-2-yl)-(1-methylpyrazol-4-yl)amino]propanamide<br>(enantiomer 1) | Example 78 | $^1$H-NMR (400 MHz, DMSO-d6): δ ppm = 1.19 (d, J = 7.35 Hz, 3 H), 3.83 (s, 3 H), 4.99-5.18 (m, 1 H), 7.18 (s, 1 H), 7.37-7.44 (m, 3H), 7.48 (s, 1 H), 7.49-7.53 (m, 3 H), 7.80-8.48 (m, 2 H), 7.90 (s, 1 H).<br>$[\alpha]_D^{20}$ = −82.8° (c = 1.00, chloroform)<br>6% yield |

Chiral HPLC Example 78.1

HPLC separation of rac-2-[(4-amino-5-benzoyl-thiazol-2-yl)-(1-methylpyrazol-4-yl)amino]propanamide (240 mg, 0.64 mmol; Example 78) on a chiral column gave 89 mg (36% yield) of 2-[(4-amino-5-benzoyl-thiazol-2-yl)-(1-methylpyrazol-4-yl)amino]propanamide, enantiomer 1.

Preparative chiral HPLC

Instrument: Sepiatec: Prep SFC100; Column: Chiralpak IC 5µ 250 × 30mm; eluent A: CO$_2$; eluent B: methanol + 0.2 vol % aqueous ammonia (32%); isocratic: 40% B; flow: 100 mL/min; temperature: 40° C.; BPR: 150 bar; UV: 254 nm Analytical chiral HPLC: Rt = 1.77 min Instrument: Agilent: 1260, Aurora SFC-Modul; Column: Chiralpak IC 5µ 100 × 4.6 mm; eluent A: CO2 eluent B: methanol + 0.2 vol % aqueous ammonia (32%); isocratic: 40% B; flow: 4 mL/min; temperature: 37.5° C.; BPR: 100 bar; UV: 254 nm

| 78.2 | 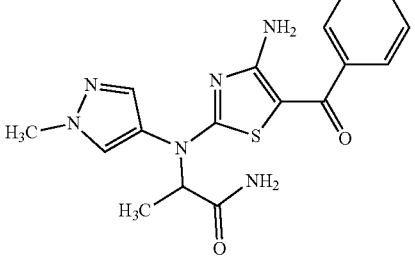<br>2-[(4-amino-5-benzoyl-thiazol-2-yl)-(1-methylpyrazol-4-yl)amino]propanamide<br>(enantiomer 2) | Example 78 | $^1$H-NMR (400 MHz, DMSO-d6): δ ppm = 1.19 (d, J = 7.35 Hz, 3 H), 3.83 (s, 3 H), 4.99-5.18 (m, 1 H), 7.18 (s, 1 H), 7.37-7.44 (m, 3 H), 7.48 (s, 1 H), 7.49-7.53 (m, 3 H), 7.80-8.48 (m, 2 H), 7.90 (s, 1 H).<br>$[\alpha]_D^{20}$ = +72.6° (c = 1.00, chloroform)<br>6% yield |

Chiral HPLC Example 78.2

HPLC separation of rac-2-[(4-amino-5-benzoyl-thiazol-2-yl)-(1-methylpyrazol-4-yl)amino]propanamide (240 mg, 0.64 mmol; Example 78) on a chiral column gave 80 mg (33% yield) of 2-[(4-amino-5-benzoyl-thiazol-2-yl)-(1-methylpyrazol-4-yl)amino]propanamide, enantiomer 2.

Preparative chiral HPLC

Instrument: Sepiatec: Prep SFC100; Column: Chiralpak IC 5µ 250 × 30mm; eluent A: CO$_2$; eluent B: methanol + 0.2 vol % aqueous ammonia (32%); isocratic: 40% B; flow: 100 mL/min; temperature: 40° C.; BPR: 150 bar; UV: 254 nm Analytical chiral HPLC: Rt = 2.66 min Instrument: Agilent: 1260, Aurora SFC-Modul; Column: Chiralpak IC 5µ 100 × 4.6 mm; eluent A: CO$_2$; eluent B: methanol + 0.2 vol % aqueous ammonia (32%); isocratic: 40% B; flow: 4 mL/min; temperature: 37.5° C.; BPR: 100 bar; UV: 254 nm TABLE 6-continued Examples 2-80

| Example number | Chemical structure Compound name | Starting materials | Analytics/purification/yield |
|---|---|---|---|
| 79 | rac-2-[(4-amino-5-benzoyl-thiazol-2-yl)-(3-pyridyl)amino]propanamide | Intermediate 95; rac-2-bromo-propanamide | $^1$H-NMR (400 MHz, DMSO-d6): δ ppm = 1.17 (d, J =7.35 Hz, 3 H), 5.07 (q, J =7.10 Hz, 1 H), 5.76 (s, 1 H), 7.30 (s, 1 H), 7.35-7.43 (m, 3 H), 7.47-7.51 (m, 2 H), 7.54 (dd, J = 8.1 1, 4.82 Hz, 1 H), 7.64 (s, 1 H), 7.90-8.44 (m, 2 H), 8.04-8.08 (m, 1 H), 8.63 (dd, J = 4.56, 1.52 Hz, 1 H), 8.74 (d, J = 2.03 Hz, 1 H). LC-MS (method 2) Rt = 0.84 min; MS (ESIpos): m/z = 368.5 [M + H]$^+$ preparative flash chromatography (method Z, 0-3%) 10% yield |
| 79.1 and 79.2 | (R)-2-[(4-amino-5-benzoyl-thiazol-2-yl)-(3-pyridyl)amino]propanamide and (S)-2-[(4-amino-5-benzoyl-thiazol-2-yl)-(3-pyridyl)amino]propanamide | | |
| 79.1 | 2-[(4-amino-5-benzoyl-thiazol-2-yl)-(3-pyridyl)amino]propanamide (enantiomer 1) | Example 79 | $^1$H-NMR (400 MHz, DMSO-d6): δ ppm = 1.17 (d, J = 7.35 Hz, 3 H), 5.07 (q, J = 7.10 Hz, 1 H), 5.76 (s, 1 H), 7.30 (s, 1 H), 7.35-7.43 (m, 3 H), 7.47-7.51 (m, 2 H), 7.54 (dd, J = 8.11, 4.82 Hz, 1 H), 7.64 (s, 1 H), 7.90-8.44 (m, 2 H), 8.04-8.08 (m, 1 H), 8.63 (dd, J = 4.56, 1.52 Hz, 1 H), 8.74 (d, J = 2.03 Hz, 1 H). $[α]_D^{20}$ = −119.3° (c = 1.00, chloroform) 3% yield |

Chiral HPLC Example 79.1

HPLC separation of rac-2-[(4-amino-5-benzoyl-thiazol-2-yl)-(3-pyridyl)amino]propanamide (200 mg, 0.52 mmol; Example 79) on a chiral column gave 50 mg (25% yield) of 2-[(4-amino-5-benzoyl-thiazol-2-yl)-(3-pyridyl)amino]propanamide, enantiomer 1.

Preparative chiral HPLC

Instrument: PrepCon Labomatic HPLC; Column: YMC Cellulose SB 10μ, 250 × 50; eluent A: hexane + 0.1 vol % diethylamine; eluent B: ethanol; isocratic: 60% A + 40% B; flow: 150 mL/min; temperature: 25° C.; UV: 254 nm Analytical chiral HPLC: Rt = 2.15 min Instrument: Waters Alliance 2695; Column: YMC Cellulose SB 3μ, 100 × 4.6; eluent A: hexane + 0.1 vol % diethylamine; eluent B: ethanol; isocratic: 60% A + 40% B; flow: 1.4 ml/min; temperature: 25° C.; UV: 254 nm TABLE 6-continued Examples 2-80

| Example number | Chemical structure Compound name | Starting materials | Analytics/purification/yield |
|---|---|---|---|
| 79.2 | 2-[(4-amino-5-benzoyl-thiazol-2-yl)-(3-pyridyl)amino]propanamide (enantiomer 2) | Example 79 | $^1$H-NMR (400 MHz, DMSO-d6): δ ppm = 1.17 (d, J = 7.35 Hz, 3 H), 5.07 (q, J = 7.10 Hz, 1 H), 5.76 (s, 1 H), 7.30 (s, 1 H), 7.35-7.43 (m, 3 H), 7.47-7.51 (m, 2 H), 7.54 (dd, J = 8.11, 4.82 Hz, 1 H), 7.64 (s, 1 H), 7.90-8.44 (m, 2 H), 8.04-8.08 (m, 1 H), 8.63 (dd, J = 4.56, 1.52 Hz, 1 H), 8.74 (d, J = 2.03 Hz, 1 H). $[\alpha]_D^{20}$ = +138.1% (c = 1.00, chloroform) 3% yield |

Chiral HPLC Example 79.2

HPLC separation of rac-2-[(4-amino-5-benzoyl-thiazol-2-yl)-(3-pyridyl)amino]propanamide (200 mg, 0.52 mmol; Example 79) on a chiral column gave 50 mg (25% yield) of 2-[(4-amino-5-benzoyl-thiazol-2-yl)-(3-pyridyl)amino]propanamide, enantiomer 2.

Preparative chiral HPLC

Instrument: PrepCon Labomatic HPLC; Column: YMC Cellulose SB 10μ, 250 × 50; eluent A: hexane + 0.1 vol % diethylamine; eluent B: ethanol; isocratic: 60% A + 40% B; flow: 150 mL/min; temperature: 25° C.; UV: 254 nm Analytical chiral HPLC: Rt = 2.15 min Instrument: Waters Alliance 2695; Column: YMC Cellulose SB 3μ, 100 × 4.6; eluent A: hexane + 0.1 vol % diethylamine; eluent B: ethanol; isocratic: 60% A + 40% B; flow: 1.4 ml/min; temperature: 25° C.; UV: 254 nm

| | | | |
|---|---|---|---|
| 80 | rac-2-(N-[4-amino-5-(4-bromobenzoyl)thiazol-2-yl]-4-fluoro-anilino)propanamide | Intermediate 96; rac-2-bromo-propanamide | $^1$H-NMR (400 MHz, DMSO-d6): δ ppm = 1.16 (d, J = 7.35 Hz, 3 H), 5.06 (q, J = 6.25 Hz, 1 H), 7.25 (s, 1 H), 7.33 (t, J = 8.74 Hz, 2 H), 7.40-7.46 (m, 2 H), 7.57-7.67 (m, 5 H), 7.82-8.54 (m, 2 H). LC-MS (method 2) Rt = 1.20 min; MS (ESIpos): m/z = 463.4 [M + H]$^+$ preparative flash chromatography (method Z, 0-3%) 19% yield |

Example 81 rac-ethyl 2-[4-[4-amino-2-(4-fluoro-N-[2-amino-1-methyl-2-oxo-ethyl]anilino)thiazole-5-carbonyl]phenoxy]acetate

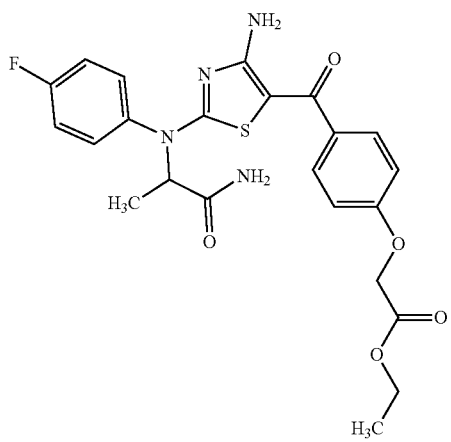

Ethyl 2-[4-[4-amino-2-(4-fluoroanilino)thiazole-5-carbonyl]phenoxy]acetate (18.54 g, 44.6 mmol; Intermediate 80) was dissolved in N,N-dimethylformamide (493 mL), followed by the addition of potassium carbonate (30.84 g, 223.1 mmol) and rac-2-bromopropanamide (8.14 g, 53.6 mmol). The reaction mixture was stirred at 90° C. for 1 h. After cooling down the reaction mixture was partitioned between water and ethyl acetate. The organic layer was separated and washed with saturated aqueous ammonium chloride solution and brine. Afterwards, the organic layer was filtrated by a water repellent filter circle (MN 617 WA) and evaporated to dryness. Water was added to the residue and the resulting suspension was dried by lyophilization to give 6.16 g (27% yield) of rac-ethyl 2-[4-[4-amino-2-(4-fluoro-N-[2-amino-1-methyl-2-oxo-ethyl]anilino)thiazole-5-carbonyl]phenoxy]-acetate.

$^1$H-NMR (400 MHz, DMSO-d6): δ ppm=1.16 (d, J=7.86 Hz, 3H), 1.18 (t, J=6.84 Hz, 3H), 4.15 (q, J=7.10 Hz, 2H), 4.80 (s, 2H), 5.06 (q, J=6.25 Hz, 1H), 6.91 (d, J=8.87 Hz, 2H), 7.25 (s, 1H), 7.33 (t, J=8.74 Hz, 2H), 7.47 (d, J=8.87 Hz, 2H), 7.58 (s, 1H), 7.64 (dd, J=8.87, 5.07 Hz, 2H), 8.15 (br s, 2H).

LC-MS (method 2) Rt=1.09 min; MS (ESIpos): m/z=487.5 [M+H]$^+$

Example 81.1 and 81.2

(R)-ethyl 2-[4-[4-amino-2-(4-fluoro-N-[2-amino-1-methyl-2-oxo-ethyl]anilino)thiazole-5-carbonyl]phenoxy]acetate and (S)-ethyl 2-[4-[4-amino-2-(4-fluoro-N-[2-amino-1-methyl-2-oxo-ethyl]anilino)thiazole-5-carbonyl]phenoxy]acetate

Example 81.1 ethyl 2-[4-[4-amino-2-(4-fluoro-N-[2-amino-1-methyl-2-oxo-ethyl]anilino)thiazole-5-carbonyl]phenoxy]acetate (enantiomer 1)

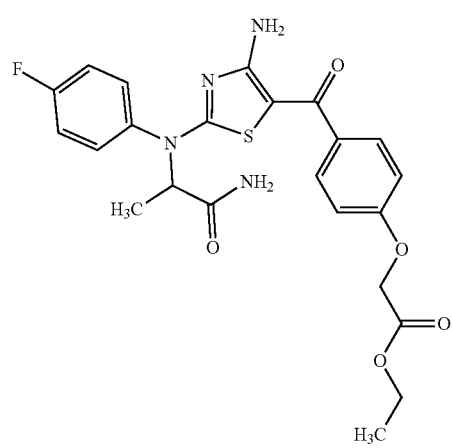 [SMILES: CCOC(=O)COc1ccc(C(=O)c2sc(N(c3ccc(F)cc3)C(C)C(N)=O)nc2N)cc1]

enantiometer 1

HPLC separation of rac-ethyl 2-[4-[4-amino-2-(4-fluoro-N-[2-amino-1-methyl-2-oxo-ethyl]anilino)thiazole-5-carbonyl]phenoxy]acetate (6.16 g, 12.66 mmol; Example 81) on a chiral column gave 2.50 g (39% yield) of ethyl 2-[4-[4-amino-2-(4-fluoro-N-[2-amino-1-methyl-2-oxo-ethyl]anilino)thiazole-5-carbonyl]phenoxy]acetate, enantiomer 1.

Preparative Chiral HPLC

Labomatic HD3000, Knauer Pump 100, Labcol Vario 4000 Plus, Knauer DAD 2600; column: Amylose SB 5μ 250×50 mm Nr.34; Eluent A: hexane; Eluent B: ethanol; isocratic: 70% A+30% B; flow 150.0 mL/min; UV @ 254 nm Analytical chiral HPLC: Rt=7.31 min Instrument: Agilent HPLC 1260; column: Amylose SB 3μ 100×4, 6 mm; Eluent A: hexane; Eluent B: ethanol; isocratic: 70% A+30% B; flow 1.4 mL/min; temperature: 25° C.; DAD 254 nm

Example 81.2 ethyl 2-[4-[4-amino-2-(4-fluoro-N-[2-amino-1-methyl-2-oxo-ethyl]anilino)thiazole-5-carbonyl]phenoxy]acetate (enantiomer 2)

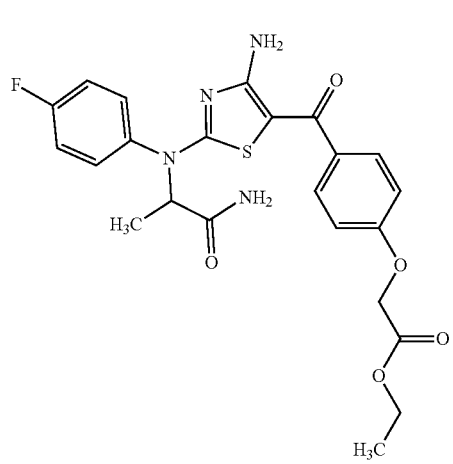

enantiomer 2

HPLC separation of rac-ethyl 2-[4-[4-amino-2-(4-fluoro-N-[2-amino-1-methyl-2-oxo-ethyl]anilino)thiazole-5-carbonyl]phenoxy]acetate (6.16 g, 12.66 mmol; Example 81) on a chiral column gave 2.60 g (40% yield) of ethyl 2-[4-[4-amino-2-(4-fluoro-N-[2-amino-1-methyl-2-oxo-ethyl]anilino)thiazole-5-carbonyl]phenoxy]acetate, enantiomer 2.

Preparative Chiral HPLC

Labomatic HD3000, Knauer Pump 100, Labcol Vario 4000 Plus, Knauer DAD 2600; column: Amylose SB 5μ 250×50 mm Nr.34; Eluent A: hexane; Eluent B: ethanol; isocratic: 70% A+30% B; flow 150.0 mL/min; UV @ 254 nm Analytical chiral HPLC: Rt=10.17 min Instrument: Agilent HPLC 1260; column: Amylose SB 3μ 100×4, 6 mm; Eluent A: hexane; Eluent B: ethanol; isocratic: 70% A+30% B; flow 1.4 mL/min; temperature: 25° C.; DAD 254 nm

Example 82 rac-2-(N-[4-amino-5-[4-[2-(isopropylamino)-2-oxo-ethoxy]benzoyl]thiazol-2-yl]-4-fluoro-anilino)propanamide

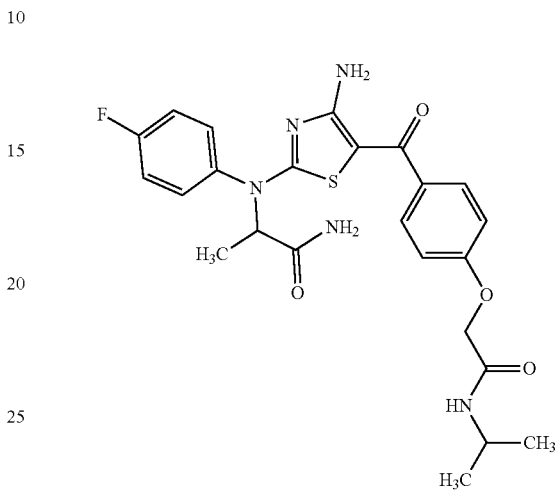

Rac-2-[4-[4-amino-2-(N-[2-amino-1-methyl-2-oxo-ethyl]-4-fluoro-anilino)thiazole-5-carbonyl]phenoxy]acetic acid (12 mg, 26 μmol, intermediate 100) and isopropylamine (3 mg, 51 μmol) were dissolved in dimethylformamide (0.4 mL). N,N-diisopropylethylamine (13 mg, 102 μmol), 4-dimethylaminopyridine (0.2 mg, 1 μmol) and HATU (19 mg, 51 μmol) were added. The reaction mixture was stirred at rt for 2 h.

The reaction mixture was filtrated and purified by RP-HPLC (method C, basic) to give 6 mg (42% yield) of the title compound.

$^1$H-NMR (400 MHz, DMSO-d6): δ ppm=1.04-1.07 (m, 6H), 1.16 (d, J=7.35 Hz, 3H), 3.86-3.97 (m, 1H), 4.45 (s, 2H), 5.05 (q, J=6.34 Hz, 1H), 6.92 (d, J=8.87 Hz, 2H), 7.24 (s, 1H), 7.33 (t, J=8.87 Hz, 2H), 7.47 (d, J=8.87 Hz, 2H), 7.58 (s, 1H), 7.64 (dd, J=8.87, 5.07 Hz, 2H), 7.88 (br d, J=7.86 Hz, 1H), 8.13 (br s, 2H).

LC-MS (method 2) Rt=1.00 min; MS (ESIpos): m/z=500.6 [M+H]$^+$

The following examples were prepared from the starting materials stated in Table 7, below, using the procedure as for Example 82.

The crude product was purified by method F (individual gradient given, depending on retention time in analytical HPLC) after filtration of the reaction mixture.

TABLE 7

Examples 83-141

| Example number | Chemical structure / Compound name | Starting materials | Analytics/ purification/yield |
|---|---|---|---|
| 83 | rac-2-(N-[4-amino-5-[4-[2-(m-tolylmethylamino)-2-oxo-ethoxy]benzoyl]thiazol-2-yl]-4-fluoro-anilino)propanamide | Intermediate 100, 1-(3-methylphenyl)methanamine | LC-MS (method 3) Rt = 1.12 min; MS (ESIpos): m/z = 562.2 [M + H]$^+$ Method F: Prep_30-60% B 11% yield |
| 84 | rac-2-(N-[4-amino-5-[4-[2-(o-tolylmethylamino)-2-oxo-ethoxy]benzoyl]thiazol-2-yl]-4-fluoro-anilino)propanamide | Intermediate 100, 1-(2-methylphenyl)methanamine | LC-MS (method 3) Rt = 1.11 min; MS (ESIpos): m/z = 562.1 [M + H]$^+$ Method F: Prep_30-60% B 11% yield |
| 85 | rac-2-(N-(4-amino-5-[4-[2-1(3-chlorophenyl)methylamino]-2-oxo-ethoxy]benzoyl]thiazol-2-yl)-4-fluoro-anilino)propanamide | Intermediate 100, 1-(3-chlorophenyl)methanamine | LC-MS(method 3) Rt = 1.13 min; MS (ESIpos): m/z = 582.1 [M + H]$^+$ Method F: Prep_35-65% B 10% yield |

TABLE 7-continued

Examples 83-141

| Example number | Chemical structure / Compound name | Starting materials | Analytics/ purification/yield |
|---|---|---|---|
| 86 | 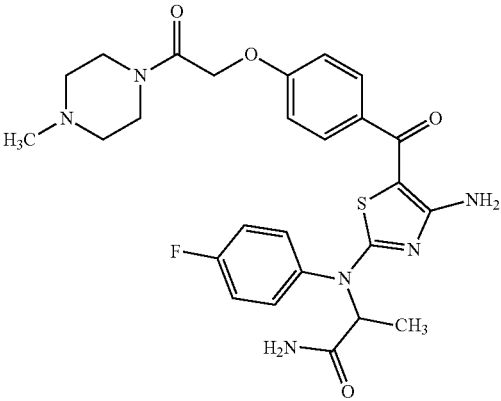 [SMILES: CC(C(N)=O)N(c1ccc(F)cc1)c1nc(N)c(C(=O)c2ccc(OCC(=O)N3CCN(C)CC3)cc2)s1]<br>rac-2-(N-[4-amino-5-[4-[2-(4-methylpiperazin-1-yl)-2-oxo-ethoxy]benzoyl]thiazol-2-yl]-4-fluoro-anilino)propanamide | Intermediate 100, 1-methylpiperazine | LC-MS (method 3) Rt = 0.88 min; MS (ESIpos): m/z = 541.1 [M + H]$^+$<br>Method F: Prep_20-50% B<br>12% yield |
| 87 | 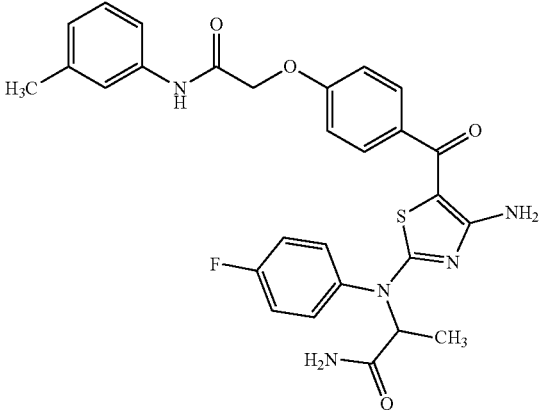 [SMILES: Cc1cccc(NC(=O)COc2ccc(C(=O)c3sc(N(c4ccc(F)cc4)C(C)C(N)=O)nc3N)cc2)c1]<br>rac-2-(N-[4-amino-5-[4-[2-(3-methylanilino)-2-oxo-ethoxy] benzoyl]thiazol-2-yl]-4-fluoro-anilino)propanamide | Intermediate 100, m-toluidine | LC-MS (method 3) Rt = 1.15 min; MS (ESIpos): m/z = 548.1 [M + H]$^+$<br>Method F: Prep_40-70% B<br>12% yield |
| 88 | 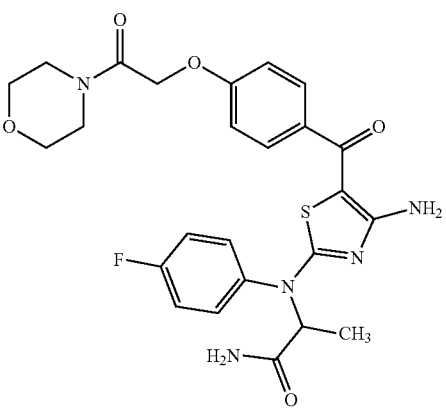 [SMILES: CC(C(N)=O)N(c1ccc(F)cc1)c1nc(N)c(C(=O)c2ccc(OCC(=O)N3CCOCC3)cc2)s1]<br>rac-2-(N-[4-amino-5-[4-(2-morpholino-2-oxo-ethoxy) benzoyl]thiazol-2-yl]-4-fluoro-anilino)propanamide | Intermediate 100, morpholine | LC-MS (method 3) Rt = 0.90 min; MS (ESIpos): m/z = 528.1 [M + H]$^+$<br>Method F: Prep_20-50% B<br>13% yield |

TABLE 7-continued

Examples 83-141

| Example number | Chemical structure Compound name | Starting materials | Analytics/ purification/yield |
|---|---|---|---|
| 89 | 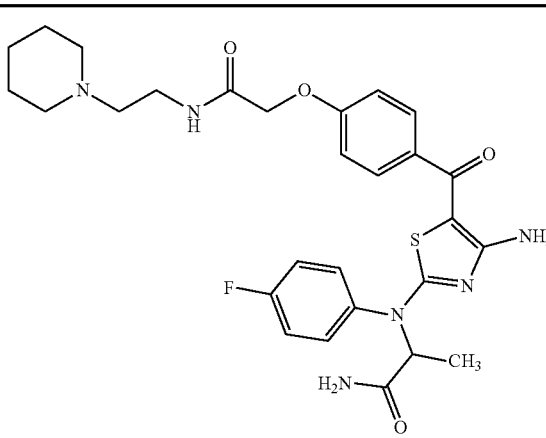<br>rac-2-(N-[4-amino-5-[4-[2-oxo-2-[2-(1-piperidyl)ethylamino]ethoxy]benzoyl]thiazol-2-yl]-4-fluoro-anilino)propanamide | Intermediate 100, 2-(piperidin-1-yl)ethanamine | LC-MS (method 3) Rt = 1.07 min; MS (ESIpos): m/z = 569.2 [M + H]$^+$<br>Method F: Prep_30-60% B<br>5% yield |
| 90 | 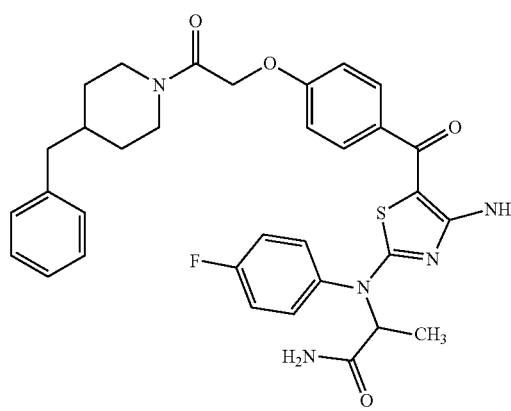<br>rac-2-(N-[4-amino-5-[4-[2-(4-benzyl-1-piperidyl)-2-oxo-ethoxy]benzoyl]thiazol-2-yl]-4-fluoro-anilino)propanamide | Intermediate 100, 4-benzylpiperidine | LC-MS (method 3) Rt = 1.26 min; MS (ESIpos): m/z = 616.2 [M + H]$^+$<br>Method F: Prep_45-75% B<br>5% yield |
| 91 | 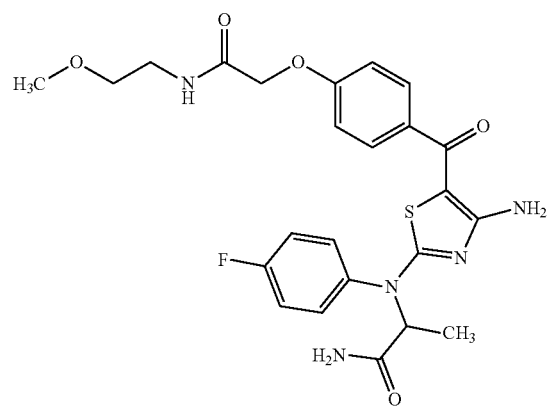 [SMILES: COCCNC(=O)COc1ccc(C(=O)c2sc(N(c3ccc(F)cc3)C(C)C(N)=O)nc2N)cc1]<br>rac-2-(N-(4-amino-5-[4-[2-(2-methoxyethylamino)-2-oxo-ethoxy]benzoyl]thiazol-2-yl]-4-fluoro-anilino)propanamide | Intermediate 100, 2-methoxyethanamine | LC-MS (method 3) Rt = 0.90 min; MS (ESIpos): m/z = 516.1 [M + H]$^+$<br>Method F: Prep_20-50% B<br>5% yield |

TABLE 7-continued

Examples 83-141

| Example number | Chemical structure Compound name | Starting materials | Analytics/ purification/yield |
|---|---|---|---|
| 92 | 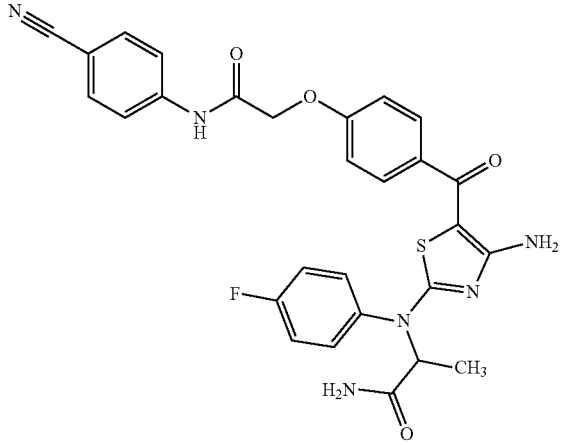 [SMILES: CC(C(N)=O)N(c1ccc(F)cc1)c1nc(N)c(C(=O)c2ccc(OCC(=O)Nc3ccc(C#N)cc3)cc2)s1]<br>rac-2-(N-[4-amino-5-[4-[2-(4-cyanoanilino)-2-oxo-ethoxy]benzoyl]thiazol-2-yl]-4-fluoro-anilino)propanamide | Intermediate 100, 4-aminobenzonitrile | LC-MS (method 3) Rt = 1.06 min; MS (ESIpos): m/z = 559.1 [M + H]$^+$<br>Method F: Prep_30-60% B<br>9% yield |
| 93 | 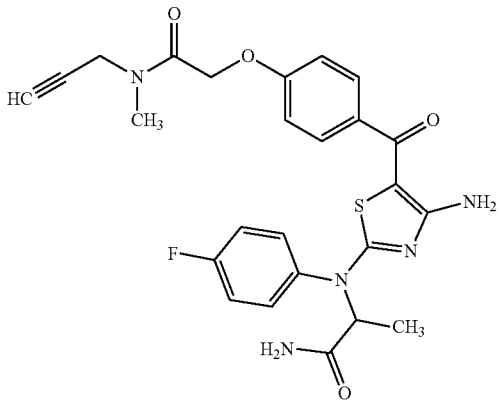 [SMILES: C#CCN(C)C(=O)COc1ccc(C(=O)c2sc(N(c3ccc(F)cc3)C(C)C(N)=O)nc2N)cc1]<br>rac-2-(N-[4-amino-5-[4-[2-[methyl(prop-2-ynyl)amino]-2-oxo-ethoxy]benzoyl]thiazol-2-yl]-4-fluoro-anilino)propanamide | Intermediate 100, N-methylprop-2-yn-1-amine | LC-MS (method 3) Rt = 0.96 min; MS (ESIpos): m/z = 510.1 [M + H]$^+$<br>Method F: Prep_25-55% B<br>9% yield |
| 94 | 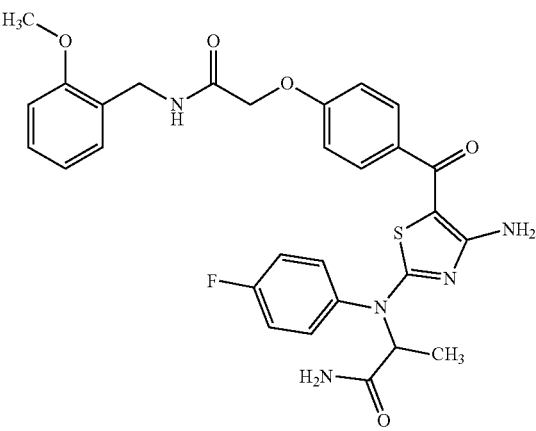 [SMILES: COc1ccccc1CNC(=O)COc1ccc(C(=O)c2sc(N(c3ccc(F)cc3)C(C)C(N)=O)nc2N)cc1]<br>rac-2-(N-[4-amino-5-[4-[2-[(2-methoxyphenyl)methylamino]-2-oxo-ethoxy]benzoyl]thiazol-2-yl]-4-fluoro-anilino)propanamide | Intermediate 100, 1-(2-methoxyphenyl)methanamine | LC-MS (method 3) Rt = 1.08 min; MS (ESIpos): m/z = 578.1 [M + H]$^+$<br>Method F: Prep_30-60% B<br>13% yield |

TABLE 7-continued

Examples 83-141

| Example number | Chemical structure Compound name | Starting materials | Analytics/ purification/yield |
|---|---|---|---|
| 95 | rac-2-(N-(4-amino-5-[4-[2-[(3-methoxyphenyl)methylamino]-2-oxo-ethoxy]benzoyl]thiazol-2-yl]-4-fluoro-anilino)propanamide | Intermediate 100, 1-(3-methoxyphenyl) methanamine | LC-MS (method 3) Rt = 1.06 min; MS (ESIpos): m/z = 578.1 $[M + H]^+$ Method F: Prep_30-60% B 10% yield |
| 96 | rac-2-(N-[4-amino-5-[4-[2-[(2-fluorophenyl)methylamino]-2-oxo-ethoxy]benzoyl]thiazol-2-yl]-4-fluoro-anilino)propanamide | Intermediate 100, 1-(2-fluorophenyl) methanamine | LC-MS (method 3) Rt = 1.07 min; MS (ESIpos): m/z = 566.1 $[M + H]^+$ Method F: Prep_30-60% B 10% yield |
| 97 | rac-2-(N-[4-amino-5-[4-[2-[(4-fluorophenyl)methylamino]-2-oxo-ethoxy]benzoyl]thiazol-2-yl]-4-fluoro-anilino)propanamide | Intermediate 100, 1-(4-fluorophenyl) methanamine | LC-MS (method 3) Rt = 1.07 min; MS (ESIpos): m/z = 566.1 $[M + H]^+$ Method F: Prep_30-60% B 13% yield |

TABLE 7-continued

Examples 83-141

| Example number | Chemical structure Compound name | Starting materials | Analytics/ purification/yield |
|---|---|---|---|
| 98 | 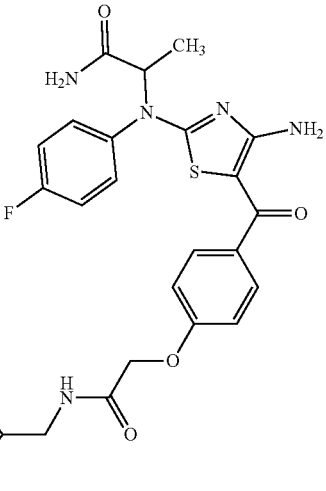<br>rac-2-(N-[4-amino-5-[4-[2-(1H-benzimidazol-2-ylmethylamino)-2-oxo-ethoxy]benzoyl]thiazol-2-yl]-4-fluoro-anilino)propanamide | Intermediate 100, 1-(1H-benzimidazol-2-yl)methanamine | LC-MS (method 3) Rt = 0.93 min; MS (ESIpos): m/z = 588.1 $[M + H]^+$<br>Method F: Prep_25-55% B<br>7% yield |
| 99 | 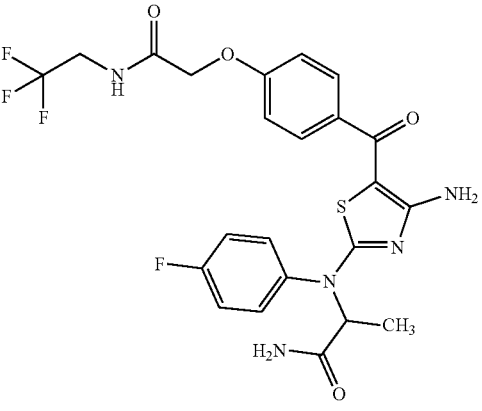 [SMILES: CC(C(N)=O)N(c1ccc(F)cc1)c1nc(N)c(C(=O)c2ccc(OCC(=O)NCC(F)(F)F)cc2)s1]<br>rac-2-(N-[4-amino-5-[4-[2-oxo-2-(2,2,2-trifluoroethylamino) ethoxy]benzoyl]thiazol-2-yl]-4-fluoro-anilino)propanamide | Intermediate 100, 2,2,2-trifluoroethanamine | LC-MS (method 3) Rt = 1.00 min; MS (ESIpos): m/z = 540.0 $[M + H]^+$<br>Method F: Prep_25-55% B<br>21% yield |
| 100 | 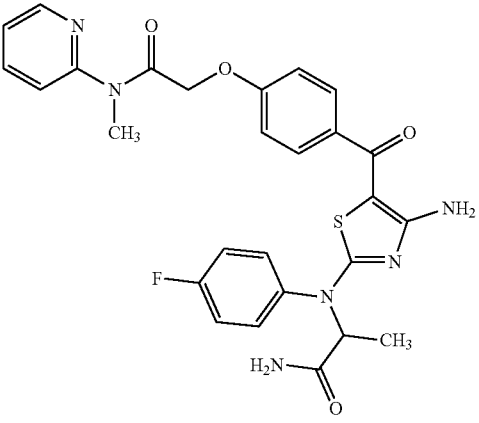 [SMILES: CC(C(N)=O)N(c1ccc(F)cc1)c1nc(N)c(C(=O)c2ccc(OCC(=O)N(C)c3ccccn3)cc2)s1]<br>rac-2-(N-[4-amino-5-[4-[2-[methyl(2-pyridyl)amino]-2-oxo-ethoxy]benzoyl]thiazol-2-yl]-4-fluoro-anilino)propanamide | Intermediate 100, N-methylpyridin-2-amine | LC-MS (method 3) Rt = 0.99 min; MS (ESIpos): m/z = 549.1 $[M + H]^+$<br>Method F: Prep_25-55% B<br>9% yield |

TABLE 7-continued

Examples 83-141

| Example number | Chemical structure Compound name | Starting materials | Analytics/ purification/yield |
|---|---|---|---|
| 101 | 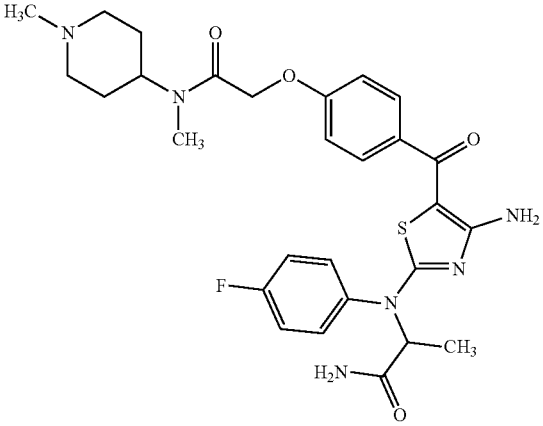 [SMILES: CC(C(N)=O)N(c1ccc(F)cc1)c1nc(N)c(C(=O)c2ccc(OCC(=O)N(C)C3CCN(C)CC3)cc2)s1]<br>rac-2-(N-[4-amino-5-[4-[2-[methyl-(1-methyl-4-piperidyl)amino]-2-oxo-ethoxy]benzoyl]thiazol-2-yl]-4-fluoro-anilino)propanamide | Intermediate 100, N,1-dimethylpiperidin-4-amine | LC-MS (method 3) Rt = 0.94 min; MS (ESIpos): m/z = 569.1 [M + H]$^+$<br>Method F: Prep_25-55% B<br>23% yield |
| 102 | 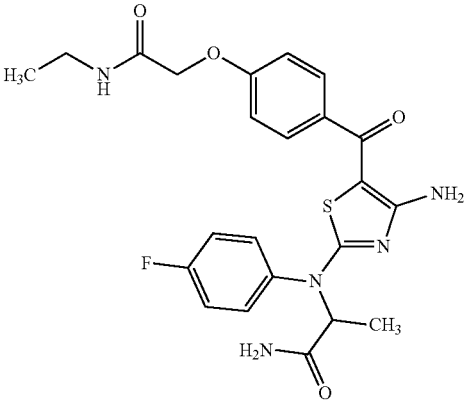 [SMILES: CCNC(=O)COc1ccc(C(=O)c2sc(N(c3ccc(F)cc3)C(C)C(N)=O)nc2N)cc1]<br>rac-2-(N-[4-amino-5-[4-[2-(methoxyamino)-2-oxo-ethoxy]benzoyl]thiazol-2-yl]-4-fluoro-anilino)propanamide | Intermediate 100, O-methylhydroxy-lamine | LC-MS (method 3) Rt = 0.90 min; MS (ESIpos): m/z = 488.1 [M + H]$^+$<br>Method F: Prep_20-50% B<br>22% yield |
| 103 | 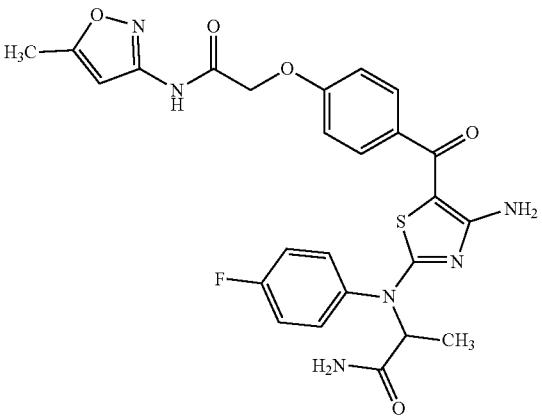 [SMILES: Cc1cc(NC(=O)COc2ccc(C(=O)c3sc(N(c4ccc(F)cc4)C(C)C(N)=O)nc3N)cc2)no1]<br>rac-2-(N-[4-amino-5-[4-[2-[(5-methylisoxazol-3-yl)amino]-2-oxo-ethoxy]benzoyl]thiazol-2-yl]-4-fluoro-anilino)propanamide | Intermediate 100, 5-methyl-1,2-oxazol-3-amine | LC-MS (method 3) Rt = 0.99 min; MS (ESIpos): m/z = 539.1 [M + H]$^+$<br>Method F: Prep_25-55% B<br>7% yield |

TABLE 7-continued

Examples 83-141

| Example number | Chemical structure Compound name | Starting materials | Analytics/ purification/yield |
|---|---|---|---|
| 104 | rac-2-(N-[4-amino-5-[4-[2-(ethylamino)-2-oxo-ethoxy] benzoyl]thiazol-2-yl]-4-fluoro-anilino)propanamide | Intermediate 100, ethanamine | LC-MS (method 3) Rt = 0.92 min; MS (ESIpos): m/z = 486.0 $[M + H]^+$<br>Method F: Prep_25-55% B<br>33% yield |
| 105 | rac-2-(N-[4-amino-5-[4-[2-(4-methylanilino)-2-oxo-ethoxy] benzoyl]thiazol-2-yl]-4-fluoro-anilino)propanamide | Intermediate 100, p-toluidine | LC-MS (method 3) Rt = 1.15 min; MS (ESIpos): m/z = 548.1 $[M + H]^+$<br>Method F: Prep_40-70% B<br>37% yield |
| 106 | rac-2-(N-(4-amino-5-[4-[2-(cyclohexylamino)-2-oxo-ethoxy] benzoyl]thiazol-2-yl]-4-fluoro-anilino)propanamide | Intermediate 100, cyclohexanamine | LC-MS (method 3) Rt = 1.12 min; MS (ESIpos): m/z = 540.1 $[M + H]^+$<br>Method F: Prep_35-65% B<br>11% yield |

TABLE 7-continued

Examples 83-141

| Example number | Chemical structure Compound name | Starting materials | Analytics/ purification/yield |
|---|---|---|---|
| 107 | 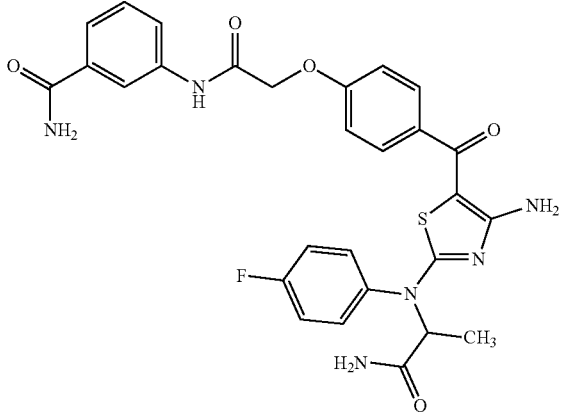 [SMILES: CC(C(N)=O)N(c1ccc(F)cc1)c1nc(N)c(C(=O)c2ccc(OCC(=O)Nc3cccc(C(N)=O)c3)cc2)s1]<br>rac-3-[[2-[4-[4-amino-2-(N-[2-amino-1-methyl-2-oxo-ethyl]-4-fluoro-anilino)thiazole-5-carbonyl]phenoxy]acetyl]amino]benzamide | Intermediate 100, 3-aminobenzamide | LC-MS (method 3) Rt = 0.89 min; MS (ESIpos): m/z = 577.1 [M + H]$^+$<br>Method F: Prep_20-50% B<br>20% yield |
| 108 | 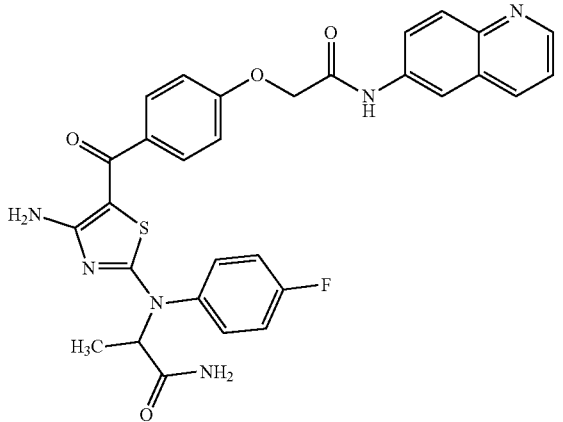 [SMILES: CC(C(N)=O)N(c1ccc(F)cc1)c1nc(N)c(C(=O)c2ccc(OCC(=O)Nc3ccc4ncccc4c3)cc2)s1]<br>rac-2-(N-(4-amino-5-[4-[2-oxo-2-(6-quinolylamino)ethoxy]benzoyl]thiazol-2-yl]-4-fluoro-anilino)propanamide | Intermediate 100, quinolin-6-amine | LC-MS (method 3) Rt = 1.01 min; MS (ESIpos): m/z = 585.1 [M + H]$^+$<br>Method F: Prep_25-55% B<br>30% yield |
| 109 | 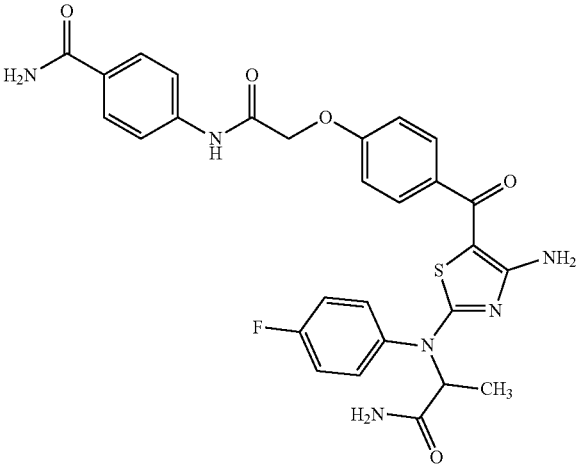 [SMILES: CC(C(N)=O)N(c1ccc(F)cc1)c1nc(N)c(C(=O)c2ccc(OCC(=O)Nc3ccc(C(N)=O)cc3)cc2)s1]<br>rac-4-[[2-[4-[4-amino-2-(N-[2-amino-1-methyl-2-oxo-ethyl]-4-fluoro-anilino)thiazole-5-carbonyl]phenoxy]acetyl]amino]benzamide | Intermediate 100, 4-aminobenzamide | LC-MS (method 3) Rt = 1.01 min; MS (ESIpos): m/z = 577.1 [M + H]$^+$<br>Method F: Prep_20-50% B<br>7% yield |

TABLE 7-continued

Examples 83-141

| Example number | Chemical structure Compound name | Starting materials | Analytics/ purification/yield |
|---|---|---|---|
| 110 | 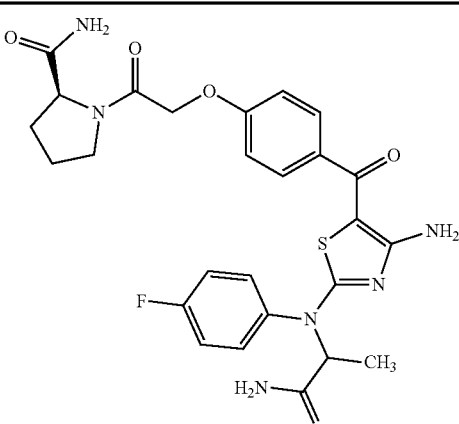<br>(2S)-1-[2-[4-[4-amino-2-(N-[2-amino-(1RS)-methyl-2-oxo-ethyl]-4-fluoro-anilino)thiazole-5-carbonyl]phenoxy]acetyl]pyrrolidine-2-carboxamide (mixture of two diastereomers) | Intermediate 100, L-prolinamide | LC-MS (method 3) Rt = 0.82 min; MS (ESIpos): m/z = 555.1 [M + H]$^+$<br>Method F: Prep_15-45% B<br>15% yield |
| 111 | 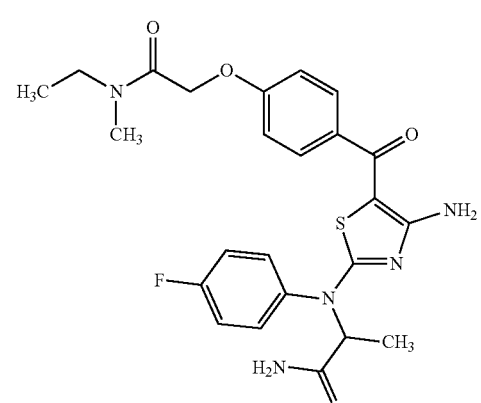<br>rac-2-(N-[4-amino-5-[4-[2-[ethyl(methyl)amino]-2-oxo-ethoxy]benzoyl]thiazol-2-yl]-4-fluoro-anilino)propanamide | Intermediate 100, N-methylethanamine | LC-MS (method 3) Rt = 0.96 min; MS (ESIpos): m/z = 500.1 [M + H]$^+$<br>Method F: Prep_25-55% B<br>23% yield |
| 112 | 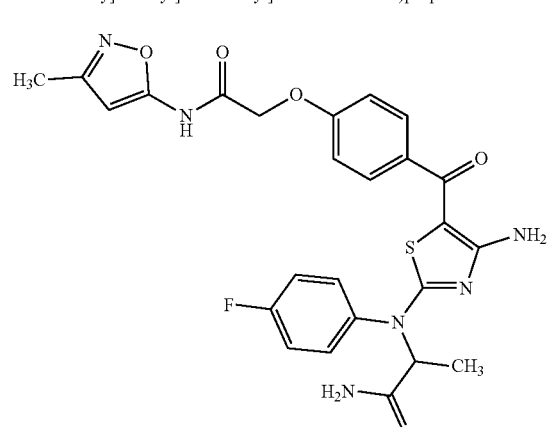<br>rac-2-(N-(4-amino-5-[4-[2-[(3-methylisoxazol-5-yl)amino]-2-oxo-ethoxy]benzoyl]thiazol-2-yl]-4-fluoro-anilino)propanamide | Intermediate 100, 3-methyl-1,2-oxazol-5-amine | LC-MS (method 3) Rt = 0.80 min; MS (ESIpos): m/z = 539.1 [M + H]$^+$<br>Method F: Prep_10-40% B<br>4% yield |

TABLE 7-continued

Examples 83-141

| Example number | Chemical structure Compound name | Starting materials | Analytics/ purification/yield |
| --- | --- | --- | --- |
| 113 | 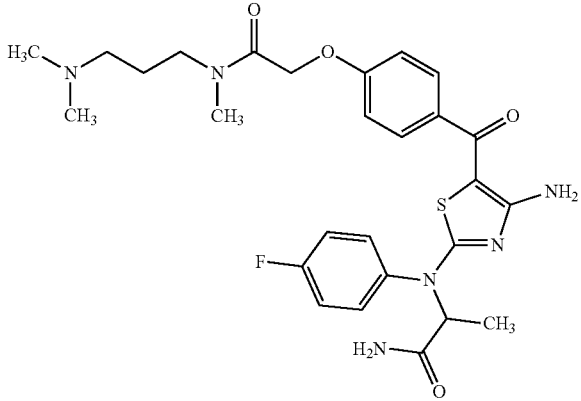 [SMILES: CC(C(N)=O)N(c1ccc(F)cc1)c1nc(N)c(C(=O)c2ccc(OCC(=O)N(C)CCCN(C)C)cc2)s1]<br>rac-2-(N-(4-amino-5-[4-[2-[3-(dimethylamino)propyl-methyl-amino]-2-oxo-ethoxy]benzoyl]thiazol-2-yl]-4-fluoro-anilino)propanamide | Intermediate 100, N,N,N'-trimethylpropane-1,3-diamine | LC-MS (method 3) Rt = 1.02 min; MS (ESIpos): m/z = 557.2 [M + H]$^+$<br>Method F: Prep_25-55% B<br>12% yield |
| 114 | 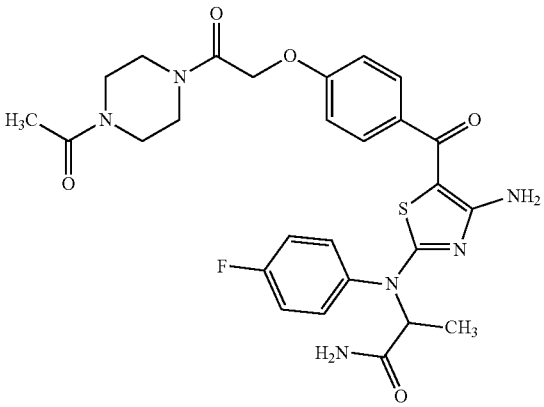 [SMILES: CC(=O)N1CCN(C(=O)COc2ccc(C(=O)c3sc(N(c4ccc(F)cc4)C(C)C(N)=O)nc3N)cc2)CC1]<br>rac-2-(N-[5-[4-[2-(4-acetylpiperazin-1-yl)-2-oxo-ethoxy]benzoyl]-4-amino-thiazol-2-yl]-4-fluoro-anilino)propanamide | Intermediate 100, 1-(piperazin-1-yl)ethanone | LC-MS (method 3) Rt = 0.84 min; MS (ESIpos): m/z = 569.1 [M + H]$^+$<br>Method F: Prep_15-45% B<br>14% yield |
| 115 | 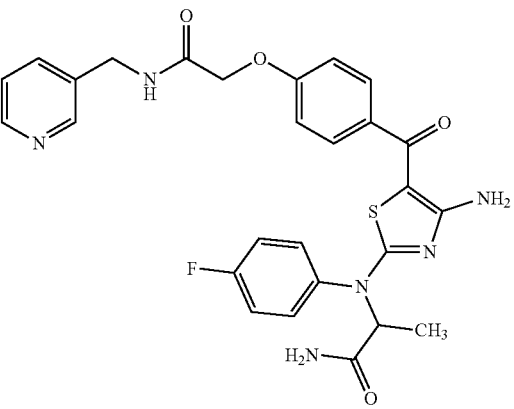 [SMILES: CC(C(N)=O)N(c1ccc(F)cc1)c1nc(N)c(C(=O)c2ccc(OCC(=O)NCc3cccnc3)cc2)s1]<br>rac-2-(N-[4-amino-5-[4-[2-oxo-2-(3-pyridylmethylamino)ethoxy]benzoyl]thiazol-2-yl]-4-fluoro-anilino)propanamide | Intermediate 100, 1-(pyridin-3-yl)methanamine | LC-MS (method 3) Rt = 0.90 min; MS (ESIpos): m/z = 549.1 [M + H]$^+$<br>Method F: Prep_20-50% B<br>4% yield |

TABLE 7-continued

Examples 83-141

| Example number | Chemical structure Compound name | Starting materials | Analytics/ purification/yield |
|---|---|---|---|
| 116 | 2-(N-[4-amino-5-(4-[2-(2,3-dihydroxypropylamino)-2-oxo-ethoxy] benzoyl]thiazol-2-yl]-4-fluoro-anilino)propanamide (mixture of stereoisomers) | Intermediate 100, rac-3-aminopropane-1,2-diol | LC-MS (method 3) Rt = 0.77 min; MS (ESIpos): m/z = 532.0 [M + H]$^+$ Method F: Prep_10-40% B 12% yield |
| 117 | rac-2-(N-[4-amino-5-[4-[2-(4-methoxyanilino)-2-oxo-ethoxy]benzoyl]thiazol-2-yl]-4-fluoro-anilino)propanamide | Intermediate 100, 4-methoxyaniline | LC-MS (method 3) Rt = 1.07 min; MS (ESIpos): m/z = 564.1 [M + H]$^+$ Method F: Prep_30-60% B 21% yield |
| 118 | rac-2-(N-[4-amino-5-[4-[2-[benzyl(methyl)amino]-2-oxo-ethoxy]benzoyl]thiazol-2-yl]-4-fluoro-anilino)propanamide | Intermediate 100, N-methyl-1-phenylmethanamine | LC-MS (method 3) Rt = 1.10 min; MS (ESIpos): m/z = 562.1 [M + H]$^+$ Method F: Prep_30-60% B 14% yield |

TABLE 7-continued

Examples 83-141

| Example number | Chemical structure Compound name | Starting materials | Analytics/ purification/yield |
|---|---|---|---|
| 119 | 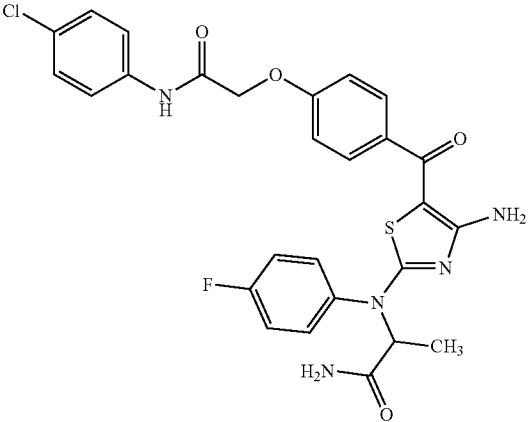 [SMILES: CC(C(N)=O)N(c1ccc(F)cc1)c1nc(N)c(C(=O)c2ccc(OCC(=O)Nc3ccc(Cl)cc3)cc2)s1]<br>rac-2-(N-[4-amino-5-[4-[2-(4-chloroanilino)-2-oxo-ethoxy]benzoyl]thiazol-2-yl]-4-fluoro-anilino)propanamide | Intermediate 100, 4-chloroaniline | LC-MS (method 3) Rt = 1.18 min; MS (ESIpos): m/z = 568.1 [M + H]$^+$<br>Method F: Prep_40-70% B<br>22% yield |
| 120 | 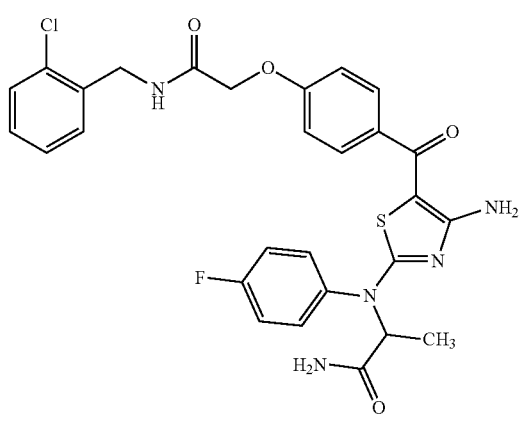 [SMILES: CC(C(N)=O)N(c1ccc(F)cc1)c1nc(N)c(C(=O)c2ccc(OCC(=O)NCc3ccccc3Cl)cc2)s1]<br>rac-2-(N-[4-amino-5-[4-[2-[(2-chlorophenyl)methylamino]-2-oxo-ethoxy]benzoyl]thiazol-2-yl]-4-fluoro-anilino)propanamide | Intermediate 100, 1-(2-chlorophenyl)methanamine | LC-MS (method 3) Rt = 1.13 min; MS (ESIpos): m/z = 582.1 [M + H]$^+$<br>Method F: Prep_35-65% B<br>12% yield |
| 121 | 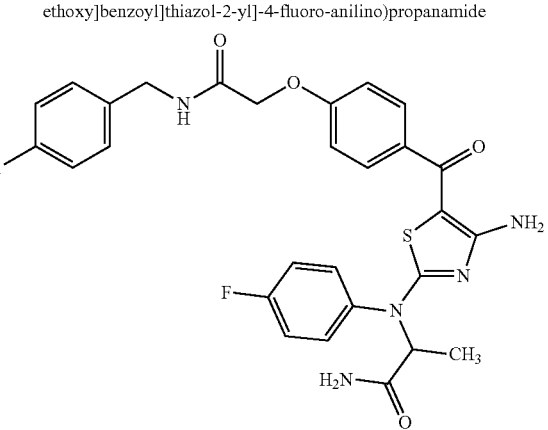<br>rac-2-(N-(4-amino-5-[4-[2-[(4-chlorophenyl)methylamino]-2-oxo-ethoxy]benzoyl]thiazol-2-yl]-4-fluoro-anilino)propanamide | Intermediate 100, 1-(4-chlorophenyl)methanamine | LC-MS (method 3) Rt = 1.13 min; MS (ESIpos): m/z = 582.1 [M + H]$^+$<br>Method F: Prep_35-65% B<br>15% yield |

TABLE 7-continued

Examples 83-141

| Example number | Chemical structure / Compound name | Starting materials | Analytics/ purification/yield |
|---|---|---|---|
| 122 | 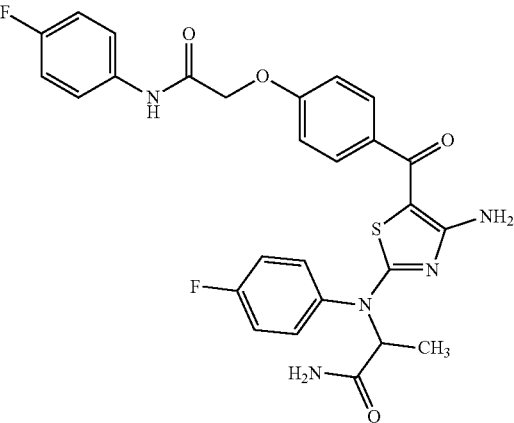 [SMILES: CC(C(N)=O)N(c1ccc(F)cc1)c1nc(N)c(C(=O)c2ccc(OCC(=O)Nc3ccc(F)cc3)cc2)s1]<br>rac-2-(N-[4-amino-5-[4-[2-(4-fluoroanilino)-2-oxo-ethoxy]benzoyl]thiazol-2-yl]-4-fluoro-anilino)propanamide | Intermediate 100, 4-fluoroaniline | LC-MS (method 3) Rt = 1.10 min; MS (ESIpos): m/z = 552.1 [M + H]$^+$<br>Method F: Prep_30-60% B<br>24% yield |
| 123 | 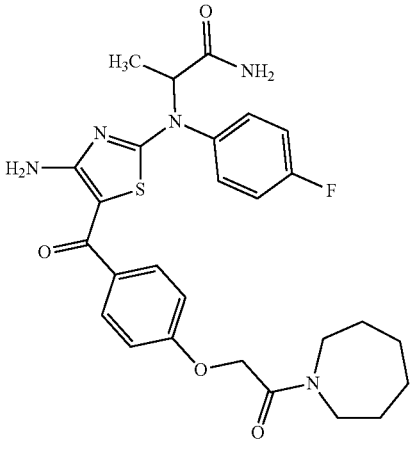 [SMILES: CC(C(N)=O)N(c1ccc(F)cc1)c1nc(N)c(C(=O)c2ccc(OCC(=O)N3CCCCCC3)cc2)s1]<br>rac-2-(N-[4-amino-5-[4-[2-(azepan-1-yl)-2-oxo-ethoxy]benzoyl]thiazol-2-yl]-4-fluoro-anilino)propanamide | Intermediate 100, azepane | LC-MS (method 3) Rt = 1.08 min; MS (ESIpos): m/z = 540.1 [M + H]$^+$<br>Method F: Prep_30-60% B<br>6% yield |
| 124 | 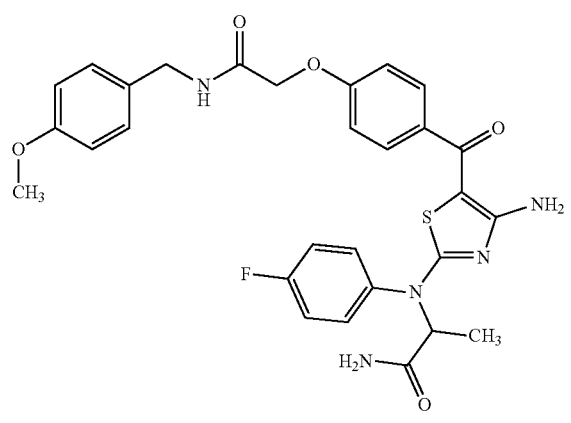 [SMILES: COc1ccc(CNC(=O)COc2ccc(C(=O)c3sc(N(c4ccc(F)cc4)C(C)C(N)=O)nc3N)cc2)cc1]<br>rac-2-(N-[4-amino-5-[4-[2-[(4-methoxyphenyl)methylamino]-2-oxo-ethoxy]benzoyl]thiazol-2-yl]-4-fluoro-anilino)propanamide | Intermediate 100, 1-(4-methoxyphenyl)methanamine | LC-MS (method 3) Rt = 1.05 min; MS (ESIpos): m/z = 578.1 [M + H]$^+$<br>Method F: Prep_30-60% B<br>8% yield |

TABLE 7-continued

Examples 83-141

| Example number | Chemical structure / Compound name | Starting materials | Analytics/ purification/yield |
|---|---|---|---|
| 125 | 2-(N-[4-amino-5-[4-[2-oxo-2-(1-phenylethylamino)ethoxy]benzoyl]thiazol-2-yl]-4-fluoro-anilino)propanamide (mixture of stereoisomers) | Intermediate 100, rac-1-phenylethanamine | LC-MS (method 3) Rt = 1.10 min; MS (ESIpos): m/z = 562.1 [M + H]$^+$<br>Method F: Prep_30-60% B<br>9% yield |
| 126 | rac-2-(N-[4-amino-5-[4-[2-oxo-2-(p-tolylmethylamino)ethoxy]benzoyl]thiazol-2-yl]-4-fluoro-anilino)propanamide | Intermediate 100, 1-(4-methylphenyl)methanamine | LC-MS (method 3) Rt = 1.12 min; MS (ESIpos): m/z = 562.1 [M + H]$^+$<br>Method F: Prep_35-65% B<br>13% yield |
| 127 | rac-2-(N-[4-amino-5-[4-[2-[methyl(2-phenylethyl)amino]-2-oxo-ethoxy]benzoyl]thiazol-2-yl]-4-fluoro-anilino)propanamide | Intermediate 100, N-methyl-2-phenylethanamine | LC-MS (method 3) Rt = 1.11 min; MS (ESIpos): m/z = 576.1 [M + H]$^+$<br>Method F: Prep_30-60% B<br>23% yield |

TABLE 7-continued

Examples 83-141

| Example number | Chemical structure / Compound name | Starting materials | Analytics/ purification/yield |
|---|---|---|---|
| 128 | 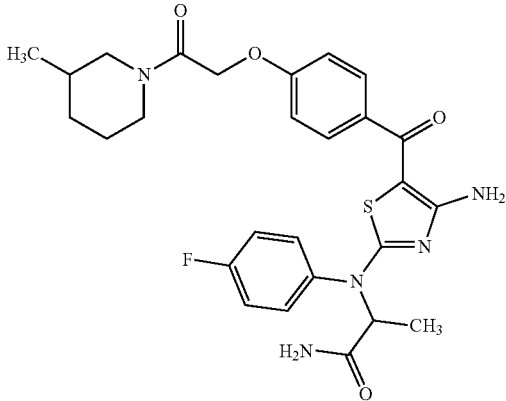 [SMILES: CC1CCCN(C(=O)COc2ccc(C(=O)c3sc(N(c4ccc(F)cc4)C(C)C(N)=O)nc3N)cc2)C1]<br>2-(N-[4-amino-5-[4-[2-(3-methyl-1-piperidyl)-2-oxo-ethoxy]benzoyl]thiazol-2-yl]-4-fluoro-anilino)propanamide<br>(mixture of stereoisomers) | Intermediate 100, rac-3-methylpiperidine | LC-MS (method 3) Rt = 1.11 min; MS (ESIpos): m/z = 540.1 [M + H]$^+$<br>Method F: Prep_30-60% B<br>4% yield |
| 129 | 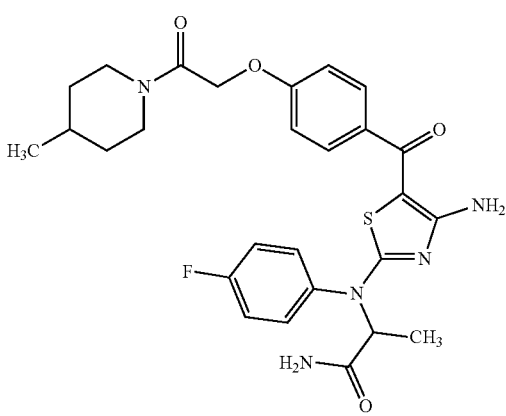 [SMILES: CC1CCN(C(=O)COc2ccc(C(=O)c3sc(N(c4ccc(F)cc4)C(C)C(N)=O)nc3N)cc2)CC1]<br>rac-2-(N-[4-amino-5-(4-[2-(4-methyl-1-piperidyl)-2-oxo-ethoxy]benzoyl]thiazol-2-yl]-4-fluoro-anilino)propanamide | Intermediate 100, 4-methylpiperidine | LC-MS (method 3) Rt = 1.11 min; MS (ESIpos): m/z = 540.1 [M + H]$^+$<br>Method F: Prep_30-60% B<br>5% yield |
| 130 | 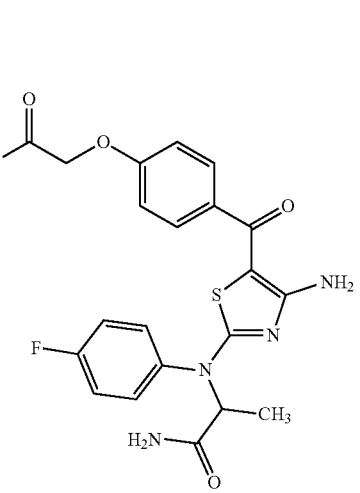<br>rac-2-(N-[5-[4-[2-(4-acetamidoanilino)-2-oxo-ethoxy]benzoyl]-4-amino-thiazol-2-yl]-4-fluoro-anilino)propanamide | Intermediate 100, N-(4-aminophenyl)acetamide | LC-MS (method 3) Rt = 0.92 min; MS (ESIpos): m/z = 591.1 [M + H]$^+$<br>Method F: Prep_25-55% B<br>25% yield |

TABLE 7-continued

Examples 83-141

| Example number | Chemical structure Compound name | Starting materials | Analytics/ purification/yield |
|---|---|---|---|
| 131 | rac-2-(N-[4-amino-5-[4-[2-oxo-2-(1H-pyrazolo[3,4-d]pyrimidin-4-ylamino)ethoxy]benzoyl]thiazol-2-yl]-4-fluoro-anilino)propanamide | Intermediate 100, 1H-pyrazolo[3,4-d]pyrimidin-4-amine | LC-MS (method 3) Rt = 0.80 min; MS (ESIpos): m/z = 576.1 [M + H]$^+$ Method F: Prep_10-40% B 7% yield |
| 132 | rac-2-(N-[4-amino-5-[4-[2-(cyclopentylamino)-2-oxo-ethoxy]benzoyl]thiazol-2-yl]-4-fluoro-anilino)propanamide | Intermediate 100, cyclopentanamine | LC-MS (method 3) Rt = 1.06 min; MS (ESIpos): m/z = 526.1 [M + H]$^+$ Method F: Prep_30-60% B 8% yield |
| 133 | rac-2-(N-[4-amino-5-[4-[2-(3,4-dihydro-1H-isoquinolin-2-yl)-2-oxo-ethoxy]benzoyl]thiazol-2-yl]-4-fluoro-anilino)propanamide | Intermediate 100, 1,2,3,4-tetrahydroiso-quinoline | LC-MS (method 3) Rt = 1.13 min; MS (ESIpos): m/z = 574.1 [M + H]$^+$ Method F: Prep_35-65% B 8% yield |

TABLE 7-continued

Examples 83-141

| Example number | Chemical structure Compound name | Starting materials | Analytics/ purification/yield |
|---|---|---|---|
| 134 | 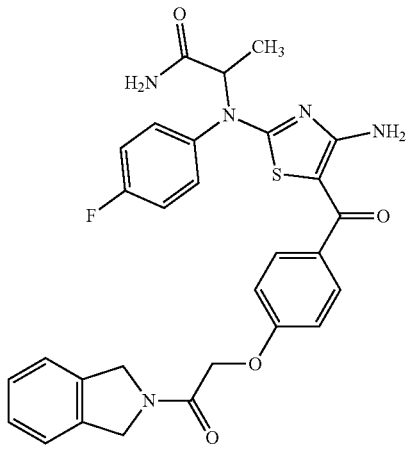 [SMILES: CC(C(N)=O)N(c1ccc(F)cc1)c1nc(N)c(C(=O)c2ccc(OCC(=O)N3Cc4ccccc4C3)cc2)s1]<br>rac-2-(N-[4-amino-5-[4-(2-isoindolin-2-yl-2-oxo-ethoxy)benzoyl]thiazol-2-yl]-4-fluoro-anilino)propanamide | Intermediate 100, isoindoline | LC-MS (method 3) Rt = 1.09 min; MS (ESIpos): m/z = 560.1 [M + H]$^+$<br>Method F: Prep_30-60% B<br>6% yield |
| 135 | 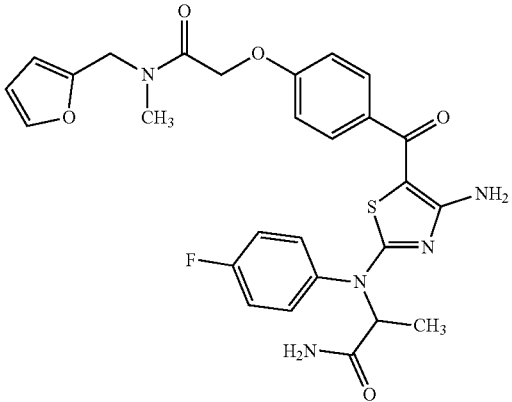 [SMILES: CC(C(N)=O)N(c1ccc(F)cc1)c1nc(N)c(C(=O)c2ccc(OCC(=O)N(C)Cc3ccco3)cc2)s1]<br>rac-2-(N-[4-amino-5-[4-[2-[2-furylmethyl(methyl)amino]-2-oxo-ethoxy]benzoyl]thiazol-2-yl]-4-fluoro-anilino)propanamide | Intermediate 100, 1-(2-furyl)-N-methylmethanamine | LC-MS (method 3) Rt = 1.04 min; MS (ESIpos): m/z = 552.1 [M + H]$^+$<br>Method F: Prep_30-60% B<br>12% yield |
| 136 | 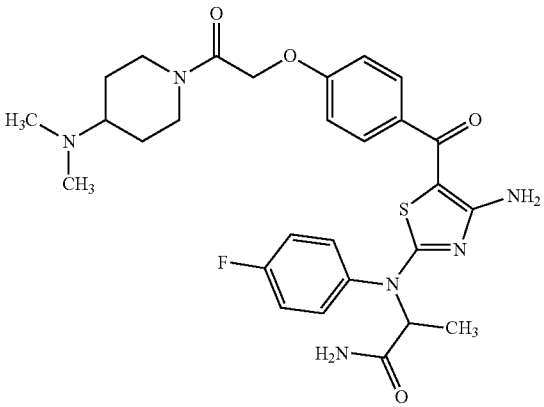 [SMILES: CC(C(N)=O)N(c1ccc(F)cc1)c1nc(N)c(C(=O)c2ccc(OCC(=O)N3CCC(N(C)C)CC3)cc2)s1]<br>rac-2-(N-[4-amino-5-[4-[2-[4-(dimethylamino)-1-piperidyl]-2-oxo-ethoxy]benzoyl]thiazol-2-yl]-4-fluoro-anilino)propanamide | Intermediate 100, N,N-dimethylpiperidin-4-amine | LC-MS (method 3) Rt = 0.97 min; MS (ESIpos): m/z = 569.2 [M + H]$^+$<br>Method F: Prep_25-55% B<br>13% yield |

TABLE 7-continued

Examples 83-141

| Example number | Chemical structure Compound name | Starting materials | Analytics/ purification/yield |
|---|---|---|---|
| 137 | 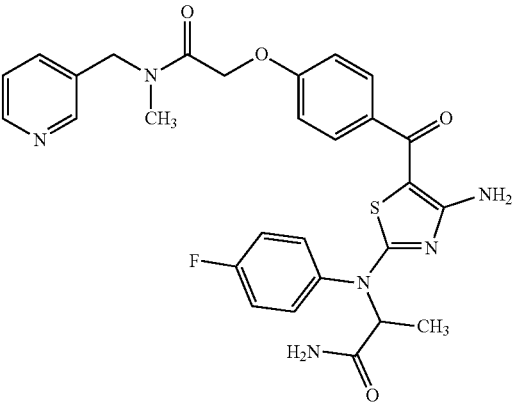 [SMILES: CC(C(N)=O)N(c1ccc(F)cc1)c1nc(N)c(C(=O)c2ccc(OCC(=O)N(C)Cc3cccnc3)cc2)s1]  rac-2-(N-[4-amino-5-[4-[2-[methyl(3-pyridylmethyl)amino]-2-oxo-ethoxy]benzoyl]thiazol-2-yl]-4-fluoro-anilino)propanamide | Intermediate 100, N-methyl-1-(pyridin-3-yl)methanamine | LC-MS (method 3) Rt = 0.92 min; MS (ESIpos): m/z = 563.1 [M + H]$^+$ Method F: Prep_25-55% B 24% yield |
| 138 | 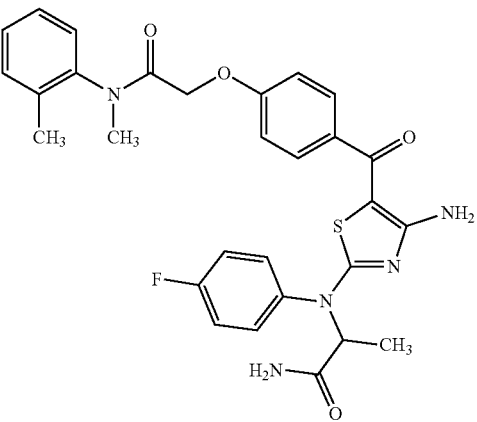 [SMILES: Cc1ccccc1N(C)C(=O)COc1ccc(C(=O)c2sc(N(c3ccc(F)cc3)C(C)C(N)=O)nc2N)cc1]  rac-2-(N-[4-amino-5-[4-[2-(N,2-dimethylanilino)-2-oxo-ethoxy]benzoyl]thiazol-2-yl]-4-fluoro-anilino)propanamide | Intermediate 100, N,2-dimethylaniline | LC-MS (method 3) Rt = 1.13 min; MS (ESIpos): m/z = 562.1 [M + H]$^+$ Method F: Prep_35-65% B 13% yield |
| 139 | 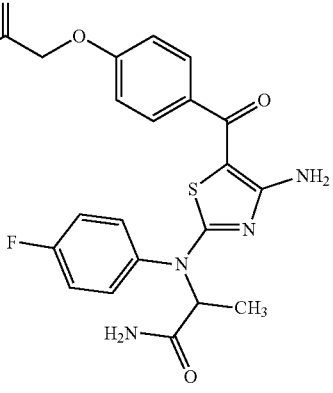  rac-2-(N-[4-amino-5-[4-[2-(N,4-dimethylanilino)-2-oxo-ethoxy]benzoyl]thiazol-2-yl]-4-fluoro-anilino)propanamide | intermediate 100, N,4-dimethylaniline | LC-MS (method 3) Rt = 1.16 min; MS (ESIpos): m/z = 562.1 [M + H]$^+$ Method F: Prep_40-70% B 26% yield |

TABLE 7-continued

Examples 83-141

| Example number | Chemical structure Compound name | Starting materials | Analytics/ purification/yield |
|---|---|---|---|
| 140 | 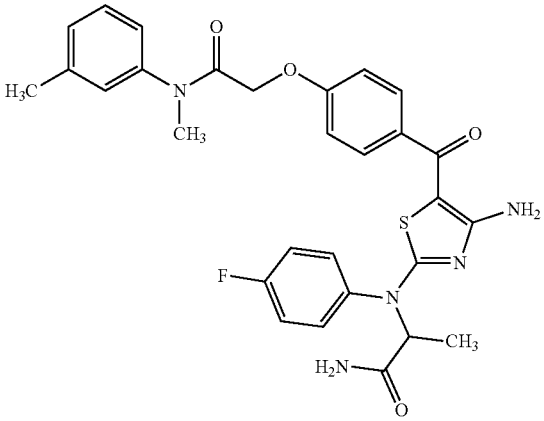 [SMILES: Cc1cccc(N(C)C(=O)COc2ccc(C(=O)c3sc(N(c4ccc(F)cc4)C(C)C(N)=O)nc3N)cc2)c1]<br>rac-2-(N-[4-amino-5-[4-[2-(N,3-dimethylanilino)-2-oxo-ethoxy]benzoyl]thiazol-2-yl]-4-fluoro-anilino)propanamide | Intermediate 100, N,3-dimethylaniline | LC-MS (method 3) Rt = 1.15 min; MS (ESIpos): m/z = 562.1 [M + H]$^+$<br>Method F: Prep_40-70% B<br>31% yield |
| 141 | 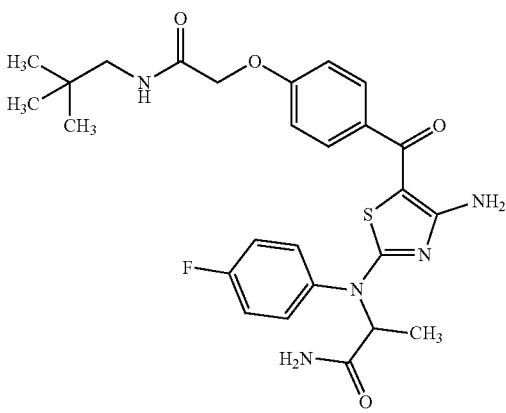 [SMILES: CC(C(N)=O)N(c1ccc(F)cc1)c1nc(N)c(C(=O)c2ccc(OCC(=O)NCC(C)(C)C)cc2)s1]<br>rac-2-(N-[4-amino-5-[4-[2-(2,2-dimethylpropylamino)-2-oxo-ethoxy]benzoyl]thiazol-2-yl]-4-fluoro-anilino)propanamide | Intermediate 100, 2,2-dimethylpropan-1-amine | LC-MS (method 3) Rt = 1.08 min; MS (ESIpos): m/z = 528.1 [M + H]$^+$<br>Method F: Prep_30-60% B<br>4% yield |

Example 142

2-(N-[5-[4-[2-(1-adamantylamino)-2-oxo-ethoxy]benzoyl]-4-amino-thiazol-2-yl]-4-fluoro-anilino)propanamide (single stereoisomer)

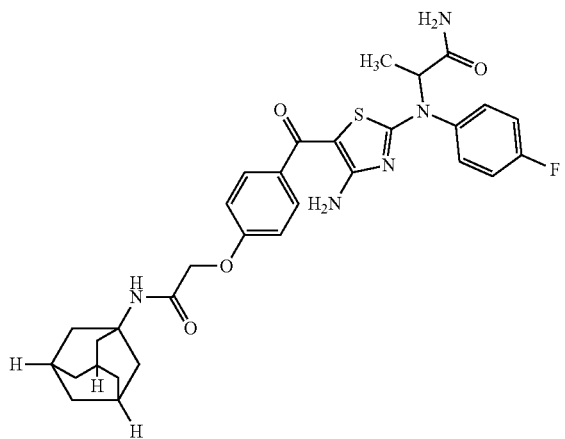 [SMILES: CC(C(N)=O)N(c1ccc(F)cc1)c1nc(N)c(C(=O)c2ccc(OCC(=O)NC34CC5CC(CC(C5)C3)C4)cc2)s1]

2-[4-[4-amino-2-(N-[2-amino-1-methyl-2-oxo-ethyl]-4-fluoro-anilino)thiazole-5-carbonyl]phenoxy]acetic acid (enantiomer 2) (30 mg, 65 μmol; Intermediate 100.2) and adamantan-1-amine (20 mg, 131 μmol) were dissolved in dimethylformamide (0.5 mL). N,N-diisopropylethylamine (25 mg, 196 μmol), 4-dimethylaminopyridine (0.4 mg, 3 μmol) and HATU (50 mg, 131 μmol) were added. The reaction mixture was stirred overnight at rt.

The reaction mixture was filtrated and purified by RP-HPLC (method E, basic) to give 12 mg (29% yield) of the title compound.

$^1$H-NMR (400 MHz, DMSO-d6): δ ppm=1.16 (d, J=7.60 Hz, 3H), 1.59-1.63 (m, 6H), 1.92 (d, J=2.53 Hz, 6H), 2.00 (br d, J=1.77 Hz, 3H), 4.41 (s, 2H), 5.00-5.13 (m, 1H), 6.89 (d, J=8.87 Hz, 2H), 7.24 (s, 1H), 7.30-7.36 (m, 3H), 7.46 (d, J=8.87 Hz, 2H), 7.57 (s, 1H), 7.64 (dd, J=9.00, 5.20 Hz, 2H), 8.11 (br s, 2H).

LC-MS (method 2) Rt=1.32 min; MS (ESIpos): m/z=592.5 [M+H]$^+$

The following examples were prepared from the starting materials stated in Table 8, below, using the procedure as for Example 142.

TABLE 8

Examples 143-155

| Example number | Chemical structure Compound name | Starting materials | Analytics/purification/yield |
|---|---|---|---|
| 143 | 2-(N-[5-[4-[2-(1-adamantylmethylamino)-2-oxo-ethoxy]benzoyl]-4-amino-thiazol-2-yl]-4-fluoro-anilino)propanamide (single stereoisomer) | Intermediate 100.2; 1-adamantyl-methanamine | $^1$H-NMR (400 MHz, DMSO-d6): δ ppm = 1.15 (d, J = 7.35 Hz, 3 H), 1.31 (d, J = 2.03 Hz, 6 H), 1.44-1.48 (m, 3 H), 1.55-1.61 (m, 3 H), 1.80 (br s, 3 H), 2.78 (d, J = 6.59 Hz, 2 H), 4.54 (s, 2 H), 5.02-5.11 (m, 1 H), 6.94 (d, J = 8.87 Hz, 2 H), 7.25 (s, 1 H), 7.32 (t, J = 8.74 Hz, 2 H), 7.48 (d, J = 8.62 Hz, 2 H), 7.57 (s, 1 H), 7.63 (dd, J = 8.87, 4.82 Hz, 2 H), 7.82 (t, J = 6.21 Hz, 1 H), 8.19 (br s, 2 H). LC-MS (method 1) Rt = 1.29 min; MS (ESIpos): m/z = 606.5 [M + H]$^+$ RP-HPLC (method E, basic) 41% yield |

TABLE 8-continued

Examples 143-155

| Example number | Chemical structure Compound name | Starting materials | Analytics/purification/yield |
| --- | --- | --- | --- |
| 144 | 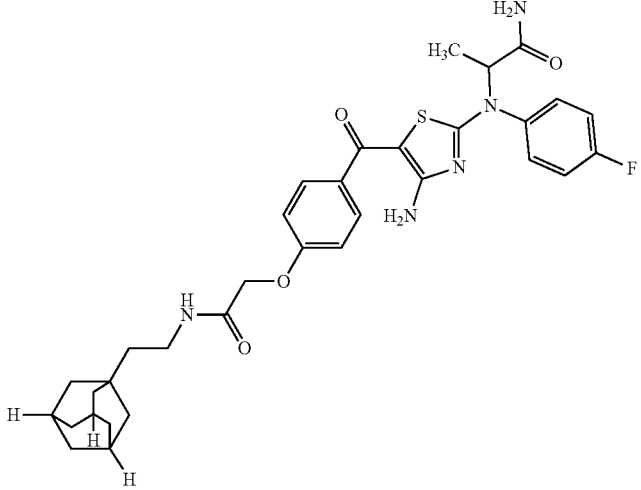 [SMILES: CC(C(N)=O)N(c1ccc(F)cc1)c1nc(N)c(C(=O)c2ccc(OCC(=O)NCCC34CC5CC(CC(C5)C3)C4)cc2)s1]<br>2-(N-[5-[4-[2-2-(1-adamantyl)ethylamino]-2-oxo-ethoxy]benzoyl]-4-amino-thiazol-2-yl]-4-fluoro-anilino)propanamide(single stereoisomer) | Intermediate 100.2; 2-(1-adamantyl) ethanamine | ¹H-NMR (400 MHz, DMSO-d6): δ ppm = 1.13-1.17 (m, 3 H), 1.17-1.24 (m, 2 H), 1.44 (d, J = 2.03 Hz, 6 H), 1.55-1.61 (m, 3 H), 1.62-1.68 (m, 3 H), 1.87-1.91 (m, 3 H), 3.07-3.15 (m, 2 H), 4.45 (s, 2 H), 5.01-5.10 (m, 1 H), 6.92 (d, J = 8.87 Hz, 2 H), 7.24 (s, 1 H), 7.33 (t, J = 8.87 Hz, 2 H), 7.47 (d, J = 8.87 Hz, 2 H), 7.57 (s, 1 H), 7.64 (dd, J = 8.87, 5.07 Hz, 2 H), 8.30 (br s, 2 H), 7.97 (t, J = 5.83 Hz, 1 H).<br>LC-MS (method 1) Rt = 1.40 min; MS (ESIpos): m/z = 620.6 [M + H]⁺<br>RP-HPLC (method E, basic) |
| 145 | 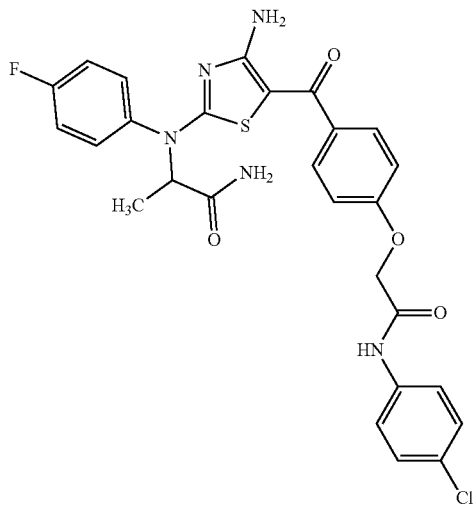 [SMILES: CC(C(N)=O)N(c1ccc(F)cc1)c1nc(N)c(C(=O)c2ccc(OCC(=O)Nc3ccc(Cl)cc3)cc2)s1]<br>2-(N-[4-amino-5-[4-[2-(4-chloroanilino)-2-oxo-ethoxy]benzoyl]thiazol-2-yl]-4-fluoro-anilino)propanamide(single stereoisomer) | Intermediate 100.2; 4-chloroaniline | ¹H-NMR (400 MHz, DMSO-d6): δ ppm = 1.16 (d, J = 7.35 Hz, 3 H), 4.73 (s, 2 H), 5.00-5.11 (m, 1 H), 6.98 (d, J = 8.87 Hz, 2 H), 7.24 (s, 1 H), 7.33 (t, J = 8.87 Hz, 2 H), 7.38 (d, J = 8.87 Hz, 2 H), 7.49 (d, J = 8.87 Hz, 2 H), 7.57 (s, 1 H), 7.61-7.67 (m, 4 H), 8.08 (br s, 2 H), 10.24 (s, 1 H).<br>LC-MS (method 1) Rt = 1.20 min; MS (ESIpos): m/z = 568.4 [M + H]⁺<br>RP-HPLC (method D, basic)<br>59% yield |

TABLE 8-continued

Examples 143-155

| Example number | Chemical structure Compound name | Starting materials | Analytics/purification/yield |
|---|---|---|---|
| 146 | 4-[[2-[4-[4-amino-2-(4-fluoro-N-[2-amino-1-methyl-2-oxo-ethyl]anilino)thiazole-5-carbonyl]phenoxy]acetyl]amino]benzamide(single stereoisomer) | Intermediate 100.2; 4-aminobenzamide | $^1$H-NMR (400 MHz, DMSO-d6): δ ppm = 1.16 (d, J = 7.35 Hz, 3 H), 4.76 (s, 2 H), 5.01-5.09 (m, 1 H), 6.99 (d, J = 8.87 Hz, 2 H), 7.24 (s, 1 H), 7.26 (br s, 1 H), 7.33 (t, J = 8.74 Hz, 2 H), 7.49 (d, J = 8.62 Hz, 2 H), 7.58 (s, 1 H), 7.64 (dd, J = 9.00, 5.20 Hz, 2 H), 7.68 (d, J = 8.87 Hz, 2 H), 7.84 (d, J = 8.87 Hz, 2 H), 7.87-7.90 (m, 1 H), 8.10 (br s, 2 H), 10.31 (s, 1 H). LC-MS (method 1) Rt = 0.88 min; MS (ESIpos): m/z = 577.4 [M + H]$^+$ RP-HPLC (method C, basic) 48% yield |
| 147 | 2-(N-[4-amino-5-[4-[2-((2RS),3-dihydroxypropylamino)-2-oxo-ethoxy]benzoyl]thiazol-2-yl]-4-fluoro-anilino)propanamide (mixture of two diastereomers) | Intermediate 100.2; rac-3-aminopropane-1,2-diol | $^1$H-NMR (400 MHz, DMSO-d6): δ ppm = 1.16 (d, J = 7.35 Hz, 3 H), 2.99-3.08 (m, 1 H), 3.24-3.30 (m, 4 H), 3.48-3.56 (m, 2 H), 4.49-4.53 (m, 2 H), 4.55-4.60 (m, 1 H), 4.75-4.85 (m, 1 H), 5.05 (br d, J = 7.10 Hz, 1 H), 6.92-6.96 (m, 2 H), 7.24 (s, 1 H), 7.33 (t, J = 8.87 Hz, 2 H), 7.48 (d, J = 8.62 Hz, 2 H), 7.58 (s, 1 H), 7.61-7.67 (m, 2 H), 7.93-7.99 (m, 1 H). LC-MS (method 1) Rt = 0.78 min; MS (ESIpos): m/z = 532.4 [M + H]$^+$ RP-HPLC (method B, basic) 54% yield |

TABLE 8-continued

Examples 143-155

| Example number | Chemical structure / Compound name | Starting materials | Analytics/purification/yield |
|---|---|---|---|
| 148 | 2-(N-[4-amino-5-[4-[2-oxo-2-[2-(1-piperidyl)ethylamino]ethoxy]benzoyl]thiazol-2-yl]-4-fluoro-anilino)propanamide (single stereoisomer) | Intermediate 100.2; 2-(piperidin-1-yl)ethanamine (salt with hydrogen chloride) | $^1$H-NMR (400 MHz, DMSO-d6): δ ppm = 1.16 (d, J = 7.60 Hz, 3 H), 1.28-1.46 (m, 7 H), 2.22-2.30 (m, 6 H), 3.16-3.24 (m, 2 H), 4.42-4.56 (m, 2 H), 4.96-5.19 (m, 1 H), 6.90-6.95 (m, 2 H), 7.23-7.26 (m, 1 H), 7.33 (t, J = 8.74 Hz, 2 H), 7.45-7.50 (m, 2 H), 7.56-7.59 (m, 1 H), 7.61-7.66 (m, 2 H), 7.87 (t, J = 5.32 Hz, 1 H). LC-MS (method 1) Rt = 0.77 min; MS (ESIpos): m/z = 569.5 [M + H]$^+$ RP-HPLC (method C, basic) 54% yield |
| 149 | 2-(N-[4-amino-5-[4-(2-amino-2-oxo-ethoxy)benzoyl]thiazol-2-yl]-4-fluoro-anilino)propanamide (single stereoisomer) | Intermediate 100.2; ammonia in dioxane | $^1$H-NMR (400 MHz, DMSO-d6): δ ppm = 1.16 (d, J = 7.35 Hz, 3 H), 4.44 (s, 2 H), 5.05 (q, J = 6.84 Hz, 1 H), 6.92 (d, J = 8.87 Hz, 2 H), 7.24 (s, 1 H), 7.33 (t, J = 8.87 Hz, 2 H), 7.38 (br s, 1 H), 7.47 (d, J = 8.87 Hz, 2 H), 7.52 (br s, 1 H), 7.58 (s, 1 H), 7.64 (dd, J = 8.87, 5.07 Hz, 2 H), 8.07 (br s, 2 H). LC-MS (method 1) Rt = 0.82 min; MS (ESIpos): m/z = 458.3 [M + H]$^+$ RP-HPLC (method B, basic) 60% yield |
| 150 and 151 | (R)-2-(N-[4-amino-5-[4-[2-(methylamino)-2-oxo-ethoxy]benzoyl]thiazol-2-yl]-4-fluoro-anilino)propanamide and (S)-2-(N-[4-amino-5-[4-[2-(methylamino)-2-oxo-ethoxy]benzoyl]thiazol-2-yl]-4-fluoro-anilino)propanamide | | |

TABLE 8-continued

Examples 143-155

| Example number | Chemical structure Compound name | Starting materials | Analytics/purification/yield |
|---|---|---|---|
| 150 | 2-(N-[4-amino-5-[4-[2-(methylamino)-2-oxo-ethoxy]benzoyl]thiazol-2-yl]-4-fluoro-anilino)propanamide (enantiomer 1) | Intermediate 100.1; methanamine in tetrahydrofurane 2.0M | $^1$H-NMR (400 MHz, DMSO-d6): δ ppm = 1.16 (d, J = 7.60 Hz, 3 H), 2.63 (d, J = 4.82 Hz, 3 H), 4.47 (s, 2 H), 5.05 (q, J = 6.00 Hz, 1 H), 6.93 (d, J = 8.87 Hz, 2 H), 7.24 (s, 1 H), 7.33 (t, J = 8.74 Hz, 2 H), 7.48 (d, J = 8.62 Hz, 2 H), 7.58 (s, 1 H), 7.64 (dd, J = 8.87, 5.07 Hz, 2 H), 8.15 (br s, 2 H), 8.00-8.04 (m, 1 H).<br>LC-MS (method 1) Rt = 0.88 min; MS (ESIpos): m/z = 472.3 [M + H]$^+$<br>RP-HPLC (method C, basic)<br>64% yield |
| 151 | 2-(N-[4-amino-5-[4-[2-(methylamino)-2-oxo-ethoxy]benzoyl]thiazol-2-yl]-4-fluoro-anilino)propanamide (enantiomer 2) | Intermediate 100.2; methanamine in tetrahydrofurane 2.0M | $^1$H-NMR (400 MHz, DMSO-d6): δ ppm = 1.16 (d, J = 7.60 Hz, 3 H), 2.63 (d, J = 4.82 Hz, 3 H), 4.47 (s, 2 H), 5.05 (q, J = 7.35 Hz, 1 H), 6.93 (d, J = 8.87 Hz, 2 H), 7.25 (s, 1 H), 7.33 (t, J = 8.74 Hz, 2 H), 7.48 (d, J = 8.62 Hz, 2 H), 7.58 (s, 1 H), 7.64 (dd, J = 8.87, 5.07 Hz, 2 H), 8.07 (br s, 2 H), 7.99-8.05 (m, 1 H).<br>LC-MS (method 1) Rt = 0.88 min; MS (ESIpos): m/z = 472.3 [M + H]$^+$<br>RP-HPLC (method C, basic)<br>29% yield |
| 152 and 153 | (R)-2-(N-[4-amino-5-[4-[2-(isopropylamino)-2-oxo-ethoxy]benzoyl]thiazol-2-yl]-4-fluoro-anilino)propanamide and (S)-2-(N-[4-amino-5-[4-[2-(isopropylamino)-2-oxo-ethoxy]benzoyl]thiazol-2-yl]-4-fluoro-anilino)propanamide | | |

TABLE 8-continued

Examples 143-155

| Example number | Chemical structure Compound name | Starting materials | Analytics/purification/yield |
|---|---|---|---|
| 152 | 2-(N-[4-amino-5-[4-[2-(isopropylamino)-2-oxo-ethoxy]benzoyl]thiazol-2-yl]-4-fluoro-anilino)propanamide (enantiomer 1) | Intermediate 100.1; propan-2-amine | $^1$H-NMR (400 MHz, DMSO-d6): δ ppm = 1.04-1.08 (m, 6 H), 1.16 (d, J = 7.35 Hz, 3 H), 3.86-3.96 (m, 1 H), 4.45 (s, 2 H), 5.05 (br q, J = 7.10 Hz, 1 H), 6.92 (d, J = 8.87 Hz, 2 H), 7.24 (s, 1 H), 7.33 (t, J = 8.87 Hz, 2 H), 7.47 (d, J = 8.87 Hz, 2 H), 7.57 (s, 1 H), 7.64 (dd, J = 9.00, 5.20 Hz, 2 H), 8.08 (br s, 2 H), 7.87 (brd, J = 8.11 Hz, 1 H). LC-MS (method 1) Rt = 1.00 min; MS (ESIpos): m/z = 500.4 [M + H]$^+$ RP-HPLC (method C, basic) 75% yield |
| 153 | 2-(N-[4-amino-5-[4-[2-(isopropylamino)-2-oxo-ethoxy]benzoyl]thiazol-2-yl]-4-fluoro-anilino)propanamide (enantiomer 2) | Intermediate 100.2; propan-2-amine | $^1$H-NMR (400 MHz, DMSO-d6): δ ppm = 1.06 (d, J = 6.59 Hz, 6 H), 1.16 (d, J = 7.35 Hz, 3 H), 3.87-3.96 (m, 1 H), 4.45 (s, 2 H), 5.05 (q, J = 7.86 Hz, 1 H), 6.92 (d, J = 8.87 Hz, 2 H), 7.24 (s, 1 H), 7.33 (t, J = 8.87 Hz, 2 H), 7.47 (d, J = 8.87 Hz, 2 H), 7.57 (s, 1 H), 7.64 (dd, J = 9.00, 5.20 Hz, 2 H), 8.06 (br s, 2 H), 7.87 (br d, J = 7.86 Hz, 1 H). LC-MS (method 1) Rt = 1.00 min; MS (ESIpos): m/z = 500.4 [M + H]$^+$ RP-HPLC (method C, basic) 72% yield |
| 154 | | Intermediate 82; propan-2-amine | $^1$H-NMR (400 MHz, DMSO-d$_6$): δ ppm = 0.94 (d, J = 6.59 Hz, 6 H), 1.16 (d, J = 7.35 Hz, 3 H), 1.43 (s, 6 H), 3.83-3.96 (m, 1 H), 4.99-5.11 (m, 1 H), 6.79 (d, J = 8.62 Hz, 2 H), 7.24 (s, 1 H), 7.32 (t, J = 8.87 Hz, 2 H), 7.42 (d, J = 8.62 Hz, 2 H), 7.57 (s, 1 H), 7.63 (dd, J = 8.74, 5.20 Hz, 2 H), 7.75 (d, J = 8.11 Hz, 1 H), 7.80-8.50 (m, 2 H). LC-MS (method 1) Rt = 1.10 min; MS (ESIpos): m/z = 528.4 [M + H]$^+$ RP-HPLC (method D, basic) 23% yield |

TABLE 8-continued

Examples 143-155

| Example number | Chemical structure Compound name | Starting materials | Analytics/purification/yield |
|---|---|---|---|
| 155 | rac-2-[4-[4-amino-2-(N-(2-amino-1-methyl-2-oxo-ethyl)-4-fluoro-anilino)thiazole-5-carbonyl]phenoxy]-N-isopropyl-2-methyl-propanamide<br>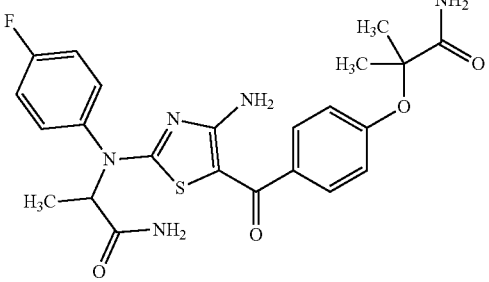<br>rac-2-[4-[4-amino-2-(N-(2-amino-1-methyl-2-oxo-ethyl)-4-fluoro-anilino)thiazole-5-carbonyl]phenoxy]-2-methyl-propanamide | Intermediate 82; ammonia | $^1$H-NMR (400 MHz, DMSO-d6): δ ppm = 1.15 (d, J = 7.35 Hz, 3 H), 1.43 (s, 6 H), 4.99-5.11 (m, 1 H), 6.82 (d, J = 8.87 Hz, 2 H), 7.25 (br d, J = 7.86 Hz, 2 H), 7.33 (t, J = 8.87 Hz, 2 H), 7.44 (d, J = 8.62 Hz, 2 H), 7.50-7.52 (m, 1 H), 7.57-7.59 (m, 1 H), 7.64 (dd, J = 8.74, 5.20 Hz, 2 H), 7.82-8.34 (m, 2 H).<br>LC-MS (method 1) Rt = 0.93 min; MS (ESIpos): m/z = 486.3 [M + H]$^+$<br>RP-HPLC (method C, basic)<br>42% yield |

Example 156 rac-2-(N-(5-benzoyl-4-methyl-thiazol-2-yl)-4-fluoro-anilino)propanamide

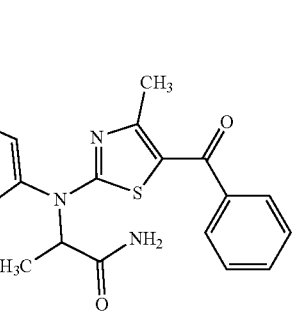

[2-(4-fluoroanilino)-4-methyl-thiazol-5-yl]-phenyl-methanone (40 mg, 0.13 mmol; Intermediate 81) was dissolved in N,N-dimethylformamide (1.4 mL), followed by the addition of potassium carbonate (177 mg, 1.28 mmol) and rac-2-bromopropanamide (97 mg, 0.64 mmol). The reaction mixture was stirred at 90° C. for 1 h. The reaction mixture was filtrated and purified by RP-HPLC (method D, basic) to give 24 mg (48% yield) of the title compound.

$^1$H-NMR (400 MHz, DMSO-d6): δ ppm=1.16 (d, J=7.35 Hz, 3H), 2.24-2.27 (m, 3H), 5.11 (q, J=7.35 Hz, 1H), 7.20 (s, 1H), 7.36 (t, J=8.87 Hz, 2H), 7.43-7.48 (m, 2H), 7.51-7.57 (m, 3H), 7.62 (s, 1H), 7.67 (dd, J=9.13, 5.07 Hz, 2H).

LC-MS (method 2) Rt=1.16 min; MS (ESIpos): m/z=384.4 [M+H]$^+$

Example 157 rac-2-(N-[4-amino-5-(4-hydroxybenzoyl)thiazol-2-yl]-4-fluoro-anilino)propanamide

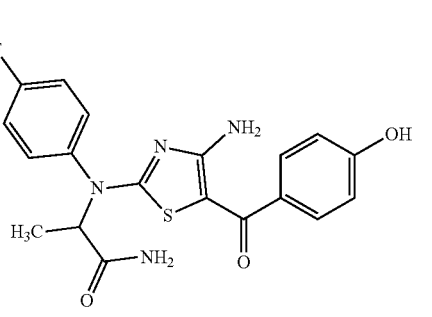

Rac-2-(N-[4-amino-5-(4-benzyloxybenzoyl)thiazol-2-yl]-4-fluoro-anilino)propanamide (100 mg, 204 µmol, Example 158) was dissolved in ethanol (2.5 mL). Under nitrogen atmosphere was added palladium on carbon (325 mg, 10% purity, 306 µmol; CAS-RN 7440-05-3) and then the nitrogen atmosphere was evacuated and was replaced with hydrogen. The mixture was stirred for 3.5 h at rt under hydrogen atmosphere. Further palladium on carbon (100 µmol) was added and the mixture was stirred for a further 3 h at rt under hydrogen atmosphere. The reaction mixture was filtered over celite, washed with ethanol and the filtrate was concentrated under reduced pressure. The residue was purified by RP-HPLC (method B, basic) to give 27 mg (31% yield) of the title compound.

LC-MS (method 2) Rt=0.69 min; MS (ESIpos): m/z=401.2 [M+H]$^+$

¹H-NMR (400 MHz, DMSO-d6): δ ppm=1.16 (d, J=7.35 Hz, 3H), 2.08 (s, 1H), 5.01-5.09 (m, 1H), 6.70-6.75 (m, 2H), 7.24 (s, 1H), 7.33 (t, J=8.87 Hz, 2H), 7.37-7.41 (m, 2H), 7.57 (s, 1H), 7.64 (dd, J=9.00, 4.94 Hz, 2H), 7.76-8.21 (m, 2H), 9.90 (br s, 1H)

Example 158 rac-2-(N-[4-amino-5-(4-benzyloxybenzoyl)thiazol-2-yl]-4-fluoro-anilino)propanamide

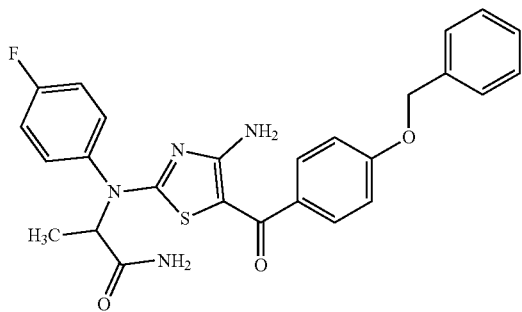 [SMILES: CC(C(N)=O)N(c1ccc(F)cc1)c1nc(N)c(C(=O)c2ccc(OCc3ccccc3)cc2)s1]

[4-amino-2-(4-fluoroanilino)-1,3-thiazol-5-yl][4-(benzyloxy)phenyl]methanone (610 mg, 1.45 mmol, Intermediate 77) was suspended in DMF (10 mL), rac-2-bromopropanamide (265 mg, 1.75 mmol) and potassium carbonate (301 mg, 2.18 mmol) were added. The reaction mixture was stirred for 3.5 h at rt. Further rac-2-bromopropanamide (265 mg, 1.75 mmol) and potassium carbonate (301 mg, 2.18 mmol) were added and the mixture was stirred overnight at rt. The mixture was treated with water and stirred for 30 min. The resulting precipitate was isolated by filtration, washed with water and dried to give 641 mg (98% purity, 88% yield) of the title compound.

¹H-NMR (400 MHz, DMSO-d6): δ ppm=1.16 (d, J=7.35 Hz, 3H), 5.02-5.09 (m, 1H), 5.11 (s, 2H), 7.00 (d, J=8.87 Hz, 2H), 7.25 (s, 1H), 7.31-7.45 (m, 7H), 7.46-7.50 (m, 2H), 7.57 (s, 1H), 7.64 (dd, J=8.87, 5.07 Hz, 2H), 7.78-8.38 (m, 2H).

LC-MS (method 2) Rt=1.25 min; MS (ESIpos): m/z=491.3 [M+H]⁺

The following examples were prepared from the starting materials stated in Table 9, below, using the procedure as for Example 1.

The crude product was either purified by RP-HPLC (methods A-D depending on polarity) or by preparative flash chromatography (methods X, Y or Z depending on polarity) after precipitation, extraction or filtration of the reaction mixture if necessary.

Enantiomers were separated from their racemate by chiral HPLC using the column and solvent conditions stated.

TABLE 9

Example 159-256

| Example number | Chemical structure Compound name | Starting materials | Analytics/purification/yield |
|---|---|---|---|
| 159 | rac-2-(N-[4-amino-5-[6-(difluoromethyl)pyridine-3-carbonyl]thiazol-2-yl]-4-fluoro-anilino)propanamide | Intermediate 101; rac-2-bromopropanamide | ¹H NMR (400 MHz, DMSO-d₆) δ ppm = 1.16 (d, J = 7.35 Hz, 3 H), 5.04-5.08 (m, 1 H), 6.94 (t, J = 60 Hz, 1 H), 7.29-7.33 (m, 3 H), 7.60-7.65 (m, 3 H), 7.72 (d, J = 8.11 Hz, 1 H), 8.04 (dd, J = 7.98, 2.15 Hz, 1 H), 8.30 8.34 (m, 2 H), 8.76 (d, J = 1.52 Hz, 1 H). RP-HPLC (method C basic) LC-MS (method 2) Rt = 1.00 min MS (ESIpos): m/z = 436.4 [M + H]⁺ 48% yield |
| 160 | | Intermediate 102; rac-2-bromopropanamide | ¹H NMR (400 MHz, DMSO-d₆) δ ppm = 1.18 (d, J = 7.35 Hz, 3 H), 5.00-5.04 (m, 1 H), 7.31 (s, 1 H), 7.40-7.44 (m, 2 H), 7.55-7.58 (m, 1 H), 7.63-7.67 (m, 2 H), 7.91 (dd, J = 6.84, 2.28 Hz, 1 H), 8.27-8.31 (m, 2 H), 8.60-8.64 (m, 2 H). Isolated via precipitation LC-MS (method 2) Rt = 0.94 min MS (ESIpos): m/z = 420.3 [M + H]⁺ 60% yield |

TABLE 9-continued

Example 159-256

| Example number | Chemical structure Compound name | Starting materials | Analytics/purification/yield |
|---|---|---|---|
| 160.1 and 160.2 | rac-2-(N-[4-amino-5-(pyridine-4-carbonyl)thiazol-2-yl]-3-chloro-4-fluoro-anilino)propanamide (R)-2-(N-[4-amino-5-(pyridine-4-carbonyl)thiazol-2-yl]-3-chloro-4-fluoro-anilino)propanamide and (S)-2-(N-[4-amino-5-(pyridine-4-carbonyl)thiazol-2-yl]-3-chloro-4-fluoro-anilino)propanamide | | |
| 160.1 | 2-(N-[4-amino-5-(pyridine-4-carbonyl)thiazol-2-yl]-3-chloro-4-fluoro-anilino)propanamide (enantiomer 1) | Example 160 | $^1$H NMR (400 MHz, DMSO-d$_6$) δ ppm = 1.18 (d, J = 7.35 Hz, 4 H), 5.00-5.05 (m, 1 H), 7.31 (s, 1 H), 7.42 (d, J = 6.08 Hz, 2 H), 7.57 (m, 1 H), 7.62-7.67 (m, 2 H), 7.92 (dd, J = 6.84, 2.53 Hz, 1 H), 8.25-8.29 (m, 2 H), 8.63 (d, J = 5.83 Hz, 2 H). LC-MS (method 1) Rt = 0.86 min; MS (ESIpos): m/z = 420.3 [M + H]$^+$ 34% yield |

Chiral HPLC Example 160.1
HPLC separation of rac-2-(N-[4-amino-5-(pyridine-4-carbonyl)thiazol-2-yl]-3-chloro-4-fluoro-anilino)propanamide(560 mg, 1.33 mmol, Example 160) on a chiral column gave 190 mg (34% yield) of 2-(N-[4-amino-5-(pyridine-4-carbonyl)thiazol-2-yl]-3-chloro-4-fluoro-anilino)propanamide, enantiomer 1.
Preparative chiral HPLC
PrepCon Labomatic HPLC; Column: YMC Amylose SA 10μ, 250 × 50;
eluent A: methyl tert-butyl ether + 0.1 vol % diethylamine; eluent B: acetonitrile; isocratic:
50% A + 50% B; flow: 120 mL/min; temperature: 25° C.; UV: 254 nm
Analytical chiral HPLC: Rt = 1.23 min
Waters Alliance 2695; Column: YMC Amylose SA 3μ, 100 × 4.6;
eluent A: methyl tert-butyl ether + 0.1 vol % diethylamine; eluent B: acetonitrile; isocratic:
50% A + 50% B; flow: 1.4 mL/min; temperature: 25° C.; UV: 254 nm

| | | | |
|---|---|---|---|
| 160.2 | 2-(N-[4-amino-5-(pyridine-4-carbonyl)thiazol-2-yl]-3-chloro-4-fluoro-anilino)propanamide (enantiomer 2) | Example 160 | $^1$H NMR (400 MHz, DMSO-d$_6$) δ ppm = 1.18 (d, J = 7.35 Hz, 4 H), 5.00-5.04 (m, 1 H), 7.31 (s, 1 H), 7.42 (d, J = 6.08 Hz, 2 H), 7.55-7.59 (m, 1 H), 7.63-7.67 (m, 2 H), 7.92 (dd, J = 6.84, 2.53 Hz, 1 H), 8.24-8.30 (m, 2 H), 8.63 (d, J = 5.83 Hz, 2 H). LC-MS (method 1) Rt = 0.86 min; MS (ESIpos): m/z = 420.3 [M + H]$^+$ 33% yield |

Chiral HPLC Example 160.2
HPLC separation of rac-2-(N-[4-amino-5-(pyridine-4-carbonyl)thiazol-2-yl]-3-chloro-4-fluoro-anilino)propanamide(560 mg, 1.33 mmol, Example 160) on a chiral column gave 185 mg (33% yield) of 2-(N-[4-amino-5-(pyridine-4-carbonyl)thiazol-2-yl]-3-chloro-4-fluoro-anilino)propanamide, enantiomer 2.

TABLE 9-continued

Example 159-256

| Example number | Chemical structure Compound name | Starting materials | Analytics/purification/yield |
|---|---|---|---|
| | Preparative chiral HPLC PrepCon Labomatic HPLC; Column: YMC Amylose SA 10μ, 250 × 50; eluent A: methyl tert-butyl ether + 0.1 vol % diethylamine; eluent B: acetonitrile; isocratic: 50% A + 50% B; flow: 120 mL/min; temperature: 25° C.; UV: 254 nm Analytical chiral HPLC: Rt = 1.67 min Waters Alliance 2695; Column: YMC Amylose SA 3μ, 100 × 4.6; eluent A: methyl tert-butyl ether + 0.1 vol % diethylamine; eluent B: acetonitrile; isocratic: 50% A + 50% B; flow: 1.4 mL/min; temperature: 25° C.; UV: 254 nm | | |
| 161 161.1 and 161.2 | rac-2-(N-[4-amino-5-(4-methoxybenzoyl)thiazol-2-yl]-3-chloro-4-fluoro-anilino)propanamide (R)-2-(N-[4-amino-5-(4-methoxybenzoyl)thiazol-2-yl]-3-chloro-4-fluoro-anilino)propanamide and (S)-2-(N-[4-amino-5-(4-methoxybenzoyl)thiazol-2-yl]-3-chloro-4-fluoro-anilino)propanamide | Intermediate 103; rac-2-bromopropanamide | $^1$H NMR (500 MHz, DMSO-$d_6$) δ ppm = 1.18 (d, J = 7.57 Hz, 3 H), 3.76 (s, 3 H), 5.00-5.04 (m, 1 H), 6.94 (d, J = 8.83 Hz, 2 H), 7.29 (s, 1 H), 7.50 (d, J = 8.83 Hz, 2 H), 7.57-7.59 (m, 1 H), 7.63 (s, 1 H), 7.64-7.68 (m, 1 H), 7.92 (m, 1 H), 8.12-8.17 (m, 2 H). LC-MS (method 2) Rt = 1.17 min Isolated via precipitation MS (ESIpos): m/z = 449.3 [M + H]$^+$ 70% yield |
| 161.1 | 2-(N-[4-amino-5-(4-methoxybenzoyl)thiazol-2-yl]-3-chloro-4-fluoro-anilino)propanamide (enantiomer 1) | Example 161 | $^1$H NMR (500 MHz, DMSO-$d_6$) δ ppm = 1.18 (d, J = 7.57 Hz, 3 H), 3.76 (s, 3 H), 5.00-5.04 (m, 1 H), 6.94 (d, J = 8.83 Hz, 2 H), 7.29 (s, 1 H), 7.50 (d, J = 8.83 Hz, 2 H), 7.55-7.59 (m, 1 H), 7.63 (s, 1 H), 7.64-7.66 (m, 1 H), 7.90-7.94 (m, 1 H), 8.14 (m, 2 H). LC-MS (method 1) Rt = 1.13 min MS (ESIpos): m/z = 449.4 [M + H]$^+$ $[α]_D^{20}$ = 85° C. = 10.3 mg/mL in DMSO 31% yield |

Chiral HPLC Example 161.1
HPLC separation of rac-2-(N-[4-amino-5-(4-methoxybenzoyl)thiazol-2-yl]-3-chloro-4-fluoro-anilino)propanamide (1300 mg, 2.9 mmol, Example 161) on a chiral column followed by trituration in MTBE gave 401 mg (31% yield) of 2-(N-[4-amino-5-(4-methoxybenzoyl)thiazol-2-yl]-3-chloro-4-fluoro-anilino)propanamide, enantiomer 1.
Preparative chiral HPLC
Instrument: PrepCon Labomatic HPLC; Column: YMC Cellulose SB 5μ, 250 × 30; eluent A: hexane + 0.1 vol % diethylamine; eluent B: 2-propanol; isocratic: 60% A + 40% B; flow: 40 mL/min; temperature: 25° C.; UV: 254 nm
Analytical chiral HPLC: Rt = 2.11 min
Instrument: Thermo Fisher UltiMate 3000; Column: YMC Cellulose SB 3μ, 100 × 4.6; eluent A: hexane + 0.1 vol % diethylamine; eluent B: 2-propanol; isocratic: 60% B + 40% B; flow: 1.4 mL/min; temperature: 25° C.; UV: 254 nm

TABLE 9-continued

Example 159-256

| Example number | Chemical structure Compound name | Starting materials | Analytics/purification/yield |
|---|---|---|---|
| 161.2 | 2-(N-[4-amino-5-(4-methoxybenzoyl)thiazol-2-yl]-3-chloro-4-fluoro-anilino)propanamide (enantiomer 2) | Example 161 | $^1$H NMR (500 MHz, DMSO-d$_6$) δ ppm = 1.18 (d, J = 7.57 Hz, 3 H), 3.76 (s, 3 H), 5.00-5.04 (m, 1 H), 6.94 (d, J = 8.83 Hz, 2 H), 7.29 (s, 1 H), 7.50 (d, J = 8.83 Hz, 2 H), 7.58 (m, 1 H), 7.63 (s, 1 H), 7.66 (m, 1 H), 7.90-7.94 (m, 1 H), 8.10-8.16 (m, 2 H). LC-MS (method 1) Rt = 1.13 min; MS (ESIpos): m/z = 449.4 [M + H]$^+$ [α]$_D^{20}$ = −89° C. = 10.1 mg/mL in DMSO 29% yield |

Chiral HPLC Example 161.2
HPLC separation of rac-2-(N-[4-amino-5-(4-methoxybenzoyl)thiazol-2-yl]-3-chloro-4-fluoro-anilino)propanamide(1300 mg, 2.9 mmol, Example 161) on a chiral column followed by trituration in MTBE gave 375 mg (29% yield) of 2-(N-[4-amino-5-(4-methoxybenzoyl)thiazol-2-yl]-3-chloro-4-fluoro-anilino)propanamide, enantiomer 2.
Preparative chiral HPLC
Instrument: PrepCon Labomatic HPLC; Column: YMC Cellulose SB 5μ, 250 × 30; eluent A: hexane + 0.1 vol % diethylamine; eluent B: 2-propanol; isocratic: 60% A + 40% B; flow: 40 mL/min; temperature: 25° C.; UV: 254 nm
Analytical chiral HPLC: Rt = 5.48 min
Instrument: Thermo Fisher UltiMate 3000; Column: YMC Cellulose SB 3μ, 100 × 4.6; eluent A: hexane + 0.1 vol % diethylamine; eluent B: 2-propanol; isocratic: 60% B + 40% B; flow: 1.4 mL/min; temperature: 25° C.; UV: 254 nm

| 162 | | Intermediate 104; rac-2-bromopropanamide | $^1$H-NMR (400 MHz, DMSO-d$_6$): δ ppm = 1.13-1.20 (m, 3 H), 5.00-5.12 (m, 1 H), 7.10 (d, J = 8.62 Hz, 1 H), 7.23-7.28 (m, 1 H), 7.34 (t, J = 8.87 Hz, 2 H), 7.52-7.68 (m, 3 H), 7.97-8.03 (m, 1 H), 8.06-8.35 (m, 1 H), 8.35-8.42 (m, 1 H). LC-MS (method 2) Rt = 1.10 min Isolated via precipitation MS (ESIpos): m/z = 452.2 [M + H]$^+$ 61% yield |
|---|---|---|---|
| 162.1 and 162.2 | rac-2-(N-[4-amino-5-[6-(difluoromethoxy)pyridine-3-carbonyl]thiazol-2-yl]-4-fluoro-anilino)propanamide (R)-2-(N-[4-amino-5-(6-(difluoromethoxy)pyridine-3-carbonyl]thiazol-2-yl]-4-fluoro-anilino)propanamide and (S)-2-(N-[4-amino-5-[6-(difluoromethoxy)pyridine-3-carbonyl]thiazol-2-yl]-4-fluoro-anilino)propanamide | | |

TABLE 9-continued

Example 159-256

| Example number | Chemical structure Compound name | Starting materials | Analytics/purification/yield |
|---|---|---|---|
| 162.1 | 2-(N-[4-amino-5-[6-(difluoromethoxy)pyridine-3-carbonyl]thiazol-2-yl]-4-fluoro-anilino)propanamide (enantiomer 1) | Example 162 | $^1$H NMR (400 MHz, DMSO-d$_6$) δ ppm = 1.16 (d, J = 7.35 Hz, 3 H), 5.06 (m, 1 H), 7.11 (d, J = 8.62 Hz, 1 H), 7.26 (s, 1 H), 7.34 (m, 2 H), 7.59 (s, 1 H), 7.65 (br d, J = 3.80 Hz, 2 H), 7.71 (t, J = 72 Hz, 1 H), 8.00 (dd, J = 8.49, 2.41 Hz, 1 H), 8.19 (m, 1 H), 8.38 (d, J = 2.03 Hz, 1 H), 8.38 (m, 1 H). LC-MS (method 2) Rt = 1.13 min; MS (ESIpos): m/z = 452.3 [M + H]$^+$ [α]$_D^{20}$ = −71° C. = 8 mg/mL in DMSO 37% yield |

Chiral HPLC Example 162.1
HPLC separation of rac-2-(N-[4-amino-5-[6-(difluoromethoxy)pyridine-3-carbonyl]thiazol-2-yl]-4-fluoro-anilino)propanamide(105 mg, 0.23 mmol, Example 162) on a chiral column gave 39 mg (37% yield) of 2-(N-[4-amino-5-[6-(difluoromethoxy)pyridine-3-carbonyl]thiazol-2-yl]-4-fluoro-anilino)propanamide, enantiomer 1.
Preparative chiral HPLC
Instrument: PrepCon Labomatic HPLC-4; column: YMC Cellulose SB 5μ, 250 × 30;
eluent A: hexane + 0.1 vol % diethylamine; eluent B: ethanol + 0.1 vol % diethylamine; isocratic:
70% A + 30% B; flow: 50 mL/min; temperature: 25° C.; UV: 254 nm
Analytical chiral HPLC: Rt = 3.07 min
Instrument: Waters Alliance 2695; column: YMC Cellulose SB 3μ, 100 × 4.6;
eluent A: hexane + 0.1 vol % diethylamine; eluent B: ethanol; isocratic: 70% A + 30% B; flow: 1.4
mL/min; temperature: 25° C.; UV: 254 nm

| | | | |
|---|---|---|---|
| 162.2 | 2-(N-[4-amino-5-[6-(difluoromethoxy)pyridine-3-carbonyl]thiazol-2-yl]-4-fluoro-anilino)propanamide (enantiomer 2) | Example 162 | $^1$H NMR (400 MHz, DMSO-d$_6$) δ ppm = 1.16 (d, J = 7.35 Hz, 3 H), 5.02-5.08 (m, 1 H), 7.11 (d, J = 8.62 Hz, 1 H), 7.26 (s, 1 H), 7.34 (m, 2 H), 7.59 (s, 1 H), 7.65 (br d, J = 3.80 Hz, 2 H), 7.71 (t, J = 72 Hz, 1 H), 8.00 (dd, J = 8.49, 2.41 Hz, 1 H), 8.17-8.21 (m, 1 H), 8.38 (d, J = 2.03 Hz, 1 H), 8.38 (m, 1 H). LC-MS (method 2) Rt = 1.13 min; MS (ESIpos): m/z = 452.3 [M + H]$^+$ [α]$_D^{20}$ = 74° C. = 8.7 mg/mL in DMSO 39% yield |

Chiral HPLC Example 162.2
HPLC separation of rac-2-(N-[4-amino-5-[6-(difluoromethoxy)pyridine-3-carbonyl]thiazol-2-yl]-4-fluoro-anilino)propanamide(105 mg, 0.23 mmol, Example 162) on a chiral column gave 41 mg (39% yield) of 2-(N-[4-amino-5-[6-(difluoromethoxy)pyridine-3-carbonyl]thiazol-2-yl]-4-fluoro-anilino)propanamide, enantiomer 2.
Preparative chiral HPLC
Instrument: PrepCon Labomatic HPLC-4; column: YMC Cellulose SB 5μ, 250 × 30;
eluent A: hexane + 0.1 vol % diethylamine; eluent B: ethanol + 0.1 vol % diethylamine; isocratic:
70% A + 30% B; flow: 50 mL/min; temperature: 25° C.; UV: 254 nm

TABLE 9-continued

Example 159-256

| Example number | Chemical structure Compound name | Starting materials | Analytics/purification/yield |
|---|---|---|---|
| | Analytical chiral HPLC: Rt = 2.40 min  Instrument: Waters Alliance 2695; column: YMC Cellulose SB 3μ, 100 × 4.6; eluent A: hexane + 0.1 vol % diethylamine; eluent B: ethanol; isocratic: 70% A + 30% B; flow: 1.4 mL/min; temperature: 25° C.; UV: 254 nm | | |
| 163 | 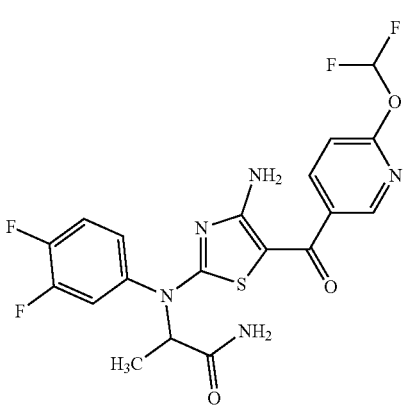 [SMILES: CC(C(N)=O)N(c1ccc(F)c(F)c1)c1nc(N)c(C(=O)c2ccc(OC(F)F)nc2)s1]<br>rac-2-(N-[4-amino-5-[6-(difluoromethoxy)pyridine-3-carbonyl]thiazol-2-yl]-3,4-difluoro-anilino)propanamide | Intermediate 105; rac-2-bromopropanamide | $^1$H NMR (400 MHz, DMSO-$d_6$) δ ppm = 1.19 (d, J = 8 Hz, 3 H), 5.03 (q, J = 6.84 Hz, 1 H), 7.09-7.12 (m, 1 H), 7.30 (s, 1 H), 7.58 (m, 3 H), 7.71 (t, J = 72 Hz, 1 H), 7.79 (m, 1 H), 8.02 (dd, J = 8.49, 2.41 Hz, 1 H), 8.19-8.23 (m, 2 H), 8.41 (d, J = 2.03 Hz, 1 H). LC-MS (method 2) Rt = 1.15 min Biotage (method X) MS (ESIpos): m/z = 470.3 [M + H]$^+$ 56% yield |
| 163.1 and 163.2 | (R)-(N-[4-amino-5-[6-(difluoromethoxy)pyridine-3-carbonyl]thiazol-2-yl]-3,4-difluoro-anilino)propanamide and (S)-(N-[4-amino-5-[6-(difluoromethoxy)pyridine-3-carbonyl]thiazol-2-yl]-3,4-difluoro-anilino)propanamide | | |
| 163.1 | 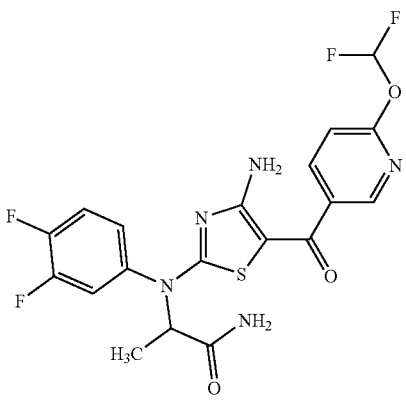<br>2-(N-[4-amino-5-[6-(difluoromethoxy)pyridine-3-carbonyl]thiazol-2-yl]-3,4-difluoro-anilino)propanamide (enantiomer 1) | Example 163 | $^1$H NMR (400 MHz, DMSO-$d_6$) δ ppm = 1.16 (d, J = 7.35 Hz, 3 H), 5.02-5.06 (m, 1 H), 7.11 (d, J = 8.62 Hz, 1 H), 7.26 (s, 1 H), 7.34 (m, 2 H), 7.59 (s, 1 H), 7.65 (br d, J = 3.80 Hz, 2 H), 7.71 (t, J = 72 Hz, 1 H), 8.00 (dd, J = 8.49, 2.41 Hz, 1 H), 8.17-8.22 (m, 1 H), 8.38 (d, J = 2.03 Hz, 1 H), 8.35-8.37 (m, 1 H). LC-MS (method 2) Rt = 1.15 min 41% yield |

Chiral HPLC Example 163.1
HPLC separation of rac-2-(N-[4-amino-5-[6-(difluoromethoxy)pyridine-3-carbonyl]thiazol-2-yl]-3,4-difluoro-anilino)propanamide(120 mg, 0.26 mmol, Example 163) on a chiral column gave 49 mg (41% yield) of 2-(N-[4-amino-5-[6-(difluoromethoxy)pyridine-3-carbonyl]thiazol-2-yl]-3,4-difluoro-anilino)propanamide, enantiomer 1.
Preparative chiral HPLC
Instrument: PrepCon Labomatic HPLC-2; Column: YMC Amylose SA 10μ, 250 × 50; eluent A: methyl tert-butyl ether + 0.1 vol % diethylamine; eluent B: acetonitrile; isocratic: 95% A + 5% B; flow: 100 mL/min; temperature: 25° C.; UV: 280 nm

TABLE 9-continued

Example 159-256

| Example number | Chemical structure Compound name | Starting materials | Analytics/purification/yield |
|---|---|---|---|
| | Analytical chiral HPLC: Rt = 2.42 min Instrument: Thermo Fisher UltiMate 3000; Column: YMC Amylose SA 3µ, 100 × 4.6; eluent A: methyl tert-butyl ether + 0.1 vol % diethylamine; eluent B: acetonitrile; isocratic: 95% A + 5% B; flow: 1.4 mL/min; temperature: 25° C.; UV: 280 nm | | |
| 163.2 | 2-(N-[4-amino-5-[6-(difluoromethoxy)pyridine-3-carbonyl]thiazol-2-yl]-3,4-difluoro-anilino)propanamide (enantiomer 2) | Example 163 | $^1$H NMR (400 MHz, DMSO-$d_6$) δ ppm = 1.19 (d, J = 7.35 Hz, 3 H), 5.02-5.06 (m, 1 H), 7.12 (d, J = 8.62 Hz, 1 H), 7.30 (s, 1 H), 7.48-7.52 (m, 1 H), 7.58-7.62 (m, 2 H), 7.72 (t, J = 72 Hz, 1 H), 7.77-7.82 (m, 1 H), 8.02 (dd, J = 8.49, 2.41 Hz, 1 H), 8.20-8.25 (m, 2 H), 8.41 (d, J = 2.53 Hz, 1 H). LC-MS (method 2) Rt = 1.15 min 56% yield |
| | Chiral HPLC Example 163.2 HPLC separation of rac-2-(N-[4-amino-5-[6-(difluoromethoxy)pyridine-3-carbonyl]thiazol-2-yl]-3,4-difluoro-anilino)propanamide(120 mg, 0.26 mmol, Example 163) on a chiral column gave 68 mg (56% yield) of 2-(N-[4-amino-5-[6-(difluoromethoxy)pyridine-3-carbonyl]thiazol-2-yl]-3,4-difluoro-anilino)propanamide, enantiomer 2. Preparative chiral HPLC Instrument: PrepCon Labomatic HPLC-2; Column: YMC Amylose SA 10µ, 250 × 50; eluent A: methyl tert-butyl ether + 0.1 vol % diethylamine; eluent B: acetonitrile; isocratic: 95% A + 5% B; flow: 100 mL/min; temperature: 25° C.; UV: 280 nm Analytical chiral HPLC: Rt = 3.72 min Instrument: Thermo Fisher UltiMate 3000; Column: YMC Amylose SA 3µ, 100 × 4.6; eluent A: methyl tert-butyl ether + 0.1 vol % diethylamine; eluent B: acetonitrile; isocratic: 95% A + 5% B; flow: 1.4 mL/min; temperature: 25° C.; UV: 280 nm | | |
| 164 | rac-2-(N-[4-amino-5-[6-(difluoromethoxy)pyridine-3-carbonyl]thiazol-2-yl]-4-chloro-3-fluoro-anilino)propanamide | Intermediate 106, rac-2-bromopropanamide | $^1$H NMR (400 MHz, DMSO-$d_6$) δ ppm = 1.20 (d, J = 8.11 Hz, 3 H), 5.01-5.05 (m, 1 H), 7.12 (d, J = 8.62 Hz, 1 H), 7.32 (s, 1 H), 7.53 (m, 1 H), 7.64 (s, 1 H), 7.71 (t, J = 72 Hz, 1 H), 7.72-7.76 (m, 2 H), 8.03 (dd, J = 8.62, 2.53 Hz, 1 H), 8.20-8.25 (m, 2 H), 8.41 (d, J = 2.28 Hz, 1 H). Biotage (method X) LC-MS (method 2) Rt = 1.21 min MS (ESIpos): m/z = 486.3 [M + H]$^+$ 53% yield |
| 164.1 and 164.2 | (R)-2-(N-[4-amino-5-[6-(difluoromethoxy)pyridine-3-carbonyl]thiazol-2-yl]-4-chloro-3-fluoro-anilino)propanamide and (S)-2-(N-[4-amino-5-[6- | | |

TABLE 9-continued

Example 159-256

| Example number | Chemical structure Compound name | Starting materials | Analytics/purification/yield |
|---|---|---|---|
| | (difluoromethoxy)pyridine-3-carbonyl]thiazol-2-yl]-4-chloro-3-fluoro-anilino)propanamide | | |
| 164.1 | 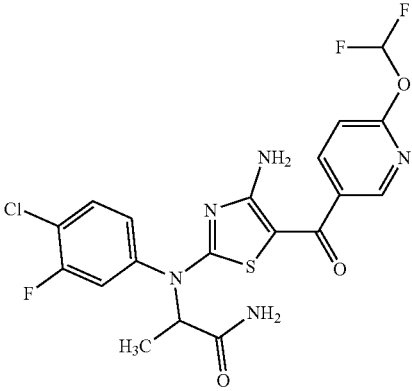 [SMILES: CC(C(N)=O)N(c1ccc(Cl)c(F)c1)c1nc(N)c(C(=O)c2ccc(OC(F)F)nc2)s1]<br>2-(N-[4-amino-5-[6-(difluoromethoxy)pyridine-3-carbonyl]thiazol-2-yl]-4-chloro-3-fluoro-anilino)propanamide (enantiomer 1) | Example 164 | $^1$H NMR (400 MHz, DMSO-d$_6$) δ ppm = 1.20 (d, J = 7.35 Hz, 3 H), 5.01-5.05 (m, 1 H), 7.12 (m, 1 H), 7.32 (s, 1 H), 7.53 (m, 1 H), 7.64 (s, 1 H), 7.71 (t, J = 72 Hz, 1 H), 7.72-7.77 (m, 2 H), 8.03 (dd, J = 8.62, 2.53 Hz, 1 H), 8.21-8.26 (m, 2 H), 8.39-8.42 (m, 1 H). 45% yield |

Chiral HPLC Example 164.1
HPLC separation of rac-2-(N-[4-amino-5-[6-(difluoromethoxy)pyridine-3-carbonyl]thiazol-2-yl]-4-chloro-3-fluoro-anilino)propanamide(113 mg, 0.23 mmol, Example 164) on a chiral column gave 51 mg (45% yield) of 2-(N-[4-amino-5-[6-(difluoromethoxy)pyridine-3-carbonyl]thiazol-2-yl]-4-chloro-3-fluoro-anilino)propanamide, enantiomer 1.
Preparative chiral HPLC
Instrument: PrepCon Labomatic HPLC-2; Column: YMC Amylose SA 10μ, 250 × 50; eluent A: methyl tert-butyl ether + 0.1 vol % diethylamine; eluent B: acetonitrile; isocratic: 95% A + 5% B; flow: 100 mL/min; temperature: 25° C.; UV: 280 nm
Analytical chiral HPLC: Rt = 2.6 min
Instrument: Thermo Fisher UltiMate 3000; Column: YMC Amylose SA 3μ, 100 × 4.6; eluent A: methyl tert-butyl ether + 0.1 vol % diethylamine; eluent B: acetonitrile; isocratic: 95% A + 5% B; flow: 1.4 mL/min; temperature: 25° C.; UV: 280 nm

| 164.2 | 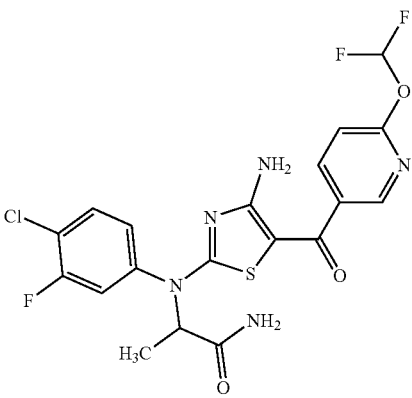 [SMILES: CC(C(N)=O)N(c1ccc(Cl)c(F)c1)c1nc(N)c(C(=O)c2ccc(OC(F)F)nc2)s1]<br>2-(N-[4-amino-5-[6-(difluoromethoxy)pyridine-3-carbonyl]thiazol-2-yl]-4-chloro-3-fluoro-anilino)propanamide (enantiomer 2) | Example 164 | $^1$H NMR (400 MHz, DMSO-d$_6$) δ ppm = 1.20 (d, J = 7.35 Hz, 3 H), 5.01-5.05 (m, 1 H), 7.10-7.14 (m, 1 H), 7.32 (s, 1 H), 7.50-7.56 (m, 1 H), 7.64 (s, 1 H), 7.71 (t, J = 72 Hz, 1 H), 7.70-7.78 (m, 2 H), 8.03 (dd, J = 8.62, 2.53 Hz, 1 H), 8.20-8.25 (m, 2 H), 8.40-8.43 (m, 1 H). 45% yield |

Chiral HPLC Example 164.2
HPLC separation of rac-2-(N-[4-amino-5-[6-(difluoromethoxy)pyridine-3-carbonyl]thiazol-2-yl]-4-chloro-3-fluoro-anilino)propanamide(113 mg, 0.23 mmol, Example 164) on a chiral column gave 51 mg (45% yield) of 2-(N-[4-amino-5-[6-(difluoromethoxy)pyridine-3-carbonyl]thiazol-2-yl]-4-chloro-3-fluoro-anilino)propanamide, enantiomer 2.

TABLE 9-continued

Example 159-256

| Example number | Chemical structure Compound name | Starting materials | Analytics/purification/yield |
|---|---|---|---|
| | Preparative chiral HPLC Instrument: PrepCon Labomatic HPLC-2; Column: YMC Amylose SA 10μ, 250 × 50; eluent A: methyl tert-butyl ether + 0.1 vol % diethylamine; eluent B: acetonitrile; isocratic: 95% A + 5% B; flow: 100 mL/min; temperature: 25° C.; UV: 280 nm Analytical chiral HPLC: Rt = 3.87 min Instrument: Thermo Fisher UltiMate 3000; Column: YMC Amylose SA 3μ, 100 × 4.6; eluent A: methyl tert-butyl ether + 0.1 vol % diethylamine; eluent B: acetonitrile; isocratic: 95% A + 5% B; flow: 1.4 mL/min; temperature: 25° C.; UV: 280 nm | | |
| 165 | 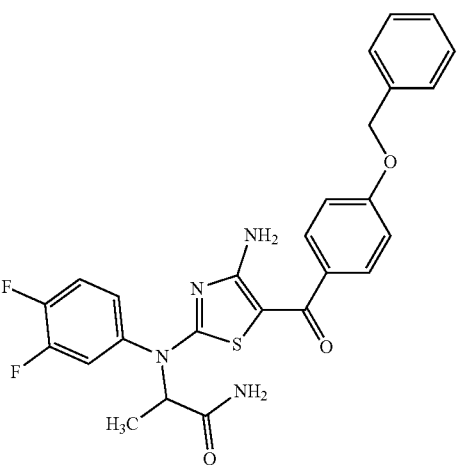 [SMILES: CC(C(N)=O)N(c1ccc(F)c(F)c1)c1nc(N)c(C(=O)c2ccc(OCc3ccccc3)cc2)s1] rac-2-(N-[4-amino-5-(4-benzyloxybenzoyl)thiazol-2-yl]-3,4-difluoro-anilino)propanamide | Intermediate 107, rac-2-bromopropanamide | $^1$H NMR (400 MHz, DMSO-d$_6$) δ ppm = 1.18 (d, J = 7.35 Hz, 3 H), 5.00-5.04 (m, 1 H), 5.12 (s, 2 H), 7.00-7.05 (m, 2 H), 7.24-7.64 (m, 11 H), 7.77-7.81 (m, 1 H), 8.03-8.07 (m, 2 H). Biotage (method X) LC-MS (method 2) Rt = 1.32 min MS (ESIpos): m/z = 509.4 [M + H]$^+$ 57% yield |
| 165.1 and 165.2 | (R)-2-(N-[4-amino-5-(4-benzyloxybenzoyl)thiazol-2-yl-3,4-difluoro-anilino)propanamide and (S)-2-(N-[4-amino-5-(4-benzyloxybenzoyl)thiazol-2-yl]-3,4-difluoro-anilino)propanamide | | |
| 165.1 | 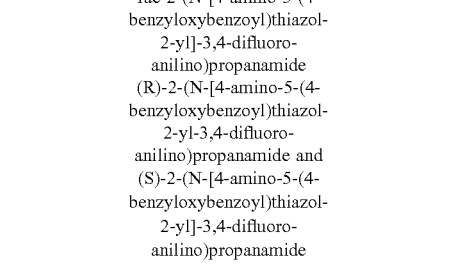 2-(N-[4-amino-5-(4-benzyloxybenzoyl)thiazol-2-yl]-3,4-difluoro-anilino)propanamide (enantiomer 1) | Example 165 | $^1$H NMR (400 MHz, DMSO-d$_6$) δ ppm = 1.19 (d, J = 7.35 Hz, 4 H), 5.00-5.04 (m, 1 H), 5.12 (s, 2 H), 7.00-7.05 (m, 2 H), 7.28 (s, 1 H), 7.36-7.44 (m, 5 H), 7.47-7.52 (m, 3 H), 7.59-7.63 (m, 2 H), 7.78 (ddd, J = 11.34, 7.54, 2.41 Hz, 1 H), 8.02-8.06 (m, 2 H) 46% yield |

TABLE 9-continued

Example 159-256

| Example number | Chemical structure Compound name | Starting materials | Analytics/purification/yield |
|---|---|---|---|
| | Chiral HPLC Example 165.1 HPLC separation of rac-2-(N-[4-amino-5-(4-benzyloxybenzoyl)thiazol-2-yl]-3,4-difluoro-anilino)propanamide(340 mg, 0.67 mmol, Example 165) on a chiral column gave 155 mg (46% yield) of 2-(N-[4-amino-5-(4-benzyloxybenzoyl)thiazol-2-yl]-3,4-difluoro-anilino)propanamide, enantiomer 1. Preparative chiral HPLC Instrument: PrepCon Labomatic HPLC-4; Column: YMC Amylose SA 5μ, 250 × 30; eluent A: methyl tert-butyl ether + 0.1 vol % diethylamine; eluent B: acetonitrile; isocratic: 80% A + 20% B; flow: 50 mL/min; temperature: 25° C.; UV: 280 nm Analytical chiral HPLC: Rt = 1.73 min Instrument: Waters Alliance 2695; Column: YMC Amylose SA 3μ, 100 × 4.6; eluent A: methyl tert-butyl ether + 0.1 vol % diethylamine; eluent B: acetonitrile; isocratic: 80% A + 20% B; flow: 1.4 mL/min; temperature: 25° C.; UV: 280 nm | | |
| 165.2 | 2-(N-[4-amino-5-(4-benzyloxybenzoyl)thiazol-2-yl]-3,4-difluoro-anilino)propanamide (enantiomer 2) | Example 165 | $^1$H NMR (400 MHz, DMSO-d$_6$) δ ppm = 1.19 (d, J = 7.35 Hz, 4 H), 5.00-5.04 (m, 1 H), 5.12 (s, 2 H), 7.02 (m, 2 H), 7.28 (s, 1 H), 7.35-7.45 (m, 5 H), 7.47-7.52 (m, 3 H), 7.58-7.62 (m, 2 H), 7.78 (ddd, J = 11.34, 7.54, 2.41 Hz, 1 H), 8.02-8.05 (m, 2 H) 46% yield |
| | Chiral HPLC Example 165.2 HPLC separation of rac-2-(N-[4-amino-5-(4-benzyloxybenzoyl)thiazol-2-yl]-3,4-difluoro-anilino)propanamide(340 mg, 0.67 mmol, Example 165) on a chiral column gave 156 mg (46% yield) of 2-(N-[4-amino-5-(4-benzyloxybenzoyl)thiazol-2-yl]-3,4-difluoro-anilino)propanamide, enantiomer 2. Preparative chiral HPLC Instrument: PrepCon Labomatic HPLC-4; Column: YMC Amylose SA 5μ, 250 × 30; eluent A: methyl tert-butyl ether + 0.1 vol % diethylamine; eluent B: acetonitrile; isocratic: 80% A + 20% B; flow: 50 mL/min; temperature: 25° C.; UV: 280 nm Analytical chiral HPLC: Rt = 2.32 min Instrument: Waters Alliance 2695; Column: YMC Amylose SA 3μ, 100 × 4.6; eluent A: methyl tert-butyl ether + 0.1 vol % diethylamine; eluent B: acetonitrile; isocratic: 80% A + 20% B; flow: 1.4 mL/min; temperature: 25° C.; UV: 280 nm | | |

TABLE 9-continued

Example 159-256

| Example number | Chemical structure Compound name | Starting materials | Analytics/purification/yield |
|---|---|---|---|
| 166 | rac-2-(N-[4-amino-5-(4-benzyloxybenzoyl)thiazol-2-yl]-4-chloro-3-fluoro-anilino)propanamide | Intermediate 108, rac-2-bromopropanamide | $^1$H NMR (400 MHz, DMSO-d$_6$) δ ppm = 1.20 (d, J = 7.35 Hz, 3 H), 5.00-5.04 (m, 1 H), 5.12 (s, 2 H), 7.00-7.05 (m, 2 H), 7.30-7.42 (m, 6 H), 7.47-7.52 (m, 3 H), 7.63 (s, 1 H), 7.73-7.77 (m, 2 H), 8.09-8.13 (m, 2 H) Biotage (method X) LC-MS (method 2) Rt = 1.36 min MS (ESIpos): m/z = 525.3 [M + H]$^+$ 57% yield |
| 166.1 and 166.2 | (R)-2-(N-[4-amino-5-(4-benzyloxybenzoyl)thiazol-2-yl]-4-chloro-3-fluoro-anilino)propanamide and (S)-2-(N-[4-amino-5-(4-benzyloxybenzoyl)thiazol-2-yl]-4-chloro-3-fluoro-anilino)propanamide | | |
| 166.1 | 2-(N-[4-amino-5-(4-benzyloxybenzoyl)thiazol-2-yl]-4-chloro-3-fluoro-anilino)propanamide (enantiomer 1) | Example 166 | $^1$H NMR (400 MHz, DMSO-d$_6$) δ ppm = 1.20 (d, J = 7.35 Hz, 3 H), 5.01-5.04 (m, 1 H), 5.12 (s, 2 H), 7.00-7.05 (m, 2 H), 7.35-7.45 (m, 9 H), 7.63 (s, 1 H), 7.73-7.77 (m, 2 H), 8.08-8.13 (m, 2 H) 39% yield |

Chiral HPLC Example 166.1
HPLC separation of rac-2-(N-[4-amino-5-(4-benzyloxybenzoyl)thiazol-2-yl]-4-chloro-3-fluoro-anilino)propanamide(790 mg, 1.5 mmol, Example 166) on a chiral column gave 313 mg (39% yield) of 2-(N-[4-amino-5-(4-benzyloxybenzoyl)thiazol-2-yl]-4-chloro-3-fluoro-anilino)propanamide, enantiomer 1.
Preparative chiral HPLC
Instrument: PrepCon Labomatic HPLC-4; Column: YMC Cellulose SC 10μ, 250 × 50; eluent A: methyl tert-butyl ether + 0.1 vol % diethylamine; eluent B: acetonitrile; isocratic: 90% A + 10% B; flow: 100 mL/min; temperature: 25° C.; UV: 325 nm TABLE 9-continued Example 159-256

| Example number | Chemical structure Compound name | Starting materials | Analytics/purification/yield |
|---|---|---|---|
| | Analytical chiral HPLC: Rt = 2.94 min Instrument: Thermo Fisher UltiMate 3000; Column: YMC Cellulose SC 3μ, 100 × 4.6; eluent A: methyl tert-butyl ether + 0.1 vol % diethylamine; eluent B: acetonitrile; isocratic: 90% A + 10% B; flow: 1.4 mL/min; temperature: 25° C.; UV: 325 nm | | |
| 166.2 | 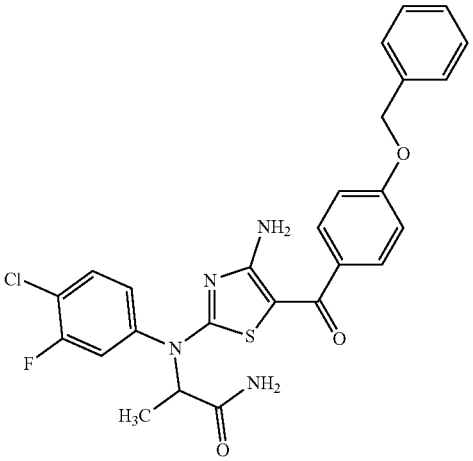 [SMILES: CC(C(N)=O)N(c1ccc(Cl)c(F)c1)c1nc(N)c(C(=O)c2ccc(OCc3ccccc3)cc2)s1]<br>2-(N-[4-amino-5-(4-benzyloxybenzoyl)thiazol-2-yl]-4-chloro-3-fluoro-anilino)propanamide (enantiomer 2)<br>HPLC separation of rac-2-(N-[4-amino-5-(4-benzyloxybenzoyl)thiazol-2-yl]-4-chloro-3-fluoro-anilino)propanamide(790 mg, 1.5 mmol, Example 166) on a chiral column gave 276 mg (35% yield) of 2-(N-[4-amino-5-(4-benzyloxybenzoyl)thiazol-2-yl]-4-chloro-3-fluoro-anilino)propanamide, enantiomer 2.<br>Preparative chiral HPLC<br>Instrument: PrepCon Labomatic HPLC-4; Column: YMC Cellulose SC 10μ, 250 × 50; eluent A: methyl tert-butyl ether + 0.1 vol % diethylamine; eluent B: acetonitrile; isocratic: 90% A + 10% B; flow: 100 mL/min; temperature: 25° C.; UV: 325 nm<br>Analytical chiral HPLC: Rt = 3.51 min<br>Instrument: Thermo Fisher UltiMate 3000; Column: YMC Cellulose SC 3μ, 100 × 4.6; eluent A: methyl tert-butyl ether + 0.1 vol % diethylamine; eluent B: acetonitrile; isocratic: 90% A + 10% B; flow: 1.4 mL/min; temperature: 25° C.; UV: 325 nm | Example 166 | $^1$H NMR (400 MHz, DMSO-$d_6$) δ ppm = 1.20 (d, J = 7.35 Hz, 3 H), 5.01-5.05 (m, 1 H), 5.12 (s, 2 H), 7.00-7.05 (m, 2 H), 7.35-7.45 (m, 9 H), 7.63 (s, 1 H), 7.73-7.77 (m, 2 H), 8.08-8.13 (m, 2 H)<br>35% yield |
| 167 | 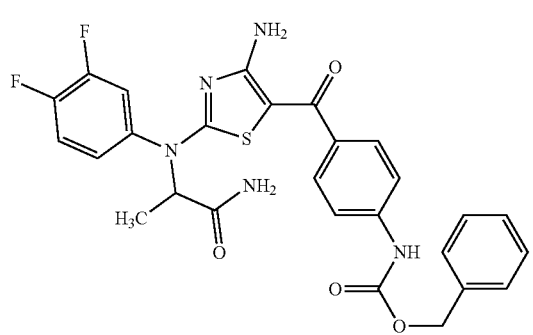 [SMILES: CC(C(N)=O)N(c1ccc(F)c(F)c1)c1nc(N)c(C(=O)c2ccc(NC(=O)OCc3ccccc3)cc2)s1]<br>rac-benzyl N-[4-[4-amino-2-(N-(2-amino-1-methyl-2-oxo-ethyl)-3,4-difluoro-anilino)thiazole-5-carbonyl]phenyl]carbamate | Intermediate 109, rac-2-bromopropanamide | $^1$H NMR (400 MHz, DMSO-$d_6$) δ ppm = 1.18 (d, J = 7.60 Hz, 3 H), 5.01 (br d, J = 7.35 Hz, 1 H), 5.15 (s, 2 H), 7.28 (s, 1 H), 7.40 (m, 6 H), 7.48 (m, 5H), 7.57 (m, 1 H), 7.61 (s, 1 H), 7.77 (ddd, J = 11.41, 7.48, 2.41 Hz, 1 H), 7.95 (m, 2 H)<br>Biotage (method X)<br>LC-MS (method 2) Rt = 1.22 min<br>MS (ESIpos): m/z = 552.4 [M + H]$^+$<br>64% yield |

TABLE 9-continued

Example 159-256

| Example number | Chemical structure Compound name | Starting materials | Analytics/purification/yield |
|---|---|---|---|
| 167.1 and 167.2 | (R)-benzyl N-[4-[4-amino-2-(N-(2-amino-1-methyl-2-oxo-ethyl)-3,4-difluoro-anilino)thiazole-5-carbonyl]phenyl]carbamate and (S)-benzyl N-[4-[4-amino-2-(N-(2-amino-1-methyl-2-oxo-ethyl)-3,4-difluoro-anilino)thiazole-5-carbonyl]phenyl]carbamate | | |
| 167.1 | Benzyl N-[4-[4-amino-2-(N-(2-amino-1-methyl-2-oxo-ethyl)-3,4-difluoro-anilino)thiazole-5-carbonyl]phenyl]carbamate (enantiomer 1) | Example 167 | $^1$H NMR (400 MHz, DMSO-d$_6$) δ ppm = 1.18 (d, J = 7.35 Hz, 3 H), 5.01 (q, J = 7.35 Hz, 1 H), 5.15 (s, 2 H), 5.76 (s, 1 H), 7.28 (s, 1 H), 7.35-7.42 (m, 5 H), 7.46-7.52 (m, 5 H), 7.57 (m, 1 H), 7.61 (s, 1 H), 7.78 (m, 1 H), 8.18 (m, 2 H), 10.00 (s, 1 H) 32% yield |

Chiral HPLC Example 167.1
HPLC separation of rac-benzyl N-[4-[4-amino-2-(N-(2-amino-1-methyl-2-oxo-ethyl)-3,4-difluoro-anilino)thiazole-5-carbonyl]phenyl]carbamate(385 mg, 0.7 mmol, Example 167) on a chiral column followed by trituration in MTBE gave 123 mg (32% yield) of benzyl N-[4-[4-amino-2-(N-(2-amino-1-methyl-2-oxo-ethyl)-3,4-difluoro-anilino)thiazole-5-carbonyl]phenyl]carbamate, enantiomer 1.
Preparative chiral HPLC
Instrument: PrepCon Labomatic HPLC-3; Column: YMC Amylose SA 10μ, 250 × 50; eluent A: methyl tert-butyl ether + 0.1 vol % diethylamine; eluent B: acetonitrile; isocratic: 90% A + 10% B; flow: 100 mL/min; temperature: 25° C.; UV: 280 nm
Analytical chiral HPLC: Rt = 2.87 min
Instrument: Thermo Fisher UltiMate 3000; Column: YMC Cellulose SC 3μ, 100 × 4.6; eluent A: methyl tert-butyl ether + 0.1 vol % diethylamine; eluent B: acetonitrile; isocratic: 90% A + 10% B; flow: 1.4 mL/min; temperature: 25° C.; UV: 325 nm

| | | | |
|---|---|---|---|
| 167.2 | Benzyl N-[4-[4-amino-2-(N-(2-amino-1-methyl-2-oxo-ethyl)-3,4-difluoro-anilino)thiazole-5-carbonyl]phenyl]carbamate (enantiomer 2) | Example 167 | $^1$H NMR (400 MHz, DMSO-d$_6$) δ ppm = 1.18 (d, J = 7.35 Hz, 3 H), 5.01 (q, J = 7.35 Hz, 1 H), 5.15 (s, 2 H), 5.76 (s, 1 H), 7.28 (s, 1 H), 7.40 (m, 5 H), 7.48 (m, 5 H), 7.57 (m, 1 H), 7.61 (s, 1 H), 7.78 (m, 1 H), 8.18 (m, 2 H), 10.00 (s, 1 H) 34% yield |

TABLE 9-continued

Example 159-256

| Example number | Chemical structure Compound name | Starting materials | Analytics/purification/yield |
|---|---|---|---|
| | Chiral HPLC Example 167.2 HPLC separation of rac-benzyl N-[4-[4-amino-2-(N-(2-amino-1-methyl-2-oxo-ethyl)-3,4-difluoro-anilino)thiazole-5-carbonyl]phenyl]carbamate(385 mg, 0.7 mmol, Example 167) on a chiral column followed by trituration in MTBE gave 129 mg (34% yield) of benzyl N-[4-[4-amino-2-(N-(2-amino-1-methyl-2-oxo-ethyl)-3,4-difluoro-anilino)thiazole-5-carbonyl]phenyl]carbamate, enantiomer 2. Preparative chiral HPLC Instrument: PrepCon Labomatic HPLC-3; Column: YMC Amylose SA 10μ, 250 × 50; eluent A: methyl tert-butyl ether + 0.1 vol % diethylamine; eluent B: acetonitrile; isocratic: 90% A + 10% B; flow: 100 mL/min; temperature: 25° C.; UV: 280 nm Analytical chiral HPLC: Rt = 3.90 min Instrument: Thermo Fisher UltiMate 3000; Column: YMC Cellulose SC 3μ, 100 × 4.6; eluent A: methyl tert-butyl ether + 0.1 vol % diethylamine; eluent B: acetonitrile; isocratic: 90% A + 10% B; flow: 1.4 mL/min; temperature: 25° C.; UV: 325 nm | | |
| 168 | 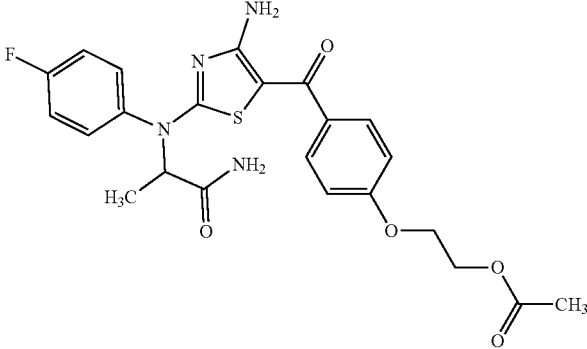 [SMILES: CC(=O)OCCOc1ccc(C(=O)c2sc(N(c3ccc(F)cc3)C(C)C(N)=O)nc2N)cc1] rac-2-[4-[4-amino-2-(N-(2-amino-1-methyl-2-oxo-ethyl)-4-fluoro-anilino)thiazole-5-carbonyl]phenoxy]ethyl acetate | Intermediate 112, rac-2-bromopropanamide | $^1$H NMR (400 MHz, DMSO-d$_6$) δ ppm = 1.15 (d, J = 7.60 Hz, 3 H), 2.01 (s, 3 H), 4.18 (dd, J = 5.32, 3.55 Hz, 2 H), 4.30 (dd, J = 5.45, 3.42 Hz, 2 H), 5.06 (m, 1 H), 6.94 (m, 2 H), 7.23 (s, 1 H), 7.33 (t, J = 8.74 Hz, 2 H), 7.47 (d, J = 8.87 Hz, 2 H), 7.58 (s, 1 H), 7.63 (m, 2 H), 8.06 (m, 2 H) RP-HPLC (method C basic) LC-MS (method 1) Rt = 1.04 min MS (ESIpos): m/z = 487.6 [M + H]$^+$ 54% yield |
| 169 169.1 and 169.2 | 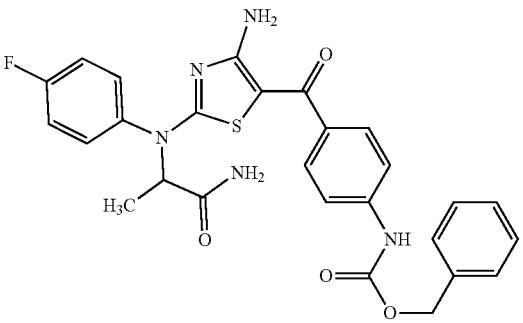 [SMILES: CC(C(N)=O)N(c1ccc(F)cc1)c1nc(N)c(C(=O)c2ccc(NC(=O)OCc3ccccc3)cc2)s1] rac-benzyl N-[4-[4-amino-2-(N-(2-amino-1-methyl-2-oxo-ethyl)-4-fluoro-anilino)thiazole-5-carbonyl]phenyl]carbamate (R)-benzyl N-[4-[4-amino-2-(N-(2-amino-1-methyl-2-oxo-ethyl)-4-fluoro-anilino)thiazole-5-carbonyl]phenyl]carbamate and (S)-benzyl N-[4-[4-amino-2-(N-(2-amino-1-methyl-2-oxo-ethyl)-4-fluoro-anilino)thiazole-5-carbonyl]phenyl]carbamate | Intermediate 132, rac-2-bromopropanamide | $^1$H NMR (400 MHz, DMSO-d$_6$) δ ppm = 1.16 (d, J = 7.35 Hz, 3 H), 5.05 (q, J = 7.35 Hz, 1 H), 5.15 (s, 2 H), 7.25 (s, 1 H), 7.40 (m, 11 H), 7.58 (s, 1 H), 7.64 (m, 2 H), 8.12 (m, 2 H), 9.99 (m, 1 H) Biotage (method X) LC-MS (method 1) Rt = 1.19 min MS (ESIpos): m/z = 534.4 [M + H]$^+$ 65% yield |

TABLE 9-continued

Example 159-256

| Example number | Chemical structure Compound name | Starting materials | Analytics/purification/yield |
|---|---|---|---|
| 169.1 | Benzyl N-[4-[4-amino-2-(N-(2-amino-1-methyl-2-oxo-ethyl)-4-fluoro-anilino)thiazole-5-carbonyl]phenyl]carbamate (enantiomer 1) | Example 169 | $^1$H NMR (400 MHz, DMSO-$d_6$) δ ppm = 1.16 (d, J = 7.35 Hz, 3 H), 5.05 (q, J = 7.35 Hz, 1 H), 5.15 (s, 2 H), 7.25 (s, 1 H), 7.40 (m, 11 H), 7.58 (s, 1 H), 7.64 (m, 2 H), 8.12 (m, 2 H), 9.99 (m, 1 H) LC-MS (method 1) Rt = 1.19 min MS (ESIpos): m/z = 534.4 [M + H]$^+$ 14% yield |

Chiral HPLC Example 169.1
HPLC separation of rac-benzyl N-[4-[4-amino-2-(N-(2-amino-1-methyl-2-oxo-ethyl)-4-fluoro-anilino)thiazole-5-carbonyl]phenyl]carbamate(422 mg, 0.76 mmol, Example 169) on a chiral column followed by trituration in MTBE gave 88 mg (14% yield) of benzyl N-[4-[4-amino-2-(N-(2-amino-1-methyl-2-oxo-ethyl)-4-fluoro-anilino)thiazole-5-carbonyl]phenyl]carbamate, enantiomer 1.
Preparative chiral HPLC
Instrument: PrepCon Labomatic HPLC-3; Column: YMC Amylose SA 10μ, 250 × 50; eluent A: methyl tert-butyl ether + 0.1 vol % diethylamine; eluent B: acetonitrile; isocratic: 50% A + 50% B; flow: 80 mL/min; temperature: 25° C.; UV: 280 nm
Analytical chiral HPLC: Rt = 1.39 min
Instrument: Thermo Fisher UltiMate 3000; Column: YMC Amylose SA 3μ, 100 × 4.6; eluent A: methyl tert-butyl ether + 0.1 vol % diethylamine; eluent B: acetonitrile; isocratic: 50% A + 50% B; flow: 1.4 mL/min; temperature: 25° C.; UV: 280 nm

| | | | |
|---|---|---|---|
| 169.2 | Benzyl N-[4-[4-amino-2-(N-(2-amino-1-methyl-2-oxo-ethyl)-4-fluoro-anilino)thiazole-5-carbonyl]phenyl]carbamate (enantiomer 2) | Example 169 | $^1$H NMR (400 MHz, DMSO-$d_6$) δ ppm = 1.16 (d, J = 7.35 Hz, 3 H), 5.05 (q, J = 7.35 Hz, 1 H), 5.15 (s, 2 H), 7.25 (s, 1 H), 7.40 (m, 11 H), 7.58 (s, 1 H), 7.64 (m, 2 H), 8.12 (m, 2 H), 9.99 (m, 1 H) LC-MS (method 1) Rt = 1.19 min MS (ESIpos): m/z = 534.4 [M + H]$^+$ 16% yield |

Chiral HPLC Example 169.2
HPLC separation of rac-benzyl N-[4-[4-amino-2-(N-(2-amino-1-methyl-2-oxo-ethyl)-4-fluoro-anilino)thiazole-5-carbonyl]phenyl]carbamate(422 mg, 0.76 mmol, Example 169) on a chiral column followed by trituration in MTBE gave 106 mg (14% yield) of benzyl N-[4-[4-amino-2-(N-(2-amino-1-methyl-2-oxo-ethyl)-4-fluoro-anilino)thiazole-5-carbonyl]phenyl]carbamate, enantiomer 2.
Preparative chiral HPLC
Instrument: PrepCon Labomatic HPLC-3; Column: YMC Amylose SA 10μ, 250 × 50; eluent A: methyl tert-butyl ether + 0.1 vol % diethylamine; eluent B: acetonitrile; isocratic: 50% A + 50% B; flow: 80 mL/min; temperature: 25° C.; UV: 280 nm
Analytical chiral HPLC: Rt = 1.80 min
Instrument: Thermo Fisher UltiMate 3000; Column: YMC Amylose SA 3μ, 100 × 4.6; eluent A: methyl tert-butyl ether + 0.1 vol % diethylamine; eluent B: acetonitrile; isocratic: 50% A + 50% B; flow: 1.4 mL/min; temperature: 25° C.; UV: 280 nm

TABLE 9-continued

Example 159-256

| Example number | Chemical structure Compound name | Starting materials | Analytics/purification/yield |
|---|---|---|---|
| 170 | rac-2-(N-[4-amino-5-(4-benzyloxybenzoyl)thiazol-2-yl]-4-fluoro-anilino)propanamide | Intermediate 110, rac-2-bromopropanamide | $^1$H NMR (400 MHz, DMSO-d$_6$) δ ppm = 1.16 (d, J = 7.35 Hz, 3 H), 5.05 (m, 1 H), 5.11 (s, 2 H), 7.00 (m, 2 H), 7.25 (s, 1 H), 7.37 (m, 7 H), 7.48 (m, 2 H), 7.57 (s, 1 H), 7.64 (m, 2 H), 8.11 (m, 2H) RP-HPLC (method B basic) LC-MS (method 2) Rt = 1.25 min MS (ESIpos): m/z = 491.3 [M + H]$^+$ 88% yield |
| 170.1 and 170.2 | (R)-2-(N-[4-amino-5-(4-benzyloxybenzoyl)thiazol-2-yl]-4-fluoro-anilino)propanamide and (S)-2-(N-[4-amino-5-(4-benzyloxybenzoyl)thiazol-2-yl]-4-fluoro-anilino)propanamide | | |
| 170.1 | 2-(N-[4-amino-5-(4-benzyloxybenzoyl)thiazol-2-yl]-4-fluoro-anilino)propanamide (enantiomer 1) | Example 170 | $^1$H NMR (400 MHz, DMSO-d$_6$) δ ppm = 1.16 (d, J = 7.35 Hz, 3 H), 5.02-5.06 (m, 1 H), 5.11 (s, 2 H), 7.00 (m, 2 H), 7.25 (s, 1 H), 7.30-7.40 (m, 7 H), 7.46-7.50 (m, 2 H), 7.57 (s, 1 H), 7.62-7.66 (m, 2 H), 8.08-8.12 (m, 2H) LC-MS (method 2) Rt = 1.25 min MS (ESIpos): m/z = 491.3 [M + H]$^+$ 35% yield |

Chiral HPLC Example 170.1

HPLC separation of rac-2-(N-[4-amino-5-(4-benzyloxybenzoyl)thiazol-2-yl]-4-fluoro-anilino)propanamide(150 mg, 0.3 mmol, Example 170) on a chiral column gave 53 mg (35% yield) of 2-(N-[4-amino-5-(4-benzyloxybenzoyl)thiazol-2-yl]-4-fluoro-anilino)propanamide, enantiomer 1.

Preparative chiral HPLC

Instrument: Sepiatec: Prep SFC100; Column: Chiralpak IB 5μ 250 × 30 mm; eluent A: CO$_2$; eluent B: 2-propanol + 0.4 vol % diethylamine; isocratic: 35% B; flow: 100 mL/min; temperature: 40° C.; BPR: 150 bar; UV: 254 nm Analytical chiral HPLC: Rt = 3.08 min Instrument: Agilent: 1260, Aurora SFC-Modul; Column: Chiralpak IB 5μ 100 × 4.6 mm; eluent A: CO$_2$; eluent B: 2-propanol + 0.4 vol % diethylamine; isocratic: 35% B; flow: 4 mL/min; temperature: 37.5° C.; BPR: 100 bar; UV: 254 nm TABLE 9-continued Example 159-256

| Example number | Chemical structure Compound name | Starting materials | Analytics/purification/yield |
|---|---|---|---|
| 170.2 | 2-(N-[4-amino-5-(4-benzyloxybenzoyl)thiazol-2-yl]-4-fluoro-anilino)propanamide (enantiomer 2) | Example 170 | $^1$H NMR (400 MHz, DMSO-$d_6$) δ ppm = 1.16 (d, J = 7.35 Hz, 3 H), 5.04-5.07 (m, 1 H), 5.11 (s, 2 H), 6.97-7.02 (m, 2 H), 7.25 (s, 1 H), 7.30-7.40 (m, 7 H), 7.46-7.50 (m, 2 H), 7.57 (s, 1 H), 7.62-7.66 (m, 2 H), 8.09-8.11 (m, 2H)<br>LC-MS (method 2) Rt = 1.25 min<br>MS (ESIpos): m/z = 491.3 [M + H]$^+$<br>34% yield |

Chiral HPLC Example 170.2
HPLC separation of rac-2-(N-[4-amino-5-(4-benzyloxybenzoyl)thiazol-2-yl]-4-fluoro-anilino)propanamide(150 mg, 0.3 mmol, Example 170) on a chiral column gave 51 mg (34% yield) of 2-(N-[4-amino-5-(4-benzyloxybenzoyl)thiazol-2-yl]-4-fluoro-anilino)propanamide, enantiomer 2.
Preparative chiral HPLC
Instrument: Sepiatec: Prep SFC100; Column: Chiralpak IB 5μ 250 × 30 mm; eluent A: CO$_2$; eluent B: 2-propanol + 0.4 vol % diethylamine; isocratic: 35% B; flow: 100 mL/min; temperature: 40° C.; BPR: 150 bar; UV: 254 nm
Analytical chiral HPLC: Rt = 4.42 min
Instrument: Agilent: 1260, Aurora SFC-Modul; Column: Chiralpak IB 5μ 100 × 4.6 mm; eluent A: CO$_2$; eluent B: 2-propanol + 0.4 vol % diethylamine; isocratic: 35% B; flow: 4 mL/min; temperature: 37.5° C.; BPR: 100 bar; UV: 254 nm

| | | | |
|---|---|---|---|
| 171 | rac-2-(N-[4-amino-5-(4-iodobenzoyl)thiazol-2-yl] 4-fluoro-anilino)propanamide | Intermediate 111, rac-2-bromopropanamide | $^1$H NMR (400 MHz, DMSO-$d_6$) δ ppm = 1.16 (d, J = 7.35 Hz, 3 H), 5.07 (q, J = 7.35 Hz, 1 H), 7.29 (m, 5 H), 7.58 (m, 1 H), 7.63 (m, 2 H), 7.76 (m, 2 H), 8.21 (m, 2 H)<br>Biotage (method X)<br>LC-MS (method 2) Rt = 1.21 min<br>MS (ESIpos): m/z = 511.0 [M + H]$^+$<br>39% yield |
| 172 | rac-2-(N-[4-amino-5-(6-methoxypyridine-3-carbonyl)thiazol-2-yl]-4-chloro-3-fluoro-anilino)propanamide | Intermediate 113, rac-2-bromopropanamide | $^1$H NMR (400 MHz, DMSO-$d_6$) δ ppm = 1.20 (d, J = 7.35 Hz, 3 H), 3.87 (s, 3 H), 5.03 (q, J = 7.35 Hz, 1 H), 6.85 (dd, J = 8.62, 0.76 Hz, 1 H), 7.31 (s, 1 H), 7.52 (m, 1 H), 7.64 (s, 1 H), 7.76 (m, 2 H), 7.84 (dd, J = 8.49, 2.41 Hz, 1 H), 8.14 (m, 2 H), 8.37 (m, 1 H)<br>Biotage (method Y)<br>LC-MS (method 2) Rt = 1.14 min<br>MS (ESIpos): m/z = 450.3 [M + H]$^+$<br>38% yield |

TABLE 9-continued

Example 159-256

| Example number | Chemical structure Compound name | Starting materials | Analytics/purification/yield |
|---|---|---|---|
| 172.1 and 172.2 | (R)-2-(N-[4-amino-5-(6-methoxypyridine-3-carbonyl)thiazol-2-yl]-4-chloro-3-fluoro-anilino)propanamide and (S)-2-(N-[4-amino-5-(6-methoxypyridine-3-carbonyl)thiazol-2-yl]-4-chloro-3-fluoro-anilino)propanamide | | |
| 172.1 | 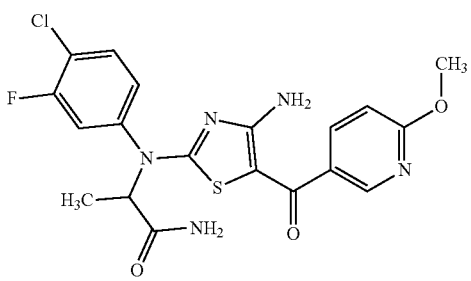 [SMILES: COc1ccc(C(=O)c2sc(N(c3ccc(Cl)c(F)c3)C(C)C(N)=O)nc2N)cn1]<br>2-(N-[4-amino-5-(6-methoxypyridine-3-carbonyl)thiazol-2-yl]-4-chloro-3-fluoro-anilino)propanamide (enantiomer 1) | Example 172 | $^1$H NMR (400 MHz, DMSO-d$_6$) δ ppm = 1.20 (d, J = 7.35 Hz, 3 H), 3.87 (s, 3 H), 5.03 (q, J = 7.35 Hz, 1 H), 6.85 (dd, J = 8.62, 0.76 Hz, 1 H), 7.31 (s, 1 H), 7.52 (m, 1 H), 7.64 (s, 1 H), 7.76 (m, 2 H), 7.84 (dd, J = 8.49, 2.41 Hz, 1 H), 8.14 (m, 2 H), 8.37 (m, 1 H)<br>LC-MS (method 2) Rt = 1.14 min<br>MS (ESIpos): m/z = 450.3 [M + H]$^+$<br>24% yield |

Chiral HPLC Example 172.1
HPLC separation of rac-2-(N-[4-amino-5-(6-methoxypyridine-3-carbonyl)thiazol-2-yl]-4-chloro-3-fluoro-anilino)propanamide(312 mg, 0.69 mmol, Example 172) on a chiral column gave 78 mg (24% yield) of 2-(N-[4-amino-5-(6-methoxypyridine-3-carbonyl)thiazol-2-yl]-4-chloro-3-fluoro-anilino)propanamide, enantiomer 1.
Preparative chiral HPLC
Instrument: Sepiatec: Prep SFC100; Column: Chiralpak IG 5µ 250 × 30 mm; eluent A: CO$_2$; eluent B: methanol + 0.2 vol % aqueous ammonia (32%); isocratic: 30% B; flow: 100 mL/min; temperature: 40° C.; BPR: 150 bar; UV: 254 nm
Analytical chiral HPLC: Rt = 2.61 min
Instrument: Agilent: 1260, Aurora SFC-Modul; Column: Chiralpak IG 5µ 100 × 4.6 mm; eluent A: CO$_2$; eluent B: methanol + 0.2 vol % aqueous ammonia (32%); isocratic: 30% B; flow: 4 mL/min; temperature: 37.5° C.; BPR: 100 bar; UV: 254 nm

| 172.2 | 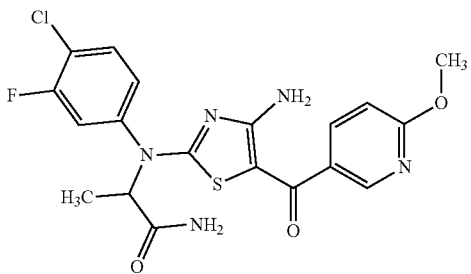 [SMILES: COc1ccc(C(=O)c2sc(N(c3ccc(Cl)c(F)c3)C(C)C(N)=O)nc2N)cn1]<br>2-(N-[4-amino-5-(6-methoxypyridine-3-carbonyl)thiazol-2-yl]-4-chloro-3-fluoro-anilino)propanamide (enantiomer 2) | Example 172 | $^1$H NMR (400 MHz, DMSO-d$_6$) δ ppm = 1.20 (d, J = 7.35 Hz, 3 H), 3.87 (s, 3 H), 5.03 (q, J = 7.35 Hz, 1 H), 6.85 (dd, J = 8.62, 0.76 Hz, 1 H), 7.31 (s, 1 H), 7.52 (m, 1 H), 7.64 (s, 1 H), 7.76 (m, 2 H), 7.84 (dd, J = 8.49, 2.41 Hz, 1 H), 8.14 (m, 2 H), 8.37 (m, 1 H)<br>LC-MS (method 2) Rt = 1.14 min<br>MS (ESIpos): m/z = 450.3 [M + H]$^+$<br>23% yield |

Chiral HPLC Example 172.2
HPLC separation of rac-2-(N-[4-amino-5-(6-methoxypyridine-3-carbonyl)thiazol-2-yl]-4-chloro-3-fluoro-anilino)propanamide(312 mg, 0.69 mmol, Example 172) on a chiral column gave 73 mg (23% yield) of 2-(N-[4-amino-5-(6-methoxypyridine-3-carbonyl)thiazol-2-yl]-4-chloro-3-fluoro-anilino)propanamide, enantiomer 2.
Preparative chiral HPLC
Instrument: Sepiatec: Prep SFC100; Column: Chiralpak IG 5µ 250 × 30 mm; eluent A: CO$_2$; eluent B: methanol + 0.2 vol % aqueous ammonia (32%); isocratic: 30% B; flow: 100 mL/min; temperature: 40° C.; BPR: 150 bar UV: 254 nm
Analytical chiral HPLC: Rt = 3.40 min TABLE 9-continued Example 159-256

| Example number | Chemical structure Compound name | Starting materials | Analytics/purification/yield |
|---|---|---|---|
| | Instrument: Agilent: 1260, Aurora SFC-Modul; Column: Chiralpak IG 5μ 100 × 4.6 mm; eluent A: CO$_2$; eluent B: methanol + 0.2 vol % aqueous ammonia (32%); isocratic: 30% B; flow: 4 mL/min; temperature: 37.5° C.; BPR: 100 bar; UV: 254 nm | | |
| 173 | 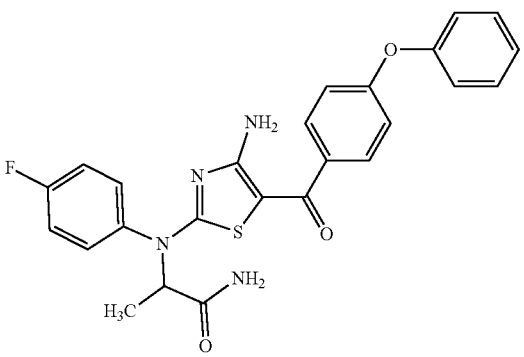 [SMILES: CC(C(N)=O)N(c1ccc(F)cc1)c1nc(N)c(C(=O)c2ccc(Oc3ccccc3)cc2)s1]<br>rac-2-(N-[4-amino-5-(4-phenoxybenzoyl)thiazol-2-yl]-4-fluoro-anilino)propanamide | Intermediate 114, rac-2-bromopropanamide | $^1$H NMR (400 MHz, DMSO-d$_6$) δ ppm = 1.16 (d, J = 7.35 Hz, 3 H), 5.07 (m, 1 H), 6.94 (m, 2 H), 7.06 (m, 2 H), 7.20 (m, 1 H), 7.25 (s, 1 H), 7.33 (dd, J = 8.87 Hz, 2 H), 7.41 (m, 2 H), 7.53 (m, 2 H), 7.58 (s, 1 H), 7.64 (m, 2 H), 8.14 (m, 2 H)<br>Biotage (method X)<br>LC-MS (method 2) Rt = 1.26 min<br>MS (ESIpos): m/z = 477.2 [M + H]$^+$<br>56% yield |
| 174 | 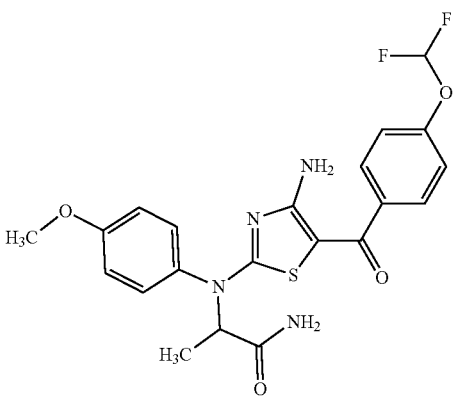 [SMILES: COc1ccc(N(c2nc(N)c(C(=O)c3ccc(OC(F)F)cc3)s2)C(C)C(N)=O)cc1]<br>rac-2-(N-[4-amino-5-[4-(difluoromethoxy)benzoyl]thiazol-2-yl]-4-methoxy-anilino)propanamide | Intermediate 115, rac-2-bromopropanamide | $^1$H NMR (400 MHz, DMSO-d$_6$) δ ppm = 1.15 (d, J = 7.35 Hz, 3 H), 3.73 (s, 3H), 5.06 (q, J = 7.35 Hz, 1 H), 7.01 (d, J = 9.13 Hz, 2 H), 7.16 (m, 2 H), 7.21 (s, 1 H), 7.27 (t, J = 72 Hz, 1 H), 7.46 (m, 2 H), 7.54 (m, 3 H), 8.15 (m, 2 H)<br>Biotage (method X)<br>LC-MS (method 2) Rt = 1.08 min<br>MS (ESIpos): m/z = 463.2 [M + H]$^+$<br>77% yield |
| 174.1 and 174.2 | (R)-2-(N-[4-amino-5-[4-(difluoromethoxy)benzoyl]thiazol-2-yl]-4-methoxy-anilino)propanamide and (S)-2-(N-[4-amino-5-[4-(difluoromethoxy)benzoyl]thiazol-2-yl]-4-methoxy-anilino)propanamide | | |

TABLE 9-continued

Example 159-256

| Example number | Chemical structure Compound name | Starting materials | Analytics/purification/yield |
|---|---|---|---|
| 174.1 | 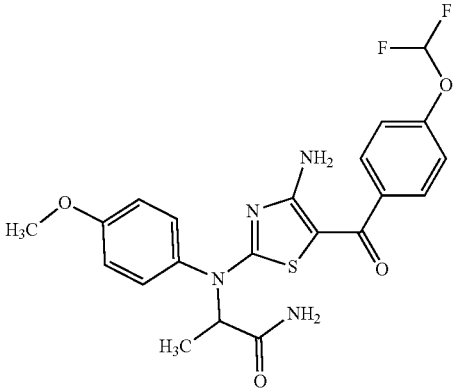 [SMILES: COc1ccc(N(c2nc(N)c(C(=O)c3ccc(OC(F)F)cc3)s2)C(C)C(N)=O)cc1]<br>2-(N-[4-amino-5-[4-(difluoromethoxy)benzoyl]thiazol-2-yl]-4-methoxy-anilino)propanamide (enantiomer 1) | Example 174 | $^1$H NMR (400 MHz, DMSO-d$_6$) δ ppm = 1.15 (d, J = 7.35 Hz, 3 H), 3.73 (s, 3H), 5.06 (q, J = 7.35 Hz, 1 H), 7.01 (d, J = 9.13 Hz, 2 H), 7.16 (m, 2 H), 7.21 (s, 1 H), 7.27 (t, J = 72 Hz, 1 H), 7.46 (m, 2 H), 7.54 (m, 3 H), 8.15 (m, 2 H) LC-MS (method 2) Rt = 1.08 min MS (ESIpos): m/z = 463.2 [M + H]$^+$ 31% yield |

Chiral HPLC Example 174.1
HPLC separation of rac-2-(N-[4-amino-5-[4-(difluoromethoxy)benzoyl]thiazol-2-yl]-4-methoxy-anilino)propanamide(316 mg, 0.66 mmol, Example 174 on a chiral column gave 121 mg (31% yield) of 2-(N-[4-amino-5-[4-(difluoromethoxy)benzoyl]thiazol-2-yl]-4-methoxy-anilino)propanamide, enantiomer 1.
Preparative chiral HPLC
Instrument: PrepCon Labomatic HPLC-3; Column: YMC Amylose SA 10μ, 250 × 50; eluent A: methyl tert-butyl ether + 0.1 vol % diethylamine; eluent B: methanol; isocratic: 50% A + 50% B; flow: 100 mL/min; temperature: 25° C.; UV: 254 nm
Analytical chiral HPLC: Rt = 1.28 min
Instrument: Thermo Fisher UltiMate 3000; Column: YMC Amylose SA 3μ, 100 × 4.6; eluent A: methyl tert-butyl ether + 0.1 vol % diethylamine; eluent B: acetonitrile; isocratic: 50% A + 50% B; flow: 1.4 mL/min; temperature: 25° C.; UV: 254 nm

| 174.2 | 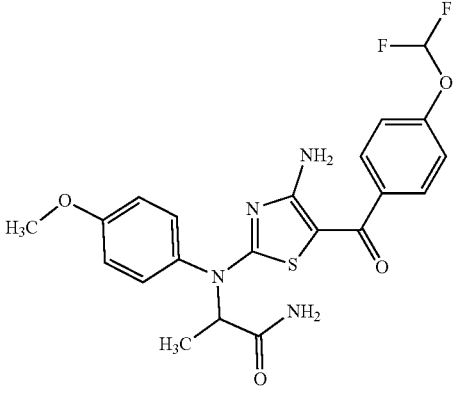 [SMILES: COc1ccc(N(c2nc(N)c(C(=O)c3ccc(OC(F)F)cc3)s2)C(C)C(N)=O)cc1]<br>2-(N-[4-amino-5-[4-(difluoromethoxy)benzoyl]thiazol-2-yl]-4-methoxy-anilino)propanamide (enantiomer 2) | Example 174 | $^1$H NMR (400 MHz, DMSO-d$_6$) δ ppm = 1.15 (d, J = 7.35 Hz, 3 H), 3.73 (s, 3H), 5.06 (q, J = 7.35 Hz, 1 H), 7.01 (d, J = 9.13 Hz, 2 H), 7.16 (m, 2 H), 7.21 (s, 1 H), 7.27 (t, J = 72 Hz, 1 H), 7.46 (m, 2 H), 7.54 (m, 3 H), 8.15 (m, 2 H) LC-MS (method 2) Rt = 1.08 min MS (ESIpos): m/z = 463.2 [M + H]$^+$ 31% yield |

Chiral HPLC Example 174.2
HPLC separation of rac-2-(N-[4-amino-5-[4-(difluoromethoxy)benzoyl]thiazol-2-yl]-4-methoxy-anilino)propanamide(316 mg, 0.66 mmol, Example 174 on a chiral column gave 121 mg (31% yield) of 2-(N-[4-amino-5-[4-(difluoromethoxy)benzoyl]thiazol-2-yl]-4-methoxy-anilino)propanamide, enantiomer 2.
Preparative chiral HPLC
Instrument: PrepCon Labomatic HPLC-3; Column: YMC Amylose SA 10μ, 250 × 50; eluent A: methyl tert-butyl ether + 0.1 vol % diethylamine; eluent B: methanol; isocratic: 50% A + 50% B; flow: 100 mL/min; temperature: 25° C.; UV: 254 nm TABLE 9-continued Example 159-256

| Example number | Chemical structure Compound name | Starting materials | Analytics/purification/yield |
|---|---|---|---|
| | Analytical chiral HPLC: Rt = 1.62 min Instrument: Thermo Fisher UltiMate 3000; Column: YMC Amylose SA 3μ, 100 × 4.6; eluent A: methyl tert-butyl ether + 0.1 vol % diethylamine; eluent B: acetonitrile; isocratic: 50% A + 50% B; flow: 1.4 mL/min; temperature: 25° C.; UV: 254 nm | | |
| 175 | 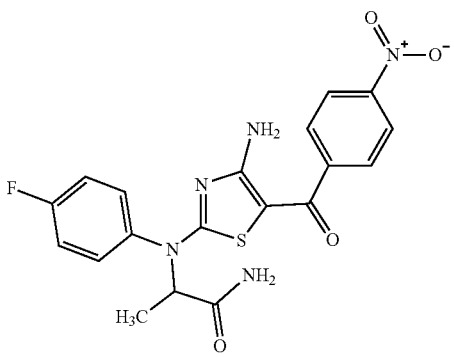 [SMILES: CC(C(N)=O)N(c1ccc(F)cc1)c1nc(N)c(C(=O)c2ccc([N+](=O)[O-])cc2)s1]<br>rac-2-(N-[4-amino-5-(4-nitrobenzoyl)thiazol-2-yl]-4-fluoro-anilino)propanamide | Intermediate 116, rac-2-bromopropanamide | $^1$H NMR (400 MHz, DMSO-d$_6$) δ ppm = 1.16 (d, J = 7.35 Hz, 3 H), 5.07 (q, J = 7.35 Hz, 1 H), 7.26 (br s, 1 H), 7.33 (m, 3 H), 7.59 (br s, 1 H), 7.63 (m, 3 H), 7.71 (m, 2 H), 8.23 (m, 3 H), 8.38 (m, 1 H) Biotage (method X) LC-MS (method 2) Rt = 1.05 min MS (ESIpos): m/z = 430.1 [M + H]$^+$ 66% yield |
| 176 | 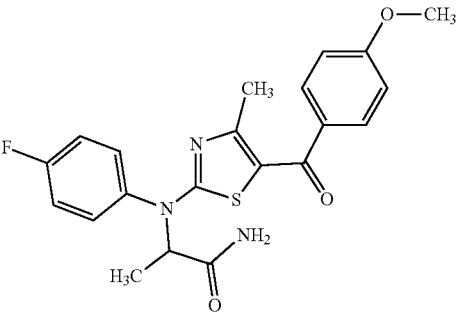 [SMILES: COc1ccc(C(=O)c2sc(N(c3ccc(F)cc3)C(C)C(N)=O)nc2C)cc1]<br>rac-2-(4-fluoro-N-[5-(4-methoxybenzoyl)-4-methyl-thiazol-2-yl]anilino)propanamide | Intermediate 117, rac-2-bromopropanamide | $^1$H NMR (500 MHz, DMSO-d$_6$) δ ppm = 1.16 (d, J = 7.57 Hz, 3 H), 2.29 (s, 3 H), 3.80 (s, 3 H), 5.11 (q, J = 7.35 Hz, 1 H), 6.99 (d, J = 8.83 Hz, 2 H), 7.20 (s, 1 H), 7.36 (dd, J = 8.83 Hz, 2 H), 7.58 (m, 2 H), 7.61 (s, 1 H), 7.68 (m, 2 H) LC-MS (method 2) Rt = 1.16 min MS (ESIpos): m/z = 414.5 [M + H]$^+$ 79% yield |
| 176.1 and 176.2 | (R)-2-(4-fluoro-N-[5-(4-methoxybenzoyl)-4-methyl-thiazol-2-yl]anilino)propanamide and (S)-2-(4-fluoro-N-[5-(4-methoxybenzoy)-4-methyl-thiazol-2-yl]anilino)propanamide | | |
| 176.1 | 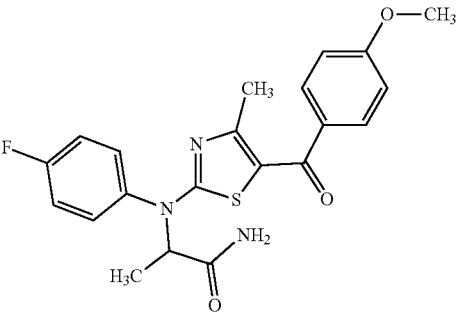 [SMILES: COc1ccc(C(=O)c2sc(N(c3ccc(F)cc3)C(C)C(N)=O)nc2C)cc1] | Example 176 | $^1$H NMR (500 MHz, DMSO-d$_6$) δ ppm = 1.16 (d, J = 7.57 Hz, 3 H), 2.29 (s, 3 H), 3.80 (s, 3 H), 5.11 (q, J = 7.35 Hz, 1 H), 6.99 (d, J = 8.83 Hz, 2 H), 7.20 (s, 1 H), 7.36 (dd, J = 8.83 Hz, 2 H), 7.58 (m, 2 H), 7.61 (s, 1 H), 7.68 (m, 2 H) LC-MS (method 2) Rt = 1.16 min MS (ESIpos): m/z = 414.5 [M + H]$^+$ 49% yield |

TABLE 9-continued

Example 159-256

| Example number | Chemical structure Compound name | Starting materials | Analytics/purification/yield |
|---|---|---|---|
| | 2-(4-fluoro-N-[5-(4-methoxybenzoyl)-4-methyl-thiazol-2-yl]anilino)propanamide (enantiomer 1) Chiral HPLC Example 176.1 HPLC separation of rac-2-(4-fluoro-N-[5-(4-methoxybenzoyl)-4-methyl-thiazol-2-yl]anilino)propanamide(80 mg, 0.19 mmol, Example 176 on a chiral column gave 39 mg (49% yield) of 2-(4-fluoro-N-[5-(4-methoxybenzoyl)-4-methyl-thiazol-2-yl]anilino)propanamide, enantiomer 1. Preparative chiral HPLC Instrument: PrepCon Labomatic HPLC-4; Column: YMC Cellulose SC 10μ, 250 × 50; eluent A: hexane + 0.1 vol % diethylamine; eluent B: ethanol; isocratic: 80% A + 20% B; flow: 100 mL/min; temperature: 25° C.; UV: 254 nm Analytical chiral HPLC: Rt = 4.20 min Instrument: Thermo Fisher UltiMate 3000; Column: YMC Cellulose SC 3μ, 100 × 4.6; eluent A: hexane + 0.1 vol % diethylamine; eluent B: ethanol; isocratic: 80% A + 20% B; flow: 1.4 mL/min; temperature: 25° C.; UV: 254 nm | | |
| 176.2 | 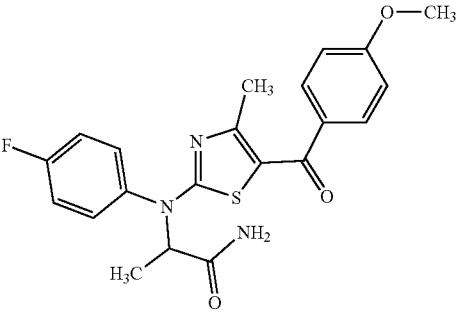 [SMILES: COc1ccc(C(=O)c2sc(N(c3ccc(F)cc3)C(C)C(N)=O)nc2C)cc1] 2-(4-fluoro-N-[5-(4-methoxybenzoyl)-4-methyl-thiazol-2-yl]anilino)propanamide (enantiomer 2) Chiral HPLC Example 176.2 HPLC separation of rac-2-(4-fluoro-N-[5-(4-methoxybenzoyl)-4-methyl-thiazol-2-yl]anilino)propanamide(80 mg, 0.19 mmol, Example 176 on a chiral column gave 31 mg (39% yield) of 2-(4-fluoro-N-[5-(4-methoxybenzoyl)-4-methyl-thiazol-2-yl]anilino)propanamide, enantiomer 2. Preparative chiral HPLC Instrument: PrepCon Labomatic HPLC-4; Column: YMC Cellulose SC 10μ, 250 × 50; eluent A: hexane + 0.1 vol % diethylamine; eluent B: ethanol; isocratic: 80% A + 20% B; flow: 100 mL/min; temperature: 25° C.; UV: 254 nm Analytical chiral HPLC: Rt = 4.84 min Instrument: Thermo Fisher UltiMate 3000; Column: YMC Cellulose SC 3μ, 100 × 4.6; eluent A: hexane + 0.1 vol % diethylamine; eluent B: ethanol; isocratic: 80% A + 20% B; flow: 1.4 mL/min; temperature: 25° C.; UV: 254 nm | Example 176 | $^1$H NMR (500 MHz, DMSO-$d_6$) δ ppm = 1.16 (d, J = 7.57 Hz, 3 H), 2.29 (s, 3 H), 3.80 (s, 3 H), 5.11 (q, J = 7.35 Hz, 1 H), 6.99 (d, J = 8.83 Hz, 2 H), 7.20 (s, 1 H), 7.36 (dd, J = 8.83 Hz, 2 H), 7.58 (m, 2 H), 7.61 (s, 1 H), 7.68 (m, 2 H) LC-MS (method 2) Rt = 1.16 min MS (ESIpos): m/z = 414.5 [M + H]$^+$ 49% yield |
| 177 | 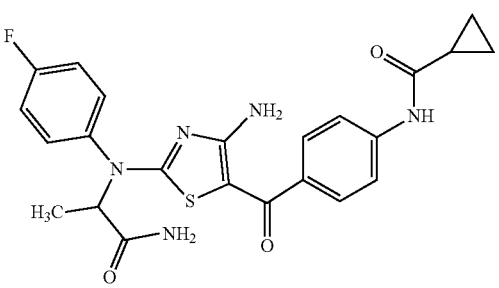 [SMILES: CC(C(N)=O)N(c1ccc(F)cc1)c1nc(N)c(C(=O)c2ccc(NC(=O)C3CC3)cc2)s1] rac-4-[4-[4-amino-2-(N-(2-amino-1-methyl-2-oxo-ethyl)-4-fluoro-anilino)thiazole-5-carbonyl]phenyl]cyclopropanecarboxamide | Intermediate 118, rac-2-bromopropanamide | $^1$H NMR (500 MHz, DMSO-$d_6$) δ ppm = 0.75-0.80 (m, 4 H), 1.16 (d, J = 7.31 Hz, 3 H), 1.77 (m, 1 H), 5.05 (m, 1 H), 7.24 (br s, 1 H), 7.32 (dd, J = 8.74 Hz, 2 H), 7.45 (d, J = 8.58 Hz, 2 H), 7.57 (m, 3 H), 7.64 (dd, J = 8.74, 4.93 Hz, 2 H), 8.11 (m, 2 H), 10.34 (s, 1 H) RP-HPLC (method C basic) LC-MS (method 1) Rt = 0.99 min MS (ESIpos): m/z = 468.5 [M + H]$^+$ 57% yield |

TABLE 9-continued

Example 159-256

| Example number | Chemical structure Compound name | Starting materials | Analytics/purification/yield |
|---|---|---|---|
| 178 | 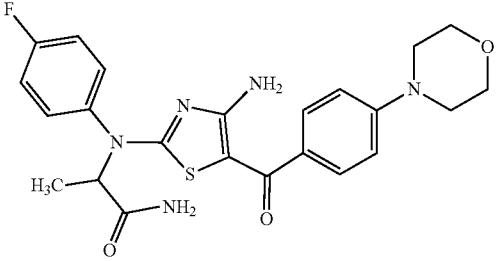 [SMILES: CC(C(N)=O)N(c1ccc(F)cc1)c1nc(N)c(C(=O)c2ccc(N3CCOCC3)cc2)s1]<br>rac-2-(N-[4-amino-5-(4-morpholinobenzoyl)thiazol-2-yl]-4-fluoro-anilino)propanamide | Intermediate 119, rac-2-bromopropanamide | $^1$H NMR (400 MHz, DMSO-$d_6$) δ ppm = 1.16 (d, J = 7.35 Hz, 3 H), 3.16 (m, 4 H), 3.70 (m, 4 H), 5.06 (q, J = 7.35 Hz, 1 H), 6.90 (d, J = 8.87 Hz, 2 H), 7.24 (br s, 1 H), 7.34 (dd, J = 8.74 Hz, 2 H), 7.43 (m, J = 8.87 Hz, 2 H), 7.57 (br s, 1 H), 7.65 (m, 2H), 7.97 (m, 2 H) LC-MS (method 2) Rt = 1.01 min MS (ESIpos): m/z = 470.3 [M + H]$^+$ 48% yield |
| 179 | 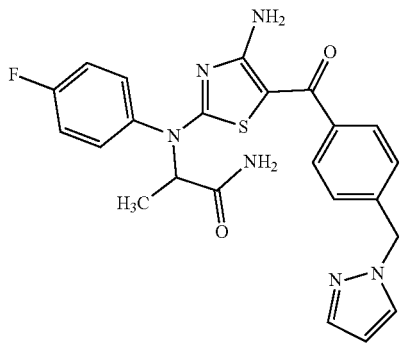 [SMILES: CC(C(N)=O)N(c1ccc(F)cc1)c1nc(N)c(C(=O)c2ccc(Cn3cccn3)cc2)s1]<br>rac-2-(N-[4-amino-5-[4-(pyrazol-1-ylmethyl)benzoyl]thiazol-2-yl]-4-fluoro-anilino)propanamide | Intermediate 120, rac-2-bromopropanamide | $^1$H NMR (400 MHz, DMSO-$d_6$) δ ppm = 1.14 (d, J = 7.35 Hz, 3 H), 5.04 (q, J = 7.35 Hz, 1 H), 5.32 (m, 2 H), 6.27 (dd, J = 2.03 Hz, 1 H), 7.15 (d, J = 8.36 Hz, 2 H), 7.23 (s, 1 H), 7.31 (m, 2 H), 7.43 (m, 2 H), 7.45 (m, 1 H), 7.60 (m, 3 H), 7.82 (dd, J = 2.28, 0.76 Hz, 1 H), 8.18 (m, 2 H) RP-HPLC (method C basic) LC-MS (method 1) Rt = 1.0 min MS (ESIpos): m/z = 465.6 [M + H]$^+$ 66% yield |
| 180 | 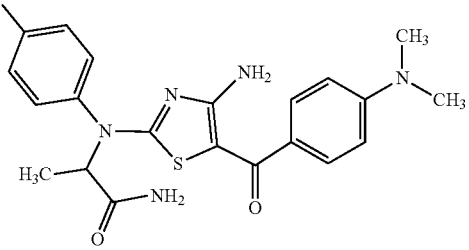<br>rac-2-(N-[4-amino-5-[4-(dimethylamino)benzoyl]thiazol-2-yl]-4-fluoro-anilino)propanamide | Intermediate 121, rac-2-bromopropanamide | $^1$H NMR (400 MHz, DMSO-$d_6$) δ ppm = 1.16 (d, J = 7.35 Hz, 3 H), 2.92 (s, 6 H), 5.05 (q, J = 7.35 Hz, 1 H), 6.65 (m, 2 H), 7.23 (s, 1 H), 7.34 (dd, J = 8.87 Hz, 2 H), 7.43 (m, 2 H), 7.57 (br d, J = 0.76 Hz, 1 H), 7.65 (m, 2H), 7.96 (m, 2 H) RP-HPLC (method D basic) LC-MS (method 2) Rt = 1.13 min MS (ESIpos): m/z = 428.5 [M + H]$^+$ 63% yield |
| 181 | 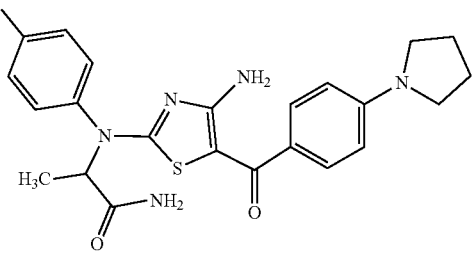 | Intermediate 122, rac-2-bromopropanamide | $^1$H NMR (400 MHz, DMSO-$d_6$) δ ppm = 1.16 (br d, J = 7.35 Hz, 3 H), 1.93 (m, 4H), 3.23 (m, 4 H), 5.06 (m, 1 H), 6.47 (br d, J = 8.62 Hz, 2 H), 7.24 (m, 1 H), 7.34 (s, 2 H), 7.42 (brd, J = 8.36 Hz, 2 H), 7.57 (br s, 1 H), 7.65 (m, 2 H), 7.97 (m, 2 H) LC-MS (method 2) Rt = 1.21 min MS (ESIpos): m/z = 454.3 [M + H]$^+$ 82% yield |

TABLE 9-continued

Example 159-256

| Example number | Chemical structure Compound name | Starting materials | Analytics/purification/yield |
|---|---|---|---|
| 182 | rac-2-(N-[4-amino-5-(4-pyrrolidin-1-ylbenzoyl)thiazol-2-yl]-4-fluoro-anilino)propanamide | Intermediate 123, rac-2-bromopropanamide | ¹H NMR (400 MHz, DMSO-d₆) δ ppm = 1.15 (d, J = 7.35 Hz, 3 H), 5.03-5.06 (m, 1 H), 5.08-5.12 (m, 2 H), 7.09-7.14 (m, 4 H), 7.22 (s, 1 H), 7.28 (s, 1 H), 7.35-7.45-7.62 (m, 10 H), 8.10-8.15 (m, 2 H)<br>Biotage (method X)<br>LC-MS (method 2) Rt = 1.29 min<br>MS (ESIpos): m/z = 539.4 [M + H]⁺<br>73% yield |
| 182.1 and 182.2 | rac-2-(N-[4-amino-5-[4-(difluoromethoxy)benzoyl]thiazol-2-yl]-4-benzyloxy-anilino)propanamide<br>(R)-2-(N-[4-amino-5-[4-(difluoromethoxy)benzoyl]thiazol-2-yl]-4-benzyloxy-anilino)propanamide and (S)-2-(N-[4-amino-5-[4-(difluoromethoxy)benzoyl]thiazol-2-yl]-4-benzyloxy-anilino)propanamide | | |
| 182.1 | 2-(N-[4-amino-5-[4-(difluoromethoxy)benzoyl]thiazol-2-yl]-4-benzyloxy-anilino)propanamide (enantiomer 1) | Example 182 | ¹H NMR (400 MHz, DMSO-d₆) δ ppm = 1.15 (d, J = 7.35 Hz, 3 H), 5.05 (m, 1 H), 5.11 (m, 2 H), 7.13 (m, 4 H), 7.22 (s, 1 H), 7.28 (s, 1 H), 7.35-7.55 (m, 10 H), 8.13 (m, 2 H)<br>LC-MS (method 2) Rt = 1.29 min<br>MS (ESIpos): m/z = 539.4 [M + H]⁺<br>44% yield |

Chiral HPLC Example 182.1
HPLC separation of rac-2-(N-[4-amino-5-[4-(difluoromethoxy)benzoyl]thiazol-2-yl]-4-benzyloxy-anilino)propanamide(813 mg, 1.51 mmol, Example 182) on a chiral column gave 360 mg (44% yield) of 2-(N-[4-amino-5-[4-(difluoromethoxy)benzoyl]thiazol-2-yl]-4-benzyloxy-anilino)propanamide, enantiomer 1.
Preparative chiral HPLC
Instrument: PrepCon Labomatic HPLC-3; Column: YMC Cellulose SB 10μ, 250 × 50;
eluent A: hexane + 0.1 vol % diethylamine; eluent B: ethanol + 0.1 vol % diethylamine; isocratic:
60% A + 40% B; flow: 100 mL/min; temperature: 25° C.; UV: 254 nm
Analytical chiral HPLC: Rt = 2.76 min
Instrument: Waters Alliance 2695; Column: YMC Cellulose SB 3μ, 100 × 4.6;
eluent A: hexane + 0.1 vol % diethylamine; eluent B: ethanol; isocratic: 60% A + 40% B; flow: 1.4
mL/min; temperature: 25° C.; UV: 254 nm TABLE 9-continued Example 159-256

| Example number | Chemical structure Compound name | Starting materials | Analytics/purification/yield |
|---|---|---|---|
| 182.2 | 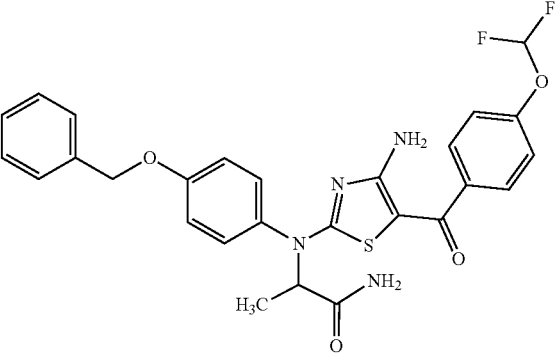 [SMILES: CC(C(N)=O)N(c1ccc(OCc2ccccc2)cc1)c1nc(N)c(C(=O)c2ccc(OC(F)F)cc2)s1]<br>2-(N-[4-amino-5-[4-(difluoromethoxy)benzoyl]thiazol-2-yl]-4-benzyloxy-anilino)propanamide (enantiomer 2) | Example 182 | $^1$H NMR (400 MHz, DMSO-$d_6$) δ ppm = 1.15 (d, J = 7.35 Hz, 3 H), 5.03-5.06 (m, 1 H), 5.09-5.12 (m, 2 H), 7.09-7.14 (m, 4 H), 7.22 (s, 1 H), 7.28 (s, 1 H), 7.35-7.55 (m, 10 H), 8.10-8.15 (m, 2 H)<br>LC-MS (method 2) Rt = 1.29 min<br>MS (ESIpos): m/z = 539.4 [M + H]$^+$<br>45% yield |
| | Chiral HPLC Example 182.2<br>HPLC separation of rac-2-(N-[4-amino-5-[4-(difluoromethoxy)benzoyl]thiazol-2-yl]-4-benzyloxy-anilino)propanamide(813 mg, 1.51 mmol, Example 182) on a chiral column gave 365 mg (45% yield) of 2-(N-[4-amino-5-[4-(difluoromethoxy)benzoyl]thiazol-2-yl]-4-benzyloxy-anilino)propanamide, enantiomer 2.<br>Preparative chiral HPLC<br>Instrument: PrepCon Labomatic HPLC-3; Column: YMC Cellulose SB 10µ, 250 × 50; eluent A: hexane + 0.1 vol % diethylamine; eluent B: ethanol + 0.1 vol % diethylamine; isocratic: 60% A + 40% B; flow: 100 mL/min; temperature: 25° C.; UV: 254 nm<br>Analytical chiral HPLC: Rt = 3.49 min<br>Instrument: Waters Alliance 2695; Column: YMC Cellulose SB 3µ, 100 × 4.6; eluent A: hexane + 0.1 vol % diethylamine; eluent B: ethanol; isocratic: 60% A + 40% B; flow: 1.4 mL/min; temperature: 25° C.; UV: 254 nm | | |
| 183 | 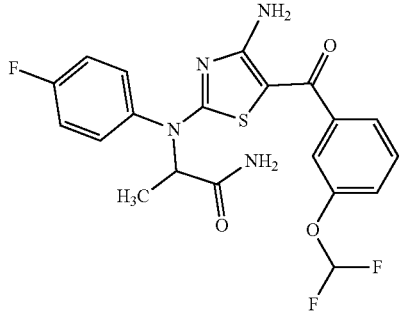 [SMILES: CC(C(N)=O)N(c1ccc(F)cc1)c1nc(N)c(C(=O)c2cccc(OC(F)F)c2)s1]<br>rac-2-(N-[4-amino-5-[3-(difluoromethoxy)benzoyl]thiazol-2-yl]-4-fluoro-anilino)propanamide | Intermediate 124, rac-2-bromopropanamide | $^1$H NMR (400 MHz, DMSO-$d_6$) δ ppm = 1.15 (d, J = 7.35 Hz, 3 H), 5.03-5.06 (m, 1 H), 7.20-7.28 (m, 4 H), 7.33 (d, J = 8.87 Hz, 3 H), 7.42 (d, J = 8.11 Hz, 1 H), 7.59-7.63 (m, 3 H), 8.17-8.21 (m, 2 H)<br>RP-HPLC (method D basic)<br>LC-MS (method 2) Rt = 1.13 min<br>MS (ESIpos): m/z = 451.5 [M + H]$^+$<br>41% yield |
| 184 | 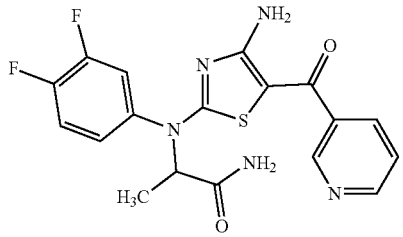 [SMILES: CC(C(N)=O)N(c1ccc(F)c(F)c1)c1nc(N)c(C(=O)c2cccnc2)s1]<br>rac-2-(N-[4-amino-5-(pyridine-3-carbonyl)thiazol-2-yl]-3,4-difluoro-anilino)propanamide | Intermediate 125, rac-2-bromopropanamide | $^1$H NMR (400 MHz, DMSO-$d_6$) δ ppm = 1.19 (d, J = 7.35 Hz, 3 H), 4.97-5.09 (m, 1 H), 7.30 (s, 1 H), 7.40-7.48 (m, 1 H), 7.48-7.53 (m, 1 H), 7.55-7.61 (m, 1 H), 7.63 (s, 1 H), 7.74-7.81 (m, 1 H), 7.85-7.90 (m, 1 H), 8.07-8.41 (m, 2 H), 8.61 (dd, J = 4.82, 1.52 Hz, 1 H), 8.69 (dd, J = 2.28, 0.76 Hz, 1 H)<br>RP-HPLC (method D basic)<br>LC-MS (method 2) Rt = 0.92 min<br>MS (ESIpos): m/z = 404.3 [M + H]$^+$<br>54% yield |

TABLE 9-continued

Example 159-256

| Example number | Chemical structure Compound name | Starting materials | Analytics/purification/yield |
|---|---|---|---|
| 184.1 and 184.2 | (R)-2-(N-[4-amino-5-(pyridine-3-carbonyl)thiazol-2-yl]-3,4-difluoro-anilino)propanamide and (S)-2-(N-[4-amino-5-(pyridine-3-carbonyl)thiazol-2-yl]-3,4-difluoro-anilino)propanamide | | |
| 184.1 | 2-(N-[4-amino-5-(pyridine-3-carbonyl)thiazol-2-yl]-3,4-difluoro-anilino)propanamide (enantiomer 1) | Example 184 | $^1$H NMR (400 MHz, DMSO-d$_6$) δ ppm = 1.19 (d, J = 7.35 Hz, 3 H), 4.97-5.09 (m, 1 H), 7.30 (s, 1 H), 7.40-7.48 (m, 1 H), 7.48-7.53 (m, 1 H), 7.55-7.61 (m, 1 H), 7.63 (s, 1 H), 7.74-7.81 (m, 1 H), 7.85-7.90 (m, 1 H), 8.07-8.41 (m, 2 H), 8.61 (dd, J = 4.82, 1.52 Hz, 1 H), 8.69 (dd, J = 2.28, 0.76 Hz, 1 H) LC-MS (method 2) Rt = 0.92 min MS (ESIpos): m/z = 404.3 [M + H]$^+$ 39% yield |

Chiral HPLC Example 184.1
HPLC separation of rac-2-(N-[4-amino-5-(pyridine-3-carbonyl)thiazol-2-yl]-3,4-difluoro-anilino)propanamide(115 mg, 0.29 mmol, Example 184) on a chiral column gave 45 mg (39% yield) of 2-(N-[4-amino-5-(pyridine-3-carbonyl)thiazol-2-yl]-3,4-difluoro-anilino)propanamide, enantiomer 1.
Preparative chiral HPLC
Instrument: PrepCon Labomatic HPLC-4; Column: YMC Cellulose SC 10μ, 250 × 50; eluent A: methyl tert-butyl ether + 0.1 vol % diethylamine; eluent B: acetonitrile; isocratic: 50% A + 50% B; flow: 100 mL/min; temperature: 25° C.; UV: 280 nm
Analytical chiral HPLC: Rt = 2.11 min
Instrument: Thermo Fisher UltiMate 3000; Column: YMC Cellulose SC 3μ, 100 × 4.6; eluent A: methyl tert-butyl ether + 0.1 vol % diethylamine; eluent B: acetonitrile; isocratic: 50% A + 50% B; flow: 1.4 mL/min; temperature: 25° C.; UV: 254 nm

| 184.2 | 2-(N-[4-amino-5-(pyridine-3-carbonyl)thiazol-2-yl]-3,4-difluoro-anilino)propanamide (enantiomer 2) | Example 184 | $^1$H NMR (400 MHz, DMSO-d$_6$) δ ppm = 1.19 (d, J = 7.35 Hz, 3 H), 4.97-5.09 (m, 1 H), 7.30 (s, 1 H), 7.40-7.48 (m, 1 H), 7.48-7.53 (m, 1 H), 7.55-7.61 (m, 1 H), 7.63 (s, 1 H), 7.74-7.81 (m, 1 H), 7.85-7.90 (m, 1 H), 8.07-8.41 (m, 2 H), 8.61 (dd, J = 4.82, 1.52 Hz, 1 H), 8.69 (dd, J = 2.28, 0.76 Hz, 1 H) LC-MS (method 2) Rt = 0.92 min MS (ESIpos): m/z = 404.3 [M + H]$^+$ 43% yield |

Chiral HPLC Example 184.2
HPLC separation of rac-2-(N-[4-amino-5-(pyridine-3-carbonyl)thiazol-2-yl]-3,4-difluoro-anilino)propanamide(115 mg, 0.29 mmol, Example 184) on a chiral column gave 50 mg (43% yield) of 2-(N-[4-amino-5-(pyridine-3-carbonyl)thiazol-2-yl]-3,4-difluoro-anilino)propanamide, enantiomer 2.
Preparative chiral HPLC
Instrument: PrepCon Labomatic HPLC-4; Column: YMC Cellulose SC 10μ, 250 × 50; eluent A: methyl tert-butyl ether + 0.1 vol % diethylamine; eluent B: acetonitrile; isocratic: 50% A + 50% B; flow: 100 mL/min; temperature: 25° C.; UV: 280 nm
Analytical chiral HPLC: Rt = 2.83 min
Instrument: Thermo Fisher UltiMate 3000; Column: YMC Cellulose SC 3μ, 100 × 4.6; eluent A: methyl tert-butyl ether + 0.1 vol % diethylamine; eluent B: acetonitrile; isocratic: 50% A + 50% B; flow: 1.4 mL/min; temperature: 25° C.; UV: 254 nm

TABLE 9-continued

Example 159-256

| Example number | Chemical structure Compound name | Starting materials | Analytics/purification/yield |
|---|---|---|---|
| 185 | 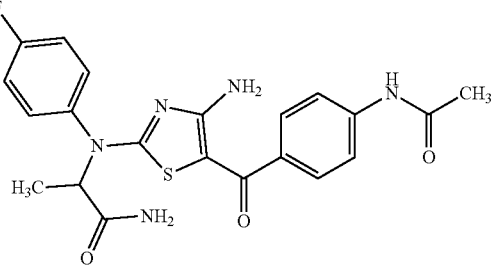<br>rac-2-(N-[5-(4-acetamidobenzoyl)-4-amino-thiazol-2-yl]-4-fluoro-anilino)propanamide | Intermediate 126, rac-2-bromopropanamide | $^1$H NMR (400 MHz, DMSO-d$_6$) δ ppm = 1.15 (d, J = 7.35 Hz, 3 H), 2.03 (s, 3 H), 5.05 (q, J = 7.35 Hz, 1 H), 7.24 (s, 1 H), 7.32 (dd, J = 8.87 Hz, 2 H), 7.44 (d, J = 8.87 Hz, 2 H), 7.55 (d, J = 8.62 Hz, 2 H), 7.58 (br s, 1 H), 7.61-7.66 (m, 2 H), 7.81-8.39 (m, 2 H), 10.11 (br s, 1 H)<br>RP-HPLC (method C basic)<br>LC-MS (method 1) Rt = 0.87 min<br>MS (ESIpos): m/z = 442.4 [M + H]$^+$<br>54% yield |
| 186 | 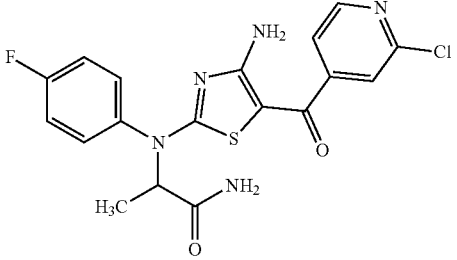 [SMILES: CC(C(N)=O)N(c1ccc(F)cc1)c1nc(N)c(C(=O)c2ccnc(Cl)c2)s1]<br>rac-2-(N-[4-amino-5-(2-chloropyridine-4-carbonyl)thiazol-2-yl]-4-fluoro-anilino)propanamide | Intermediate 127, rac-2-bromopropanamide | $^1$H NMR (400 MHz, DMSO-d$_6$) δ ppm = 1.16 (d, J = 7.60 Hz, 3 H), 5.00-5.13 (m, 1 H), 7.27 (s, 1 H), 7.34 (dd, J = 8.87 Hz, 2 H), 7.41 (dd, J = 5.07, 1.27 Hz, 1 H), 7.49 (s, 1 H), 7.59 (s, 1 H), 7.64 (dd, J = 8.87, 5.07 Hz, 2 H), 8.20-8.42 (m, 2 H), 8.45 (d, J = 5.07 Hz, 1 H)<br>RP-HPLC (method C basic)<br>LC-MS (method 2) Rt = 1.03 min<br>MS (ESIpos): m/z = 420.3 [M + H]$^+$<br>25% yield |
| 187 | 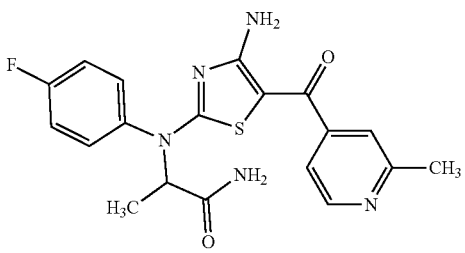 [SMILES: Cc1cc(C(=O)c2sc(N(c3ccc(F)cc3)C(C)C(N)=O)nc2N)ccn1]<br>rac-2-(N-[4-amino-5-(2-methylpyridine-4-carbonyl)thiazol-2-yl]-4-fluoro-anilino)propanamide | Intermediate 128, rac-2-bromopropanamide | $^1$H NMR (400 MHz, DMSO-d$_6$) δ ppm = 1.15 (d, J = 7.60 Hz, 3 H), 2.45 (s, 3 H), 5.06 (br s, 1 H), 7.10-7.23 (m, 1 H), 7.23-7.28 (m, 2 H), 7.33 (dd, J = 8.74 Hz, 2 H), 7.59 (br s, 1 H), 7.63 (dd, J = 8.87, 5.07 Hz, 2 H), 8.05-8.42 (m, 2 H), 8.46 (d, J = 5.07 Hz, 1 H)<br>RP-HPLC (method C basic)<br>LC-MS (method 2) Rt = 0.90 min<br>MS (ESIpos): m/z = 400.5 [M + H]$^+$<br>66% yield |
| 187.1 and 187.2 | (R)-2-(N-[4-amino-5-(2-methylpyridine-4-carbonyl)thiazol-2-yl]-4-fluoro-anilino)propanamide and (S)-2-(N-[4-amino-5-(2-methylpyridine-4-carbonyl)thiazol-2-yl]-4-fluoro-anilino)propanamide | | |
| 187.1 | 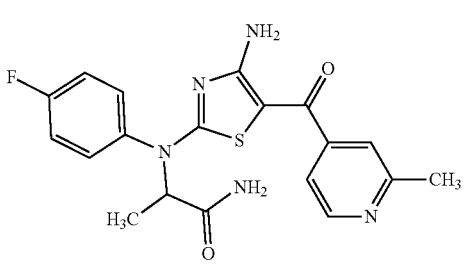 [SMILES: Cc1cc(C(=O)c2sc(N(c3ccc(F)cc3)C(C)C(N)=O)nc2N)ccn1] | Example 187 | $^1$H NMR (400 MHz, DMSO-d$_6$) δ ppm = 1.15 (d, J = 7.60 Hz, 3 H), 2.45 (s, 3 H), 5.06 (br s, 1 H), 7.10-7.23 (m, 1 H), 7.23-7.28 (m, 2 H), 7.33 (dd, J = 8.74 Hz, 2 H), 7.59 (br s, 1 H), 7.63 (dd, J = 8.87, 5.07 Hz, 2 H), 8.05-8.42 (m, 2 H), 8.46 (d, J = 5.07 Hz, 1 H)<br>32% yield |

TABLE 9-continued

Example 159-256

| Example number | Chemical structure Compound name | Starting materials | Analytics/purification/yield |
|---|---|---|---|
| | 2-(N-[4-amino-5-(2-methyipyridine-4-carbonyl)thiazol-2-yl]-4-fluoro-anilino)propanamide (enantiomer 1) Chiral HPLC Example 187.1 HPLC separation of rac-2-(N-[4-amino-5-(2-methylpyridine-4-carbonyl)thiazol-2-yl]-4-fluoro-anilino)propanamide(333 mg, 0.83 mmol, Example 187) on a chiral column gave 105 mg (32% yield) of 2-(N-[4-amino-5-(2-methylpyridine-4-carbonyl)thiazol-2-yl]-4-fluoro-anilino)propanamide, enantiomer 1. Preparative chiral HPLC Instrument: Sepiatec: Prep SFC100; Column: Chiralpak IG 5μ 250 × 30 mm; eluent A: $CO_2$; eluent B: ethanol + 0.2 vol % aqueous ammonia (32%); isocratic: 15% B; flow: 100 mL/min; temperature: 40° C.; BPR: 150 bar; UV: 254 nm Analytical chiral HPLC: Rt = 2.81 min Instrument: Agilent: 1260, Aurora SFC-Modul; Column: Chiralpak IG 5μ 100 × 4.6 mm; eluent A: $CO_2$; eluent B: ethanol + 0.2 vol % aqueous ammonia (32%); isocratic: 25% B; flow: 4 mL/min; temperature: 37.5° C.; BPR: 100 bar; UV: 254 nm | | |
| 187.2 | 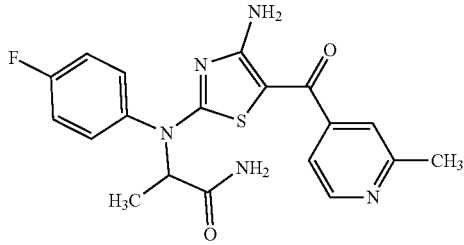 [SMILES: Cc1cc(C(=O)c2sc(N(c3ccc(F)cc3)C(C)C(N)=O)nc2N)ccn1] 2-(N-[4-amino-5-(2-methylpyridine-4-carbonyl)thiazol-2-yl]-4-fluoro-anilino)propanamide (enantiomer 2) Chiral HPLC Example 187.2 HPLC separation of rac-2-(N-[4-amino-5-(2-methylpyridine-4-carbonyl)thiazol-2-yl]-4-fluoro-anilino)propanamide(333 mg, 0.83 mmol, Example 187) on a chiral column gave 78 mg (23% yield) of 2-(N-[4-amino-5-(2-methylpyridine-4-carbonyl)thiazol-2-yl]-4-fluoro-anilino)propanamide, enantiomer 2. Preparative chiral HPLC Instrument: Sepiatec: Prep SFC100; Column: Chiralpak IG 5μ 250 × 30 mm; eluent A: $CO_2$; eluent B: ethanol + 0.2 vol % aqueous ammonia (32%); isocratic: 15% B; flow: 100 mL/min; temperature: 40° C.; BPR: 150 bar; UV: 254 nm Analytical chiral HPLC: Rt = 3.56 min Instrument: Agilent: 1260, Aurora SFC-Modul; Column: Chiralpak IG 5μ 100 × 4.6 mm; eluent A: $CO_2$; eluent B: ethanol + 0.2 vol % aqueous ammonia (32%); isocratic: 25% B; flow: 4 mL/min; temperature: 37.5° C.; BPR: 100 bar; UV: 254 nm | Example 187 | $^1$H NMR (400 MHz, DMSO-$d_6$) δ ppm = 1.15 (d, J = 7.60 Hz, 3 H), 2.45 (s, 3 H), 5.06 (br s, 1 H), 7.10-7.23 (m, 1 H), 7.23-7.28 (m, 2 H), 7.33 (dd, J = 8.74 Hz, 2 H), 7.59 (br s, 1 H), 7.63 (dd, J = 8.87, 5.07 Hz, 2 H), 8.05-8.42 (m, 2 H), 8.46 (d, J = 5.07 Hz, 1 H) 23% yield |
| 188 | 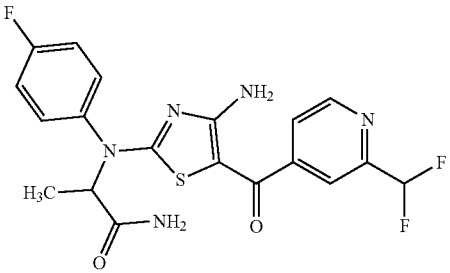 [SMILES: CC(C(N)=O)N(c1ccc(F)cc1)c1nc(N)c(C(=O)c2ccnc(C(F)F)c2)s1] rac-2-(N-[4-amino-5-[2-(difluoromethyl)pyridine-4-carbonyl]thiazol-2-yl]-4-fluoro-anilino)propanamide | Intermediate 129, rac-2-bromopropanamide | $^1$H NMR (400 MHz, DMSO-$d_6$) δ ppm = 1.16 (d, J = 7.35 Hz, 3 H), 4.99-5.13 (m, 1 H), 6.97 (t, J = 52 Hz, 1 H), 7.27 (s, 1 H), 7.33 (t J = 8.87 Hz, 2 H), 7.56-7.61 (m, 2 H), 7.64 (dd, J = 8.87, 5.07 Hz, 2 H), 7.67 (s, 1 H), 8.20-8.57 (m, 2 H), 8.73 (d, J = 4.56 Hz, 1 H) RP-HPLC (method C basic) LC-MS (method 2) Rt = 1.00 min MS (ESIpos): m/z = 436.3 [M + H]$^+$ 13% yield |

TABLE 9-continued

Example 159-256

| Example number | Chemical structure Compound name | Starting materials | Analytics/purification/yield |
|---|---|---|---|
| 189 | 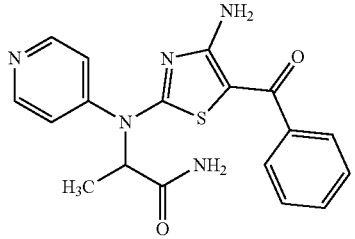 [SMILES: CC(C(N)=O)N(c1ccncc1)c1nc(N)c(C(=O)c2ccccc2)s1]<br>rac-2-[(4-amino-5-benzoyl-thiazol-2-yl)-(4-pyridyl)amino]propanamide | Intermediate 130, rac-2-bromopropanamide | $^1$H NMR (400 MHz, DMSO-d$_6$) δ ppm = 1.22 (d, J = 7.35 Hz, 3 H), 5.05 (q, J = 7.35 Hz, 1 H), 5.74 (s, 1 H), 7.32 (s, 1 H), 7.37-7.44 (m, 2 H), 7.48-7.55 (m, 2 H), 7.56-7.65 (m, 3 H), 8.06-8.42 (m, 2 H), 8.68-8.73 (m, 2 H)<br>RP-HPLC (method C basic)<br>LC-MS (method 2) Rt = 0.80 min<br>MS (ESIpos): m/z = 368.2 [M + H]$^+$<br>17% yield |
| 190 | 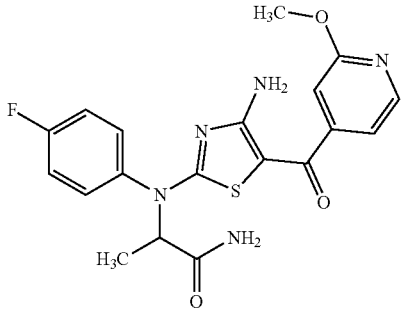 [SMILES: COc1cc(C(=O)c2sc(N(c3ccc(F)cc3)C(C)C(N)=O)nc2N)ccn1]<br>rac-2-(N-[4-amino-5-(2-methoxypyridine-4-carbonyl)thiazol-2-yl]-4-fluoro-anilino)propanamide | Intermediate 131, rac-2-bromopropanamide | $^1$H NMR (400 MHz, DMSO-d$_6$) δ ppm = 1.15 (d, J = 7.35 Hz, 3 H), 3.83 (s, 3H), 5.00-5.11 (m, 1 H), 6.76 (s, 1 H), 6.99 (dd, J = 5.20, 1.39 Hz, 1 H), 7.26 (s, 1 H), 7.30-7.37 (m, 2 H), 7.59 (s, 1 H), 7.63 (dd, J = 8.87, 5.07 Hz, 2 H), 8.17-8.20 (m, 1 H), 8.21-8.48 (m, 2 H)<br>RP-HPLC (method C basic)<br>LC-MS (method 2) Rt = 0.98 min<br>MS (ESIpos): m/z = 416.2 [M + H]$^+$<br>29% yield |
| 191 | 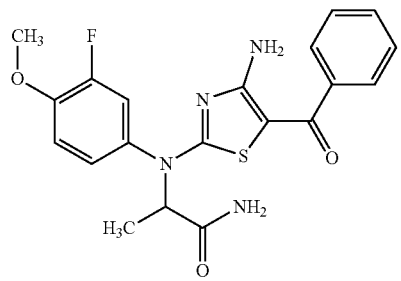 [SMILES: COc1ccc(N(c2nc(N)c(C(=O)c3ccccc3)s2)C(C)C(N)=O)cc1F]<br>rac-2-(N-(4-amino-5-benzoyl-thiazol-2-yl)-3-fluoro-4-methoxy-anilino)propanamide | Intermediate 133; rac-2-bromopropanamide | $^1$H NMR (400 MHz, DMSO-d$_6$) δ ppm = 8.12 (br s, 2H), 7.57 (s, 1H), 7.46-7.53 (m, 3H), 7.34-7.44 (m, 4H), 7.21-7.28 (m, 2H), 4.98-5.10 (m, 1H), 3.87 (s, 3H), 1.16 (d, J = 7.4 Hz, 3H).<br>LC-MS (method 2) Rt = 1.06 min<br>MS (ESIpos): m/z = 415.3 [M + H]$^+$<br>78% yield |
| 192 | 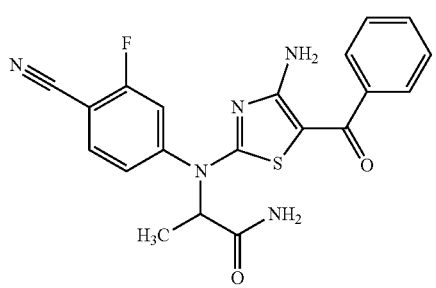 [SMILES: CC(C(N)=O)N(c1ccc(C#N)c(F)c1)c1nc(N)c(C(=O)c2ccccc2)s1]<br>rac-2-(N-(4-amino-5-benzoyl-thiazol-2-yl)-4-cyano-3-fluoro-anilino)propanamide | Intermediate 134; rac-2-bromopropanamide | $^1$H NMR (400 MHz, DMSO-d$_6$) δ ppm = 1H NMR (400 MHz, DMSO-d6, 22° C.): Shift = 7.95-8.40 (m, 3H), 7.86 (dd, J = 10.4, 1.8 Hz, 1H), 7.64-7.72 (m, 2H), 7.50-7.55 (m, 2H), 7.38-7.48 (m, 3H), 7.36 (s, 1H), 5.01 (q, J = 7.4 Hz, 1H), 1.22 (d, J = 7.4 Hz, 3H)<br>LC-MS (method 2) Rt = 1.04 min<br>MS (ESIpos): m/z = 410.3 [M + H]$^+$<br>18% yield |

TABLE 9-continued

Example 159-256

| Example number | Chemical structure Compound name | Starting materials | Analytics/purification/yield |
|---|---|---|---|
| 193 | 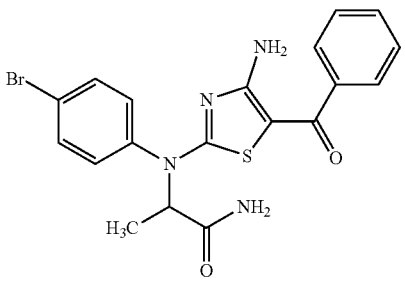 [SMILES: CC(C(N)=O)N(c1ccc(Br)cc1)c1nc(N)c(C(=O)c2ccccc2)s1]<br>rac-2-(N-(4-amino-5-benzoyl-thiazol-2-yl)-4-bromo-anilino)propanamide | Intermediate 135; rac-2-bromopropanamide | $^1$H NMR (400 MHz, DMSO-d$_6$) δ ppm = 8.17 (br s, 2H), 7.66-7.72 (m, 2H), 7.59 (s, 1H), 7.51-7.57 (m, 2H), 7.46-7.51 (m, 2H), 7.36-7.44 (m, 3H), 7.26 (s, 1H), 5.05 (q, J = 7.3 Hz, 1H), 1.16 (d, J = 7.6 Hz, 3H).<br>LC-MS (method 2) Rt = 1.19 min MS (ESIpos): m/z = 445.3 [M + H]$^+$ 47% yield |
| 194 | 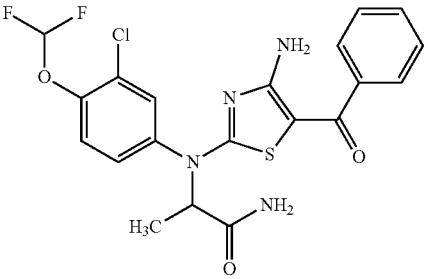 [SMILES: CC(C(N)=O)N(c1ccc(OC(F)F)c(Cl)c1)c1nc(N)c(C(=O)c2ccccc2)s1]<br>rac-2-[N-(4-amino-5-benzoyl-thiazol-2-yl)-3-chloro-4-(difluoromethoxy)anilino]propanamide | Intermediate 136; rac-2-bromopropanamide | $^1$H NMR (400 MHz, DMSO-d$_6$) δ ppm = 8.13 (br s, 2H), 7.90 (d, J = 2.5 Hz, 1H), 7.60-7.68 (m, 2H), 7.45-7.52 (m, 3H), 7.39-7.44 (m, 3H), 7.39 (t, J = 73.0 Hz, 1H), 7.29 (s, 1H), 5.02 (q, J = 7.1 Hz, 1H), 1.18 (d, J = 7.4 Hz, 3H).<br>LC-MS (method 2) Rt = 1.18 min MS (ESIpos): m/z = 467.4 [M + H]$^+$ 68% yield |
| 195 | 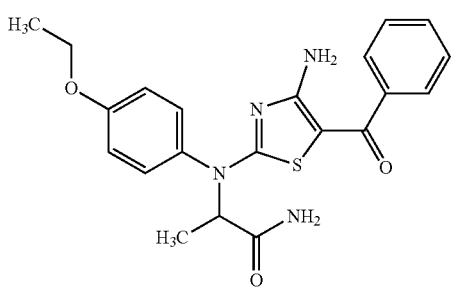 [SMILES: CCOc1ccc(N(c2nc(N)c(C(=O)c3ccccc3)s2)C(C)C(N)=O)cc1]<br>rac-2-(N-(4-amino-5-benzoyl-thiazol-2-yl)-4-ethoxy-anilino)propanamide | Intermediate 137; rac-2-bromopropanamide | $^1$H NMR (400 MHz, DMSO-d$_6$) δ ppm = 8.11 (br s, 2H), 7.52 (s, 1H), 7.41-7.49 (m, 4H), 7.34-7.41 (m, 3H), 7.20 (s, 1H), 6.98 (d, J = 9.1 Hz, 2H), 5.00-5.12 (m, 1H), 4.03 (q, J = 6.8 Hz, 2H), 1.32 (t, J = 7.0 Hz, 3H), 1.14 (d, J = 7.4 Hz, 3H).<br>LC-MS (method 2) Rt = 1.15 min MS (ESIpos): m/z = 411.5 [M + H]$^+$ 61% yield |
| 196 | 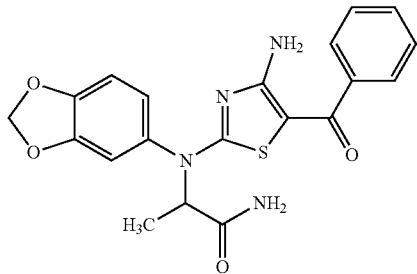 [SMILES: CC(C(N)=O)N(c1ccc2c(c1)OCO2)c1nc(N)c(C(=O)c2ccccc2)s1] | Intermediate 138; rac-2-bromopropanamide | $^1$H NMR (400 MHz, DMSO-d$_6$) δ ppm = 8.08 (br s, 2H), 7.54 (s, 1H), 7.46-7.51 (m, 2H), 7.36-7.44 (m, 3H), 7.22 (s, 1H), 7.14 (d, J = 1.8 Hz, 1H), 7.01-7.07 (m, 1H), 6.96-7.00 (m, 1H), 6.10 (s, 2H), 4.97-5.09 (m, 1H), 1.18 (d, J = 7.4 Hz, 3H).<br>LC-MS (method 2) Rt = 1.03 min MS (ESIpos): m/z = 411.4 [M + H]$^+$ 67% yield |

TABLE 9-continued

Example 159-256

| Example number | Chemical structure Compound name | Starting materials | Analytics/purification/yield |
|---|---|---|---|
| | rac-2-[(4-amino-5-benzoyl-thiazol-2-yl)-(1,3-benzodioxol-5-yl)amino]propanamide | | |
| 197 | rac-2-[(4-amino-5-benzoyl-thiazol-2-yl)-(2,2-difluoro-1,3-benzodioxol-5-yl)amino]propanamide | Intermediate 139; rac-2-bromopropanamide | $^1$H NMR (400 MHz, DMSO-d$_6$) δ ppm = 8.13 (br s, 2H), 7.71 (d, J = 2.0 Hz, 1H), 7.61 (s, 1H), 7.45-7.56 (m, 4H), 7.35-7.44 (m, 3H), 7.28 (s, 1H), 5.03 (br d, J = 6.8 Hz, 1H), 1.18 (d, J = 7.4 Hz, 3H). LC-MS (method 2) Rt = 1.2 min MS (ESIpos): m/z = 447.3 [M + H]$^+$ 51% yield |
| 198 | rac-2-[N-(4-amino-5-benzoyl-thiazol-2-yl)-4-(difluoromethoxy)-3-fluoro-anilino]propanamide | Intermediate 140; rac-2-bromopropanamide | $^1$H NMR (400 MHz, DMSO-d$_6$) δ ppm = 8.14 (br s, 2H), 7.69-7.76 (m, 1H), 7.62 (s, 1H), 7.46-7.52 (m, 4H), 7.36-7.46 (m, 3H), 7.34 (t, J = 73.0 Hz, 1H), 7.29 (s, 1H), 5.03 (q, J = 7.1 Hz, 1H), 1.18 (d, J = 7.4 Hz, 3H). LC-MS (method 2) Rt = 1.12 min MS (ESIpos): m/z = 451.3 [M + H]$^+$ 49% yield |
| 199 | rac-2-(N-(4-amino-5-benzoyl-thiazol-2-yl)-4-benzyloxy-anilino)propanamide | Intermediate 141; rac-2-bromopropanamide | $^1$H NMR (400 MHz, DMSO-d$_6$) δ ppm = 8.12 (br s, 2H), 7.53 (s, 1H), 7.44-7.51 (m, 6H), 7.32-7.43 (m, 6H), 7.21 (s, 1H), 7.09 (d, J = 9.1 Hz, 2H), 4.99-5.15 (m, 3H), 1.15 (d, J = 7.4 Hz, 3H). LC-MS (method 2) Rt = 1.28 min MS (ESIpos): m/z = 473.4 [M + H]$^+$ 57% yield |

TABLE 9-continued

Example 159-256

| Example number | Chemical structure Compound name | Starting materials | Analytics/purification/yield |
|---|---|---|---|
| 200 | 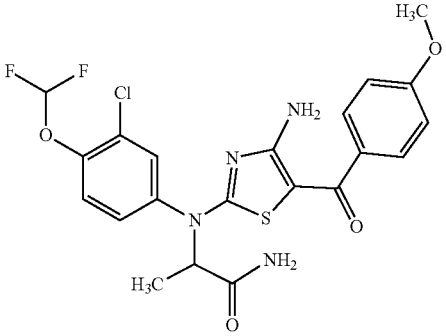 [SMILES: COc1ccc(C(=O)c2sc(N(c3ccc(OC(F)F)c(Cl)c3)C(C)C(N)=O)nc2N)cc1]<br>rac-2-[N-[4-amino-5-(4-methoxybenzoyl)thiazol-2-yl]-3-chloro-4-(difluoromethoxy)anilino] propanamide | Intermediate 142; rac-2-bromopropanamide | $^1$H NMR (400 MHz, DMSO-d$_6$) δ ppm = 7.93-8.45 (m, 2H), 7.91 (d, J = 2.3 Hz, 1H), 7.63-7.67 (m, 1H), 7.62 (s, 1H), 7.47-7.53 (m, 3H), 7.40 (t, J = 73.0 Hz, 1H), 7.29 (s, 1H), 6.92-6.96 (m, 2H), 4.98-5.07 (m, 1H), 3.76 (s, 3H), 1.18 (d, J = 7.4 Hz, 3H).<br>LC-MS (method 2) Rt = 1.17 min<br>MS (ESIpos): m/z = 497.3 [M + H]$^+$<br>63% yield |
| 201 | 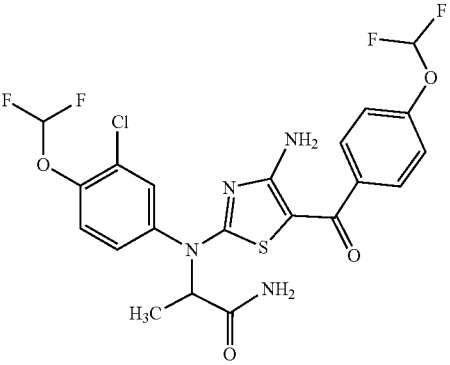 [SMILES: CC(C(N)=O)N(c1ccc(OC(F)F)c(Cl)c1)c1nc(N)c(C(=O)c2ccc(OC(F)F)cc2)s1]<br>rac-2-[N-[4-amino-5-[4-(difluoromethoxy)benzoyl] thiazol-2-yl]-3-chloro-4-(difluoromethoxy)anilino] propanamide | Intermediate 143; rac-2-bromopropanamide | $^1$H NMR (400 MHz, DMSO-d$_6$) δ ppm = 7.93-8.54 (m, 2H), 7.91 (d, J = 2.5 Hz, 1H), 7.61-7.68 (m, 2H), 7.55-7.61 (m, 2H), 7.08-7.53 (m, 6H), 4.98-5.08 (m, 1H), 1.18 (d, J = 7.4 Hz, 3H).<br>LC-MS (method 2) Rt = 1.21 min<br>MS (ESIpos): m/z = 533.3 [M + H]$^+$<br>58% yield |
| 202 | 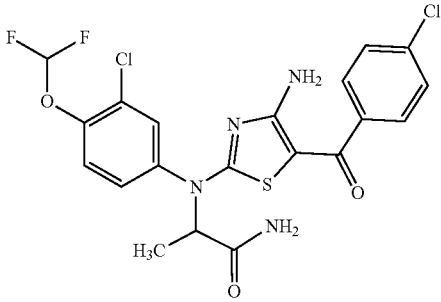 [SMILES: CC(C(N)=O)N(c1ccc(OC(F)F)c(Cl)c1)c1nc(N)c(C(=O)c2ccc(Cl)cc2)s1]<br>rac-2-[N-[4-amino-5-(4-chlorobenzoyl)thiazol-2-yl]-3-chloro-4-(difluoromethoxy)anilino] propanamide | Intermediate 144; rac-2-bromopropanamide | $^1$H NMR (400 MHz, DMSO-d$_6$) δ ppm = 7.92-8.51 (m, 2H), 7.90 (d, J = 2.5 Hz, 1H), 7.60-7.68 (m, 2H), 7.50-7.55 (m, 2H), 7.45-7.50 (m, 3H), 7.39 (t, J = 73.0 Hz, 1H), 7.30 (s, 1H), 4.98-5.08 (m, 1H), 1.18 (d, J = 7.4 Hz, 3H).<br>LC-MS (method 2) Rt = 1.28 min<br>MS (ESIpos): m/z = 501.3 [M + H]$^+$<br>56% yield |

TABLE 9-continued

Example 159-256

| Example number | Chemical structure Compound name | Starting materials | Analytics/purification/yield |
|---|---|---|---|
| 203 | 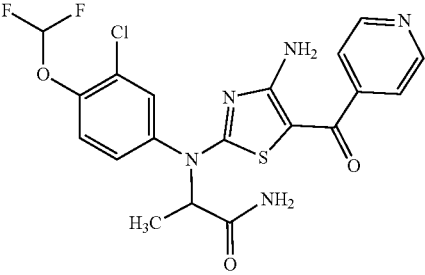 [SMILES: CC(C(N)=O)N(c1ccc(OC(F)F)c(Cl)c1)c1nc(N)c(C(=O)c2ccncc2)s1]<br>rac-2-[N-[4-amino-5-(pyridine-4-carbonyl)thiazol-2-yl]-3-chloro-4-(difluoromethoxy)anilino]propanamide | Intermediate 145; rac-2-bromopropanamide | $^1$H NMR (400 MHz, DMSO-d$_6$) δ ppm = 8.61-8.66 (m, 2H), 8.06-8.54 (m, 2H), 7.90 (d, J = 2.5 Hz, 1H), 7.61-7.67 (m, 2H), 7.48 (d, J = 8.6 Hz, 1H), 7.40-7.45 (m, 2H), 7.39 (t, J = 72.7 Hz, 1H), 7.31 (s, 1H), 4.98-5.07 (m, 1H), 1.18 (d, J = 7.4 Hz, 3H).<br>LC-MS (method 2) Rt = 0.98 min<br>MS (ESIpos): m/z = 468.3 [M + H]$^+$<br>47% yield |
| 204 | 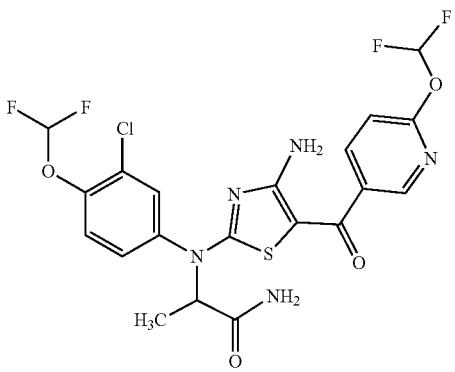 [SMILES: CC(C(N)=O)N(c1ccc(OC(F)F)c(Cl)c1)c1nc(N)c(C(=O)c2ccc(OC(F)F)nc2)s1]<br>rac-2-[N-[4-amino-5-[6-(difluoromethoxy)pyridine-3-carbonyl]thiazol-2-yl]-3-chloro-4-(difluoromethoxy)anilino]propanamide | Intermediate 146; rac-2-bromopropanamide | $^1$H NMR (400 MHz, DMSO-d$_6$) δ ppm = 8.41 (d, J = 1.8 Hz, 1H), 8.05-8.38 (m, 2H), 8.02 (dd, J = 8.6, 2.5 Hz, 1H), 7.91 (d, J = 2.5 Hz, 1H), 7.72 (t, J = 72.5 Hz, 1H), 7.61-7.68 (m, 2H), 7.47-7.52 (m, 1H), 7.40 (t, J = 72.8 Hz, 1H), 7.31 (s, 1H), 7.10-7.15 (m, 1H), 4.98-5.08 (m, 1H), 1.19 (d, J = 7.4 Hz, 3H).<br>LC-MS (method 2) Rt = 1.21 min<br>MS (ESIpos): m/z = 534.3 [M + H]$^+$<br>42% yield |
| 205 | 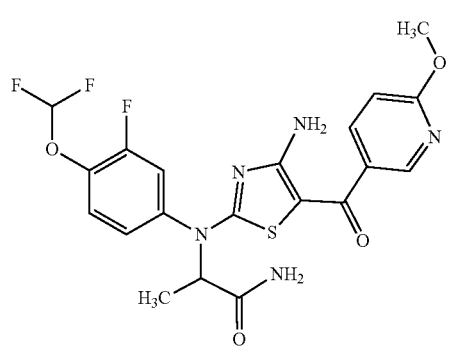 [SMILES: COc1ccc(C(=O)c2sc(N(c3ccc(OC(F)F)c(F)c3)C(C)C(N)=O)nc2N)cn1]<br>rac-2-[N-[4-amino-5-(4-methoxybenzoyl)thiazol-2-yl]-4-(difluoromethoxy)-3-fluoro-anilino]propanamide | Intermediate 147; rac-2-bromopropanamide | $^1$H NMR (400 MHz, DMSO-d$_6$) δ ppm = 7.77-8.42 (m, 2H), 7.74 (dd, J = 11.4, 1.3 Hz, 1H), 7.62 (s, 1H), 7.47-7.53 (m, 4H), 7.35 (t, J = 73.0 Hz, 1H), 6.91-6.97 (m, 2H), 4.99-5.08 (m, 1H), 3.76 (s, 3H), 1.19 (d, J = 7.4 Hz, 3H).<br>LC-MS (method 2) Rt = 1.13 min<br>MS (ESIpos): m/z = 481.3 [M + H]$^+$<br>57% yield |

TABLE 9-continued

Example 159-256

| Example number | Chemical structure Compound name | Starting materials | Analytics/purification/yield |
|---|---|---|---|
| 206 | 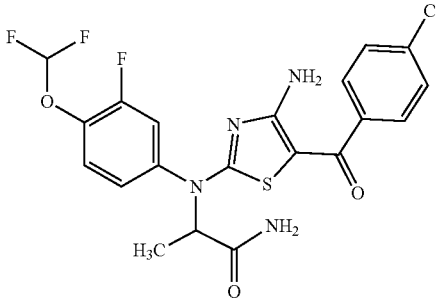<br>rac-2-[N-[4-amino-5-(4-chlorobenzoyl)thiazol-2-yl]-4-(difluoromethoxy)-3-fluoro-anilino]propanamide | Intermediate 148; rac-2-bromopropanamide | $^1$H NMR (400 MHz, DMSO-d$_6$) δ ppm = 7.80-8.55 (m, 2H), 7.73 (dd, J = 11.3, 1.4 Hz, 1H), 7.62 (s, 1H), 7.46-7.55 (m, 6H), 7.35 (t, J = 72.8 Hz, 1H), 7.30 (s, 1H), 4.99-5.08 (m, 1H), 1.19 (d, J = 7.4 Hz, 3H).<br>LC-MS (method 2) Rt = 1.24 min<br>MS (ESIpos): m/z = 485.3 [M + H]$^+$<br>53% yield |
| 207 | 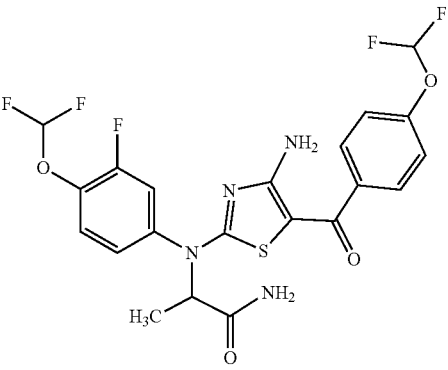 [SMILES: CC(C(N)=O)N(c1ccc(OC(F)F)c(F)c1)c1nc(N)c(C(=O)c2ccc(OC(F)F)cc2)s1]<br>rac-2-[N-[4-amino-5-[4-(difluoromethoxy)benzoyl]thiazol-2-yl]-4-(difluoromethoxy)-3-fluoro-anilino]propanamide | Intermediate 149; rac-2-bromopropanamide | $^1$H NMR (400 MHz, DMSO-d$_6$) δ ppm = 7.78-8.47 (m, 2H), 7.73 (dd, J = 11.2, 1.3 Hz, 1H), 7.62 (s, 1H), 7.55-7.60 (m, 2H), 7.34-7.54 (m, 3H), 7.09-7.32 (m, 4H), 4.98-5.08 (m, 1H), 1.19 (d, J = 7.4 Hz, 3H).<br>LC-MS (method 2) Rt = 1.18 min<br>MS (ESIpos): m/z = 517.3 [M + H]$^+$<br>50% yield |
| 208 | 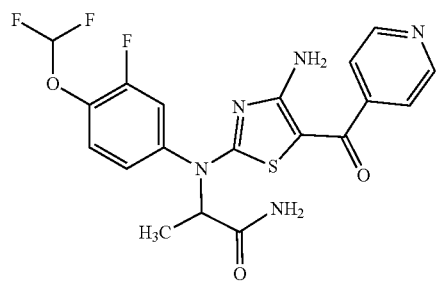<br>rac-2-[N-[4-amino-5-(pyridine-4-carbonyl)thiazol-2-yl]-4-(difluoromethoxy)-3-fluoro-anilino]propanamide | Intermediate 150; rac-2-bromopropanamide | $^1$H NMR (400 MHz, DMSO-d$_6$) δ ppm = 8.61-8.65 (m, 2H), 8.30 (br s, 2H), 7.73 (dd, J = 11.0, 1.4 Hz, 1H), 7.63 (s, 1H), 7.48-7.52 (m, 2H), 7.39-7.45 (m, 2H), 7.35 (t, J = 73.0 Hz, 1H), 7.31 (s, 1H), 4.98-5.08 (m, 1H), 1.19 (d, J = 7.4 Hz, 3H).<br>LC-MS (method 2) Rt = 0.94 min<br>MS (ESIpos): m/z = 452.3 [M + H]$^+$<br>48% yield |
| 209 | 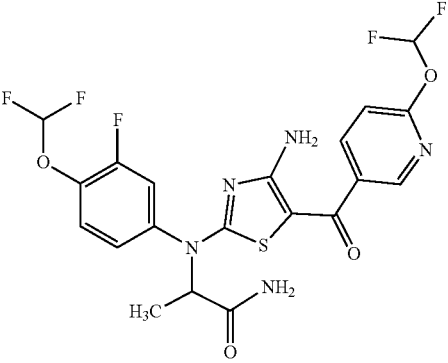 [SMILES: CC(C(N)=O)N(c1ccc(OC(F)F)c(F)c1)c1nc(N)c(C(=O)c2ccc(OC(F)F)nc2)s1] | Intermediate 151; rac-2-bromopropanamide | $^1$H NMR (400 MHz, DMSO-d$_6$) δ ppm = 8.41 (d, J = 2.0 Hz, 1H), 8.02 (dd, J = 8.5, 2.4 Hz, 3H), 7.74 (dd, J = 11.4, 1.3 Hz, 1H), 7.72 (t, J = 72.5 Hz, 1H), 7.63 (s, 1H), 7.49-7.53 (m, 2H), 7.36 (t, J = 73.0 Hz, 1H), 7.31 (s, 1H), 7.10-7.15 (m, 1H), 4.99-5.09 (m, 1H), 1.19 (d, J = 7.4 Hz, 3H).<br>LC-MS (method 2) Rt = 1.18 min<br>MS (ESIpos): m/z = 518.3 [M + H]$^+$<br>51% yield |

TABLE 9-continued

Example 159-256

| Example number | Chemical structure Compound name | Starting materials | Analytics/purification/yield |
|---|---|---|---|
| 218 | 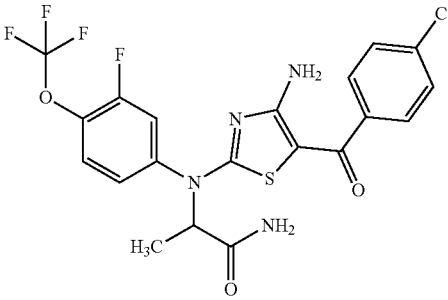<br>rac-2-[N-[4-amino-5-(4-chlorobenzoyl)thiazol-2-yl]-3-fluoro-4-(trifluoromethoxy)anilino]propanamide | Intermediate 160; rac-2-bromopropanamide | $^1$H NMR (400 MHz, DMSO-d$_6$) δ ppm = 7.90-8.49 (m, 2H), 7.85 (dd, J = 11.2, 2.3 Hz, 1H), 7.75 (td, J = 8.7, 1.0 Hz, 1H), 7.65 (s, 1H), 7.58-7.62 (m, 1H), 7.51-7.56 (m, 2H), 7.45-7.50 (m, 2H), 7.32 (s, 1H), 4.97-5.06 (m, 1H), 1.20 (d, J = 7.4 Hz, 3H).<br>LC-MS (method 2) Rt = 1.34 min MS (ESIpos): m/z = 503.3 [M + H]$^+$<br>46% yield |
| 219 | 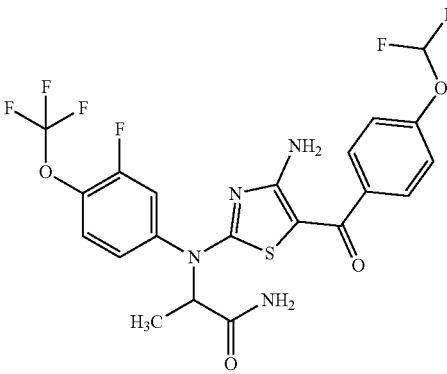<br>rac-2-[N-[4-amino-5-[4-(difluoromethoxy)benzoyl]thiazol-2-yl]-3-fluoro-4-(trifluoromethoxy)anilino]propanamide | Intermediate 161; rac-2-bromopropanamide | $^1$H NMR (400 MHz, DMSO-d$_6$) δ ppm = 7.89-8.50 (m, 2H), 7.85 (dd, J = 11.2, 2.3 Hz, 1H), 7.70-7.80 (m, 1H), 7.65 (s, 1H), 7.57-7.63 (m, 3H), 7.32 (s, 1H), 7.29 (t, J = 73.8 Hz, 1H), 7.19 (d, J = 8.6 Hz, 2H), 5.02 (q, J = 7.4 Hz, 1H), 1.20 (d, J = 7.4 Hz, 3H).<br>LC-MS (method 2) Rt = 1.26 min MS (ESIpos): m/z = 525.3 [M + H]$^+$<br>40% yield |
| 220 | 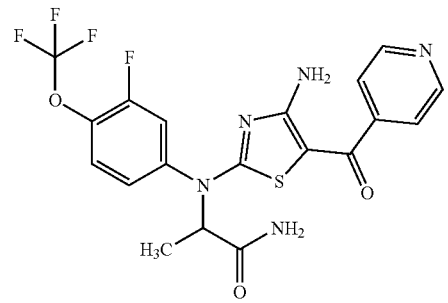 [SMILES: CC(C(N)=O)N(c1ccc(OC(F)(F)F)c(F)c1)c1nc(N)c(C(=O)c2ccncc2)s1]<br>rac-2-[N-[4-amino-5-(pyridine-4-carbonyl)thiazol-2-yl]-3-fluoro-4-(trifluoromethoxy)anilino]propanamide | Intermediate 162; rac-2-bromopropanamide | $^1$H NMR (400 MHz, DMSO-d$_6$) δ ppm = 8.61-8.66 (m, 2H), 8.05-8.54 (m, 2H), 7.85 (dd, J = 11.2, 2.3 Hz, 1H), 7.71-7.78 (m, 1H), 7.66 (s, 1H), 7.60 (dd, J = 8.7, 1.4 Hz, 1H), 7.41-7.46 (m, 2H), 7.33 (s, 1H), 4.97-5.06 (m, 1H), 1.20 (d, J = 7.4 Hz, 3H).<br>LC-MS (method 2) Rt = 1.04 min MS (ESIpos): m/z = 470.3 [M + H]$^+$<br>40% yield |

TABLE 9-continued

Example 159-256

| Example number | Chemical structure Compound name | Starting materials | Analytics/purification/yield |
|---|---|---|---|
| 221 | 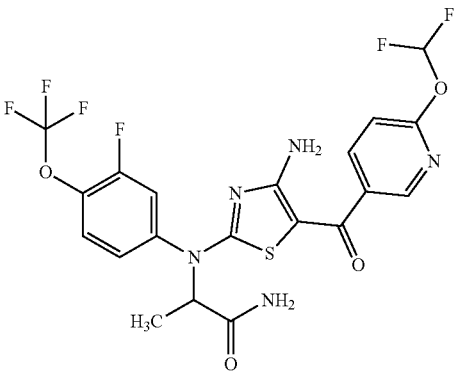 [SMILES: CC(C(N)=O)N(c1ccc(OC(F)(F)F)c(F)c1)c1nc(N)c(C(=O)c2ccc(OC(F)F)nc2)s1]<br>rac-2-[N-[4-amino-5-[6-(difluoromethoxy)pyridine-3-carbonyl]thiazol-2-yl]-3-fluoro-4-(trifluoromethoxy)anilino]propanamide | Intermediate 163; rac-2-bromopropanamide | $^1$H NMR (400 MHz, DMSO-$d_6$) δ ppm = 8.42 (d, J = 2.0 Hz, 1H), 8.23 (br s, 2H), 8.03 (dd, J = 8.5, 2.4 Hz, 1H), 7.86 (dd, J = 11.2, 2.3 Hz, 1H), 7.73-7.79 (m, 1H), 7.72 (t, J = 72.5 Hz, 1H), 7.66 (s, 1H), 7.58-7.64 (m, 1H), 7.34 (s, 1H), 7.13 (dd, J = 8.6, 0.8 Hz, 1H), 4.97-5.06 (m, 1H), 1.20 (d, J = 7.4 Hz, 3H).<br>LC-MS (method 2) Rt = 1.29 min<br>MS (ESIpos): m/z = 536.3 [M + H]$^+$<br>51% yield |
| 222 | 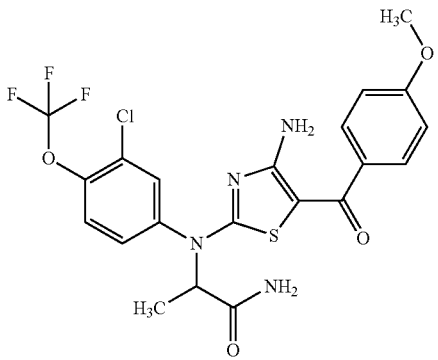 [SMILES: COc1ccc(C(=O)c2sc(N(c3ccc(OC(F)(F)F)c(Cl)c3)C(C)C(N)=O)nc2N)cc1]<br>rac-2-[N-[4-amino-5-(4-methoxybenzoyl)thiazol-2-yl]-3-chloro-4-(trifluoromethoxy)anilino]propanamide | Intermediate 164; rac-2-bromopropanamide | $^1$H NMR (400 MHz, DMSO-$d_6$) δ ppm = 7.78-8.36 (m, 2H), 7.74 (s, 2H), 7.66 (s, 1H), 7.49-7.55 (m, 2H), 7.32 (s, 1H), 6.91-6.98 (m, 2H), 5.00 (q, J = 7.0 Hz, 1H), 3.77 (s, 3H), 1.19 (d, J = 7.4 Hz, 3H).<br>LC-MS (method 2) Rt = 1.29 min<br>MS (ESIpos): m/z = 515.3 [M + H]$^+$<br>46% yield |
| 223 | 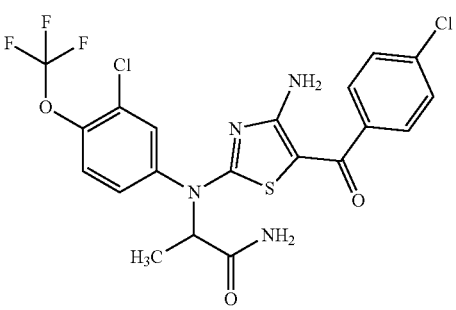 [SMILES: CC(C(N)=O)N(c1ccc(OC(F)(F)F)c(Cl)c1)c1nc(N)c(C(=O)c2ccc(Cl)cc2)s1]<br>rac-2-[N-[4-amino-5-(4-chlorobenzoyl)thiazol-2-yl]-3-chloro-4-(trifluoromethoxy)anilino]propanamide | Intermediate 165; rac-2-bromopropanamide | $^1$H NMR (400 MHz, DMSO-$d_6$) δ ppm = 8.03-8.45 (m, 2H), 8.01 (t, J = 1.4 Hz, 1H), 7.74 (s, 2H), 7.66 (s, 1H), 7.51-7.57 (m, 2H), 7.45-7.50 (m, 2H), 7.33 (s, 1H), 4.96-5.05 (m, 1H), 1.19 (d, J = 7.4 Hz, 3H).<br>LC-MS (method 2) Rt = 1.4 min<br>MS (ESIpos): m/z = 519.2 [M + H]$^+$<br>40% yield |

TABLE 9-continued

Example 159-256

| Example number | Chemical structure Compound name | Starting materials | Analytics/purification/yield |
|---|---|---|---|
| 224 | 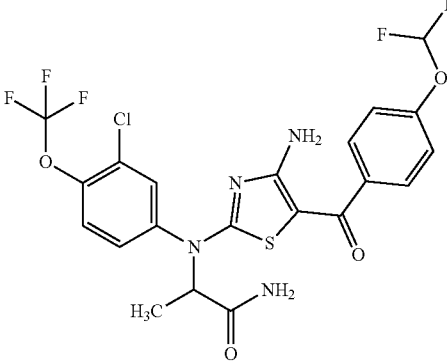<br>rac-2-[N-[4-amino-5-[4-(difluoromethoxy)benzoyl]thiazol-2-yl]-3-chloro-4-(trifluoromethoxy)anilino]propanamide | Intermediate 166; rac-2-bromopropanamide | $^1$H NMR (400 MHz, DMSO-$d_6$) δ ppm = 8.04-8.37 (m, 2H), 8.01 (t, J = 1.3 Hz, 1H), 7.74 (s, 2H), 7.66 (s, 1H), 7.57-7.62 (m, 2H), 7.33 (s, 1H), 7.29 (t, J = 73.8 Hz, 1H), 7.19 (d, J = 8.6 Hz, 2H), 5.00 (q, J = 7.0 Hz, 1H), 1.19 (d, J = 7.6 Hz, 3H).<br>LC-MS (method 2) Rt = 1.32 min<br>MS (ESIpos): m/z = 551.3 [M + H]$^+$<br>42% yield |
| 225 | 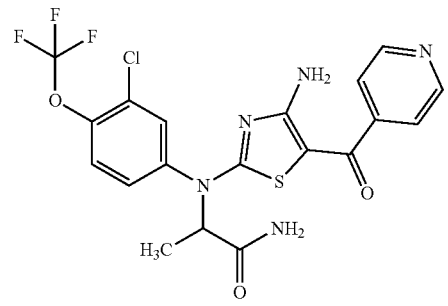 [SMILES: CC(C(N)=O)N(c1ccc(OC(F)(F)F)c(Cl)c1)c1nc(N)c(C(=O)c2ccncc2)s1]<br>rac-2-[N-[4-amino-5-(pyridine-4-carbonyl)thiazol-2-yl]-3-chloro-4-(trifluoromethoxy)anilino]propanamide | Intermediate 167; rac-2-bromopropanamide | $^1$H NMR (400 MHz, DMSO-$d_6$) δ ppm = 8.62-8.66 (m, 2H), 8.03-8.60 (m, 2H), 8.01 (t, J = 1.4 Hz, 1H), 7.74 (s, 2H), 7.67 (s, 1H), 7.41-7.46 (m, 2H), 7.34 (s, 1H), 4.95-5.04 (m, 1H), 1.19 (d, J = 7.4 Hz, 3H).<br>LC-MS (method 2) Rt = 1.09 min<br>MS (ESIpos): m/z = 486.2 [M + H]$^+$<br>42% yield |
| 226 | 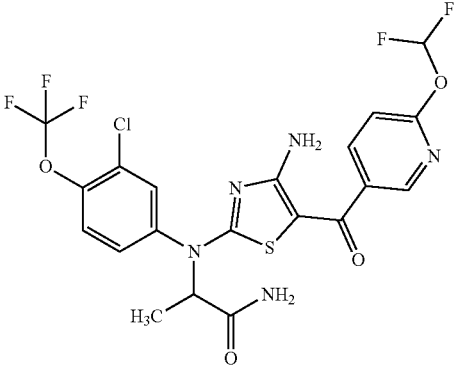 [SMILES: CC(C(N)=O)N(c1ccc(OC(F)(F)F)c(Cl)c1)c1nc(N)c(C(=O)c2ccc(OC(F)F)nc2)s1]<br>rac-2-[N-[4-amino-5-[6-(difluoromethoxy)pyridine-3-carbonyl]thiazol-2-yl]-3-chloro-4-(trifluoromethoxy)anilino]propanamide | Intermediate 168; rac-2-bromopropanamide | $^1$H NMR (400 MHz, DMSO-$d_6$) δ ppm = 8.42 (d, J = 1.8 Hz, 1H), 8.07-8.40 (m, 2H), 8.01-8.06 (m, 2H), 7.75 (s, 2H), 7.72 (t, J = 72.2 Hz, 1H), 7.67 (s, 1H), 7.34 (s, 1H), 7.13 (d, J = 9.1 Hz, 1H), 4.96-5.05 (m, 1H), 1.20 (d, J = 7.6 Hz, 3H).<br>LC-MS (method 2) Rt = 1.33 min<br>MS (ESIpos): m/z = 552.2 [M + H]$^+$<br>34% yield |

TABLE 9-continued

Example 159-256

| Example number | Chemical structure Compound name | Starting materials | Analytics/purification/yield |
|---|---|---|---|
| 227 | 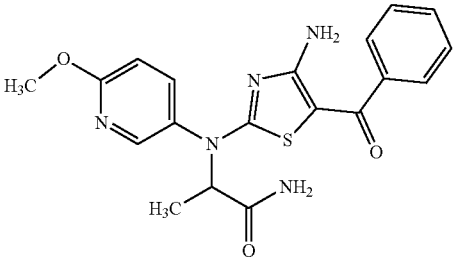 [SMILES: COc1ccc(N(c2nc(N)c(C(=O)c3ccccc3)s2)C(C)C(N)=O)cn1]<br>rac-2-[(4-amino-5-benzoyl-thiazol-2-yl)-(6-methoxy-3-pyridyl)amino]propanamide | Intermediate 169; rac-2-bromopropanamide | $^1$H NMR (400 MHz, DMSO-d$_6$) δ ppm = 8.32 (d, J = 2.5 Hz, 1H), 7.93 (dd, J = 8.9, 2.8 Hz, 3H), 7.61 (s, 1H), 7.47-7.52 (m, 2H), 7.35-7.44 (m, 3H), 7.26 (s, 1H), 6.93 (d, J = 8.9 Hz, 1H), 4.98-5.16 (m, 1H), 3.87 (s, 3H), 1.17 (d, J = 7.4 Hz, 3H).<br>LC-MS (method 2) Rt = 1.01 min<br>MS (ESIpos): m/z = 398.3 [M + H]$^+$<br>75% yield |
| 228 | 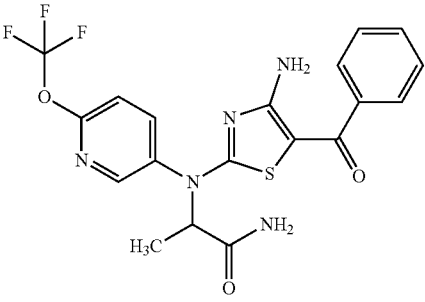 [SMILES: CC(C(N)=O)N(c1ccc(OC(F)(F)F)nc1)c1nc(N)c(C(=O)c2ccccc2)s1]<br>rac-2-[(4-amino-5-benzoyl-thiazol-2-yl)-[6-(trifluoromethoxy)-3-pyridyl]amino]propanamide | Intermediate 170; rac-2-bromopropanamide | $^1$H NMR (400 MHz, DMSO-d$_6$) δ ppm = 8.56 (d, J = 2.5 Hz, 1H), 8.30 (dd, J = 8.7, 2.7 Hz, 1H), 8.15 (br s, 2H), 7.68 (s, 1H), 7.52 (dd, J = 7.6, 1.5 Hz, 2H), 7.37-7.48 (m, 4H), 7.33 (s, 1H), 4.97-5.07 (m, 1H), 1.19 (d, J = 7.4 Hz, 3H).<br>LC-MS (method 2) Rt = 1.16 min<br>MS (ESIpos): m/z = 452.3 [M + H]$^+$<br>50% yield |
| 229 | 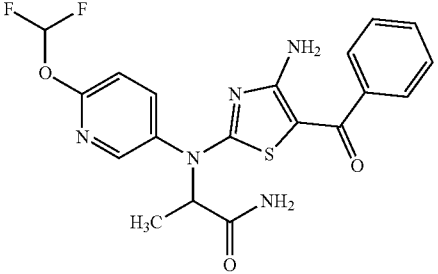 [SMILES: CC(C(N)=O)N(c1ccc(OC(F)F)nc1)c1nc(N)c(C(=O)c2ccccc2)s1]<br>rac-2-[(4-amino-5-benzoyl-thiazol-2-yl)-[6-(difluoromethoxy)-3-pyridyl]amino]propanamide | Intermediate 171; rac-2-bromopropanamide | $^1$H NMR (400 MHz, DMSO-d$_6$) δ ppm = 8.46 (d, J = 2.3 Hz, 1H), 8.18 (dd, J = 8.7, 2.7 Hz, 3H), 7.74 (t, J = 72.2 Hz, 1H), 7.66 (s, 1H), 7.47-7.53 (m, 2H), 7.36-7.46 (m, 3H), 7.31 (s, 1H), 7.23 (d, J = 8.6 Hz, 1H), 5.04 (br d, J = 5.6 Hz, 1H), 1.18 (d, J = 7.4 Hz, 3H).<br>LC-MS (method 2) Rt = 1.1 min<br>MS (ESIpos): m/z = 434.3 [M + H]$^+$<br>68% yield |
| 230 | 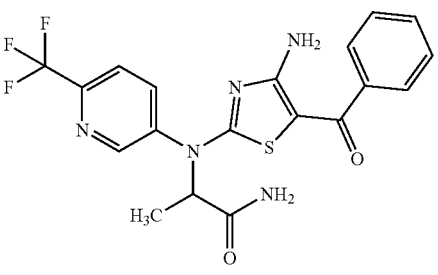 [SMILES: CC(C(N)=O)N(c1ccc(C(F)(F)F)nc1)c1nc(N)c(C(=O)c2ccccc2)s1]<br>rac-2-[(4-amino-5-benzoyl-thiazol-2-yl)-[6-(trifluoromethyl)-3-pyridyl]amino]propanamide | Intermediate 172; rac-2-bromopropanamide | $^1$H NMR (400 MHz, DMSO-d$_6$) δ ppm = 8.95 (s, 1H), 8.35-8.40 (m, 1H), 8.09 (brd, J = 8.4 Hz, 3H), 7.72 (s, 1H), 7.50-7.56 (m, 2H), 7.34-7.47 (m, 4H), 4.97-5.04 (m, 1H), 1.21 (brd, J = 7.1 Hz, 3H).<br>LC-MS (method 2) Rt = 1.1 min<br>MS (ESIpos): m/z = 436.3 [M + H]$^+$<br>20% yield |

TABLE 9-continued

Example 159-256

| Example number | Chemical structure Compound name | Starting materials | Analytics/purification/yield |
|---|---|---|---|
| 231 | 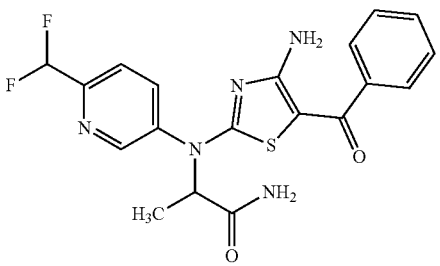 [SMILES: CC(C(N)=O)N(c1ccc(C(F)F)nc1)c1nc(N)c(C(=O)c2ccccc2)s1]<br>rac-2-[(4-amino-5-benzoyl-thiazol-2-yl)-[6-(difluoromethyl)-3-pyridyl]amino]propanamide | Intermediate 173; rac-2-bromopropanamide | $^1$H NMR (400 MHz, DMSO-d$_6$) δ ppm = 8.86 (d, J = 2.3 Hz, 1H), 7.89-8.50 (m, 3H), 7.86 (d, J = 8.4 Hz, 1H), 7.70 (s, 1H), 7.49-7.54 (m, 2H), 7.37-7.46 (m, 3H), 7.34 (s, 1H), 7.03 (t, J = 54.7 Hz, 1H), 5.03 (q, J = 7.4 Hz, 1H), 1.19 (d, J = 7.4 Hz, 3H).<br>LC-MS (method 2) Rt = 1.0 min<br>MS (ESIpos): m/z = 418.3 [M + H]$^+$<br>39% yield |
| 232 | 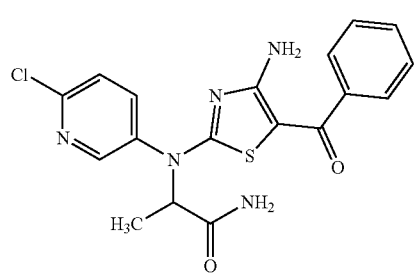 [SMILES: CC(C(N)=O)N(c1ccc(Cl)nc1)c1nc(N)c(C(=O)c2ccccc2)s1]<br>rac-2-[(4-amino-5-benzoyl-thiazol-2-yl)-(6-chloro-3-pyridyl)amino]propanamide | Intermediate 174; rac-2-bromopropanamide | $^1$H NMR (400 MHz, DMSO-d$_6$) δ ppm = 8.61 (d, J = 2.8 Hz, 1H), 8.14 (dd, J = 8.4, 2.8 Hz, 3H), 7.69 (d, J = 8.6 Hz, 2H), 7.48-7.55 (m, 2H), 7.37-7.46 (m, 3H), 7.33 (br s, 1H), 4.96-5.07 (m, 1H), 1.19 (d, J = 7.4 Hz, 3H).<br>LC-MS (method 2) Rt = 1.03 min<br>MS (ESIpos): m/z = 402.2 [M + H]$^+$<br>49% yield |
| 233 | 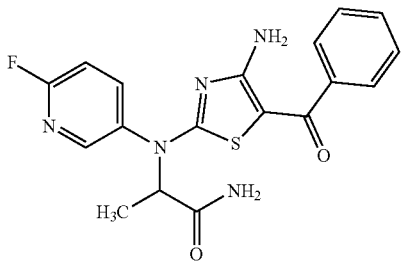<br>rac-2-[(4-amino-5-benzoyl-thiazol-2-yl)-(6-fluoro-3-pyridyl)amino]propanamide | Intermediate 175; rac-2-bromopropanamide | $^1$H NMR (400 MHz, DMSO-d$_6$) δ ppm = 8.46 (d, J = 2.3 Hz, 1H), 7.72-8.42 (m, 3H), 7.67 (s, 1H), 7.48-7.54 (m, 2H), 7.33-7.47 (m, 4H), 7.32 (s, 1H), 4.97-5.10 (m, 1H), 1.19 (d, J = 7.6 Hz, 3H).<br>LC-MS (method 2) Rt = 0.97 min<br>MS (ESIpos): m/z = 386.3 [M + H]$^+$<br>65% yield |
| 234 | 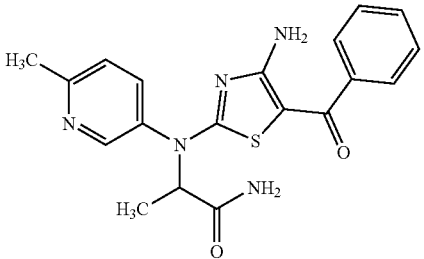<br>rac-2-[(4-amino-5-benzoyl-thiazol-2-yl)-(6-methyl-3-pyridyl)amino]propanamide | Intermediate 176; rac-2-bromopropanamide | $^1$H NMR (400 MHz, DMSO-d$_6$) δ ppm = 8.58 (d, J = 2.3 Hz, 1H), 7.90 (dd, J = 8.1, 2.5 Hz, 3H), 7.62 (s, 1H), 7.46-7.52 (m, 2H), 7.35-7.44 (m, 4H), 7.27 (s, 1H), 5.01-5.12 (m, 1H), 1.16 (d, J = 7.6 Hz, 3H).<br>LC-MS (method 2) Rt = 0.91 min<br>MS (ESIpos): m/z = 382.3 [M + H]$^+$<br>69% yield |

TABLE 9-continued

Example 159-256

| Example number | Chemical structure Compound name | Starting materials | Analytics/purification/yield |
|---|---|---|---|
| 235 | 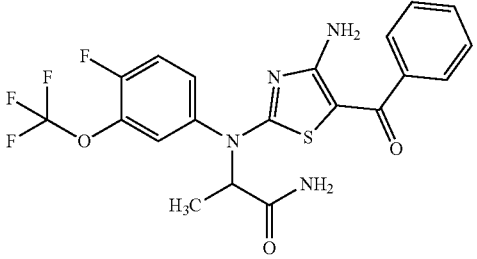 [SMILES: CC(C(N)=O)N(c1ccc(F)c(OC(F)(F)F)c1)c1nc(N)c(C(=O)c2ccccc2)s1]<br>rac-2-[N-(4-amino-5-benzoyl-thiazol-2-yl)-4-fluoro-3-(trifluoromethoxy)anilino]propanamide | Intermediate 177; rac-2-bromopropanamide | $^1$H NMR (400 MHz, DMSO-d$_6$) δ ppm = 7.78-8.47 (m, 3H), 7.73 (td, J = 4.3, 2.5 Hz, 1H), 7.62-7.70 (m, 2H), 7.47-7.54 (m, 2H), 7.35-7.46 (m, 3H), 7.30 (s, 1H), 5.02 (brd, J = 6.8 Hz, 1H), 1.17 (d, J = 7.4 Hz, 3H).<br>LC-MS (method 2) Rt = 1.26 min<br>MS (ESIpos): m/z = 469.3 [M + H]$^+$<br>52% yield |
| 236 | 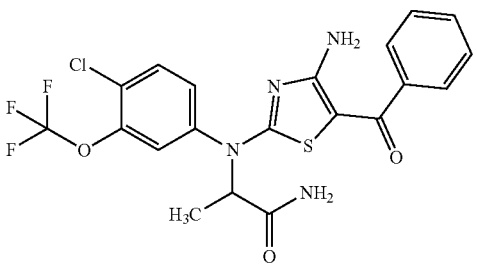 [SMILES: CC(C(N)=O)N(c1ccc(Cl)c(OC(F)(F)F)c1)c1nc(N)c(C(=O)c2ccccc2)s1]<br>rac-2-[N-(4-amino-5-benzoyl-thiazol-2-yl)-4-chloro-3-(trifluoromethoxy)anilino]propanamide | Intermediate 178; rac-2-bromopropanamide | $^1$H NMR (400 MHz, DMSO-d$_6$) δ ppm = 7.97 (dd, J = 2.0, 1.3 Hz, 3H), 7.85 (d, J = 8.6 Hz, 1H), 7.65-7.73 (m, 2H), 7.48-7.55 (m, 2H), 7.36-7.47 (m, 3H), 7.32 (s, 1H), 5.03 (q, J = 7.4 Hz, 1 H), 1.18 (d, J = 7.6 Hz, 3H).<br>LC-MS (method 2) Rt = 1.33 min<br>MS (ESIpos): m/z = 485.2 [M + H]$^+$<br>44% yield |
| 237 | 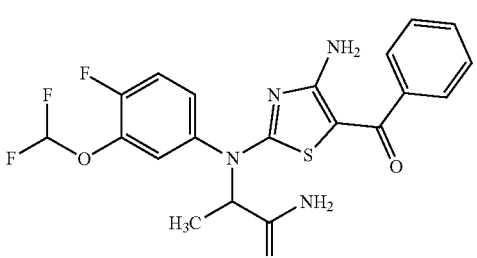<br>rac-2-[N-(4-amino-5-benzoyl-thiazol-2-yl)-3-(difluoromethoxy)-4-fluoro-anilino]propanamide | Intermediate 179; rac-2-bromopropanamide | $^1$H NMR (400 MHz, DMSO-d$_6$) δ ppm = 7.77-8.54 (m, 2H), 7.72 (d, J = 7.6 Hz, 1H), 7.62 (s, 1H), 7.48-7.58 (m, 4H), 7.36-7.44 (m, 3H), 7.27 (s, 1H), 7.26 (t, J = 72.8 Hz, 1H), 4.97-5.08 (m, 1H), 1.18 (d, J = 7.4 Hz, 3H).<br>LC-MS (method 2) Rt = 1.15 min<br>MS (ESIpos): m/z = 451.3 [M + H]$^+$<br>66% yield |
| 238 | 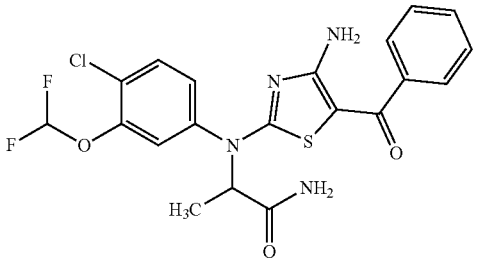 [SMILES: CC(C(N)=O)N(c1ccc(Cl)c(OC(F)F)c1)c1nc(N)c(C(=O)c2ccccc2)s1]<br>rac-2-[N-(4-amino-5-benzoyl-thiazol-2-yl)-4-chloro-3-(difluoromethoxy)anilino]propanamide | Intermediate 180; rac-2-bromopropanamide | $^1$H NMR (400 MHz, DMSO-d$_6$) δ ppm = 7.78-8.54 (m, 2H), 7.69-7.77 (m, 2H), 7.63 (s, 1H), 7.48-7.55 (m, 3H), 7.36-7.45 (m, 3H), 7.09-7.33 (m, 2H), 5.02 (q, J = 7.4 Hz, 1H), 1.19 (d, J = 7.6 Hz, 3H).<br>LC-MS (method 2) Rt = 1.22 min<br>MS (ESIpos): m/z = 467.3 [M + H]$^+$<br>51% yield |

TABLE 9-continued

Example 159-256

| Example number | Chemical structure Compound name | Starting materials | Analytics/purification/yield |
|---|---|---|---|
| 239 | 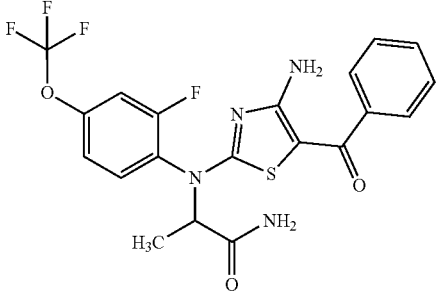 [SMILES: CC(C(N)=O)N(c1nc(N)c(C(=O)c2ccccc2)s1)c1ccc(OC(F)(F)F)cc1F]<br>rac-2-[N-(4-amino-5-benzoyl-thiazol-2-yl)-2-fluoro-4-(trifluoromethoxy)anilino]propanamide | Intermediate 181; rac-2-bromopropanamide | $^1$H NMR (400 MHz, DMSO-d$_6$) δ ppm = 8.03-8.39 (m, 2H), 7.93-8.03 (m, 1H), 7.61-7.72 (m, 2H), 7.52 (brd, J = 4.3 Hz, 2H), 7.42 (br d, J = 7.1 Hz, 4H), 7.34 (br s, 1H), 4.65-5.38 (m, 1H), 1.09-1.27 (m, 3H).<br>LC-MS (method 2) Rt = 1.19 min<br>MS (ESIpos): m/z = 469.2 [M + H]$^+$<br>50% yield |
| 240 | 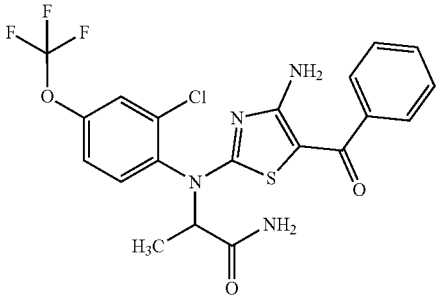<br>rac-2-[N-(4-amino-5-benzoyl-thiazol-2-yl)-2-chloro-4-(trifluoromethoxy)anilino]propanamide | Intermediate 182; rac-2-bromopropanamide | $^1$H NMR (400 MHz, DMSO-d$_6$) δ ppm = 7.88-8.43 (m, 3H), 7.64-7.87 (m, 2H), 7.60 (br d, J = 8.4 Hz, 1H), 7.27-7.56 (m, 6H), 4.93-5.30 (m, 1H), 1.09 (d, J = 7.4 Hz, 3H).<br>LC-MS (method 2) Rt = 1.24 min<br>MS (ESIpos): m/z = 485.1 [M + H]$^+$<br>41% yield |
| 241 | 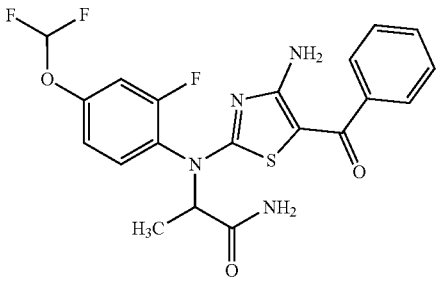<br>rac-2-[N-(4-amino-5-benzoyl-thiazol-2-yl)-4-(difluoromethoxy)-2-fluoro-anilino]propanamide | Intermediate 183; rac-2-bromopropanamide | $^1$H NMR (400 MHz, DMSO-d$_6$) δ ppm = 7.94-8.49 (m, 2H), 7.88 (br s, 1H), 7.63 (br s, 1H), 7.50 (br s, 2H), 7.39-7.45 (m, 3H), 7.38 (t, J = 73.3 Hz, 1H), 7.35 (brd, J = 2.0 Hz, 1H), 7.31 (br s, 1H), 7.18 (br d, J = 8.9 Hz, 1H), 4.82-5.40 (m, 1H), 1.15 (brd, J = 1.3 Hz, 3H).<br>LC-MS (method 2) Rt = 1.09 min<br>MS (ESIpos): m/z = 451.2 [M + H]$^+$<br>38% yield |
| 242 | 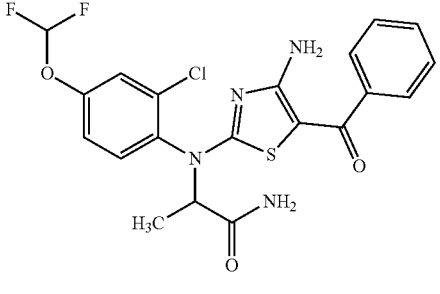 [SMILES: CC(C(N)=O)N(c1nc(N)c(C(=O)c2ccccc2)s1)c1ccc(OC(F)F)cc1Cl] | Intermediate 184; rac-2-bromopropanamide | $^1$H NMR (400 MHz, DMSO-d$_6$) δ ppm = 8.01 (d, J = 8.9 Hz, 3H), 7.60-7.72 (m, 1H), 7.20-7.59 (m, 9H), 4.97-5.21 (m, 1H), 1.09 (d, J = 7.4 Hz, 3H).<br>LC-MS (method 2) Rt = 1.13 min<br>MS (ESIpos): m/z = 467.1 [M + H]$^+$<br>44% yield |

TABLE 9-continued

Example 159-256

| Example number | Chemical structure Compound name | Starting materials | Analytics/purification/yield |
|---|---|---|---|
| | rac-2-[N-(4-amino-5-benzoyl-thiazol-2-yl)-2-chloro-4-(difluoromethoxy)anilino]propanamide | | |
| 243 | rac-2-[N-[4-amino-5-(4-methoxybenzoyl)thiazol-2-yl]-4-(difluoromethyl)anilino]propanamide | Intermediate 185; rac-2-bromopropanamide | $^1$H NMR (400 MHz, DMSO-d$_6$) δ ppm = 7.77-8.41 (m, 2H), 7.67-7.76 (m, 4H), 7.60 (s, 1H), 7.45-7.52 (m, 2H), 7.27 (s, 1H), 7.10 (t, J = 55.8 Hz, 1H), 6.90-6.95 (m, 2H), 5.08 (q, J = 7.3 Hz, 1H), 3.75 (s, 3H), 1.17 (d, J = 7.4 Hz, 3H). LC-MS (method 2) Rt = 1.05 min MS (ESIpos): m/z = 447.2 [M + H]$^+$ 54% yield |
| 244 | rac-2-[N-[4-amino-5-(4-chlorobenzoyl)thiazol-2-yl]-4-(difluoromethyl)anilino]propanamide | Intermediate 186; rac-2-bromopropanamide | $^1$H NMR (400 MHz, DMSO-d$_6$) δ ppm = 7.81-8.54 (m, 2H), 7.67-7.75 (m, 4H), 7.60 (s, 1H), 7.48-7.53 (m, 2H), 7.43-7.48 (m, 2H), 7.28 (s, 1H), 7.09 (t, J = 55.5 Hz, 1H), 5.08 (q, J = 7.3 Hz, 1H), 1.17 (d, J = 7.4 Hz, 3H). LC-MS (method 2) Rt = 1.15 min MS (ESIpos): m/z = 451.1 [M + H]$^+$ 48% yield |
| 245 | rac-2-[N-[4-amino-5-[4-(difluoromethoxy)benzoyl]thiazol-2-yl]-4-(difluoromethyl)anilino]propanamide | Intermediate 187; rac-2-bromopropanamide | $^1$H NMR (400 MHz, DMSO-d$_6$) δ ppm = 7.76-8.57 (m, 2H), 7.67-7.76 (m, 4H), 7.61 (s, 1H), 7.52-7.59 (m, 2H), 7.14-7.20 (m, 2H), 6.93-7.48 (m, 3H), 5.08 (q, J = 7.5 Hz, 1H), 1.17 (d, J = 7.4 Hz, 3H). LC-MS (method 2) Rt = 1.09 min MS (ESIpos): m/z = 483.2 [M + H]$^+$ 45% yield |

TABLE 9-continued

Example 159-256

| Example number | Chemical structure Compound name | Starting materials | Analytics/purification/yield |
|---|---|---|---|
| 246 | 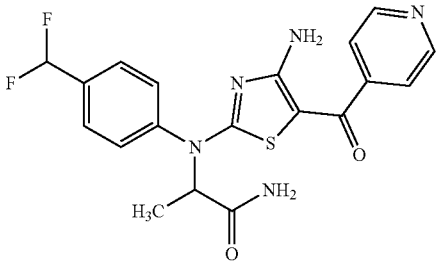 [SMILES: CC(C(N)=O)N(c1ccc(C(F)F)cc1)c1nc(N)c(C(=O)c2ccncc2)s1]<br>rac-2-[N-[4-amino-5-(pyridine-4-carbonyl)thiazol-2-yl]-4-(difluoromethyl)anilino]propanamide | Intermediate 188; rac-2-bromopropanamide | $^1$H NMR (400 MHz, DMSO-d$_6$) δ ppm = 8.59-8.64 (m, 2H), 8.06-8.55 (m, 2H), 7.67-7.76 (m, 4H), 7.62 (s, 1H), 7.37-7.43 (m, 2H), 7.29 (s, 1H), 7.09 (t, J = 55.8 Hz, 1H), 5.02-5.13 (m, 1H), 1.17 (d, J = 7.4 Hz, 3H).<br>LC-MS (method 2) Rt = 0.85 min<br>MS (ESIpos): m/z = 418.2 [M + H]$^+$<br>49% yield |
| 247 | 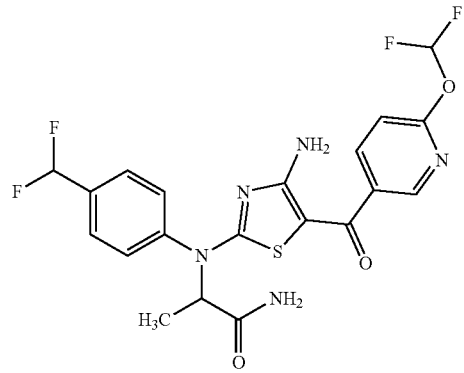 [SMILES: CC(C(N)=O)N(c1ccc(C(F)F)cc1)c1nc(N)c(C(=O)c2ccc(OC(F)F)nc2)s1]<br>rac-2-[N-[4-amino-5-[6-(difluoromethoxy)pyridine-3-carbonyl]thiazol-2-yl]-4-(difluoromethyl)anilino]propanamide | Intermediate 189; rac-2-bromopropanamide | $^1$H NMR (400 MHz, DMSO-d$_6$) δ ppm = 8.03-8.53 (m, 3H), 8.00 (dd, J = 8.5, 2.4 Hz, 1H), 7.50-7.91 (m, 6H), 7.29 (s, 1H), 6.94-7.26 (m, 2H), 5.08 (q, J = 7.1 Hz, 1H), 1.18 (d, J = 7.6 Hz, 3H).<br>LC-MS (method 2) Rt = 1.13 min<br>MS (ESIpos): m/z = 484.5 [M + H]$^+$<br>53% yield |
| 248 | 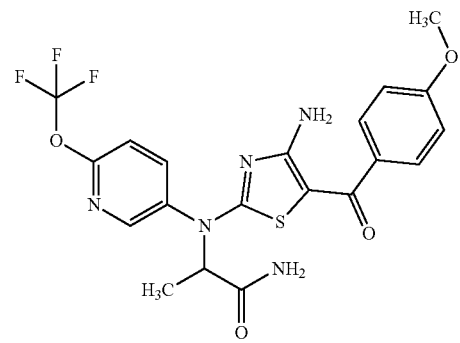 [SMILES: COc1ccc(C(=O)c2sc(N(c3ccc(OC(F)(F)F)nc3)C(C)C(N)=O)nc2N)cc1]<br>rac-2-[[4-amino-5-(4-methoxybenzoyl)thiazol-2-yl]-[6-(trifluoromethoxy)-3-pyridyl]amino]propanamide | Intermediate 190; rac-2-bromopropanamide | $^1$H NMR (400 MHz, DMSO-d$_6$) δ ppm = 8.57 (d, J = 2.5 Hz, 1H), 8.31 (dd, J = 8.6, 2.5 Hz, 1H), 7.90-8.28 (m, 2H), 7.65-7.71 (m, 1H), 7.50-7.55 (m, 2H), 7.46 (d, J = 8.6 Hz, 1H), 7.33 (s, 1H), 6.92-6.97 (m, 2H), 5.03 (q, J = 6.8 Hz, 1H), 3.77 (s, 3H), 1.20 (d, J = 7.4 Hz, 3H).<br>LC-MS (method 2) Rt = 1.14 min<br>MS (ESIpos): m/z = 482.4 [M + H]$^+$<br>47% yield |

TABLE 9-continued

Example 159-256

| Example number | Chemical structure Compound name | Starting materials | Analytics/purification/yield |
|---|---|---|---|
| 249 | rac-2-[[4-amino-5-(4-chlorobenzoyl)thiazol-2-yl]-[6-(trifluoromethoxy)-3-pyridyl]amino]propanamide | Intermediate 191; rac-2-bromopropanamide | $^1$H NMR (400 MHz, DMSO-$d_6$) δ ppm = 8.56 (d, J = 2.5 Hz, 1H), 8.30 (dd, J = 8.7, 2.7 Hz, 3H), 7.69 (s, 1H), 7.51-7.57 (m, 2H), 7.43-7.50 (m, 3H), 7.34 (s, 1H), 5.03 (brd, J = 7.1 Hz, 1H), 1.19 (d, J = 7.4 Hz, 3H). LC-MS (method 2) Rt = 1.24 min MS (ESIpos): m/z = 486.3 [M + H]$^+$ 23% yield |
| 250 | rac-2-[[4-amino-5-[4-(difluoromethoxy)benzoyl]thiazol-2-yl]-[6-(trifluoromethoxy)-3-pyridyl]amino]propanamide | Intermediate 192; rac-2-bromopropanamide | $^1$H NMR (400 MHz, DMSO-$d_6$) δ ppm = 8.57 (d, J = 2.5 Hz, 1H), 8.30 (dd, J = 8.7, 2.7 Hz, 1H), 8.11 (br s, 2H), 7.68 (s, 1H), 7.57-7.62 (m, 2H), 7.45 (d, J = 9.1 Hz, 1H), 7.34 (s, 1H), 7.29 (t, J = 73.8 Hz, 1H), 7.19 (d, J = 8.6 Hz, 2H), 5.03 (brd, J = 6.6 Hz, 1H), 1.20 (d, J = 7.4 Hz, 3H). LC-MS (method 2) Rt = 1.19 min MS (ESIpos): m/z = 518.3 [M + H]$^+$ 31% yield |
| 251 | rac-2-[[4-amino-5-[6-(difluoromethoxy)pyridine-3-carbonyl]thiazol-2-yl]-[6-(trifluoromethoxy)-3-pyridyl]amino]propanamide | Intermediate 293; rac-2-bromopropanamide | $^1$H NMR (400 MHz, DMSO-$d_6$) δ ppm = 8.57 (d, J = 2.5 Hz, 1H), 8.43 (d, J = 2.3 Hz, 1H), 8.31 (dd, J = 8.7, 2.7 Hz, 3H), 8.04 (dd, J = 8.5, 2.4 Hz, 1H), 7.72 (t, J = 72.5 Hz, 1H), 7.70 (s, 1H), 7.46 (d, J = 9.1 Hz, 1H), 7.35 (s, 1H), 7.13 (d, J = 9.1 Hz, 1H), 5.03 (brd, J = 6.8 Hz, 1H), 1.20 (d, J = 7.4 Hz, 3H). LC-MS (method 2) Rt = 1.21 min MS (ESIpos): m/z = 519.4 [M + H]$^+$ 26% yield |

TABLE 9-continued

Example 159-256

| Example number | Chemical structure Compound name | Starting materials | Analytics/purification/yield |
|---|---|---|---|
| 252 | 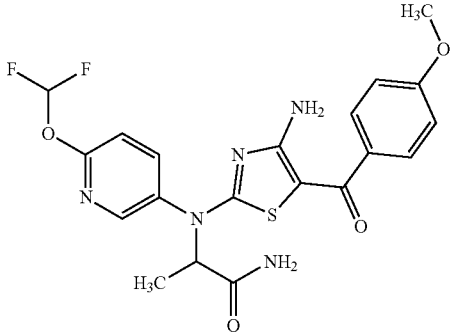 [SMILES: COc1ccc(C(=O)c2sc(N(c3ccc(OC(F)F)nc3)C(C)C(N)=O)nc2N)cc1]<br>rac-2-[[4-amino-5-(4-methoxybenzoyl)thiazol-2-yl]-[6-(difluoromethoxy)-3-pyridyl]amino]propanamide | Intermediate 194; rac-2-bromopropanamide | $^1$H NMR (400 MHz, DMSO-$d_6$) δ ppm = 8.47 (d, J = 2.5 Hz, 1H), 8.19 (dd, J = 8.6, 2.8 Hz, 3H), 7.75 (t, J = 72.2 Hz, 1H), 7.65 (s, 1H), 7.48-7.53 (m, 2H), 7.30 (s, 1H), 7.25 (d, J = 8.1 Hz, 1H), 6.92-6.96 (m, 2H), 5.05 (br d, J = 5.8 Hz, 1H), 3.76 (s, 3H), 1.19 (d, J = 7.4 Hz, 3H).<br>LC-MS (method 2) Rt = 1.09 min<br>MS (ESIpos): m/z = 464.3 [M + H]$^+$<br>65% yield |
| 253 | 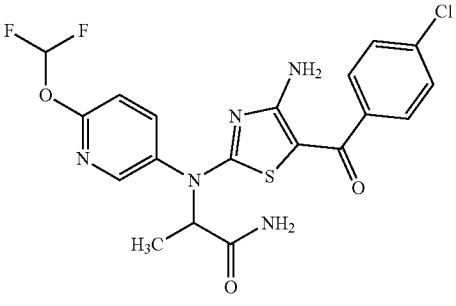 [SMILES: CC(C(N)=O)N(c1ccc(OC(F)F)nc1)c1nc(N)c(C(=O)c2ccc(Cl)cc2)s1]<br>rac-2-[[4-amino-5-(4-chlorobenzoyl)thiazol-2-yl]-[6-(difluoromethoxy)-3-pyridyl]amino]propanamide | Intermediate 195; rac-2-bromopropanamide | $^1$H NMR (400 MHz, DMSO-$d_6$) δ ppm = 8.46 (d, J = 2.3 Hz, 1H), 8.18 (dd, J = 8.7, 2.7 Hz, 3H), 7.74 (t, J = 72.5 Hz, 1H), 7.66 (s, 1H), 7.50-7.55 (m, 2H), 7.44-7.49 (m, 2H), 7.31 (s, 1H), 7.22-7.27 (m, 1H), 5.05 (br s, 1H), 1.18 (d, J = 7.4 Hz, 3H).<br>LC-MS (method 2) Rt = 1.19 min<br>MS (ESIpos): m/z = 468.3 [M + H]$^+$<br>51% yield |
| 254 | 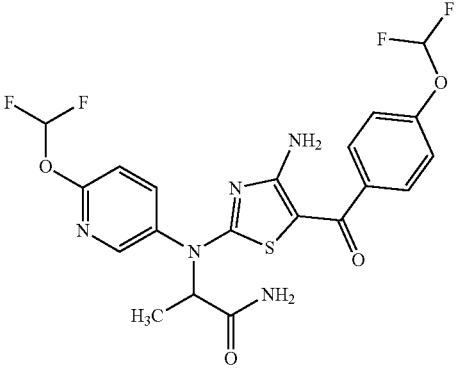 [SMILES: CC(C(N)=O)N(c1ccc(OC(F)F)nc1)c1nc(N)c(C(=O)c2ccc(OC(F)F)cc2)s1]<br>rac-2-[[4-amino-5-[4-(difluoromethoxy)benzoyl]thiazol-2-yl]-[6-(difluoromethoxy)-3-pyridyl]amino]propanamide | Intermediate 196; rac-2-bromopropanamide | $^1$H NMR (400 MHz, DMSO-$d_6$) δ ppm = 8.47 (d, J = 2.5 Hz, 1H), 8.19 (dd, J = 8.7, 2.7 Hz, 3H), 7.75 (t, J = 72.5 Hz, 1H), 7.66 (s, 1H), 7.56-7.61 (m, 2H), 7.31 (s, 1H), 7.29 (t, J = 73.8 Hz, 1H), 7.25 (d, J = 8.6 Hz, 1H), 7.18 (d, J = 8.6 Hz, 2H), 5.05 (br s, 1H), 1.19 (d, J = 7.4 Hz, 3H).<br>LC-MS (method 2) Rt = 1.14 min<br>MS (ESIpos): m/z = 500.4 [M + H]$^+$<br>44% yield |

TABLE 9-continued

Example 159-256

| Example number | Chemical structure Compound name | Starting materials | Analytics/purification/yield |
|---|---|---|---|
| 255 | 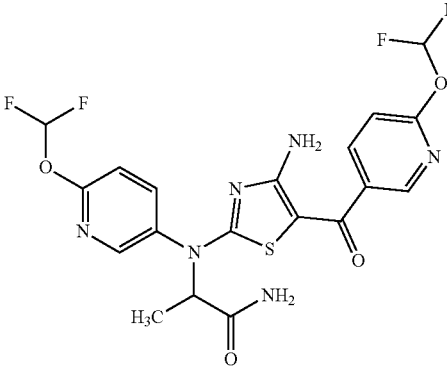<br>rac-2-[[4-amino-5-[6-(difluoromethoxy)pyridine-3-carbonyl]thiazol-2-yl]-[6-(difluoromethoxy)-3-pyridyl]amino]propanamide | Intermediate 197; rac-2-bromopropanamide | $^1$H NMR (400 MHz, DMSO-d$_6$) δ ppm = 8.47 (d, J = 2.5 Hz, 1H), 8.41 (d, J = 2.0 Hz, 1H), 8.19 (dd, J = 8.6, 2.5 Hz, 3H), 8.03 (dd, J = 8.6, 2.5 Hz, 1H), 7.75 (t, J = 72.5 Hz, 1H), 7.72 (t, J = 72.3 Hz, 1H), 7.67 (s, 1H), 7.32 (s, 1H), 7.25 (d, J = 9.1 Hz, 1H), 7.12 (d, J = 8.6 Hz, 1H), 5.06 (br s, 1H), 1.19 (d, J = 7.4 Hz, 3H).<br>LC-MS (method 2) Rt = 1.13 min<br>MS (ESIpos): m/z = 501.5 [M + H]$^+$<br>56% yield |
| 256 | 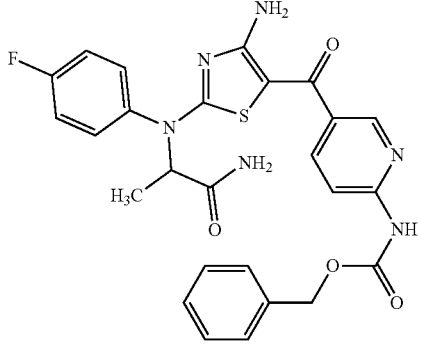 [SMILES: CC(C(N)=O)N(c1ccc(F)cc1)c1nc(N)c(C(=O)c2ccc(NC(=O)OCc3ccccc3)nc2)s1]<br>rac-benzyl N-[5-[4-amino-2-(N-(2-amino-1-methyl-2-oxo-ethyl)-4-fluoro-anilino)thiazole-5-carbonyl]-2-pyridyl]carbamate | Intermediate 217, rac-2-bromopropanamide | $^1$H NMR (400 MHz, DMSO-d$_6$) δ ppm = 1.17 (d, J = 7.35 Hz, 3 H), 5.05 (m, J = 6.34 Hz, 1 H), 5.18 (s, 2 H), 7.26 (s, 1 H), 7.29-7.44 (m, 7 H), 7.59 (s, 1 H), 7.64 (dd, J = 8.87, 5.07 Hz, 2 H), 7.80-7.85 (m, 1 H), 7.85-7.91 (m, 1 H), 7.94-8.36 (m, 2 H), 8.40 (d, J = 1.77 Hz, 1 H), 10.49 (s, 1 H)<br>RP-HPLC (method C)<br>LC-MS (method 2) Rt = 1.16 min<br>MS (ESIpos): m/z = 535.4 [M + H]$^+$<br>7% yield |

Example 257 rac-Ethyl 4-[4-amino-2-(N-(2-amino-1-methyl-2-oxo-ethyl)-4-fluoro-anilino)thiazole-5-carbonyl]benzoate

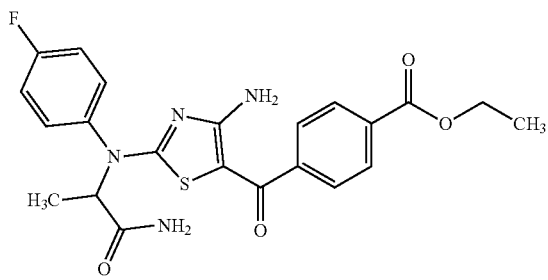 [SMILES: CCOC(=O)c1ccc(C(=O)c2sc(N(c3ccc(F)cc3)C(C)C(N)=O)nc2N)cc1]

Ethyl 4-[4-amino-2-(4-fluoroanilino)thiazole-5-carbonyl]benzoate (14.2 g, 36.9 mmol, Intermediate 210) was suspended in DMF (300 mL) and treated with rac-2-bromo propionamide (7.9 g, 52 mmol) and potassium carbonate (9 g, 65 mmol). The reaction mixture was stirred at rt overnight and then treated with water. After 30 min the reaction mixture was extracted three times with ethyl acetate. The combined organic phases were washed with brine, filtered through a water repellent filter circle (MN 617 WA) and evaporated to dryness to give 15.47 g (33 mmol, 89% yield) of the title compound.

LC-MS (method 2): Rt=1.17 min; MS(ESIpos) m/z=457.3 [M+H]$^+$

Example 258 rac-Ethyl 4-[4-amino-2-(N-(2-amino-1-methyl-2-oxo-ethyl)-4-chloro-3-fluoro-anilino)thiazole-5-carbonyl]benzoate

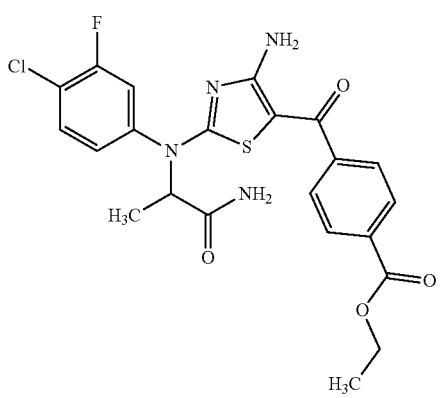 [SMILES: CCOC(=O)c1ccc(C(=O)c2sc(N(c3ccc(Cl)c(F)c3)C(C)C(N)=O)nc2N)cc1]

Ethyl 4-[4-amino-2-(4-chloro-3-fluoro-anilino)thiazole-5-carbonyl]benzoate (1.24 g, 2.52 mmol, Intermediate 212) was suspended in DMF (18 mL) and treated with rac-2-bromo propionamide (765.5 mg, 5.04 mmol) and potassium carbonate (522 mg, 3.78 mmol). The reaction mixture was stirred for 3 h and then treated with water. After 30 min the reaction mixture was extracted three times with ethyl acetate. The combined organic phases were washed with brine, filtered through a water repellent filter circle (MN 617 WA) and evaporated to dryness. The crude product was purified by Biotage (method X) to give 1.02 g (82% yield) of the title compound.

$^1$H NMR (400 MHz, DMSO-d$_6$) δ ppm=1.19 (m, J=8.0 Hz, 3H), 1.31 (t, J=7.1 Hz, 3H), 4.30 (q, J=7.10 Hz, 2H), 5.02 (m, 1H), 7.31 (s, 1H), 7.51 (dt, J=8.49, 1.20 Hz, 1H), 7.62 (m, 3H), 7.74 (m, 2H), 7.97 (m, 2H), 8.28 (m, 2H).

LC-MS (method 2): Rt=1.20 min; MS(ESIpos) m/z=491.2 [M+H]$^+$

Example 259 rac-Ethyl 2-[4-[4-amino-2-(N-(2-amino-1-methyl-2-oxo-ethyl)-4-fluoro-anilino)thiazole-5-carbonyl]phenoxy]-2-methyl-propanoate

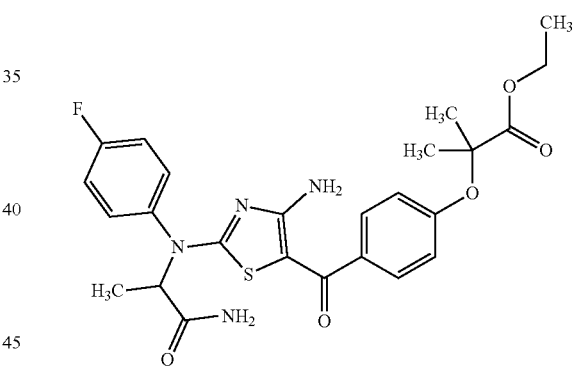

rac-Ethyl 2-[4-[4-amino-2-(4-fluoroanilino)thiazole-5-carbonyl]phenoxy]-2-methyl-propanoate (1.01 g, 2.28 mmol, Intermediate 214) was suspended in DMF (20 mL) and treated with rac-2-bromo propionamide (519 mg, 3.4 mmol) and potassium carbonate (1.57 g, 11.4 mmol). The reaction mixture was stirred overnight at rt and then treated with water. After 30 min the reaction mixture was extracted three times with ethyl acetate. The combined organic phases were washed with brine, filtered through a water repellent filter circle (MN 617 WA) and evaporated to dryness. The crude product was purified by Biotage (method X) to give 926 mg (1.79 mmol, 78% yield) of the title compound.

$^1$H NMR (400 MHz, DMSO-d$_6$) δ ppm=1.07 (t, J=7.1 Hz, 3H), 1.16 (d, J=7.35 Hz, 3H), 1.53 (s, 6H), 4.13 (q, J=7.1 Hz, 2H), 5.06 (m, 1H), 6.74 (m, 2H), 7.24 (s, 1H), 7.33 (t, J=8.74 Hz, 2H), 7.44 (m, 2H), 7.57 (s, 1H), 7.63 (m, 2H), 8.13 (m, 2H).

LC-MS (method 2): Rt=1.22 min; MS(ESIpos) m/z=515.5 [M+H]$^+$

Example 260 rac-4-[4-amino-2-(N-(2-amino-1-methyl-2-oxo-ethyl)-4-fluoro-anilino)thiazole-5-carbonyl]-N-cyclohexyl-benzamide

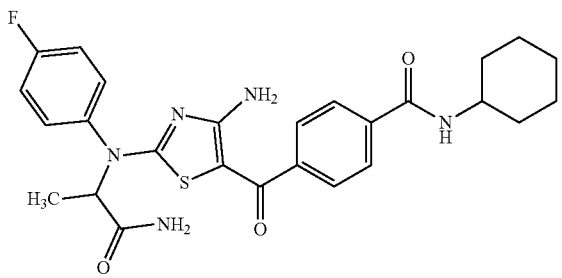 [SMILES: CC(C(N)=O)N(c1ccc(F)cc1)c1nc(N)c(C(=O)c2ccc(C(=O)NC3CCCCC3)cc2)s1]

4-[(4-amino-2-{[(2RS)-1-amino-1-oxopropan-2-yl](4-fluorophenyl)amino}-1,3-thiazol-5-yl)carbonyl]benzoic acid (Intermediate 211, 75 mg, 0.175 mmol) and cyclohexane amine (35 mg, 0.35 mmol) were solved in 1 mL DMF and treated with HATU (133 mg, 0.35 mmol), N,N-diisopropylethylamine (68 mg, 0.53 mmol) and DMAP (1 mg, 9 µM). The reaction mixture was stirred at rt overnight, filtrated and purified by RP-HPLC (method D) to yield 48 mg (0.09 mmol, 53%) of the title compound.

$^1$H NMR (400 MHz, DMSO-de) δ ppm=1.06-1.14 (m, 1H), 1.16 (d, J=7.35 Hz, 3H), 1.20-1.36 (m, 4H), 1.55-1.64 (m, 1H), 1.68-1.76 (m, 2H), 1.76-1.83 (m, 2H), 3.66-3.79 (m, 1H), 5.01-5.12 (m, 1H), 7.25 (s, 1H), 7.32 (t, J=8.74 Hz, 2H), 7.52 (d, J=8.36 Hz, 2H), 7.58 (s, 1H), 7.64 (dd, J=8.87, 5.07 Hz, 2H), 7.78 (d, J=8.36 Hz, 2H), 7.98-8.12 (br s, 1H), 8.23 (d, J=7.86 Hz, 1H), 8.20-8.50 (br s, 1H).

LC-MS (method 2): Rt=1.15 min; MS(ESIpos) m/z=510.4 [M+H]$^+$

The following examples were prepared from the starting materials stated in Table 10, below, using the procedure as for Example 260.

The crude product was either purified by RP-HPLC (methods A-D depending on polarity) or by preparative flash chromatography (methods X, Y or Z depending on polarity) after precipitation, extraction or filtration of the reaction mixture if necessary.

Enantiomers were separated from their racemate by chiral HPLC using the column and solvent conditions stated.

TABLE 10

Examples 261-273

| Example number | Chemical structure / Compound name | Starting materials | Analytics/purification/yield |
|---|---|---|---|
| 261 | rac-4-[4-amino-2-(N-(2-amino-1-methyl-2-oxo-ethyl)-4-fluoro-anilino)thiazole-5-carbonyl]-N-isopropyl-benzamide | Intermediate 211, propan-2-amine | $^1$H NMR (400 MHz, DMSO-d$_6$) δ ppm = 1.11-1.19 (m, 9H), 3.99-4.11 (m, 1H), 5.00-5.13 (m, 1H), 7.25 (s, 1H), 7.32 (t, J = 8.87 Hz, 2H), 7.53 (d, J = 8.62 Hz, 2H), 7.58 (s, 1H), 7.60-7.67 (m, 2H), 7.79 (d, J = 8.36 Hz, 2H), 7.94-8.22 (m, 1H), 8.24 (d, J = 7.86 Hz, 1H), 8.27-8.48 (m, 1H) RP-HPLC (method C basic) LC-MS (method 2) Rt = 1.00 min MS (ESIpos): m/z = 470.7 [M + H]$^+$ 73% yield |
| 262 | rac-4-[4-amino-2-(N-(2-amino-1-methyl-2-oxo-ethyl)-4-fluoro-anilino)thiazole-5-carbonyl]-N-benzyl-benzamide | Intermediate 211, 1-phenylmethan-amine | $^1$H NMR (400 MHz, DMSO-d$_6$) δ ppm = 1.16 (d, J = 7.35 Hz, 3H), 4.46 (d, J = 6.08 Hz, 2H), 5.01-5.11 (m, 1H), 7.21-7.28 (m, 2H), 7.28-7.35 (m, 6H), 7.53-7.57 (m, 2H), 7.58 (s, 1H), 7.60-7.66 (m, 2H), 7.83-7.87 (m, 2H), 8.09 (br s, 1H), 8.38 (br s, 1H), 9.07 (t, J = 5.96 Hz, 1H) RP-HPLC (method C basic) LC-MS (method 2) Rt = 1.10 min MS (ESIpos): m/z = 518.4 [M + H]$^+$ 59% yield |

TABLE 10-continued

Examples 261-273

| Example number | Chemical structure Compound name | Starting materials | Analytics/purification/yield |
|---|---|---|---|
| 263 | 4-[4-amino-2-(N-(2-amino-1-methyl-2-oxo-ethyl)-4-fluoro-anilino)thiazole-5-carbonyl]-N-[(2S)-2-hydroxypropyl]benzamide (mixture of stereoisomers) | Intermediate 211, S-1-aminopropan-2-ol | $^1$H NMR (400 MHz, DMSO-$d_6$) δ ppm = 1.04 (d, J = 6.34 Hz, 3H), 1.13-1.19 (m, 3H), 3.17 (td, J = 5.96, 1.52 Hz, 2H), 3.70-3.81 (m, 1H), 4.73 (d, J = 4.82 Hz, 1H), 5.01-5.13 (m, 1H), 7.26 (s, 1H), 7.32 (t, J = 8.74 Hz, 2H), 7.53 (d, J = 8.36 Hz, 2H), 7.58 (s, 1H), 7.61-7.66 (m, 2H), 7.81 (d, J = 8.62 Hz, 2H), 7.91-8.14 (m, 1H), 8.17-8.38 (m, 1H), 8.43 (t, J = 5.83 Hz, 1H)<br>RP-HPLC (method C basic)<br>LC-MS (method 2) Rt = 0.83 min<br>MS (ESIpos): m/z = 486.6 [M + H]$^+$<br>73% yield |
| 264 | rac-4-[4-amino-2-(N-(2-amino-1-methyl-2-oxo-ethyl)-4-fluoro-anilino)thiazole-5-carbonyl]-N-(2-methoxyethyl)benzamide | Intermediate 211, 2-methoxy-ethanamine | $^1$H NMR (400 MHz, DMSO-$d_6$) δ ppm = 1.16 (d, J = 7.35 Hz, 3H), 3.25 (s, 3H), 3.36-3.46 (m, 4H), 5.00-5.12 (m, 1H), 7.26 (s, 1H), 7.29-7.36 (m, 2H), 7.54 (d, J = 8.36 Hz, 2H), 7.58 (s, 1H), 7.63 (dd, J = 8.87, 5.07 Hz, 2H), 7.80 (d, J = 8.36 Hz, 2H), 7.90-8.16 (m, 1H), 8.17-8.47 (m, 1H), 8.55 (t, J = 5.20 Hz, 1H)<br>RP-HPLC (method C basic)<br>LC-MS (method 2) Rt = 0.90 min<br>MS (ESIpos): m/z = 486.6 [M + H]$^+$<br>68% yield |
| 265 | 4-[4-amino-2-(N-(2-amino-1-methyl-2-oxo-ethyl)-4-fluoro-anilino)thiazole-5-carbonyl]-N-[(2R)-2-hydroxypropyl]benzamide (mixture of stereoisomers) | Intermediate 211, R-1-aminopropan-2-ol | $^1$H NMR (400 MHz, DMSO-$d_6$) δ ppm = 1.04 (d, J = 6.08 Hz, 3H), 1.16 (d, J = 7.60 Hz, 3H), 3.17 (td, J = 6.02, 1.65 Hz, 2H), 3.70-3.80 (m, 1H), 4.73 (d, J = 4.82 Hz, 1H), 5.01-5.12 (m, 1H), 7.25 (s, 1H), 7.32 (t, J = 8.74 Hz, 2H), 7.51-7.57 (m, 2H), 7.58 (s, 1H), 7.60-7.67 (m, 2H), 7.81 (d, J = 8.36 Hz, 2H), 7.92-8.17 (m, 1H), 8.18-8.38 (m, 1H), 8.43 (t, J = 5.70 Hz, 1H)<br>RP-HPLC (method C basic)<br>LC-MS (method 2) Rt = 0.83 min<br>MS (ESIpos): m/z = 486.6 [M + H]$^+$<br>64% yield |
| 266 | rac-4-[4-amino-2-(N-(2-amino-1-methyl-2-oxo-ethyl)-4-fluoro-anilino)thiazole-5-carbonyl]-N-cyclopropyl-benzamide | Intermediate 211, cyclopropan-amine | $^1$H NMR (400 MHz, DMSO-$d_6$) δ ppm = 0.51-0.58 (m, 2H), 0.64-0.71 (m, 2H), 1.16 (d, J = 7.35 Hz, 3H), 2.82 (m, J = 4.06 Hz, 1H), 5.06 (m, J = 7.10 Hz, 1H), 7.25 (s, 1H), 7.32 (t, J = 8.87 Hz, 2H), 7.52 (d, J = 8.36 Hz, 2H), 7.58 (s, 1H), 7.61-7.67 (m, 2H), 7.73-7.81 (m, 2H), 7.92-8.17 (m, 1H), 8.18-8.40 (m, 1H), 8.44 (d, J = 4.31 Hz, 1H)<br>RP-HPLC (method C basic)<br>LC-MS (method 2) Rt = 0.93 min<br>MS (ESIpos): m/z = 468.5 [M + H]$^+$<br>68% yield |

TABLE 10-continued

Examples 261-273

| Example number | Chemical structure Compound name | Starting materials | Analytics/purification/yield |
|---|---|---|---|
| 267 | 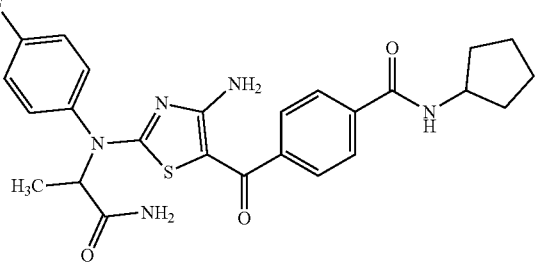<br>rac-4-[4-amino-2-(N-(2-amino-1-methyl-2-oxo-ethyl)-4-fluoro-anilino)thiazole-5-carbonyl]-N-cyclopentyl-benzamide | Intermediate 211, cyclopentan-amine | $^1$H NMR (400 MHz, DMSO-$d_6$) δ ppm = 1.16 (d, J = 7.35 Hz, 3H), 1.47-1.58 (m, 4H), 1.63-1.73 (m, 2H), 1.81-1.93 (m, 2H), 4.14-4.26 (m, 1H), 5.01-5.13 (m, 1H), 7.25 (s, 1H), 7.32 (t, J = 8.87 Hz, 2H), 7.50-7.55 (m, 2H), 7.58 (s, 1H), 7.61-7.66 (m, 2H), 7.75-7.82 (m, 2H), 7.94-8.11 (m, 1H), 8.12-8.27 (m, 1H), 8.31 (d, J = 7.35 Hz, 1H)<br>RP-HPLC (method C basic)<br>LC-MS (method 2) Rt = 1.08 min<br>MS (ESIpos): m/z = 496.4 [M + H]$^+$<br>47% yield |
| 268 | 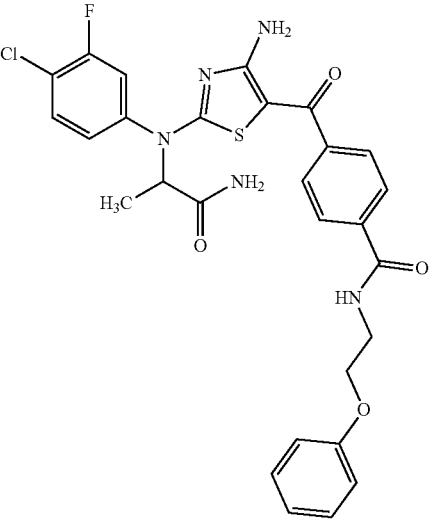 [SMILES: CC(C(N)=O)N(c1ccc(Cl)c(F)c1)c1nc(N)c(C(=O)c2ccc(C(=O)NCCOc3ccccc3)cc2)s1]<br>rac-4-[4-amino-2-(N-(2-amino-1-methyl-2-oxo-ethyl)-4-chloro-3-fluoro-anilino)thiazole-5-carbonyl]-N-(2-phenoxyethyl)benzamide | Intermediate 213, 2-phenoxy-ethanamine | $^1$H NMR (400 MHz, DMSO-$d_6$) δ ppm = 1.19 (d, J = 7.35 Hz, 3H), 3.58-3.65 (m, 2H), 4.09 (t, J = 5.83 Hz, 2H), 4.98-5.08 (m, 1H), 6.90-6.97 (m, 3H), 7.23-7.34 (m, 3H), 7.48-7.53 (m, 1H), 7.55-7.59 (m, 2H), 7.61-7.66 (m, 1H), 7.71-7.78 (m, 2H), 7.81-7.87 (m, 2H), 7.96-8.57 (m, 2H), 8.71-8.77 (m, 1H)<br>RP-HPLC (method D basic)<br>LC-MS (method 2) Rt = 1.15 min<br>MS (ESIpos): m/z = 582.2 [M + H]$^+$<br>16% yield |
| 269 | (structure shown) | Intermediate 213, 2-(trifluoro-methoxy) ethanamine hydrochloride (1:1) | $^1$H NMR (400 MHz, DMSO-$d_6$) δ ppm = 1.20 (d, J = 7.35 Hz, 3H), 3.55 (q, J = 5.35 Hz, 2H), 4.18 (dd, J = 5.35 Hz, 2H), 4.99-5.07 (m, 1H), 7.30 (s, 1H), 7.51 (dt, J = 8.62, 1.14 Hz, 1H), 7.56-7.61 (m, 2H), 7.63 (s, 1H), 7.72-7.78 (m, 2H), 7.79-7.88 (m, 2H), 8.02-8.47 (m, 2H), 8.78 (t, J = 5.58 Hz, 1H)<br>RP-HPLC (method D basic)<br>LC-MS (method 2) Rt = 1.11 min<br>MS (ESIpos): m/z = 574.1 [M + H]$^+$<br>32% yield |

TABLE 10-continued

Examples 261-273

| Example number | Chemical structure Compound name | Starting materials | Analytics/purification/yield |
|---|---|---|---|
| 270 | rac-4-[4-amino-2-(N-(2-amino-1-methyl-2-oxo-ethyl)-4-chloro-3-fluoro-anilino)thiazole-5-carbonyl]-N-[2-(trifluoromethoxy)ethyl]benzamide | Intermediate 213, 2-(difluoromethoxy)ethanamine | $^1$H NMR (400 MHz, DMSO-d$_6$) δ ppm = 1.20 (d, J = 7.35 Hz, 3H), 3.48 (q, J = 5.58 Hz, 2H), 3.91-3.96 (m, 2H), 4.98-5.09 (m, 1H), 6.68 (t, J = 76 Hz, 1H), 7.30 (s, 1H), 7.48-7.53 (m, 1H), 7.56-7.60 (m, 2H), 7.63 (s, 1H), 7.70-7.79 (m, 2H), 7.79-7.86 (m, 2H), 7.95-8.51 (m, 2H), 8.66-8.71 (m, 1H) RP-HPLC (method D basic) LC-MS (method 2) Rt = 1.02 min MS (ESIpos): m/z = 556.1 [M + H]$^+$ 18% yield |
| | rac-4-[4-amino-2-(N-(2-amino-1-methyl-2-oxo-ethyl)-4-chloro-3-fluoro-anilino)thiazole-5-carbonyl]-N-2-(difluoromethoxy)ethyl]benzamide | | |
| 271 | | Intermediate 213, 2-tert-butoxyethanamine hydrochloride (1:1) | $^1$H NMR (400 MHz, DMSO-d$_6$) δ ppm = 1.12 (s, 9H), 1.20 (d, J = 7.35 Hz, 3H), 3.27-3.33 (m, 2H), 3.37-3.43 (m, 2H), 4.98-5.07 (m, 1H), 7.30 (s, 1H), 7.47-7.54 (m, 1H), 7.54-7.59 (m, 2H), 7.63 (s, 1H), 7.71-7.78 (m, 2H), 7.79-7.84 (m, 2H), 7.97-8.45 (m, 2H), 8.52 (t, J = 5.58 Hz, 1H) RP-HPLC (method D basic) LC-MS (method 2) Rt = 1.02 min MS (ESIpos): m/z = 562.2 [M + H]$^+$ 33% yield |
| | rac-4-[4-amino-2-(N-(2-amino-1-methyl-2-oxo-ethyl)-4-chloro-3-fluoro-anilino)thiazole-5-carbonyl]-N-(2-tert-butoxyethyl)benzamide | | |

TABLE 10-continued

Examples 261-273

| Example number | Chemical structure Compound name | Starting materials | Analytics/purification/yield |
|---|---|---|---|
| 272 | 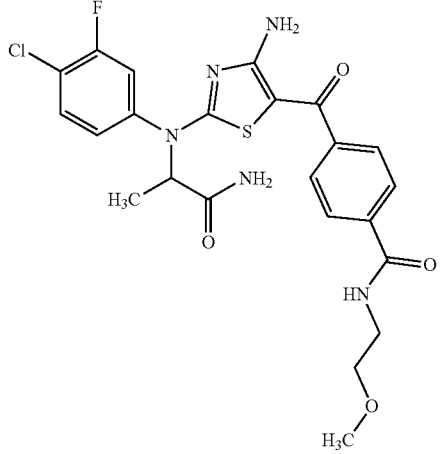 [SMILES: COCCNC(=O)c1ccc(C(=O)c2sc(N(c3ccc(Cl)c(F)c3)C(C)C(N)=O)nc2N)cc1]<br>rac-4-[4-amino-2-(N-(2-amino-1-methyl-2-oxo-ethyl)-4-chloro-3-fluoro-anilino)thiazole-5-carbonyl]-N-(2-methoxyethyl)benzamide | Intermediate 213, 2-methoxyethan-amine | $^1$H NMR (400 MHz, DMSO-$d_6$) δ ppm = 1.20 (d, J = 7.35 Hz, 3H), 3.25 (s, 3H), 3.37-3.47 (m, 4H), 4.98-5.08 (m, 1H), 7.31 (s, 1H), 7.49-7.54 (m, 1H), 7.54-7.59 (m, 2H), 7.63 (s, 1H), 7.71-7.78 (m, 2H), 7.80-7.85 (m, 2H), 7.97-8.46 (m, 2H), 8.53-8.59 (m, 1H)<br>RP-HPLC (method C basic)<br>LC-MS (method 2) Rt = 0.95 min<br>MS (ESIpos): m/z = 520.2 [M + H]$^+$<br>17% yield |
| 273 | 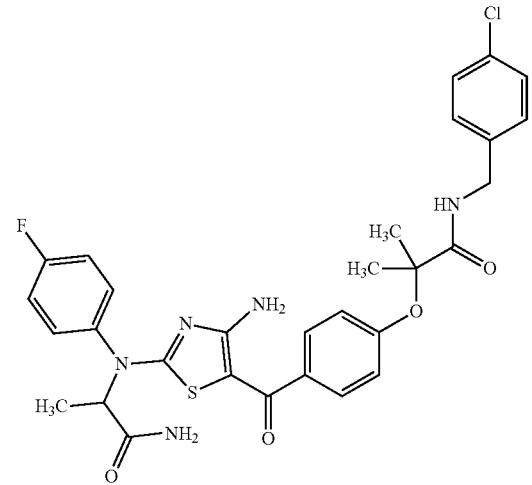 [SMILES: CC(C(N)=O)N(c1ccc(F)cc1)c1nc(N)c(C(=O)c2ccc(OC(C)(C)C(=O)NCc3ccc(Cl)cc3)cc2)s1]<br>rac-2-[4-[4-amino-2-(N-(2-amino-1-methyl-2-oxo-ethyl)-4-fluoro-anilino)thiazole-5-carbonyl]phenoxy]-N-[(4-chlorophenyl)methyl]-2-methyl-propanamide | Intermediate 215, 1-(4-chlorophenyl)methan-amine | $^1$H NMR (400 MHz, DMSO-$d_6$) δ ppm = 1.16 (d, J = 7.35 Hz, 3H), 1.45 (s, 6H), 4.23 (d, J = 6.08 Hz, 2H), 5.00-5.13 (m, 1H), 6.77-6.82 (m, 2H), 7.13-7.19 (m, 2H), 7.24 (s, 1H), 7.27-7.36 (m, 4H), 7.38-7.45 (m, 2H), 7.57 (s, 1H), 7.64 (dd, J = 8.87, 5.07 Hz, 2H), 7.80-8.57 (m, 2H), 8.68 (t, J = 6.08 Hz, 1H)<br>RP-HPLC (method C basic)<br>LC-MS (method 2) Rt = 1.23 min<br>MS (ESIpos): m/z = 610.4 [M + H]$^+$<br>77% yield |

Example 274 rac-2-(N-[4-amino-5-(6-bromopyridine-3-carbonyl)thiazol-2-yl]-4-fluoro-anilino)propanamide

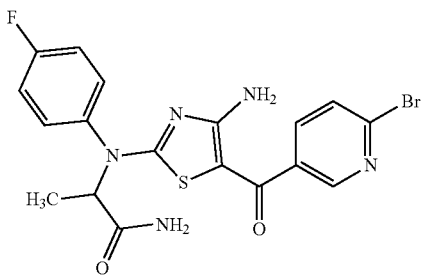 [SMILES: CC(C(N)=O)N(c1ccc(F)cc1)c1nc(N)c(C(=O)c2ccc(Br)nc2)s1]

[4-amino-2-(4-fluoroanilino)-1,3-thiazol-5-yl](6-bromopyridin-3-yl)methanone (2.52 g, 6.4 mmol, Intermediate 218) was suspended in DMF (100 mL) and treated with rac-2-bromo propionamide (1.46 g, 9.6 mmol) and potassium carbonate (4.43 g, 32 mmol). The reaction mixture was stirred overnight at rt and then treated with water. After 30 min the precipitate was filtered off, washed with water and dried in vacuo to give 2.2 g (4.4 mmol, 69% yield) of the title compound.

$^1$H NMR (400 MHz, DMSO-da) δ ppm=1.16 (d, J=7.35 Hz, 3H), 5.05 (m, 1H), 7.27 (m, 1H), 7.34 (t, J=8.87 Hz, 2H), 7.65 (m, 4H), 7.80 (dd, J=8.24, 2.41 Hz, 1H), 8.25 (m, 2H), 8.48 (d, J=2.03 Hz, 1H).

LC-MS (method 2): Rt=1.08 min; MS(ESIpos) m/z=466.1 [M+H]$^+$

Example 275 rac-2-(N-[4-amino-5-[6-[4-(trifluoromethyl)-1-piperidyl]pyridine-3-carbonyl]thiazol-2-yl]-4-fluoro-anilino)propanamide

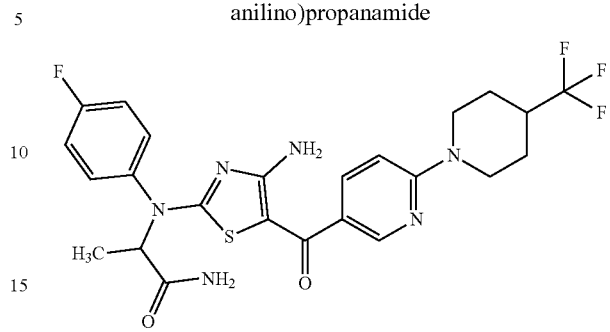

2-(N-[4-amino-5-(6-bromopyridine-3-carbonyl)thiazol-2-yl]-4-fluoro-anilino)propanamide (50 mg, 0.11 mmol, Example 274), 4-(trifluoromethyl)piperidine (25 mg, 0.16 mmol), tetrabutylammonium iodide (4 mg, 0.01 mmol) and potassium carbonate (18 mg, 0.13 mmol) were suspended in DMSO and stirred overnight at 50° C. The reaction mixture was filtrated and purified by RP-HPLC (method D) to yield 24 mg (0.04 mmol, 41%) of the title compound.

$^1$H NMR (400 MHz, DMSO-de) δ ppm=1.17 (d, J=7.35 Hz, 3H), 1.30-1.43 (m, 2H), 1.84 (br d, J=11.15 Hz, 2H), 2.56-2.65 (m, 1H), 2.87 (td, J=12.86, 2.15 Hz, 2H), 4.42-4.51 (m, 2H), 5.00-5.11 (m, 1H), 6.84 (d, J=8.87 Hz, 1H), 7.25 (s, 1H), 7.35 (t, J=8.87 Hz, 2H), 7.58 (s, 1H), 7.61-7.72 (m, 3H), 7.80-8.26 (m, 2H), 8.31 (d, J=2.28 Hz, 1H).

LC-MS (method 2): Rt=1.25 min; MS(ESIpos) m/z=537.5 [M+H]$^+$

The following examples were prepared from the starting materials stated in Table 11, below, using the procedure as for Example 275.

The crude product was either purified by RP-HPLC (methods A-D depending on polarity) or by preparative flash chromatography (methods X, Y or Z depending on polarity) after precipitation, extraction or filtration of the reaction mixture if necessary.

Enantiomers were separated from their racemate by chiral HPLC using the column and solvent conditions stated.

TABLE 11

Examples 276-285.2

| Example number | Chemical structure Compound name | Starting materials | Analytics/purification/yield |
|---|---|---|---|
| 276 | rac-2-(N-[4-amino-5-[6-(4-methyl-1-piperidyl)pyridine-3-carbonyl]thiazol-2-yl]-4-fluoro-anilino)propanamide | Example 274, 4-methylpiperidine | $^1$H NMR (400 MHz, DMSO-d$_6$) δ ppm = 0.89 (d, J = 6.08 Hz, 3H), 0.97-1.09 (m, 2H), 1.17 (d, J = 7.35 Hz, 3H), 1.57-1.68 (m, 3H), 2.76-2.87 (m, 2H), 4.32 (br d, J = 13.18 Hz, 2H), 5.01-5.10 (m, 1H), 6.78 (d, J = 8.87 Hz, 1H), 7.25 (s, 1H), 7.35 (t, J = 8.87 Hz, 2H), 7.58 (br s, 1H), 7.62-7.69 (m, 3H), 7.86-8.24 (m, 2H), 8.29 (d, J = 2.28 Hz, 1H) RP-HPLC (method D basic) LC-MS (method 2) Rt = 1.28 min MS (ESIpos): m/z = 438.3 [M + H]$^+$ 56% yield |

TABLE 11-continued

Examples 276-285.2

| Example number | Chemical structure Compound name | Starting materials | Analytics/purification/yield |
|---|---|---|---|
| 277 | rac-2-(N-[4-amino-5-[6-[4-(oxetan-3-yl)-1-piperidyl]pyridine-3-carbonyl]thiazol-2-yl]-4-fluoro-anilino)propanamide | Example 274, 4-(oxetan-3-yl)piperidine | $^1$H NMR (400 MHz, DMSO-$d_6$) δ ppm = 0.94 (br dd, J = 12.29, 3.42 Hz, 2H), 1.16 (d, J = 7.35 Hz, 3H), 1.61 (br d, J = 11.15 Hz, 2H), 1.81-1.94 (m, 1H), 2.63-2.73 (m, 1H), 2.79-2.89 (m, 2H), 4.30-4.40 (m, 4H), 4.59 (dd, J = 7.86, 6.08 Hz, 2H), 5.05 (q, J = 7.10 Hz, 1H), 6.79 (d, J = 8.87 Hz, 1H), 7.25 (s, 1H), 7.34 (t, J = 8.87 Hz, 2H), 7.58 (s, 1H), 7.60-7.70 (m, 3H), 7.80-8.23 (m, 2H), 8.29 (d, J = 2.53 Hz, 1H) RP-HPLC (method D basic) LC-MS (method 2) Rt = 1.06 min MS (ESIpos): m/z = 525.5 [M + H]$^+$ 60% yield |
| 278 | rac-2-(N-[4-amino-5-[6-(dimethylamino)pyridine-3-carbonyl]thiazol-2-yl]-4-fluoro-anilino)propanamide | Example 274, N-methylmethanamine | $^1$H NMR (500 MHz, DMSO-$d_6$) δ ppm = 1.17 (d, J = 7.25 Hz, 3H), 3.03 (s, 6H), 5.01-5.09 (m, 1H), 6.61 (d, J = 8.83 Hz, 1H), 7.25 (s, 1H), 7.35 (t, J = 8.83 Hz, 2H), 7.58 (s, 1H), 7.63-7.70 (m, 3H), 7.82-8.26 (m, 2H), 8.30 (d, J = 2.21 Hz, 1H) RP-HPLC (method D basic) LC-MS (method 2) Rt = 1.04 min MS (ESIpos): m/z = 429.5 [M + H]$^+$ 51% yield |
| 279 | rac-2-(N-[4-amino-5-[6-(4,4-dimethyl-1-piperidyl)pyridine-3-carbonyl]thiazol-2-yl]-4-fluoro-anilino)propanamide | Example 274, 4,4-dimethylpiperidine hydrochloride (1:1) | $^1$H NMR (400 MHz, DMSO-$d_6$) δ ppm = 0.95 (s, 6H), 1.17 (d, J = 7.35 Hz, 3H), 1.28-1.34 (m, 4H), 3.52-3.60 (m, 4H), 5.00-5.12 (m, 1H), 6.78 (d, J = 9.13 Hz, 1H), 7.25 (s, 1H), 7.35 (t, J = 8.87 Hz, 2H), 7.55-7.61 (m, 1H), 7.62-7.69 (m, 3H), 7.80-8.24 (m, 2H), 8.29 (d, J = 2.53 Hz, 1H) RP-HPLC (method D basic) LC-MS (method 2) Rt = 1.37 min MS (ESIpos): m/z = 497.5 [M + H]$^+$ 59% yield |
| 280 | rac-2-(N-[4-amino-5-[6-(3-azabicyclo[3.2.1]octan-3-yl)pyridine-3-carbonyl]thiazol-2-yl]-4-fluoro-anilino)propanamide | Example 274, 3-azabicyclo[3.2.1]octane hydrochloride (1:1) | $^1$H NMR (400 MHz, DMSO-$d_6$) δ ppm = 1.16 (d, J = 7.35 Hz, 3H), 1.37-1.46 (m, 2H), 1.50-1.56 (m, 2H), 1.56-1.67 (m, 2H), 2.26-2.32 (m, 2H), 2.85 (d, J = 10.39 Hz, 2H), 3.93 (br d, J = 10.65 Hz, 2H), 4.99-5.10 (m, 1H), 6.67 (d, J = 8.87 Hz, 1H), 7.25 (s, 1H), 7.34 (t, J = 8.87 Hz, 2H), 7.58 (s, 1H), 7.61-7.69 (m, 3H), 7.75-8.25 (m, 2H), 8.29 (d, J = 2.53 Hz, 1H) RP-HPLC (method D basic) LC-MS (method 2) Rt = 1.29 min MS (ESIpos): m/z = 495.3 [M + H]$^+$ 60% yield |

TABLE 11-continued

Examples 276-285.2

| Example number | Chemical structure / Compound name | Starting materials | Analytics/purification/yield |
|---|---|---|---|
| 281 | rac-2-(N-[4-amino-5-[6-(3,5-dimethyl-1-piperidyl)pyridine-3-carbonyl]thiazol-2-yl]-4-fluoro-anilino)propanamide | Example 274, 3,5-dimethylpiperidine | $^1$H NMR (400 MHz, DMSO-d$_6$) δ ppm = 0.87 (d, J = 6.59 Hz, 6H), 1.17 (d, J = 7.60 Hz, 3H), 1.44-1.57 (m, 2H), 1.75 (br d, J = 12.42 Hz, 1H), 2.25-2.34 (m, 2H), 4.34 (br d, J = 9.89 Hz, 2H), 5.01-5.12 (m, 1H), 6.80 (d, J = 8.87 Hz, 1H), 7.25 (s, 1H), 7.35 (t, J = 8.74 Hz, 2H), 7.58 (s, 1H), 7.62-7.70 (m, 3H), 7.81-8.26 (m, 2H), 8.29 (d, J = 2.53 Hz, 1H), 0.78 (q, J = 12 Hz, 1H) RP-HPLC (method D basic) LC-MS (method 2) Rt = 1.37 min MS (ESIpos): m/z = 497.3 [M + H]$^+$ 59% yield |
| 282 | rac-2-(N-[4-amino-5-[6-(3-azabicyclo[3.1.0]hexan-3-yl)pyridine-3-carbonyl]thiazol-2-yl]-4-fluoro-anilino)propanamide | Example 274, 3-azabicyclo[3.1.0]hexane hydrochloride (1:1) | $^1$H NMR (400 MHz, DMSO-d$_6$) δ ppm = 0.13 (d, J = 4.31 Hz, 1H), 0.72 (td, J = 7.67, 4.69 Hz, 1H), 1.16 (d, J = 7.35 Hz, 3H), 1.63-1.69 (m, 2H), 3.34-3.41 (m, 2H), 3.63 (br d, J = 10.39 Hz, 2H), 5.05 (br d, J = 7.35 Hz, 1H), 6.42 (d, J = 8.62 Hz, 1H), 7.25 (s, 1H), 7.34 (t, J = 8 74 Hz, 2H), 7.58 (s, 1H), 7.60-7.70 (m, 3H), 7.83-8.22 (m, 2H), 8.27 (d, J = 2.28 Hz, 1H) RP-HPLC (method D basic) LC-MS (method 2) Rt = 1.12 min MS (ESIpos): m/z = 467.3 [M + H]$^+$ 72% yield |
| 283 | rac-2-(N-[4-amino-5-[6-(1-piperidyl)pyridine-3-carbonyl]thiazol-2-yl]-4-fluoro-anilino)propanamide | Example 274, piperidine | $^1$H NMR (400 MHz, DMSO-d$_6$) δ ppm = 1.17 (d, J = 7.35 Hz, 3H), 1.45-1.55 (m, 4H), 1.56-1.64 (m, 2H), 3.53-3.59 (m, 4H), 5.00-5.10 (m, 1H), 6.78 (d, J = 9.12 Hz, 1H), 7.25 (s, 1H), 7.35 (t, J = 8.74 Hz, 2H), 7.58 (s, 1H), 7.62-7.70 (m, 3H), 7.80-8.23 (m, 2H), 8.29 (d, J = 2.28 Hz, 1H) RP-HPLC (method D basic) LC-MS (method 2) Rt = 1.22 min MS (ESIpos): m/z = 469.5 [M + H]$^+$ 100% yield |
| 284 | rac-2-(N-[4-amino-5-[6-(4,4-difluoro-1-piperidyl) pyridine-3-carbonyl]thiazol-2-yl]-4-fluoro-anilino)propanamide | Example 274, 4,4-difluoropiperidine hydrochloride (1:1) | $^1$H NMR (400 MHz, DMSO-d$_6$) δ ppm = 1.17 (d, J = 7.60 Hz, 3H), 1.90-2.03 (m, 4H), 3.69-3.76 (m, 4H), 5.00-5.11 (m, 1H), 6.93 (d, J = 9.13 Hz, 1H), 7.25 (s, 1H), 7.35 (t, J = 8.74 Hz, 2H), 7.58 (s, 1H), 7.62-7.72 (m, 3H), 7.80-8.26 (m, 2H), 8.31-8.34 (m, 1H) RP-HPLC (method D basic) LC-MS (method 2) Rt = 1.09 min MS (ESIpos): m/z = 466.2 [M + H]$^+$ 26% yield |

TABLE 11-continued

Examples 276-285.2

| Example number | Chemical structure Compound name | Starting materials | Analytics/purification/yield |
|---|---|---|---|
| 285 | rac-2-(N-[4-amino-5-[6-(4-cyano-4-methyl-1-piperidyl)pyridine-3-carbonyl]thiazol-2-yl]-4-fluoro-anilino)propanamide | Example 274, 4-methylpiper-idine-4-carbonitrile hydrochloride (1:1) | $^1$H NMR (500 MHz, DMSO-$d_6$) δ ppm = 1.17 (d, J = 7.25 Hz, 3H), 1.35 (s, 3H), 1.49 (td, J = 12.77, 4.10 Hz, 2H), 1.90 (br d, J = 13.87 Hz, 2H), 2.97-3.05 (m, 2H), 4.36 (br d, J = 13.87 Hz, 2H), 5.01-5.10 (m, 1H), 6.86 (d, J = 8.83 Hz, 1H), 7.25 (s, 1H), 7.35 (t, J = 8.83 Hz, 2H), 7.58 (s, 1H), 7.63-7.70 (m, 3H), 7.78-8.29 (m, 2H), 8.31 (d, J = 2.21 Hz, 1H) RP-HPLC (method D basic) LC-MS (method 2) Rt = 1.04 min<br><br>MS (ESIpos): m/z = 508.8 [M + H]$^+$<br>64% yield |
| 285.1 and 285.2 | (R)-2-(N-[4-amino-5-[6-(4-cyano-4-methyl-1-piperidyl)pyridine-3-carbonyl]thiazol-2-yl]-4-fluoro-anilino)propanamide and (S)-2-(N-[4-amino-5-[6-(4-cyano-4-methyl-1-piperidyl)pyridine-3-carbonyl]thiazol-2-yl]-4-fluoro-anilino)propanamide | | |
| 285.1 | 2-(N-[4-amino-5-[6-(4-cyano-4-methyl-1-piperidyl)pyridine-3-carbonyl]thiazol-2-yl]-4-fluoro-anilino)propanamide (enantiomer 1) | Example 285 | $^1$H NMR (500 MHz, DMSO-$d_6$) δ ppm = 1.17 (d, J = 7.25 Hz, 3H), 1.35 (s, 3H), 1.49 (td, J = 12.77, 4.10 Hz, 2H), 1.90 (br d, J = 13.87 Hz, 2H), 2.97-3.05 (m, 2H), 4.36 (br d, J = 13.87 Hz, 2H), 5.01-5.10 (m, 1H), 6.86 (d, J = 8.83 Hz, 1H), 7.25 (s, 1H), 7.35 (t, J = 8.83 Hz, 2H), 7.58 (s, 1H), 7.63-7.70 (m, 3H), 7.78-8.29 (m, 2H), 8.31 (d, J = 2.21 Hz, 1H) LC-MS (method 2) Rt = 1.04 min<br><br>MS (ESIpos): m/z = 508.8 [M + H]$^+$<br>39% yield |

Chiral HPLC Example 285.1
HPLC separation of rac-2-(N-[4-amino-5-[6-(4-cyano-4-methyl-1-piperidyl)pyridine-3-carbonyl]thiazol-2-yl]-4-fluoro-anilino)propanamide (98 mg, 0.19 mmol, Example 285) on a chiral column gave 38 mg (39% yield) of 2-(N-[4-amino-5-[6-(4-cyano-4-methyl-1-piperidyl)pyridine-3-carbonyl]tiazol-2-yl]-4-fluoro-anilino)propanamide, enantiomer 1.
Preparative chiral HPLC
Instrument: PrepCon Labomatic HPLC-4; Column: YMC Cellulose SC 10µ, 250 × 50; eluent A: methyl tert-butyl ether + 0.1 vol % diethylamine; eluent B: acetonitrile; isocratic: 50% A + 50% B; flow: 100 mL/min; temperature: 25° C.; UV: 254 nm
Analytical chiral HPLC: Rt = 2.37 min
Instrument: Thermo Fisher UltiMate 3000; Column: YMC Cellulose SC 3µ, 100 × 4.6; eluent A: methyl tert-butyl ether + 0.1 vol % diethylamine; eluent B: acetonitrile; isocratic: 50% A + 50% B; flow: 1.4 mL/min; temperature: 25° C.; UV: 254 nm

| | | | |
|---|---|---|---|
| 285.2 | | Example 285 | $^1$H NMR (500 MHz, DMSO-$d_6$) δ ppm = 1.17 (d, J = 7.25 Hz, 3H), 1.35 (s, 3H), 1.49 (td, J = 12.77, 4.10 Hz, 2H), 1.90 (br d, J = 13.87 Hz, 2H), 2.97-3.05 (m, 2H), 4.36 (br d, J = 13.87 Hz, 2H), 5.01-5.10 (m, 1H), 6.86 (d, J = 8.83 Hz, 1H), 7.25 (s, 1H), 7.35 (t, J = 8.83 Hz, 2H), 7.58 (s, 1H), 7.63-7.70 (m, 3H), 7.78-8.29 (m, 2H), 8.31 (d, J = 2.21 Hz, 1H) LC-MS (method 2) Rt = 1.04 min<br>MS (ESIpos): m/z = 508.8 [M + H]$^+$ |

TABLE 11-continued

Examples 276-285.2

| Example number | Chemical structure Compound name | Starting materials | Analytics/purification/yield |
|---|---|---|---|
| | 2-(N-[4-amino-5-[6-(4-cyano-4-methyl-1-piperidyl)pyridine-3-carbonyl]thiazol-2-yl]-4-fluoro-anilino)propanamide (enantiomer 2) | | 42% yield |
| | Chiral HPLC Example 285.2 HPLC separation of rac-2-(N-[4-amino-5-[6-(4-cyano-4-methyl-1-piperidyl)pyridine-3-carbonyl]thiazol-2-yl]-4-fluoro-anilino)propanamide (98 mg, 0.19 mmol, Example 285) on a chiral column gave 41 mg (42% yield) of 2-(N-[4-amino-5-[6-(4-cyano-4-methyl-1-piperidyl)pyridine-3-carbonyl]thiazol-2-yl]-4-fluoro-anilino)propanamide, enantiomer 2. Preparative chiral HPLC Instrument: PrepCon Labomatic HPLC-4; Column: YMC Cellulose SC 10µ, 250 × 50; eluent A: methyl tert-butyl ether + 0.1 vol % diethylamine; eluent B: acetonitrile; isocratic: 50% A + 50% B; flow: 100 mL/min; temperature: 25° C.; UV: 254 nm Analyticalchiral HPLC: Rt = 3.22 min Instrument: Thermo Fisher UltiMate 3000; Column: YMC Cellulose SC 3µ, 100 × 4.6; eluent A: methyl tert-butyl ether + 0.1 vol % diethylamine; eluent B: acetonitrile; isocratic: 50% A + 50% B; flow: 1.4 mL/min; temperature: 25° C.; UV: 254 nm | | |

Example 286

2-(N-[4-amino-5-(4-hydroxybenzoyl)thiazol-2-yl]-4-fluoro-anilino)propanamide (single enantiomer)

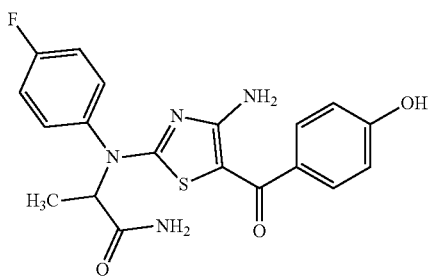 [SMILES: CC(C(N)=O)N(c1ccc(F)cc1)c1nc(N)c(C(=O)c2ccc(O)cc2)s1]

2-(N-[4-amino-5-(4-benzyloxybenzoyl)thiazol-2-yl]-4-fluoro-anilino)propanamide (enantiomer 2, example 170.2, 41 mg, 0.084 mmol) was solved in ethanol (1 mL). Under nitrogen, Pd/C (133 mg) was added and the reaction mixture was purged with $H_2$ and stirred under atmospheric $H_2$ for 5 h at rt. The mixture was filtrated via Celite and the solvent was evaporated under reduced pressure. The residue was purified by RP-HPLC (method B) to yield 22 mg (0.05 mmol, 61%) of the title compound.

$^1$H NMR (400 MHz, DMSO-$d_6$) δ ppm=1.16 (d, J=7.35 Hz, 3H), 4.99-5.10 (m, 1H), 6.70-6.75 (m, 2H), 7.24 (s, 1H), 7.30-7.40 (m, 4H), 7.57 (s, 1H), 7.61-7.66 (m, 2H), 7.84-8.32 (m, 2H), 9.90 (br s, 1H).

LC-MS (method 2): Rt=0.68 min; MS(ESIpos) m/z=401.3 [M+H]$^+$

The following examples were prepared from the starting materials stated in Table 12, below, using the procedure as for Example 286.

The crude product was either purified by RP-HPLC (methods A-D depending on polarity) or by preparative flash chromatography (methods X, Y or Z depending on polarity) after precipitation, extraction or filtration of the reaction mixture if necessary.

Enantiomers were separated from their racemate by chiral HPLC using the column and solvent conditions stated.

TABLE 12

Examples 287-291

| Example number | Chemical structure Compound name | Starting materials | Analytics/purification/yield |
|---|---|---|---|
| 287 | 2-(N-[4-amino-5-(4-hydroxybenzoyl)thiazol-2-yl]-3,4-difluoro-anilino)propanamide (enantiomer 1) | Example 165.1 | $^1$H NMR (400 MHz, DMSO-$d_6$) δ ppm = 1.18 (d, J = 7.35 Hz, 3H), 4.96-5.06 (m, 1H), 6.72 (d, J = 8.62 Hz, 2H), 7.28 (s, 1H), 7.37-7.43 (m, 2H), 7.48-7.54 (m, 1H), 7.55-7.64 (m, 2H), 7.72-7.83 (m, 1H), 7.83-8.25 (m, 2H) RP-HPLC (method B basic) LC-MS (method 2) Rt = 0.68 min MS (ESIpos): m/z = 419.3 [M + H]$^+$ 49% yield |

TABLE 12-continued

Examples 287-291

| Example number | Chemical structure Compound name | Starting materials | Analytics/purification/yield |
|---|---|---|---|
| 288 | 2-(N-[4-amino-5-(4-hydroxybenzoyl)thiazol-2-yl]-3,4-difluoro-anilino)propanamide (enantiomer 2) | Example 165.2 | $^1$H NMR (400 MHz, DMSO-d$_6$) δ ppm = 1.18 (d, J = 7.35 Hz, 3H), 4.96-5.06 (m, 1H), 6.72 (d, J = 8.62 Hz, 2H), 7.28 (s, 1H), 7.37-7.43 (m, 2H), 7.48-7.54 (m, 1H), 7.55-7.64 (m, 2H), 7.72-7.83 (m, 1H), 7.83-8.25 (m, 2H)<br>RP-HPLC (method B basic)<br>LC-MS (method 2) Rt = 0.68 min<br>MS (ESIpos): m/z = 419.3 [M + H]$^+$<br>43% yield |
| 289 | 2-(N-[4-amino-5-(4-hydroxybenzoyl)thiazol-2-yl]-4-chloro-3-fluoro-anilino)propanamide (enantiomer 1) | Example 166.1 | $^1$H NMR (400 MHz, DMSO-d$_6$) δ ppm = 1.19 (d, J = 7.35 Hz, 3H), 4.97-5.06 (m, 1H), 6.72-6.78 (m, 2H), 7.29 (s, 1H), 7.38-7.46 (m, 2H), 7.51 (dt, J = 8.49, 1.20 Hz, 1H), 7.62 (s, 1H), 7.71-7.79 (m, 2H), 7.83-8.26 (m, 2H), 9.93 (s, 1H)<br>Biotage (method X)<br>LC-MS (method 2) Rt = 0.76 min<br>MS (ESIpos): m/z = 435.2 [M + H]$^+$<br>21% yield |
| 290 | 2-(N-[4-amino-5-(4-hydroxybenzoyl)thiazol-2-yl]-4-chloro-3-fluoro-anilino)propanamide (enantiomer 2) | Example 166.2 | $^1$H NMR (400 MHz, DMSO-d$_6$) δ ppm = 1.19 (d, J = 7.35 Hz, 3H), 4.97-5.06 (m, 1H), 6.72-6.78 (m, 2H), 7.29 (s, 1H), 7.38-7.46 (m, 2H), 7.51 (dt, J = 8.49, 1.20 Hz, 1H), 7.62 (s, 1H), 7.71-7.79 (m, 2H), 7.83-8.26 (m, 2H), 9.93 (s, 1H)<br>Biotage (method X)<br>LC-MS (method 2) Rt = 0.76 min<br>MS (ESIpos): m/z = 435.2 [M + H]$^+$<br>27% yield |

TABLE 12-continued

Examples 287-291

| Example number | Chemical structure Compound name | Starting materials | Analytics/purification/yield |
|---|---|---|---|
| 291 | 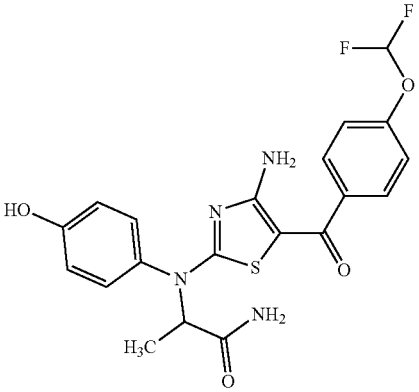 [SMILES: CC(C(N)=O)N(c1ccc(O)cc1)c1nc(N)c(C(=O)c2ccc(OC(F)F)cc2)s1]

2-(N-[4-amino-5-[4-(difluoromethoxy)benzoyl]thiazol-2-yl]-4-hydroxy-anilino)propanamide (single enantiomer) | Example 182.2 | $^1$H NMR (400 MHz, DMSO-$d_6$) δ ppm = 1.14 (d, J = 7.35 Hz, 3H), 4.96-5.13 (m, 1H), 6.80 (d, J = 8.87 Hz, 2H), 7.14-7.21 (m, 3H), 7.27 (t, J = 72 Hz, 1H), 7.32 (d, J = 8.62 Hz, 2H), 7.49 (s, 1H), 7.52-7.58 (m, 2H), 7.78-8.55 (m, 2H), 9.85 (s, 1H) RP-HPLC (method B basic) LC-MS (method 2) Rt = 0.68 min MS (ESIpos): m/z = 449.3 [M + H]$^+$ 47% yield |

Example 292 rac-2-(N-[4-amino-5-[4-(2-hydroxyethoxy)benzoyl]thiazol-2-yl]-4-fluoro-anilino)propanamide

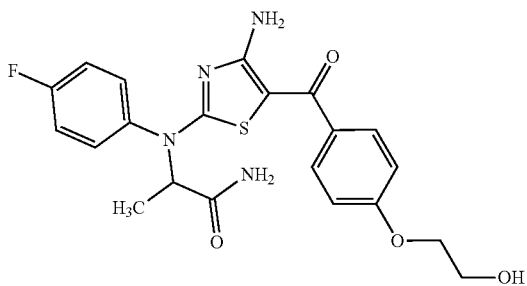 [SMILES: CC(C(N)=O)N(c1ccc(F)cc1)c1nc(N)c(C(=O)c2ccc(OCCO)cc2)s1]

[4-amino-2-(4-fluoroanilino)thiazol-5-yl]-[4-(2-hydroxyethoxy)phenyl]methanone (Intermediate 209, 74 mg, 0.2 mmol) was suspended in DMF (4 mL) and treated with rac-2-bromopropamide (30 mg, 0.2 mmol) and potassium carbonate (137 mg, 0.2 mmol). The reaction mixture was stirred at rt for 4 days. The filtrate was purified by RP-HPLC (method C, basic) to give 47 mg (53% yield) of the title compound.

$^1$H NMR (400 MHz, DMSO-$d_6$) δ ppm=1.15 (d, J=7.35 Hz, 3H) 3.64-3.71 (m, 2H) 3.98 (t, J=4.94 Hz, 2H) 4.87-4.93 (m, 1H) 5.00-5.11 (m, 1H) 6.88-6.95 (m, 2H) 7.23 (s, 1H) 7.30-7.36 (m, 2H) 7.44-7.49 (m, 2H) 7.56-7.60 (m, 1H) 7.61-7.66 (m, 2H) 7.74-8.34 (m, 2H) 9.02-9.07 (m, 1H).

LC-MS (method 1): Rt=0.84 min; MS(ESIpos) m/z=445.6 [M+H]$^+$.

EXPERIMENTAL SECTION—DETERMINATION OF ABSOLUTE STEREOCHEMISTRY BY MEANS OF X-RAY-ANALYSIS

Determination of the Absolute Configuration of Example 49.2

(R)-2-(N-[4-amino-5-[4-(difluoromethoxy)benzoyl]thiazol-2-yl]-3,4-difluoro-anilino)propanamide The crystallographic data of Example 49.2 as well as a figure depicting the thermal ellipsoids and numbering of the structure, are shown in Table 13 and FIG. 6. Colorless crystals of Example 49.2 were obtained by slow evaporation of an ethanol solution. A single crystal was mounted on a cryoloop using a protective oil. Single-crystal X-ray diffraction data were collected at 100 K on a Rigaku XtaLAB Synergy S system with a kappa goniometer and a HyPix-6000HE hybrid photon detector using Cu X-ray radiation (CuKα, =1.54178 Å). Data were integrated using the program CrysAlisPRO. SHELXM was used for structure solution and SHELXL was used for full-matrix least-squares refinement on F2. In the asymmetric unit two molecules of Example 49.2 and two water molecules are present. The di-fluorinated phenyl rings in both molecules are disordered via a 180° rotation of the ring systems. The occupancies for the alternative positions were refined to 0.25/0.75 in Molecule A and 0.35/0.65 in Molecule B, respectively. All non-hydrogen atoms were refined anisotropically. All hydrogen atoms were added in calculated positions and refined riding on their resident atoms. Hydrogens attached to the nitrogen atoms in 49.2 as well as at the water molecules were located in the difference Fourier map and placed manually. The isotropic temperature factors of the hydrogen atoms were refined as 1.2 and 1.5 times the size of the temperature factors of the corresponding heavy atoms, respectively. The absolute stereochemistry (R-configuration) could be assigned unambiguously with a Flack Parameter of 0.008(7). The program XP was used for molecular representations.

TABLE 13

Crystal data and structure refinement for Example 49.2

| | |
|---|---|
| Identification code | Example 49.2 |
| Empirical formula | C40 H36 F8 N8 O8 S2 |
| Formula weight | 972.89 |
| Temperature | 100(2) K |
| Wavelength | 1.54184 Å |
| Crystal system | Triclinic |
| Space group | P1 |
| Unit cell dimensions | a = 7.59740(10) Å   a = 78.1410(10)°. |
| | b = 9.28630(1) Å   b = 89.0340(10)°. |
| | c = 15.1835(2) Å   g = 83.8330(10)°. |
| Volume | 1042.28(2) Å$^3$ |
| Z | 1 |
| Density (calculated) | 1.550 Mg/m$^3$ |
| Absorption coefficient | 2.049 mm$^{-1}$ |
| F(000) | 500 |
| Crystal size | 0.050 × 0.040 × 0.160 mm$^3$ |
| Theta range for data collection | 2.974 to 68.246°. |
| Index ranges | −9 <= h <= 9, −11 <= k <= 11, −18 <= l <= 18 |
| Reflections collected | 74868 |
| Independent reflections | 7441 [R(int) = 0.0428] |
| Completeness to theta = 67.684° | 99.9% |
| Refinement method | Full-matrix least-squares on F$^2$ |
| Data/restraints/parameters | 7441/153/651 |
| Goodness-of-fit on F$^2$ | 1.044 |
| Final R indices (I > 2sigma(I)) | R1 = 0.0425, wR2 = 0.1062 |
| R indices (all data) | R1 = 0.0437, wR2 = 0.1072 |
| Absolute structure parameter | 0.008(7) |
| Extinction coefficient | n/a |
| Largest diff. peak and hole | 0.879 and −0.502 e.Å$^{-3}$ |

Determination of the Absolute Configuration of Example 59.1

Figure 7:
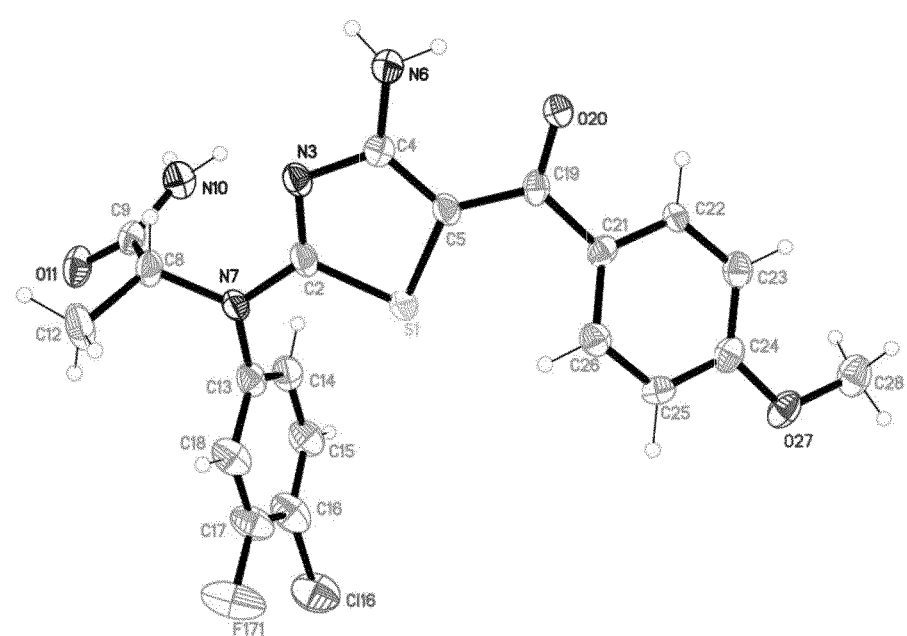
FIG. 7: 50% thermal ellipsoids of Example 59.1, Molecule 1

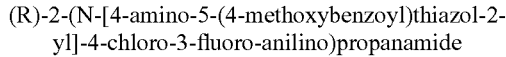
(R)-2-(N-[4-amino-5-(4-methoxybenzoyl)thiazol-2-yl]-4-chloro-3-fluoro-anilino)propanamide The crystallographic data of Example 59.1 as well as a figure depicting the thermal ellipsoids and numbering of the structure, are shown in Table 14 and FIG. 7. Colorless crystals of Example 59.1 were obtained by slow evaporation from a toluene solution. A single crystal was mounted on a cryoloop using a protective oil. Single-crystal X-ray diffraction data were collected at 100 K on a Rigaku XtaLAB Synergy S system with a kappa goniometer and a HyPix-6000HE hybrid photon detector using Cu X-ray radiation (CuKα, =1.54178 Å). Data were integrated using the program CrysAlisPRO. SHELXM was used for structure solution and SHELXL was used for full-matrix least-squares refinement on F2. In the asymmetric unit four molecules of Example 59.1 and one disordered toluene molecules are present. The fluorinated phenyl ring systems in three of the four molecules are disordered via a 180° rotation of the ring systems. The occupancies for the alternative positions were refined to 0.30/0.70 in Molecule B, 0.20/0.80 in Molecule C and 0.15/0.85 in Molecule D, respectively. The toluene solvent molecule is disordered over a pseudo 2-fold axis and the occupancies for both alternative positions refined with a ratio of 0.45/0.55. All non-hydrogen atoms were refined anisotropically. Hydrogen atoms were added in calculated positions and refined riding on their resident atoms. Hydrogens attached to amine and amide nitrogen atoms were either located in the difference Fourier map and placed manually or were refined using the riding model. The isotropic temperature factors of the hydrogen atoms were refined as 1.2 and 1.5 times the size of the temperature factors of the corresponding heavy atoms, respectively. The absolute stereochemistry (R-configuration) could be assigned unambiguously with a Flack Parameter of 0.015 (11). The program XP was used for molecular representations.

TABLE 14

Crystal data and structure refinement for Example 59.1

| | |
|---|---|
| Identification code | 59.1 |
| Empirical formula | C20 H18 N4 O3 F Cl S + 0.25 (C7 H8) |
| Formula weight | 448.9 + 23.0 |
| Temperature | 100(2) K |
| Wavelength | 1.54178 Å |
| Crystal system | Triclinic |
| Space group | P1 |
| Unit cell dimensions | a = 8.9781(2) Å   a = 103.099(2)°. |
| | b = 13.3867(3) Å   b = 92.827(2)°. |
| | c = 18.9350(3) Å   g = 101.417(2)°. |
| Volume | 2162.07(8) Å$^3$ |
| Z | 4 |
| Density (calculated) | 1.450 Mg/m$^3$ |
| Absorption coefficient | 2.827 mm$^{-1}$ |
| F(000) | 978 |
| Crystal size | 0.070 × 0.060 × 0.005 mm$^3$ |
| Theta range for data collection | 2.407 to 68.401°. |
| Index ranges | −10 <= h <= 10, −16 <= k <= 16, −22 <= l <= 22 |
| Reflections collected | 76934 |
| Independent reflections | 15381 [R(int) = 0.0650] |
| Completeness to theta = 67.679° | 100.0% |
| Refinement method | Full-matrix least-squares on F$^2$ |
| Data/restraints/parameters | 15381/1400/1272 |
| Goodness-of-fit on F$^2$ | 1.003 |
| Final R indices (I > 2sigma(I)) | R1 = 0.0496, wR2 = 0.1120 |
| R indices (all data) | R1 = 0.0605, wR2 = 0.1185 |
| Absolute structure parameter | 0.015(11) |
| Extinction coefficient | n/a |
| Largest diff. peak and hole | 0.462 and −0.430 e.Å$^{-3}$ |

Determination of the Absolute Configuration of Example 61.2

Figure 8:
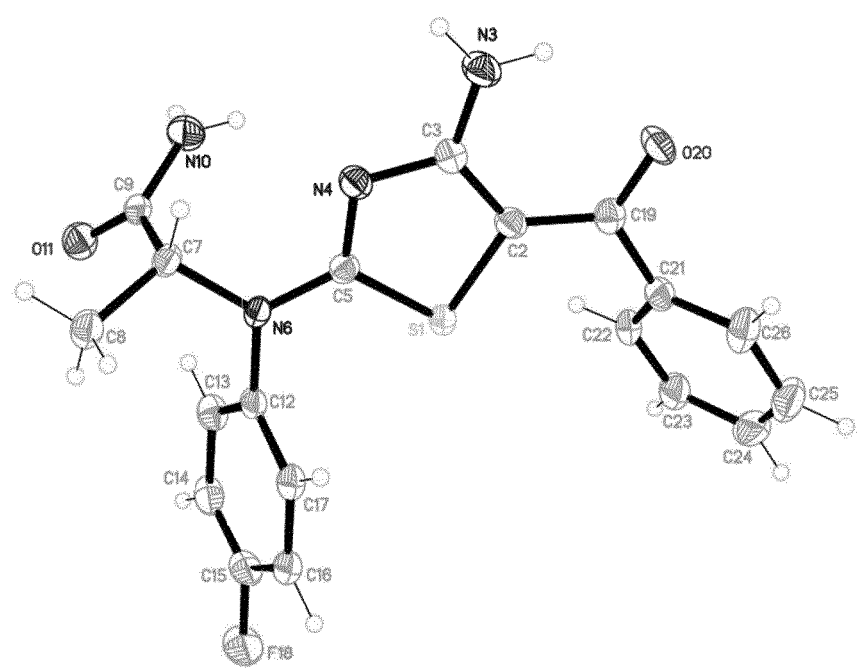
FIG. 8: 50% thermal ellipsoids of Example 61.2, Molecule 1

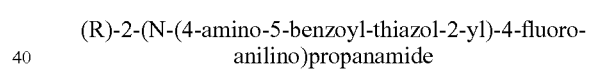
(R)-2-(N-(4-amino-5-benzoyl-thiazol-2-yl)-4-fluoro-anilino)propanamide The crystallographic data of Example 61.2 as well as a figure depicting the thermal ellipsoids and numbering of the structure, are shown in Table 15 and FIG. 8. Colorless crystals of Example 61.2 were obtained by slow evaporation from an acetonitrile solution. A single crystal was mounted on a cryoloop using a protective oil. Single-crystal X-ray diffraction data were collected at 100 K on a Rigaku XtaLAB Synergy S system with a kappa goniometer and a HyPix-6000HE hybrid photon detector using Cu X-ray radiation (CuKα, =1.54178 Å). Data were integrated using the program CrysAlisPRO. SHELXM was used for structure solution and SHELXL was used for full-matrix least-squares refinement on F2. In the asymmetric unit eight molecules of Example 61.2 and two water molecules are present. All non-hydrogen atoms were refined anisotropically. All hydrogen atoms were added in calculated positions and refined riding on their resident atoms. Hydrogens attached to amine and amide nitrogen atoms were either located in the difference Fourier map and placed manually or were refined using the riding model. The isotropic temperature factors of the hydrogen atoms were refined as 1.2 and 1.5 times the size of the temperature factors of the corresponding heavy atoms, respectively. The absolute stereochemistry (R-configuration) could be assigned unambiguously with a Flack Parameter of 0.027(11). The program XP was used for molecular representations.

TABLE 15

Crystal data and structure refinement for Example 61.2

| | |
|---|---|
| Identification code | Example 61.2 |
| Empirical formula | C19 H20 F N4 O2 S + 0.1875 H2 O |
| Formula weight | 390.45 |
| Temperature | 100(2) K |
| Wavelength | 1.54178 Å |
| Crystal system | Tetragonal |
| Space group | P4(1) |
| Unit cell dimensions | a = 17.135 Å    a = 90°. |
| | b = 17.135 Å    b = 90°. |
| | c = 49.3911(2) Å  g = 90°. |
| Volume | 14502.48(6) Å$^3$ |
| Z | 32 |
| Density (calculated) | 1.431 Mg/m$^3$ |
| Absorption coefficient | 1.886 mm$^{-1}$ |
| F(000) | 6544 |
| Crystal size | 0.3 × 0.2 × 0.1 mm$^3$ |
| Theta range for data collection | 2.58 to 77.25°. |
| Index ranges | −14 <= h <= 15, 0 <= k <= 21, −59 <= l <= 61 |
| Reflections collected | 178451 |
| Independent reflections | 26790 [R(int) = 0.0513] |
| Completeness to theta = 77.25° | 91.2% |
| Refinement method | Full-matrix least-squares on F$^2$ |
| Data/restraints/parameters | 26790/1889/2043 |
| Goodness-of-fit on F$^2$ | 1.315 |
| Final R indices (I > 2sigma(I)] | R1 = 0.0508, wR2 = 0.1276 |
| R indices (all data) | R1 = 0.0538, wR2 = 0.1292 |
| Absolute structure parameter | 0.027(11) |
| Largest diff. peak and hole | 0.475 and −0.425 e.Å$^{-3}$ |

Determination of the Absolute Configuration of Example 62.2

Figure 9:
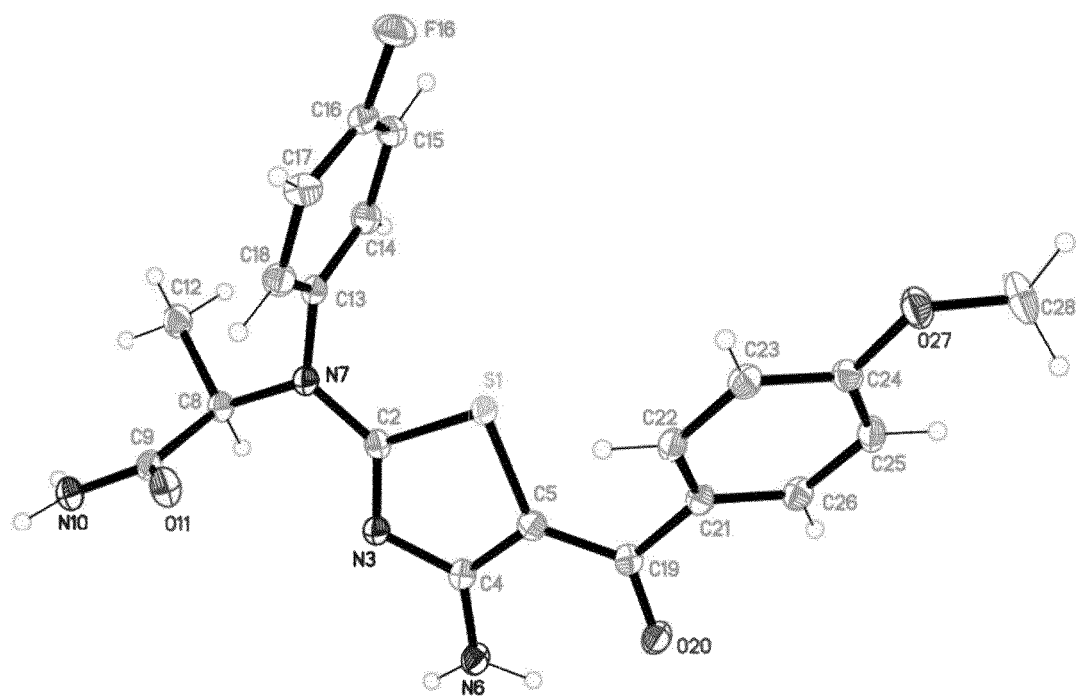
FIG. 9: 50% thermal ellipsoids of Example 62.2, Molecule 1

(R)-2-(N-[4-amino-5-(4-methoxybenzoyl)thiazol-2-yl]-4-fluoro-anilino)propanamide The crystallographic data of Example 62.2 as well as a figure depicting the thermal ellipsoids and numbering of the structure, are shown in Table 16 and FIG. 9. Colorless crystals of Example 62.2 were already present in the purified sample. A single crystal was mounted on a cryoloop using a protective oil. Single-crystal X-ray diffraction data were collected at 100 K on a Rigaku XtaLAB Synergy S system with a kappa goniometer and a HyPix-6000HE hybrid photon detector using Cu X-ray radiation (CuKα, =1.54178 Å). Data were integrated using the program CrysAlisPRO. SHELXM was used for structure solution and SHELXL was used for full-matrix least-squares refinement on F2. In the asymmetric unit two molecules of Example 62.2 are present. All non-hydrogen atoms were refined anisotropically. All hydrogen atoms were added in calculated positions and refined riding on their resident atoms. Hydrogens attached to the nitrogen atoms were located in the difference Fourier map and placed manually. The isotropic temperature factors of the hydrogen atoms were refined as 1.2 and 1.5 times the size of the temperature factors of the corresponding heavy atoms, respectively. The absolute stereochemistry (R-configuration) could be assigned unambiguously with a Flack Parameter of 0.004(3). The program XP was used for molecular representations.

TABLE 16

Crystal data and structure refinement for Example 62.2

| | |
|---|---|
| Identification code | Example 62.2 |
| Empirical formula | C40 H38 F2 N8 O6 S2 |
| Formula weight | 828.90 |
| Temperature | 100(2) K |
| Wavelength | 1.54184 Å |
| Crystal system | Monoclinic |
| Space group | I2 |
| Unit cell dimensions | a = 14.128 Å    a = 90°. |
| | b = 13.01730(10) Å  b = 92.60°. |
| | c = 21.74910(10) Å  g = 90°. |
| Volume | 3995.63(4) Å$^3$ |
| Z | 4 |
| Density (calculated) | 1.378 Mg/m$^3$ |
| Absorption coefficient | 1.778 mm$^{-1}$ |
| F(000) | 1728 |
| Crystal size | 0.100 × 0.070 × 0.020 mm$^3$ |
| Theta range for data collection | 3.656 to 77.353°. |
| Index ranges | −17 <= h <= 17, −16 <= k <= 15, −27 <= l <= 27 |
| Reflections collected | 75900 |
| Independent reflections | 8071 [R(int) = 0.0302] |
| Completeness to theta = 67.684° | 100.0% |
| Refinement method | Full-matrix least-squares on F$^2$ |
| Data/restraints/parameters | 8071/1/551 |
| Goodness-of-fit on F$^2$ | 1.065 |
| Final R indices [I > 2sigma(I)] | R1 = 0.0226, wR2 = 0.0591 |
| R indices (all data) | R1 = 0.0227, wR2 = 0.0592 |
| Absolute structure parameter | −0.004(3) |
| Extinction coefficient | n/a |
| Largest diff. peak and hole | 0.151 and −0.239 e.Å$^{-3}$ |

EXPERIMENTAL SECTION—BIOLOGICAL ASSAYS AND BIOLOGICAL DATA

Table 17, below, lists the abbreviations used in this paragraph and in the Assays section as far as they are not explained within the text body. Other abbreviations have their meanings customary per se to the skilled person.

TABLE 17

Abbreviations

| | |
|---|---|
| nL | nanoliter |
| μL | microliter |
| mL | milliliter |
| nM | nanomolar |
| μM | micromolar |
| mM | millimolar |
| min | minute(s) |
| s | second(s) |
| kDa | kilodalton |
| MW | molecular weight |
| cAMP | cyclic adenosine monophosphat |
| ADP | adenosine diphosphate |
| ATP | adenosine triphosphate |
| FCS | fetal calf serum |
| FBS | fetal bovine serum |
| PBS | phosphate buffered saline |
| RPMI | Roswell Park Memorial Institute |
| ACK lysing buffer | ammonium-chloride-potassium lysis buffer |
| DMEM | Dulbecco's Modified Eagle's Medium |
| HEPES | 2-[4-(2-hydroxyethyl)piperazin-1-yl]ethanesulfonic acid |
| MOPS | 3-(N-morpholino)propanesulfonic acid |
| Pen/Strep | penicillin and streptomycin |
| HBS-P+ | buffer containing 0.1M HEPES, 1.5M NaCl and 0.5% v/v Surfactant P20 |
| DTT | DL-Dithiothreitol |
| BGG | bovine gamma globulin |
| PBMC | peripheral blood mononuclear cells |
| APC | antigen presenting cells |
| CD | cluster of differentiation |
| IgG | immunoglobulin G |
| OKT3 | CD3 monoclonal antibody |
| FLAG-Tag | amino acid sequence DYKDDDDK |
| DNA | deoxyribonucleic acid |
| CFSE | carboxyfluorescein succinimidyl ester |

TABLE 17-continued

Abbreviations

| | |
|---|---|
| OVA | ovalbumin antigen |
| FACS | fluorescence-activated cell sorting |
| s.c. | subcutaneous |
| i.v. | intravenous |
| i.p. | intraperitoneal |
| n.d. | not determined |

Examples were tested in selected biological assays one or more times. When tested more than once, data are reported as either average values or as median values, wherein
the average value, also referred to as the arithmetic mean value, represents the sum of the values obtained divided by the number of times tested, and
the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

Human DGKζ Kinase Activity Inhibition Assay.

Human diacylglycerol kinase zeta (DGKζ) inhibitory activity of compounds of the present invention was quantified employing the human DGKζ kinase activity assay as described in the following paragraphs. In essence, the enzyme activity was measured by quantification of the adenosine-di-phosphate (ADP) generated as a co-product of the enzyme reaction via the "ADP-Glo™ Kinase Assay" kit from the company Promega. This detection system works as follows: In a first step the adenosine-tri-phosphate (ATP) not consumed in the kinase reaction is quantitatively converted to cyclic adenosine-mono-phosphate (cAMP) employing an adenylate cyclase ("ADP-Glo-reagent"), then the adenylate cyclase is stopped and the ADP generated in the kinase reaction is converted to ATP, which subsequently generates in a luciferase-based reaction a glow-luminescence signal ("Kinase Detection Reagent").

C-terminally FLAG-tagged, recombinant full-length human DGKζ (in house expressed in baculovirus infected insect cells, purified using anti-Flag pulldown and size exclusion chromatography) was used as enzyme. As an alternative, commercially available enzyme by Carnabio can be used. As substrate for the kinase, 1,2-dioleoyl-sn-glycerol, reconstituted in octyl-β-D-glucopyranoside micelles, was used. For the preparation of the micelles, 1 volume of a 16.1 mM solution of 1,2-dioleoyl-sn-glycerol (Avanti, Cat. #O8001-25G) in chloroform was slowly evaporated using a nitrogen stream. Subsequently, 22.55 volumes of a 510 mM solution of octyl-β-D-glucopyranoside (Sigma-Aldrich, Cat. #O8001-10G) in 50 mM MOPS buffer (pH 7.4) were added, and the mixture was sonicated in an ultrasonic bath for 20 s. Then 35 volumes of 50 mM MOPS buffer (pH 7.4) were added to yield a solution of 0.28 mM 1,2 dioleoyl-sn-glycerol and 200 mM octyl-β-D-glucopyranoside, which was aliquoted, flash-frozen in liquid nitrogen, and stored at −20° C. until use. For each experiment, a fresh aliquot was quickly thawed and diluted 24-fold with aqueous assay buffer (described below) containing 95.7 µM adenosine triphosphate (Promega) to yield a 1.67-fold concentrated substrate solution.

For the assay 50 nl of a 100-fold concentrated solution of the test compound in dimethyl sulfoxide (DMSO, Sigma) was pipetted into either a white 1536-well or a white low-volume 384-well microtiter plate (both Greiner Bio-One, Frickenhausen, Germany). Subsequently, 2 µl of a solution of human DGKζ in aqueous assay buffer [50 mM (3-(N-morpholino)propanesulfonic acid (MOPS, pH 7.4, Sigma-Aldrich), 1 mM dithiothreitol (DTT, Sigma-Aldrich), 100 mM NaCl (Sigma-Aldrich), 10 mM MgCl$_2$ (Sigma-Aldrich), 0.1% (w/v) bovine gamma globulin (BGG, Sigma-Aldrich), 1 µM CaCl$_2$ (Sigma-Aldrich)] were added to the wells, and the mixture was incubated for 15 min at 22° C. to allow pre-binding of the test compounds to the enzyme. The reaction was initiated by the addition of 3 µL of substrate solution [preparation described above; 11.7 µM 1,2-dioleoyl-sn-glycerol (=>final conc. in the 5 µL assay volume is 7 µM), 8.33 mM octyl-β-D-glucopyranoside (=>final conc. in 5 µL assay volume is 5 mM), and 91.67 µM adenosine triphosphate (=>final conc. in 5 µL assay volume is 55 µM) in assay buffer] and the resulting mixture was incubated for a reaction time of 20 min at 22° C. The concentration of DGKζ was adjusted depending of the activity of the enzyme lot and was chosen appropriate to have the assay in the linear range, a typical concentration is about 0.1 nM. The reaction was stopped by the addition of 2.5 µL of "ADP-Glo-reagent" (1 to 1.5 diluted with water) and the resulting mixture was incubated at 22° C. for 1 h to convert the ATP not consumed in the kinase reaction completely to cAMP. Subsequently 2.5 µl of the "kinase detection reagent" (1.2 fold more concentrated than recommended by the producer) were added, the resulting mixture was incubated at 22° C. for 1 h and then the luminescence measured with a suitable measurement instrument (e.g. Viewlux™ from Perkin-Elmer). The amount of emitted light was taken as a measure for the amount of ADP generated and thereby for the activity of the DGKζ.

The data were normalised (enzyme reaction without inhibitor=0% inhibition, all other assay components but no enzyme=100% inhibition). Usually the test compounds were tested on the same microtiterplate in 11 different concentrations in the range of 20 µM to 0.07 nM (20 µM, 5.7 µM, 1.6 µM, 0.47 µM, 0.13 µM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and IC$_{50}$ values were calculated using Genedata Screener™ software.

TABLE 18

IC$_{50}$ values of examples in in vitro human DGKζ kinase activity inhibition assays.

| Example number | IC$_{50}$ [nM] |
|---|---|
| 1 | 946 |
| 2 | 935 |
| 3 | 927 |
| 4 | 833 |
| 5 | 757 |
| 6 | 740 |
| 7 | 705 |
| 8 | 618 |
| 9 | 536 |
| 10 | 425 |

TABLE 18-continued

IC$_{50}$ values of examples in in vitro human DGKζ kinase activity inhibition assays.

| Example number | IC$_{50}$ [nM] |
|---|---|
| 11 | 406 |
| 12 | 364 |
| 13 | 357 |
| 14 | 334 |
| 15 | 266 |
| 16 | 283 |
| 17 | 261 |
| 18 | 207 |
| 19 | 200 |
| 20 | 161 |
| 21 | 142 |
| 21.1 | 5510 |
| 21.2 | 51 |
| 22 | 130 |
| 23 | 130 |
| 24 | 115 |
| 25 | 101 |
| 26 | 74.8 |
| 27 | 69.6 |
| 27.1 | 8650 |
| 27.2 | 43.6 |
| 28 | 61 |
| 29 | 58.4 |
| 29.1 | 12500 |
| 29.2 | 46.2 |
| 30 | 57.5 |
| 31 | 43.5 |
| 32 | 38.7 |
| 33 | 42.8 |
| 33.1 | 8610 |
| 33.2 | 22.8 |
| 34 | 34.4 |
| 35 | 25.3 |
| 36 | 22.2 |
| 37 | 19.8 |
| 37.1 | 2000 |
| 37.2 | 9.46 |
| 38 | 19.3 |
| 38.1 | 2000 |
| 38.2 | 7.37 |
| 39 | 19 |
| 40 | 15.4 |
| 40.1 | 792 |
| 40.2 | 7.08 |
| 41 | 13.5 |
| 41.1 | 2930 |
| 41.2 | 7.73 |
| 42 | 11.3 |
| 43 | 11.1 |
| 43.1 | 2730 |
| 43.2 | 5.93 |
| 44 | 8.83 |
| 44.1 | 1390 |
| 44.2 | 6.72 |
| 45 | 338 |
| 45.1 | 201 |
| 45.2 | 8910 |
| 45.3 | 1050 |
| 45.4 | >20000 |
| 46 | 7.07 |
| 46.1 | 1470 |
| 46.2 | 5.69 |
| 47 | 3.77 |
| 47.1 | 1020 |
| 47.2 | 1.96 |
| 48 | 3.72 |
| 48.1 | 1.76 |
| 48.2 | 120 |
| 49 | 2.76 |
| 49.1 | 1030 |
| 49.2 | 2.1 |
| 50 | 378 |
| 50.1 | 127 |
| 50.2 | 14300 |
| 51 | 16.6 |
| 51.1 | 8.85 |
| 51.2 | 872 |
| 52 | 99.2 |
| 52.1 | 72.7 |
| 52.2 | 11400 |
| 53 | 30.8 |
| 53.1 | 20.3 |
| 53.2 | 1780 |
| 54 | 20.7 |
| 55 | 9.74 |
| 55.1 | 6 |
| 55.2 | 835 |
| 56 | 120 |
| 56.1 | 50.5 |
| 56.2 | 7640 |
| 57 | 155 |
| 57.1 | 137 |
| 57.2 | 14638 |
| 58 | 16.7 |
| 58.1 | 8 |
| 58.2 | 1047 |
| 59 | 10.3 |
| 59.1 | 4 |
| 59.2 | 424 |
| 60 | 403 |
| 61 | 93.2 |
| 61.1 | 5180 |
| 61.2 | 108 |
| 62 | 32.2 |
| 62.1 | 4620 |
| 62.2 | 23.2 |
| 63 | 33.9 |
| 63.1 | 5170 |
| 63.2 | 18.5 |
| 64 | 55.8 |
| 65 | 101 |
| 66 | 363 |
| 67 | 2270 |
| 68 | 457 |
| 69 | 64.1 |
| 70 | 196 |
| 71 | 2310 |
| 72 | 985 |
| 73 | 148 |
| 73.1 | 3720 |
| 73.2 | 82.1 |
| 74 | 190 |
| 74.1 | 17100 |
| 74.2 | 81.4 |
| 75 | 419 |
| 75.1 | >20000 |
| 75.2 | 214 |
| 76 | 252 |
| 76.1 | 114 |
| 76.2 | 11000 |
| 77 | 533 |
| 77.1 | 234 |
| 77.2 | 10200 |
| 78 | 7220 |
| 78.1 | >20000 |
| 78.2 | 7550 |
| 79 | 6790 |
| 79.1 | 1660 |
| 79.2 | 2390 |
| 80 | 10.8 |
| 81 | 8.71 |
| 81.1 | 1020 |
| 81.2 | 10.1 |
| 82 | 89.6 |
| 83 | 24.3 |
| 84 | 24.6 |
| 85 | 20.3 |
| 86 | 759 |
| 87 | 8.53 |
| 88 | 667 |

TABLE 18-continued

IC$_{50}$ values of examples in in vitro human DGKζ kinase activity inhibition assays.

| Example number | IC$_{50}$ [nM] |
|---|---|
| 89 | 131 |
| 90 | 63.3 |
| 91 | 701 |
| 92 | 16.7 |
| 93 | 187 |
| 94 | 25.7 |
| 95 | 39 |
| 96 | 31.4 |
| 97 | 24.7 |
| 98 | 73.5 |
| 99 | 75.8 |
| 100 | 176 |
| 101 | 329 |
| 102 | 506 |
| 103 | 41.9 |
| 104 | 234 |
| 105 | 6.45 |
| 106 | 33.3 |
| 107 | 77.3 |
| 108 | 19.4 |
| 109 | 51.7 |
| 110 | 366 |
| 111 | 334 |
| 112 | 300 |
| 113 | 703 |
| 114 | 658 |
| 115 | 272 |
| 116 | 581 |
| 117 | 14.9 |
| 118 | 22.4 |
| 119 | 4.54 |
| 120 | 16.7 |
| 121 | 19.9 |
| 122 | 9.07 |
| 123 | 100 |
| 124 | 48.3 |
| 125 | 44 |
| 126 | 28.8 |
| 127 | 73.1 |
| 128 | 72.2 |
| 129 | 97.1 |
| 130 | 46.5 |
| 131 | 180 |
| 132 | 93.3 |
| 133 | 42.5 |
| 134 | 76.8 |
| 135 | 49.5 |
| 136 | 740 |
| 137 | 238 |
| 138 | 61.6 |
| 139 | 56.9 |
| 140 | 37.5 |
| 141 | 389 |
| 142 | 14.5 |
| 143 | 12.7 |
| 144 | 8.79 |
| 145 | 2.66 |
| 146 | 21.6 |
| 147 | 291 |
| 148 | 76.4 |
| 149 | 405 |
| 150 | 372 |
| 151 | 387 |
| 152 | 111 |
| 153 | 107 |
| 154 | 55.6 |
| 155 | 200 |
| 156 | 231 |
| 157 | 190 |
| 158 | 6.71 |
| 159 | 214 |
| 160 | 187 |
| 160.1 | 115 |
| 160.2 | 8448 |
| 161 | 15 |
| 161.1 | 9 |
| 161.2 | 2573 |
| 162 | 22 |
| 162.1 | 12 |
| 162.2 | 6574 |
| 163 | 9 |
| 163.1 | 5 |
| 163.2 | 1091 |
| 164 | 7 |
| 164.1 | 5 |
| 164.2 | 944 |
| 165 | 3 |
| 165.1 | 2 |
| 165.2 | 331 |
| 166 | 3 |
| 166.1 | 2 |
| 166.2 | 129 |
| 167 | 2 |
| 167.1 | 3 |
| 167.2 | 303 |
| 168 | 19 |
| 169 | 3 |
| 169.1 | 3 |
| 169.2 | 859 |
| 170 | 7 |
| 170.1 | 5 |
| 170.2 | 1000 |
| 171 | 11 |
| 172 | 46 |
| 172.1 | 24 |
| 172.2 | 4892 |
| 173 | 25 |
| 174 | 51 |
| 174.1 | 26 |
| 174.2 | 3793 |
| 175 | 20 |
| 176 | 91 |
| 176.1 | 34 |
| 176.2 | 672 |
| 177 | 40 |
| 178 | 48 |
| 179 | 57 |
| 180 | 62 |
| 181 | 65 |
| 182 | 91 |
| 182.1 | 84 |
| 182.2 | 10527 |
| 183 | 222 |
| 184 | 428 |
| 184.1 | 297 |
| 184.2 | >20000 |
| 185 | 301 |
| 186 | 392 |
| 187 | 1400 |
| 187.1 | 553 |
| 187.2 | >20000 |
| 188 | 1240 |
| 189 | 6352 |
| 190 | 553 |
| 191 | 356 |
| 192 | 224 |
| 193 | 35 |
| 194 | 66 |
| 195 | 1000 |
| 196 | 128 |
| 197 | 90 |
| 198 | 88 |
| 199 | 396 |
| 200 | 70 |
| 201 | 25 |
| 202 | 69 |
| 203 | 381 |
| 204 | 73 |
| 205 | 54 |
| 206 | 48 |

TABLE 18-continued

IC$_{50}$ values of examples in in vitro human DGKζ kinase activity inhibition assays.

| Example number | IC$_{50}$ [nM] |
|---|---|
| 207 | 22 |
| 208 | 672 |
| 209 | 45 |
| 210 | 69 |
| 211 | 183 |
| 212 | 41 |
| 213 | 42 |
| 214 | 16 |
| 215 | 279 |
| 216 | 32 |
| 217 | 41 |
| 218 | 64 |
| 219 | 13 |
| 220 | 219 |
| 221 | 31 |
| 222 | 108 |
| 223 | 235 |
| 224 | 45 |
| 225 | 252 |
| 226 | 87 |
| 227 | 393 |
| 228 | 218 |
| 229 | 193 |
| 230 | 199 |
| 231 | 662 |
| 232 | 112 |
| 233 | 267 |
| 234 | 1640 |
| 235 | 542 |
| 236 | 730 |
| 237 | 749 |
| 238 | 667 |
| 239 | 236 |
| 240 | 1328 |
| 241 | 382 |
| 242 | 2031 |
| 243 | 51 |
| 244 | 30 |
| 245 | 22 |
| 246 | 662 |
| 247 | 40 |
| 248 | 136 |
| 249 | 120 |
| 250 | 36 |
| 251 | 87 |
| 252 | 106 |
| 253 | 59 |
| 254 | 32 |
| 255 | 76 |
| 256 | 9 |
| 257 | n.d. |
| 258 | 19 |
| 259 | 19 |
| 260 | 29 |
| 261 | 90 |
| 262 | 6 |
| 263 | 539 |
| 264 | 376 |
| 265 | 459 |
| 266 | 287 |
| 267 | 63 |
| 268 | 3 |
| 269 | 12 |
| 270 | 13 |
| 271 | 18 |
| 272 | 39 |
| 273 | 20 |
| 274 | 107 |
| 275 | 29 |
| 276 | 29 |
| 277 | 494 |
| 278 | 230 |
| 279 | 48 |
| 280 | 43 |
| 281 | 98 |
| 282 | 53 |
| 283 | 36 |
| 284 | 33 |
| 285 | 68 |
| 285.1 | 34 |
| 285.2 | 432 |
| 286 | 31 |
| 287 | 18 |
| 288 | 3442 |
| 289 | 10 |
| 290 | 936 |
| 291 | 178 |
| 292 | 282 |

TABLE 19

IC$_{50}$ values of intermediates in in vitro human DGKζ kinase activity inhibition assays.

| Intermediate number | IC$_{50}$ [nM] |
|---|---|
| 41 | >20000 |
| 43 | >20000 |
| 62 | >20000 |
| 63 | >20000 |
| 64 | >20000 |
| 65 | >20000 |
| 66 | >20000 |
| 67 | >20000 |

Transactivation Assay in Jurkat IL2-Reporter Cell Line

Transactivation assays were carried out in Jurkat cells purchased from Promega (Promega, #CS187001) stably transfected with a firefly luciferase reporter gene construct under the control of the IL2-promoter. Cells were cultured as specified by the manufacturer. Bulk cells were harvested at a culture density of approx. 1E+06 cells/mL, suspended in cryo-storage medium (70% RPMI/20% FCS/10% DMSO), frozen at controlled rate of −1°/min in 1.8 mL cryo-vials with cell densities of 1E+07 to 1E+08 cells per vial, and stored at −150° C. or below until further use. Frozen cells were thawed and cultured in medium at a starting density of 3.5E+05 cells/mL for 6 days. On day 6 cells were centrifuged for 5 min at 300×g, medium was decanted and cell concentration was adjusted to 5.0E+06 cells/mL with fresh assay medium (500 mL RPMI (Gibco, #22400)+5 mL L-Glutamin (Sigma, #G7513)+5 mL Penicillin/Streptomycin (Sigma #P0781)+5 mL Non-essential amino acids (Invitrogen, #11140)+5 mL sodium-pyruvate (Gibco #1136088), 5 mL FBS (Biochrom, #S0615)). Cell working stock was split in two parts: neutral control and compounds with EC30 stimulation, high control with EC100 stimulation.

An antibody premix was prepared by diluting anti-CD3 (BD Pharmingen, #555329), anti-CD28 (BD Pharmingen, #555725) and goat anti mouse anti-IgG (ThermoFisher, #31160) antibodies at 1/1/4 ratio in assay medium at 2-fold of final concentration (final concentrations depend on cell batch, typically for neutral control 0.055/0.055/0.22 μg/mL, for high control 0.5/0.5/2 mg/mL). The premix solutions were added to the cells in 1+1 volume prior use.

Fifty nL of a 100-fold concentrated solution of the test compounds in DMSO were transferred into a white microtiter test plate (384, Greiner Bio-One, Germany). For this, either a Hummingbird liquid handler (Digilab, USA) or an Echo acoustic system (Labcyte, USA) was used. Five µL of the freshly prepared cell suspension was added to the wells of a test plate and incubated at 37° C. in a 5% $CO_2$ atmosphere. After completion of the incubation for 4 hours, 3 µl of Bio-Glo Luciferase assay reagent (Promega, #G7941, prepared as recommended by the supplier) were added to all wells. The test plate was incubated at 20° C. for 10 min before measurement of the luminescence in a microplate reader (typically Pherastar by BMG, Germany, or ViewLux by Perkin-Elmer, USA). Data were normalized (neutral control=0% effect, high control=100% effect). Compounds were tested in duplicates at up to 11 concentrations (typically 20 µM, 5.7 µM, 1.6 µM, 0.47 µM, 0.13 µM, 38 nM, 11 nM, 3.1 nM, 0.89 nM, 0.25 nM and 0.073 nM). Dilution series were made prior to the assay in a 100-fold concentrated form by serial dilution. $EC_{50}$ values were calculated by 4-Parameter fitting using a commercial software package (Genedata Analyzer, Switzerland).

Polyclonal Activation of Human PBMCs

To test the effect of DGKζ inhibitors of the present invention on IL-2 and IFN-γ secretion of human Peripheral Blood Mononuclear Cells (PBMCs) a 24 h human PBMC assay was performed as screening assay. For this, a 96 well flat bottom plate was coated with a suboptimal stimulation condition (EC 10-30) of human aCD3 (Invitrogen, clone OKT3) antibody in 50 µL PBS/well at 4° C. overnight. PBMCs isolated and frozen at liquid $N_2$ from leucapherese samples was thawed and resuspended in culture medium (X-Vivo-20). $4 \times 10^5$ cells/well were plated. Wells were treated with the DGKζ inhibitors of the present invention at the respective concentrations (5-fold dilution steps from 10 µM to 3 nM) and the final DMSO concentration per well is 0.1%. Medium+DMSO (0.1%) was used as baseline value. As positive controls 1000 ng/mL aCD3+aCD28 (1 µg/mL) and a DGKζ reference inhibitor was used. After 24 h the medium was collected and hIL-2 or hIFN-γ ELISA were performed. The following parameters were calculated: $EC_{50}$ value, concentration at 50% increase; max increase in % and respective concentration and maximum effect normalized to max concentration (10 µM) of a selected DGKζ reference inhibitor.

In Vitro Activation of Mouse OT-I Antigen-Specific T-Cells

To test the effect of DGKζ inhibitors of the present invention in murine antigen-specific T-cells, spleens and lymph nodes of OT-I mice were collected and mashed through a 40 µm cell strainer and incubated for 1 min in 1 mL ACK lysing buffer (Gibco)/spleen. 4×106 cells/mL were incubated in medium containing 0.05 ng/mL SIINFEKL (FIG. 2) in a 50 mL falcon at 37° C. for 30 min. Afterwards cells were centrifuged and 4×106 cells/mL were resuspended in fresh medium (DMEM; 10% FCS, 1% Pen/Strep, 0.1% β-mercaptoethanol, 1% HEPES). 4×105 cells were plated per well in a 96-well round bottom plate. Wells were treated with DGKζ inhibitors of the present invention at the respective concentrations (5-fold dilution steps from 10 µM to 3 nM) in a final DMSO concentration of 0.1%. Medium+DMSO (0.1%) was used as baseline value. As positive controls cells incubated with the 4× SIINFEKL concentration (0.2 ng/ml) and a DGKζ reference inhibitor were used. The plates were centrifuged to reduce the distance between T-cells and APCs before incubation. After 24 h the medium was collected and mIL-2 or mIFN-γ ELISAs were performed. The following parameters were calculated: $EC_{50}$ value, concentration at 50% increase; max increase in % and respective concentration and maximum effect normalized to max concentration (10 µM) of a selected DGKζ reference inhibitor.

DGKζ Surface Plasmon Resonance Interaction Assay

The ability of the compounds described in this invention to bind to DGKζ were determined using surface plasmon resonance (SPR). This allows for the quantification of binding in terms of the equilibrium dissociation constant ($K_D$ [M]), as well as association and dissociation rate constants ($k_{on}$ [1/Ms] and $k_{off}$ [1/s], respectively). The measurements were performed using Biacore® T200, Biacore® S200 or Biacore® 8K (GE Healthcare).

All buffers described in this section were prepared with 10×HBS-P+ Buffer (GE Healthcare, #BR100671) supplemented with additional buffer components as indicated below, dithiothreitol (DTT from Sigma, #D0632-25G), Adenosine 5'-triphosphate (ATP from Sigma, #A26209-10G), $MgCl_2$ (Sigma, #M1028-100ML), dimethyl sulfoxide (DMSO from Biomol, #54686.500).

For SPR measurements, recombinant and biotinylated human DGKζ (obtained from Cama Biosciences, Product number: 12-410-20N) was immobilized via the streptavidin-biotin interaction onto a Series S Sensor Chip SA (GE Healthcare, #BR-1005-31). Briefly, DGKζ was diluted to a concentration of 10 µg/mL in Immobilization Buffer (10 mM HEPES, 150 mM NaCl, 0.05% v/v Surfactant P20.2 mM $MgCl_2$, 1 mM DTT, pH 7.4) and captured on the SA Chip surface using a flow rate of 10 µL/min for 500 seconds at a temperature of 10° C. Immobilization levels of approximately 6000 RU were typically achieved. The reference surface consisted of a streptavidin surface without immobilized protein. Compounds were diluted from 10 mM DMSO stock solution into Running Buffer (10 mM HEPES, 150 mM NaCl, 0.05% v/v Surfactant P20, 2 mM $MgCl_2$, 1 mM DTT, 0.2 mM ATP and 1% v/v DMSO, pH 7.4). For SPR-binding measurements serial dilutions (typically 1:3 dilutions resulting in 8 concentrations up to 2 µM or 20 µM) were injected over immobilized protein. Binding affinity and kinetics were measured at 18° C. and at a flow rate of 100 µL/min.

A variation of the assay with an additional regeneration step was performed by injection of Regeneration Buffer without ATP (10 mM HEPES, 150 mM NaCl, 0.05% v/v Surfactant P20, 1 mM DTT and 1% v/v DMSO, pH 7.4) for 200 s at a flow rate of 30 µL/min The double-referenced sensorgrams were fit to a simple reversible Langmuir 1:1 reaction mechanism as implemented in the Biacore® T200, S200 and 8K evaluation software (Biacore T200 Evaluation Software version 2.0, Biacore S200 Evaluation Software version 1.0, Biacore 8K Evaluation Software, GE Healthcare).

Expression of DGKζ in Insect Cells Using the Baculovirus System

Expression Constructs:

The cDNA encoding the full length sequence of human DGKζ (Uniprot O13574-2) was optimized for expression in eukaryotic cells and synthesized by the GeneArt Technology at Life Technologies.

The DNA sequence encoded the following sequence:

Construct DGKζ_hu amino acid M1 to V928

Additionally the expression construct encoded: a Kozak DNA sequence for translation initiation (GCCACC), a translational start codon for methionine followed by amino acid glycine, a Flag (DYKDDDDK) sequence at the N-terminus of DGKζ, and at the C-terminus of DGKζ two stop codons and moreover 5' and 3' att-DNA sequences for Gateway Cloning.

The DGKζ construct was subcloned using the Gateway Technology into the Destination vector pD-INS. The vector pD-INS is a Baculovirus transfer vector (based on vector pVL1393, Pharmingen) which enables the expression of the Flag-DGKζ protein. The respective protein was named DGKz_hu_1.

Generation of Recombinant Baculovirus

The DGKζ transfer vector was co-transfected in Sf9 cells with Baculovirus DNA (Flashbac Gold DNA, Oxford Expression Technologies) using Fugene HD (Roche). After 5 days the supernatant of the transfected cells containing the recombinant Baculovirus encoding the various DGK proteins was used for further infection of Sf9 cells for virus amplification whereby the virus titer was monitored using qPCR.

DGKζ Expression in Sf9 Cells Using Bioreactor

Sf9 cells cultured (Insect-xpress medium, Lonza, 27° C.) in a Wave-bioreactor with a disposable culture bag were infected at a cell density of $10^6$ cells/mL with one of the recombinant baculovirus stocks at a multiplicity of infection of 1 and incubated for 72. Subsequently, the cells were harvested by centrifugation (800×g) and the cell pellet frozen at −80° C.

Purification of the DGKz_hu_1 Protein:

Purification of the DGKz_hu_1 protein was achieved by a two-step chromatography procedure as follows.

The pelleted cells (from 8 L cell culture) were resuspended in Lysis-Buffer (25 mM Tris HCl 8.0; 500 mM NaCl; 250 mM Sucrose, 1 mM DTT; 0.1% Triton X-100; Complete Protease Inhibitor Cocktail-(Roche)) and lysed by a freeze-thaw cycle followed by an incubation on ice for 60 min in the presence of Benzonase (25 U/mL). The lysate was centrifuged at 63.000×g for 30 min at 4° C. The soluble supernatant was than incubated with 40 mL anti-Flag M2 Agarose (Sigma) in a plastic flask rotating for 16 h at 4° C. for binding of the tagged DGKζ proteins, subsequently rinsed with 5×50 mL Wash-Buffer (25 mM Tris HCl 8.0; 500 mM NaCl; 250 mM Sucrose; 1 mM DTT) and finally the bound protein was eluted using Elution-Buffer (Wash-Buffer with 250 µg/mL FLAG-Peptide, incubated 30 min. at 4° C. with 3×25 mL).

The elution fractions from the affinity chromatography were concentrated (using Amicon Ultra 15, Centrifugal Filters, 30 kDa MW cut-off; Millipore #UFC903024) to 25 mL and applied to a size exclusion chromatography column (S200 prep grade 26/60, GE Healthcare) and the resulting monomeric peak fraction was collected, pooled and again concentrated. Wash-buffer with 300 mM NaCl was used for size exclusion chromatography and the final concentrated sample. The final protein sample concentration was 5 to 10 mg/mL and the yield was 5 mg final protein per L cell culture.

The in vivo activity of the compounds of the present invention can be demonstrated in the following assays:

In Vivo Activation of Murine Antigen Specific OT-I T Cells

Oral Administration of compounds enhances antigen-specific T cell activation in vivo.

Direct detection of antigen-specific T cell proliferation in vivo is technically challenging, since it requires the presence of T cells specific for a cognate antigen and also a specific measurement procedure for cell proliferation. Both these requirements are fulfilled in the OT-I transfer model, which utilizes the direct transfer of CD8 T cells transgenic for a T cell receptor recognizing an Ovalbumin-derived peptide as antigen.

Before transfer, the OT-I T cells were labeled with the fluorescent dye CFSE, which was diluted by every cell division and therefore allowed detection of cell proliferation. After transfer of the CFSE-labeled T cells, mice were vaccinated with the Ovalbumin antigen OVA-30 (FIG. 3). Only transferred OT-I cells were able to recognize the OVA-antigen presented by APC and only these transferred T cells then got activated. Flow cytometric analysis of CFSE-levels in the OT-I cells can be combined with measurement of multiple activation markers like CD69, CD25 and PD1. In particular, Wild type C57Bl6 mice received 2×10×6 CFSE-labeled OT-I T cells and were vaccinated one day later by intravenous application of 2.5 µg OVA-30. Mice were then divided into groups which received vehicle only, DGKζ inhibitors of the present invention alone or in combination with other immune modulating agents. Mice were treated for 2 to 20 days and T cell composition (incl. transferred OT-1 cells) of spleen, blood and lymph nodes were analysed by FACS.

In Vivo Syngeneic Tumor Models

Mice were assigned to a study at the age of 6-8 weeks. Animal husbandry, feeding and health conditions were according to animal welfare guidelines. Syngeneic tumor cell lines were cultivated with appropriate medium and split at least 3 times before inoculation. Female mice were inoculated with appropriate amount of tumor cells in medium or a medium/matrigel mixture s.c, i.v., or i.p, depending on the model. After 4-10 days the mice were randomized and therapeutic treatment started when tumors had reached a size of approx. 40-70 mm².

Tumor size was measured using calipers determining length (a) and width (b). Tumor volume was calculated according to:

$$v=(a \times b^2)/2$$

Significance of monotherapies and combination treatment was calculated versus control group as determined by 2-Way ANOVA analysis.

The invention claimed is:

1. A compound having the structure:

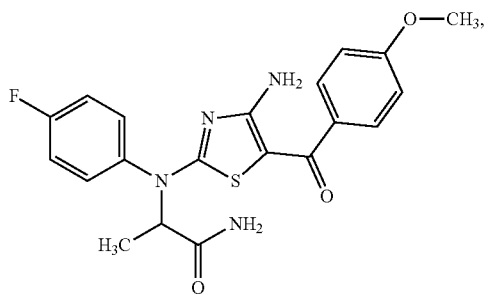 [SMILES: COc1ccc(C(=O)c2sc(N(c3ccc(F)cc3)C(C)C(N)=O)nc2N)cc1]

or a tautomer, hydrate, or solvate thereof, or a pharmaceutically acceptable salt of any of the foregoing.

2. The compound of claim 1, wherein the compound is

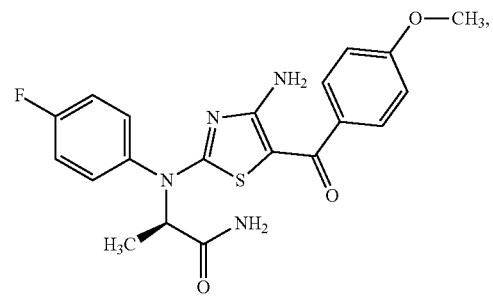 [SMILES: COc1ccc(C(=O)c2sc(N(c3ccc(F)cc3)[C@H](C)C(N)=O)nc2N)cc1]

or a tautomer, hydrate, or solvate thereof, or a pharmaceutically acceptable salt of any of the foregoing.

3. The compound of claim 1, wherein the compound is

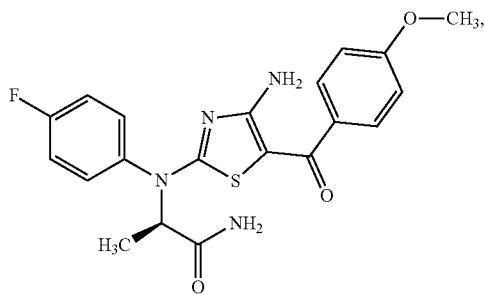 [SMILES: COc1ccc(C(=O)c2sc(N(c3ccc(F)cc3)[C@H](C)C(N)=O)nc2N)cc1]

or a pharmaceutically acceptable salt thereof.

4. The compound of claim 1, wherein the compound is

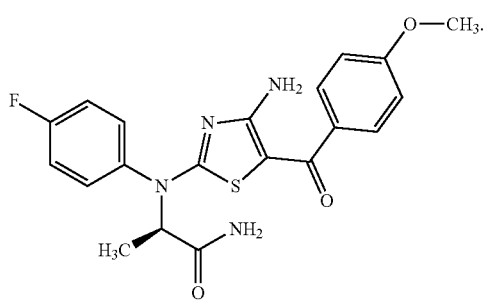

5. A pharmaceutical composition comprising a compound of claim 2, or a tautomer, hydrate, or solvate thereof, or a pharmaceutically acceptable salt of any of the foregoing, and at least one pharmaceutically acceptable excipient.

6. A pharmaceutical composition comprising a compound of claim 3, or a pharmaceutically acceptable salt thereof, and at least one pharmaceutically acceptable excipient.

7. A pharmaceutical composition comprising a compound of claim 4 and at least one pharmaceutically acceptable excipient.

8. A method of treating a disease or condition associated with dysregulated immune responses or aberrant DGKζ signaling in a mammal, comprising administering an effective amount of a compound of claim 2, or a tautomer, hydrate, or solvate thereof, or a pharmaceutically acceptable salt of any of the foregoing, to the mammal.

9. The method of claim 8, wherein the mammal is a human.

10. The method of claim 8, wherein the disease is cancer.

11. The method of claim 8, wherein the disease is non-small cell lung cancer, gastric adenocarcinoma, cancer of the gastroesophageal junction, clear cell renal cell carcinoma, or melanoma.

12. The method of claim 8, wherein the disease is non-small cell lung cancer.

13. The method of claim 8, wherein the disease is gastric adenocarcinoma.

14. The method of claim 8, wherein the disease is cancer of the gastroesophageal junction.

15. The method of claim 8, wherein the disease is clear cell renal cell carcinoma.

16. The method of claim 8, wherein the disease is melanoma.

17. A method of treating a disease or condition associated with dysregulated immune responses or aberrant DGKζ signaling in a mammal, comprising administering an effective amount of a compound of claim 3, or a pharmaceutically acceptable salt thereof, to the mammal.

18. The method of claim 17, wherein the compound is

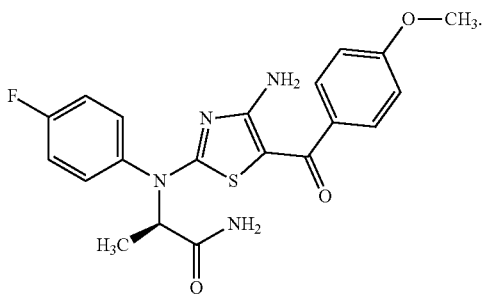

19. The method of claim 17, wherein the mammal is a human.

20. The method of claim 17, wherein the disease is cancer.

21. The method of claim 17, wherein the disease is non-small cell lung cancer, gastric adenocarcinoma, cancer of the gastroesophageal junction, clear cell renal cell carcinoma, or melanoma.

22. The method of claim 17, wherein the disease is non-small cell lung cancer.

23. The method of claim 17, wherein the disease is gastric adenocarcinoma.

24. The method of claim 17, wherein the disease is cancer of the gastroesophageal junction.

25. The method of claim 17, wherein the disease is clear cell renal cell carcinoma.

26. The method of claim 17, wherein the disease is melanoma.

* * * * *

SEQUENCE LISTING

```
Sequence total quantity: 5
SEQ ID NO: 1            moltype = AA  length = 938
FEATURE                 Location/Qualifiers
REGION                  1..938
                        note = DGKz hu 1 encoding human DGKzM1 to V928 plus
                        N-terminal Flag-Tag
source                  1..938
                        mol_type = protein
                        organism = Homo sapiens
SEQUENCE: 1
MGDYKDDDDK MEPRDGSPEA RSSDSESASA SSSGSERDAG PEPDKAPRRL NKRRFPGLRL   60
FGHRKAITKS GLQHLAPPPP TPGAPCSESE RQIRSTVDWS ESATYGEHIW FETNVSGDFC  120
```

```
YVGEQYCVAR MLKSVSRRKC AACKIVVHTP CIEQLEKINF RCKPSFRESG SRNVREPTFV    180
RHHWVHRRRQ DGKCRHCGKG FQQKFTFHSK EIVAISCSWC KQAYHSKVSC FMLQQIEEPC    240
SLGVHAAVVI PPTWILRARR PQNTLKASKK KKRASFKRKS SKKGPEEGRW RPFIIRPTPS    300
PLMKPLLVFV NPKSGGNQGA KIIQSFLWYL NPRQVFDLSQ GGPKEALEMY RKVHNLRILA    360
CGGDGTVGWI LSTLDQLRLK PPPPVAILPL GTGNDLARTL NWGGGYTDEP VSKILSHVEE    420
GNVVQLDRWD LHAEPNPEAG PEDRDEGATD RLPLDVFNNY FSLGFDAHVT LEFHESREAN    480
PEKFNSRFRN KMFYAGTAFS DFLMGSSKDL AKHIRVVCDG MDLTPKIQDL KPQCVVFLNI    540
PRYCAGTMPW GHPGEHHDFE PQRHDDGYLE VIGFTMTSLA ALQVGGHGER LTQCREVVLT    600
TSKAIPVQVD GEPCKLAASR IRIALRNQAT MVQKAKRRSA APLHSDQQPV PEQLRIQVSR    660
VSMHDYEALH YDKEQLKEAS VPLGTVVVPG DSDLELCRAH IERLQQEPDG AGAKSPTCQK    720
LSPKWCFLDA TTASRFYRID RAQEHLNYVT EIAQDEIYIL DPELLGASAR PDLPTPTSPL    780
PTSPCSPTPR SLQGDAAPPQ GEELIEAAKR NDFCKLQELH RAGGDLMHRD EQSRTLLHHA    840
VSTGSKDVVR YLLDHAPPEI LDAVEENGET CLHQAAALGQ RTICHYIVEA GASLMKTDQQ    900
GDTPRQRAEK AQDTELAAYL ENRQHYQMIQ REDQETAV                           938

SEQ ID NO: 2            moltype = AA  length = 8
FEATURE                 Location/Qualifiers
REGION                  1..8
                        note = SIINFEKL
source                  1..8
                        mol_type = protein
                        organism = Mus musculus
SEQUENCE: 2
SIINFEKL                                                            8

SEQ ID NO: 3            moltype = AA  length = 30
FEATURE                 Location/Qualifiers
REGION                  1..30
                        note = Ovalbumin antigen OVA-30
source                  1..30
                        mol_type = protein
                        organism = Gallus gallus
SEQUENCE: 3
SMLVLLPDEV SGLEQLESII NFEKLTEWTS                                    30

SEQ ID NO: 4            moltype = AA  length = 8
FEATURE                 Location/Qualifiers
REGION                  1..8
                        note = FLAG-Tag
source                  1..8
                        mol_type = protein
                        organism = synthetic construct
SEQUENCE: 4
DYKDDDDK                                                            8

SEQ ID NO: 5            moltype = AA  length = 6
FEATURE                 Location/Qualifiers
REGION                  1..6
                        note = Kozak sequence for translation initiation
source                  1..6
                        mol_type = protein
                        organism = synthetic construct
SEQUENCE: 5
GCCACC                                                              6
```